US010052342B2

(12) United States Patent
Blatt et al.

(10) Patent No.: US 10,052,342 B2
(45) Date of Patent: *Aug. 21, 2018

(54) SUBSTITUTED NUCLEOSIDES, NUCLEOTIDES AND ANALOGS THEREOF

(71) Applicant: ALIOS BIOPHARMA, INC., South San Francisco, CA (US)

(72) Inventors: Lawrence M. Blatt, Healdsburg, CA (US); Leonid Beigelman, San Mateo, CA (US); Natalia Dyatkina, Mountain View, CA (US); Julian Alexander Symons, San Carlos, CA (US); David Bernard Smith, San Mateo, CA (US)

(73) Assignee: Alios BioPharma, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/427,964

(22) Filed: Feb. 8, 2017

(65) Prior Publication Data
US 2017/0143751 A1 May 25, 2017

Related U.S. Application Data

(63) Continuation of application No. 14/746,138, filed on Jun. 22, 2015, now Pat. No. 9,603,863.

(60) Provisional application No. 62/016,219, filed on Jun. 24, 2014, provisional application No. 62/034,629, filed on Aug. 7, 2014, provisional application No. 62/061,819, filed on Oct. 9, 2014.

(51) Int. Cl.
A01N 43/04 (2006.01)
A61K 31/70 (2006.01)
A61K 31/7068 (2006.01)
A61K 31/708 (2006.01)
A61K 31/7072 (2006.01)
A61K 31/7076 (2006.01)
A61K 31/7052 (2006.01)
A61K 31/706 (2006.01)
A61K 31/7064 (2006.01)

(52) U.S. Cl.
CPC ........ A61K 31/7068 (2013.01); A61K 31/708 (2013.01); A61K 31/7072 (2013.01); A61K 31/7076 (2013.01); A61K 31/706 (2013.01); A61K 31/7052 (2013.01); A61K 31/7064 (2013.01)

(58) Field of Classification Search
None
See application file for complete search history.

(56) References Cited

U.S. PATENT DOCUMENTS

| 5,432,272 | A | 7/1995 | Benner et al. |
| 7,125,855 | B2 | 10/2006 | Bhat et al. |
| 2005/0054590 | A1 | 3/2005 | Averett |
| 2012/0070411 | A1 | 3/2012 | Beigelman et al. |
| 2012/0070415 | A1 | 3/2012 | Beigelman et al. |
| 2012/0071434 | A1 | 3/2012 | Smith et al. |
| 2012/0165286 | A1 | 6/2012 | Beigelman et al. |
| 2013/0164261 | A1 | 6/2013 | Wang et al. |
| 2013/0165400 | A1 | 6/2013 | Beigelman et al. |
| 2013/0252920 | A1 | 9/2013 | Blatt et al. |
| 2013/0253181 | A1 | 9/2013 | Serebryany et al. |
| 2013/0281687 | A1 | 10/2013 | Serebryany et al. |
| 2013/0289024 | A1 | 10/2013 | Johansen et al. |
| 2014/0178338 | A1 | 6/2014 | Mayes et al. |
| 2014/0179627 | A1 | 6/2014 | Beigelman et al. |
| 2014/0179910 | A1 | 6/2014 | Beigelman et al. |
| 2014/0303108 | A1 | 10/2014 | Beigelman et al. |
| 2014/0303113 | A1 | 10/2014 | Krop et al. |
| 2015/0011497 | A1 | 1/2015 | Beigelman et al. |
| 2015/0038451 | A1 | 2/2015 | Smith et al. |
| 2015/0051167 | A1 | 2/2015 | Wang et al. |
| 2015/0105341 | A1 | 4/2015 | Beigelman et al. |
| 2015/0141363 | A1 | 5/2015 | Wang et al. |
| 2015/0175647 | A1 | 6/2015 | Kuldipkumar et al. |
| 2015/0183819 | A1 | 7/2015 | Beigelman et al. |
| 2015/0315228 | A1 | 11/2015 | Beigelman et al. |
| 2015/0366887 | A1 | 12/2015 | Blatt et al. |
| 2015/0366888 | A1 | 12/2015 | Blatt et al. |
| 2015/0368286 | A1 | 12/2015 | Serebryany et al. |
| 2016/0016987 | A1 | 1/2016 | Beigelman et al. |
| 2016/0022724 | A1 | 1/2016 | Chanda et al. |
| 2016/0024136 | A1 | 1/2016 | Beigelman et al. |
| 2016/0039858 | A1 | 2/2016 | Beigelman et al. |
| 2016/0039861 | A1 | 2/2016 | Smith et al. |
| 2016/0115190 | A1 | 4/2016 | Serebryany et al. |
| 2016/0176910 | A1 | 6/2016 | Wang et al. |
| 2016/0176911 | A1 | 6/2016 | Beigelman et al. |

(Continued)

FOREIGN PATENT DOCUMENTS

| WO | WO 2002/069903 | 9/2002 |
| WO | WO 2006/033709 | 3/2006 |

(Continued)

OTHER PUBLICATIONS

Huggins et al. JID (1999), vol. 179 (Suppl 1), pp. S240-S247.*
Examination Report dated Jan. 9, 2018 for New Zealand Patent Application No. 727582, filed Jun. 22, 2015.
Huggins et al., "Antiviral Drug Therapy of Filovirus Infections: S-Adenosylhomocysteine Hydrolase Inhibitors Inhibit Ebola Virus In Vitro and in a Lethal Mouse Model" Journal of Infectious Disease (1999) 179 (Suppl. 1):S240-S247.

(Continued)

Primary Examiner — Patrick T Lewis
(74) Attorney, Agent, or Firm — Knobbe, Martens, Olson & Bear, LLP

(57) ABSTRACT

Disclosed herein are nucleosides, nucleotide analogs, methods of synthesizing nucleotide analogs and methods of treating diseases and/or conditions such as a Filoviridae virus infection with one or more nucleosides and/or nucleotide analogs.

22 Claims, No Drawings

(56) References Cited

U.S. PATENT DOCUMENTS

| | | |
|---|---|---|
| 2016/0264610 A1 | 9/2016 | Beigelman et al. |
| 2016/0318967 A1 | 11/2016 | Dyatkina et al. |
| 2016/0318969 A1 | 11/2016 | Kuldipkumar et al. |
| 2016/0331770 A1 | 11/2016 | Beigelman et al. |
| 2017/0002037 A1 | 1/2017 | Beigelman et al. |
| 2017/0037075 A1 | 2/2017 | Beigelman et al. |
| 2017/0037077 A1 | 2/2017 | Beigelman et al. |
| 2017/0143749 A1 | 5/2017 | Blatt et al. |
| 2018/0044369 A1 | 2/2018 | Beigelman et al. |
| 2018/0079774 A1 | 3/2018 | Beigelman et al. |

FOREIGN PATENT DOCUMENTS

| | | |
|---|---|---|
| WO | WO 2010/108135 | 9/2010 |
| WO | WO 2010/108140 | 9/2010 |
| WO | WO 2012/040126 | 3/2012 |
| WO | WO 2012/040127 | 3/2012 |
| WO | WO 2012/088155 | 6/2012 |
| WO | WO 2013/092481 | 6/2013 |
| WO | WO 2013/096679 | 6/2013 |
| WO | WO 2013/096680 | 6/2013 |
| WO | WO 2013/142124 | 9/2013 |
| WO | WO 2013/142159 | 9/2013 |
| WO | WO 2013/142525 | 9/2013 |
| WO | WO 2014/100498 | 6/2014 |
| WO | WO 2014/100505 | 6/2014 |
| WO | WO 2014/134251 | 9/2014 |
| WO | WO 2014/164533 | 10/2014 |
| WO | WO 2014/209979 | 12/2014 |
| WO | WO 2014/209983 | 12/2014 |
| WO | WO 2015/038596 | 3/2015 |
| WO | WO 2016/022464 | 2/2016 |
| WO | WO 2018/031818 | 2/2018 |

OTHER PUBLICATIONS

Simons et al., "Recent Advances in Antiviral Nucleoside and Nucleotide Therapeutics" Current Topics in Medicinal Chemistry (2005) 5(13):1191-1203.

Smith et al., "Interferon-β Therapy Prolongs Survival in Rhesus Macaque Models of Ebola and Marburg Hemorrhagic Fever" Journal of Infectious Diseases (2013) 208(2):310-318.

Uebelhoer et al., "High-throughput, luciferase-based reverse genetics systems for identifying inhibitors of Marburg and Ebola viruses" Antiviral Research (2014) 106:86-94.

Extended European Search Report dated Jan. 22, 2018 for EP Application No. 15810951.2, filed Jun. 22, 2015.

Bausch et al., "Treatment of Marburg and Ebola hemorrhagic fevers: A strategy for testing new drugs and vaccines under outbreak conditions," Antiviral Research (2008) 150-161.

Bondada, L. et al., "Adenosine Dioxolane Nucleoside Phosphoramidates as Antiviral Agents for Human Immunodeficiency and Hepatitis B Viruses" ACS Medicinal Chemistry Letters,(2013) 4(8):747-751.

Derivative, Merriam-Webster.com, Merriam-Webster, n.d. Web. Jun. 2, 2016.

Dyck, et al. "Effects of Deuterium Substitution on the Catabolism of beta-Phenylethylamine: An in Vivo Study", J Neurochem. 1986; 46(2): 399-404.

Geisbert, T.W. et al., "Postexposure protection of non-human primates against a lethal Ebola virus challenge with RNA interference: a proof-of-concept study" The Lancet (2010) 375(9729):1896-1905.

Greene, et al., Protective Groups in Organic Synthesis, 3. Ed., John Wiley & Sons, (1999) Cover & Contents pages.

"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.

Katritzky et al., Highly Diastereoselective Peptide Chain Extensions of Unprotected Amino Acids with N-(Z-α-Aminoacyl)benzotriazoles Synthesis (2004) 2004(16):2645-2652.

Lefebre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate" J. Med. Chem. (1995) 38:3941-3950.

Lewin, Benjamin, Genes V, (1994) Oxford University Press, pp. 87-90.

McOmie, J. F. W., Protective Groups in Organic Chemistry, Plenum Press, 1973. Cover & Contents pp. only.

McGuigan et al., "Phosphate Prodrugs Derived from N-Acetylglucosamine Have Enhanced Chondroprotective Activity in Explant Cultures and Represent a New Lead in Antiosteoarthritis Drug Discover" *J. Med. Chem.* (2008) 51:5807-5812.

Panchal et al., "Development of High-Content Imaging Assays for Lethal Viral Pathogens" J. Biomolecular Screening (2010) 15(7):755-765.

Pettitt, J., et al., "Therapeutic Intervention of Ebola Virus Infection in Rhesus Macaques with the MB-003 Monoclonal Antibody Cocktail" Sci Transl Med (2013) 5(199):199ra113 (1-6).

Qiu, X., et al., "Successful Treatment of Ebola Virus-Infected Cynomolgus Macaques with Monoclonal Antibodies" Sci Transl Med (2012) 4(138):138ra81 (1-11).

Reddy et al., "Stereoselective Synthesis of PSI-352938: A β-D-2'-Deoxy-2'α-fluoro-2'-β-C-methyl-3',5'-cyclic Phosphate Nucleotide Prodrug for the Treatment of HCV" *J. Org. Chem.* (2011) 76 (10):3782-3790.

Tung, R., "The development of deuterium-containing drugs" Innovations in Pharmaceutical Technology 2010; 32(32):24-28.

Villard et al., "Phenyl phosphotriester derivaties of AZT: Variations upon the SATE moiety" *Bioorg. Med. Chem.* (2008) 16:7321-7329.

Zhang et al., "Click-Connected Ligand Scaffolds: Macrocyclic Chelates for Asymmetric Hydrogenation" Org. Lett. (2008) 10:545-548.

International Preliminary Report on Patentability dated Jan. 5, 2017 for PCT Application No. PCT/US2015/036958 filed Jun. 22, 2015.

International Search Report and Written Opinion dated Aug. 6, 2015 for PCT Application No. PCT/US2015/036958, filed Jun. 22, 2015.

Office Action dated Jun. 10, 2016 for U.S. Appl. No. 14/746,138, filed Jun. 22, 2015.

Examination Report dated Jun. 7, 2017 for New Zealand Patent Application No. 727582, filed Jun. 22, 2015.

Office Action dated Aug. 11, 2017 for Eurasian Application No. 201692537, filed Jun. 22, 2015.

Search Report and Written Opinion dated Jul. 11, 2017 for SG Application No. 11201610597Q, filed Jun. 22, 2015.

\* cited by examiner

SUBSTITUTED NUCLEOSIDES, NUCLEOTIDES AND ANALOGS THEREOF

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

BACKGROUND

Field

The present application relates to the fields of chemistry, biochemistry and medicine. More particularly, disclosed herein are nucleosides, nucleotides and nucleotide analogs, pharmaceutical compositions that include one or more nucleosides, nucleotides and/or nucleotide analogs, and methods of synthesizing the same. Also disclosed herein are methods of treating diseases and/or conditions with a nucleoside, a nucleotide and/or a nucleotide analog, alone or in combination therapy with one or more other agents.

Description

Nucleoside analogs are a class of compounds that have been shown to exert antiviral and anticancer activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a method of ameliorating and/or treating a Filoviridae virus infection that can include administering to a subject identified as suffering from the Filoviridae virus infection an effective amount of one or more compounds of Formula (I), or a pharmaceutically acceptable salt of thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a Filoviridae virus infection. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a Filoviridae virus infection.

Some embodiments disclosed herein relate to a method of ameliorating and/or treating a Filoviridae virus infection that can include contacting a cell infected with the Filoviridae virus with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for ameliorating and/or treating a Filoviridae virus infection that can include contacting a cell infected with the Filoviridae virus with an effective amount of said compound(s). Still other embodiments described herein relate to one or more compounds described herein (for example, a compound of Formula (I), or a pharmaceutically acceptable salt thereof), or a pharmaceutical composition that includes one or more compounds described herein, or a pharmaceutically acceptable salt thereof, that can be used for ameliorating and/or treating a Filoviridae virus infection by contacting a cell infected with the Filoviridae virus with an effective amount of said compound(s).

Some embodiments disclosed herein relate to a method of inhibiting replication of a Filoviridae virus that can include contacting a cell infected with the Filoviridae virus with an effective amount of one or more compounds described herein (for example, a compound of Formula (I), or a pharmaceutically acceptable salt of the foregoing), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for inhibiting replication of a Filoviridae virus that can include contacting a cell infected with the Filoviridae virus with an effective amount of said compound(s). Still other embodiments described herein relate to one or more compounds described herein (for example, a compound of Formula (I), or a pharmaceutically acceptable salt of the foregoing), or a pharmaceutical composition that includes one or more compounds described herein, or a pharmaceutically acceptable salt thereof, that can be used for inhibiting replication of a Filoviridae virus by contacting a cell infected with the Filoviridae with an effective amount of said compound(s). In some embodiments, the Filoviridae virus can be an Ebola virus and/or Marburg virus.

DETAILED DESCRIPTION

The viruses of the Filoviridae family are enveloped, negative sense, single-stranded, linear RNA viruses. Three genera within the Filoviridae family are Ebolavirus, Marburgvirus and "Cuevavirus" (tentative). The five recognized species of Ebolavirus are Ebola virus (EBOV), Reston ebolavirus (REBOV), Sudan ebolavirus (SEBOV), Taï Forest ebolavirus (TAFV) and Bundibugyo ebolavirus (BEBOV). The two recognized species of Marburgvirus are Marburg virus (MARV) and Ravn virus (RAVV). Ebolavirus and Marburgvirus are highly infectious and contagious. Both viruses are transmitted by direct contact with the blood, body fluids and/or tissues of infected persons. Ebolavirus and Marburgvirus can also be transmitted by handling sick or dead infected wild animals. Ebola hemorrhagic fever (EHF) is caused by an Ebolavirus infection. Marburg virus disease (MVD) is a human disease caused by a Marburgvirus, and causes Marburgvirus hemorrhagic fever (MHF).

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^4$, $R^{5A}$, $R^{5B}$, $R^{6A}$, $R^{6B}$, $R^{6C}$, $R^{6D}$, $R^{6E}$, $R^{6F}$, $R^{6G}$, $R^{6H}$, $R^{7A}$, $R^{7B}$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{41}$, $R^{42}$, $R^{43}$ and $R^{44}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

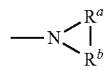

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl or a heteroalicyclyl may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heteroalicyclyl)alkyl" and "(heterocyclyl)alkyl" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aralkyl, (heteroaryl)alkyl or (heterocyclyl)alkyl is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heteroalicyclyl, aralkyl, heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an —O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl, as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl.

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-N$^6$-alkyladenine (e.g., 8-oxo-N$^6$-methyladenine), 7-deazaxanthine, 7-deazaguanine, 7-deazaadenine, N$^4$,N$^4$-ethanocytosin, N$^6$,N$^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)— and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The term "interferon" is used herein as is commonly understood by one of ordinary skill in the art. Several types of interferons are known to those skilled in the art, such as Type 1 interferons, Type 2 interferons and Type 3 interferons. A non-limiting list of examples include: alpha-interferons, beta-interferons, delta-interferons, gamma interferons, lambda interferons, omega-interferons, tau-interferons, x-interferons, consensus interferons and asialo-interferons. Interferons can be pegylated. Examples of type 1 interferons include interferon alpha 1A, interferon alpha 1B, interferon alpha 2A, interferon alpha 2B, pegylated-interferon alpha 2a (PEGASYS, Roche), recombinant interferon alpha 2a (ROFERON, Roche), inhaled interferon alpha 2b (AERX, Aradigm), pegylated-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical). Examples of type 2 interferons include interferon gamma 1, interferon gamma 2 and pegylated interferon gamma; and examples of type 3 interferons include interferon lambda 1, interferon lambda 2 and interferon lambda 3.

The terms "phosphorothioate" and "phosphothioate" refer to a compound of the general formula

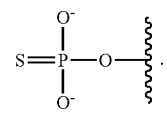

its protonated forms (for example,

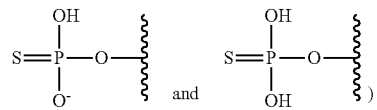 [SMILES: *OP([O-])(O)=S ; *OP(O)(O)=S]

and its tautomers (such as

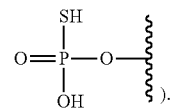

As used herein, the term "phosphate" is used in its ordinary sense as understood by those skilled in the art, and includes its protonated forms (for example,

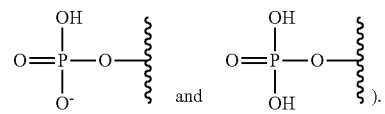 [SMILES: *OP(=O)([O-])O ; *OP(=O)(O)O]

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3- dioxolanes and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

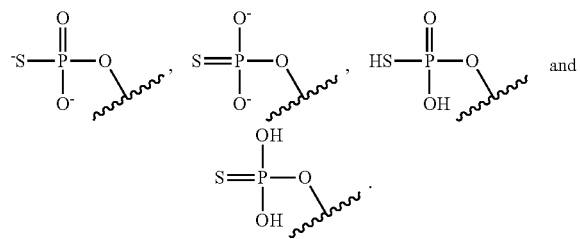

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Methods of Use

Some embodiments disclosed herein relate to a method of treating and/or ameliorating an infection caused by a Filoviridae virus that can include administering to a subject an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof). Other embodiments disclosed herein relate to a method of treating and/or ameliorating an infection caused by a Filoviridae virus that can include administering to a subject identified as suffering from the viral infection an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof).

Some embodiments described herein relate to using one or more compounds described herein (such as a compound of Formula (I), or a pharmaceutically acceptable salt thereof), in the manufacture of a medicament for ameliorating and/or treating an infection caused by a Filoviridae virus that can include administering to a subject infected with the virus an effective amount of one or more compounds described herein (such as a compound of Formula (I), or a pharmaceutically acceptable salt thereof). Still other embodiments described herein relate to one or more compounds described herein (such as a compound of Formula (I), or a pharmaceutically acceptable salt thereof) that can be used for ameliorating and/or treating an infection caused by a Filoviridae virus by administering to a subject an effective amount of one or more compounds described herein.

Some embodiments disclosed herein relate to methods of ameliorating and/or treating an infection caused by a Filoviridae virus that can include contacting a cell infected with the virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for ameliorating and/or treating an infection caused by a Filoviridae virus that can include contacting a cell infected with the virus with an effective amount of said compound(s). Still other embodiments described herein relate to one or more compounds described herein (such as a compound of Formula (I), or a pharmaceutically acceptable salt thereof), that can be used for ameliorating and/or treating an infection caused by a Filoviridae virus by contacting a cell infected with the virus with an effective amount of said compound(s).

Some embodiments disclosed herein relate to methods of inhibiting replication of a Filoviridae virus that can include contacting a cell infected with the virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for inhibiting replication of a Filoviridae virus that can include contacting a cell infected with the virus with an effective amount of said compound(s). Still other embodiments described herein relate to a compound described herein (such as a compound of Formula (I), or a pharmaceutically acceptable salt thereof), that can be used for inhibiting replication of a Filoviridae virus by contacting a cell infected with the virus with an effective amount of said compound(s). In some embodiments, a compound of Formula (I), or a pharmaceutically acceptable salt thereof, can inhibit a RNA dependent RNA polymerase of a Filoviridae virus, and thus, inhibit the replication of RNA. In some embodiments, a polymerase of a Filoviridae virus can be inhibited by contacting a cell infected with the Filoviridae virus with a compound described herein (such as a compound of Formula (I), or a pharmaceutically acceptable salt thereof).

Ebolaviruses are members of the Filoviridae virus family. In some embodiments, a compound described herein (for example, a compound of Formula (I), or a pharmaceutical acceptable salt thereof) can ameliorate and/or treat an Ebolavirus infection. In other embodiments, one or more compounds described herein (such as a compound of Formula (I), or a pharmaceutically acceptable salt thereof), can be manufactured into a medicament for ameliorating and/or treating an infection caused by an Ebolavirus that can include contacting a cell infected with the virus with an effective amount of said compound(s). In still other embodiments, one or more compounds described herein (such as a compound of Formula (I), or a pharmaceutically acceptable salt thereof), can be used for ameliorating and/or treating an infection caused by an Ebolavirus that can include contacting a cell infected with the virus with an effective amount of said compound(s). As described herein, several Ebolaviruses are known (such as EBOV, REBOV, SEBOV, TAFV and BEBOV). In some embodiments, a compound described herein (for example, a compound of Formula (I), or a pharmaceutical acceptable salt thereof) can be effective against more than one species of Ebolaviruses, such as 2, 3, 4 and/or 5 species. In some embodiments, a compound of Formula (I), or a pharmaceutical acceptable salt thereof, can be effective against an Ebolavirus, and thereby ameliorate one or more symptoms of an Ebolavirus infection. Examples of symptoms manifested by a subject infected with an Ebolavirus include severe hemorrhagic fever, malaise, fever, chills, arthralgia, myalgia, chest pain, nausea, weakness, abdominal pain, diarrhea, vomiting, weight loss, pharyngitis, sore throat, cough, dyspnea, hiccups, headaches, agitation, confusion, fatigue, depression, seizure, coma, maculopapular rash, petechiae, purpura, ecchymoses, hematomas, multiple organ dysfunction syndrome (MODS), hypotension, disseminated intravascular coagulation, focal tissue necroses, impaired kidney function, impaired liver function, low white blood cell count, low platelets, elevated liver enzymes and bleeding (internal and/or external including from the nose, mouth, rectum, eyes and/or ears).

Marburgviruses are also members of the Filoviridae virus family. In some embodiments, a compound described herein (for example, a compound of Formula (I), or a pharmaceutical acceptable salt thereof) can ameliorate and/or treat a Marburgvirus infection. In other embodiments, one or more compounds described herein (such as a compound of Formula (I), or a pharmaceutically acceptable salt thereof), can be manufactured into a medicament for ameliorating and/or treating an infection caused by a Marburgvirus that can include contacting a cell infected with the virus with an effective amount of said compound(s). In still other embodiments, one or more compounds described herein (such as a compound of Formula (I), or a pharmaceutically acceptable salt thereof), can be used for ameliorating and/or treating an infection caused by a Marburgvirus that can include contacting a cell infected with the virus with an effective amount of said compound(s). MARV and RAVV are two known Marburgviruses. In some embodiments, a compound described herein (for example, a compound of Formula (I), or a pharmaceutical acceptable salt thereof) can be effective against MARV and/or RAVV. In some embodiments, a compound of Formula (I), or a pharmaceutical acceptable salt thereof, can be effective against a Marburgvirus, and thereby ameliorate one or more symptoms of a Marburgvirus infection. Symptoms a Marburgvirus infection include severe hemorrhagic fever, fever, headaches, malaise, muscle aches, muscle pain, joint aches, joint pain, sore throat, weakness, red eyes, rash, diarrhea, abdominal pain, cramping, nausea, chest pain, cough, weight loss, vomiting, deep-set eyes, expressionless face, lethargy, rash, blood in the feces, vomiting blood, bleeding from a venepuncture site, confusion, irritability, aggression, orchitis and bleeding (internal and/or external including from the nose, mouth, rectum, eyes and/or ears).

Ebola hemorrhagic fever (EHF) is a disease caused by an Ebolavirus infection; and marburgvirus hemorrhagic fever (MHF) is a disease caused by a Marburgvirus infection. Both Ebola and Marburgvirus hemorrhagic fever are severe and often fatal diseases. In some embodiments, a compound described herein (for example, a compound of Formula (I), or a pharmaceutical acceptable salt thereof) can ameliorate and/or treat EHF and/or MHF. In other embodiments, one or more compounds described herein (such as a compound of Formula (I), or a pharmaceutically acceptable salt thereof), can be manufactured into a medicament for ameliorating and/or treating EHF and/or MHF that can include contacting a cell infected with the virus with an effective amount of said compound(s). In still other embodiments, one or more compounds described herein (such as a compound of Formula (I), or a pharmaceutically acceptable salt thereof), can be used for ameliorating and/or treating EHF and/or MHF that can include contacting a cell infected with the virus with an effective amount of said compound(s).

Various indicators for determining the effectiveness of a method for treating and/or ameliorating a Filoviridae viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator(s) of disease response. Further indicators include one or more overall quality of life health indicators, such as reduced illness duration, reduced illness severity, reduced time to return to normal health and normal activity, and reduced time to alleviation of one or more symptoms. In some embodiments, a compound of Formula (I), or a pharmaceutically acceptable salt thereof, can result in the reduction, alleviation or positive indication of one or more of the aforementioned indicators compared to a subject who is untreated subject.

In some embodiments, an effective amount of a compound of Formula (I), or a pharmaceutically acceptable salt thereof, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of markers includes measuring the levels of serum alanine aminotransferase (ALT), aspartate aminotransferase (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of a compound of Formula (I), or a pharmaceutically acceptable salt thereof, can be an amount effective to reduce ALT, AST, ALP, GGT and/or TBIL levels to with what is considered a normal level.

In some embodiments, a compound of Formula (I), or a pharmaceutically acceptable salt thereof, can result in a reduction in the length and/or severity of one or more symptoms associated with a Filoviridae virus infection compared to a subject who is an untreated subject. Table 1 provides some embodiments of the percentage improvements obtained using a compound of Formula (I), or a pharmaceutically acceptable salt thereof, as compared to an untreated subject. Examples include the following: in some embodiments, a compound of Formula (I), or a pharmaceutically acceptable salt thereof, can result in a duration of illness that is in the range of about 10% to about 30% less than compared to the duration of illness experienced by a subject who is untreated for a Filoviridae virus infection (such as Marburg virus); and in some embodiments, a compound of Formula (I), or a pharmaceutically acceptable salt thereof, results in a severity of a symptom (such as one of those described herein) that is 25% less than compared to the severity of the same symptom experienced by a subject who is untreated for an Ebola virus infection. Methods of quantifying the severity of a side effect and/or symptom are known to those skilled in the art.

TABLE 1

| Number of side effects | Severity of side effect(s) | Duration of illness | Severity of symptom(s) |
|---|---|---|---|
| 10% less | 10% less | 10% less | 10% less |
| 25% less | 25% less | 25% less | 25% less |
| 40% less | 40% less | 40% less | 40% less |
| 50% less | 50% less | 50% less | 50% less |
| 60% less | 60% less | 60% less | 60% less |
| 70% less | 70% less | 70% less | 70% less |
| 80% less | 80% less | 80% less | 80% less |
| 90% less | 90% less | 90% less | 90% less |
| about 10% to about 30% less | about 10% to about 30% less | about 10% to about 30% less | about 10% to about 30% less |
| about 20% to about 50% less | about 20% to about 50% less | about 20% to about 50% less | about 20% to about 50% less |
| about 30% to about 70% less | about 30% to about 70% less | about 30% to about 70% less | about 30% to about 70% less |
| about 20% to about 80% less | about 20% to about 80% less | about 20% to about 80% less | about 20% to about 80% less |

In some embodiments, the compound can be a compound of Formula (I), or a pharmaceutical acceptable salt thereof, wherein $R^{1A}$ can be hydrogen. In other embodiments, the compound can be a compound of Formula (I), wherein compound of Formula (I) can be a mono, di, or triphosphate, or a pharmaceutically acceptable salt of the foregoing. In still other embodiments, the compound can be a compound of Formula (I), wherein compound of Formula (I) can be a thiomonophosphate, alpha-thiodiphosphate, or alpha-thiotriphosphate, or a pharmaceutically acceptable salt of the foregoing. In some embodiments, the compound of Formula (I), or a pharmaceutical acceptable salt thereof, that can be used to ameliorate and/or treat a Filoviridae virus infection and/or inhibit replication of a Filoviridae virus can be any of the embodiments provided in any of the embodiments described in the paragraphs between the header "Compounds" to the header "Pharmaceutical Compositions".

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of another agent. In some embodiments, the total time of the treatment regime with a compound of Formula (I), or a pharmaceutically acceptable salt thereof, can less compared to the total time of the treatment regime with another agent.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, a compound of Formula (I), or a pharmaceutically acceptable salt thereof, can have a moiety(ies) that neutralize the charge of the phosphate or thiophosphate. By neutralizing the charge on the phosphate or thiophosphate, penetration of the cell membrane may be facilitated as a result of the increased lipophilicity of the compound. Once absorbed and taken inside the cell, the groups attached to the phosphorus can be easily removed by esterases, proteases and/or other enzymes. In some embodiments, the groups attached to the phosphorus can be removed by simple hydrolysis. Inside the cell, the phosphate thus released may then be metabolized by cellular enzymes to the diphosphate or the active triphosphate. Likewise, the thio-phosphate may be metabolized to the alpha-thiodiphosphate or the alpha-thiotriphosphate. Furthermore, in some embodiments, varying the substituents on a compound described herein, such as a compound of Formula (I), or a pharmaceutically acceptable salt thereof, can help maintain the efficacy of such the compound by reducing undesirable effects, such as isomerization.

In some embodiments, the phosphorylation of a thio-monophosphate of a compound of Formula (I), or a pharmaceutically acceptable salt thereof, can be stereoselective. For example, a thio-monophosphate of a compound of Formula (I) can be phosphorylated to give an alpha-thiodiphosphate and/or an alpha-thiotriphosphate compound that can be enriched in the (R) or (S) diastereomer with respect to the 5'-O-phosphorous atom. For example, one of the (R) and (S) configuration with respect to the 5'-O-phosphorous atom of the alpha-thiodiphosphate and/or the alpha-thiotriphosphate compound can be present in an amount >50%, ≥75%, ≥90%, ≥95% or ≥99% compared to the amount of the other of the (R) or (S) configuration with respect to the 5'-O-phosphorous atom. In some embodiments, phosphorylation of a compound of Formula (I), or a pharmaceutically acceptable salt thereof, can result in the formation of a compound that has the (R)-configuration at the 5'-O-phosphorous atom. In some embodiments, phosphorylation of a compound of Formula (I), or a pharmaceutically acceptable salt thereof, can result in formation of a compound that has the (S)-configuration at the 5'-O-phosphorous atom.

In some embodiments, a compound of Formula (I), or a pharmaceutically acceptable salt thereof, can act as a chain terminator of RNA synthesis. For example, compounds of Formula (I) can contain a moiety at the 2'-carbon position such that once the compound is incorporated into an RNA chain, no further elongation is observed to occur. For example, a compound of Formula (I), or a pharmaceutically acceptable salt thereof, can contain a non-hydrogen 2'-carbon modification such as an optionally substituted $C_{1-6}$ alkyl, an optionally substituted $C_{2-6}$ alkenyl or an optionally substituted $C_{2-6}$ alkynyl.

In some embodiments, a compound of Formula (I), or a pharmaceutically acceptable salt thereof, can have increased metabolic and/or plasma stability. In some embodiments, a compound of Formula (I), or a pharmaceutically acceptable salt thereof, can be more resistant to hydrolysis and/or more resistant to enzymatic transformations. For example, a compound of Formula (I), or a pharmaceutically acceptable salt thereof, can have increased metabolic stability, increased plasma stability, can be more resistant to hydrolysis and/or can be more resistant to enzymatic transformations compared to a compound that is identical in structure but for having $O^1$ as OH, $R^A$, $R^{2A}$, $R^{5A}$, $R^{a1}$ and $R^{a2}$ are each hydrogen and $R^{3A}$ and $R^{4A}$ are each OH. In some embodiments, a compound of Formula (I), or a pharmaceutically acceptable salt thereof, can have improved properties. A non-limiting list of example properties include, but are not limited to, increased biological half-life, increased bioavailability, increase potency, a sustained in vivo response, increased dosing intervals, decreased dosing amounts, decreased cytotoxicity, reduction in required amounts for treating disease conditions, reduction in viral load, reduction in time to seroconversion (i.e., the virus becomes undetectable in patient serum), increased sustained viral response, a reduction of morbidity or mortality in clinical outcomes, increased subject compliance, decreased liver conditions (such as liver fibrosis, liver cirrhosis and/or liver cancer), and compatibility with other medications. In some embodiments, a compound of Formula (I), or a pharmaceutically acceptable salt thereof, can have a biological half-life of greater than 24 hours. In some embodiments, a compound of Formula (I), or a pharmaceutically acceptable salt thereof, can have a biological half-life greater than a compound that is identical in structure but for having $O^1$ as OH, $R^A$, $R^{2A}$, $R^{5A}$, $R^{a1}$ and $R^{a2}$ are each hydrogen and $R^{3A}$ and $R^{4A}$ are each OH. In some embodiments, a compound of Formula (I), or a pharmaceutically acceptable salt thereof, can have more potent antiviral activity compared to a compound that is identical in structure but for having $O^1$ as OH, $R^A$, $R^{2A}$, $R^{5A}$, $R^{a1}$ and $R^{a2}$ are each hydrogen and $R^{3A}$ and $R^{4A}$ are each OH.

Additionally, in some embodiments, the presence of a moiety(ies) that neutralizes the charge of the phosphate or thiophosphate can increase the stability of the compound by inhibiting its degradation. Also, in some embodiments, the presence of a moiety(ies) that neutralizes the charge of the phosphate or thiophosphate can make the compound more resistant to cleavage in vivo and provide sustained, extended efficacy. In some embodiments, a moiety(ies) that neutralizes the charge of the phosphate or thiophosphate can facilitate the penetration of the cell membrane by a compound of Formula (I) by making the compound more lipophilic. In some embodiments, a moiety(ies) that neutralizes the charge of the phosphate or thiophosphate can have improved oral bioavailability, improved aqueous stability and/or reduced risk of byproduct-related toxicity. In some embodiments, for comparison purposes, a compound of Formula (I) can be compared to a compound that is identical in structure but for having $O^1$ as OH, $R^A$, $R^{2A}$, $R^{5A}R^{a1}$ and $R^{a2}$ are each hydrogen and $R^{3A}$ and $R^{4A}$ are each OH.

Combination Therapies

In some embodiments, the compounds disclosed herein, such as a compound of Formula (I), or a pharmaceutically acceptable salt thereof, or a pharmaceutical composition that includes a compound described herein, or a pharmaceutically acceptable salt thereof, can be used in combination with one or more additional agent(s) for treating, ameliorating and/or inhibiting a Filoviridae viral infection.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) can result in an additive effect. In some embodiments, the combination of a compound of Formula (I), or a pharmaceutically acceptable salt thereof, used in combination with one or more additional agent(s) can result in a synergistic effect. In some embodiments, the combination of a compound of Formula (I), or a pharmaceutically acceptable salt thereof, used in combination with one or more additional agent(s) can result in a strongly synergistic effect. In some embodiments, the combination of a compound of Formula (I), or a pharmaceutically acceptable salt thereof, in combination with one or more additional agent(s) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) may be a reduction in the required amount(s) of one or more additional agent(s) that is effective in treating a disease condition disclosed herein (for example, a Filoviridae virus infection), as compared to the amount required to achieve same therapeutic result when one or more additional agent(s) are administered without a compound of Formula (I), or a pharmaceutically acceptable salt thereof. For example, for treating a Marburg viral infection, the amount of the additional agent (including a pharmaceutically acceptable salt thereof) used in combination can be less compared to the amount of the additional agent (including a pharmaceutically acceptable salt thereof) needed to achieve the same viral load reduction when administered as a monotherapy. Another potential advantage of utilizing a compound of Formula (I), or a pharmaceutically acceptable salt thereof, in combination with one or more additional agent(s) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) may include little to no cross resistance between a compound of Formula (I), or a pharmaceutically acceptable salt thereof, and one or more additional agent(s) thereof; different routes for elimination of a compound of Formula (I), or a pharmaceutically acceptable salt thereof, and one or more additional agent(s); little to no overlapping toxicities between a compound of Formula (I), or a pharmaceutically acceptable salt thereof, and one or more additional agent(s); little to no significant effects on cytochrome P450; little to no pharmacokinetic interactions between a compound of Formula (I), or a pharmaceutically acceptable salt thereof, and one or more additional agent(s); greater percentage of subjects achieving a sustained viral response compared to when a compound is administered as monotherapy and/or a decrease in treatment time to achieve a sustained viral response compared to when a compound is administered as monotherapy.

For treating of a Filoviridae virus infection, examples of additional agents that can be used in combination with a compound of Formula (I), or a pharmaceutically acceptable salt thereof, or a pharmaceutical composition that includes a compound of Formula (I), or a pharmaceutically acceptable salt thereof, are described herein. Compounds that can be used in combination for the treatment of a Filoviridae virus infection include an interferon (for example, those described herein such as interferon-alpha 2b and/or IFN-β treatment), ribavirin, (2S,3S,4R,5R)-2-(4-amino-5H-pyrrolo[3,2-d]pyrimidin-7-yl)-5-(hydroxymethyl)pyrrolidine-3,4-diol (BCX 4430, BioCryst), 5-Fluoro-2-oxo-H-pyrazine-3-carboxamide (T-705, favipiravir), hexadecyloxypropyl-cidofovir (brincidofovir, CMX001), AVI-7537 (PMOplus oligomer that binds directly to the viral VP24 transcript RNA (GCC+ATG GT+T TT+T TC+T C+AG G), Sarepta Therapeutics), AVI-7288 (PMOplus oligomer that binds directly to viral RNA of the nucleoprotein (NP) transcript with a binding equilibrium constant of between $6.5\ 10_{-12}$M (CC+T GCC C+TT TGT+TCT+AGT+TG), Sarepta Therapeutics), ZMapp (a combination therapy of MB-003 (Pettitt, J., et al., *Sci Transl Med* (21 Aug. 2013) 5(199):199ra113) and ZMab (Qiu, X., et al., *Sci Transl Med* (13 Jun. 2012) 4(138): 138ra81, Mapp Pharmaceuticals) and TKM-Ebola (an anti-Ebola virus RNAi therapeutic (Geisbert, T. W. et al., *The Lancet* (29 May 2010) 375(9729):1896-1905), Tekmira Pharmaceuticals).

Compounds

Some embodiments disclosed herein relate to a method and/or use of a compound of Formula (I), or a pharmaceutically acceptable salt thereof:

(I)

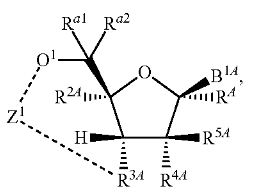

wherein: $B^{1A}$ can be an optionally substituted heterocyclic base or an optionally substituted heterocyclic base with a protected amino group; -------- can be absent or a single bond, provided that both -------- are absent or both -------- are a single bond; when -------- are both absent, then $Z^1$ can be absent, $O^1$ can be $OR^{1A}$, $R^{3A}$ can be selected from hydrogen, halogen, OH, —OC(=O)R"$^A$ and an optionally substituted O-linked amino acid, $R^{4A}$ can be selected from hydrogen, OH, halogen, $N_3$, —OC(=O)R"$^B$, an optionally substituted O-linked amino acid and NR"$^{B1}$R"$^{B2}$, or $R^{3A}$ and $R^{4A}$ can be both an oxygen atom connected via a carbonyl to form a 5-membered ring; when -------- are each a single bond, then $Z^1$ can be

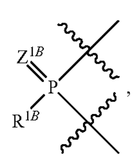

, $O^1$ can be O, $R^{3A}$ can be O; $R^{4A}$ can be selected from hydrogen, OH, halogen, $N_3$, —OC(=O)R"$^B$, an optionally substituted O-linked amino acid and NR"$^{B1}$R"$^{B2}$; and $R^{1B}$ can be selected from $O^-$, OH, an —O-optionally substituted $C_{1-6}$ alkyl.

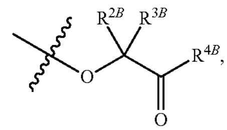

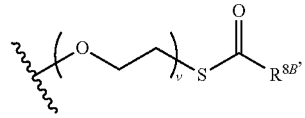

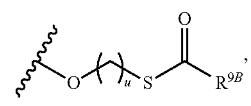

an optionally substituted N-linked amino acid and an optionally substituted N-linked amino acid ester derivative; $R^{a1}$ and $R^{a2}$ can be independently hydrogen or deuterium; $R^A$ can be hydrogen, deuterium, an unsubstituted $C_{1-3}$ alkyl, an unsubstituted $C_{2-4}$ alkenyl, an unsubstituted $C_{2-3}$ alkynyl or cyano; $R^{1A}$ can be selected from hydrogen, an optionally substituted acyl, an optionally substituted O-linked amino acid, , 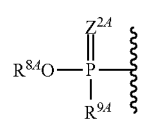  and 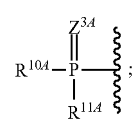 ;

$R^{2A}$ can be hydrogen, azido ($N_3$), halogen, an unsubstituted $C_{1-4}$ alkyl, an unsubstituted $C_{2-4}$ alkenyl, an unsubstituted $C_{2-4}$ alkynyl, halogen($C_{1-6}$alkyl), —$(CH_2)_{1-6}N_3$, —$(CH_2)_{1-6}NH_2$, —$(CH_2)_{1-6}$-ring A or —CN; $R^{5A}$ can be selected from hydrogen, halogen, OH, an optionally substituted $C_{1-6}$ alkyl, an optionally substituted $C_{2-6}$ alkenyl and an optionally substituted $C_{2-6}$ alkynyl; $R^{6A}$, $R^{7A}$ and $R^{8A}$ can be independently selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—$(CR^{15A}R^{16A})_p$—O—$C_{1-24}$ alkyl, an optionally substituted *—$(CR^{17A}R^{18A})_q$—O—$C_{1-24}$ alkenyl,

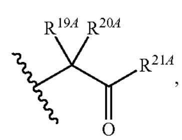

, 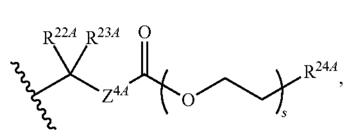 ,

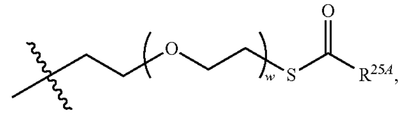

-continued

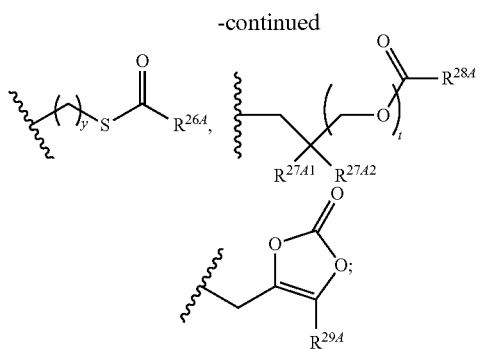

or R$^{6A}$ can be

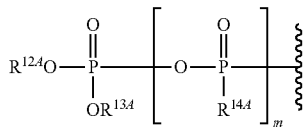

and R$^{7A}$ can be absent or hydrogen; or R$^{6A}$ and R$^{7A}$ can be taken together to form a moiety selected from an optionally substituted

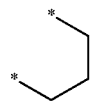

and an optionally substituted

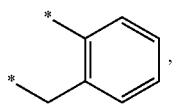

wherein the oxygens connected to R$^{6A}$ and R$^{7A}$, the phosphorus and the moiety form a six-membered to ten-membered ring system; R$^{9A}$ can be independently selected from an optionally substituted C$_{1-24}$ alkyl, an optionally substituted C$_{2-24}$ alkenyl, an optionally substituted C$_{2-24}$ alkynyl, an optionally substituted C$_{3-6}$ cycloalkyl, an optionally substituted C$_{3-6}$ cycloalkenyl, NR$^{30A}$R$^{31A}$, an optionally substituted N-linked amino acid and an optionally substituted N-linked amino acid ester derivative; R$^{10A}$ and R$^{11A}$ can be independently an optionally substituted N-linked amino acid or an optionally substituted N-linked amino acid ester derivative; R$^{12A}$ and R$^{13A}$ can be independently absent or hydrogen; R$^{14A}$ can be O$^-$, OH or methyl; each R$^{15A}$, each R$^{16A}$, each R$^{17A}$ and each R$^{18A}$ can be independently hydrogen, an optionally substituted C$_{1-24}$ alkyl or an alkoxy; R$^{19A}$, R$^{20A}$R$^{22A}$, R$^{23A}$, R$^{2B}$, R$^{3B}$, R$^{5B}$ and R$^{6B}$ can be independently selected from hydrogen, an optionally substituted C$_{1-24}$ alkyl and an optionally substituted aryl; R$^{21A}$ and R$^{4B}$ can be independently selected from hydrogen, an optionally substituted C$_{1-24}$ alkyl, an optionally substituted aryl, an optionally substituted —O—C$_{1-24}$ alkyl, an optionally substituted —O-aryl, an optionally substituted —O-heteroaryl and an optionally substituted —O-monocyclic heterocyclyl; R$^{24A}$ and R$^{7B}$ can be independently selected from of hydrogen, an optionally substituted C$_{1-24}$ alkyl, an optionally substituted aryl, an optionally substituted —O—C$_{1-24}$ alkyl, an optionally substituted —O-aryl, an optionally substituted —O-heteroaryl, an optionally substituted —O-monocyclic heterocyclyl and

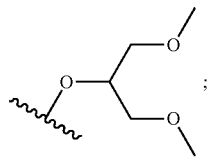 [SMILES: *OC(COC)COC]

R$^{25A}$, R$^{26A}$, R$^{29A}$, R$^{8B}$ and R$^{9B}$ can be independently selected from hydrogen, an optionally substituted C$_{1-24}$ alkyl and an optionally substituted aryl; R$^{27A1}$ and R$^{27A2}$ can be independently selected from —C≡N, an optionally substituted C$_{2-8}$ organylcarbonyl, an optionally substituted C$_{2-8}$ alkoxycarbonyl and an optionally substituted C$_{2-8}$ organylaminocarbonyl; R$^{28A}$ can be selected from hydrogen, an optionally substituted C$_{1-24}$ alkyl, an optionally substituted C$_{2-24}$ alkenyl, an optionally substituted C$_{2-24}$ alkynyl, an optionally substituted C$_{3-6}$ cycloalkyl and an optionally substituted C$_{3-6}$ cycloalkenyl; R$^{30A}$ and R$^{31A}$ can be independently selected from hydrogen, an optionally substituted C$_{1-24}$ alkyl, an optionally substituted C$_{2-24}$ alkenyl, an optionally substituted C$_{2-24}$ alkynyl, an optionally substituted C$_{3-6}$ cycloalkyl, an optionally substituted C$_{3-6}$ cycloalkenyl and an optionally substituted aryl(C$_{1-4}$ alkyl); R$'''^{A}$ and each R$'''^{B}$ can be independently an optionally substituted C$_{1-24}$ alkyl; each R$'''^{B1}$ and each R$'''^{B2}$ can be independently hydrogen or an optionally substituted C$_{1-6}$ alkyl; ring A can be an optionally substituted mono-cyclic heteroaryl or an optionally substituted mono-cyclic heterocyclyl; m and w can be independently 0 or 1; p and q can be independently 1, 2 or 3; r and s can be independently 0, 1, 2 or 3; t and v can be independently 1 or 2; u and y can be independently 3, 4 or 5; and Z$^{1A}$, Z$^{2A}$, Z$^{3A}$, Z$^{4A}$, Z$^{1B}$ and Z$^{2B}$ can be independently oxygen (O) or sulfur (S).

A compound of Formula (I) can be a nucleoside, a nucleotide (including a monophosphate, a diphosphate, a triphosphate, thiomonophosphate, alpha-thiodiphosphate and/or alpha-thiotriphosphate) or a nucleotide prodrug. In some embodiments, -------- can be both absent, Z$^1$ can be absent, O$^1$ can be OR$^{1A}$, R$^{3A}$ can be selected from hydrogen, halogen, OH, —OC(=O)R$'''^{A}$ and an optionally substituted O-linked amino acid, R$^{4A}$ can be selected from OH, halogen, —OC(=O)R$'''^{B}$ and an optionally substituted O-linked amino acid, or R$^{3A}$ and R$^{4A}$ can be both an oxygen atom connected via a carbonyl to form a 5-membered ring.

Various substituents can be attached to the 5'-position of Formula (I) when both ------ are absent. In some embodiments, R$^{1A}$ can be hydrogen. In other embodiments, R$^{1A}$ can be an optionally substituted acyl. For example, R$^{1A}$ can be —C(=O)R$^{39A}$, wherein R$^{39A}$ can be selected from an optionally substituted C$_{1-12}$ alkyl, an optionally substituted C$_{2-12}$ alkenyl, an optionally substituted C$_{2-12}$ alkynyl, an optionally substituted C$_{3-8}$ cycloalkyl, an optionally substituted C$_{5-8}$ cycloalkenyl, an optionally substituted C$_{6-10}$ aryl, an optionally substituted heteroaryl, an optionally substituted heterocyclyl, an optionally substituted aryl(C$_{1-6}$ alkyl), an optionally substituted heteroaryl(C$_{1-6}$ alkyl) and an optionally substituted heterocyclyl(C$_{1-6}$ alkyl). In some embodiments, R$^{39A}$ can be a substituted C$_{1-12}$ alkyl. In other embodiments, R$^{39A}$ can be an unsubstituted C$_{1-12}$ alkyl. In some embodiments, $R^{1A}$ can be —C(=O)-unsubstituted $C_{1-4}$ alkyl. In some embodiments, both $R^{a1}$ and $R^{a2}$ can be hydrogen. In other embodiments, $R^{a1}$ can be hydrogen and $R^{a2}$ can be deuterium. In still other embodiments, both $R^{a1}$ and $R^{a2}$ can be deuterium.

In still other embodiments, $R^{1A}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can have the structure

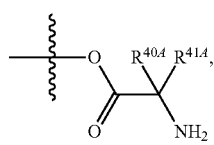

wherein $R^{40A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{41A}$ can be hydrogen or an optionally substituted $C_{1-4}$ alkyl; or $R^{40A}$ and $R^{41A}$ can be taken together to form an optionally substituted $C_{3-6}$ cycloalkyl. Those skilled in the art understand that when $R^{1A}$ is an optionally substituted O-linked amino acid, the oxygen of $R^{1A}O$— of Formula (I) is part of the optionally substituted O-linked amino acid. For example, when $R^{1A}$ is

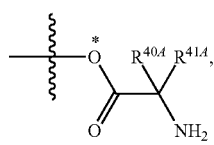

the oxygen indicated with "*" is the oxygen of $R^{1A}O$— of Formula (I).

When $R^{40A}$ is substituted, $R^{40A}$ can be substituted with one or more substituents selected from N-amido, mercapto, alkylthio, an optionally substituted aryl, hydroxy, an optionally substituted heteroaryl, O-carboxy and amino. In some embodiments, $R^{40A}$ can be an unsubstituted $C_{1-6}$ alkyl, such as those described herein. In some embodiments, $R^{40A}$ can be hydrogen. In other embodiments, $R^{40A}$ can be methyl. In some embodiments, $R^{41A}$ can be hydrogen. In other embodiments, $R^{41A}$ can be an optionally substituted $C_{1-4}$ alkyl, such as methyl, ethyl, n-propyl, isopropyl, n-butyl, isobutyl and tert-butyl. In some embodiments, $R^{41A}$ can be methyl. Depending on the groups that are selected for $R^{40A}$ and $R^{41A}$ the carbon to which $R^{40A}$ and $R^{41A}$ are attached may be a chiral center. In some embodiment, the carbon to which $R^{40A}$ and $R^{41A}$ are attached may be a (R)-chiral center. In other embodiments, the carbon to which $R^{40A}$ and $R^{41A}$ are attached may be a (S)-chiral center.

Examples of suitable

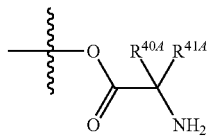

include the following:

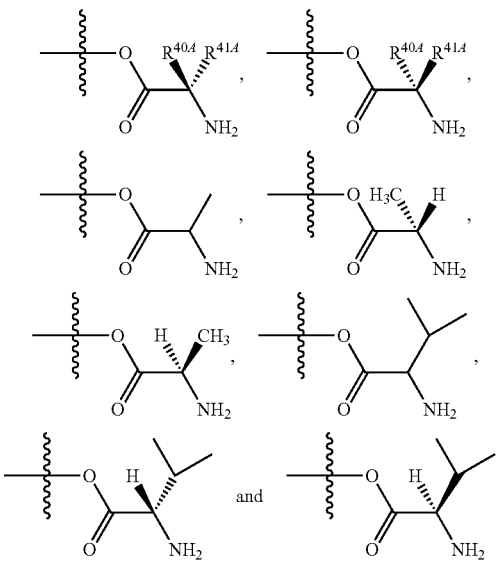

In some embodiments, $R^{1A}$ can be

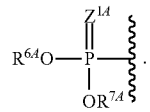

In some embodiments, $R^{6A}$ and $R^{7A}$ can be both hydrogen. In other embodiments, $R^{6A}$ and $R^{7A}$ can be both absent. In still other embodiments, at least one $R^{6A}$ and $R^{7A}$ can be absent. In yet still other embodiments, at least one $R^{6A}$ and $R^{7A}$ can be hydrogen. Those skilled in the art understand that when $R^{6A}$ and/or $R^{7A}$ are absent, the associated oxygen(s) will have a negative charge. For example, when $R^{6A}$ is absent, the oxygen associated with $R^{6A}$ will have a negative charge. In some embodiments, $Z^{1A}$ can be O (oxygen). In other embodiments, $Z^{1A}$ can be S (sulfur). In some embodiments, $R^{1A}$ can be a monophosphate. In other embodiments, $R^{1A}$ can be a monothiophosphate.

In some embodiments, $R^{1A}$ can be

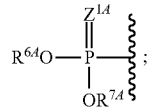

$R^{6A}$ can be

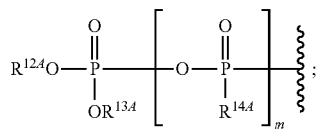

$R^{7A}$ can be absent or hydrogen; $R^{12A}$ and $R^{13A}$ can be independently absent or hydrogen; $R^{14A}$ can be O⁻, OH or methyl; and m can be 0 or 1. In some embodiments, m can be 0, and $R^{7A}$, $R^{12A}$ and $R^{13A}$ can be independently absent or hydrogen. In other embodiments, m can be 1, and $R^{7A}$, $R^{12A}$ and $R^{13A}$ can be independently absent or hydrogen; and $R^{14A}$ can be O⁻, OH or methyl. In some embodiments, m can be 1, and $R^{7A}$, $R^{12A}$ and $R^{13A}$ can be independently absent or hydrogen; and $R^{14A}$ can be O⁻ or OH. In other embodiments, m can be 1, and $R^{7A}$, $R^{12A}$ and $R^{13A}$ can be independently absent or hydrogen; and $R^{14A}$ can be methyl. Those skilled in the art understand that when m is 0, $R^{6A}$ can be a diphosphate, when $Z^{1A}$ is oxygen, or an alpha-thiodiphosphate, when $Z^{1A}$ is sulfur. Likewise, those skilled in the art understand that when m is 1, $R^{6A}$ can be a triphosphate, when $Z^{1A}$ is oxygen, or an alpha-thiotriphosphate, when $Z^{1A}$ is sulfur.

In some embodiments, when $R^{1A}$ is

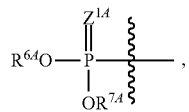

one of $R^{6A}$ and $R^{7A}$ can be hydrogen, and the other of $R^{6A}$ and $R^{7A}$ can be selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, one of $R^{6A}$ and $R^{7A}$ can be hydrogen, and the other of $R^{6A}$ and $R^{7A}$ can be an optionally substituted $C_{1-24}$ alkyl. In other embodiments, both $R^{6A}$ and $R^{7A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, both $R^{6A}$ and $R^{7A}$ can be an optionally substituted $C_{1-24}$ alkyl. In other embodiments, both $R^{6A}$ and $R^{7A}$ can be an optionally substituted $C_{2-24}$ alkenyl. In some embodiments, $R^{6A}$ and $R^{7A}$ can be independently an optionally substituted group selected from the following: myristoleyl, myristyl, palmitoleyl, palmityl, sapienyl, oleyl, elaidyl, vaccenyl, linoleyl, α-linolenyl, arachidonyl, eicosapentaenyl, erucyl, docosahexaenyl, caprylyl, capryl, lauryl, stearyl, arachidyl, behenyl, lignoceryl and cerotyl.

In some embodiments, at least one of $R^{6A}$ and $R^{7A}$ can be *—$(CR^{15A}R^{16A})_p$—O—$C_{1-24}$ alkyl. In other embodiments, $R^{6A}$ and $R^{7A}$ can be both *—$(CR^{15A}R^{16A})_p$—O—$C_{1-24}$ alkyl. In some embodiments, each $R^{15A}$ and each $R^{16A}$ can be hydrogen. In other embodiments, at least one of $R^{15A}$ and $R^{16A}$ can be an optionally substituted $C_{1-24}$ alkyl. In other embodiments, at least one of $R^{15A}$ and $R^{16A}$ can be an alkoxy (for example, benzoxy). In some embodiments, p can be 1. In other embodiments, p can be 2. In still other embodiments, p can be 3.

In some embodiments, at least one of $R^{6A}$ and $R^{7A}$ can be *—$(CR^{17A}R^{18A})_q$—O—$C_{2-24}$ alkenyl. In other embodiments, $R^{6A}$ and $R^{7A}$ can be both *—$(CR^{17A}R^{18A})_q$—O—$C_{2-24}$ alkenyl. In some embodiments, each $R^{17A}$ and each $R^{18A}$ can be hydrogen. In other embodiments, at least one of $R^{17A}$ and $R^{18A}$ can be an optionally substituted $C_{1-24}$ alkyl. In some embodiments, q can be 1. In other embodiments, q can be 2. In still other embodiments, q can be 3. When at least one of $R^{6A}$ and $R^{7A}$ is *—$(CR^{15A}R^{16A})_p$—O—$C_{1-24}$ alkyl or *—$(CR^{17A}R^{18A})_q$—O—$C_{2-24}$ alkenyl, the $C_{1-24}$ alkyl can be selected from caprylyl, capryl, lauryl, myristyl, palmityl, stearyl, arachidyl, behenyl, lignoceryl, and cerotyl, and the $C_{2-24}$ alkenyl can be selected from myristoleyl, palmitoleyl, sapienyl, oleyl, elaidyl, vaccenyl, linoleyl, α-linolenyl, arachidonyl, eicosapentaenyl, erucyl and docosahexaenyl.

In some embodiments, when $R^{1A}$ is

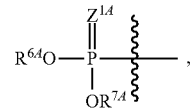

at least one of $R^{6A}$ and $R^{7A}$ can be selected from

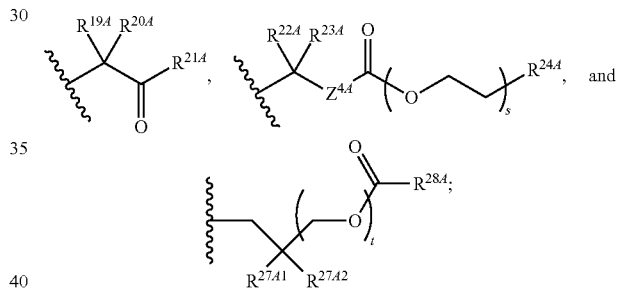

and the other of $R^{6A}$ and $R^{7A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl).

In some embodiments, at least one of $R^{6A}$ and $R^{7A}$ can be

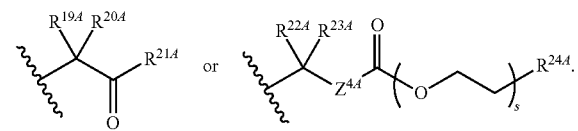

In some embodiments, both $R^{6A}$ and $R^{7A}$ can be

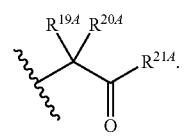

When one or both of $R^{6A}$ and $R^{7A}$ are

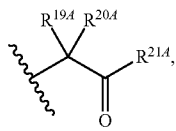

$R^{19A}$ and $R^{20A}$ can be independently selected from hydrogen, an optionally substituted $C_{1-24}$ alkyl and an optionally substituted aryl; and $R^{21A}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl. In some embodiments, $R^{19A}$ and $R^{20A}$ can be hydrogen. In other embodiments, at least one of $R^{19A}$ and $R^{20A}$ can be an optionally substituted $C_{1-24}$ alkyl or an optionally substituted aryl. In some embodiments, $R^{21A}$ can be an optionally substituted $C_{1-24}$ alkyl. In some embodiments, $R^{21A}$ can be an unsubstituted $C_{1-4}$ alkyl. In other embodiments, $R^{21A}$ can be an optionally substituted aryl. In still other embodiments, $R^{21A}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{21A}$ can be an unsubstituted —O—$C_{1-4}$ alkyl.

In some embodiments, both $R^{6A}$ and $R^{7A}$ can be

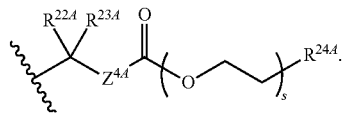

When one or both of $R^{6A}$ and $R^{7A}$ are

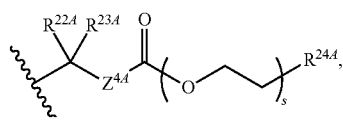

$R^{22A}$ and $R^{23A}$ can be independently selected from hydrogen, an optionally substituted $C_{1-24}$ alkyl and an optionally substituted aryl; $R^{24A}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; s can be 0, 1, 2 or 3; and $Z^{4A}$ can be independently O (oxygen) or S (sulfur). In some embodiments, $R^{22A}$ and $R^{23A}$ can be hydrogen. In other embodiments, at least one of $R^{22A}$ and $R^{23A}$ can be an optionally substituted $C_{1-24}$ alkyl or an optionally substituted aryl. In some embodiments, $R^{24A}$ can be an optionally substituted $C_{1-24}$ alkyl. In some embodiments, $R^{24A}$ can be an unsubstituted $C_{1-4}$ alkyl. In other embodiments, $R^{24A}$ can be an optionally substituted aryl. In still other embodiments, $R^{24A}$ can be an optionally substituted —O—$C_{1-24}$ alkyl, an optionally substituted —O-aryl, an optionally substituted —O-heteroaryl or an optionally substituted —O-monocyclic heterocyclyl. In yet still other embodiments, $R^{24A}$ can be In some embodiments, $R^{24A}$ can be an unsubstituted —O—$C_{1-4}$ alkyl. In some embodiments, $Z^{4A}$ can be O (oxygen). In other embodiments, $Z^{4A}$ can be or S (sulfur). In some embodiments, s can be 0. In other embodiments, s can be 1. In still other embodiments, s can be 2. In yet still other embodiments, s can be 3. In some embodiments, s can be 0 and $R^{24A}$ can be

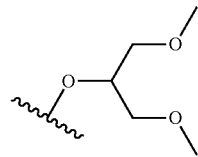

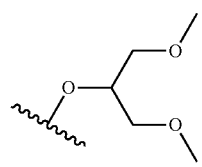

In some embodiments, one or both of $R^{6A}$ and $R^{7A}$ can be an optionally substituted isopropyloxycarbonyloxymethyl (POC). In some embodiments, $R^{6A}$ and $R^{7A}$ each can be an optionally substituted isopropyloxycarbonyloxymethyl (POC) group, and form an optionally substituted bis(isopropyloxycarbonyloxymethyl) (bis(POC)) prodrug. In other embodiments, one or both of $R^{6A}$ and $R^{7A}$ can be an optionally substituted pivaloyloxymethyl (POM). In some embodiments, $R^{6A}$ and $R^{7A}$ each can be an optionally substituted pivaloyloxymethyl (POM) group, and form an optionally substituted bis(pivaloyloxymethyl) (bis(POM)) prodrug.

In some embodiments, both $R^{6A}$ and $R^{7A}$ can be

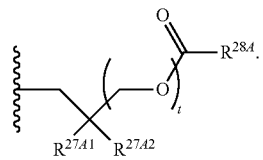

When one or both of $R^{6A}$ and $R^{7A}$ are

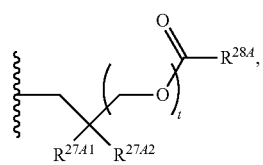

$R^{27A1}$ and $R^{27A2}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28A}$ can be selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and t can be 1 or 2. In some embodiments, $R^{27A1}$ can be —C≡N and $R^{27A2}$ can be an optionally substituted $C_{2-8}$ alkoxycarbonyl, such as —C(=O)OCH$_3$. In other embodiments, $R^{27A1}$ can be —C≡N and $R^{27A2}$ can be an optionally substituted $C_{2-8}$ organylaminocarbonyl, for example, —C(=O)NHCH$_2$CH$_3$ and —C(=O)NHCH$_2$CH$_2$phenyl. In some embodiments, both $R^{27A1}$ and $R^{27A2}$ can be an optionally substituted $C_{2-8}$ organylcarbonyl, such as —C(=O)CH$_3$. In some embodiments, both $R^{27A1}$ and $R^{27A2}$ can be an optionally substituted $C_{1-8}$ alkoxycarbonyl, for example, —C(=O)OCH$_2$CH$_3$ and —C(=O)OCH$_3$. In some embodiments, including those described in this paragraph, $R^{28A}$ can be an optionally substituted $C_{1-4}$ alkyl. In some embodiment, $R^{28A}$ can be methyl or tert-butyl. In some embodiments, t can be 1. In other embodiments, t can be 2.

In some embodiments, $R^{6A}$ and $R^{7A}$ can be both an optionally substituted aryl. In some embodiments, at least one of $R^{6A}$ and $R^{7A}$ can be an optionally substituted aryl. For example, both $R^{6A}$ and $R^{7A}$ can be an optionally substituted phenyl or an optionally substituted naphthyl. When substituted, the substituted aryl can be substituted with 1, 2, 3 or more than 3 substituents. When more the two substituents are present, the substituents can be the same or different. In some embodiments, when at least one of $R^{6A}$ and $R^{7A}$ is a substituted phenyl, the substituted phenyl can be a para-, ortho- or meta-substituted phenyl.

In some embodiments, $R^{6A}$ and $R^{7A}$ can be both an optionally substituted aryl($C_{1-6}$ alkyl). In some embodiments, at least one of $R^{6A}$ and $R^{7A}$ can be an optionally substituted aryl($C_{1-6}$ alkyl). For example, both $R^{6A}$ and $R^{7A}$ can be an optionally substituted benzyl. When substituted, the substituted benzyl group can be substituted with 1, 2, 3 or more than 3 substituents. When more the two substituents are present, the substituents can be the same or different. In some embodiments, the aryl group of the aryl($C_{1-6}$ alkyl) can be a para-, ortho- or meta-substituted phenyl.

In some embodiments, $R^{6A}$ and $R^{7A}$ can be both

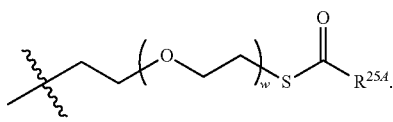

In some embodiments, at least one of $R^{6A}$ and $R^{7A}$ can be

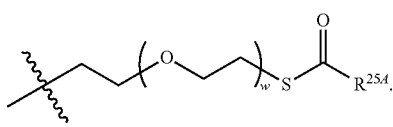

In some embodiments, $R^{25A}$ can be hydrogen. In other embodiments, $R^{25A}$ can be an optionally substituted $C_{1-24}$ alkyl. In still other embodiments, $R^{25A}$ can be an optionally substituted aryl (for example, an optionally substituted phenyl). In some embodiments, $R^{25A}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained). In some embodiments, w can be 0. In other embodiments, w can be 1. In some embodiments, $R^{6A}$ and $R^{7A}$ can be both an optionally substituted S-acylthioethyl (SATE) group and form an optionally substituted SATE ester prodrug.

In some embodiments, $R^{6A}$ and $R^{7A}$ can be both

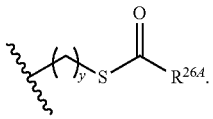

In some embodiments, at least one of $R^{6A}$ and $R^{7A}$ can be

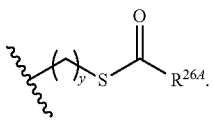

In some embodiments, $R^{26A}$ can be hydrogen. In other embodiments, $R^{26A}$ can be an optionally substituted $C_{1-24}$ alkyl. In still other embodiments, $R^{26A}$ can be an optionally substituted aryl, for example, an optionally substituted phenyl. In some embodiments, $R^{26A}$ can be an optionally substituted $C_{1-6}$ alkyl. In some embodiments, $R^{26A}$ can be an unsubstituted $C_{1-6}$ alkyl. In some embodiments, y can be 3. In other embodiments, y can be 4. In still other embodiments, y can be 5.

In some embodiments, $R^{6A}$ and $R^{7A}$ can be both

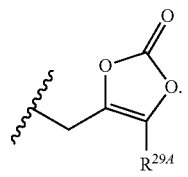

In some embodiments, at least one of $R^{6A}$ and $R^{7A}$ can be

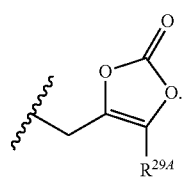

In some embodiments, $R^{29A}$ can be hydrogen. In other embodiments, $R^{29A}$ can be an optionally substituted $C_{1-24}$ alkyl. In some embodiments, $R^{29A}$ can be a $C_{1-4}$ alkyl, such as methyl, ethyl, n-propyl, iso-propyl, n-butyl, iso-butyl and t-butyl. In still other embodiments, $R^{29A}$ can be an optionally substituted aryl, such as an optionally substituted phenyl or an optionally substituted naphthyl. In some embodiments, $R^{6A}$ and $R^{7A}$ can be both an optionally substituted dioxolenone group and form an optionally substituted dioxolenone prodrug.

In some embodiments, $R^{6A}$ and $R^{7A}$ can be taken together to form an optionally substituted

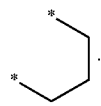

For example, $R^{1A}$ can be an optionally substituted

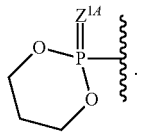

When substituted, the ring can be substituted 1, 2, 3 or more times. When substituted with multiple substituents, the substituents can be the same or different. In some embodiments, when $R^{1A}$ is

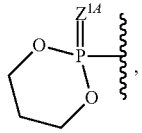

the ring can be substituted with an optionally substituted aryl group and/or an optionally substituted heteroaryl. An example of a suitable heteroaryl is pyridinyl. In some embodiments, $R^{6A}$ and $R^{7A}$ can be taken together to form an optionally substituted

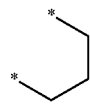

such as

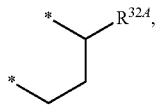

wherein $R^{32A}$ can be an optionally substituted aryl, an optionally substituted heteroaryl or an optionally substituted heterocyclyl. In some embodiments, $R^{6A}$ and $R^{7A}$ can form an optionally substituted cyclic 1-aryl-1,3-propanyl ester (HepDirect) prodrug moiety.

In some embodiments, $R^{6A}$ and $R^{7A}$ can be taken together to form an optionally substituted

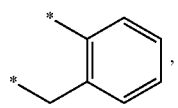

wherein the oxygens connected to $R^{6A}$ and $R^{7A}$, the phosphorus and the moiety form a six-membered to ten-membered ring system. Example of an optionally substituted

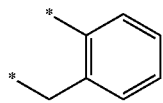 [SMILES: *Cc1ccccc1*]

include

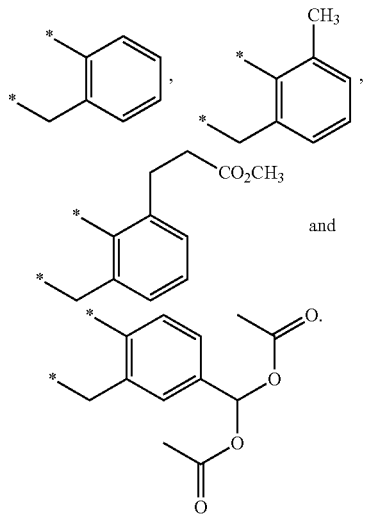

In some embodiments, $R^{6A}$ and $R^{7A}$ can form an optionally substituted cyclosaligenyl (cycloSal) prodrug.

In some embodiments, $R^{6A}$ and $R^{7A}$ can be the same. In some embodiments, $R^{6A}$ and $R^{7A}$ can be different.

In some embodiments, $Z^{1A}$ can be oxygen. In other embodiments, $Z^{1A}$ can be sulfur.

In some embodiments, $R^{1A}$ can be

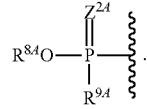

In some embodiments, $R^{8A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^{8A}$ can be hydrogen, and $R^{9A}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained), and hexyl (branched and straight-chained). In other embodiments, $R^{8A}$ can be hydrogen, and $R^{9A}$ can be $NR^{30A}R^{31A}$, wherein $R^{30A}$ and $R^{31A}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl and an optionally substituted aryl($C_{1-4}$ alkyl). In some embodiments, one of $R^{30A}$ and $R^{31A}$ can be hydrogen and the other of $R^{30A}$ and $R^{31A}$ can be an optionally substituted $C_{1-6}$ alkyl, an optionally substituted $C_{2-6}$ alkenyl, an optionally substituted $C_{2-6}$ alkynyl, an optionally substituted $C_{3-6}$ cycloalkyl, an optionally substituted $C_{3-6}$ cycloalkenyl and an optionally substituted benzyl.

In some embodiments, $R^{8A}$ can be absent or hydrogen; and $R^{9A}$ can be an optionally substituted N-linked amino acid or an optionally substituted N-linked amino acid ester derivative. In other embodiments, $R^{8A}$ can be an optionally substituted aryl; and $R^{9A}$ can be an optionally substituted N-linked amino acid or an optionally substituted N-linked amino acid ester derivative. In still other embodiments, $R^{8A}$ can be an optionally substituted heteroaryl; and $R^{9A}$ can be an optionally substituted N-linked amino acid or an optionally substituted N-linked amino acid ester derivative. In some embodiments, $R^{9A}$ can be selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. Examples of an optionally substituted N-linked amino acid ester derivatives include optionally substituted versions of the following: N-alanine isopropyl ester, N-alanine cyclohexyl ester, N-alanine neopentyl ester, N-valine isopropyl ester and N-leucine isopropyl ester. In some embodiments, $R^{9A}$ can have the structure

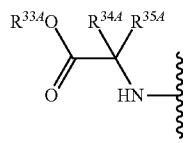

wherein $R^{33A}$ can be selected from hydrogen, an optionally substituted $C_{1-6}$ alkyl, an optionally substituted $C_{3-6}$ cycloalkyl, an optionally substituted aryl, an optionally substituted aryl($C_{1-6}$ alkyl) and an optionally substituted haloalkyl; $R^{34A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{35A}$ can be hydrogen or an optionally substituted $C_{1-4}$ alkyl; or $R^{34A}$ and $R^{35A}$ can be taken together to form an optionally substituted $C_{3-6}$ cycloalkyl.

When $R^{34A}$ is substituted, $R^{34A}$ can be substituted with one or more substituents selected from N-amido, mercapto, alkylthio, an optionally substituted aryl, hydroxy, an optionally substituted heteroaryl, O-carboxy and amino. In some embodiments, $R^{34A}$ can be an unsubstituted $C_{1-6}$ alkyl, such as those described herein. In some embodiments, $R^{34A}$ can be hydrogen. In other embodiments, $R^{34A}$ can be methyl. In some embodiments, $R^{33A}$ can be an optionally substituted $C_{1-6}$ alkyl. Examples of optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{33A}$ can be methyl or isopropyl. In some embodiments, $R^{33A}$ can be ethyl or neopentyl. In other embodiments, $R^{33A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{33A}$ can be an optionally substituted cyclohexyl. In still other embodiments, $R^{33A}$ can be an optionally substituted aryl, such as phenyl and naphthyl. In yet still other embodiments, $R^{33A}$ can be an optionally substituted aryl($C_{1-6}$ alkyl). In some embodiments, $R^{33A}$ can be an optionally substituted benzyl. In some embodiments, $R^{33A}$ can be an optionally substituted $C_{1-6}$ haloalkyl, for example, $CF_3$. In some embodiments, $R^{35A}$ can be hydrogen. In other embodiments, $R^{35A}$ can be an optionally substituted $C_{1-4}$ alkyl, such as methyl, ethyl, n-propyl, isopropyl, n-butyl, isobutyl and tert-butyl. In some embodiments, $R^{35A}$ can be methyl. In some embodiments, $R^{34A}$ and $R^{35A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{34A}$ and $R^{35A}$, the carbon to which $R^{34A}$ and $R^{35A}$ are attached may be a chiral center. In some embodiment, the carbon to which $R^{34A}$ and $R^{35A}$ are attached may be a (R)-chiral center. In other embodiments, the carbon to which $R^{34A}$ and $R^{35A}$ are attached may be a (S)-chiral center.

In some embodiments, when $R^{1A}$ is

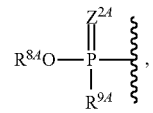

$Z^{2A}$ can be O (oxygen). In other embodiments, when $R^{1A}$ is

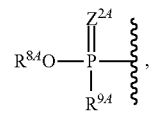

$Z^{2A}$ can be S (sulfur). In some embodiments, when $R^{1A}$ is

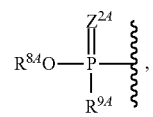

a compound of Formula (I) can be an optionally substituted phosphoroamidate prodrug, such as an optionally substituted aryl phosphoroamidate prodrug.

In some embodiments, $R^{1A}$ can be

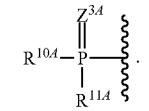

In some embodiments, $R^{10A}$ and $R^{11A}$ can be both an optionally substituted N-linked amino acid or an optionally substituted N-linked amino acid ester derivative. In some embodiments, $R^{10A}$ and $R^{11A}$ can be independently selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{10A}$ and $R^{11A}$ can be an optionally substituted version of the following: N-alanine isopropyl ester, N-alanine cyclohexyl ester, N-alanine neopentyl ester, N-valine isopropyl ester and N-leucine isopropyl ester. In some embodiments, $R^{10A}$ and $R^{11A}$ can independently have the structure

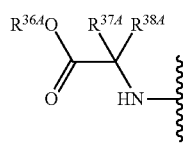

wherein $R^{36A}$ can be selected from hydrogen, an optionally substituted $C_{1-6}$ alkyl, an optionally substituted $C_{3-6}$ cycloalkyl, an optionally substituted aryl, an optionally substituted aryl($C_{1-6}$ alkyl) and an optionally substituted haloalkyl; $R^{37A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{38A}$ can be hydrogen or an optionally substituted $C_{1-4}$ alkyl; or $R^{37A}$ and $R^{38A}$ can be taken together to form an optionally substituted $C_{3-6}$ cycloalkyl.

When $R^{37A}$ is substituted, $R^{37A}$ can be substituted with one or more substituents selected from N-amido, mercapto, alkylthio, an optionally substituted aryl, hydroxy, an optionally substituted heteroaryl, O-carboxy and amino. In some embodiments, $R^{37A}$ can be an unsubstituted $C_{1-6}$ alkyl, such as those described herein. In some embodiments, $R^{37A}$ can be hydrogen. In other embodiments, $R^{37A}$ can be methyl. In some embodiments, $R^{36A}$ can be an optionally substituted $C_{1-6}$ alkyl. Examples of optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{36A}$ can be methyl or isopropyl. In some embodiments, $R^{36A}$ can be ethyl or neopentyl. In other embodiments, $R^{36A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{36A}$ can be an optionally substituted cyclohexyl. In still other embodiments, $R^{36A}$ can be an optionally substituted aryl, such as phenyl and naphthyl. In yet still other embodiments, $R^{36A}$ can be an optionally substituted aryl($C_{1-6}$ alkyl). In some embodiments, $R^{36A}$ can be an optionally substituted benzyl. In some embodiments, $R^{36A}$ can be an optionally substituted $C_{1-6}$ haloalkyl, for example, $CF_3$. In some embodiments, $R^{38A}$ can be hydrogen. In other embodiments, $R^{38A}$ can be an optionally substituted $C_{1-4}$ alkyl, such as methyl, ethyl, n-propyl, isopropyl, n-butyl, isobutyl and tert-butyl. In some embodiments, $R^{38A}$ can be methyl. In some embodiments, $R^{37A}$ and $R^{38A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{37A}$ and $R^{38A}$, the carbon to which $R^{37A}$ and $R^{38A}$ are attached may be a chiral center. In some embodiment, the carbon to which $R^{37A}$ and $R^{38A}$ are attached may be a (R)-chiral center. In other embodiments, the carbon to which $R^{37A}$ and $R^{38A}$ are attached may be a (S)-chiral center.

Examples of suitable

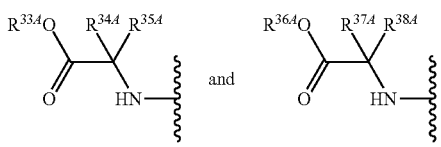

groups include the following:

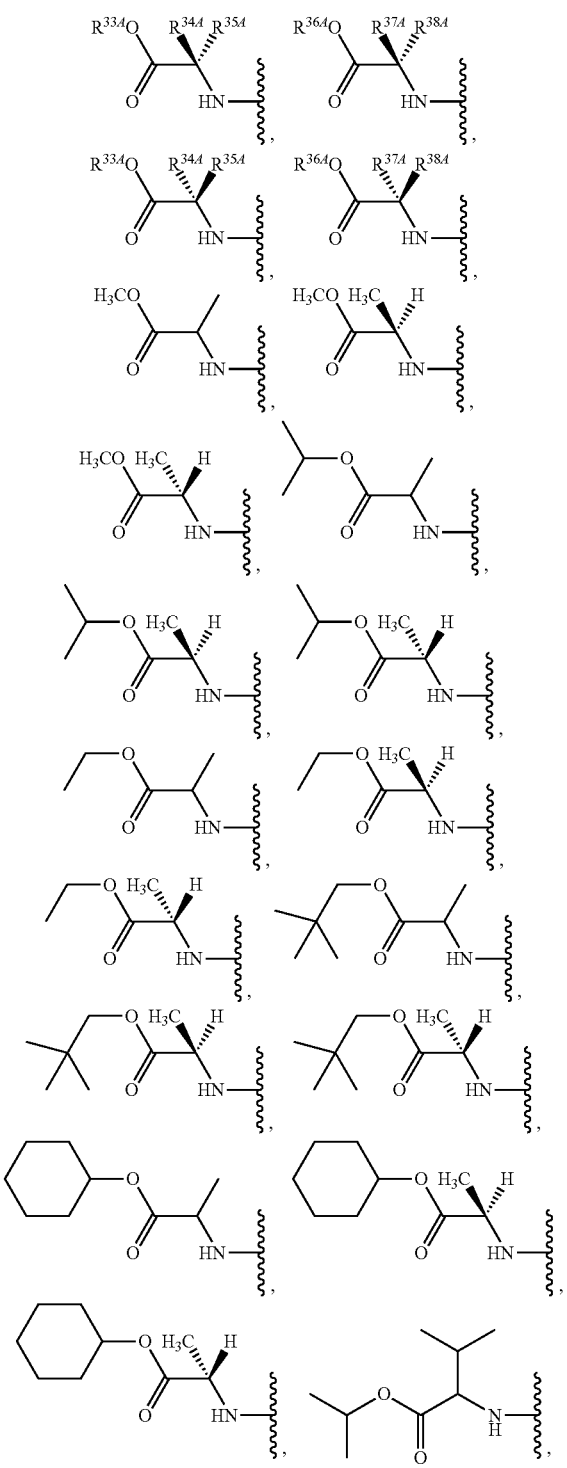

-continued

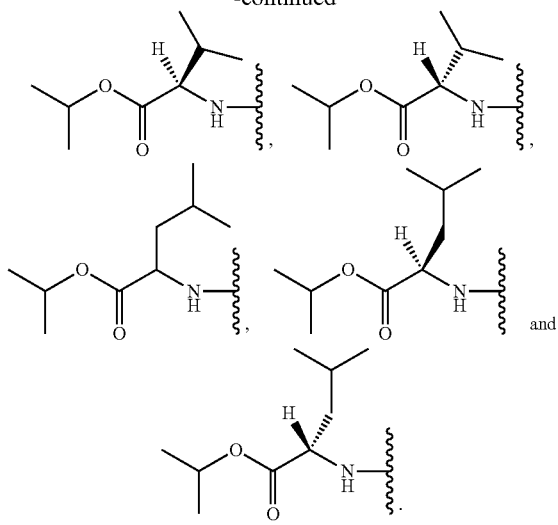

In some embodiments, $R^{10A}$ and $R^{11A}$ can be the same. In some embodiments, $R^{10A}$ and $R^{11A}$ can be different.

In some embodiments, $Z^{3A}$ can be O (oxygen). In other embodiments, $Z^{3A}$ can be S (sulfur). In some embodiments, when $R^{1A}$ is

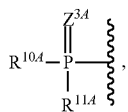

a compound of Formula (I) can be an optionally substituted phosphonic diamide prodrug.

Various substituents can be present at the 4'-position of the pentose ring. In some embodiments, $R^{2A}$ can be an unsubstituted $C_{1-4}$ alkyl. Unsubstituted $C_{1-4}$ alkyls include methyl, ethyl, n-propyl, iso-propyl, n-butyl, iso-butyl and tert-butyl. In other embodiments, $R^{2A}$ can be an unsubstituted $C_{2-4}$ alkenyl, such as ethenyl, propenyl and butenyl. In still other embodiments, $R^{2A}$ can be an unsubstituted $C_{2-4}$ alkynyl, for example, ethynyl, propynyl and butynyl. In yet still other embodiments, $R^{2A}$ can be a halogen($C_{1-6}$alkyl), such as $-(CH_2)_{0-5}(CR^{2A1}R^{2A2})$halogen, wherein $R^{2A1}$ and $R^{2A2}$ can be independently hydrogen or halogen provided that at least one of $R^{2A1}$ and $R^{2A2}$ is halogen. Examples of a halogen($C_{1-6}$alkyl) are $-(CH_2)_{1-6}$halogen, $-(CH_2)_{0-5}(CH)$(halogen)$_2$ and $-(CH_2)_{0-5}-C$(halogen)$_3$. In some embodiments, the halogen($C_{1-6}$alkyl) can be $-(CH_2)_{1-6}F$ $-(CH_2)_{1-6}Cl$. In other embodiments, the haloalkyl can be $-(CH_2)_{0-5}CHF_2$ or $-(CH_2)_{0-5}CF_3$. In some embodiments, the halogen($C_{1-6}$alkyl) can be fluoromethyl. In some embodiments, $R^{2A}$ can be $CHF_2$. In still other embodiments, $R^{2A}$ can be $CF_3$. In yet still other embodiments, $R^{2A}$ can be a $C_{1-6}$ azidoalkyl. For example, $R^{2A}$ can be an azidomethyl, azidoethyl, azidopropyl, azidobutyl, azidopentyl or azidohexyl. In some embodiments, $R^{2A}$ can be a $C_{1-6}$ aminoalkyl. For example, $R^{2A}$ can be an aminomethyl, aminoethyl, aminopropyl, aminobutyl, aminopentyl or aminohexyl. In other embodiments, $R^{2A}$ can be halogen. For example, $R^{2A}$ can be fluoro (F) or chloro (Cl). In still other embodiments, $R^{2A}$ can be hydrogen. In yet still other embodiments, $R^{2A}$ can be azido ($N_3$). In some embodiments, $R^{2A}$ can be $-(CH_2)_{1-6}$ring A. As described herein, in some embodiments, ring A can be an optionally substituted mono-cyclic heteroaryl (for example, a 5- or 6-membered optionally substituted heteroaryl). In other embodiments, ring A can be an optionally substituted mono-cyclic heterocyclyl, such as, a 5- or 6-membered optionally substituted heterocyclyl. In still other embodiments, $R^{2A}$ can be —CN.

A variety of substituents can also be present at the 2'-position of the pentose ring. In some embodiments, $R^{4A}$ can be OH. In other embodiments, $R^{4A}$ can be —OC(=O)R'''$^B$, wherein R'''$^B$ can be an optionally substituted $C_{1-24}$ alkyl. In some embodiments, $R^{4A}$ can be —OC(=O)R'''$^B$, wherein R'''$^B$ can be an unsubstituted $C_{1-4}$ alkyl. In still other embodiments, $R^{4A}$ can be halogen. In some embodiments, $R^{4A}$ can be F. In other embodiments, $R^{4A}$ can be Cl. In some embodiments, $R^{4A}$ can be $N_3$. In some embodiments, $R^{4A}$ can be NR'''$^{B1}$R'''$^{B2}$. For example, $R^{4A}$ can be $NH_2$. Other examples can be a mono-substituted $C_{1-6}$ alkyl-amine or a di-substituted $C_{1-6}$ alkyl-amine. In other embodiments, $R^{4A}$ can be hydrogen (H).

In still other embodiments, $R^{4A}$ can be an optionally substituted O-linked amino acid, such as a O-linked alpha-amino acid. In some embodiments, the O-linked amino acid can have the structure

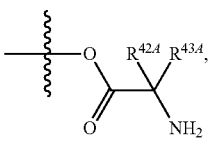

wherein $R^{42A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_{1-6}$ aryl, an optionally substituted $C_{10}$ aryl and an optionally substituted aryl($C_{1-6}$ alkyl); and $R^{43A}$ can be hydrogen or an optionally substituted $C_{1-4}$ alkyl; or $R^{42A}$ and $R^{43A}$ can be taken together to form an optionally substituted $C_{3-6}$ cycloalkyl.

When $R^{42A}$ is substituted, $R^{42A}$ can be substituted with one or more substituents selected from N-amido, mercapto, alkylthio, an optionally substituted aryl, hydroxy, an optionally substituted heteroaryl, O-carboxy and amino. In some embodiments, $R^{42A}$ can be an unsubstituted $C_{1-6}$ alkyl, such as those described herein. In some embodiments, $R^{42A}$ can be hydrogen. In other embodiments, $R^{42A}$ can be methyl. In some embodiments, $R^{43A}$ can be hydrogen. In other embodiments, $R^{43A}$ can be an optionally substituted $C_{1-4}$ alkyl, such as methyl, ethyl, n-propyl, isopropyl, n-butyl, isobutyl and tert-butyl. In some embodiments, $R^{43A}$ can be methyl. Depending on the groups that are selected for $R^{42A}$ and $R^{43A}$, the carbon to which $R^{42A}$ and $R^{43A}$ are attached may be a chiral center. In some embodiment, the carbon to which $R^{42A}$ and $R^{43A}$ are attached may be a (R)-chiral center. In other embodiments, the carbon to which $R^{42A}$ and $R^{43A}$ are attached may be a (S)-chiral center.

Examples of suitable

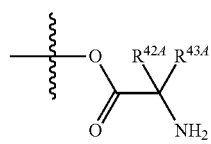

include the following:

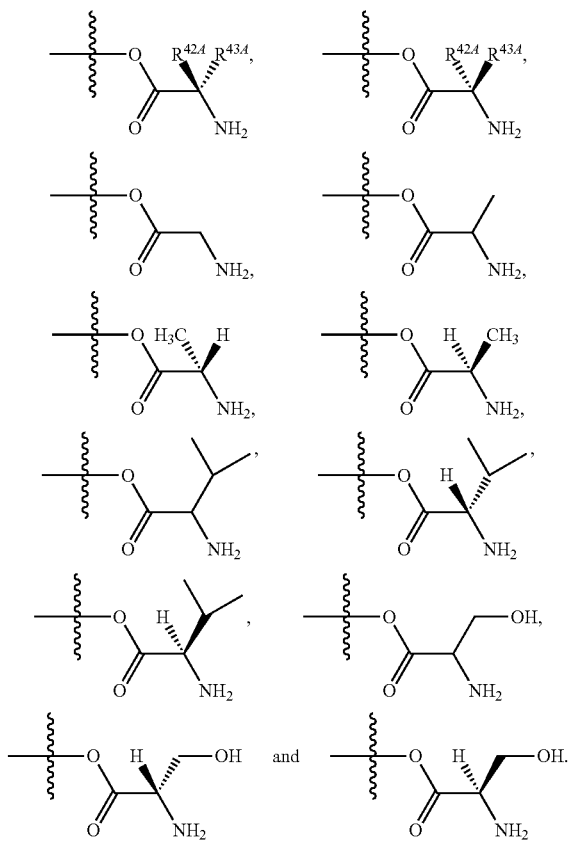

In some embodiments, $R^{5A}$ can be hydrogen. In other embodiments, $R^{5A}$ can be halogen, including F and Cl. In still other embodiments, $R^{5A}$ can be an optionally substituted $C_{1-6}$ alkyl. For example, $R^{5A}$ can be a substituted or unsubstituted version of the following: methyl, ethyl, n-propyl, iso-propyl, n-butyl, iso-butyl, tert-butyl, pentyl (branched or straight) and hexyl (branched or straight). In some embodiments, $R^{5A}$ can be a halo-substituted $C_{1-6}$ alkyl, such as —CH$_2$F. In yet still other embodiments, $R^{5A}$ can be an optionally substituted $C_{2-6}$ alkenyl. In some embodiments, $R^{5A}$ can be an optionally substituted $C_{2-6}$ alkynyl. For example, $R^{5A}$ can be ethynyl. In some embodiments, $R^{5A}$ can be hydroxy (OH).

A variety of substituents can be present at the 1'-position of the pentose ring. In some embodiments, $R^A$ can be hydrogen. In some embodiments, $R^A$ can be deuterium. In still other embodiments, $R^A$ can be an unsubstituted $C_{1-3}$ alkyl (such as methyl, ethyl, n-propyl and iso-propyl). In yet still other embodiments, $R^A$ can be an unsubstituted $C_{2-4}$ alkenyl (for example, ethenyl, propenyl (branched or straight) and butenyl (branched or straight)). In some embodiments, $R^A$ can be an unsubstituted $C_{2-3}$ alkynyl (such as ethynyl and propynyl (branched or straight)). In other embodiments, $R^A$ can be an unsubstituted cyano.

In some embodiments, ------- can be both absent such that a compound of Formula (I) has the structure:

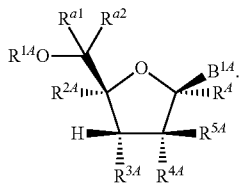

When ------- are both absent, the 3'-position can have various groups present. In some embodiments, $R^{3A}$ can be hydrogen. In other embodiments, $R^{3A}$ can be halogen. For example, $R^{3A}$ can be fluoro (F) or chloro (Cl). In still other embodiments, $R^{3A}$ can be OH. In some embodiments, $R^{3A}$ can be —OC(=O)R'''$^A$, wherein R'''$^A$ can be an optionally substituted $C_{1-24}$ alkyl. In some embodiments, $R^{3A}$ can be —OC(=O)R'''$^A$, wherein R'''$^A$ can be an unsubstituted $C_{1-4}$ alkyl. In other embodiments, $R^{3A}$ can be an optionally substituted O-linked amino acid, such as an optionally substituted O-linked alpha-amino acid. The optionally substituted O-linked amino acid can have the structure:

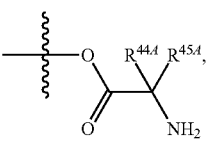

wherein $R^{44A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{45A}$ can be hydrogen or an optionally substituted $C_{1-4}$ alkyl; or $R^{44A}$ and $R^{45A}$ can be taken together to form an optionally substituted $C_{3-6}$ cycloalkyl.

When $R^{44A}$ is substituted, $R^{44A}$ can be substituted with one or more substituents selected from N-amido, mercapto, alkylthio, an optionally substituted aryl, hydroxy, an optionally substituted heteroaryl, O-carboxy and amino. In some embodiments, $R^{44A}$ can be an unsubstituted $C_{1-6}$ alkyl, such as those described herein. In some embodiments, $R^{44A}$ can be hydrogen. In other embodiments, $R^{44A}$ can be methyl. In some embodiments, $R^{45A}$ can be hydrogen. In other embodiments, $R^{45A}$ can be an optionally substituted $C_{1-4}$ alkyl, such as methyl, ethyl, n-propyl, isopropyl, n-butyl, isobutyl and tert-butyl. In some embodiments, $R^{45A}$ can be methyl. Depending on the groups that are selected for $R^{44A}$ and $R^{45A}$ the carbon to which $R^{44A}$ and $R^{45A}$ are attached may be a chiral center. In some embodiment, the carbon to which $R^{44A}$ and $R^{45A}$ are attached may be a (R)-chiral center. In other embodiments, the carbon to which $R^{44A}$ and $R^{45A}$ are attached may be a (S)-chiral center.

Examples of suitable

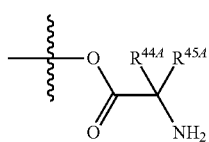

include the following:

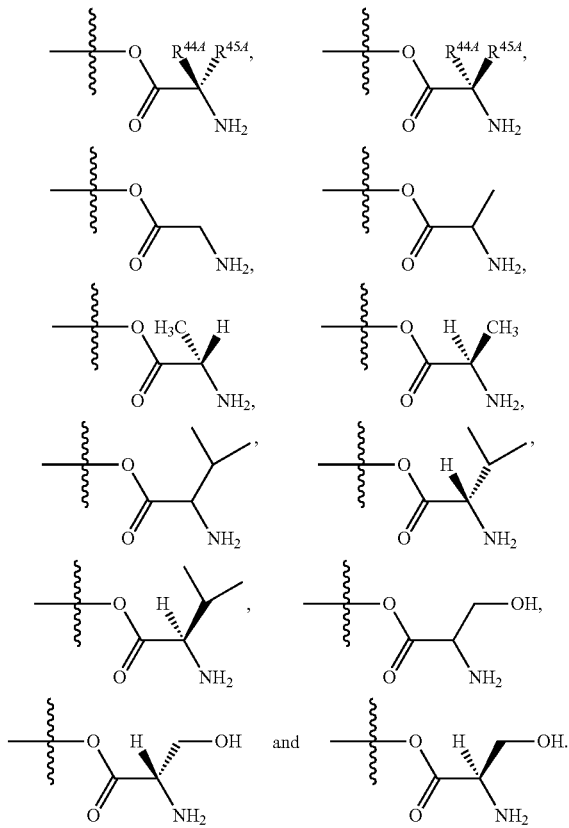

In some embodiments, $R^{3A}$ and $R^{4A}$ can be each an oxygen atom connected via a carbonyl to form a 5-membered ring.

In some embodiments, $R^{2A}$ can be fluoro and $R^{3A}$ can be fluoro. In some embodiments, $R^{2A}$ can be fluoro and $R^{4A}$ can be fluoro. In some embodiments, $R^{2A}$ can be fluoro, $R^{3A}$ can be fluoro and $R^{5A}$ can be an optionally substituted $C_{1-6}$ alkyl, an optionally substituted $C_{2-6}$ alkenyl and an optionally substituted $C_{2-6}$ alkynyl. In some embodiments, $R^{2A}$ can be fluoro, $R^{4A}$ can be fluoro and $R^{5A}$ can be an optionally substituted $C_{1-6}$ alkyl, an optionally substituted $C_{2-6}$ alkenyl and an optionally substituted $C_{2-6}$ alkynyl. In some embodiments, $R^{2A}$ can be fluoro, $R^{3A}$ can be fluoro and $R^{4A}$ can be OH or $-OC(=O)R'''^B$. In some embodiments, $R^{2A}$ can be fluoro, $R^{3A}$ can be OH or $-OC(=O)R'''^A$ and $R^{4A}$ can be fluoro. In some embodiments, $R^{4A}$ and $R^{5A}$ can be each F. In some embodiments, $R^{2A}$ can be *—$(CH_2)_{1-6}$halogen (for example, —$CH_2F$), $R^{3A}$ can be OH, —$OC(=O)R'''^A$ or an optionally substituted O-linked amino acid and $R^{4A}$ can be OH. In some embodiments, $R^{2A}$ can be —$(CH_2)_{1-6}$halogen (for example, —$CH_2F$), $R^{3A}$ can be OH, —$OC(=O)R'''^A$ or an optionally substituted O-linked amino acid, $R^{4A}$ can be OH, and $R^{5A}$ can be an unsubstituted $C_{1-6}$ alkyl. In some embodiments, $R^{2A}$ can be —$(CH_2)_{1-6}N_3$ (such as, —$CH_2N_3$), $R^{3A}$ can be OH and $R^{4A}$ can be fluoro. In other embodiments, $R^{2A}$ can be azido, $R^{3A}$ can be OH and $R^{4A}$ can be fluoro.

In some embodiments, ------ can be each a single bond such that a compound of Formula (I) has the structure:

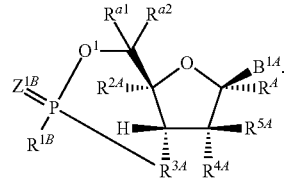

When ------ are each a single bond, $R^{3A}$ can be oxygen (O). In some embodiments, when ------ are each a single bond, $R^{1B}$ can be O⁻ or OH. In other embodiments, when ------ are each a single bond, $R^{1B}$ can be an —O-optionally substituted $C_{1-6}$ alkyl. For example, $R^{1B}$ can be an —O-unsubstituted $C_{1-6}$ alkyl.

In some embodiments, when ------ are each a single bond, $R^{1B}$ can be

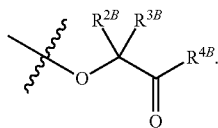

In other embodiments, $R^{1B}$ can be

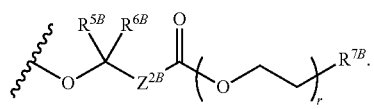

For example, $R^{1B}$ can be an optionally substituted isopropyloxycarbonyloxymethyloxy or an optionally substituted pivaloyloxymethyloxy group. In still some embodiments, $R^{1B}$ can be

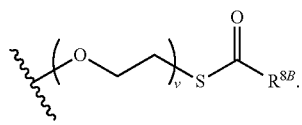

An optionally substituted S-acylthioethyl (SATE) group is an example of a

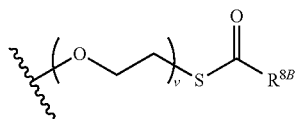

group. In yet still other embodiments, $R^{1B}$ can be an optionally substituted N-linked amino acid or an optionally substituted N-linked amino acid ester derivative, such as an optionally substituted N-linked alpha-amino acid or an optionally substituted N-linked alpha-amino acid ester derivative.

Examples of an optionally substituted N-linked amino acids and an optionally substituted N-linked amino acid ester derivatives are described herein. In some embodiments, $R^{1B}$ can be selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{1B}$ can be an optionally substituted version of the following: N-alanine isopropyl ester, N-alanine cyclohexyl ester, N-alanine neopentyl ester, N-valine isopropyl ester and N-leucine isopropyl ester. In some embodiments, $R^{1B}$ can have the structure

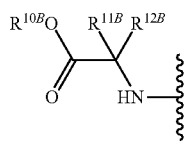

wherein $R^{10B}$ can be selected from hydrogen, an optionally substituted $C_{1-6}$ alkyl, an optionally substituted $C_{3-6}$ cycloalkyl, an optionally substituted aryl, an optionally substituted aryl($C_{1-6}$ alkyl) and an optionally substituted haloalkyl; $R^{11B}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{12B}$ can be hydrogen or an optionally substituted $C_{1-4}$ alkyl; or $R^{11B}$ and $R^{12B}$ can be taken together to form an optionally substituted $C_{3-6}$ cycloalkyl.

As described herein, $R^{11B}$ can be substituted. Examples of substituents include one or more substituents selected from N-amido, mercapto, alkylthio, an optionally substituted aryl, hydroxy, an optionally substituted heteroaryl, O-carboxy and amino. In some embodiments, $R^{11B}$ can be an unsubstituted $C_{1-6}$ alkyl, such as those described herein. In some embodiments, $R^{11B}$ can be hydrogen. In other embodiments, $R^{11B}$ can be methyl. In some embodiments, $R^{10B}$ can be an optionally substituted $C_{1-6}$ alkyl. In some embodiments, $R^{10B}$ can be methyl, ethyl, isopropyl or neopentyl. In other embodiments, $R^{10B}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{10B}$ can be an optionally substituted cyclohexyl. In still other embodiments, $R^{10B}$ can be an optionally substituted aryl, such as phenyl and naphthyl. In yet still other embodiments, $R^{10B}$ can be an optionally substituted aryl($C_{1-6}$ alkyl), for example, an optionally substituted benzyl. In some embodiments, $R^{10B}$ can be an optionally substituted $C_{1-6}$ haloalkyl, for example, $CF_3$. In some embodiments, $R^{12B}$ can be hydrogen. In other embodiments, $R^{12B}$ can be an optionally substituted $C_{1-4}$ alkyl, such as methyl, ethyl, n-propyl, isopropyl, n-butyl, isobutyl and tert-butyl. In some embodiments, $R^{12B}$ can be methyl. In some embodiments, $R^{11B}$ and $R^{12B}$ can be taken together to form an optionally substituted $C_{3-6}$ cycloalkyl. Depending on the groups that are selected for $R^{11B}$ and $R^{12B}$, the carbon to which $R^{11B}$ and $R^{12B}$ are attached may be a chiral center. In some embodiment, the carbon to which $R^{11B}$ and $R^{12B}$ are attached may be a (R)-chiral center. In other embodiments, the carbon to which $R^{11B}$ and $R^{12B}$ are attached may be a (S)-chiral center.

Examples of suitable

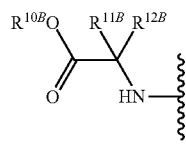

groups include the following:

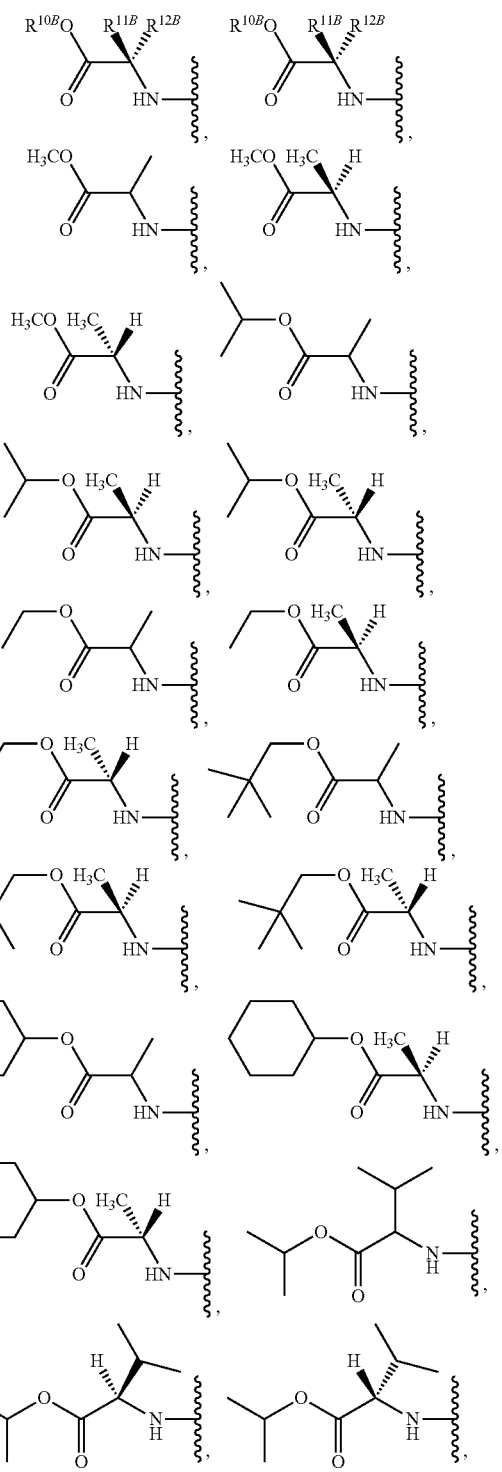

49

-continued

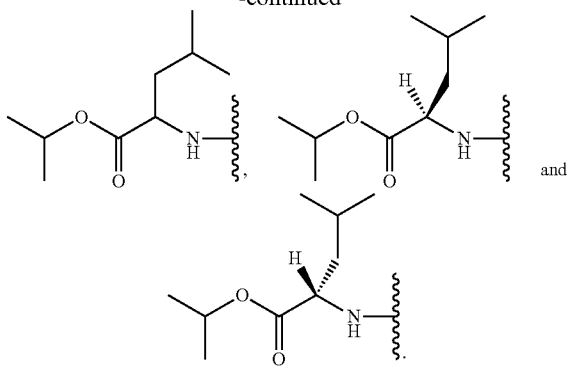

In some embodiments, R$^{1B}$ can be

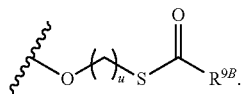

In some embodiments, R$^{9B}$ can be hydrogen. In other embodiments, R$^{9B}$ can be an optionally substituted C$_{1-24}$ alkyl. In still other embodiments, R$^{9B}$ can be an optionally substituted aryl, for example, an optionally substituted phenyl. In some embodiments, R$^{9B}$ can be an optionally substituted C$_{1-6}$ alkyl. In some embodiments, R$^{9B}$ can be an unsubstituted C$_{1-6}$ alkyl. In some embodiments, u can be 3. In other embodiments, u can be 4. In still other embodiments, u can be 5.

In some embodiments, Z$^{1B}$ can be oxygen (O). In other embodiments, Z$^{1B}$ can be S (sulfur).

Various optionally substituted heterocyclic bases can be attached to the pentose ring. In some embodiments, one or more of the amine and/or amino groups of the optionally substituted heterocyclic base may be protected with a suitable protecting group. For example, an amino group may be protected by transforming the amine and/or amino group to an amide or a carbamate. In some embodiments, an optionally substituted heterocyclic base or an optionally substituted heterocyclic base can include a group that improves the solubility of the compound (for example, —(CH$_2$)$_{1-2}$—O—P(=O)(OW$^{1A}$)$_2$). In some embodiments, an optionally substituted heterocyclic base or an optionally substituted heterocyclic base with one or more protected amino groups can have one of the following structures:

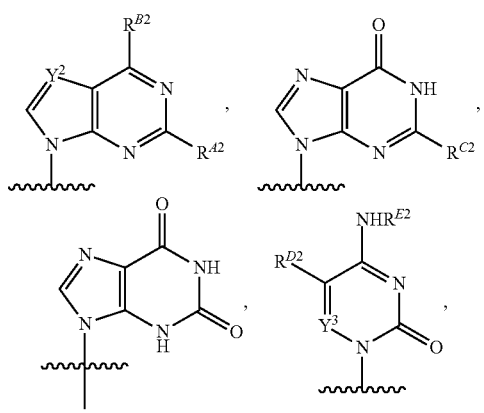

50

-continued

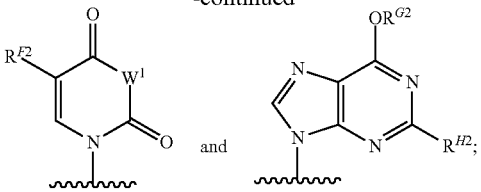

wherein: R$^{A2}$ can be selected from hydrogen, halogen and NHR$^{J2}$, wherein R$^{J2}$ can be selected from hydrogen, —C(=O)R$^{K2}$ and —C(=O)OR$^{L2}$; R$^{B2}$ can be halogen or NHR$^{W2}$, wherein R$^{W2}$ can be selected from hydrogen, an optionally substituted C$_{1-6}$ alkyl, an optionally substituted C$_{2-6}$ alkenyl, an optionally substituted C$_{3-8}$ cycloalkyl, —C(=O)R and —C(=O)OR$^{N2}$; R$^{C2}$ can be hydrogen or NHR$^{O2}$, wherein R$^{O2}$ can be selected from hydrogen, —C(=O)R$^{P2}$ and —C(=O)OR$^{Q2}$; R$^{D2}$ can be selected from hydrogen, deuterium, halogen, an optionally substituted C$_{1-6}$ alkyl, an optionally substituted C$_{2-6}$ alkenyl and an optionally substituted C$_{2-6}$ alkynyl; R$^{E2}$ can be selected from hydrogen, hydroxy, an optionally substituted C$_{1-6}$ alkyl, an optionally substituted C$_{3-8}$ cycloalkyl, —C(=O)R$^{R2}$ and —C(=O)OR$^{S2}$; R$^{F2}$ can be selected from hydrogen, halogen, an optionally substituted C$_{1-6}$ alkyl, an optionally substituted C$_{2-6}$ alkenyl and an optionally substituted C$_{2-6}$ alkynyl; Y$^2$ and Y$^3$ can be independently N (nitrogen) or CR$^2$, wherein R$^2$ can be selected from hydrogen, halogen, an optionally substituted C$_{1-6}$ alkyl, an optionally substituted C$_{2-6}$-alkenyl and an optionally substituted C$_{2-6}$-alkynyl; W$^1$ can be NH, —NCH$_2$—OC(=O)CH(NH$_2$)—CH(CH$_3$)$_2$ or —(CH$_2$)$_{1-2}$—O—P(=O)(OW$^{1A}$)$_2$, wherein W$^{1A}$ can be selected from absent, hydrogen and an optionally substituted C$_{1-6}$ alkyl; R$^{G2}$ can be an optionally substituted C$_{1-6}$ alkyl; R$^{H2}$ can be hydrogen or NHR$^{T2}$, wherein R$^{T2}$ can be independently selected from hydrogen, —C(=O)R$^{u2}$ and —C(=O)OR$^{V2}$; and R$^{K2}$, R$^{L2}$, R$^{M2}$, R$^{N2}$, R$^{P2}$, R$^{Q2}$, R$^{R2}$, R$^{S2}$, R$^{U2}$ and R$^{V2}$ can be independently selected from hydrogen, C$_{1-6}$ alkyl, C$_{2-6}$ alkenyl, C$_{2-6}$ alkynyl, C$_{3-6}$ cycloalkyl, C$_{3-6}$ cycloalkenyl, C$_{6-10}$ aryl, heteroaryl, heterocyclyl, aryl (C$_{1-6}$ alkyl), heteroaryl(C$_{1-6}$ alkyl) and heterocyclyl(C$_{1-6}$ alkyl). In some embodiments, the structures shown above can be modified by replacing one or more hydrogens with substituents selected from the list of substituents provided for the definition of "substituted." In some embodiments of B$^{1A}$, a hydrogen can be replaced with a deuterium. Those skilled in the art understand that when W$^{1A}$ is absent, the oxygen atom will have an associated negative charge. In some embodiments, the substituent on the base can result in the formation of a salt of a compound of Formula (I).

In some embodiments, B$^{1A}$ can be an optionally substituted purine base. In other embodiments, B$^{1A}$ can be an optionally substituted pyrimidine base. In some embodiments, B$^{1A}$ can be

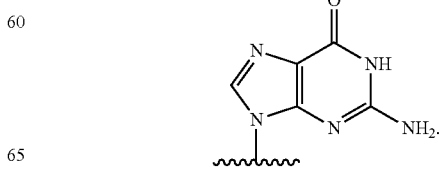

In other embodiments, $B^{1A}$ can be

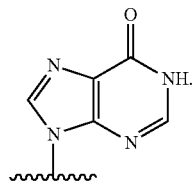 [SMILES: *n1cnc2c(=O)[nH]cnc21]

In still other embodiments, $B^{1A}$ can be

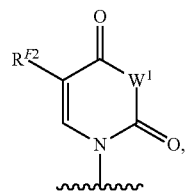

such as

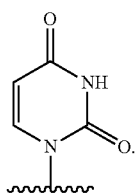 [SMILES: *n1ccc(=O)[nH]c1=O]

In yet still other embodiments, $B^{1A}$ can be

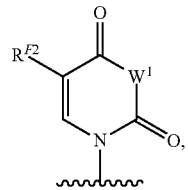

wherein $W^1$ can be —NCH$_2$—OC(=O)CH(NH$_2$)—CH(CH$_3$)$_2$ or —(CH$_2$)$_{1-2}$—O—P(=O)(OW$^{1A}$)$_2$. In some embodiments, $B^{1A}$ can be

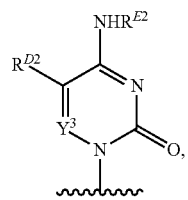

for example,

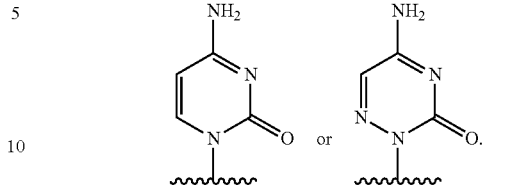

In other embodiments, $R^{D2}$ can be hydrogen. In still other embodiments, $B^{1A}$ can be

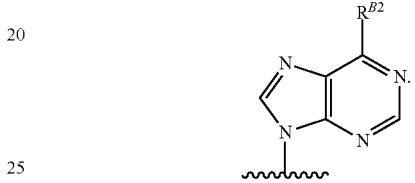

In some embodiments, $R^{B2}$ can be NH$_2$. In other embodiments, $R^{B2}$ can be NHR$^{W2}$, wherein $R^{W2}$ can be —C(=O)R$^{M2}$ or —C(=O)OR$^{N2}$. In still other embodiments, $B^{1A}$ can be

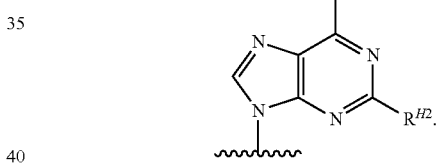

In some embodiments, $B^{1A}$ can be

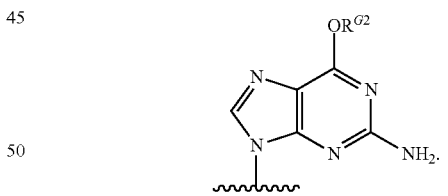

In some embodiments, when $R^{2A}$ is halogen (such as fluoro); ------ are both absent; $Z^1$ is absent; $O^1$ is OR$^{1A}$; $B^{1A}$ is selected from an optionally substituted

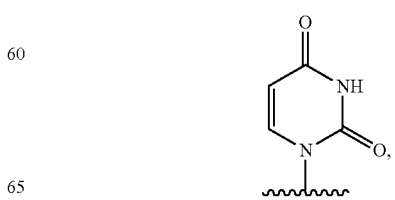

an optionally substituted

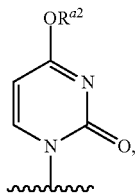

an optionally substituted

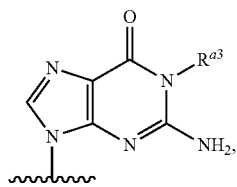

an optionally substituted

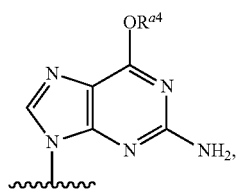

an optionally substituted

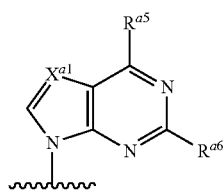

and an optionally substituted

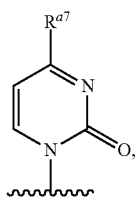

wherein $R^{a2}$ is an optionally substituted $C_{1-6}$ alkyl or an optionally substituted $C_{3-6}$ cycloalkyl, $R^{a3}$ and $R^{a4}$ are independently selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl, $R^{a5}$ is $NHR^{a8}$, and $R^{a6}$ is hydrogen, halogen or $NHR^{a9}$; $R^{a7}$ is $NHR^{a10}$; $R^{a8}$ is selected from hydrogen, an optionally substituted $C_{1-6}$ alkyl, an optionally substituted $C_{3-6}$ alkenyl, an optionally substituted $C_{3-6}$ cycloalkyl, —C(═O)$R^{a11}$ and —C(═O)O$R^{a12}$; $R^{a9}$ is selected from hydrogen, an optionally substituted $C_{1-6}$ alkyl, an optionally substituted $C_{3-6}$ alkenyl, an optionally substituted $C_{3-6}$ cycloalkyl, —C(═O)$R^{a13}$ and —C(═O)O$R^{a14}$; $R^{a10}$ is selected from hydrogen, an optionally substituted $C_{1-6}$ alkyl, an optionally substituted $C_{3-6}$ alkenyl, an optionally substituted $C_{3-6}$ cycloalkyl, —C(═O)$R^{a15}$ and —C(═O)O$R^{a16}$; $X^{a1}$ is N or —C$R^{a17}$; $R^{a17}$ is selected from hydrogen, halogen, an optionally substituted $C_{1-6}$ alkyl, an optionally substituted $C_{2-6}$ alkenyl and an optionally substituted $C_{2-6}$ alkynyl; $R^{a11}$, $R^{a12}$, $R^{a13}$, $R^{a14}$, $R^{a15}$ and $R^{a16}$ are independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl($C_{1-6}$ alkyl); then $R^{3A}$ is selected from hydrogen, halogen, and an optionally substituted O-linked amino acid; and $R^{4A}$ is selected from OH, halogen, —OC(═O)$R'''^A$ and an optionally substituted O-linked amino acid; or then $R^{4A}$ is an optionally substituted O-linked amino acid; and $R^{3A}$ is selected from hydrogen, halogen, OH, —OC(═O)$R'''^A$ and an optionally substituted O-linked amino acid; or then $R^{3A}$ and $R^{4A}$ are both an oxygen atom connected via a carbonyl to form a 5-membered ring; or then $R^{1A}$ is

wherein $R^{6A}$ and $R^{7A}$ are independently

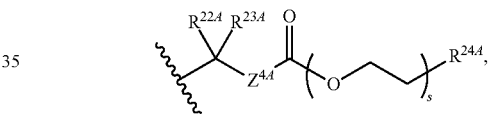

wherein s is 1, 2 or 3,

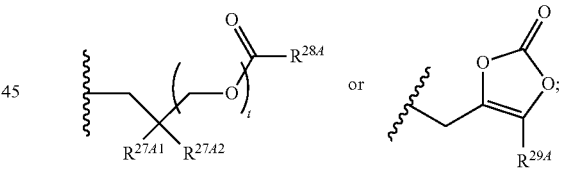

or then $R^{1A}$ is

wherein $R^{6A}$ and $R^{7A}$ are taken together to form a moiety selected from an optionally substituted

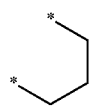

and an optionally substituted

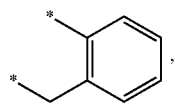

wherein the oxygens connected to $R^{6A}$ and $R^{7A}$, the phosphorus and the moiety form a six-membered to ten-membered ring system. In some embodiments, when $R^{2A}$ is halogen (such as fluoro); -------- are each a single bond; then $R^{4A}$ is —OC(=O)$R''^B$ or an optionally substituted O-linked amino acid. In some embodiments, when $R^{2A}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$N$_3$; -------- are both absent; $Z^1$ is absent; $O^1$ is OR$^{1A}$; $R^{3A}$ is OH, —OC(=O)$R''^A$ or an optionally substituted O-linked amino acid; and $R^{4A}$ is halogen; then $R^{5A}$ is selected from an optionally substituted $C_{1-6}$ alkyl, an optionally substituted $C_{2-6}$ alkenyl and an optionally substituted $C_{2-6}$ alkynyl. In some embodiments, when $R^{2A}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$N$_3$; -------- are both absent; $Z^1$ is absent; $O^1$ is OR$^{1A}$; $R^{4A}$ is halogen; and $R^{5A}$ is hydrogen or halogen; then $R^{3A}$ is hydrogen or halogen. In some embodiments, when $R^{2A}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$N$_3$; -------- are both absent; $Z^1$ is absent; $O^1$ is OR$^{1A}$; $R^{3A}$ is OH, —OC(=O)$R''^A$ or an optionally substituted O-linked amino acid; $R^{4A}$ is halogen; $R^{5A}$ is hydrogen or halogen; and $R^{1A}$ is

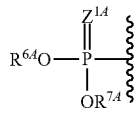

then at least one of $R^{6A}$ and $R^{7A}$ is

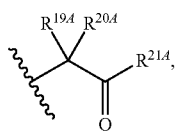

wherein $R^{21A}$ is independently selected from an optionally substituted —O-heteroaryl and an optionally substituted —O-monocyclic heterocyclyl; or then at least one of $R^{6A}$ and $R^{7A}$ is

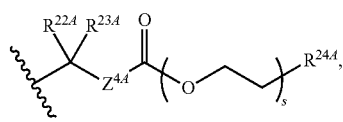

wherein s is 1, 2 or 3; or then at least one of $R^{6A}$ and $R^{7A}$ is

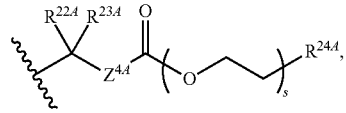

wherein s is 0 and $R^{24A}$ is an optionally substituted —O-heteroaryl or an optionally substituted —O-monocyclic heterocyclyl. In some embodiments, when $R^{2A}$ is an unsubstituted $C_{1-4}$ alkyl, an unsubstituted $C_{2-4}$ alkenyl, an unsubstituted $C_{2-4}$ alkynyl, —(CH$_2$)$_{1-6}$ halogen or —(CH$_2$)$_{1-6}$N$_3$; -- ------ are both absent; $Z^1$ is absent; $O^1$ is OR$^{1A}$; $R^{3A}$ is OH, —OC(=O)$R''^A$ or an optionally substituted O-linked amino acid; $R^{4A}$ is halogen; $R^{5A}$ is hydrogen or halogen; and $R^{1A}$ is

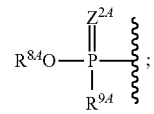

then $R^{8A}$ is

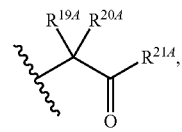

wherein $R^{21A}$ is independently selected from an optionally substituted —O-heteroaryl and an optionally substituted —O-monocyclic heterocyclyl; or then $R^{8A}$ is

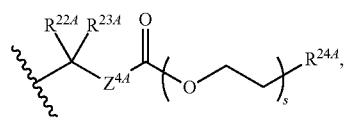

wherein s is 1, 2 or 3; or then $R^{8A}$ is

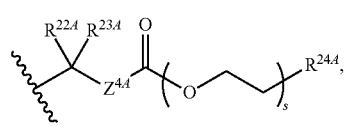

wherein s is 0 and $R^{24A}$ is an optionally substituted —O-heteroaryl, an optionally substituted —O-monocyclic heterocyclyl or

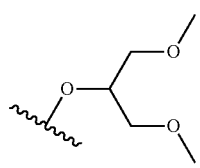

In some embodiments, when ------- are bot absent; $Z^1$ is absent; $O^1$ is OH; $R^{2A}$ is methyl; $R^{3A}$ is OH; then $R^{4A}$ is halogen, —OC(=O)R'''$^B$ or an optionally substituted O-linked amino acid. In some embodiments, when ------- are both absent; $Z^1$ is absent; $O^1$ is $OR^{1A}$; $R^{2A}$ is halogen (for example, F); $R^{3A}$ is OH or —OC(=O)R'''$^A$; $R^{4A}$ is halogen (for example, F); and $R^{5A}$ is methyl, ethyl or ethenyl; then $R^{1A}$ cannot be selected from hydrogen,

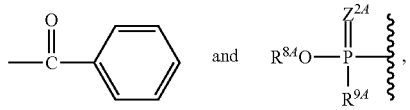

wherein $R^{8A}$ is an unsubstituted aryl; $R^{9A}$ is

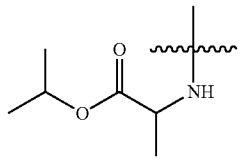 [SMILES: *NC(C)C(=O)OC(C)C]

and $Z^{2A}$ is oxygen. In some embodiments, $R^{1A}$ is not hydrogen (H), for example, when $R^{3A}$ is halo (such as fluoro) and $R^{4A}$ is OH. In some embodiments, $R^{1A}$ is not

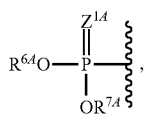

wherein $Z^{1A}$ is O and $R^{6A}$ is

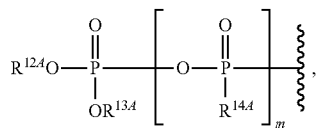

for example, when $R^{4A}$ is halo (such as fluoro) and $R^{3A}$ is OH. In some embodiments, $R^{2A}$ is not hydrogen (H). In some embodiments, $R^{2A}$ is not halogen. In some embodiments, $R^{2A}$ is not fluoro (F). In some embodiments, $R^{2A}$ is not —CN. In some embodiments, $R^{2A}$ is not —CHF$_2$. In some embodiments, $R^{2A}$ is not —CF$_3$. In some embodiments, $R^{5A}$ is not hydrogen or halo. In some embodiments, $R^{5A}$ is not —OH. In some embodiments, $R^{4A}$ is not hydrogen (H). In some embodiments, $R^{4A}$ is not halo. In some embodiments, $R^{4A}$ is not fluoro (F). In some embodiments, $R^{4A}$ is not chloro (Cl). In some embodiments, $R^{2A}$ is not an unsubstituted $C_{1-4}$ alkyl. In some embodiments, $R^{2A}$ is not an unsubstituted $C_{2-4}$ alkenyl. In some embodiments, $R^{2A}$ is not an unsubstituted $C_{2-4}$ alkynyl. In some embodiments, $R^{2A}$ is not —(CH$_2$)$_{1-6}$ halogen. In some embodiments, $R^{2A}$ is not —(CH$_2$)$_{1-6}$N$_3$. In some embodiments, $R^{4A}$ is not hydrogen, when $R^{5A}$ is fluoro. In some embodiments, $R^{6A}$ is not an optionally substituted aryl. In some embodiments, $R^{6A}$ is not an unsubstituted aryl. In some embodiments, $R^{9A}$ is not N-alanine isopropyl ester. In some embodiments, $R^{5A}$ is not an optionally substituted $C_{1-6}$ alkyl. For example, $R^{5A}$ is not an unsubstituted $C_{1-6}$ alkyl, such as methyl. In some embodiments, $B^{1A}$ is not an optionally substituted uracil, for example, a halo-substituted uracil. In some embodiments, when $R^{1A}$ is hydrogen, an optionally substituted acyl,

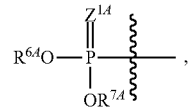

wherein $R^{6A}$ can be

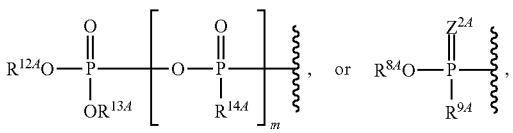

wherein $R^{8A}$ is an unsubstituted or substituted phenyl or an unsubstituted or substituted naphthyl and $R^{9A}$ is an optionally substituted N-linked amino acid or an optionally substituted N-linked amino acid ester; $R^{2A}$ is fluoro, $R^{3A}$ is OH or —C(=O)-unsubstituted or substituted phenyl; $R^{4A}$ is fluoro; and $R^{5A}$ is a $C_{1-4}$ alkyl (such as methyl); then $B^{1A}$ cannot be an optionally substituted pyrimidine base, such as

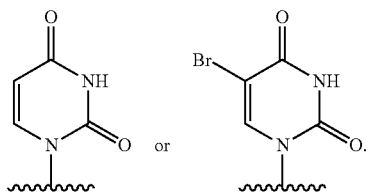 [SMILES: *n1ccc(=O)[nH]c1=O ; "or" ; *n1cc(Br)c(=O)[nH]c1=O]

In some embodiments, when $R^{1A}$ is

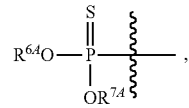

$R^{2A}$ is hydrogen, $R^{3A}$ is OH and $R^{4A}$ is OH or halogen (such as F), then $R^{5A}$ is not an optionally substituted $C_{1-6}$ alkyl, an optionally substituted $C_{2-6}$ alkenyl or an optionally substituted $C_{2-6}$ alkynyl. In some embodiments, a compound of Formulae (I) and/or (II), or a pharmaceutically acceptable salt of the foregoing, is not a compound in WO 2013/092481 (filed Dec. 17, 2012), U.S. 2014/0178338 (filed Dec. 17, 2013), U.S. 2013/0164261 (filed Dec. 20, 2012), WO 2014/100505 (filed Dec. 19, 2013), WO 2013/096679 (filed Dec. 20, 2012), WO 2013/142525 (filed Mar. 19, 2013), WO 2014/209983 (filed Jun. 24, 2014), WO 2014/209979 (filed Jun. 24, 2014) and/or U.S. 2015/0105341 (filed Oct. 9, 2014), or a pharmaceutically acceptable salt of the foregoing.

Examples of compounds of Formula (I), or a pharmaceutically acceptable salt thereof, include, but are not limited to:

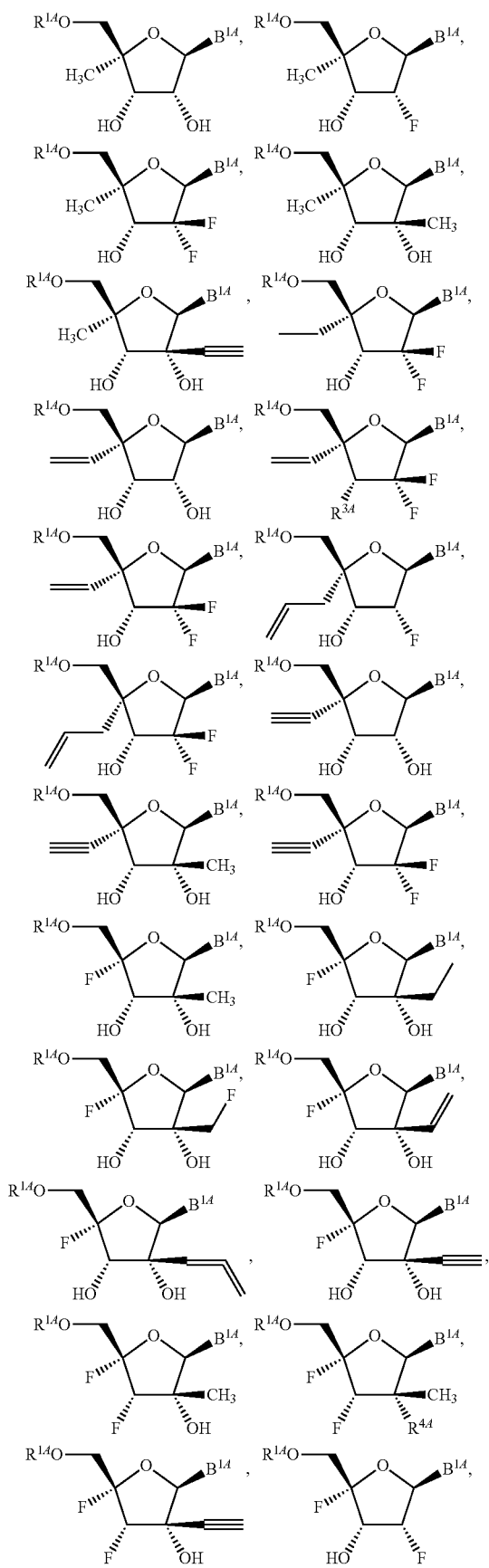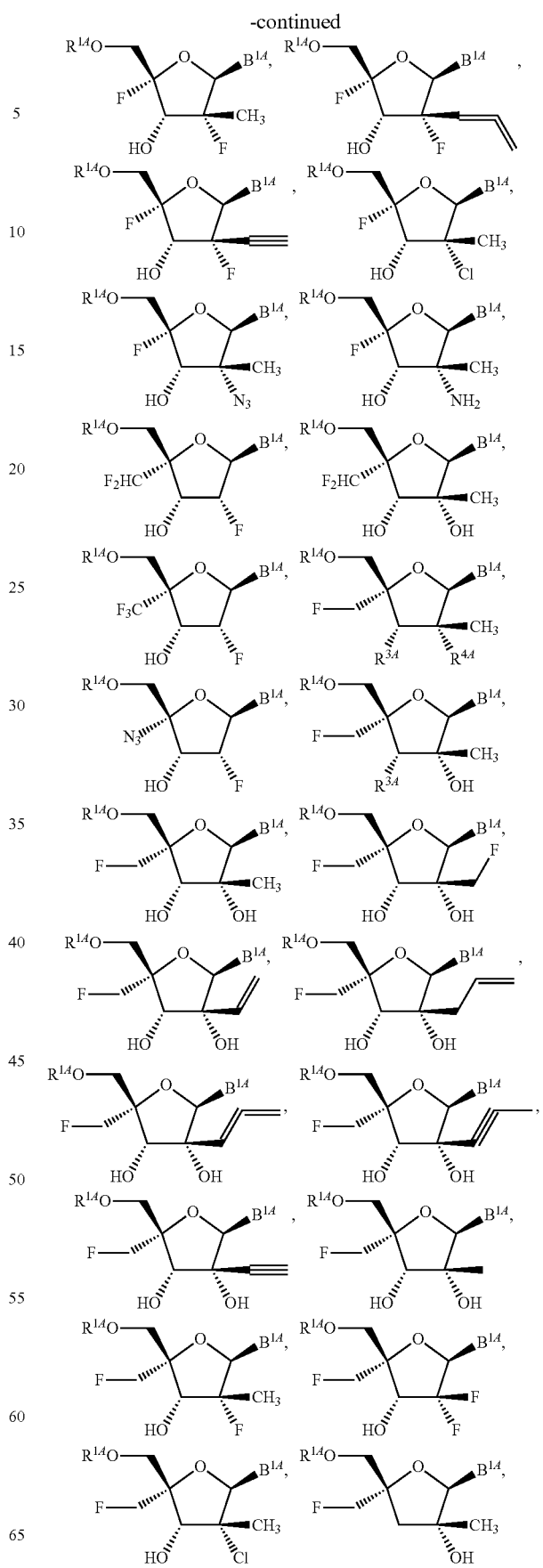

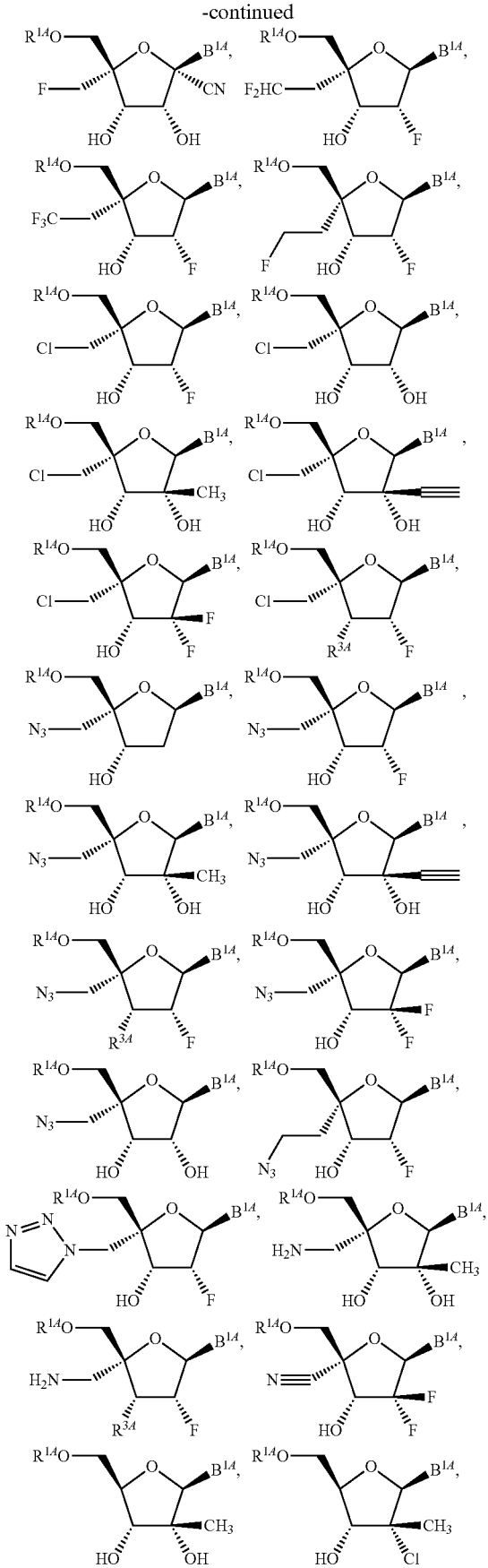
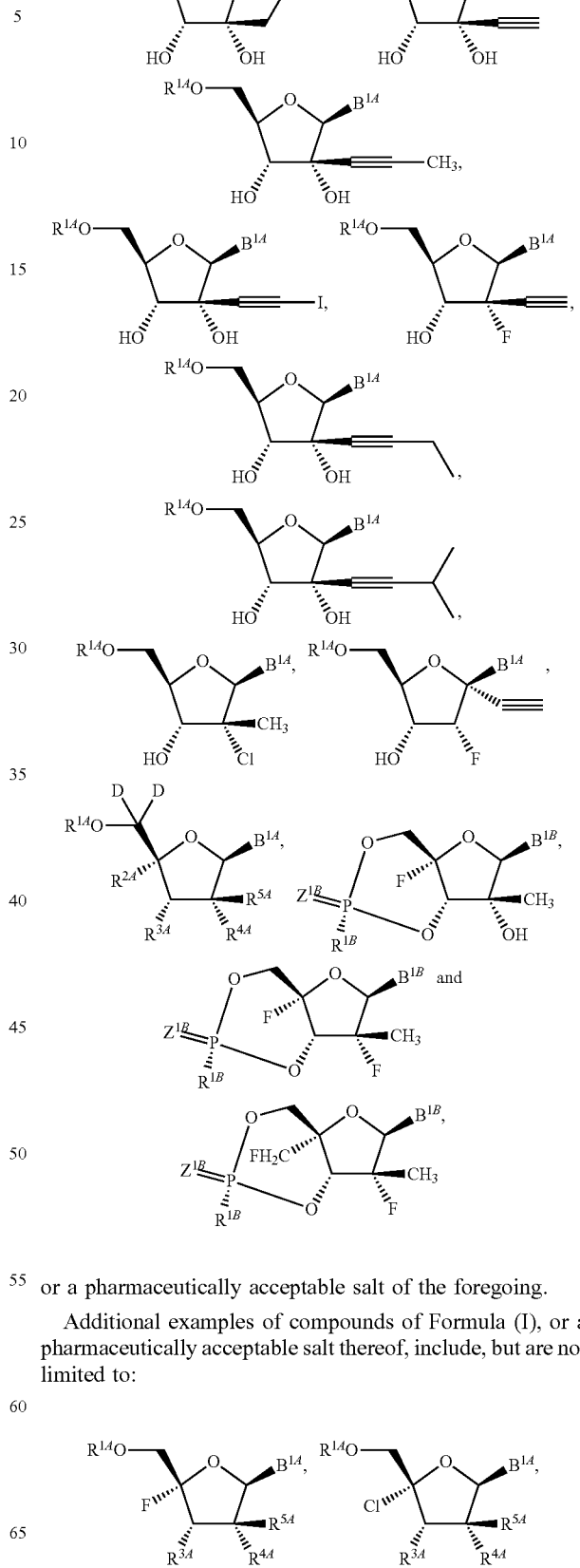
or a pharmaceutically acceptable salt of the foregoing.
Additional examples of compounds of Formula (I), or a pharmaceutically acceptable salt thereof, include, but are not limited to:

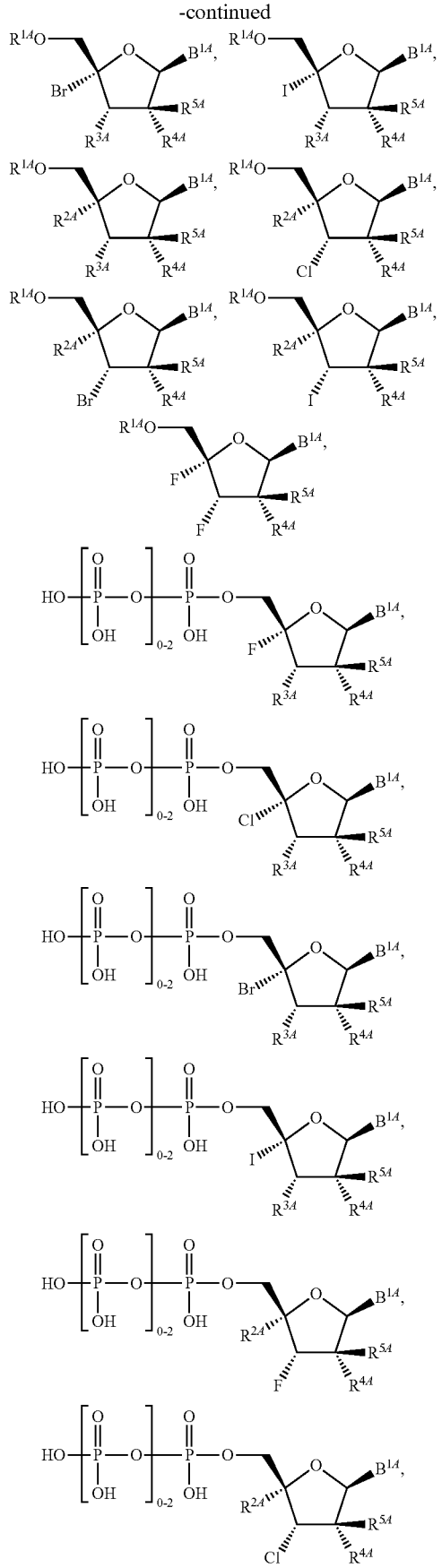
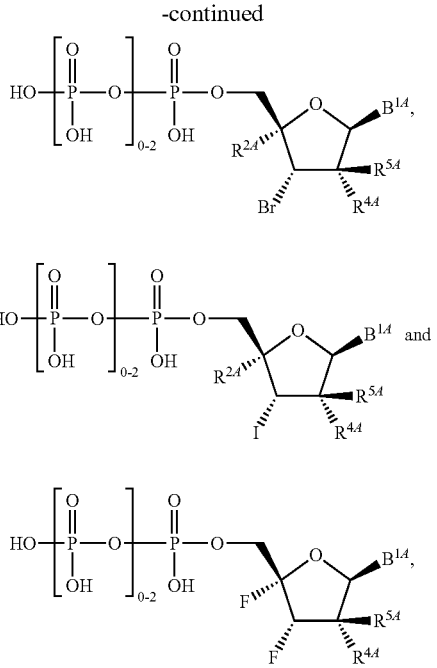
or a pharmaceutically acceptable salt of the foregoing.
In some embodiments, a compound of Formula (I), or a pharmaceutically acceptable salt thereof, may be selected from:
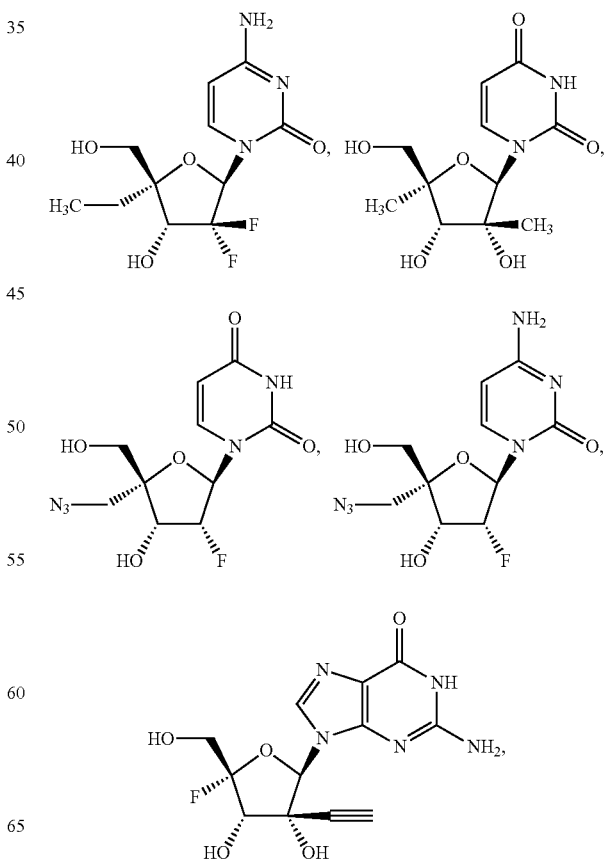

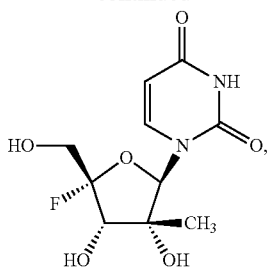
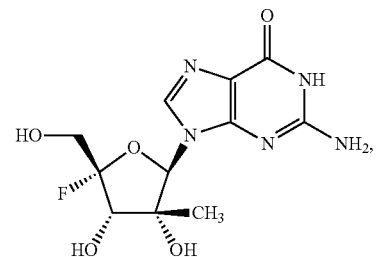
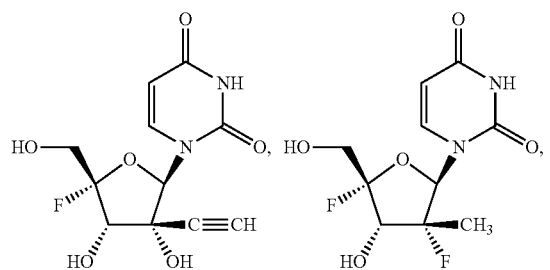
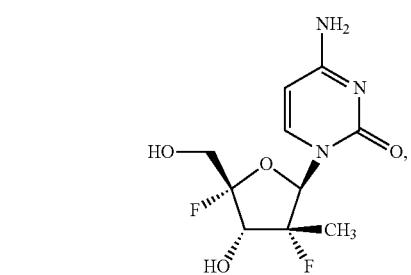
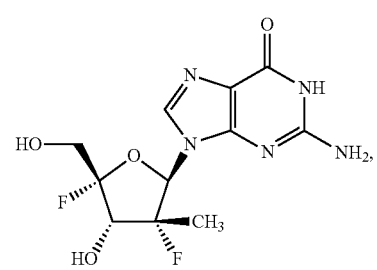
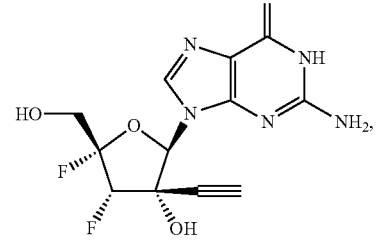
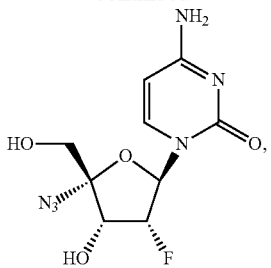
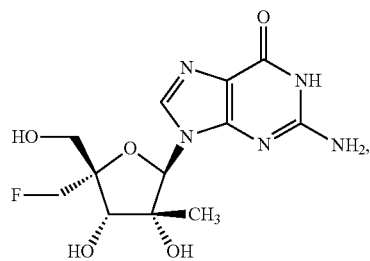
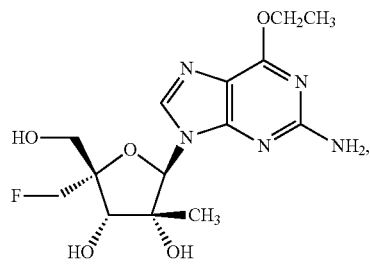
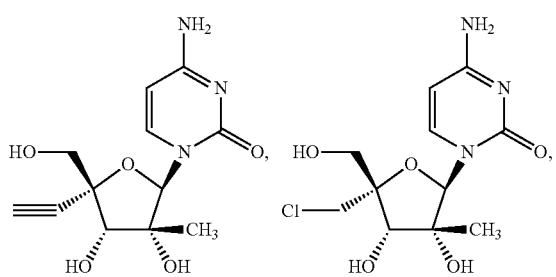
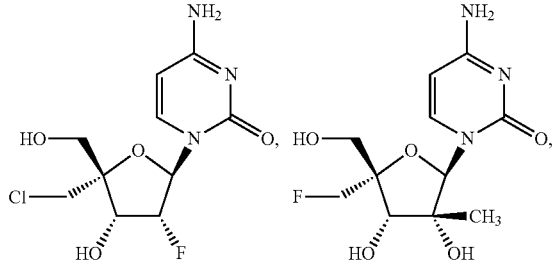
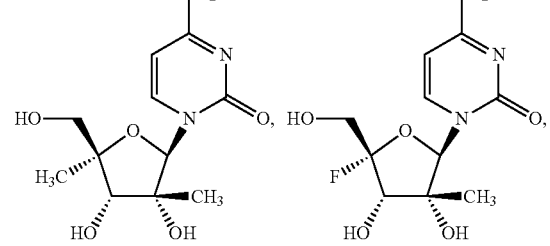

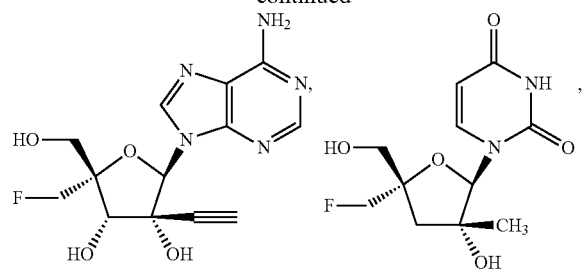
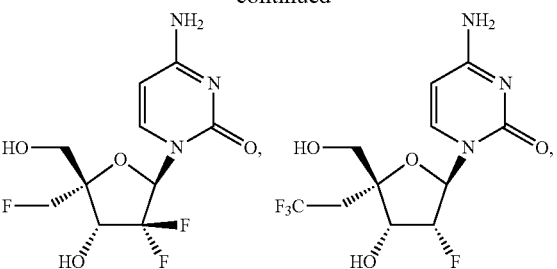
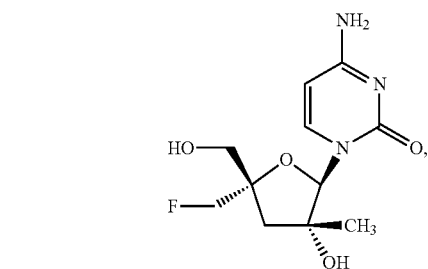
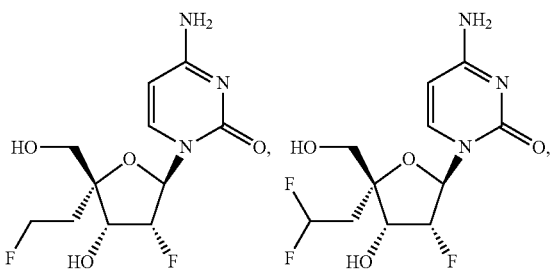
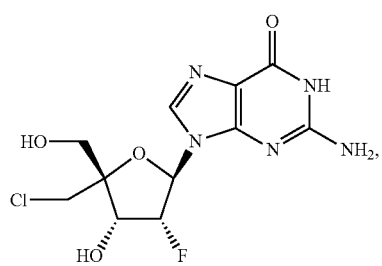
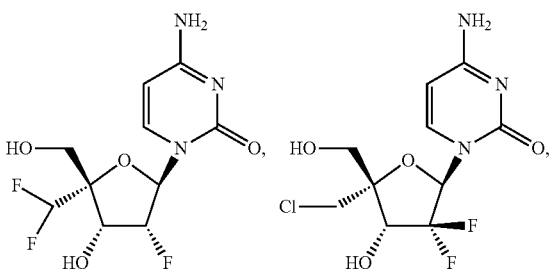
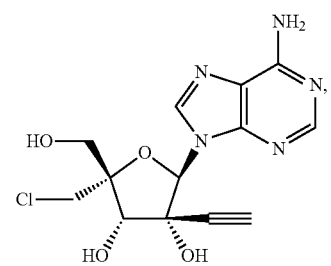
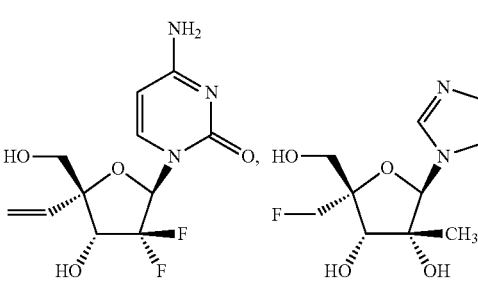
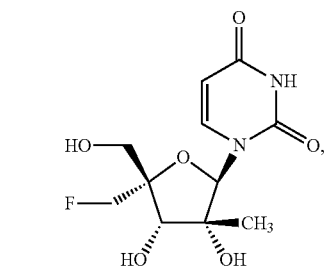
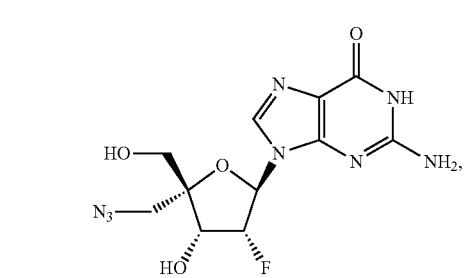
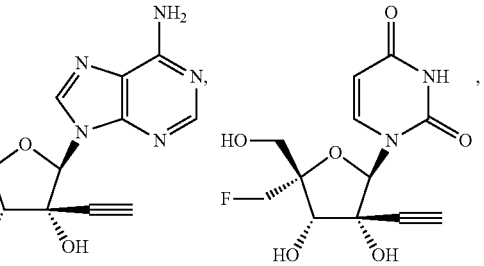
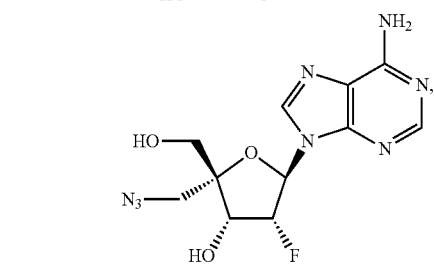

69
-continued
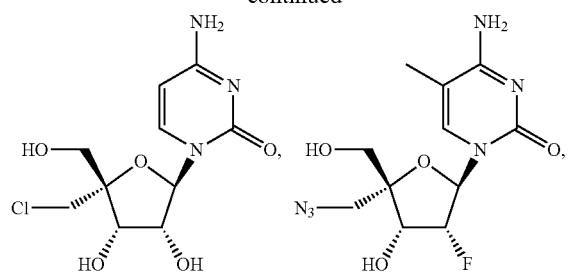
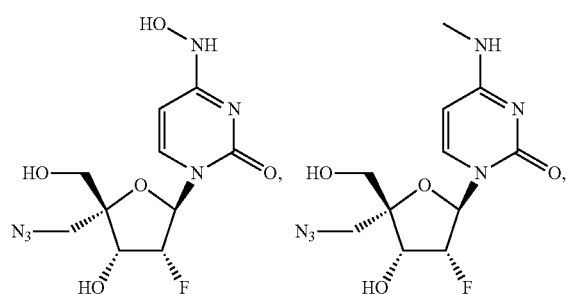
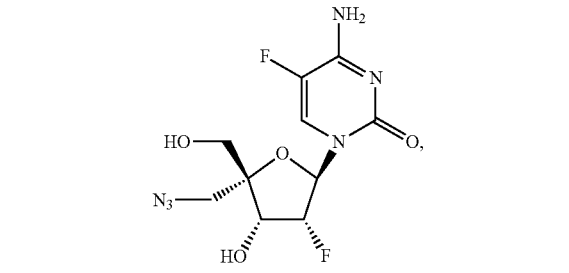
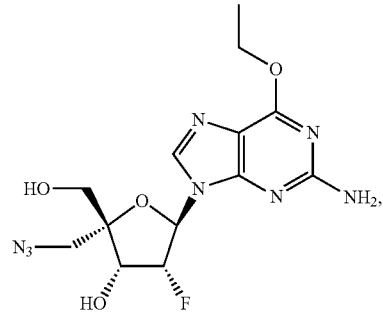
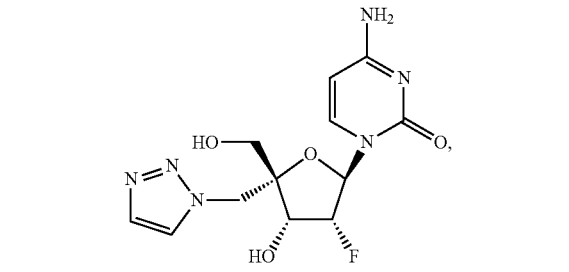
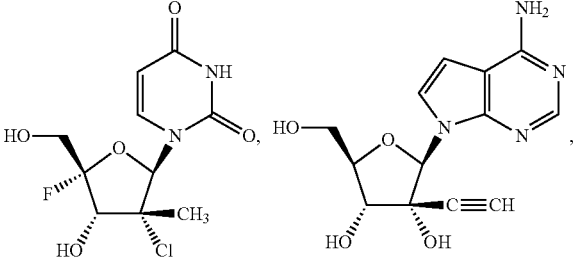
70
-continued
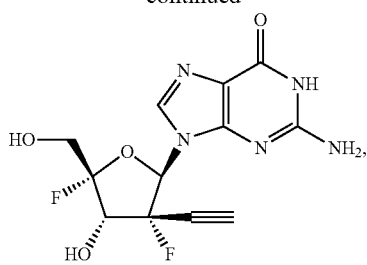
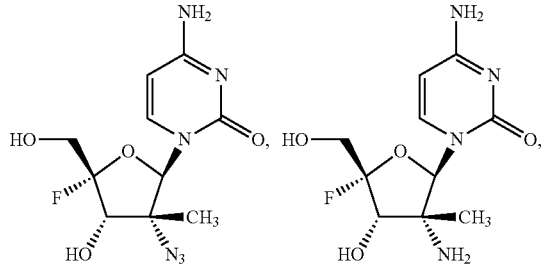
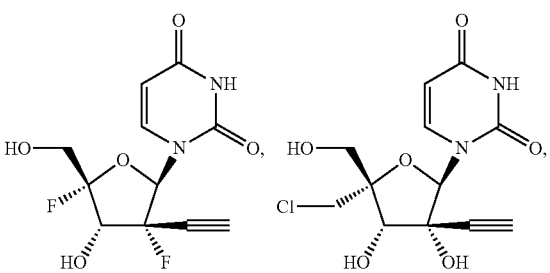
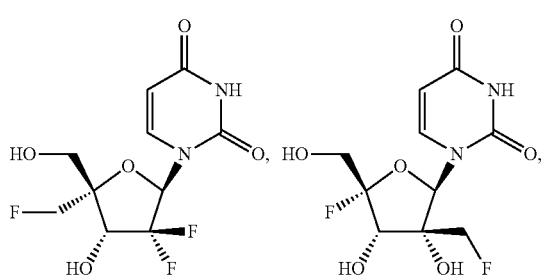
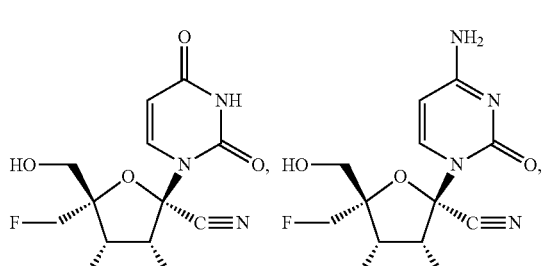
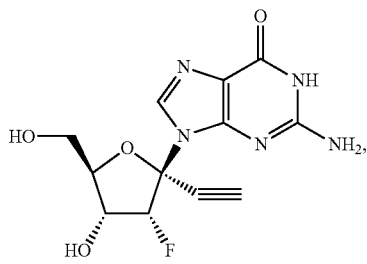

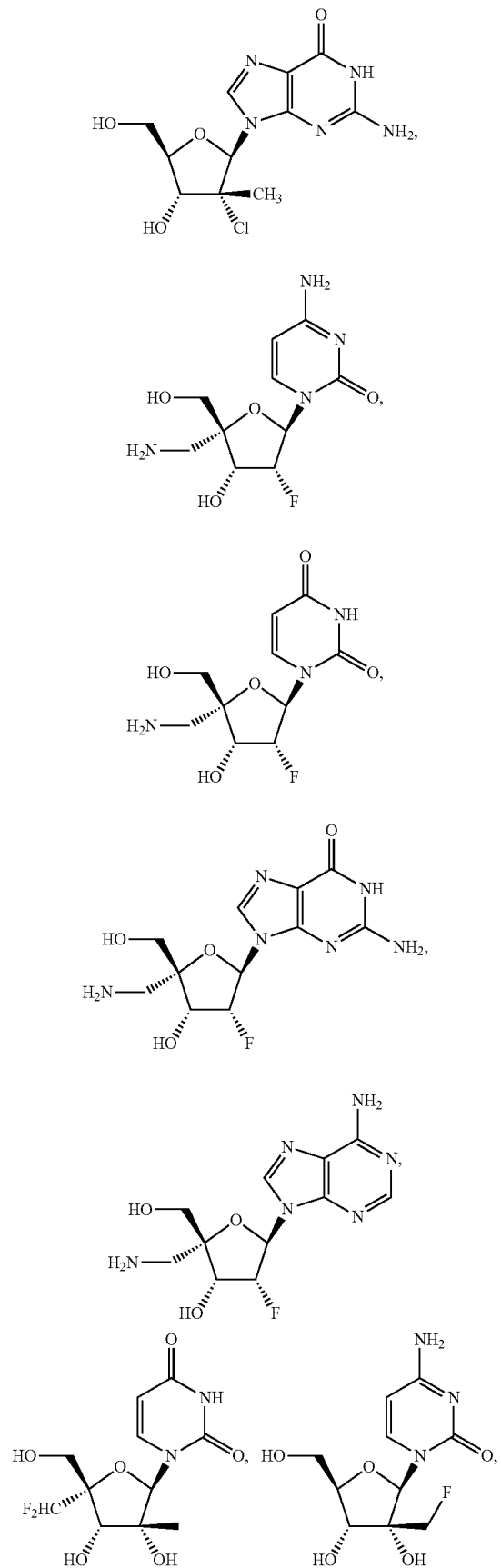
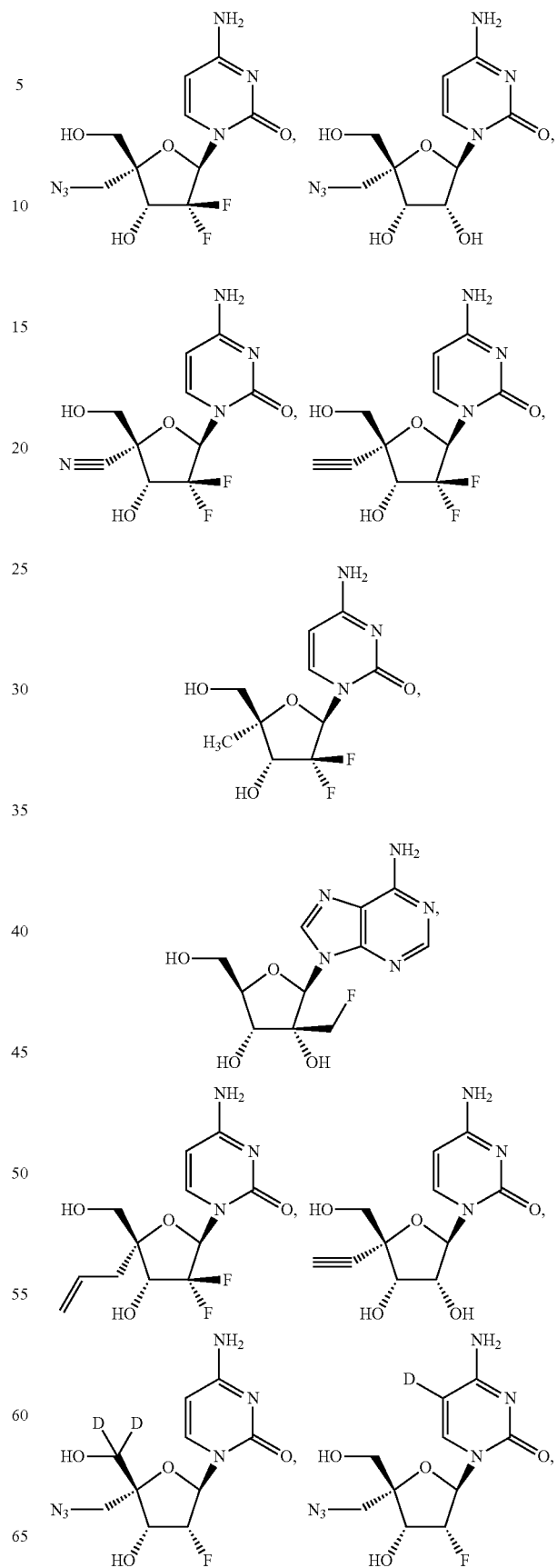

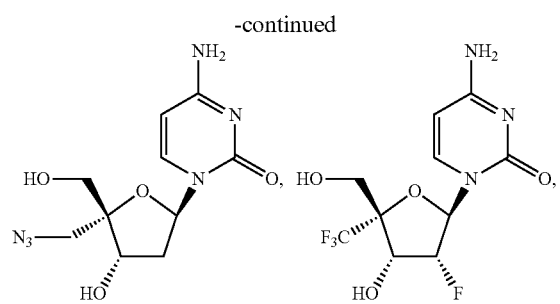
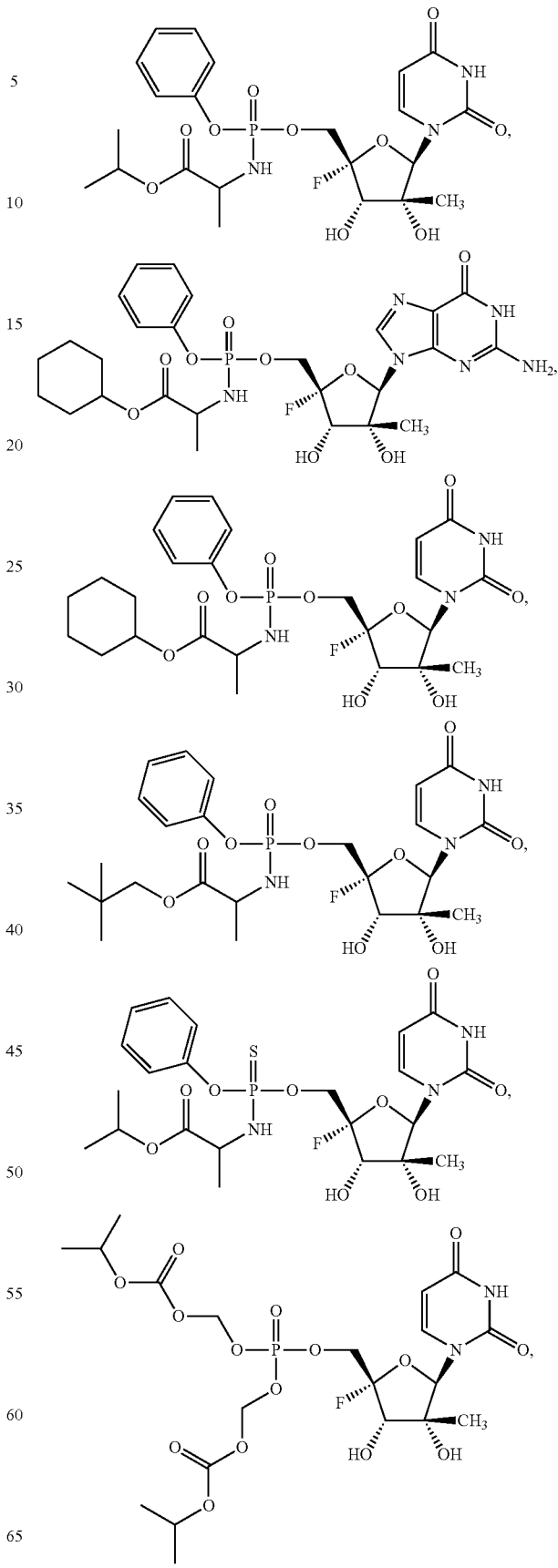
or a pharmaceutically acceptable salt of the foregoing.
In some embodiments, a compound of Formula (I), or a pharmaceutically acceptable salt thereof, may be selected from:

75
-continued
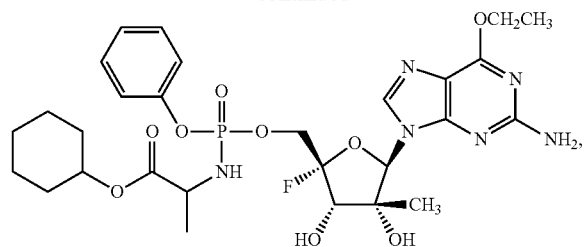
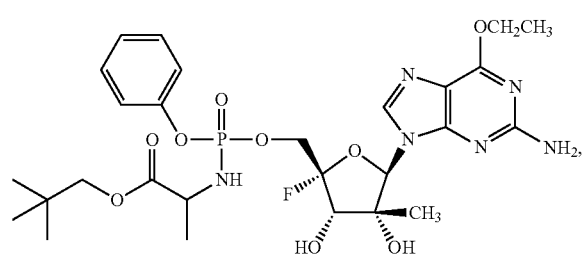
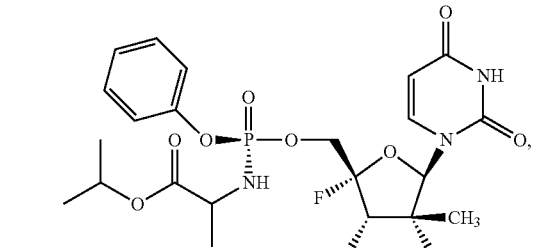
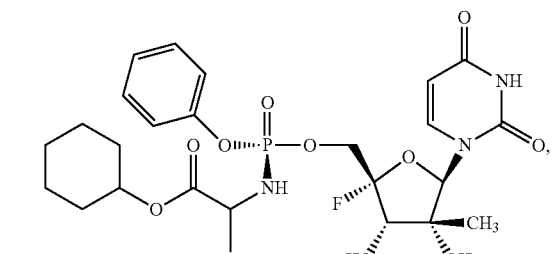
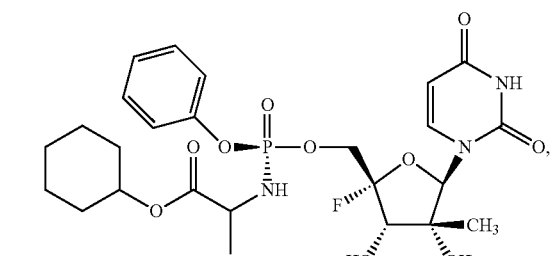
76
-continued
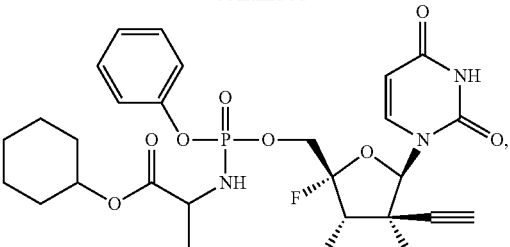
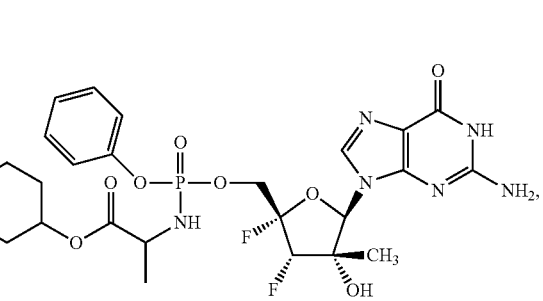
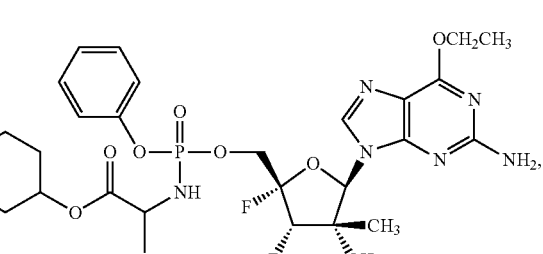
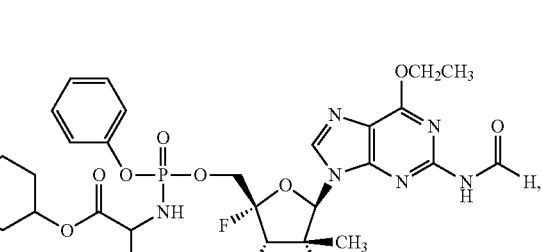
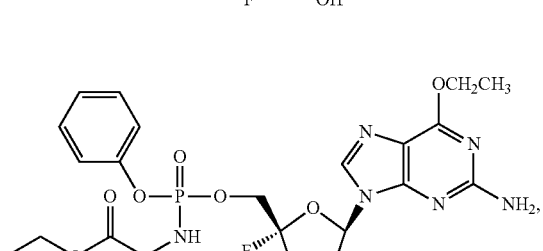

77
-continued
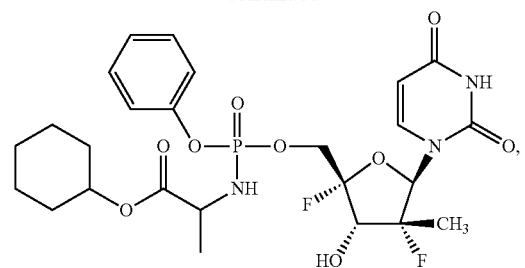
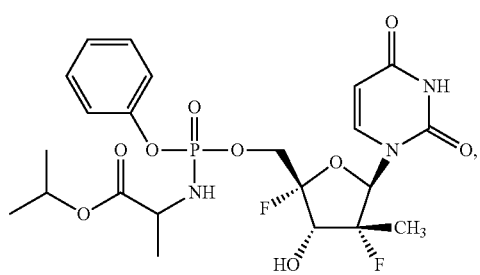
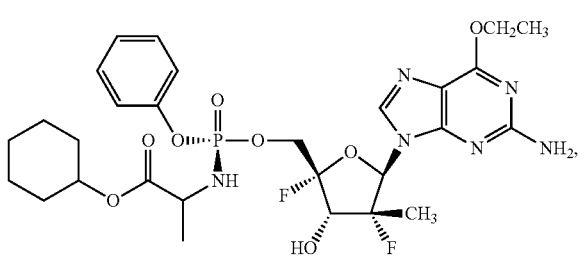
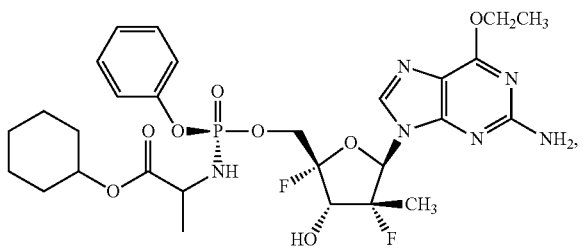
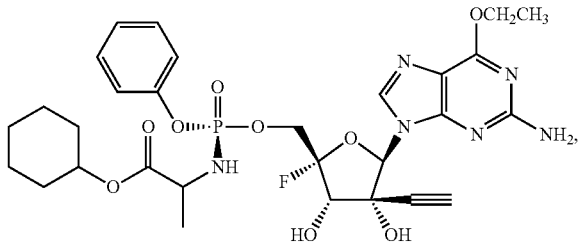
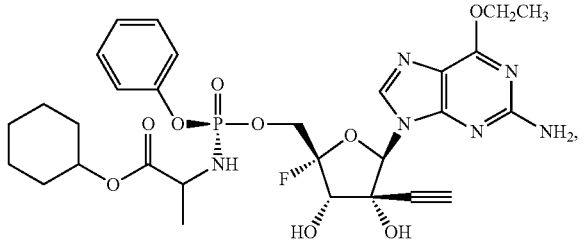
78
-continued
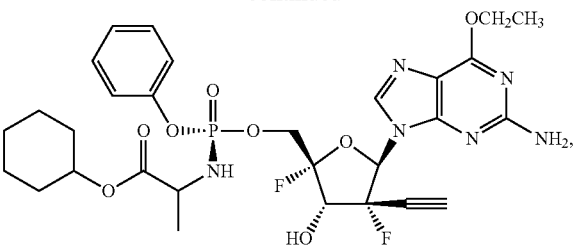
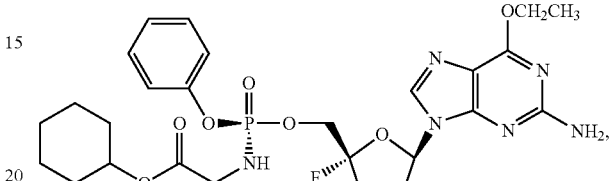
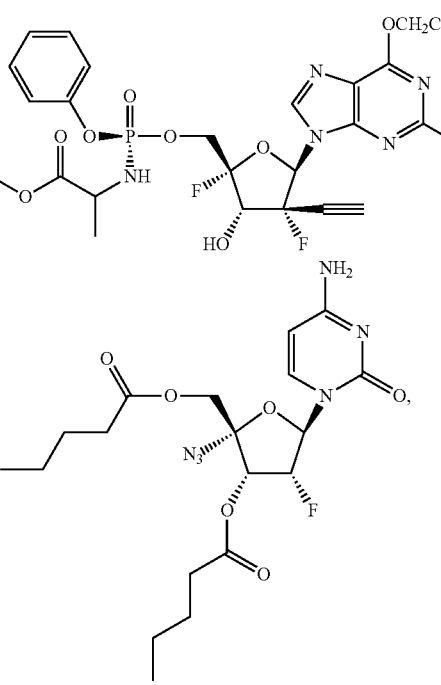
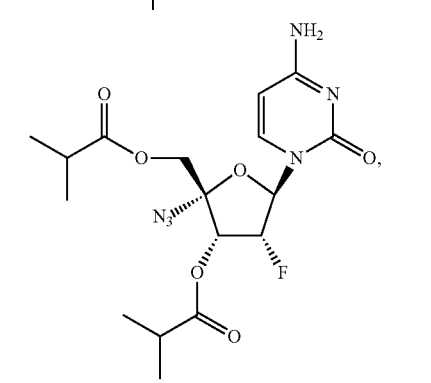
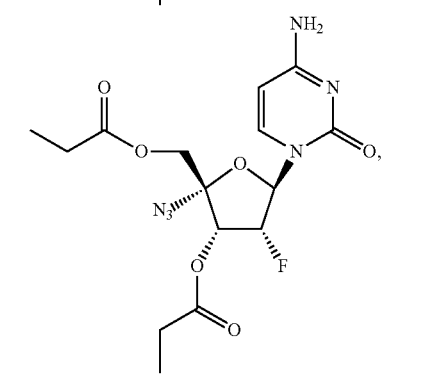

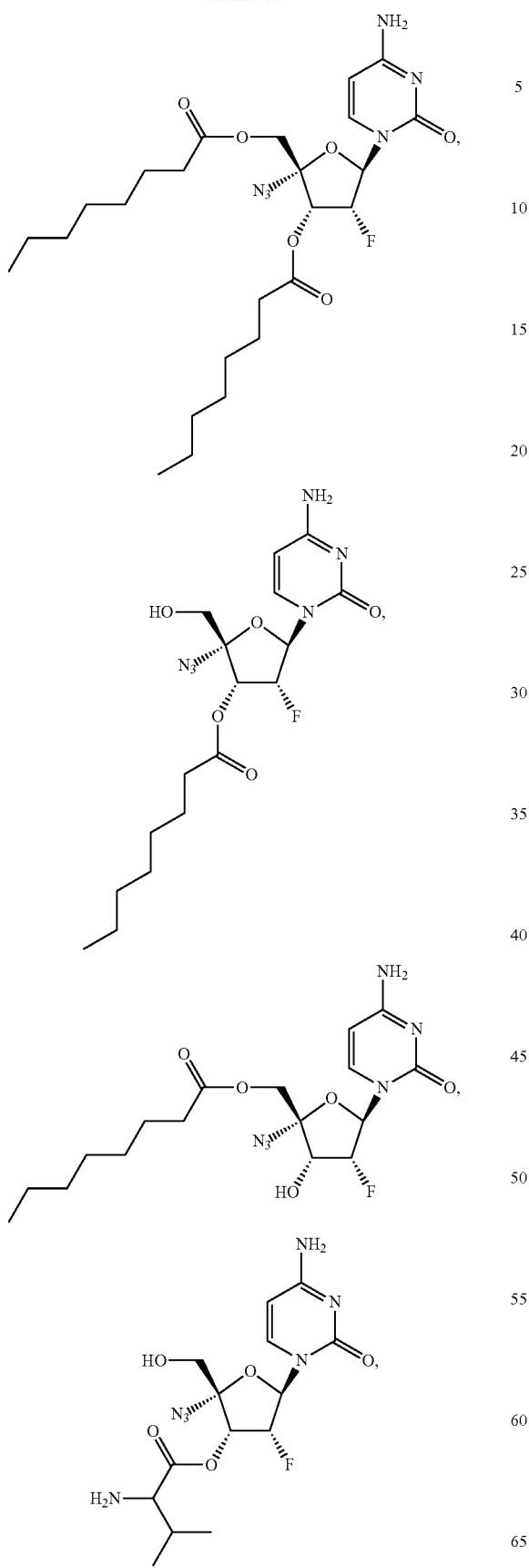
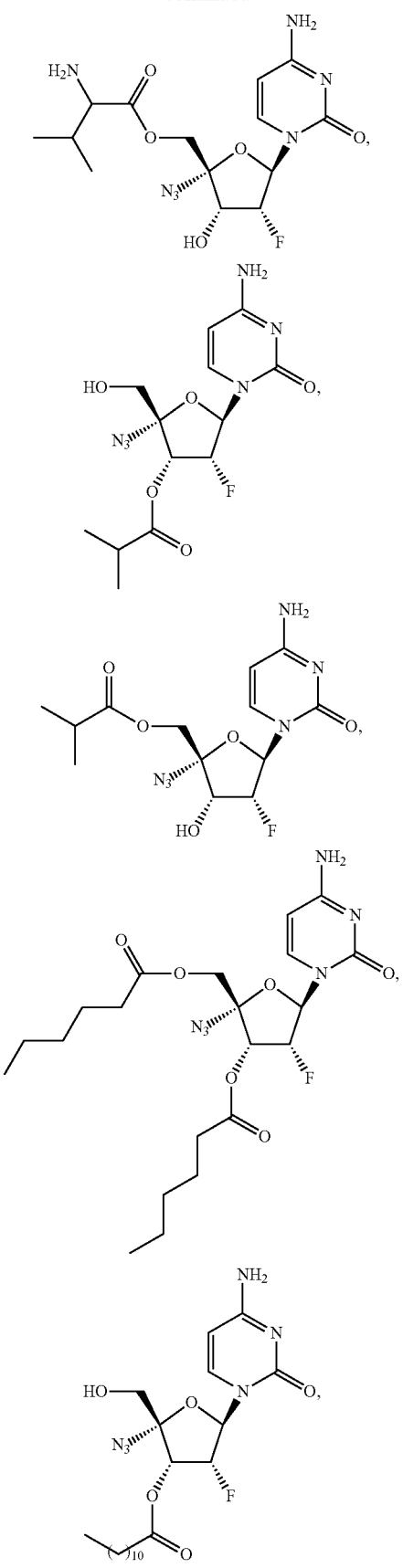

81
-continued
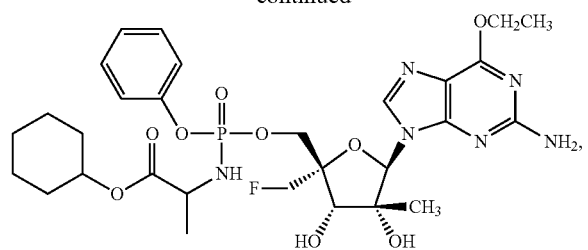
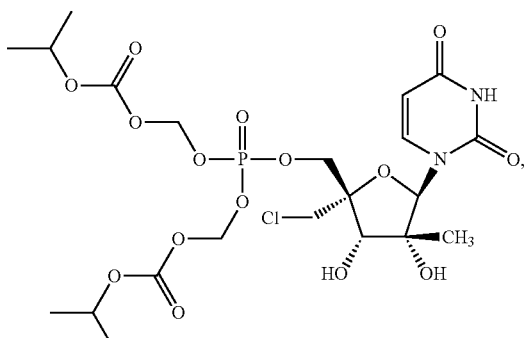
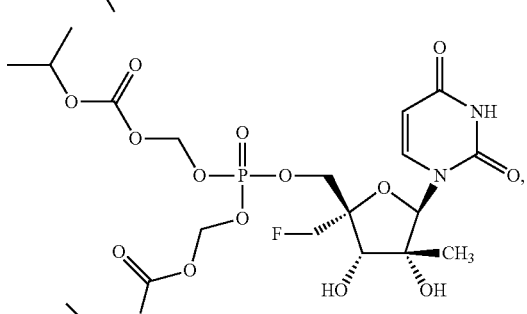
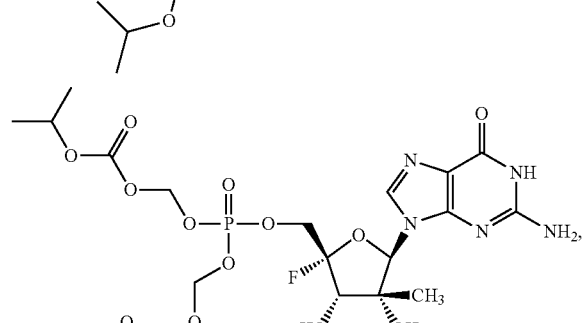
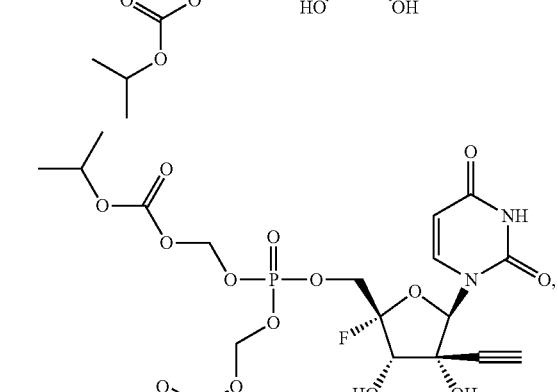
82
-continued
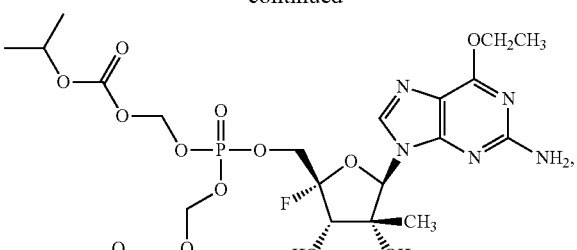
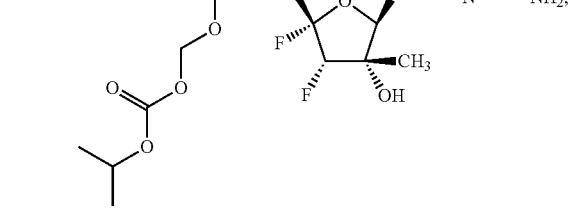
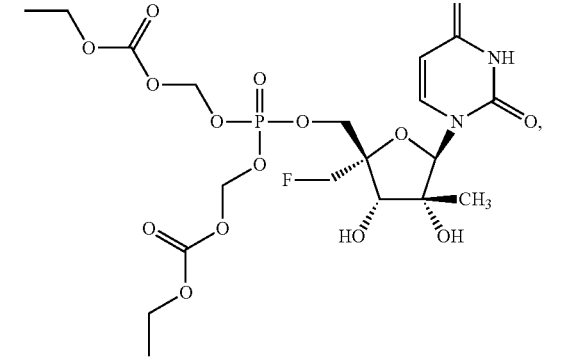
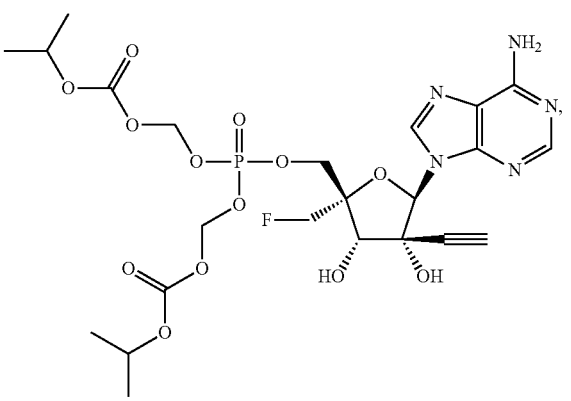

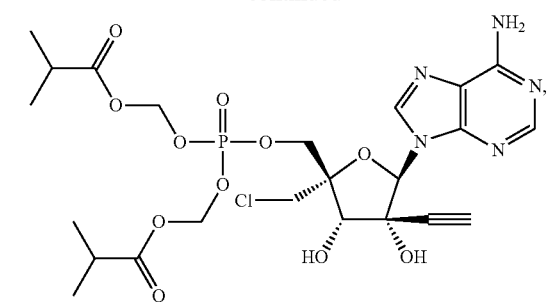
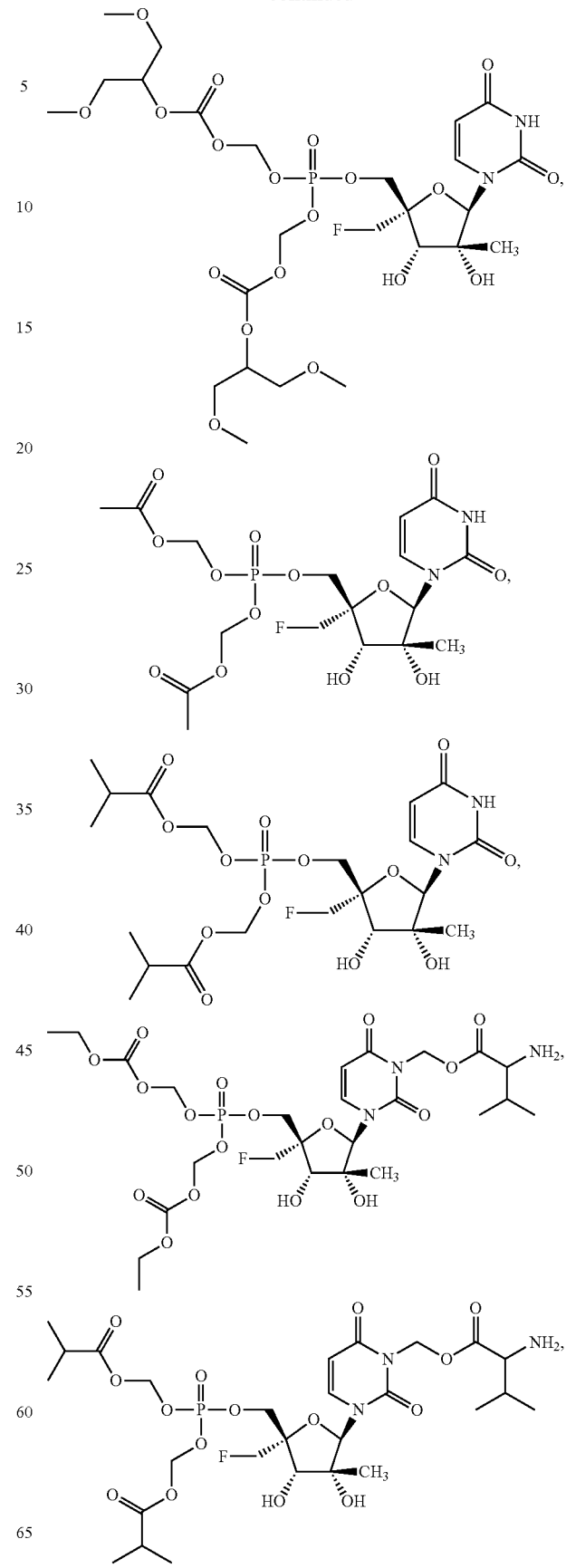

85
-continued
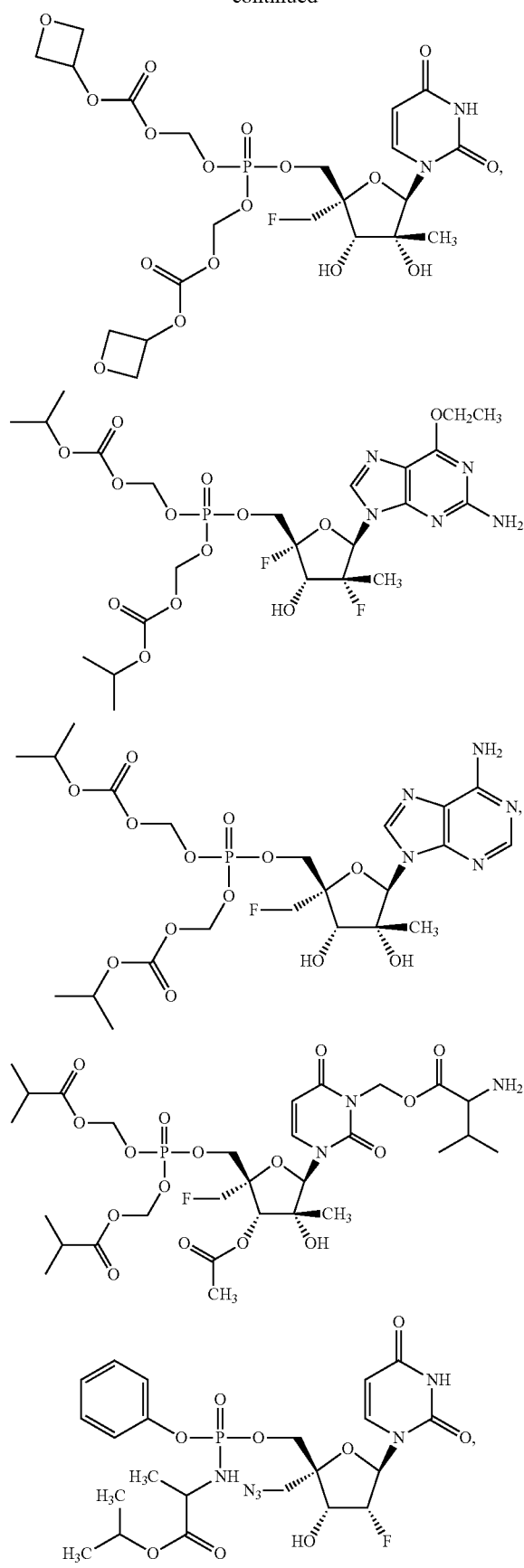
86
-continued
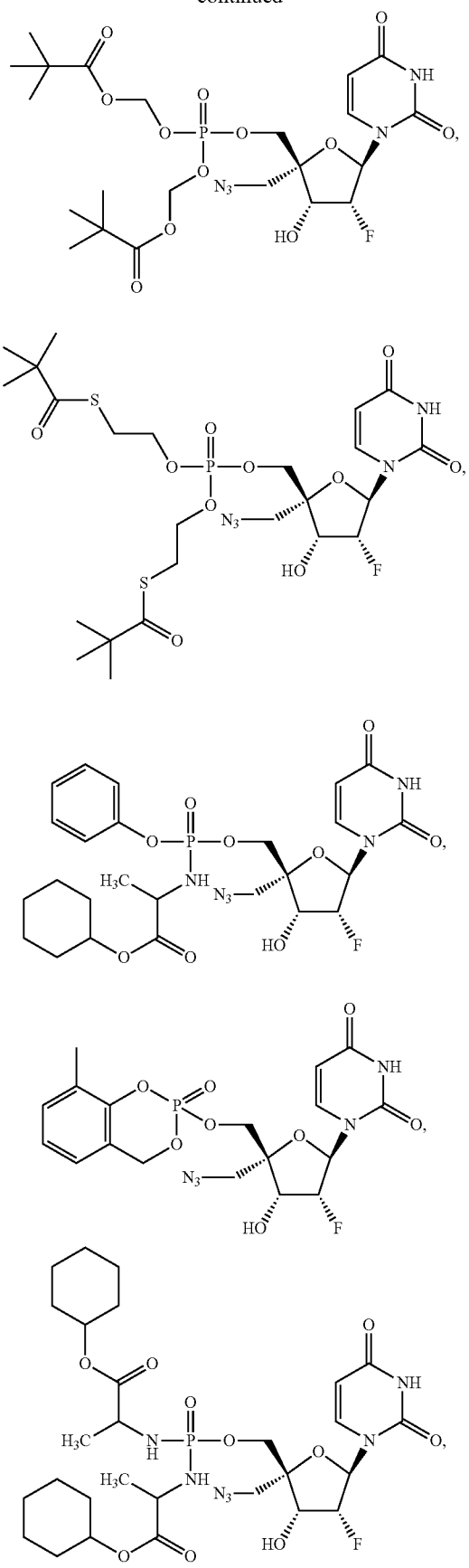

87
-continued
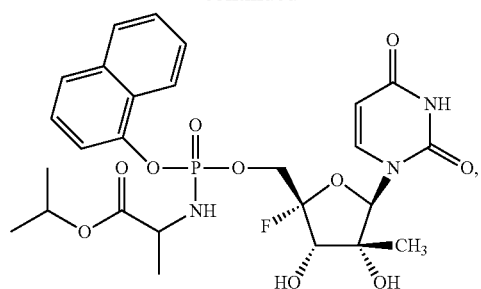
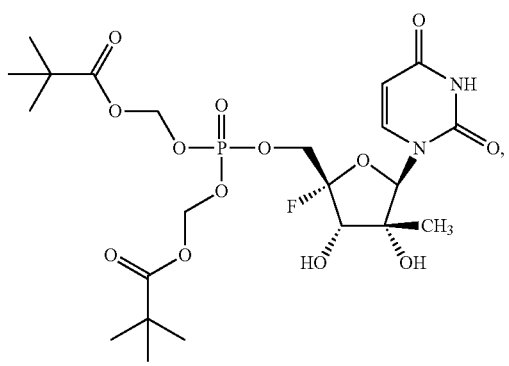
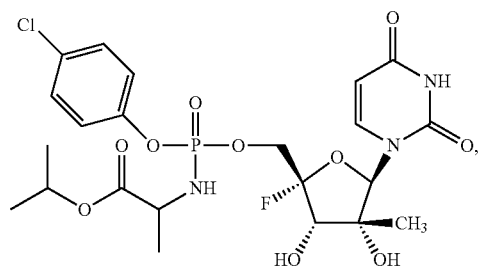
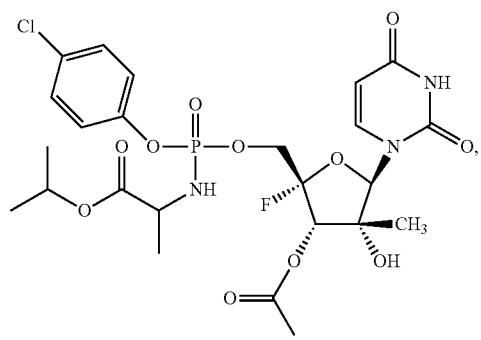
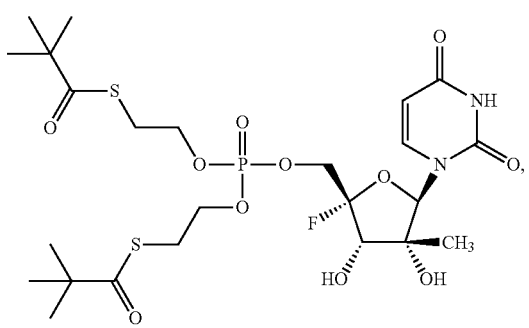
88
-continued
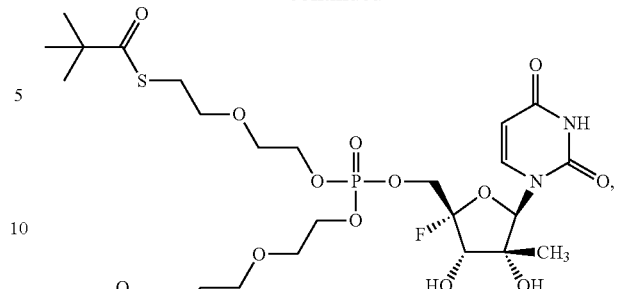
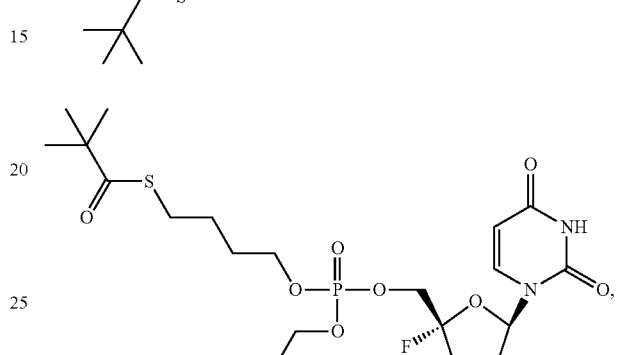
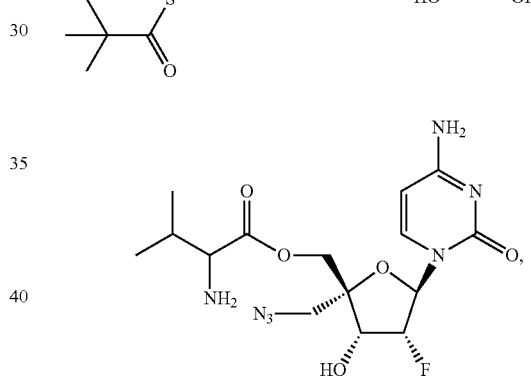
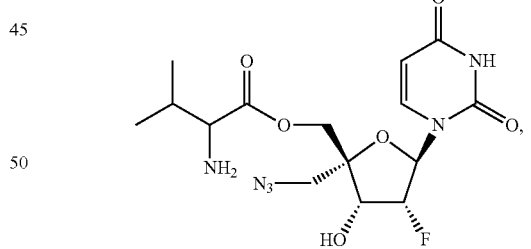
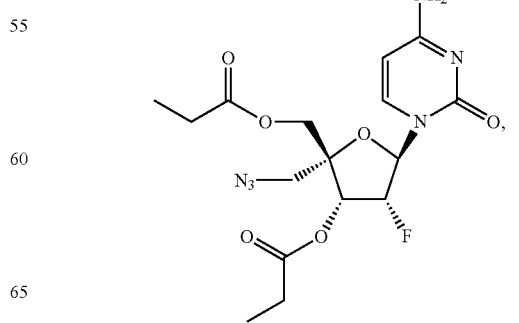

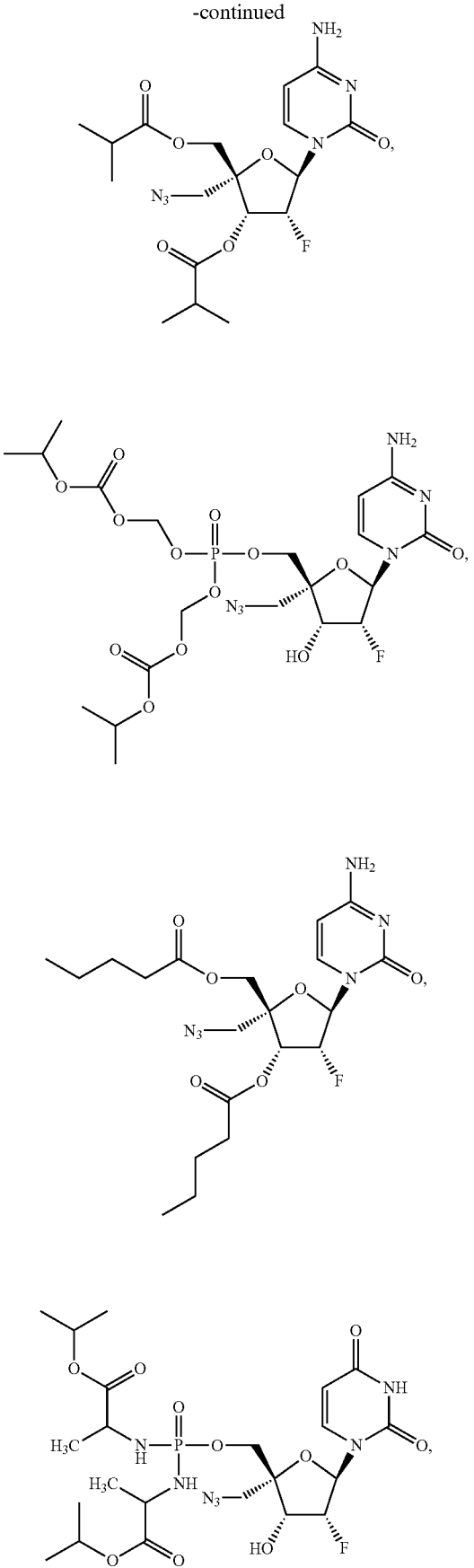
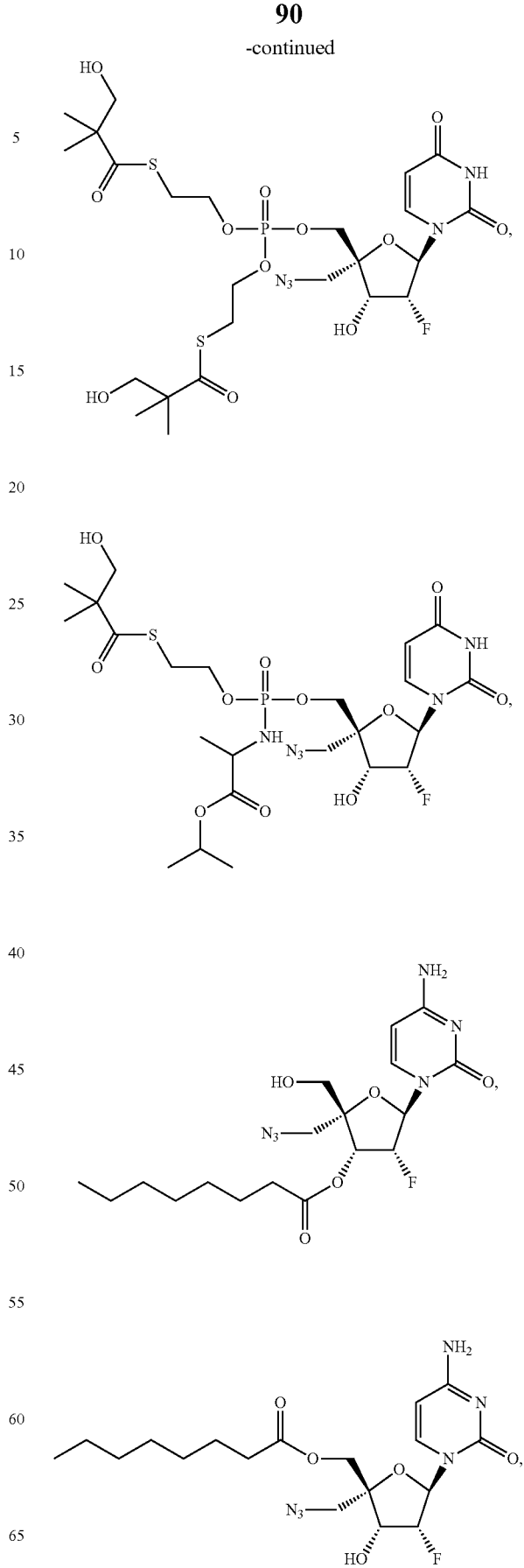

91
-continued
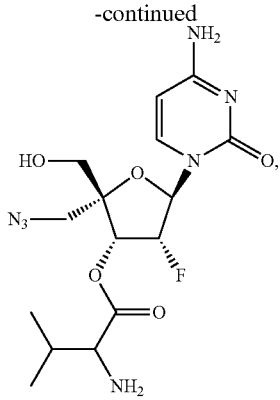
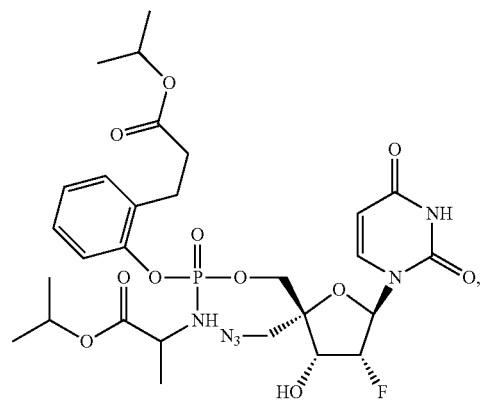
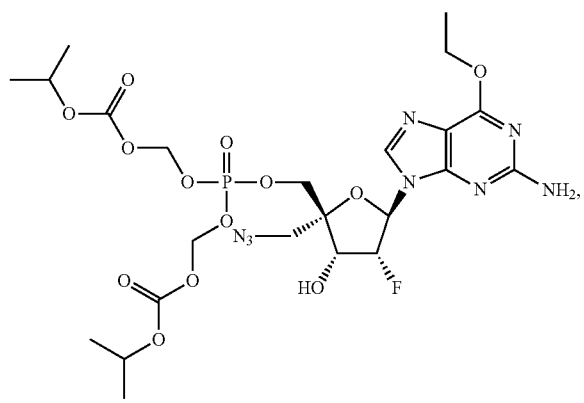
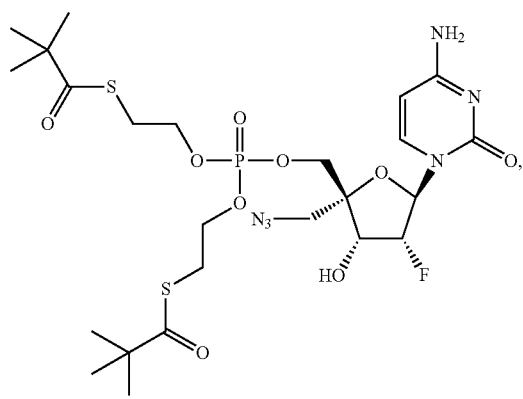
92
-continued
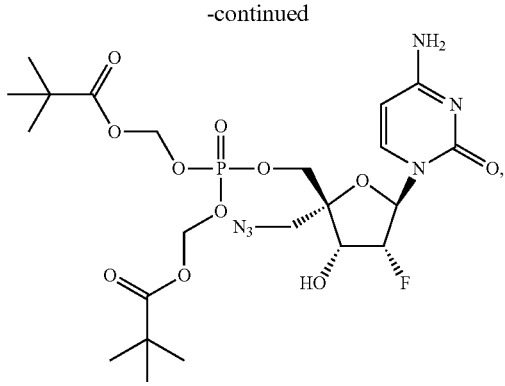
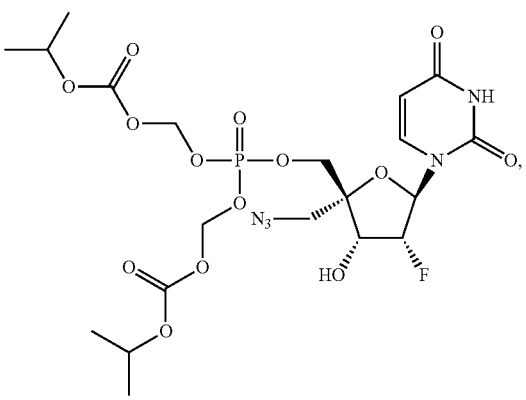
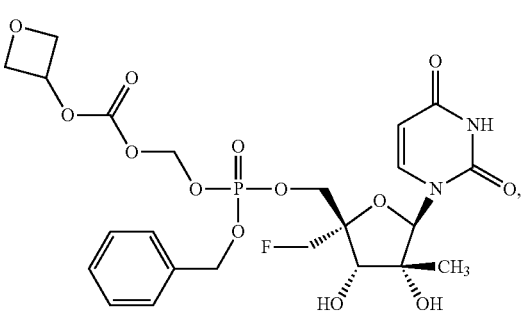
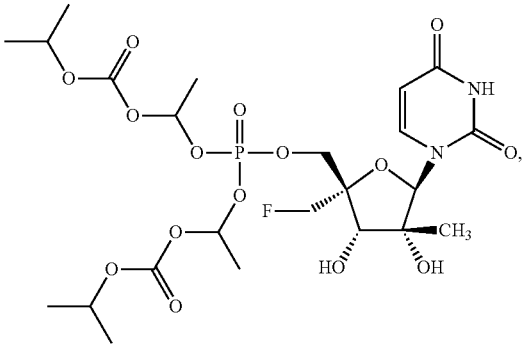

93
-continued
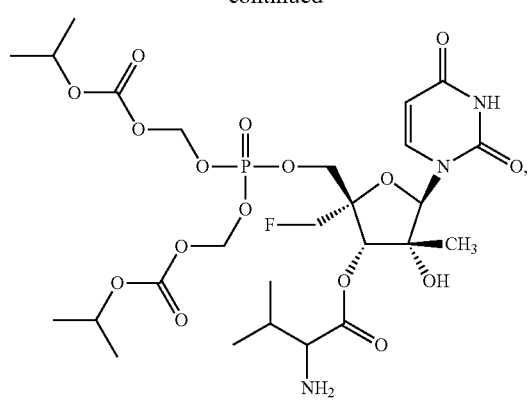
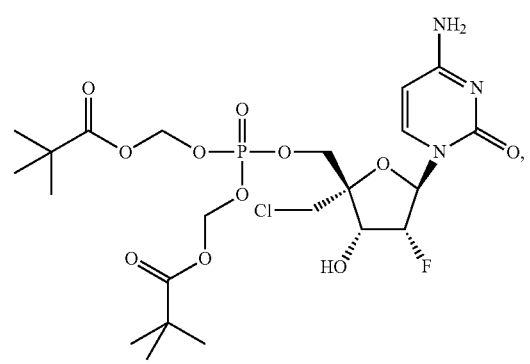
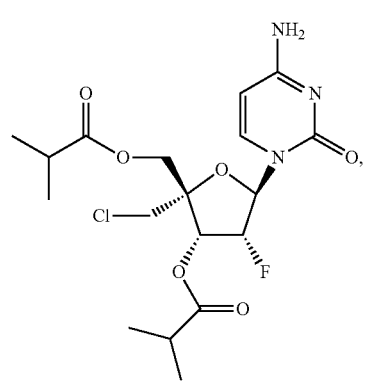
94
-continued
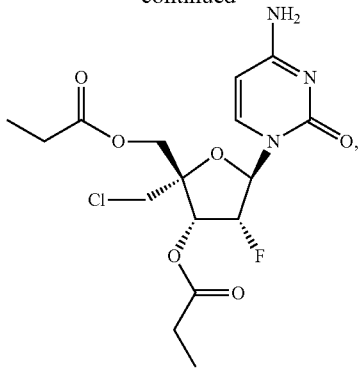
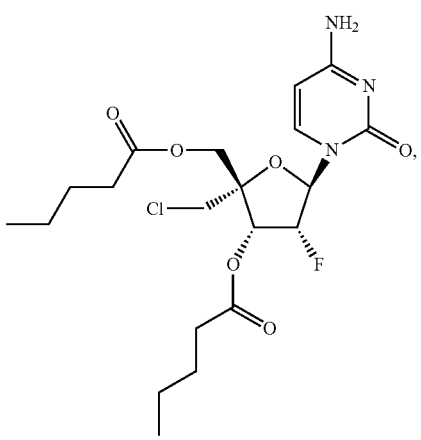
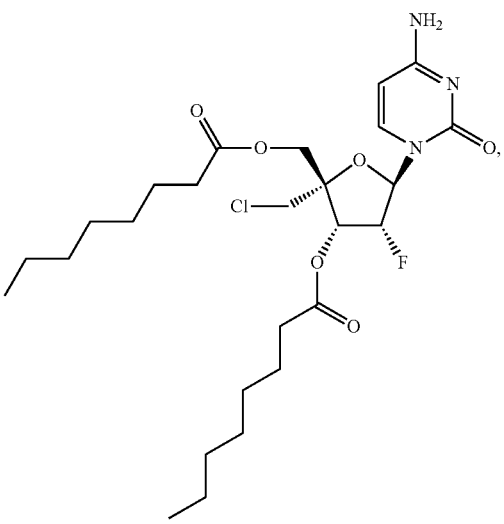

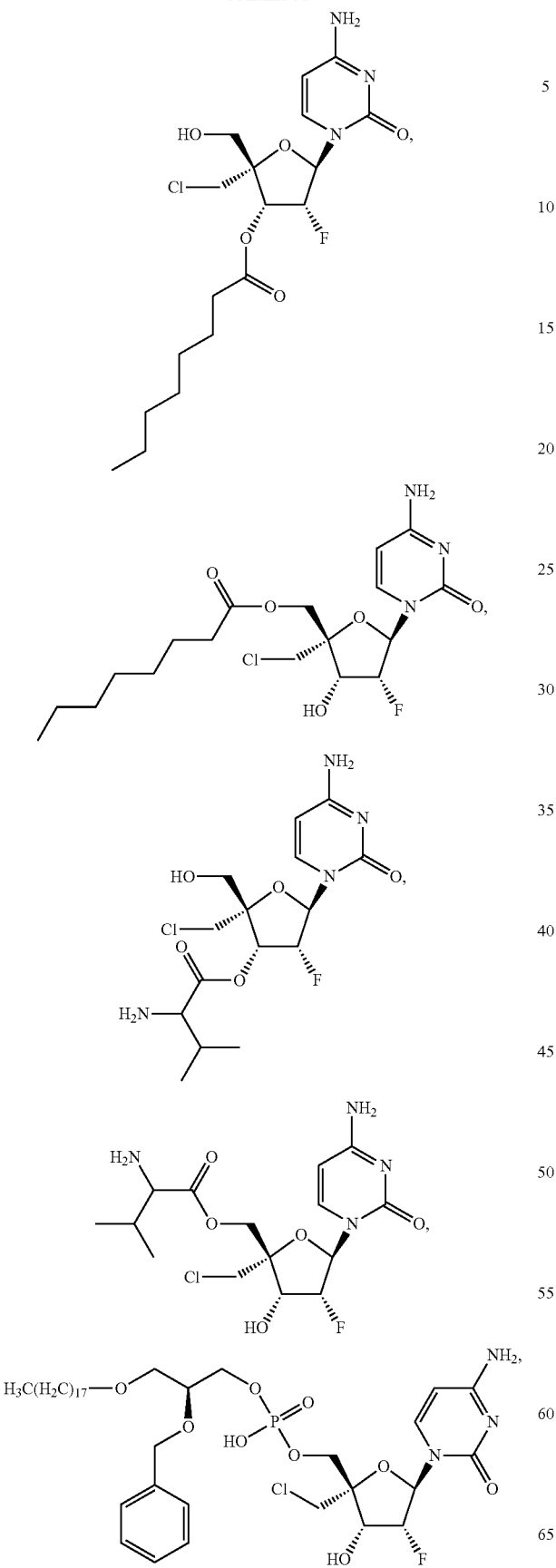
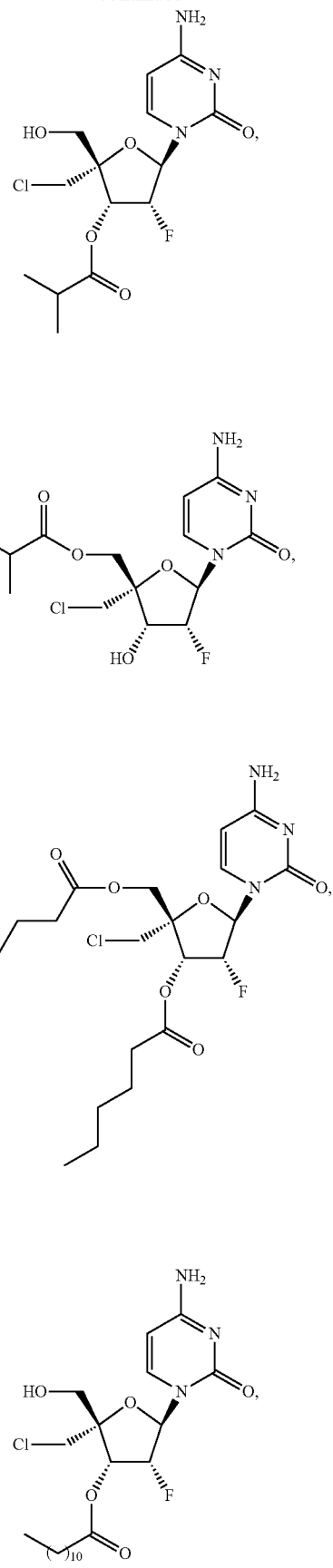

97
-continued
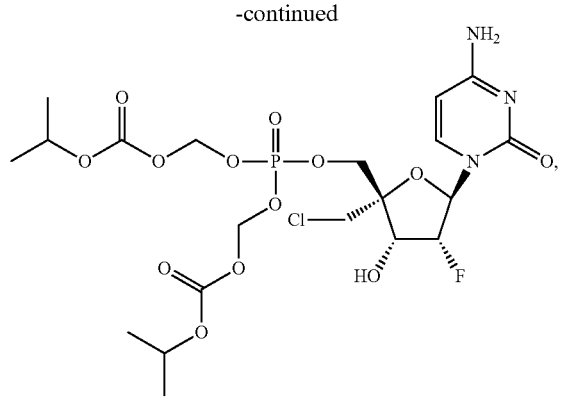
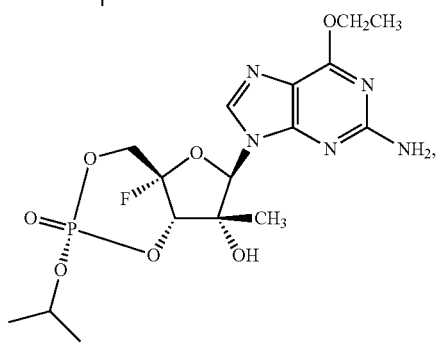
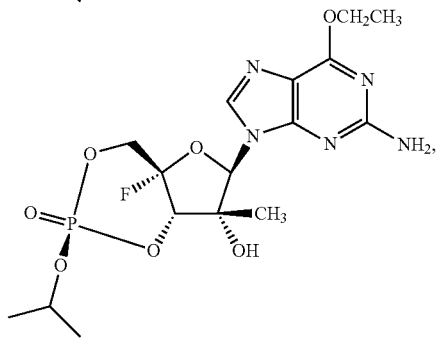
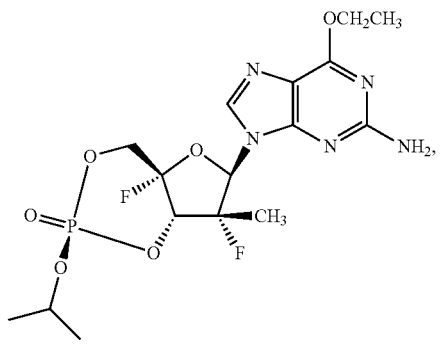
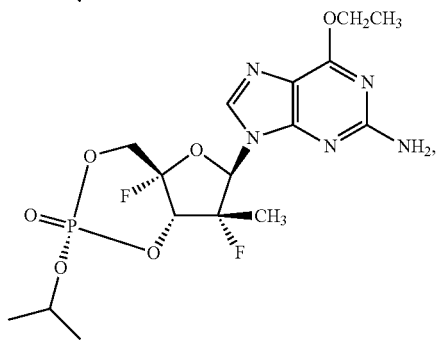
98
-continued
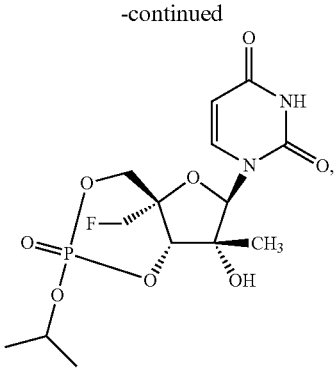
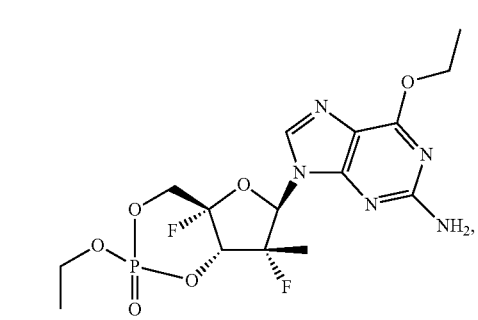
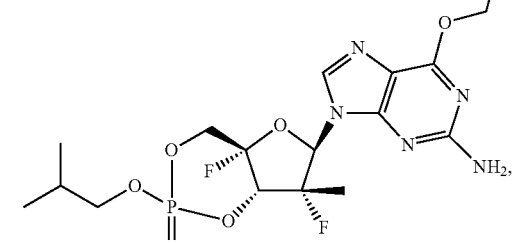
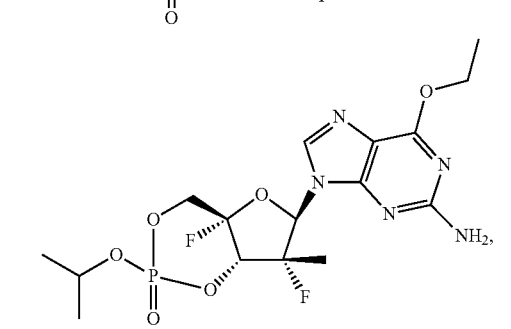

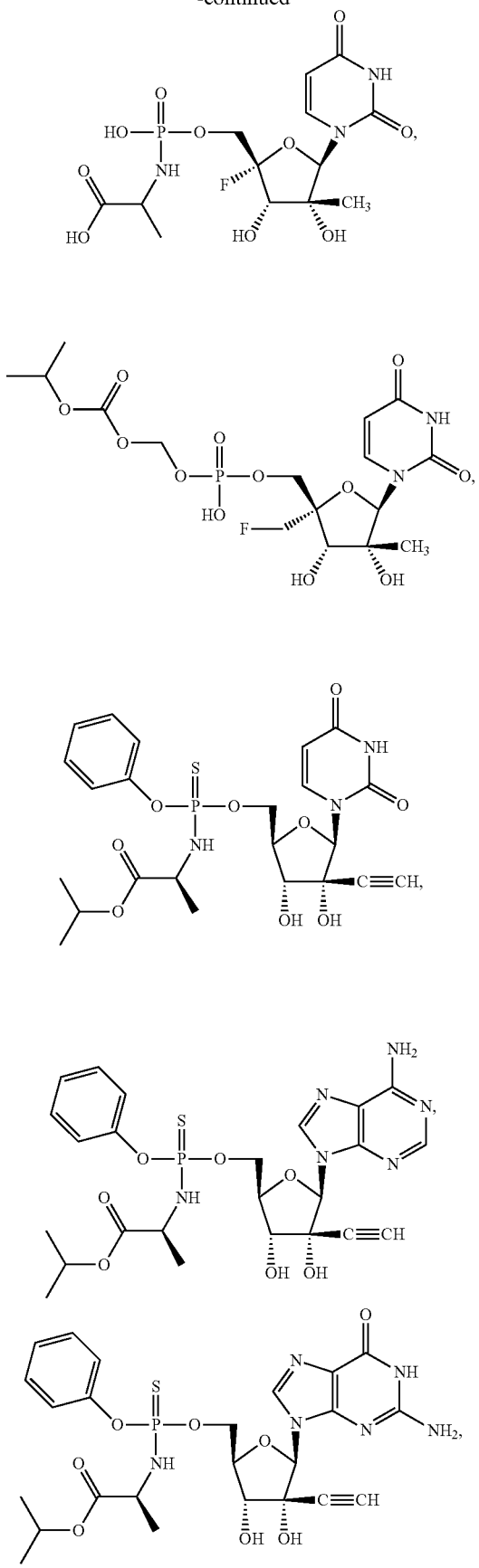
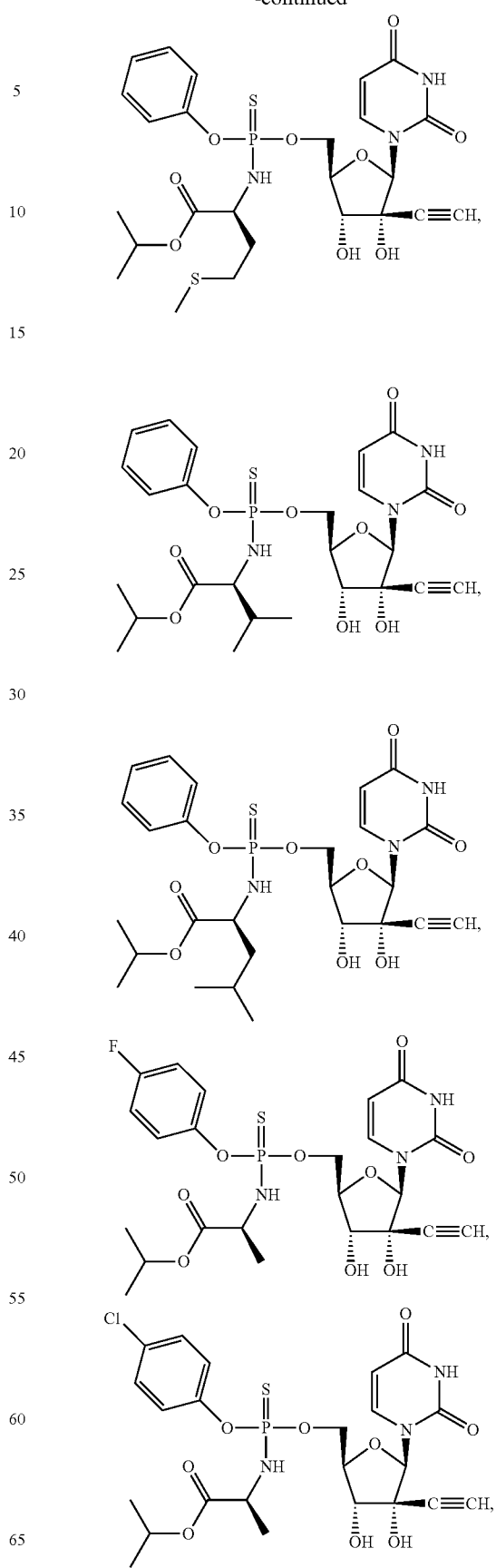

101
-continued
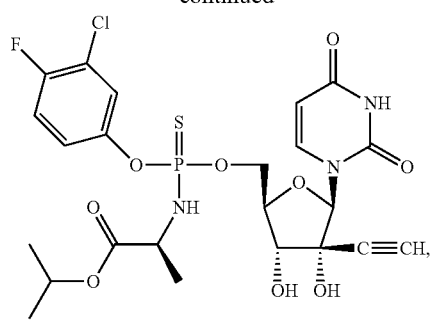
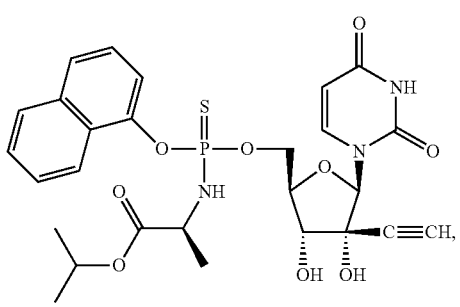
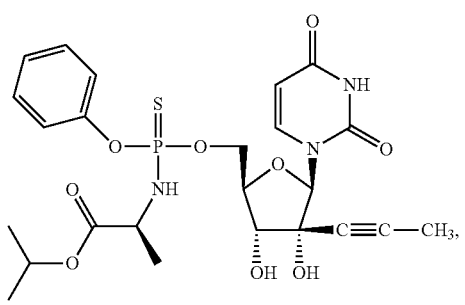
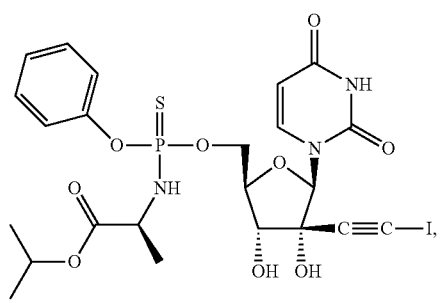
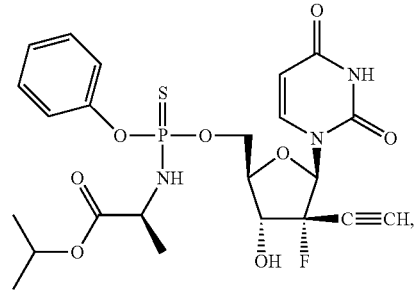
102
-continued
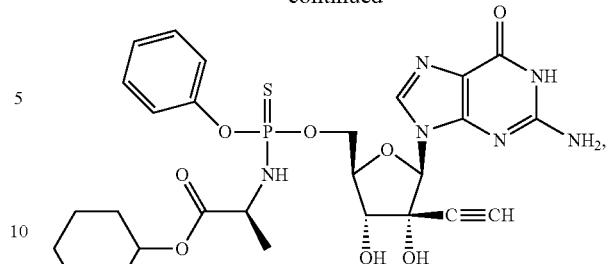
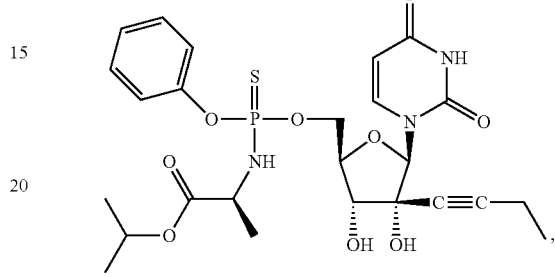
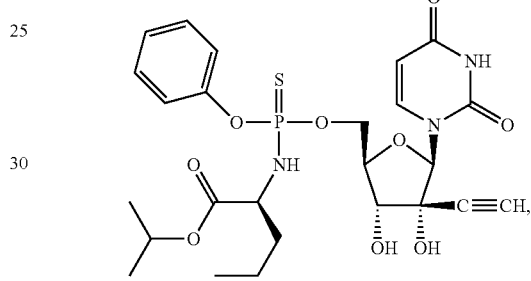
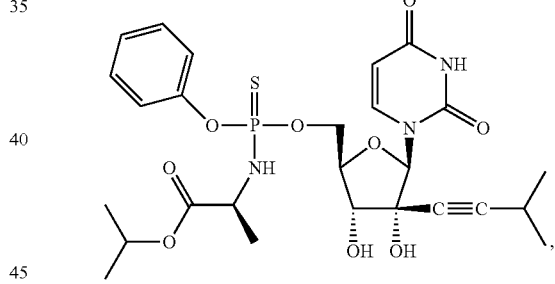
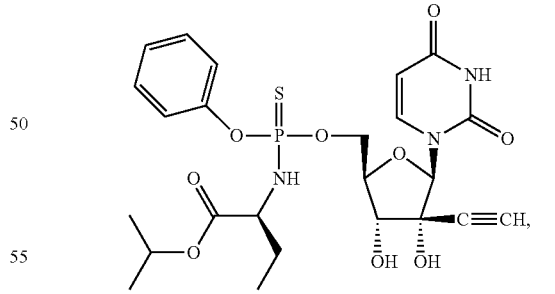
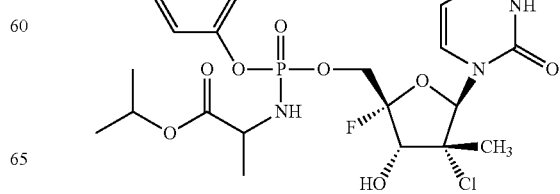

103
-continued
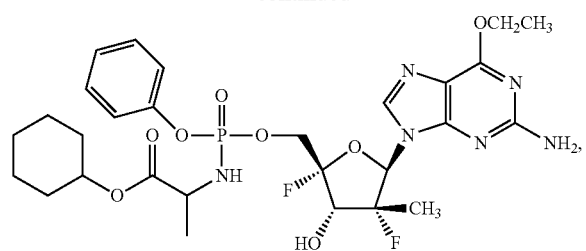
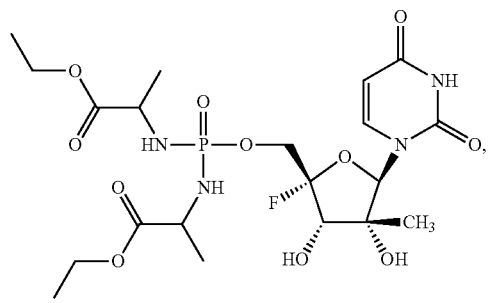
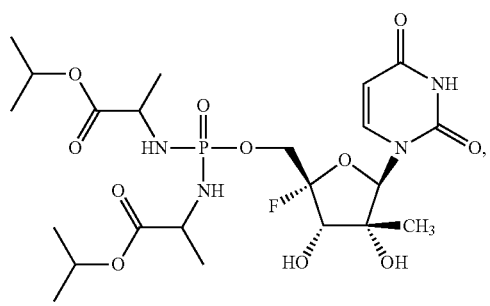
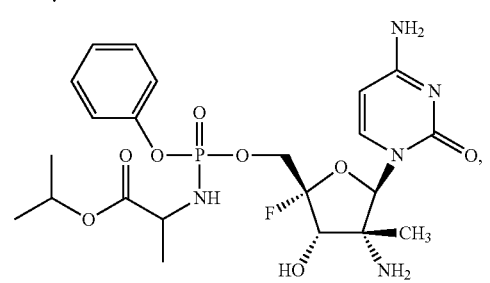
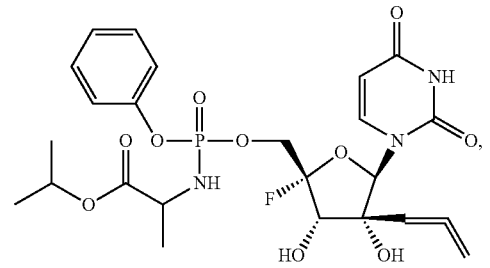
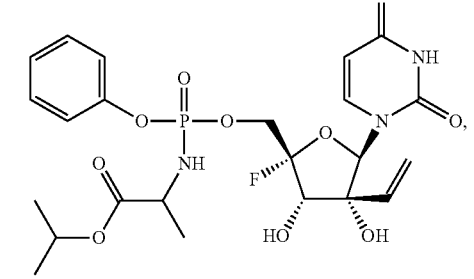
104
-continued
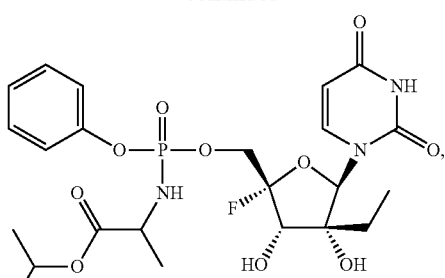
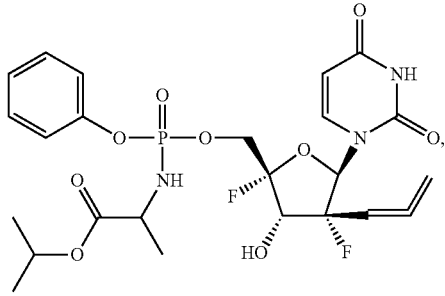
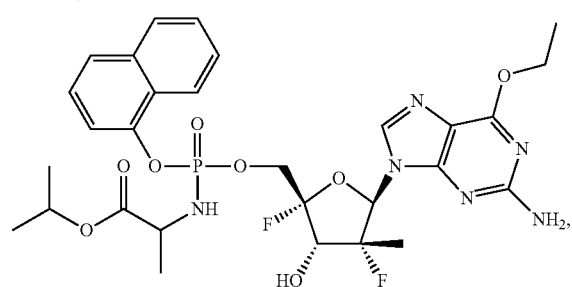
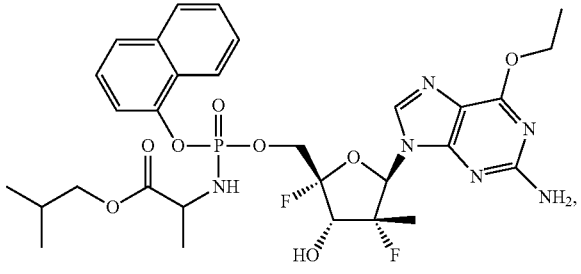
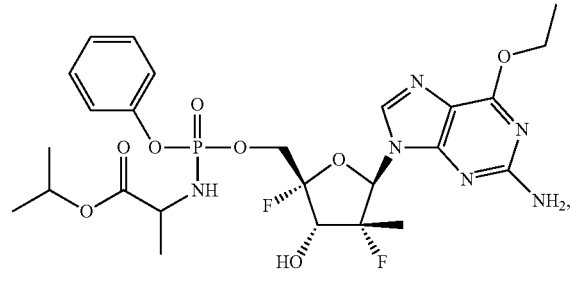
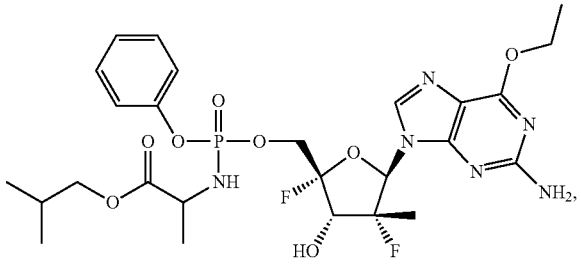

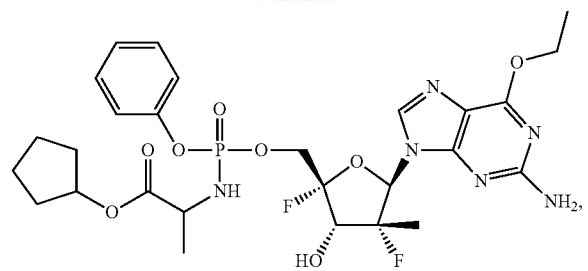
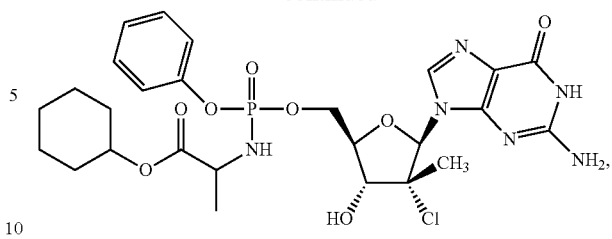
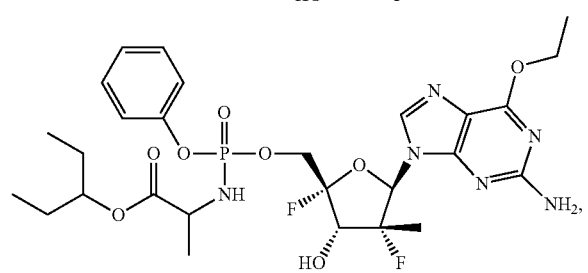
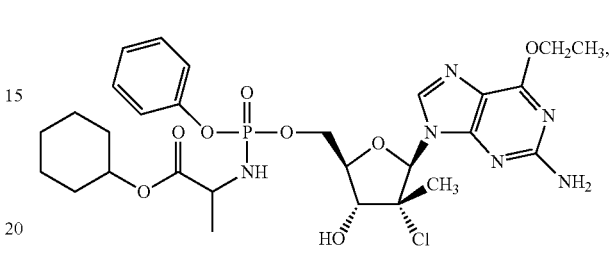
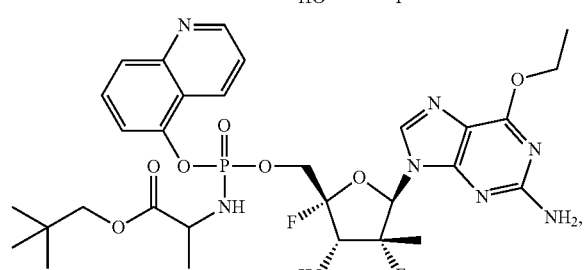
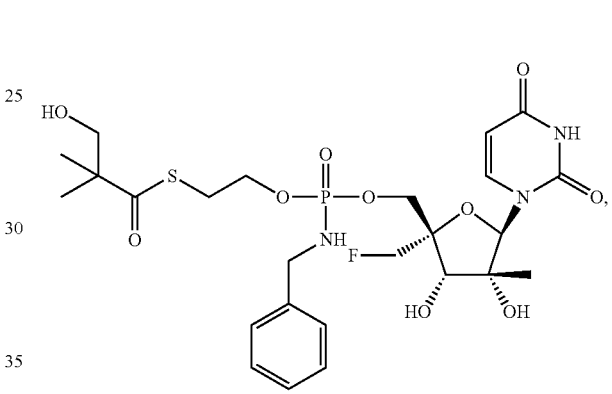
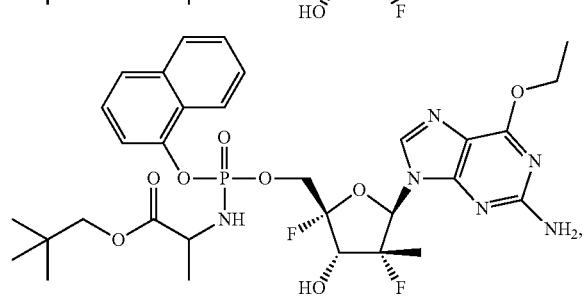
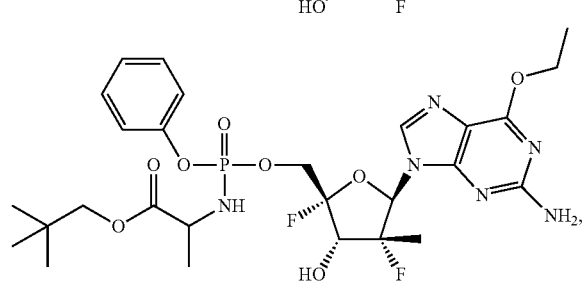
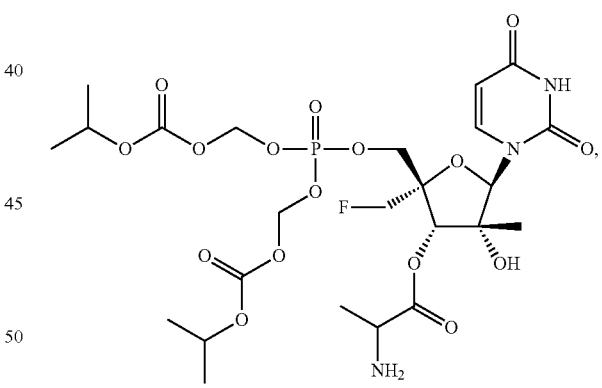
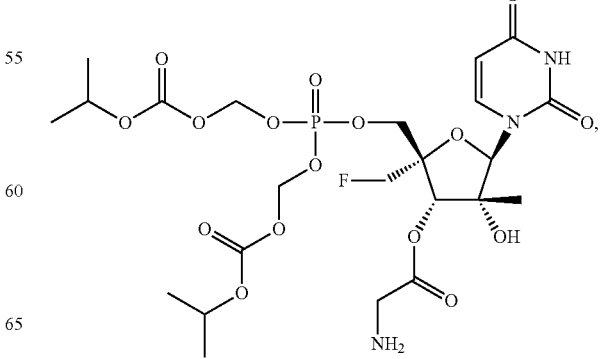

107
-continued
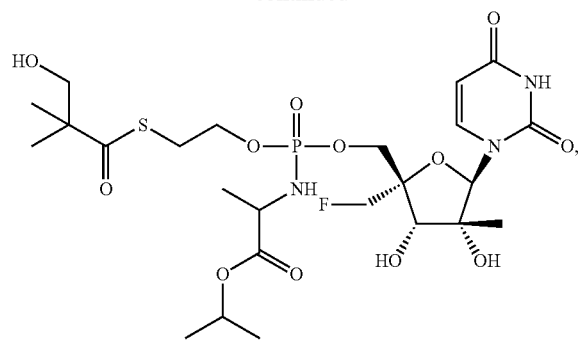
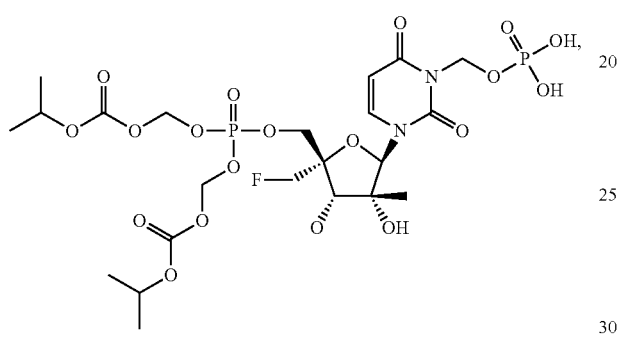
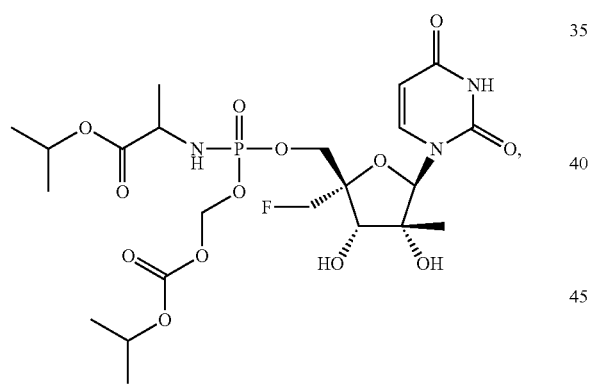
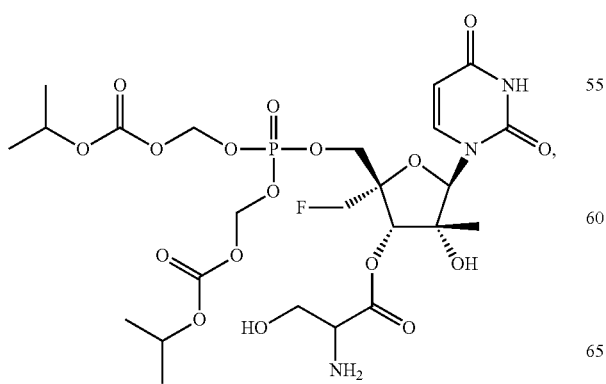
108
-continued
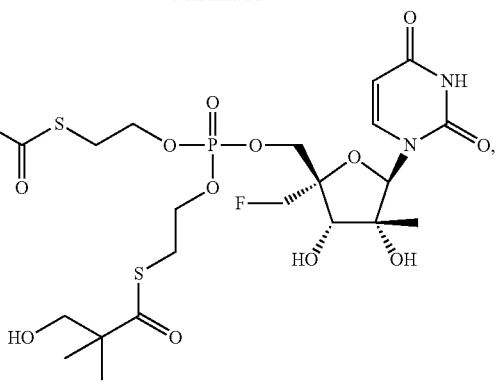
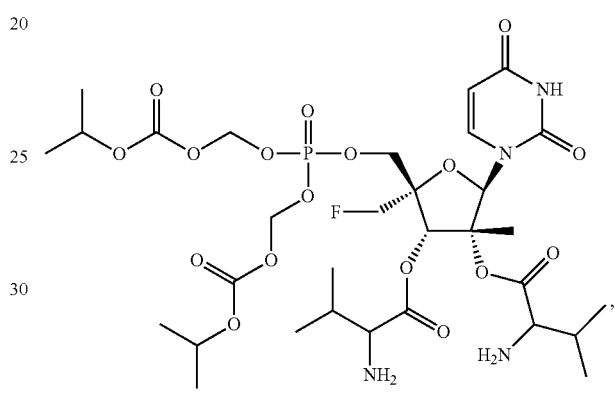
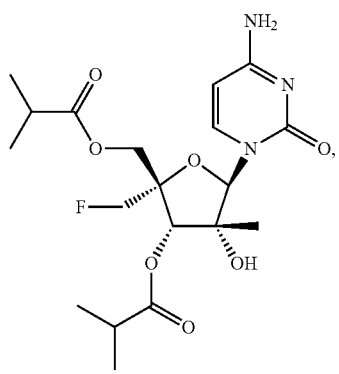
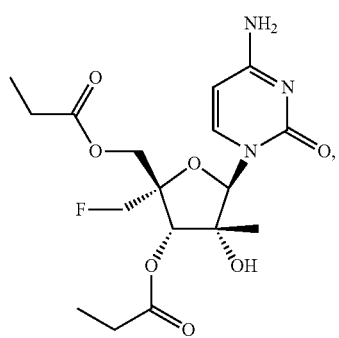

109
-continued
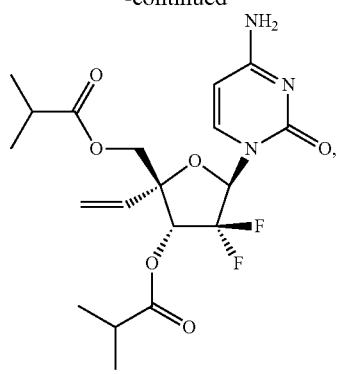
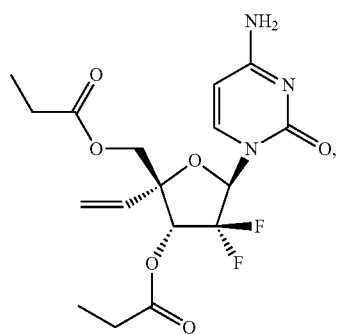
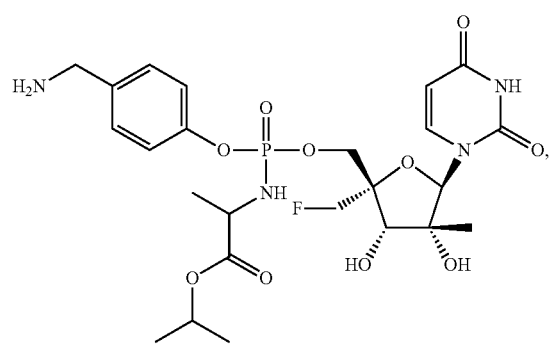
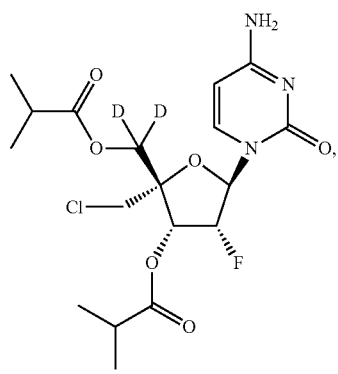
110
-continued
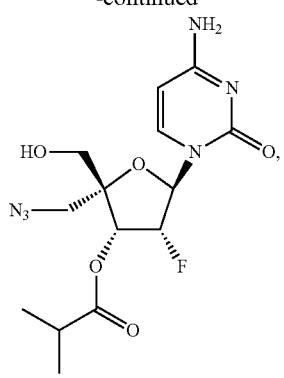
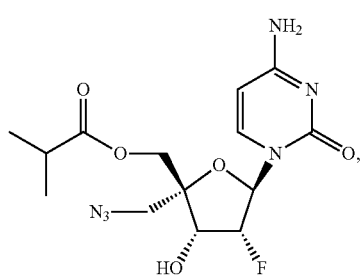
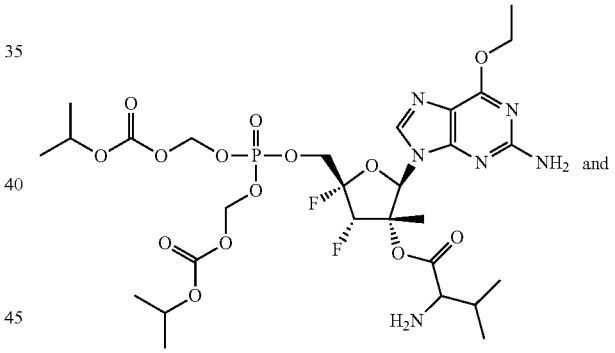
or a pharmaceutically acceptable salt of the foregoing.
In some embodiments, a compound of Formula (I), or a pharmaceutically acceptable salt thereof, may be selected from:

111
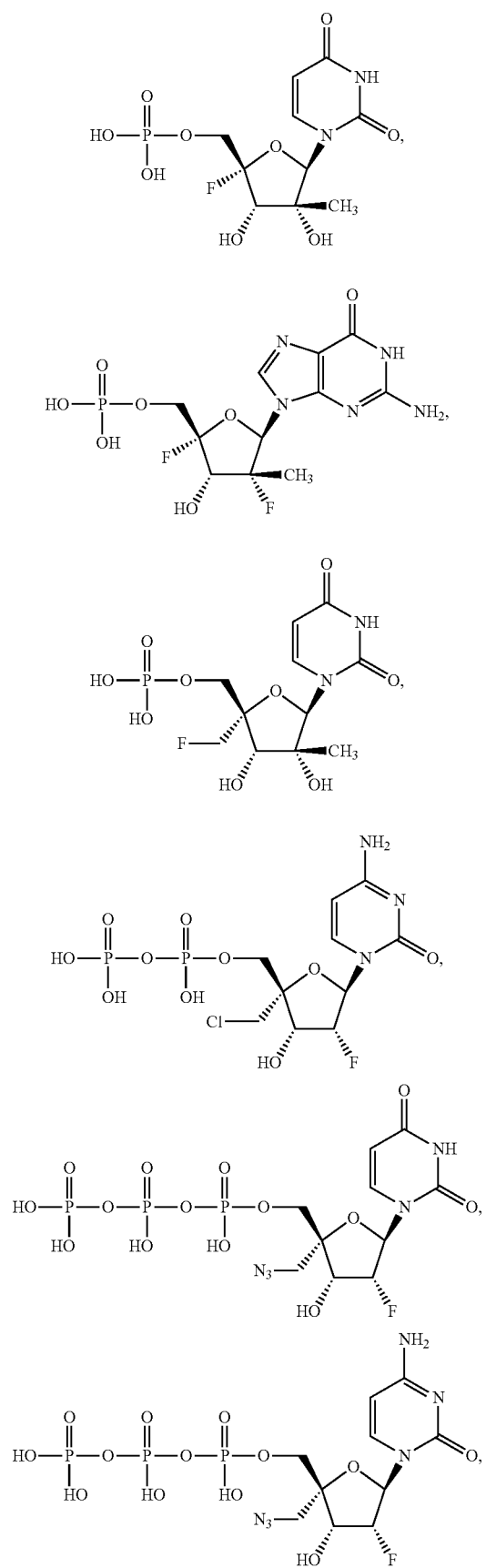
112
-continued
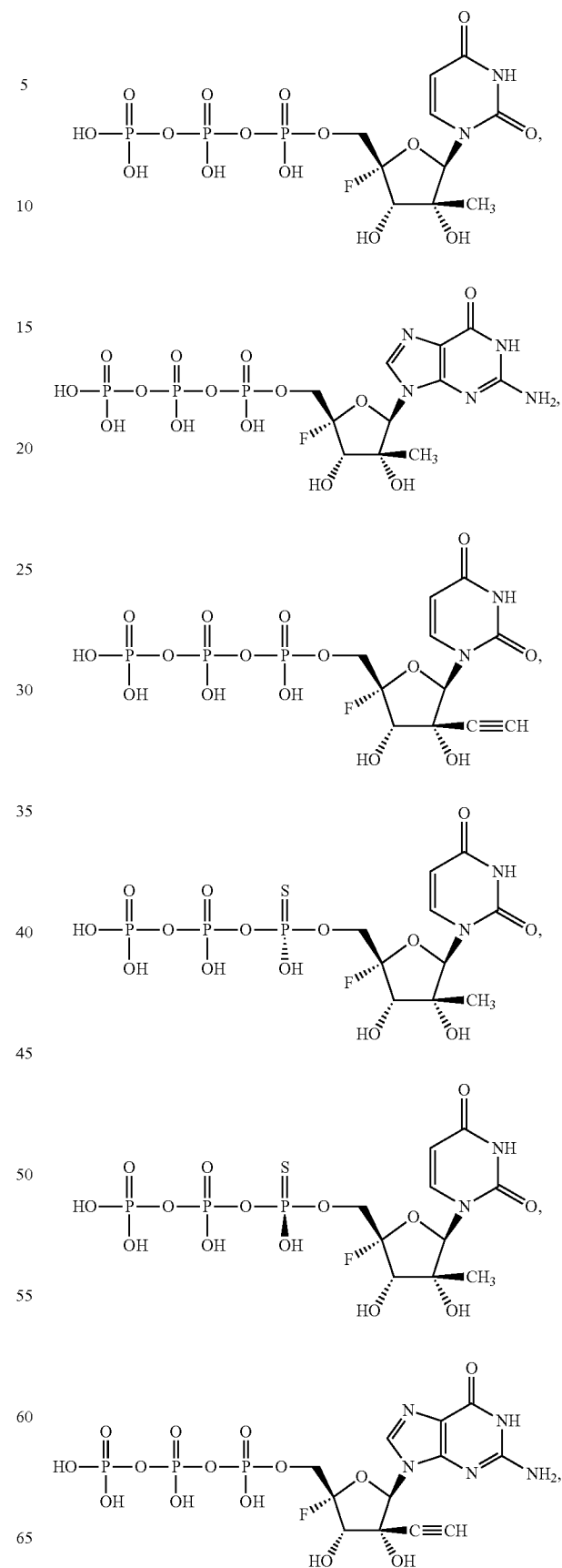

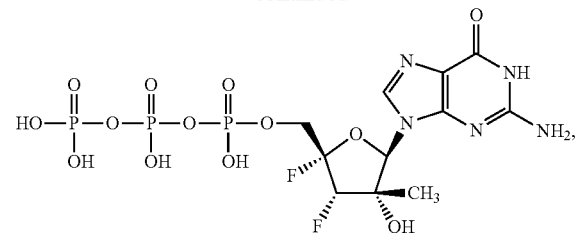
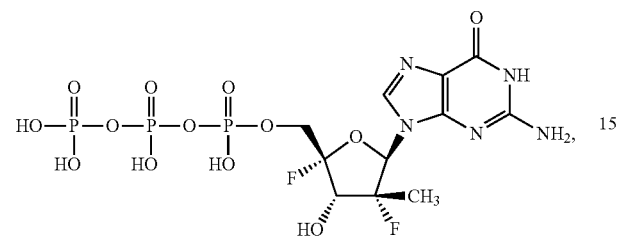
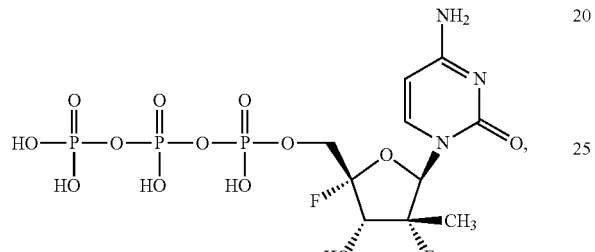
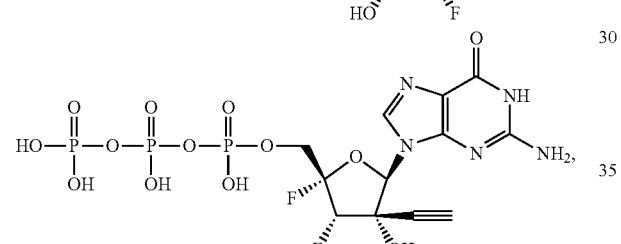
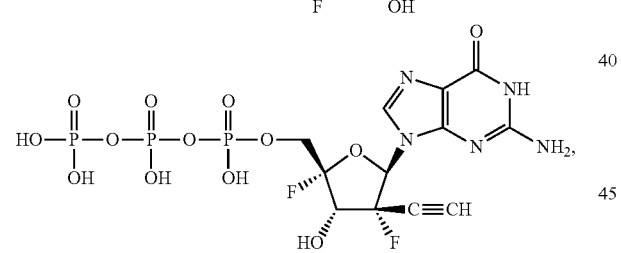
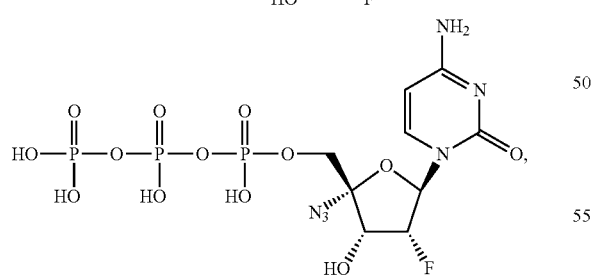
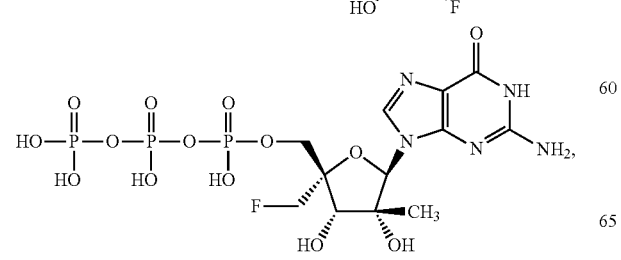
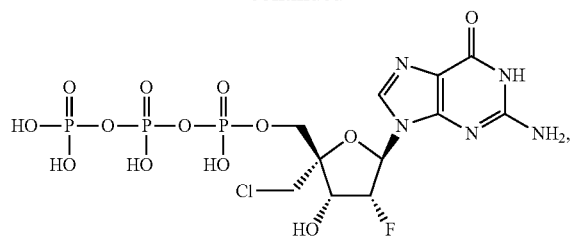
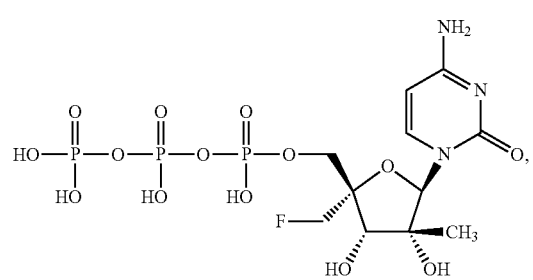
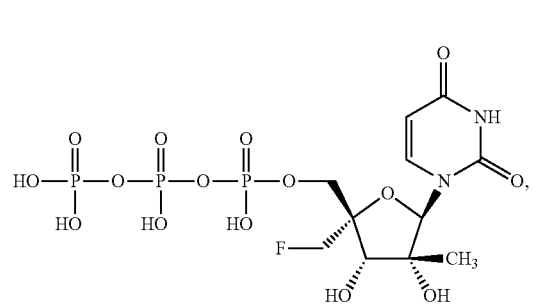
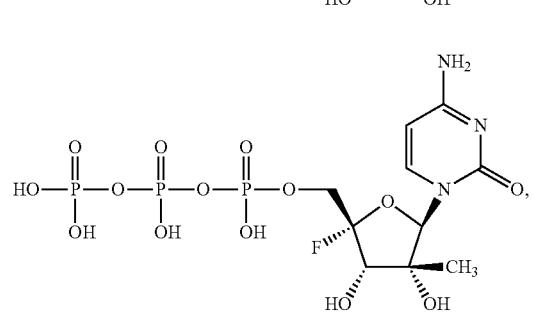
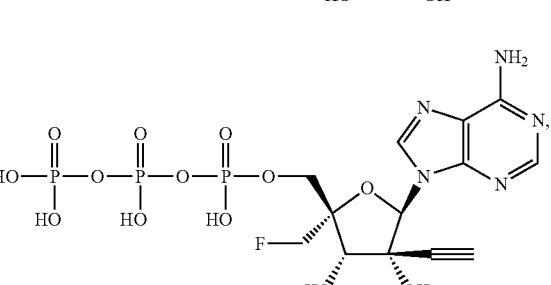
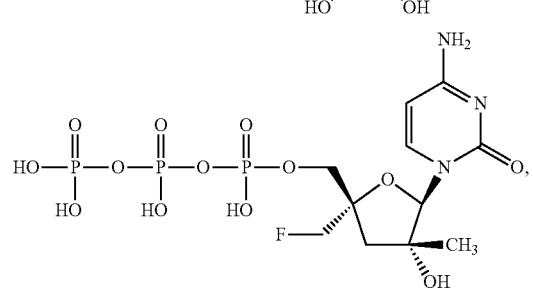

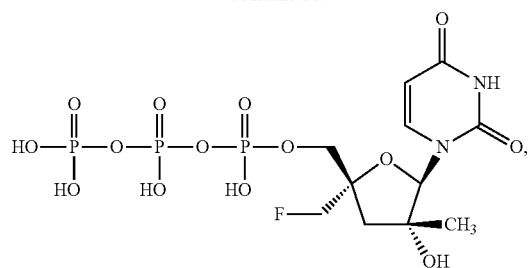
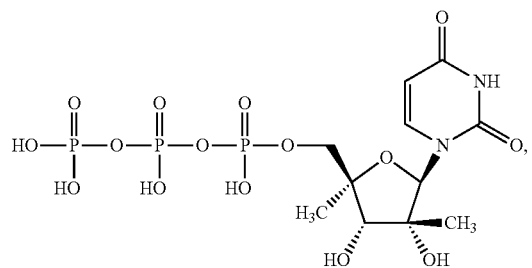
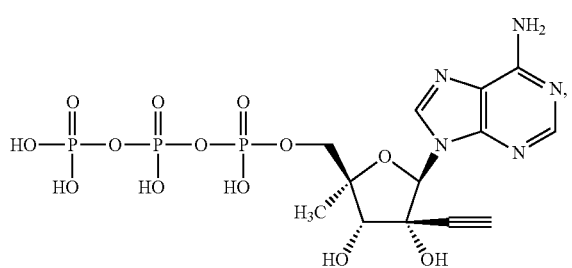
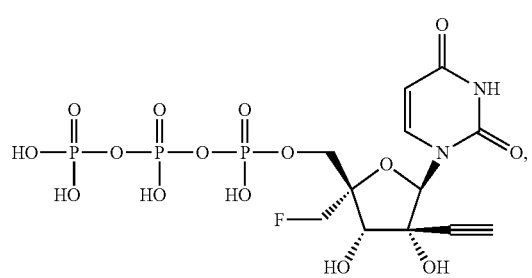
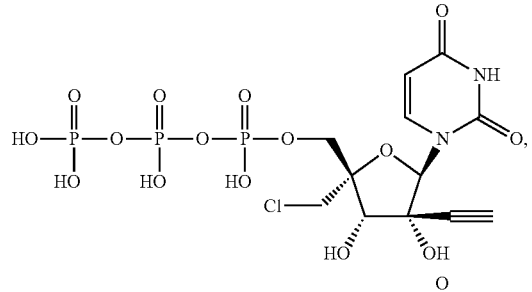
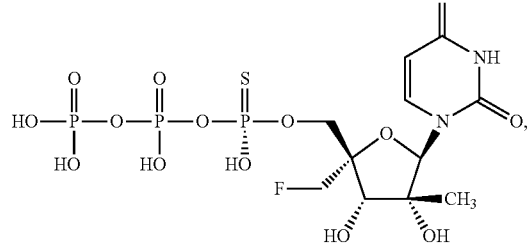
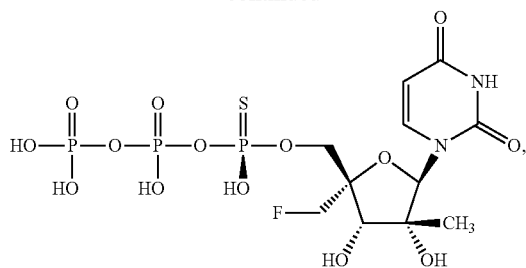
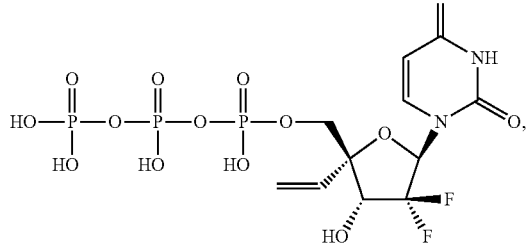
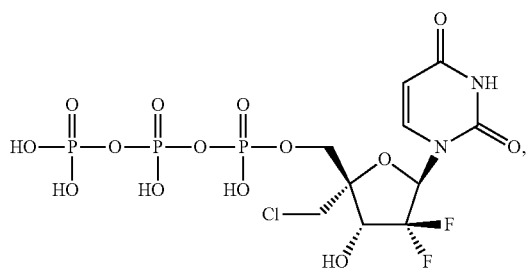
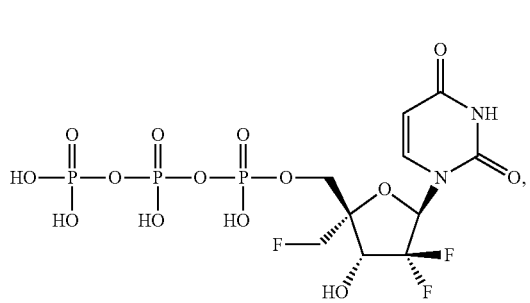
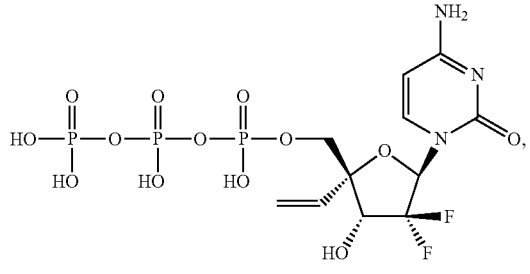
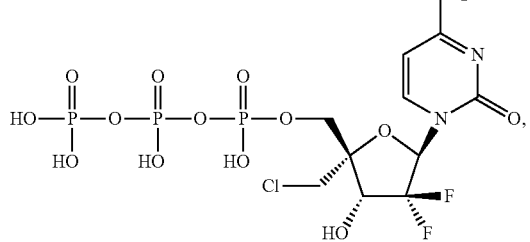

-continued
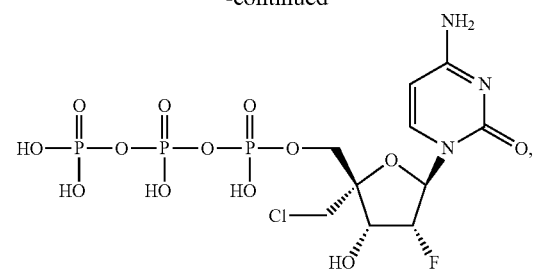
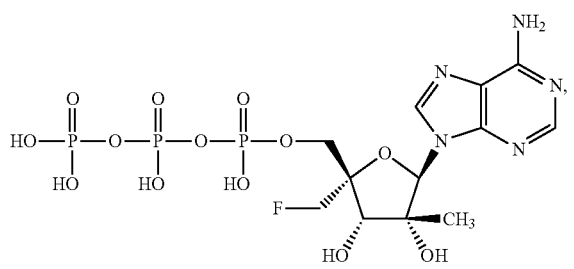
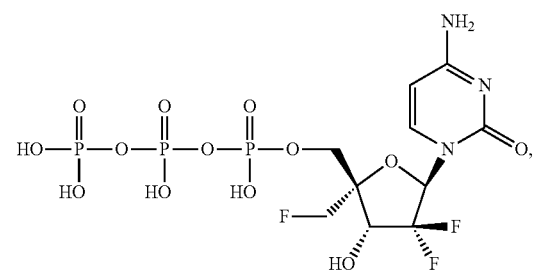
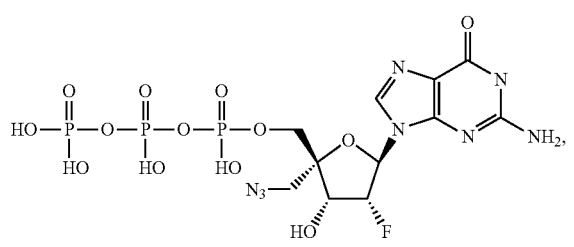
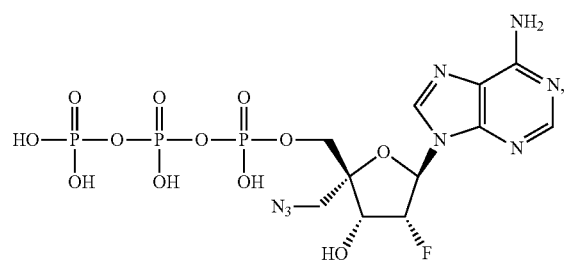
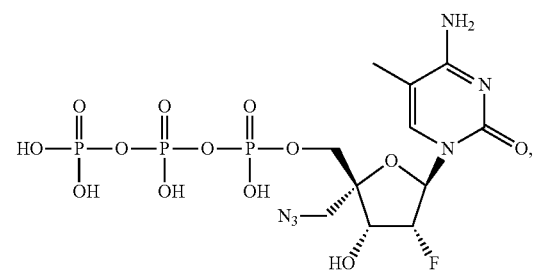
-continued
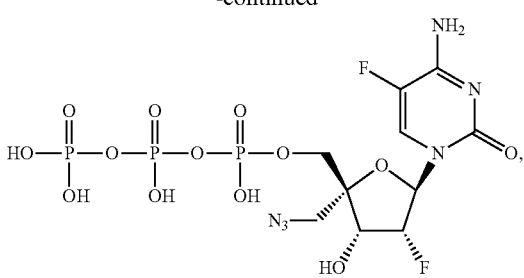
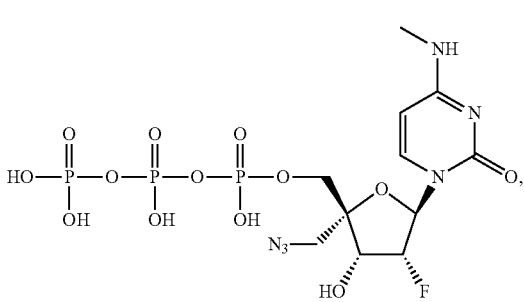
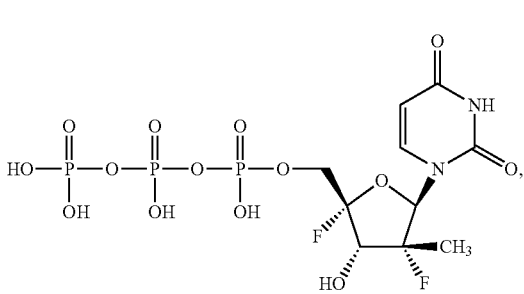
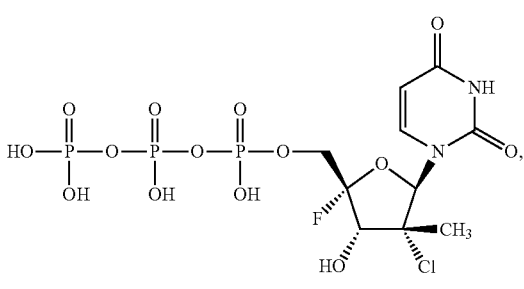
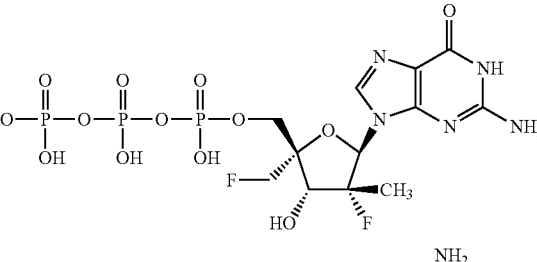
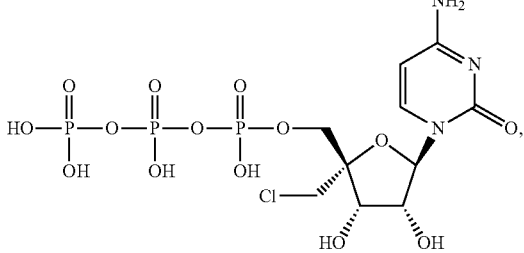

119
-continued
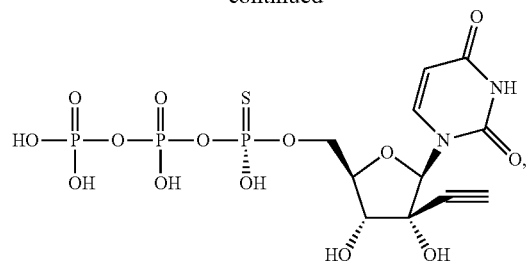
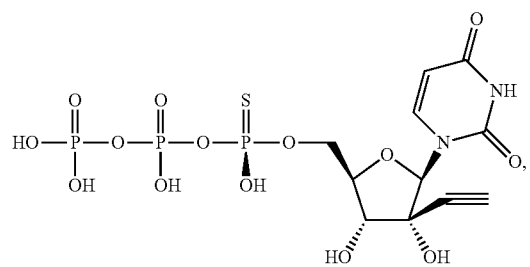
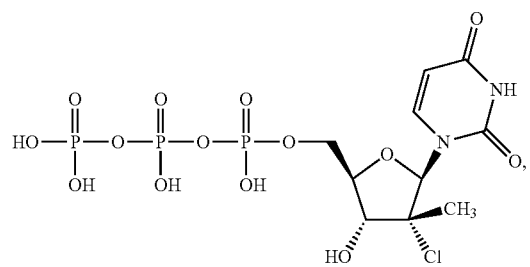
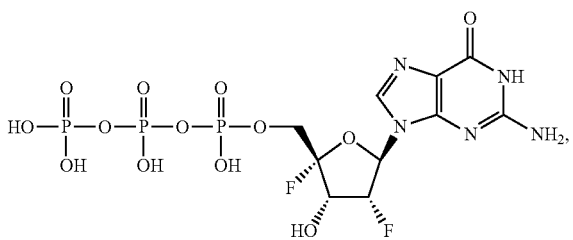
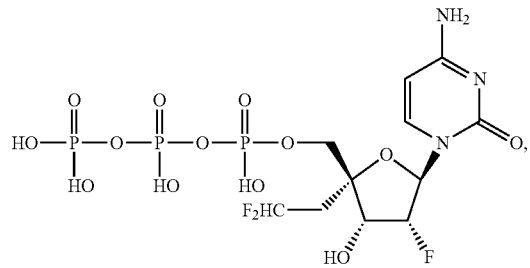
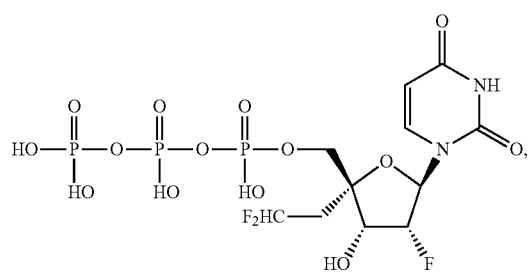
120
-continued
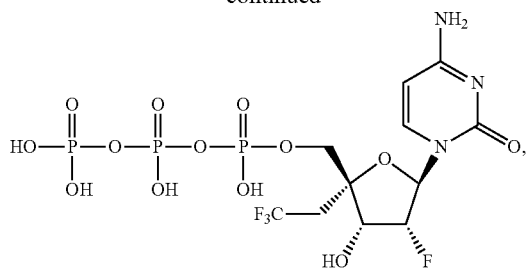
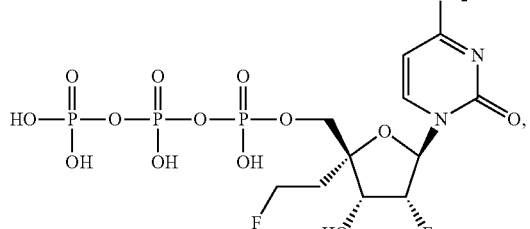
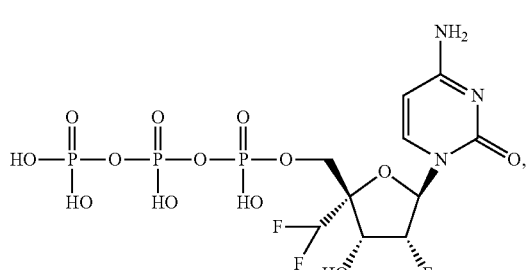
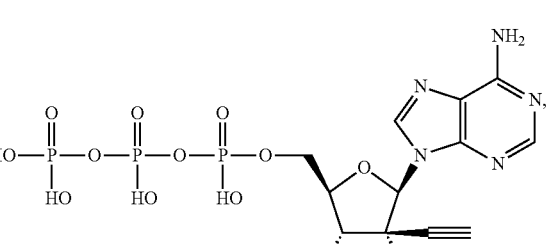
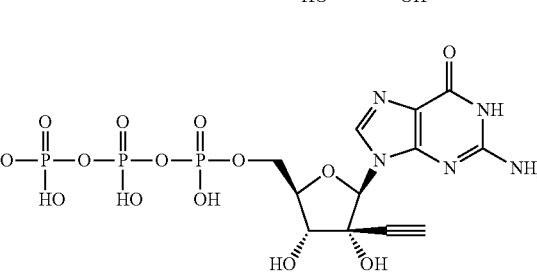
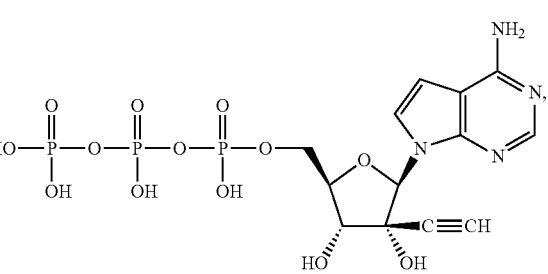

121
-continued
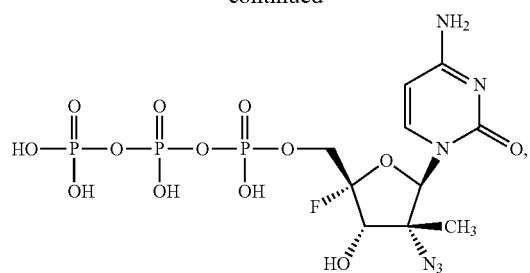
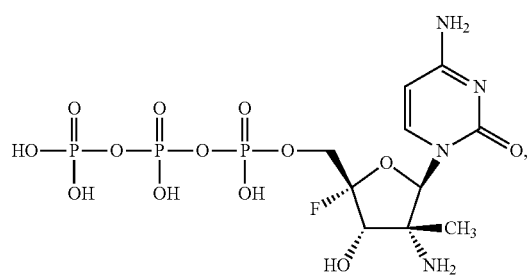
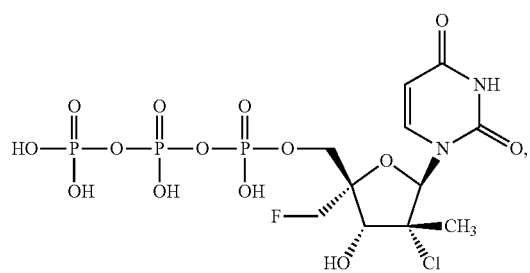
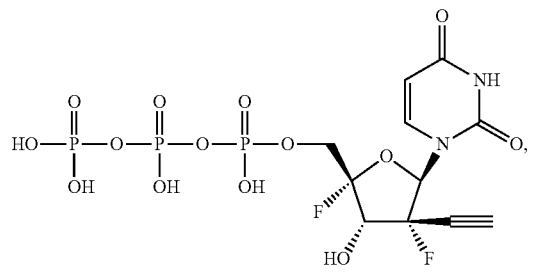
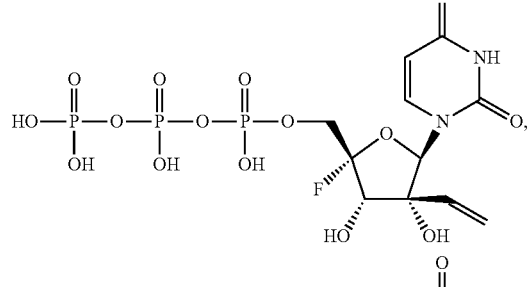
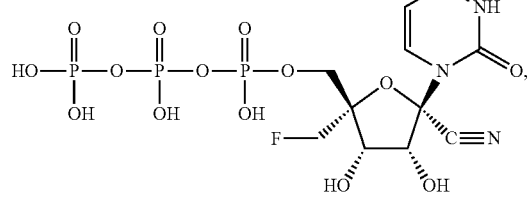
122
-continued
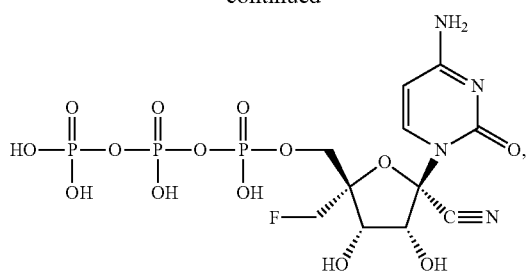
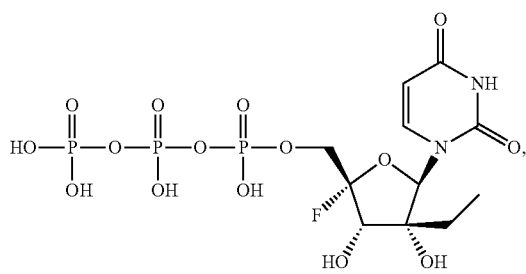
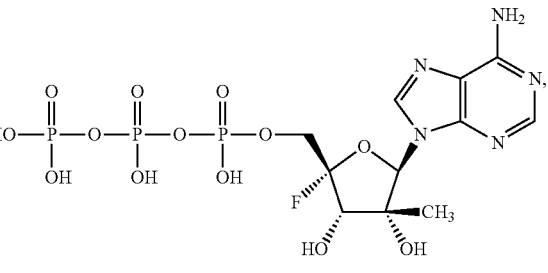
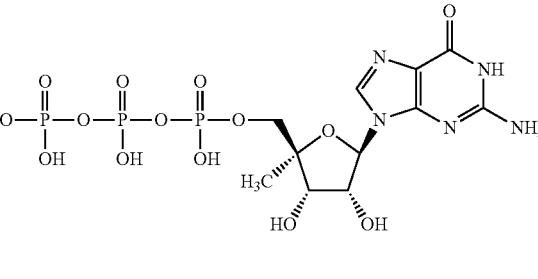
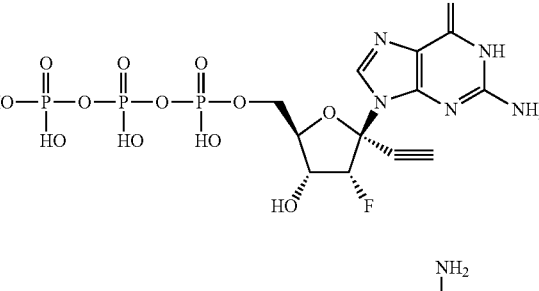
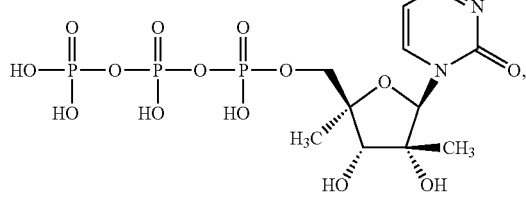

123
-continued
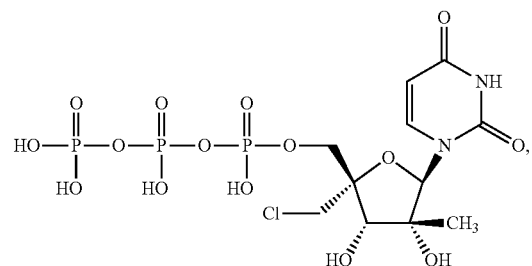
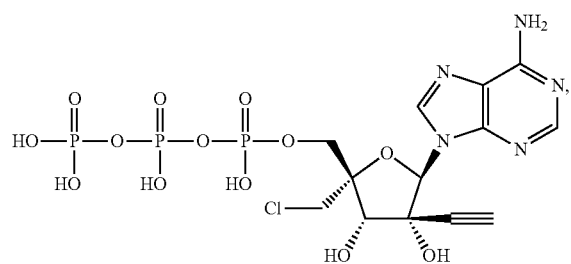
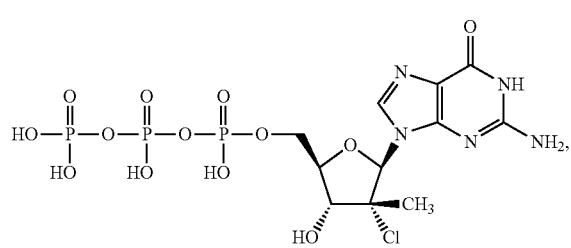
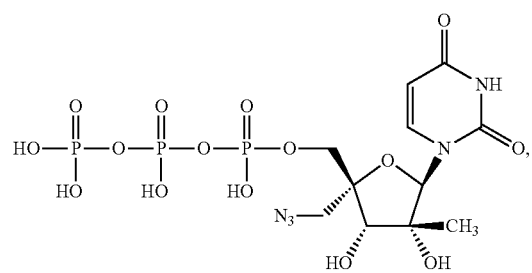
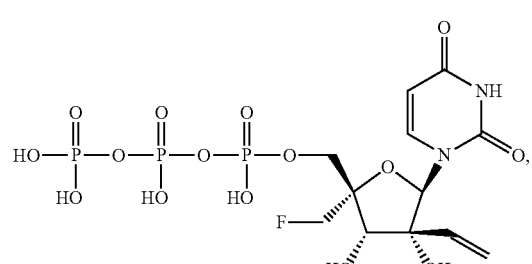
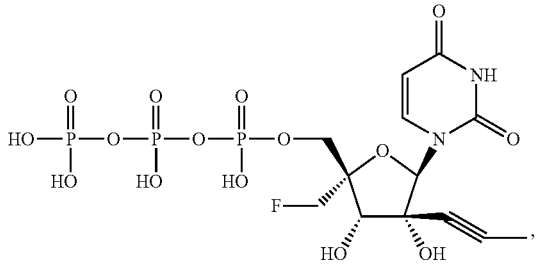
124
-continued
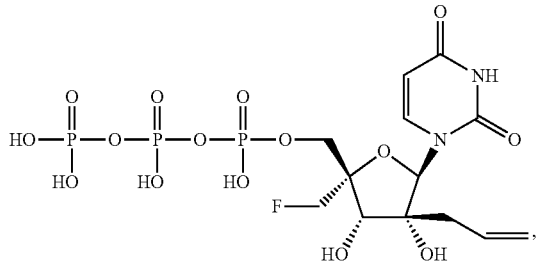
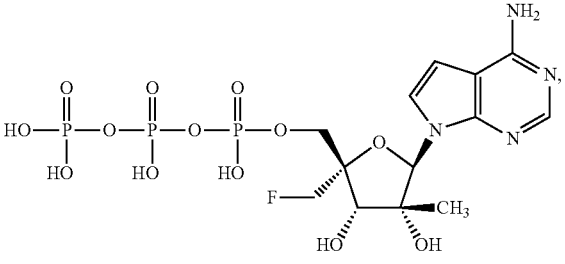
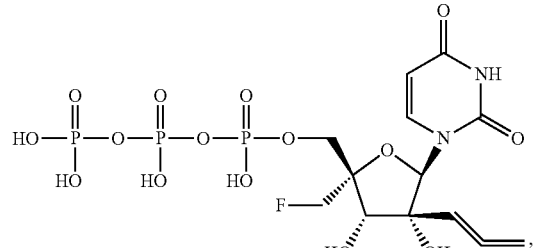
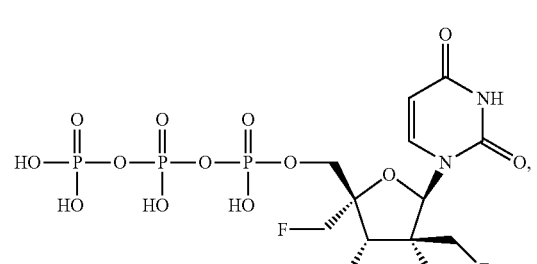
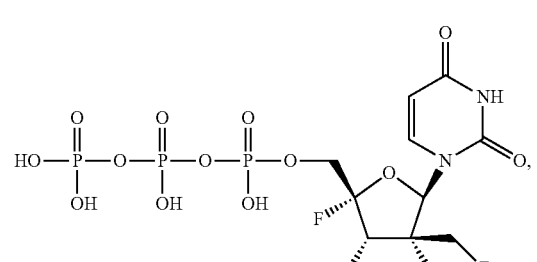
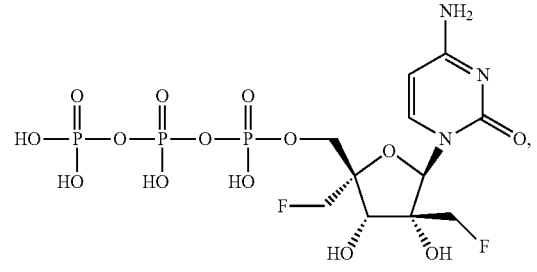

125
-continued
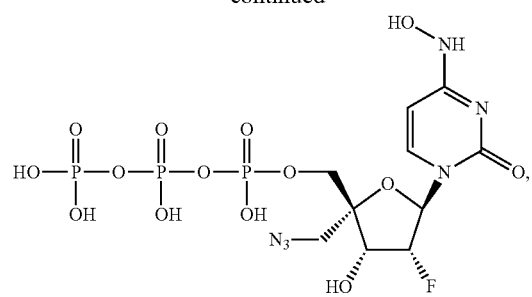
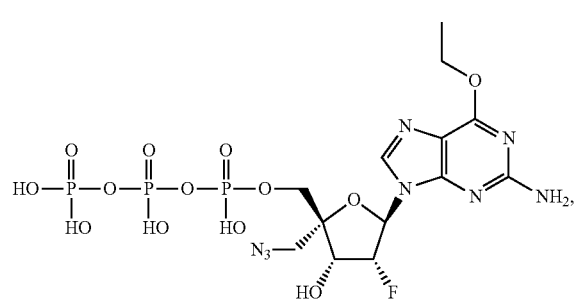
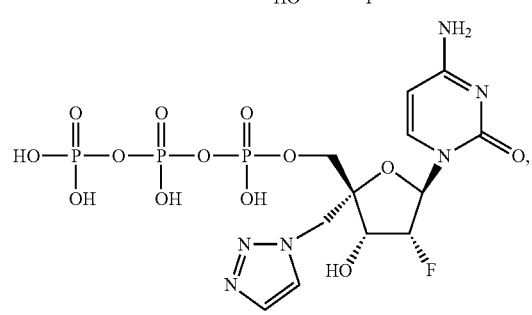
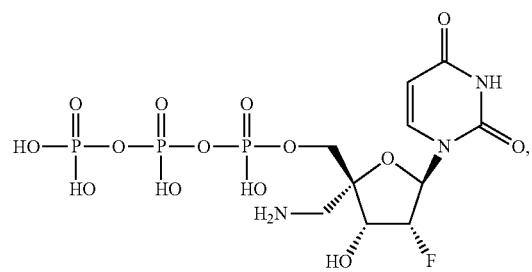
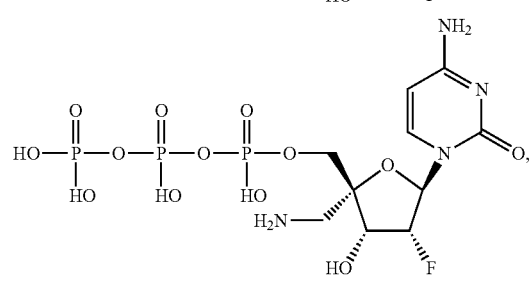
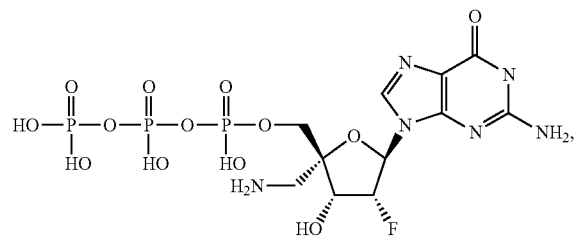
126
-continued
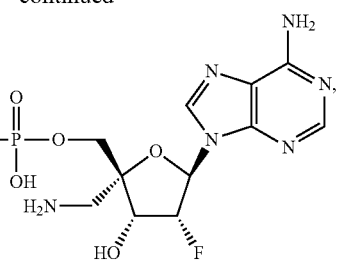
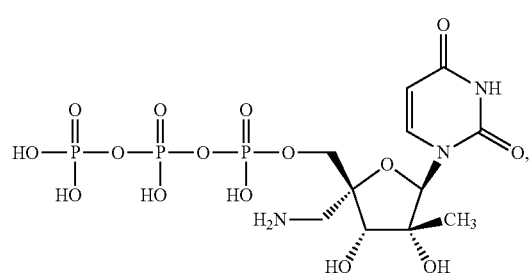
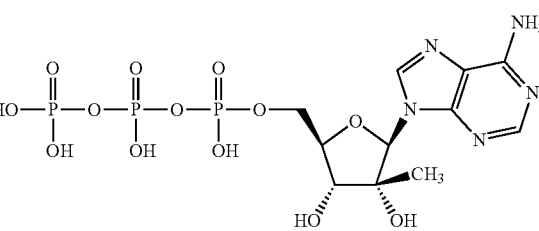
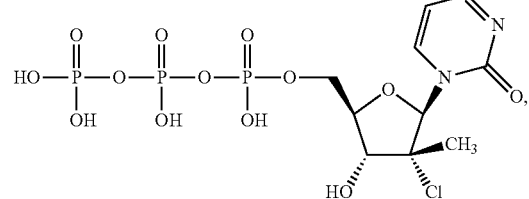
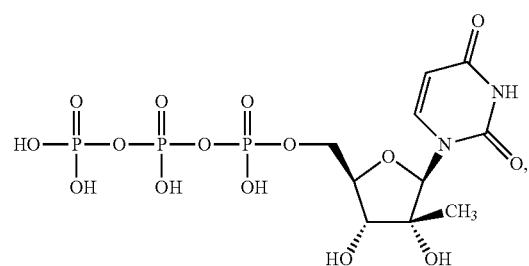
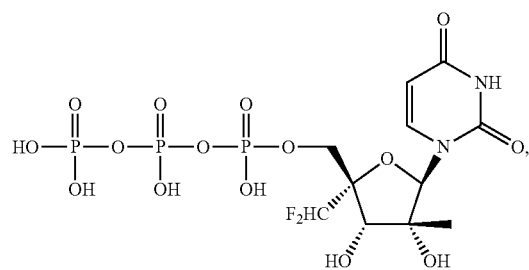

127
-continued
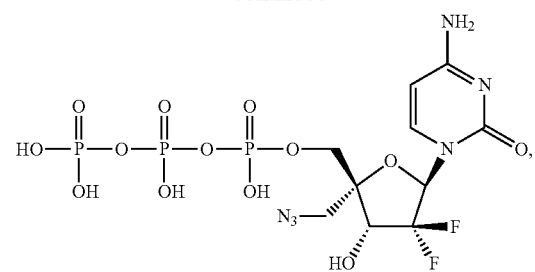
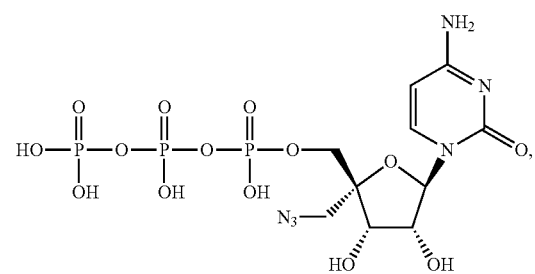
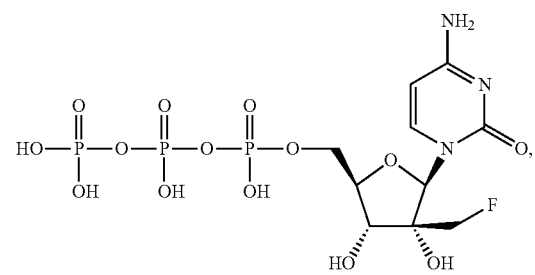
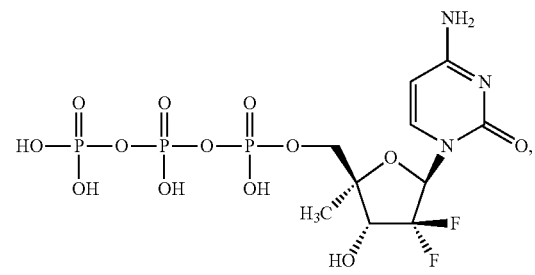
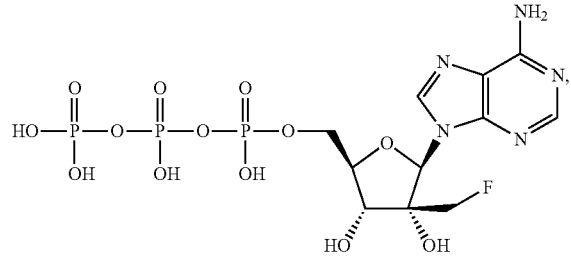
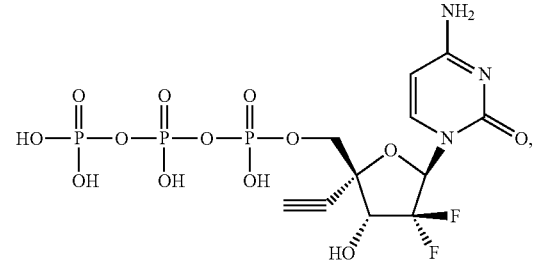
128
-continued
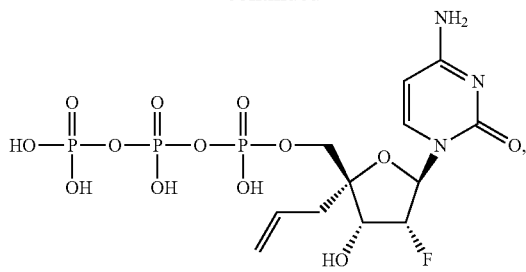
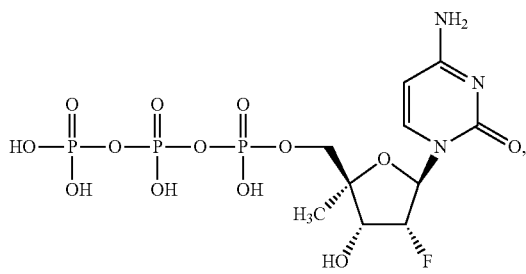
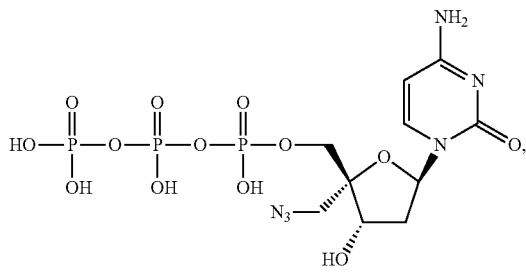
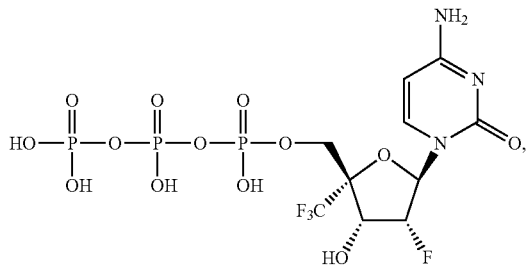
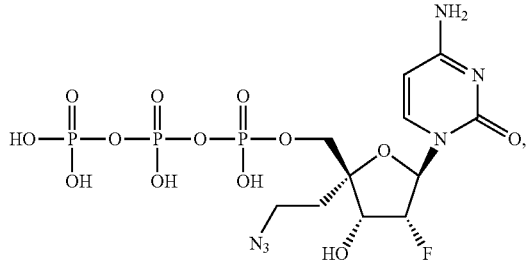
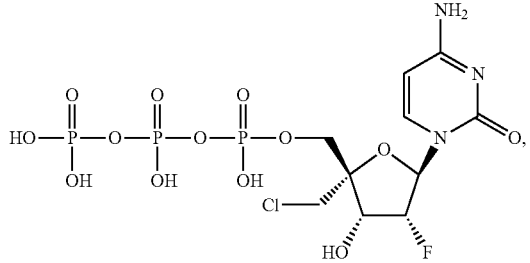

-continued

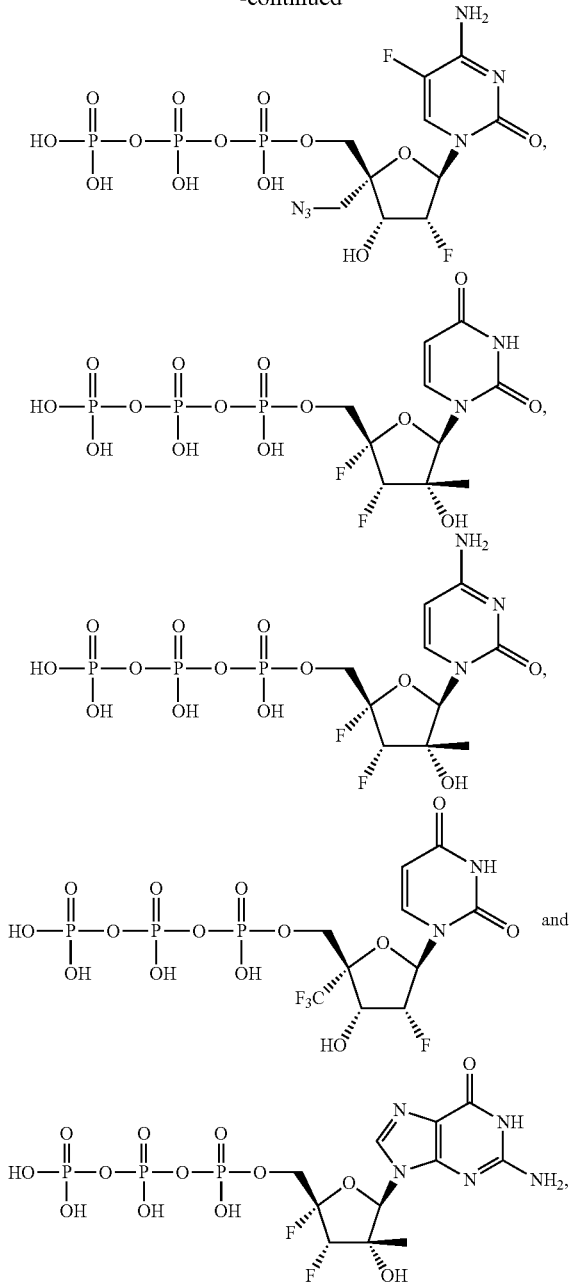

or a pharmaceutically acceptable salt of the foregoing.

Pharmaceutical Compositions

Some embodiments described herein relates to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration. A pharmaceutical composition is suitable for human and/or veterinary applications.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Synthesis

Compounds of Formula (I) and those described herein may be prepared in various ways. General synthetic routes to the compound of Formula (I) and some examples of starting materials used to synthesize the compounds of Formula (I) are shown in Scheme 1, 2, 3 and 4, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) can be prepared using various methods known to those skilled in the art. Examples of methods are shown in Schemes 1, 2, 3 and 4. Suitable phosphorus containing precursors can be commercially obtained or prepared by synthetic methods known to those skilled in the art. Examples of general structures of phosphorus containing precursors are shown in Schemes 1, 2, 3 and 4, and include phosphorochloridates and thiophosphorochloridates. Suitable phosphorochloridates and thiophosphorochloridates are commercially available and/or can be synthetically prepared.

Scheme 1

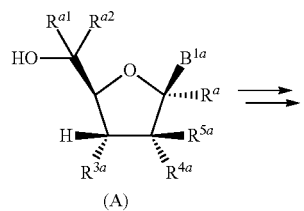

(A)

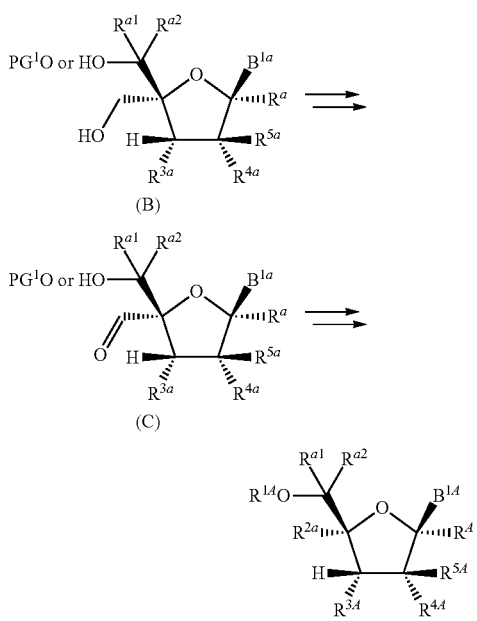

As shown in Scheme 1, compounds of Formula (I), wherein the 4'-position is a haloalkyl, can be prepared from a nucleoside, for example, a nucleoside of Formula (A). In Scheme 1, $R^a$, $R^{3a}$, $R^{4a}$, $R^{5a}$, and $B^{1a}$ can be the same as $R^A$, $R^{3A}$, $R^{4A}$, $R^{5A}$ and $B^{1A}$ as described herein for Formula (I), and $PG^1$ is a suitable protecting group. A hydroxyalkyl group can be formed at the 4'-position of the pentose ring using suitable conditions known to those skilled in the art. Examples of suitable conditions for forming a hydroxyalkyl include the use of 2-iodoxybenzoic acid (IBX) aqueous formaldehyde and sodium borohydride. A compound of Formula (B) can be transformed to a haloalkyl using a suitable agent(s), for example, to an iodide using imidazole, triphenylphosphine and iodine; to a fluoro using diethylaminosulfur trifluoride (DAST); or to a chloro using triphenylphosphine and carbontetrachloride in dichloroethylene (DCE).

Scheme 2

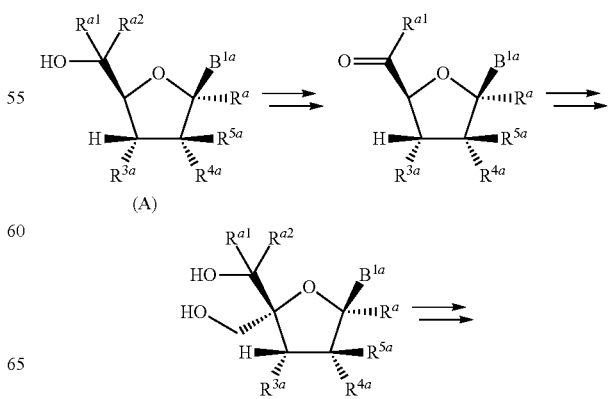

-continued

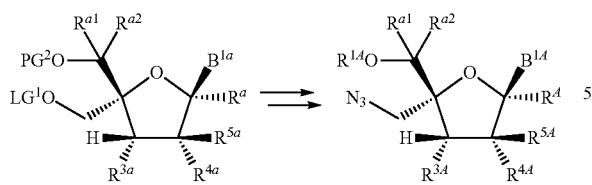

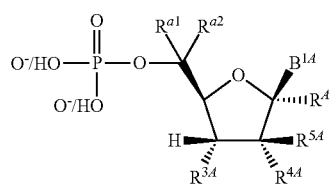

Compounds of Formula (I), where $R^{2A}$ is a $C_{1-6}$ azidoalkyl, can be prepared from a nucleoside, for example, a nucleoside of Formula (A). In Scheme 2, $R^a$, $R^{3a}R^{4a}$, $R^{5a}$ and $B^{1a}$ can be the same as $R^A$, $R^{3A}$, $R^{4A}$, $R^{5A}$ and $B^{1A}$ as described herein for Formula (I), $PG^2$ can be a suitable protecting group and $LG^2$ can be a suitable leaving group. The 5'-position of the nucleoside can be oxidized to an aldehyde using methods known to those skilled in the art. Suitable oxidation conditions include, but are not limited to, Moffatt oxidation, Swern oxidation and Corey-Kim oxidation; and suitable oxidizing agents include, but are not limited to, Dess-Martin periodinane, IBX (2-iodoxybenzoic acid), TPAP/NMO (tetrapropylammonium perruthenate/N-methylmorpholine N-oxide), Swern oxidation reagent, PCC (pyridinium chlorochromate), PDC (pyridinium dichromate), sodium periodate, Collin's reagent, ceric ammonium nitrate CAN, $Na_2Cr_2O_7$ in water, $Ag_2CO_3$ on celite, hot $HNO_3$ in aqueous glyme, $O_2$-pyridine CuCl, $Pb(OAc)_4$-pyridine and benzoyl peroxide-$NiBr_2$. A hydroxymethyl group can be added to the 4'-position of the pentose ring along with the reduction of the aldehyde to an alcohol. The hydroxymethyl group can be added via a condensation reaction using formaldehyde and a base, such as sodium hydroxide. After addition of the hydroxymethyl group, reduction of the intermediate compound with a 4'-hydroxymethyl group can be conducted using a reducing reagent. Examples of suitable reducing agents include, but are not limited to, $NaBH_4$ and $LiAlH_4$. A suitable leaving group, such as a triflate, can be formed by replacing the hydrogen of the hydroxymethyl group attached to the 4'-position, and the oxygen attached to the 5'-position can be protected with a suitable protecting group (for example, by cyclization with the base, $B^{1a}$, or with a separate protecting group). The leaving group can be replaced with an azido group using a metal azide reagent, for example, sodium azide. A $C_{1-6}$ azidoalkyl at the 4'-position can be reduced to a $C_{1-6}$ aminoalkyl. Various reduction agents/conditions known to those skilled in the art can be utilized. For example, the azido group can be reduced to an amino group via hydrogenation (for example, $H_2$—Pd/C or $HCO_2NH_4$—Pd/C), Staudinger Reaction, $NaBH_4/CoCl_2 \cdot 6H_2O$, $Fe/NH_4Cl$ or $Zn/NH_4Cl$.

Scheme 3

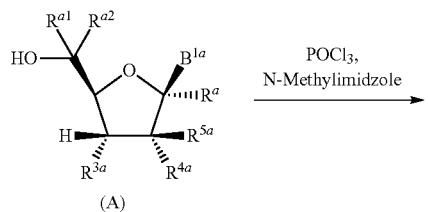

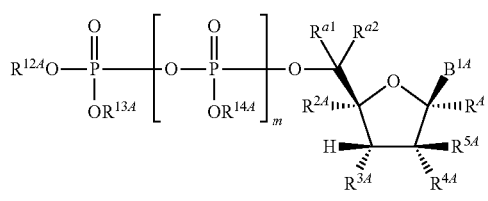

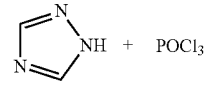

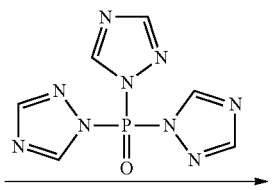

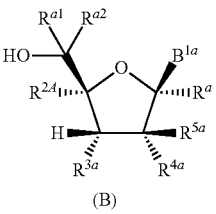

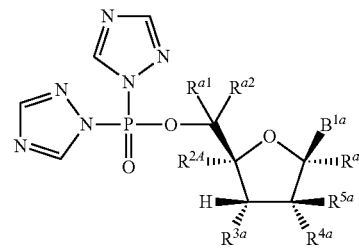

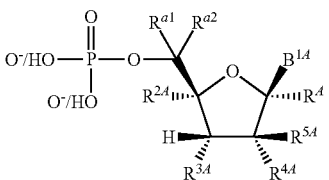

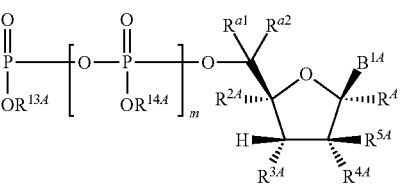

Scheme 4

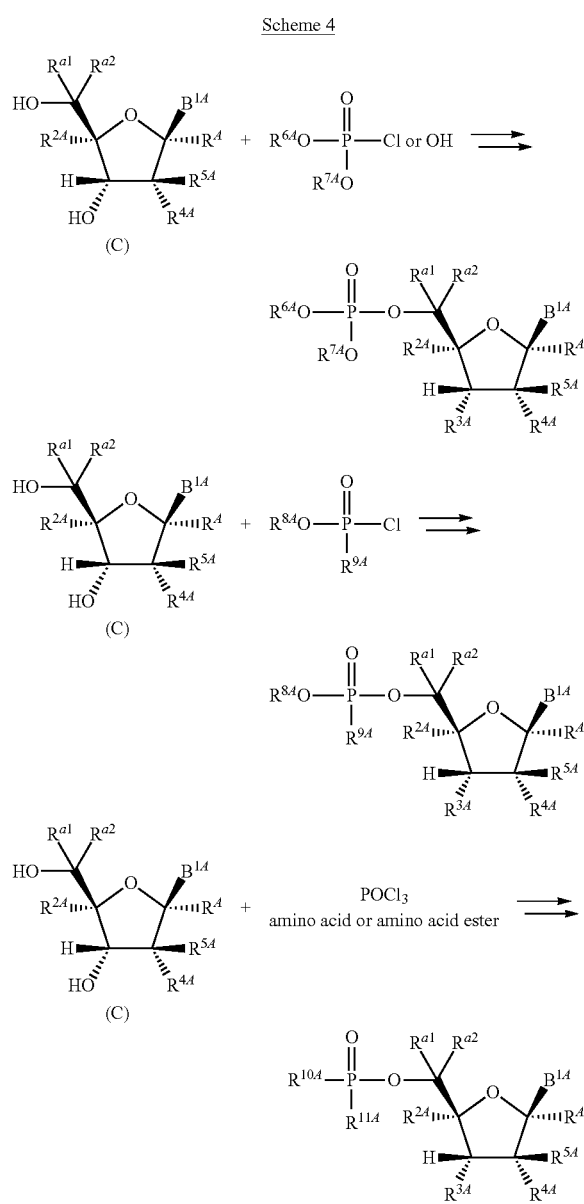

Compounds of Formula (I) having a phosphorus containing group attached to the 5'-position of the pentose ring can be prepared using various methods known to those skilled in the art. Examples of methods are shown in Schemes 3 and 4. In Schemes 3 and 4, $R^a$, $R^{2a}$, $R^{3a}$, $R^{4a}$, $R^{5a}$ and $B^{1a}$ can be the same as $R^A$, $R^{2A}$, $R^{3A}$, $R^{4A}$, $R^{5A}$ and $B^{1A}$ as described herein for Formulae (I). A phosphorus containing precursor can be coupled to the nucleoside, for example, a compound of Formula (B). Following the coupling of the phosphorus containing precursor, any leaving groups can be cleaved under suitable conditions, such as hydrolysis. Further phosphorus containing groups can be added using methods known to those skilled in the art, for example using a pyrophosphate. If desired, one or more bases can be used during the addition of each phosphorus-containing group. Examples of suitable bases are described herein.

In some embodiments, an alkoxide can be generated from a compound of Formula (C) using an organometallic reagent, such as a Grignard reagent. The alkoxide can be coupled to the phosphorus containing precursor. Suitable Grignard reagents are known to those skilled in the art and include, but are not limited to, alkylmagnesium chlorides and alkylmagnesium bromides. In some embodiments, an appropriate base can be used. Examples of suitable bases include, but are not limited to, an amine base, such as an alkylamine (including mono-, di- and tri-alkylamines (e.g., triethylamine)), optionally substituted pyridines (e.g. collidine) and optionally substituted imidazoles (e.g., N-methylimidazole)). Alternatively, a phosphorus containing precursor can be added to the nucleoside and form a phosphite. The phosphite can be oxidized to a phosphate using conditions known to those skilled in the art. Suitable conditions include, but are not limited to, meta-chloroperoxybenzoic acid (MCPBA) and iodine as the oxidizing agent and water as the oxygen donor.

When compounds of Formula (I) have $Z^{1A}$, $Z^{2A}$ or $Z^{3A}$ being sulfur, the sulfur can be added in various manners known to those skilled in the art. In some embodiments, the sulfur can be part of the phosphorus containing precursor, for example,

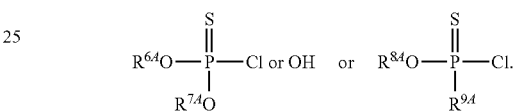

Alternatively, the sulfur can be added using a sulfurization reagent. Suitable sulfurization agents are known to those skilled in the art, and include, but are not limited to, elemental sulfur, Lawesson's reagent, cyclooctasulfur, 3H-1,2-Benzodithiole-3-one-1,1-dioxide (Beaucage's reagent), 3-((N,N-dimethylaminomethylidene)amino)-3H-1,2,4-dithiazole-5-thione (DDTT) and bis(3-triethoxysilyl)propyl-tetrasulfide (TEST).

As described herein, in some embodiments, $R^{3A}$ and $R^{4A}$ can be each an oxygen atom, wherein the oxygen atoms are linked together by a carbonyl groups. The —O—C(=O)—O— group can be formed using methods known to those skilled in the art. For example, a compound of Formula (I), wherein $R^{3A}$ and $R^{4A}$ are both hydroxy groups, can be treated with 1,1'-carbonyldiimidazole (CDI).

In some embodiments, the 2'-position and/or the 3'-position of the pentose ring can have an optionally substituted —O-acyl group attached, for example, —OC(=O)R'''$^A$. The optionally substituted —O-acyl group can be formed at the 2'- and/or 3'-position using various methods known to those skilled in the art. As an example, a compound of Formulae (I), wherein the 2'-position and the 3'-position each have an hydroxy group attached, can be treated with an alkyl anhydride (e.g., acetic anhydride and propionic anhydride) or an alkyl acid chloride (e.g., acetylchloride). If desired, a catalyst can be used to facilitate the reaction. An example of suitable catalyst is 4-dimethylaminopyridine (DMAP). Alternatively, the optionally substituted —O-acyl group group(s) can be formed at the 2'- and 3'-positions by reacting an alkyl acid (e.g. acetic acid and propionic acid) in the presences of a carbodiimide or a coupling reagent. Examples of carbodiimides include, but are not limited to, N,N'-dicyclohexylcarbodiimide (DCC), N,N'-diisopropylcarbodiimide (DIC) and 1-ethyl-3-(3-dimethylaminopropyl) carbodiimide (EDC).

To reduce the formation of side products, one or more the groups attached to the pentose ring can be protected with one or more suitable protecting groups and/or any —NH and/or NH$_2$ groups present on the B$^{1a}$, can be protected with one or more suitable protecting groups. As an example, if 2'-position and/or the 3'-position is/are hydroxy group(s), the hydroxy group(s) can be protected with suitable protecting groups, such as triarylmethyl and/or silyl groups. Examples of triarylmethyl groups include but are not limited to, trityl, monomethoxytrityl (MMTr), 4,4'-dimethoxytrityl (DMTr), 4,4',4''-trimethoxytrityl (TMTr), 4,4',4''-tris-(benzoyloxy) trityl (TBTr), 4,4',4''-tris (4,5-dichlorophthalimido) trityl (CPTr), 4,4',4''-tris (levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl) xanthen-9-yl, 1,1'-bis-(4-methoxyphenyl)-1'-pyrenylmethyl, 4,4',4''-tris-(tert-butylphenyl) methyl (TTTr) and 4,4'-di-3,5-hexadienoxytrityl. Examples of suitable silyl groups are described herein and include trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl. Alternatively, R$^{3,4}$ and/or R$^{4,4}$ can be protected by a single achiral or chiral protecting group, for example, by forming an orthoester, a cyclic acetal or a cyclic ketal. Suitable orthoesters include methoxymethylene acetal, ethoxymethylene acetal, 2-oxacyclopentylidene orthoester, dimethoxymethylene orthoester, 1-methoxyethylidene orthoester, 1-ethoxyethylidene orthoester, methylidene orthoester, phthalide orthoester 1,2-dimethoxyethylidene orthoester, and alpha-methoxybenzylidene orthoester; suitable cyclic acetals include methylene acetal, ethylidene acetal, t-butylmethylidene acetal, 3-(benzyloxy)propyl acetal, benzylidene acetal, 3,4-dimethoxybenzylidene acetal and p-acetoxybenzylidene acetal; and suitable cyclic ketals include 1-t-butylethylidene ketal, 1-phenylethylidene ketal, isopropylidene ketal, cyclopentylidene ketal, cyclohexylidene ketal, cycloheptylidene ketal and 1-(4-methoxyphenyl)ethylidene ketal.

EXAMPLES

Additional embodiments are disclosed in further detail in the following examples, which are not in any way intended to limit the scope of the claims.

Example 1

Compound 1

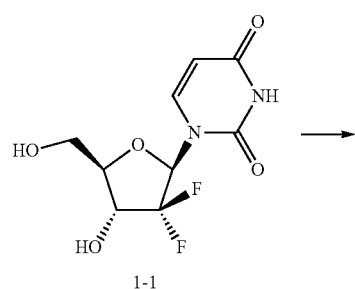

1-1

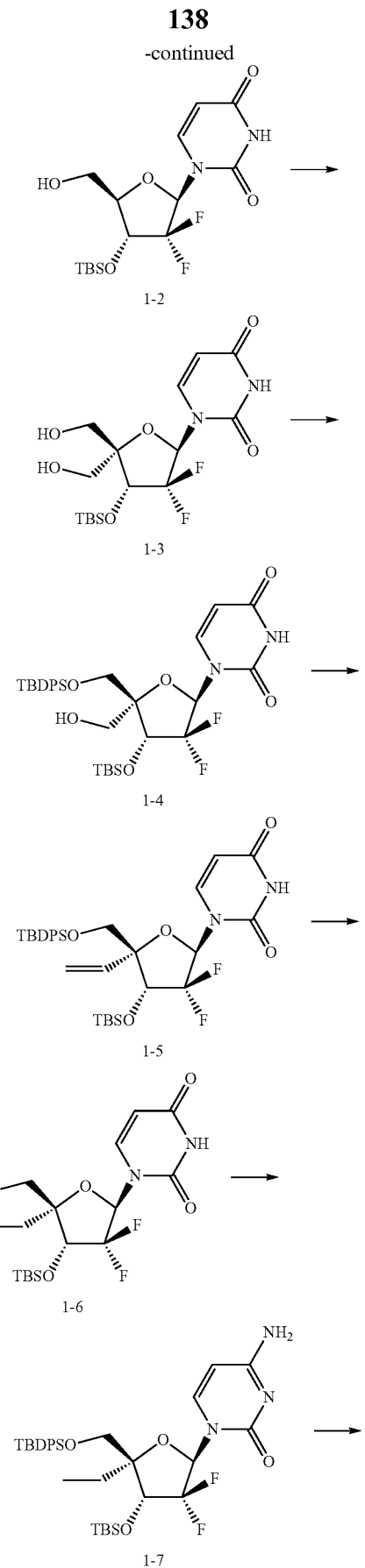

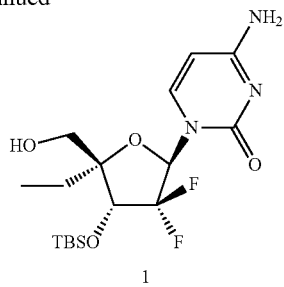

1

To a solution of 1-1 (100.0 g, 378.7 mmol) in pyridine (750 mL) was added DMTrCl (164.9 g, 487.8 mmol). The solution was stirred at RT for 15 h. MeOH (300 mL) was added, and the mixture was concentrated to dryness under reduced pressure. The residue was dissolved in EA and washed with water. The organic layer was dried over $Na_2SO_4$ and concentrated. The residue was dissolved in DCM (500 mL). To this solution were added imidazole (44.3 g, 650.4 mmol) and TBSCl (91.9 g, 609.8 mmol). The mixture was stirred at RT for 14 h. The solution was washed with $NaHCO_3$ and brine. The organic layer was dried over $Na_2SO_4$, and concentrated to give the crude product as a light yellow solid. The crude (236.4 g, 347.6 mmol) was dissolved in 80% HOAc aqueous solution (500 mL). The mixture was stirred at RT for 15 h. The mixture was diluted with EA, and washed with $NaHCO_3$ solution and brine. The organic layer was dried over $Na_2SO_4$ and purified on a silica gel column chromatography (1-2% MeOH in DCM) to give 1-2 (131.2 g, 91.9%) as a light yellow solid. ESI-MS: m/z 802 [M+H]$^+$.

To a solution of 1-2 (131.2 g, 346.9 mmol) in anhydrous $CH_3CN$ (1200 mL) was added IBX (121.2 g, 432.8 mmol) at RT. The mixture was refluxed for 3 h and then cooled to 0° C. The precipitate was filtered, and the filtrate was concentrated to give the crude aldehyde (121.3 g) as a yellow solid. The aldehyde was dissolved in 1,4-dioxane (1000 mL). 37% $CH_2O$ (81.1 mL, 1.35 mmol) and 2M NaOH aqueous solution (253.8 mL, 507.6 mmol) were added. The mixture was stirred at RT for 2 h., and then neutralized with AcOH to pH=7. To the solution were added EtOH (400 mL) and $NaBH_4$ (51.2 g, 1.35 mol). The mixture was stirred at RT for 30 mins, the reaction was quenched with sat. aq. $NH_4Cl$. The mixture was extracted with EA. The organic layer was dried over $Na_2SO_4$ and concentrated. The residue was purified by silica gel column chromatography (1-3% MeOH in DCM) to give 1-3 (51.4 g, 38.9%) as a white solid.

To a solution of 1-3 (51.4 g, 125.9 mmol) in anhydrous DCM (400 mL) were added pyridine (80 mL) and DMTrCl (49.1 g, 144.7 mmol) at 0° C. The reaction was stirred at RT for 14 h, and then treated with MeOH (30 mL). The solvent was removed, and the residue was purified by silica gel column chromatography (1-3% MeOH in DCM) to give the mono-DMTr protected intermediate as a yellow foam (57.4 g, 62.9%). The intermediate (57.4 g, 82.8 mmol) was dissolved in $CH_2Cl_2$ (400 mL), and imidazole (8.4 g, 124.2 mmol), TBDPSCl (34.1 g, 124.2 mmol) were added. The mixture was stirred at RT for 14 h. The precipitate was filtered off, and the filtrate was washed with brine and dried with $Na_2SO_4$. The solvent was removed to give a residue (72.45 g) as a white solid. The residue was dissolved in 80% HOAc aqueous solution (400 mL). The mixture was stirred RT for 15 h. The mixture was diluted with EA and washed with $NaHCO_3$ solution and brine. The organic layer was dried over $Na_2SO_4$ and purified by silica gel column chromatography (1-2% MeOH in DCM) to give 1-4 (37.6 g, 84.2%) as a white solid.

A solution of 1-4 (700 mg, 1.09 mmol) in anhydrous dichloromethane was added Dess-Martin reagent (919 mg, 2.16 mmol) at 0° C. The mixture was stirred at RT for 30 mins. The reaction was quenched with sat. sodium hydrogen carbonate and sodium thiosulfate solution, and extracted with EA. The organic layers were concentrated to give the crude aldehyde, which was used for next step without purification. A solution of $MePPh_3Br$ (3.88 g, 10.87 mmol) in anhydrous THF was treated with a solution of t-BuOK (9.81 mL, 9.81 mmol) in THF at 0° C. The mixture was warmed to RT for 1 h. After cooling to 0° C. for 1 h, a solution of the aldehyde (700 mg, 1.09 mmol) in THF was added. The mixture was stirred overnight at RT. The reaction was quenched with sat. ammonium chloride solution, and extracted with EA. The organic layers were purified by column chromatography to give 1-5 (167 mg, 30%).

To a solution of 1-5 (450 mg, 0.69 mmol) in MeOH (10 mL) was added Pd/C (200 mg) at RT. The reaction mixture was stirred at RT for 1 h under $H_2$ (balloon). Then the mixture was filtered and the filtrate was concentrated to give the crude 1-6 (440 mg, 97.1%) as a white solid.

A solution of 1-6 (317 mg, 0.49 mmol), TPSCl (373 mg, 1.23 mmol), DMAP (150 mg, 1.23 mmol) and TEA (124 mg, 1.23 mmol) in anhydrous MeCN was stirred at RT overnight. The reaction was quenched with $NH_3.H_2O$, and then stirred at RT for 3 h. The solvent was removed under reduced pressure. The residue was purified by column chromatography to give 1-7 (200 mg, 63%).

To a solution of 1-7 (280 mg, 0.44 mmol) in MeOH (10 mL) was added $NH_4F$ (1.0 g, 27.0 mmol) at RT. The mixture was refluxed for 12 h. The mixture was filtered, and the filtrate was concentrated. The residue was purified on a silica gel column (10% MeOH in DCM) to give compound 1 (81 mg, 63.3%) as a white solid. ESI-MS: m/z 291.8 [M+H]$^+$.

Example 2

Compound 2

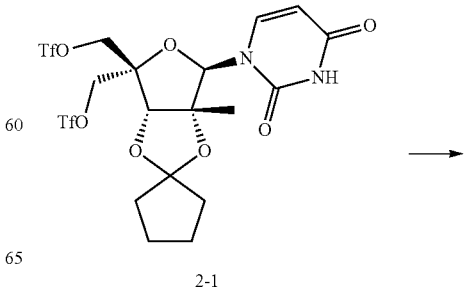

2-1

-continued

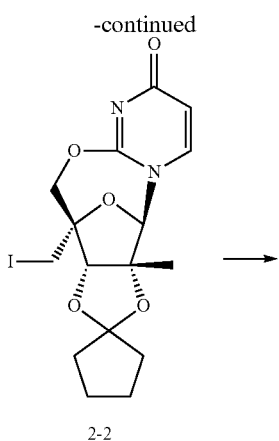

2-2

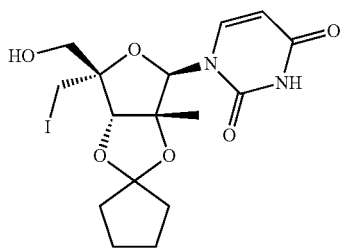

2-3

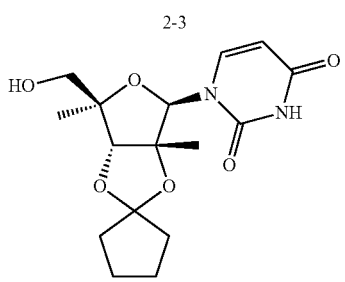

2-4

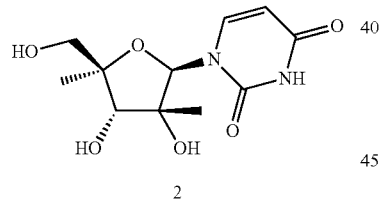

2

To a solution of 2-1 (2.5 g, 4.04 mmol) in DMF was added NaH (170 mg, 4.24 mmol, 60% purity) at 0° C. The mixture was stirred for 3 h at RT. NaI (6.1 g, 40.4 mmol) was added at RT and stirred for 3 h. The reaction was diluted with water and extracted with EA. The organic layer was dried over anhydrous $Na_2SO_4$, and concentrated at low pressure to give 2-2 (1.7 g, 94%) as a yellow solid.

To a solution of 2-2 (1.7 g, 3.81 mmol) in THF (5 mL) was added 2 M NaOH solution (4.5 mL) at 0° C. The solution was stirred for 2 h at RT. The mixture was adjusted to pH=7, and concentrated under reduced pressure. The mixture was partitioned between DCM and water. The DCM layer was dried with high vacuum to give 2-3 (1.2 g, 68%) as a white solid, which was used without further purification.

To a solution of 2-3 (1.2 g, 2.58 mmol) in EtOH (20 mL) was added $NH_4COOH$ (650 mg, 7.75 mmol) and Pd/C (120 mg). The mixture was stirred under $H_2$ (30 psi) for 1.5 h at RT. The suspension was filtered, and the filtrate was concentrated at a low pressure. The residue was purified on silica gel column (0.5% TEA and 1% MeOH in DCM) to give 2-4 (545 mg, 62%). ESI-MS: m/z 361.2 [M+23]$^+$.

Compound 2-4 was dissolved in 80% aq. HCOOH (20 mL) and kept at 20° C. for 18 h. After cooling to RT, the solvent was removed in vacuo, and the residue co-evaporated with toluene (3×25 mL). The residue was dissolved in water (3 mL) and concentrated aqueous $NH_4OH$ (1 mL) was added. After 2 h at 20° C., the solvent was removed in vacuo. The residue was purified by flash chromatography using a 5 to 50% gradient of methanol in DCM to give purified compound 2 (14 mg) as a white solid.

Example 3

Compound 4

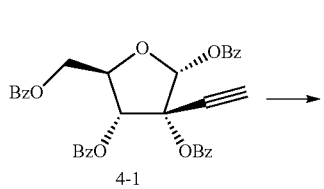

4-1

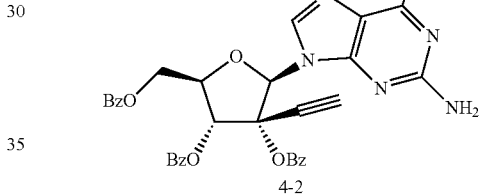

4-2

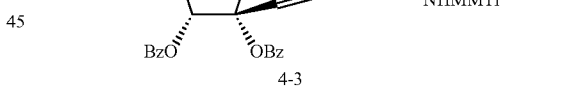

4-3

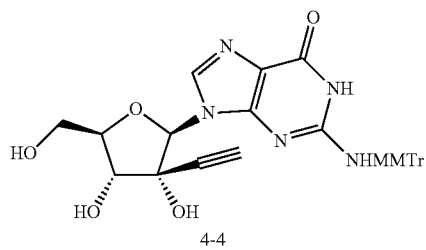

4-4

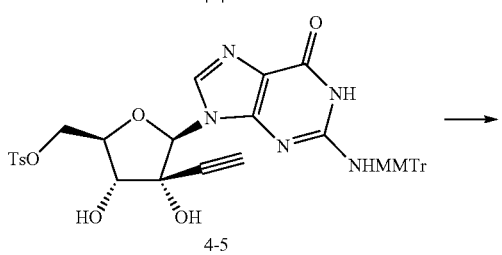

4-5

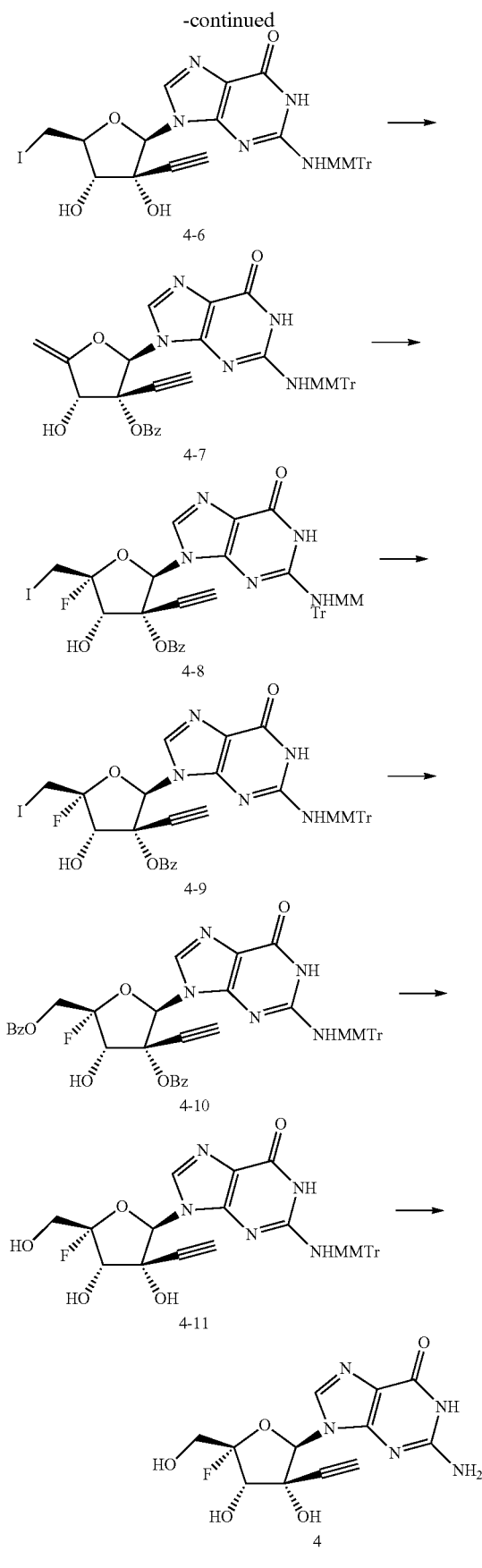

Compound 4-1 (5.0 g, 8.5 mmol) and 2-amino-6-chloropurine (3.0 g, 17.7 mmol) were co-concentrated with anhydrous toluene for 3 times. To a stirred suspension of the mixture in anhydrous MeCN (50 mL) was added DBU (7.5 g, 49 mmol) at 0° C. The mixture was stirred at 0° C. for 15 mins, and TMSOTf (15 g, 67.6 mmol) was added dropwise at 0° C. The mixture was stirred at 0° C. for 15 mins and then heated to 70° C. overnight. The mixture was cooled to RT, and diluted with EA (100 mL). The solution was washed with sat. NaHCO$_3$ solution and brine. The organic layer was dried over Na$_2$SO$_4$ and then concentrated at low pressure. The residue was purified by column on silica gel (PE/EA: from 15/1 to 3/1) to give 4-2 (2.5 g, 46.3%) as a white foam.

To a solution of 4-2 (10 g, 15.7 mmol), AgNO$_3$ (8.0 g, 47 mmol) and collidine (10 mL) in anhydrous DCM (20 mL) was added MMTrCl (14.5 g, 47 mmol) in small portions under N$_2$. The mixture was stirred at RT overnight. The mixture was filtered, and the filtrate was washed with sat. NaHCO$_3$ aqueous and brine. The organic layer was dried over anhydrous Na$_2$SO$_4$, and concentrated at low pressure. The residue was purified by silica gel column (PE/ME=20/1 to 8/1) to give 4-3 (10 g, 70%) as a yellow solid.

To a solution of 3-hydroxy-propionitrile (3.51 g, 49.4 mmol) in anhydrous THF (100 mL) was added NaH (2.8 g, 70 mmol) at 0° C., and the mixture was stirred at RT for 30 mins. To the mixture was added a solution of 4-3 (8.5 g, 9.35 mmol) in anhydrous THF (100 mL) at 0° C., and the reaction mixture was stirred at RT overnight. The reaction was quenched by water, and extracted with EA (100 mL). The organic layer was dried over anhydrous Na$_2$SO$_4$, and concentrated at low pressure. The residue was purified by silica gel column (DCM/MeOH=100/1 to 20/1) to give 4-4 (4.5 g, 83%) as a white solid.

Compound 4-4 (1.5 g, 2.6 mmol) was co-concentrated with anhydrous pyridine 3 times. To an ice cooled solution of 4-4 in anhydrous pyridine (30 mL) was added TsCl (1.086 g, 5.7 mmol), and the reaction mixture was stirred at 0° C. for 1 h. The reaction was quenched with water, and extracted with EA (80 mL). The organic layer was dried over anhydrous Na$_2$SO$_4$, and concentrated at low pressure. The residue was purified by silica gel column (DCM/MeOH=100/1 to 15/1) to give 4-5 (1.4 g, 73%) as a white solid.

To a solution of 4-5 (4.22 g, 5.7 mmol) in acetone (60 mL) was added NaI (3.45 g, 23 mmol), and the mixture was refluxed overnight. The reaction was quenched by sat. Na$_2$S$_2$O$_3$ aqueous, and then extracted with EA (100 mL). The organic layer was dried over anhydrous Na$_2$SO$_4$, and concentrated at low pressure. The residue was purified by silica gel column (DCM/MeOH=100/1 to 15/1) to give 4-6 (4 g, 73%) as a white solid.

To a solution of 4-6 (4.0 g, 5.8 mmol) in anhydrous THF (60 mL) was added DBU (3.67 g, 24 mmol), and the mixture was stirred at 60° C. overnight. The mixture was diluted with EA (80 mL). The solution was washed with brine. The organic layer was dried over anhydrous Na$_2$SO$_4$, and concentrated at low pressure. The residue was purified by silica gel column (DCM/MeOH=100/1 to 20/1) to give 4-7 (2 g, 61%) as a white solid.

To an ice cooled solution of 4-7 (500 mg, 0.89 mmol) in anhydrous DCM (20 mL) was added AgF (618 mg, 4.9 mmol) and a solution of I$_2$ (500 mg, 1.97 mmol) in anhydrous DCM (20 mL). The mixture was stirred at RT for 3 h. The reaction was quenched with sat Na$_2$S$_2$O$_3$ and NaHCO$_3$ aqueous, and the mixture was extracted with DCM (50 mL). The organic layer was separated, dried over anhydrous Na$_2$SO$_4$, and concentrated to give crude 4-8 (250 mg, crude) as a yellow solid.

To a solution of crude 4-8 (900 mg, 1.28 mmol) in anhydrous DCM (50 mL) was added DMAP (1.0 g, 8.2 mmol) and BzCl (795 mg, 5.66 mmol). The mixture was stirred at RT overnight. The mixture was washed with sat. NaHCO$_3$ aq. and brine. The organic layer was dried over anhydrous Na$_2$SO$_4$, and concentrated at low pressure. The residue was purified by prep-TLC (DCM/MeOH=15:1) to give 4-9 (300 mg, 26%) as a white solid.

To a solution of crude 4-9 (750 mg, 0.82 mmol) in anhydrous HMPA (20 mL) was added NaOBz (1.2 g, 8.3 mmol) and 15-crown-5 (1.8 g, 8.3 mmol). The mixture was stirred at 60° C. for 2 d. The mixture was diluted with EA, and the solution was washed with brine. The organic layer was dried over anhydrous Na$_2$SO$_4$, and concentrated at low pressure. The residue was purified by prep-TLC (PE/EA=1:1) to give crude 4-10 (550 mg, 73%) as a white solid.

Crude 4-10 (550 mg, 0.6 mmol) was dissolved in NH$_3$/MeOH (7N, 50 mL). The mixture was stirred at RT overnight. The mixture was concentrated, and the residue was purified by silica gel column (DCM/MeOH from 100/1 to 20/1) to give 4-11 (62 mg, 17%) as white solid. ESI-MS: m/z 598.0 [M+H]$^+$.

A solution of 4-11 (12 mg) in 80% formic acid (0.5 mL) stood at RT for 3.5 h and then was concentrated. The residue was co-evaporated with MeOH/toluene 4 times in a vial, then triturated with EtOAc at 40° C. The EtOAc solution removed with pippet, and the trituration step was repeated several times. The remaining solid was dissolved in MeOH. The solution was concentrated and dried to give compound 4 (4.7 mg) as an off white solid. ESI-MS: m/z 326.6 [M+H]$^+$.

Example 4

Compound 5

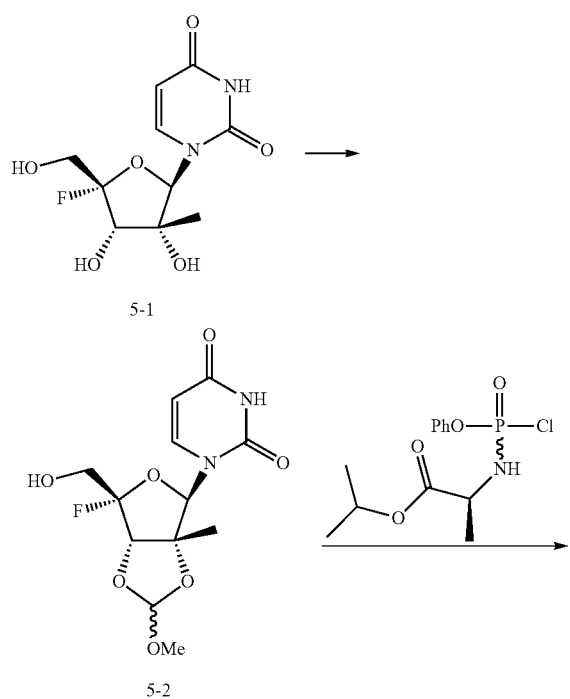

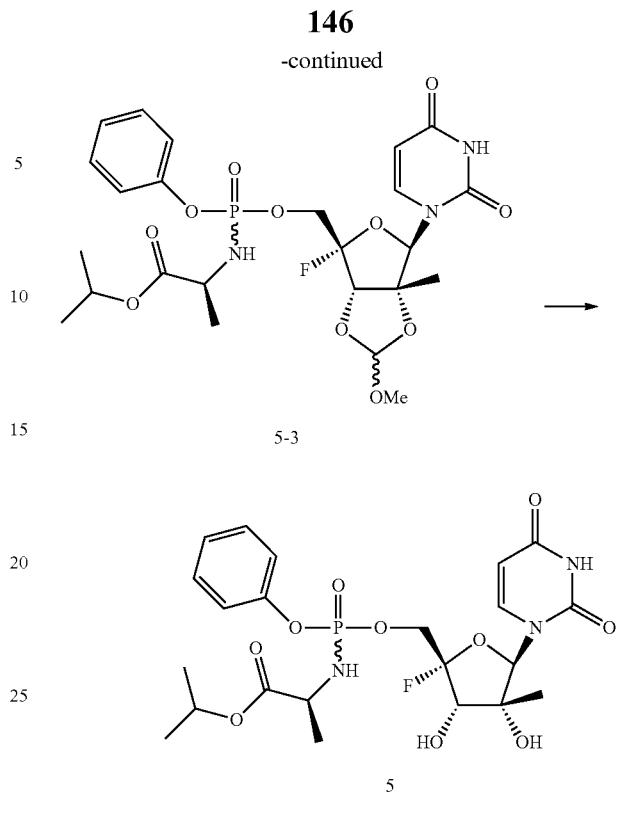

To a solution of 5-1 (1.2 g; 4.3 mmol) in dioxane (30 mL) were added p-toluenesulphonic acid monohydrate (820 mg; 1 eq.) and trimethyl orthoformate (14 mL; 30 eq.). The mixture was stirred overnight at RT. The mixture was then neutralized with methanolic ammonia and the solvent evaporated. Purification on silica gel column with CH$_2$Cl$_2$-MeOH solvent system (4-10% gradient) yielded 5-2 (1.18 g, 87%).

To an ice cooled solution of 5-2 (0.91 g; 2.9 mmol) in anhydrous THF (20 mL) was added iso-propylmagnesium chloride (2.1 mL; 2 M in THF). The mixture stirred at 0° C. for 20 mins. A solution of phosphorochloridate reagent (2.2 g; 2.5 eq.) in THF (2 mL) was added dropwise. The mixture stirred overnight at RT. The reaction was quenched with saturated aq. NH$_4$Cl solution and stirred at RT. for 10 mins. The mixture was then diluted with water and CH$_2$Cl$_2$, and the two layers were separated. The organic layer was washed with water, half saturated aq. NaHCO$_3$ and brine, and dried with Na$_2$SO$_4$. The evaporated residue was purified on silica gel column with CH$_2$Cl$_2$-iPrOH solvent system (4-10% gradient) to yield Rp/Sp-mixture of 5-3 (1.59 g; 93%).

A mixture of 5-3 (1.45 g; 2.45 mmol) and 80% aq. HCOOH (7 mL) was stirred at RT. for 1.5 h. The solvent was evaporated and coevaporated with toluene. The obtained residue was dissolved in MeOH, treated with Et$_3$N (3 drops) and the solvent was evaporated. Purification on silica gel column with CH$_2$Cl$_2$-MeOH solvent system (4-10% gradient) yielded Rp/Sp-mixture of compound 5 (950 mg; 70%). $^{31}$P-NMR (DMSO-d$_6$): δ 3.52, 3.37. MS: m/z=544 [M−1].

Example 5

Compound 6

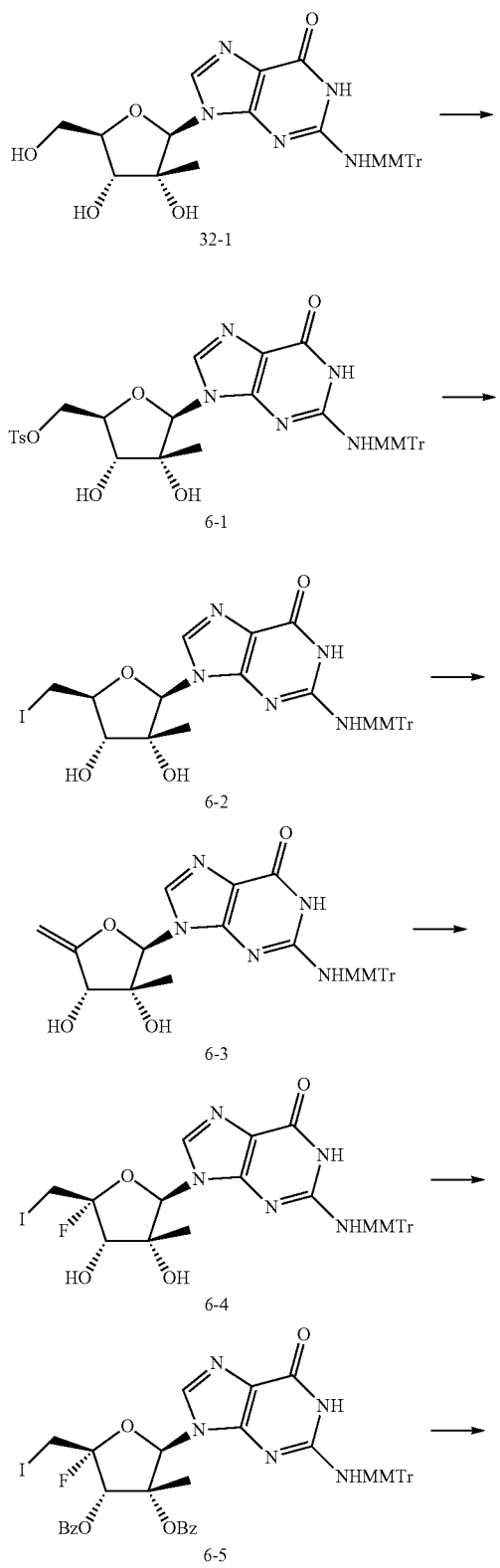

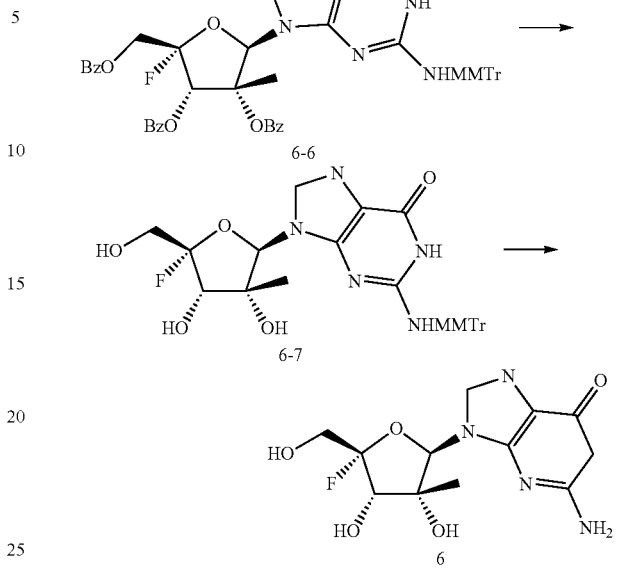

Compound 32-1 (5 g, 8.79 mmol) was co-evaporated with anhydrous pyridine. To an ice cooled solution of 32-1 in anhydrous pyridine (15 mL) was added TsCl (3.43 g, 17.58 mmol), and stirred for 1 h at 0° C. The reaction was checked by LCMS and TLC. The reaction was quenched with $H_2O$, and extracted with EA. The organic phase was dried over anhydrous $Na_2SO_4$, and evaporated at low pressure. Compound 6-1 (6.35 g, 100%) was used for next step directly.

To a solution of 6-1 (31.77 g, 43.94 mmol) in acetone (300 mL) was added NaI (65.86 g, 439.4 mmol), and heated to reflux overnight. The reaction was checked by LCMS. The reaction was quenched with sat. $Na_2S_2O_3$ solution, and extracted with EA. The organic layer was dried over anhydrous $Na_2SO_4$, and evaporated at low pressure. The residue was purified by silica gel column chromatography (MeOH in DCM from 1% to 6%) to give 6-2 (11.5 g, 38%) as a white solid.

To a solution of 6-2 (11.5 g, 16.94 mmol) in dry THF (120 mL) was added DBU (12.87 g, 84.68 mmol), and heated to 60° C. The reaction was stirred overnight and checked by LCMS. The reaction was quenched with sat. $NaHCO_3$ solution, and extracted with EA. The organic phase was dried over anhydrous $Na_2SO_4$, and evaporated at low pressure. The residue was purified by silica gel column chromatography (MeOH in DCM from 1% to 5%) to give 6-3 (5.5 g, 54%) as a white solid.

To an ice cooled solution of 6-3 (500 mg, 0.90 mmol) in dry DCM (20 mL) was added AgF (618 mg, 4.9 mmol) and a solution of $I_2$ (500 mg, 1.97 mmol) in dry DCM (20 mL). The reaction was stirred for 3 h., and checked by LCMS. The reaction was quenched with sat $Na_2S_2O_3$ solution and sat. $NaHCO_3$ solution, and the mixture was extracted with DCM. The organic layer was dried by anhydrous $Na_2SO_4$, and evaporated at low pressure to give crude 6-4 (420 mg, 66%).

To a solution of crude 6-4 (250 mg, 0.36 mmol) in dry DCM (8 mL) was added DMAP (0.28 g, 2.33 mmol), TEA (145 mg, 1.44 mmol) and BzCl (230 mg, 1.62 mmol) in a solution of DCM (2 mL). The reaction was stirred overnight, and checked by LCMS. The mixture was washed with sat. $NaHCO_3$ solution and brine. The organic layer was evaporated at low pressure. The residue was purified by prep-TLC to give crude 6-5 (150 mg, 46%).

To a solution of crude 6-5 (650 mg, 0.72 mmol) in dry HMPA (20 mL) was added NaOBz (1.03 g, 7.2 mmol) and 15-crown-5 (1.59 g, 7.2 mmol). The reaction was stirred for 2 d at 60° C. The mixture was diluted with H$_2$O, and extracted with EA. The organic layer was evaporated at low pressure. The residue was purified by prep-TLC to give 6-6 (210 mg, 32.4%). ESI-MS: m/z: 900.4 [M+H]$^+$.

A mixture of 6-6 (25 mg) and BuNH$_2$ (0.8 mL) was stirred overnight at RT. The mixture was evaporated and purified on silica gel (10 g column) with CH$_2$Cl$_2$/MeOH (4-15% gradient) to yield 6-7 (15 mg, 91%).

A mixture of 6-7 (15 mg, 0.02 mmol) in ACN (0.25 mL) and 4 N HCL/dioxane (19 μL) was stirred at RT for 45 mins. The mixture was diluted with MeOH and evaporated. The crude residue was treated with MeCN, and the solid was filtered to yield compound 6 (7 mg). MS: m/z=314 [M−1].

Example 6

Compound 7

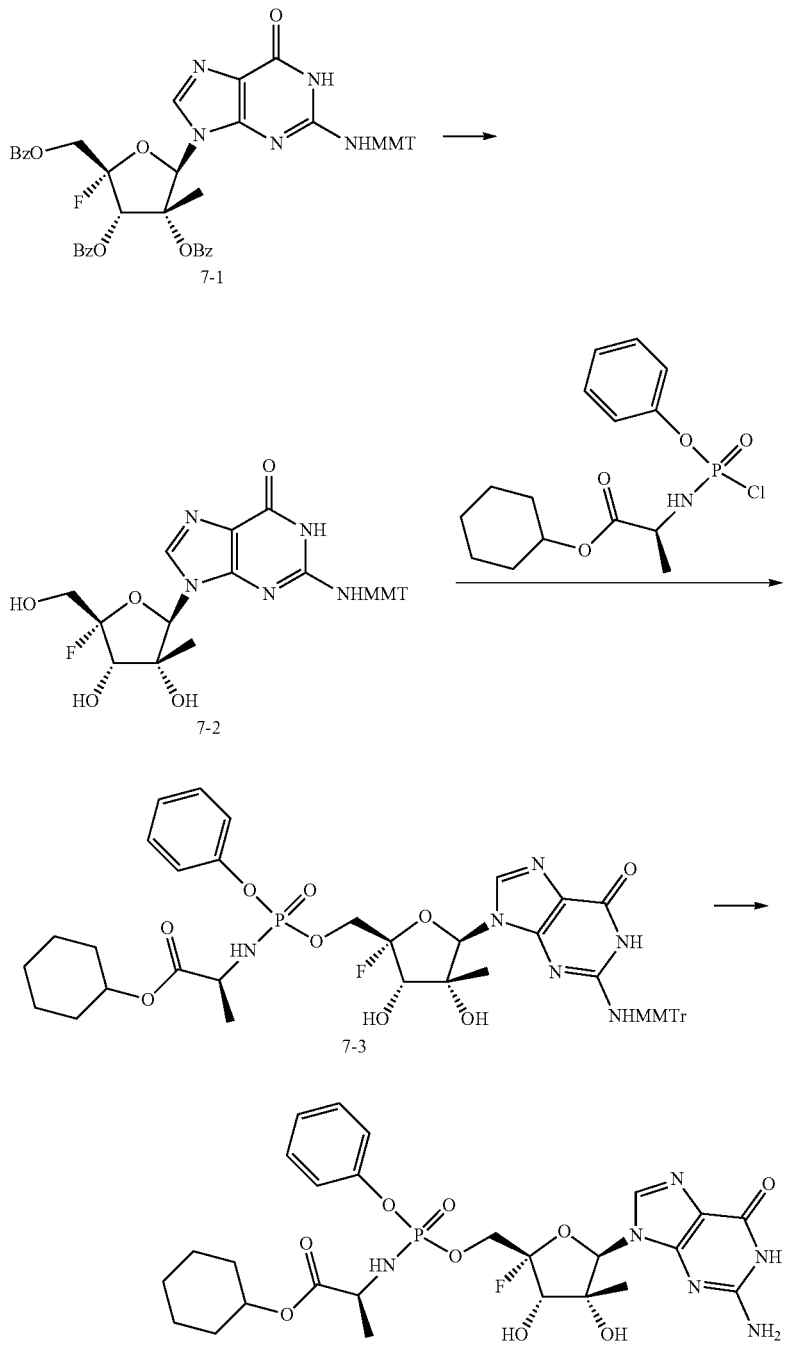

A mixture of 7-1 (170 mg, 0.19 mmol) and methanolic ammonia (7 N; 3 mL) was stirred at RT for 8 h, concentrated and purified on silica gel (10 g column) with CH$_2$Cl$_2$/MeOH (4-11% gradient) to give 7-2 (100 mg, 90%).

Compound 7-2 was rendered anhydrous by co-evaporating with pyridine, followed by toluene. To a solution of 7-2 (24 mg, 0.04 mmol), and N-methylimidazole (17 µL, 5 eq.) in acetonitrile (1 mL) was added the phosphorochloridate (50 mg, 3.5 eq.) in 2 portions in 6 h intervals. The mixture was stirred at RT for 1 d and evaporated. Purification on silica (10 g column) with CH$_2$Cl$_2$/MeOH (4-12% gradient) yielded 7-3 (10 mg, 28%).

A solution of 7-3 (9 mg, 0.01 mmol) in 80% formic acid was stirred 3 h at RT. The mixture was evaporated and purified on silica (10 g column) with CH$_2$Cl$_2$/MeOH (5-15% gradient) to give compound 7 (3 mg, 50%). MS: m/z=624 [M−1].

Example 7

Compound 8

To an ice cooled solution of 8-1 (80 mg; 015 mmol) in anhydrous THF (2 mL) was added isopropylmagnesium chloride (0.22 mL; 2 M in THF). The mixture stirred at 0° C. for 20 mins. A solution of the phosphorochloridate reagent (0.16 g; 0.45 mmol) in THF (0.5 mL) was added dropwise. The mixture stirred overnight at RT. The reaction was quenched with saturated aq. NH$_4$Cl solution and stirred at RT for 10 mins. The mixture was diluted with water and CH$_2$Cl$_2$, and the two layers were separated. The organic layer was washed with water, half saturated aq. NaHCO$_3$ and brine, and dried with Na$_2$SO$_4$. The evaporated residue was purified on silica gel column with CH$_2$Cl$_2$-MeOH solvent system (2-10% gradient) to yield Rp/Sp-mixture of 8-2 (102 mg; 80%).

A mixture of 8-2 (100 mg; 0.12 mmol) in EtOH (3 mL) and 10% Pd/C (10 mg) was stirred under the H$_2$ atmosphere for 1.5 h. The mixture was filtered through a Celite pad, evaporated and purified on silica gel column with CH$_2$Cl$_2$-MeOH solvent system (4-10% gradient) to yield Rp/Sp-mixture of compound 8 (52 mg, 74%). MS: m/z=584 [M−1].

Example 8

Compound 9

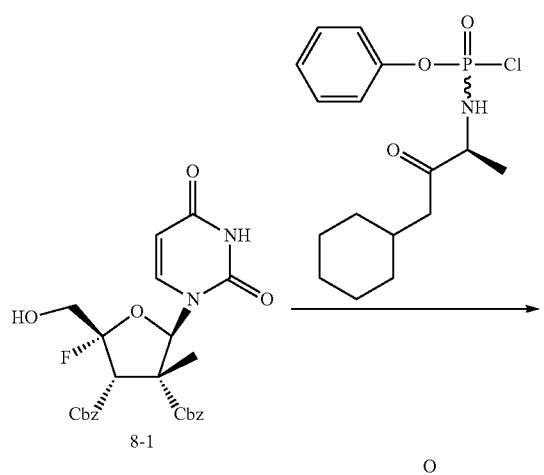

8-1

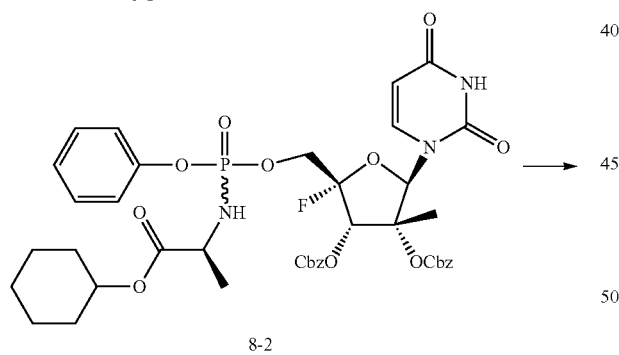

8-2

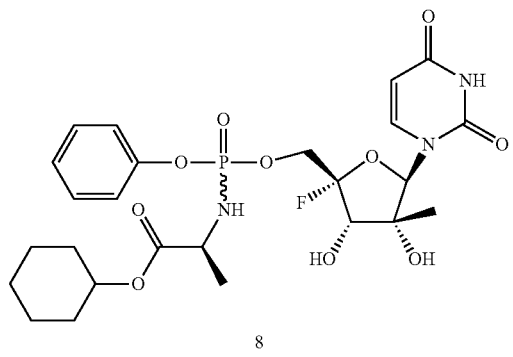

8

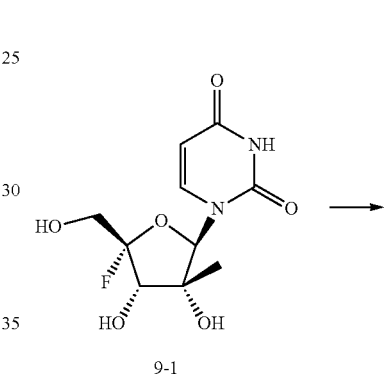

9-1

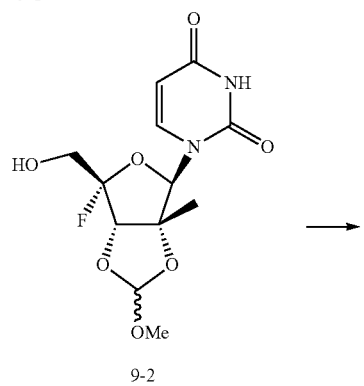

9-2

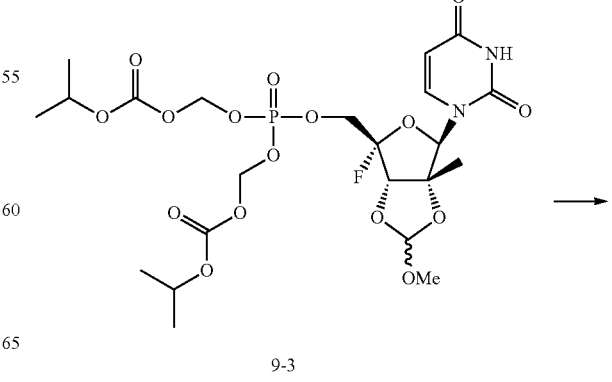

9-3

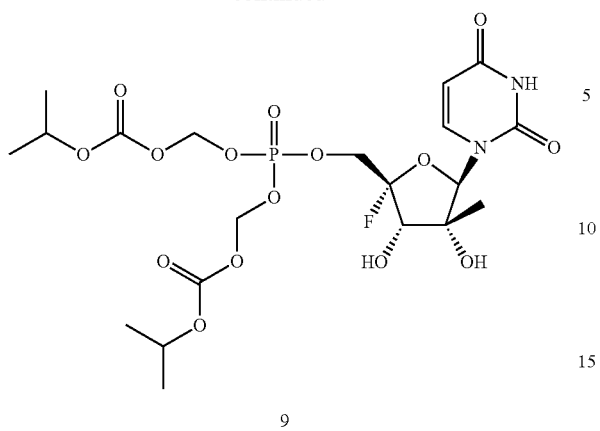

9

A mixture of 9-1 (1.2 g, 4.3 mmol), PTSA monohydrate (0.82 g, 1 eq.), and trimethyl orthoformate (14 mL, 30 eq.) in dioxane (30 mL) was stirred overnight at RT. The reaction was neutralized with 7 N NH$_3$/MeOH and a white solid removed by filtration. The residue was dissolved in THF (10 mL) and treated with 80% aq. AcOH (5 mL). The mixture was kept at RT for 45 mins and then evaporated. The residue was purified on silica gel (25 g column) with CH$_2$Cl$_2$/MeOH (4-10% gradient) to give 9-2 (1.18 g, 87%).

Compound 9-3 (137 mg, 75%) was prepared from 9-2 (93 mg, 0.29 mmol) and triethylammonium bis(isopropyloxy-carbonyloxymethyl)phosphate (0.44 mmol) with DIPEA (0.2 mL), BopCl (147 mg), and 3-nitro-1,2,4-triazole (66 mg) in THF (3 mL). Purification was done with CH$_2$Cl$_2$/i-PrOH solvent system (3-10% gradient).

A solution of 9-3 (137 mg) in 80% aq. HCOOH was stirred at RT for 2 h, and then concentrated. The residue was co-evaporated with toluene and then MeOH containing a small amount of a small amount of Et$_3$N (2 drops). Purification on silica (25 g column) with CH$_2$Cl$_2$/MeOH (4-10% gradient) gave compound 9 (100 mg, 77%). MS: m/z=1175 (2M−1).

Example 9

Compound 10

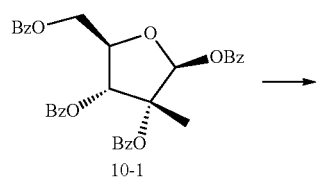

10-1

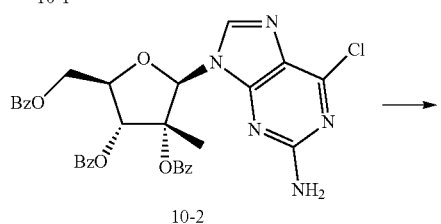

10-2

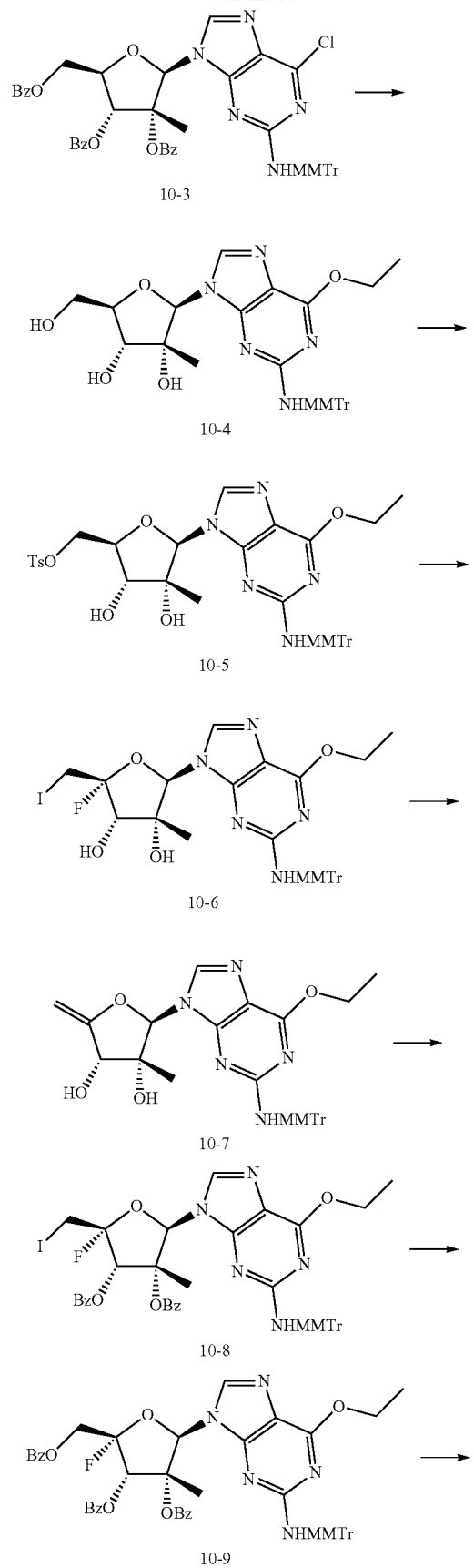

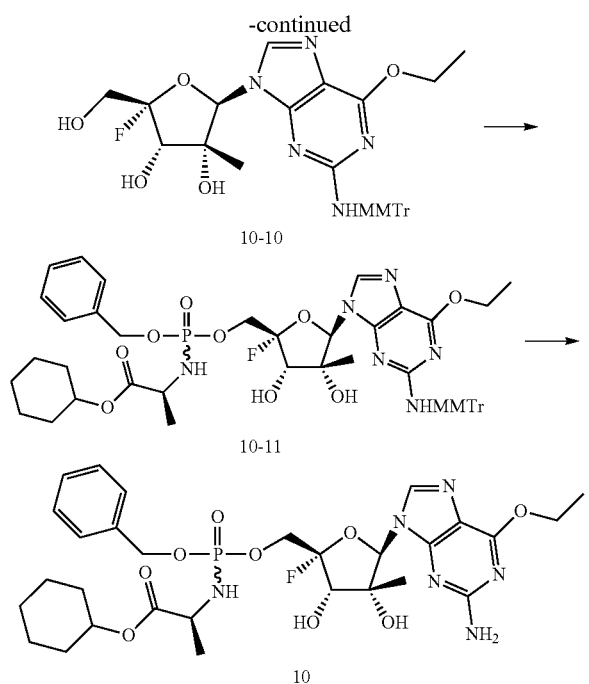

10-10

10-11

10

Compound 10-1 (50 g, 86.0 mmol) and 6-Cl-guanine (16.1 g, 98.2 mmol) were co-evaporated with anhydrous toluene 3 times. To a solution of 10-1 in MeCN (200 mL) was added DBU (39.5 g, 258.0 mmol) at 0° C. The mixture was stirred at 0° C. for 30 mins, and then TMSOTf (95.5 g, 430.0 mmol) was added dropwise at 0° C. The mixture was stirred at 0° C. for 30 mins. The mixture was heated to 70° C., and stirred overnight. The solution was cooled to RT and diluted with EA (100 mL). The solution was washed with sat. NaHCO$_3$ solution and brine. The organic layer was dried over Na$_2$SO$_4$, and concentrated at low pressure. The residue was purified by column on silica gel (EA in PE from 10% to 40%) to give 10-2 (48.0 g, yield: 88.7%) as a yellow foam. ESI-MS: m/z 628 [M+H]$^+$.

To a solution of 10-2 (48.0 g, 76.4 mol), AgNO$_3$ (50.0 g, 294.1 mmol) and collidine (40 mL) in anhydrous DCM (200 mL) was added MMTrCl (46.0 g, 149.2 mmol) in small portions under N$_2$. The mixture was stirred at RT for 3 h under N$_2$. The reaction was monitored by TLC. The mixture was filtered, and the filter was washed with sat. NaHCO$_3$ solution and brine. The organic layer was dried over anhydrous Na$_2$SO$_4$, and concentrated at low pressure. The residue was purified by silica gel column (EA in PE from 5% to 50%) to the give crude 10-3 (68 g, 98%). ESI-MS: m/z 900.1 [M+H]$^+$.

Sodium (8.7 g, 378.0 mmol) was dissolved in dry EtOH (100 mL) at 0° C., and slowly warmed to RT. Compound 10-3 (68.0 g, 75.6 mmol) was treated with freshly prepared NaOEt solution, and stirred overnight at RT. The reaction was monitored by TLC, and the mixture was concentrated at low pressure. The mixture was diluted with H$_2$O (100 mL), and extracted with EA (3×100 mL). The organic layer was dried over anhydrous Na$_2$SO$_4$, and evaporated at low pressure. The residue was purified by silica gel column chromatography (MeOH in DCM from 1% to 5%) to give 10-4 (34.0 g, 75.2%) as a yellow solid. ESI-MS: m/z 598 [M+H]$^+$.

Compound 10-4 (32.0 g, 53.5 mmol) was co-evaporated with anhydrous pyridine 3 times. To an ice cooled solution of 10-4 in anhydrous pyridine (100 mL) was added TsCl (11.2 g, 58.9 mmol) in pyridine (50 mL) dropwise at 0° C. The mixture was stirred for 18 h. at 0° C. The reaction was checked by LCMS (about 70% was the desired product). The reaction was quenched with H$_2$O, and the solution was concentrated at low pressure. The residue was dissolved in EA (100 mL), and washed with sat. NaHCO$_3$ solution. The organic layer was dried over anhydrous Na$_2$SO$_4$, and evaporated at low pressure. The residue was purified by silica gel column chromatography (MeOH in DCM from 1% to 5%) to give crude 10-5 (25.0 g, 62.2%) as a yellow solid. ESI-MS: m/z 752 [M+H]$^+$.

To a solution of 10-5 (23.0 g, 30.6 mmol) in acetone (150 mL) was added NaI (45.9 g, 306.0 mmol) and TBAI (2.0 g), and refluxed overnight. The reaction was monitored by LCMS. After the reaction was complete, the mixture was concentrated at low pressure. The residue was dissolved in EA (100 mL), washed with brine, and dried over anhydrous Na$_2$SO$_4$. The organic solution was evaporated at low pressure. The residue was purified by silica gel column chromatography (DCM:MeOH=100:1 to 20:1) to give the crude product. To a solution of the crude product in dry THF (200 mL) was added DBU (14.0 g, 91.8 mmol), and heated to 60° C. The mixture was stirred overnight, and checked by LCMS. The reaction was quenched with sat. NaHCO$_3$, and the solution was extracted with EA (100 mL). The organic layer was dried over anhydrous Na$_2$SO$_4$, and evaporated at low pressure. The residue was purified by silica gel column chromatography (MeOH in DCM from 1% to 5%) to give 10-6 (12.0 g, 67.4%) as a yellow solid. ESI-MS: m/z 580 [M+H]$^+$.

To an ice cooled solution of 10-6 (8.0 g, 13.8 mmol) in dry MeCN (100 mL) was added NIS (3.9 g, 17.2 mmol) and TEA.3HF (3.3 g, 20.7 mmol) at 0° C. The mixture was stirred at RT for 18 h and checked by LCMS. After the reaction was complete, the reaction was quenched with sat Na$_2$SO$_3$ and sat. NaHCO$_3$ solution. The solution was extracted with EA. The organic layer was dried over anhydrous Na$_2$SO$_4$, and evaporated at low pressure. The residue was purified by silica gel column chromatography (EA in PE from 10% to 50%) to give 10-7 (7.2 g, 72.0%) as a solid. ESI-MS: m/z 726 [M+H]$^+$.

To a solution of crude 10-7 (7.2 g, 9.9 mmol) in dry DCM (100 mL) was added DMAP (3.6 g, 29.8 mmol), and BzCl (2.8 g, 19.8 mmol) at 0° C. The mixture was stirred overnight, and checked by LCMS. The mixture was washed with sat. NaHCO$_3$ solution. The organic layer was dried over anhydrous Na$_2$SO$_4$, and evaporated at low pressure. The residue was purified by silica gel column chromatography (EA in PE from 10% to 30%) to give 10-8 (8.0 g, 86.4%) as a solid. ESI-MS: m/z 934 [M+H]$^+$.

To a solution of 10-8 (7.5 g, 8.0 mmol) in dry DMF (100 mL) was added NaOBz (11.5 g, 80.0 mmol) and 15-crown-5 (15.6 mL). The mixture was stirred for 36 h. at 90° C. The mixture was diluted with H$_2$O (100 mL), and extracted with EA (3×150 mL). The organic layer was dried over anhydrous Na$_2$SO$_4$, and evaporated at low pressure. The residue was purified by silica gel column chromatography (EA in PE from 10% to 30%) to give crude 10-9 (6.0 g, 80.0%) as a solid. ESI-MS: m/z 928 [M+H]$^+$.

Compound 10-9 (4.0 g, 4.3 mmol) was co-evaporated with anhydrous toluene 3 times, and treated with NH$_3$/MeOH (50 mL, 4N) at RT. The mixture was stirred for 18 h at RT. The reaction was monitored by LCMS, and the mixture was concentrated at low pressure. The residue was purified by silica gel column chromatography (EA in PE from 30% to 50%) to give 10-10 (1.9 g, 71.7%) as a solid. ESI-MS: m/z 616 [M+H]$^+$.

Compound 10-10 (300.0 mg, 0.49 mmol) was co-evaporated with anhydrous toluene 3 times, and was dissolved in MeCN (2 mL). The mixture was treated with NMI (120.5 mg, 1.47 mmol) and the phosphorochloridate reagent (338.1 mg, 0.98 mmol) in MeCN (1 mL) at 0° C. The mixture was stirred for 18 h at RT. The reaction was monitored by LCMS. The mixture was diluted with 10% NaHCO$_3$ solution, and extracted with EA. The residue was purified by silica gel column chromatography (EA in PE from 30% to 50%) to give 10-11 (240 mg, 53.3%) as a solid. ESI-MS: m/z 925 [M+H]$^+$.

Compound 10-11 (240.0 mg, 0.26 mmol) was treated with 80% AcOH (10 mL), and the mixture was stirred for 18 h at RT. The reaction was monitored by LCMS. The mixture was concentrated at low pressure. The residue was purified by silica gel column chromatography (MeOH in DCM from 1% to 3%) to give compound 10 (87.6 mg, 51.7%) as a solid. ESI-MS: m/z 653 [M+H]$^+$.

Example 10

Compound 12

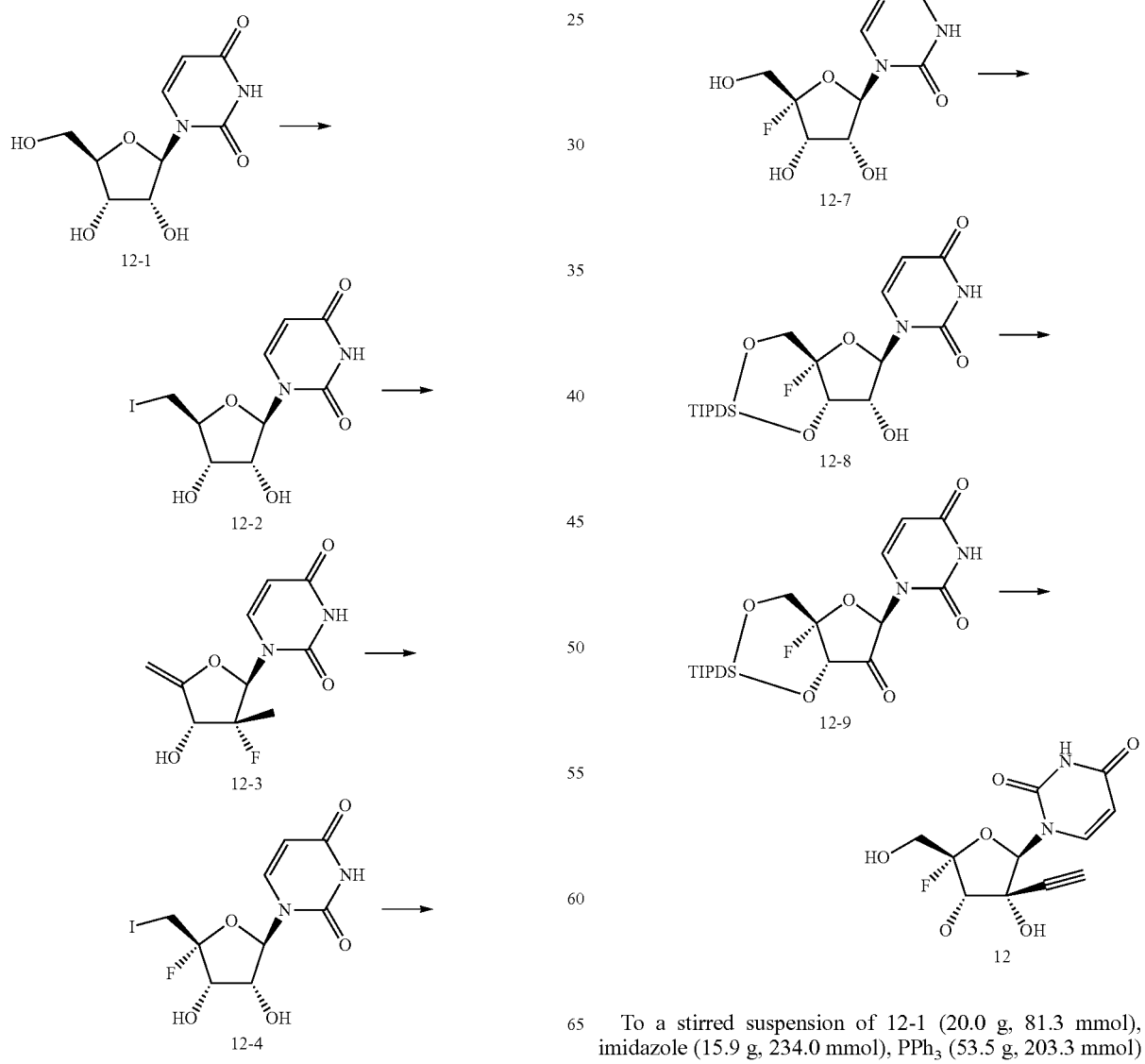

To a stirred suspension of 12-1 (20.0 g, 81.3 mmol), imidazole (15.9 g, 234.0 mmol), PPh$_3$ (53.5 g, 203.3 mmol) and pyridine (90 mL) in anhydrous THF (100 mL) was added a solution of I$_2$ (41.3 g, 162.6 mmol) in THF (150 mL) dropwise at 0° C. The mixture was slowly warmed to RT and stirred for 14 h. The reaction was quenched with sat. aq. Na$_2$S$_2$O$_3$ (150 mL) and extracted with THF/EA (1/1) (100 mL×3). The organic layer was dried over Na$_2$SO$_4$, and concentrated at a low pressure. The residue was recrystallized from EtOH to afford pure 12-2 (23 g, 79%) as a white solid.

To a stirred solution of 12-2 (23 g, 65 mmol) in anhydrous MeOH (200 mL) was added NaOCH$_3$ (10.5 g, 195 mmol) in MeOH (50 mL) at RT. The mixture was stirred at 60° C. for 3 h, and quenched with dry ice. A solid precipitated and removed by filtration. The filtrate was concentrated at a low pressure. The residue was purified on column silica gel column (MeOH in DCM from 1% to 10%) to provide 12-3 (13.1 g, 92.5%) as a white foam solid.

To a stirred solution of 12-3 (12.0 g, 53 mmol) in anhydrous CH$_3$CN was added TEA.3HF (8.5 g, 53 mmol) and NIS (10.2 g, 63.6 mmol) at 0° C. The mixture was stirred for 30 mins, and slowly warmed to RT. The mixture was stirred for another 30 mins. The solid was removed by filtration, and washed with DCM to give 12-4 (14 g, 73%) as a yellow solid. ESI-MS: m/z 373.0 [M+H]$^+$.

To a stirred solution of 12-4 (12.0 g, 32 mmol) and DMAP (1.2 g, 9.6 mmol) in pyridine (100 mL) was added Bz$_2$O (21.7 g, 96 mmol) at RT. The mixture was stirred at 50° C. for 16 h. The resulting solution was quenched with water, and concentrated to dryness at low pressure. The crude was purified on silica gel column (50% EA in PE) to give 12-5 (15 g, 81%) as a white solid. ESI-TOF-MS: m/z 581.0 [M+H]$^+$.

Tetra-butylammonium hydroxide (288 mL as 54-56% aqueous solution, 576 mmol) was adjusted to pH~4 by adding TFA (48 mL). The resulting solution was treated with a solution of 12-5 (14 g, 24 mmol) in DCM (200 mL). m-Chloroperbenzoic acid (30 g, 60-70%, 120 mmol) was added portion wise with vigorous stirring, and the mixture was stirred overnight. The organic layer was separated and washed with brine. The resulting solution was dried over magnesium sulfate and concentrated under reduced pressure. The residue was purified by column chromatography to give 12-6 (7.5 g, 68%)

Compound 12-6 (5.0 g, 10.6 mmol) was treated with 7N NH$_3$.MeOH (100 mL), and the mixture was stirred for 5 h. The mixture was then concentrated to dryness at low pressure. The residue was washed with DCM, and the solid was filtered to give 12-7 (2.1 g, 75%) as a white foam. ESI-MS: m/z 263.0 [M+H]$^+$.

To a solution of 12-7 (2.1 g, 8.0 mmol) in pyridine was added TIDPSCl (2.5 g, 8.0 mmol) dropwise at 0° C., and stirred for 12 h. at RT. The solution was quenched with water, and concentrated to dryness at low pressure. The crude was purified by column chromatography (EA in PE from 10% to 50%) to give pure 12-8 (1.6 g, 40%) as a white foam.

A solution of 12-8 (1.5 g, 3.0 mmol) and IBX (1.69 g, 6.0 mmol) in anhydrous CH$_3$CN (10 mL) was stirred at 80° C. for 3 h. The mixture was cooled down to RT and filtered. The filtrate was concentrated to dryness at low pressure. The residue was purified by column chromatography (EA in PE from 2% to 50%) to give pure 12-9 (1.2 g, 80%) as a white foam. ESI-MS: m/z 503.0 [M+H]$^+$ Compound 12-9 (500 mg, 1 mmol) was dissolved in dry THF (8 mL). Ethynyl magnesium bromide (8 mL of 0.5M solution in cyclohexane) was added at RT. After 30 mins, additional ethynyl magnesium bromide (8 mL) was added. The mixture was left for 30 mins, and then quenched with sat. solution of ammonium chloride. The product was extracted with EA. The organic extracts were washed with brine, dried, and concentrated. The residue was purified by flash chromatography on silica gel in EA to remove the dark color. The yellow compound was dissolved in THF (3 mL) and treated with TBAF (1 mL, 2M solution in THF) for 30 mins. The solvent was evaporated, and the residue was subjected to silica gel chromatography on a Biotage cartridge (25 g). EA saturated with water was used for isocratic elution. Each fractions were analyzed by TLC in DCM: MeOH (9:1 v:v). Fractions containing only the isomer with a high Rf were concentrated to give pure compound 12 (110 mg). MS: 285.1 [M−1].

Example 11

Compound 13

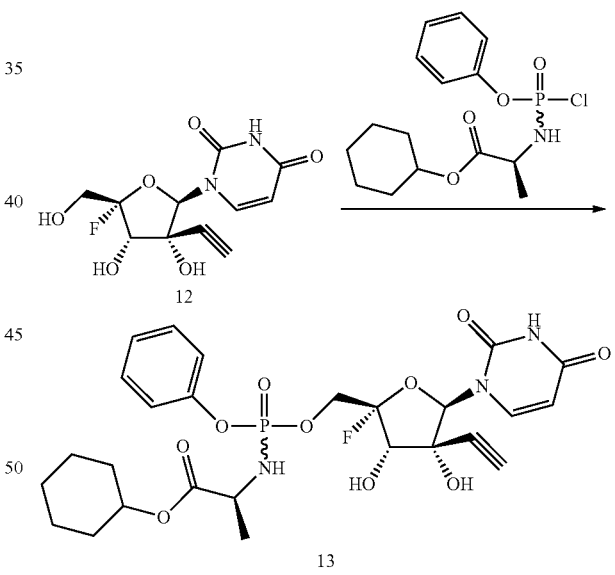

Compound 12 (57 mg, 0.2 mmol) was dissolved in CH$_3$CN (2 mL), containing N-methylimidazole (40 uL). The phosphorochloridate reagent (207 mg, 0.6 mmol) was added, and the mixture was kept overnight at 40° C. The mixture was distributed between water and EA. The organic layer was separated, washed with brine, dried and evaporated. The product was isolated by silica gel chromatography in gradient of methanol in DCM from 0% to 15%. Compound 13 was obtained (46 mg, 39%). MS: m/z 593.9 [M−1].

Example 12
Compound 14
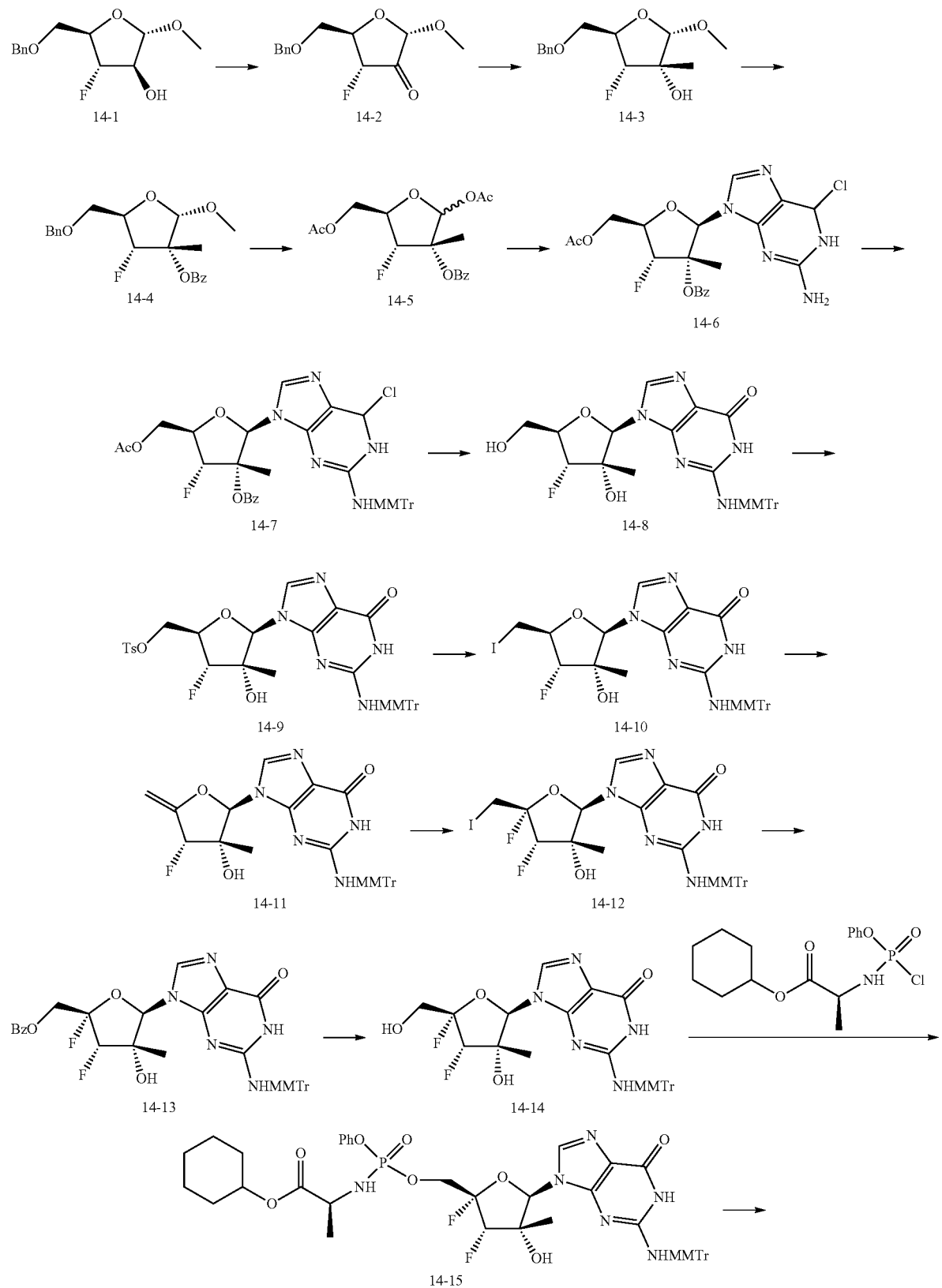

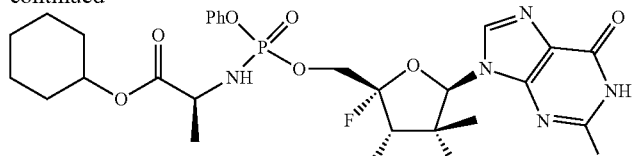

14

To a stirred solution of 14-1 (5.0 g, 19.53 mmol) in anhydrous MeCN was added IBX (7.66 g, 27.34 mmol) at RT. The mixture was heated at 80° C. for 12 h, and then slowly cooled to RT. After filtration, the filtrate was concentrated to give crude 14-2 (4.87 g, 98%).

To a solution of 14-2 (4.96 g, 19.53 mmol) in anhydrous THF at −78° C. under $N_2$ was added methyl magnesium bromide (19.53 mL, 58.59 mmol) by dropwise. The mixture was slowly warmed to RT, and stirred for 12 h. The mixture was quenched with sat. $NH_4Cl$ solution, and extracted with EA. The organic layer was dried over anhydrous $Na_2SO_4$, and evaporated at low pressure. The residue was purified by silica gel column chromatography to give 14-3 (4.37 g, 83%) as a white solid.

To a solution of 14-3 (4.37 g, 16.19 mmol) in anhydrous DCM (20 mL) was added DMAP (3.95 g, 32.38 mmol), TEA (4.91 g, 48.56 mmol), and BzCl (6.80 g, 48.56 mmol) at 0° C. The mixture was stirred at RT overnight. The reaction was quenched with sat. $NaHCO_3$ solution (30 mL), and extracted with EA (3×50 mL). The organic layer was dried over anhydrous $Na_2SO_4$, and evaporated at low pressure. The residue was purified by silica gel column chromatography to give crude 14-4 (5.3 g, 87%) as a white solid.

To a solution of 14-4 (3.0 g, 8.02 mmol) and $Ac_2O$ (4.91 g, 48.13 mmol) in acetic acid (10 mL) was added concentrated $H_2SO_4$ (98%, 2.41 g, 24.06 mmol) at 0° C. The mixture was stirred at RT for 12 h. The solution was poured into ice water (30 mL), and extracted with EA (3×50 mL). The organic layer was dried over anhydrous $Na_2SO_4$, and evaporated at low pressure. The residue was purified by silica gel column chromatography to give 14-5 (2.3 g, 81%)) as a white solid.

To a stirred solution of 6-Cl-guanine (560 mg, 3.31 mmol) and 14-5 (1.11 g, 2.76 mmol) in anhydrous MeCN (5 mL) was added DBU (1.27 g, 8.28 mmol) under $N_2$ at 0° C. The mixture was stirred at RT for 30 mins. The mixture was cooled to 0° C., and TMSOTf (2.45 g, 11.04 mmol) was added slowly in 15 mins. The mixture was then warmed RT in 30 mins. The mixture was heated at 60° C. for 4 h. The mixture was then poured into ice water (30 mL), and extracted with EA (3×50 mL). The organic layer was dried over anhydrous $Na_2SO_4$ and evaporated at low pressure. The residue was purified by silica gel column chromatography to give 14-6 (800 mg, 70%) as a white solid.

To a solution of 14-6 (839 mg, 1.64 mmol), MMTrCl (1.46 g, 4.75 mmol) and $AgNO_3$ (697 mg, 4.1 mmol) in DCM (10 mL) was added collidine (794 mg, 6.56 mmol). The mixture was stirred for 12 h at RT. The reaction was quenched with sat. $NaHCO_3$ solution (20 mL). After filtration, the filtrate was extracted with DCM (3×20 mL). The organic layer was dried over anhydrous $Na_2SO_4$, and evaporated at low pressure. The residue was purified by silica gel column chromatography to give 14-7 (1.3 g, 72.5%) as a white solid.

3-hydroxyl acrylic nitrile (4.13 g, 5.82 mmol) was dissolved in anhydrous THF (10 mL). The solution was treated with NaH (464 mg, 11.6 mmol) at 0° C., and slowly warmed to RT, and stirred for 30 mins. A solution of 14-7 (912 mg, 1.16 mmol) in anhydrous THF (5 mL) was added slowly. The mixture was stirred at RT overnight. The reaction was quenched with water (40 mL), and extracted with EA (3×50 mL). The organic layer was dried over anhydrous $Na_2SO_4$, and evaporated at low pressure. The residue was purified by silica gel column chromatography to give 14-8 (600 mg, 85%) as a white solid.

To a solution of 14-8 (6.20 g, 10.86 mmol) in anhydrous pyridine (10 mL) at 0° C. was added a solution of TsCl (4.54 g, 23.89 mmol) in anhydrous pyridine (10 mL) dropwise. The mixture was stirred at RT for 30 mins. The mixture was quenched with water (30 mL), and extracted with EA (3×50 mL). The organic layer was dried over anhydrous $Na_2SO_4$, and evaporated at low pressure. The residue was purified by silica gel column chromatography to give 14-9 (6.0 g, 76%) as a white solid.

To a solution of 14-9 (6.0 g, 8.28 mmol) in acetone (30 mL) was NaI (4.97 g, 33.12 mmol), and refluxed overnight. The mixture was evaporated under reduced pressure. The residue was dissolved in EA (50 mL), and washed with sat.$NaHCO_3$ solution (30 mL). The organic layer was dried over anhydrous $Na_2SO_4$, and evaporated at low pressure. The residue was purified by silica gel column chromatography to give 14-10 (5.43 g, 96.4%) as a white solid.

To a solution of 14-10 (5.0 g, 7.34 mmol) in anhydrous THF (20 mL) was added DBU (4.49 g, 29.37 mmol), and stirred at 60° C. overnight. The mixture was slowly cooled to RT. The mixture was quenched with water (30 mL), and extracted with EA (3×50 mL). The organic layer was dried over anhydrous $Na_2SO_4$, and evaporated at low pressure. The residue was purified by silica gel column chromatography to give 14-11 (3.5 g, 85%) as a white solid.

To a solution of 14-11 (3.5 g, 6.33 mmol) and AgF (4.42 g, 34.81 mmol) in anhydrous DCM (20 mL) was added a solution of iodine (3.54 g, 13.93 mmol) in anhydrous DCM (5 mL) dropwise at 0° C. The mixture was stirred for 3 h. The reaction mixture was washed with sat. $NaHCO_3$ solution (40 mL) and extracted with EA (3×50 mL). The organic layer was dried over anhydrous $Na_2SO_4$, and evaporated at low pressure. The residue was purified by silica gel column chromatography to give crude 14-12 (1.37 g, 31%) as a white solid.

To a solution of 14-12 (1.37 g, 1.96 mmol) in anhydrous DMF (15 mL) was added sodium benzoate (2.82 g, 19.60 mmol) and 15-crown-5 (4.31 g, 19.60 mmol), and stirred at 90° C. for 3 d. The mixture was quenched with water (30 mL), and extracted with EA (3×50 mL). The organic layer was dried over anhydrous $Na_2SO_4$, and evaporated at low pressure. The residue was purified by HPLC separation to give 14-13 (250 mg, 20%). ESI-MS: m/z: 694 [M+H]$^+$ A mixture of 14-13 (250 mg, 0.36 mmol) in liquid ammonia was kept overnight at RT in high pressure glass vessel. Ammonia was then evaporated, and the residue purified on silica gel (10 g column) with CH₂Cl₂/MeOH (4-10% gradient) to give 14-14 (180 mg, 85%).

Compound 14 (85 mg, 56%) was prepared from 14-14 (99 mg) with i-PrMgCl (0.11 mL) and the phosphorochloridate reagent (94 mg) in THF (2 mL) followed by deprotection. MS: m/z=627 [M+1].

Example 13

Compound 15

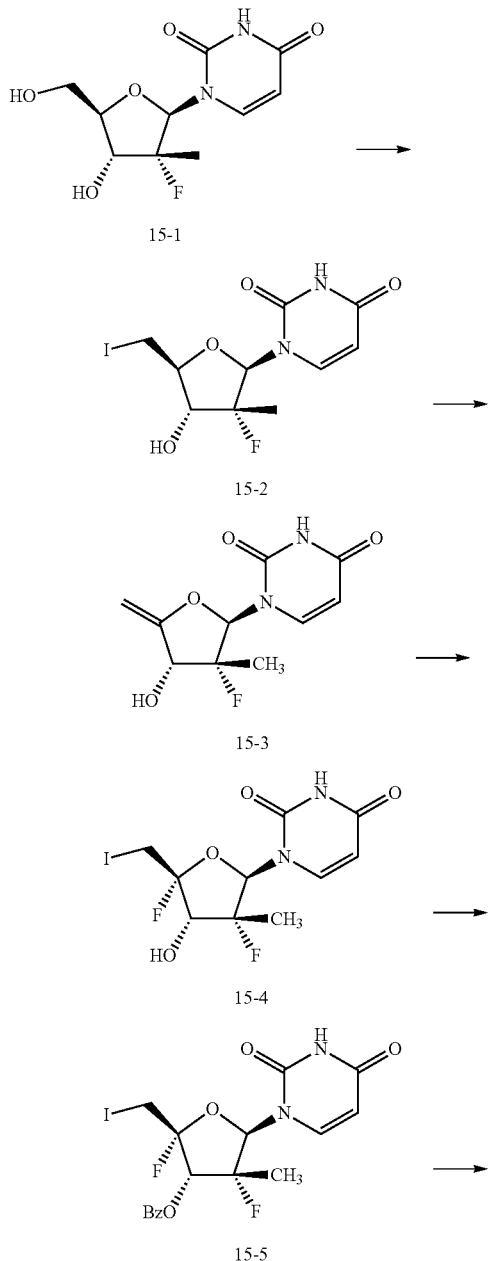

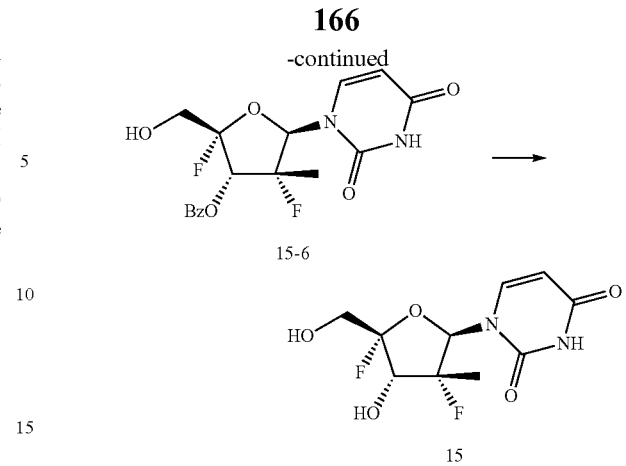

To a solution of 15-1 (260 mg, 1 mmol), PPh₃ (780 mg, 3 mmol) and pyridine (0.5 mL) in anhydrous THF (8 mL) were added I₂ (504 mg, 2 mmol) at RT, and the mixture was stirred at RT for 12 h. The mixture was diluted with EtOAc and washed with 1M HCl solution. The organic layer was dried over Na₂SO₄, filtered and concentrated at low pressure. The residue was purified by silica gel column (5% MeOH in DCM) to give 15-2 (190 mg, 85%) as a white solid.

To a solution of 15-2 (190 mg, 0.52 mmol) in THF (4 mL) was added DBU (760 mg, 5 mmol) at RT, and the mixture was heated at 50° C. overnight. The mixture was diluted with EtOAc, and washed with water. The organic layer was dried over anhydrous Na₂SO₄ and concentrated at low pressure. The residue was purified by silica gel column (30% EA in PE) to give 15-3 (75 mg, 52%) as a white solid.

To a solution of 15-3 (200 mg, 0.82 mmol) in MeCN (anhydrous, 4 mL) was added NIS (337 mg, 1.5 mmol) and TEA.3HF (213 mg, 1.25 mmol) at RT, and the mixture was stirred at RT for 7 h. The reaction was quenched with sat. Na₂SO₃ solution and sat. aq. NaHCO₃ solution. The mixture was extracted with EA. The organic layer was separated, dried over anhydrous Na₂SO₄, and concentrated at low pressure. The residue was purified by silica gel column (20% EA in PE) to give 15-4 (300 mg, 62%) as a white solid.

To a solution of 15-4 (194 mg, 0.5 mmol) in pyridine (5 mL) was added BzCl (92 mg, 0.55 mmol) at 0° C. The mixture was stirred at RT for 5 h, and the reaction was quenched with water. The mixture was concentrated at low pressure, and the residue was purified by silica gel column (20% EA in PE) to give 15-5 (397 mg, 81%) as a white solid.

To a solution of 15-5 (1.05 g, 2.13 mmol) in DCM (12 mL) was added a mixture of TFA (0.5 mL) and Bu₄NOH (1 mL), followed by addition of m-CPBA (1.3 g, 6 mmol) at RT. The mixture was stirred at RT for 5 h. The mixture was washed with sat. Na₂SO₃ solution and aq. NaHCO₃ solution. The organic layer was dried over anhydrous Na₂SO₄, and concentrated at low pressure. The residue was purified by silica gel column (30% EA in PE) to give 15-6 (450 mg, 63%) as a white solid.

Compound 15-6 (250 mg, 0.65 mmol) was dissolved in NH₃/MeOH (5 mL). The mixture was stirred at RT for 5 h, and then concentrated at low pressure. The residue was purified by silica gel column (5% MeOH in DCM) to give compound 15 (120 mg, 66%) as a white powder. ESI-MS: m/z 279.0 [M+H]⁺.

Example 14

Compound 16

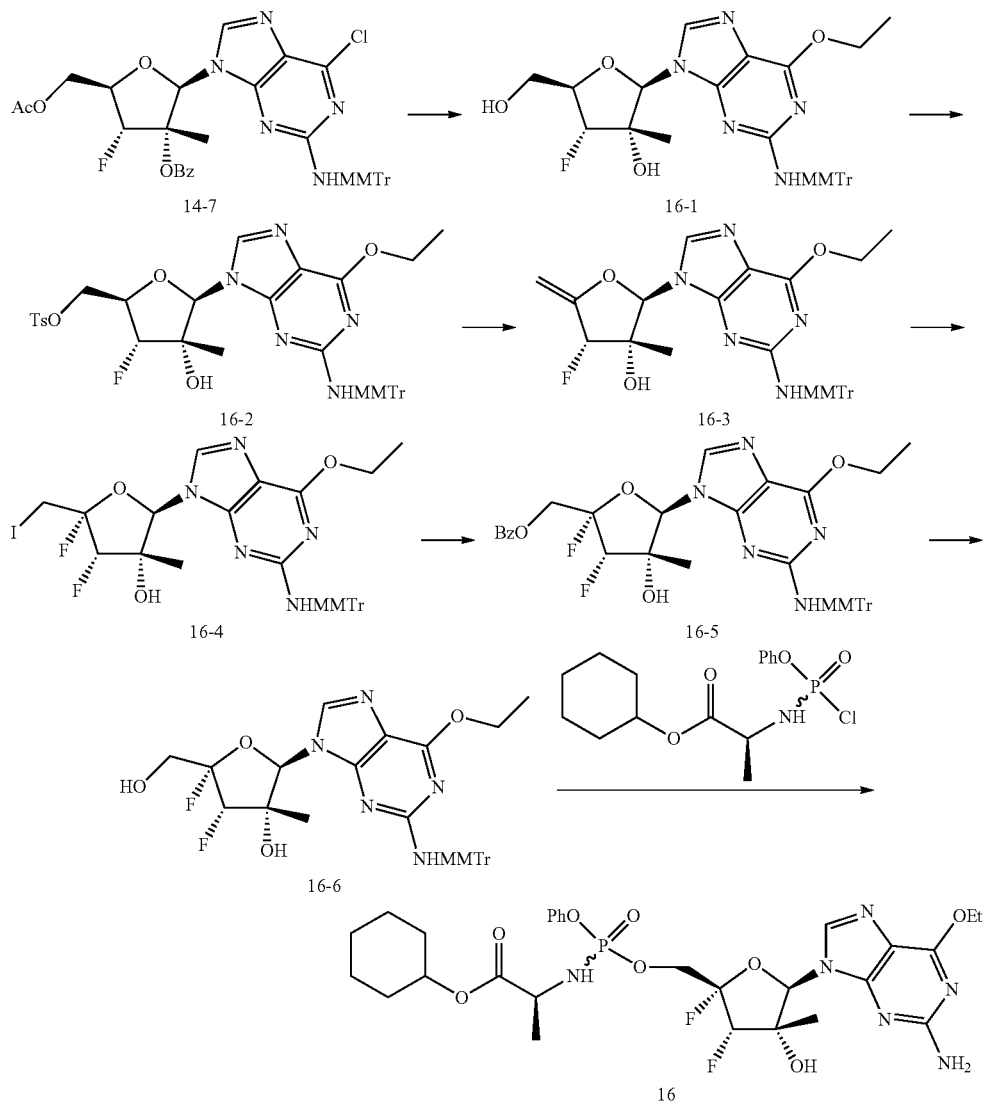

Sodium (6.0 g, 261.2 mmol) was dissolved in dry EtOH (400 mL) at 0° C., and slowly warmed to RT. Compound 14-7 (32.0 g, 43.5 mmol) was treated with a freshly prepared NaOEt solution at 0° C., and the mixture was stirred at RT overnight. The reaction was monitored by TLC and LCMS. After completion of the reaction, the mixture was concentrated at low pressure. The mixture was quenched with H$_2$O (40 mL), and extracted with EA (3×50 mL). The organic layer was dried over anhydrous Na$_2$SO$_4$, and evaporated at low pressure. The residue was purified by silica gel column chromatography (MeOH in DCM from 0.5% to 2%) to give 16-1 (20.0 g, 76.6%) as a white solid.

Compound 16-1 (20.0 g, 33.3 mmol) was co-evaporated with anhydrous pyridine 3 times. To an ice cooled solution of 16-1 in anhydrous pyridine (100 mL) was added TsCl (9.5 g, 49.9 mmol) at 0° C. After addition, the reaction was stirred for 12 h at 20° C., and monitored by LCMS. The reaction was quenched with H$_2$O, and concentrated at low pressure. The residue was dissolved in EA (50 mL). The solution was washed with sat. NaHCO$_3$ solution and brine. The organic layer was dried over anhydrous Na$_2$SO$_4$, and evaporated at low pressure. The residue was purified by silica gel column chromatography (MeOH in DCM from 0.5% to 2%) to give 16-2 (20.0 g, 80%) as a yellow solid.

To a solution of 16-2 (20.0 g, 26.5 mmol) in acetone (100 mL) was added NaI (31.8 g, 212 mmol), and heated to reflux overnight. The reaction was checked by LCMS. After the reaction was complete, the mixture was concentrated at low pressure. The residue was dissolved in EA (50 mL). The solution was washed with brine. The organic layer was dried over anhydrous Na$_2$SO$_4$, and evaporated at low pressure. The residue was purified by silica gel column chromatography (MeOH in DCM from 0.5% to 2%) to give a crude product. To a solution of the crude product in dry THF (60 mL) was added DBU (16.2 g, 106 mmol), and heated to 60° C. The mixture was stirred overnight and checked by LCMS. The reaction was quenched with sat. NaHCO$_3$ solution, and extracted with EA (3×50 mL). The organic phase was washed with brine, dried over anhydrous Na$_2$SO$_4$, and evaporated at low pressure. The residue was purified by silica gel column chromatography (MeOH in DCM from 0.5% to 2%) to give 16-3 (12.0 g, 77.9%) as a yellow solid.

To an ice-clod solution of 16-3 (11.0 g, 18.9 mmol) in dry MeCN (100 mL) was added NIS (5.4 g, 23.7 mmol) and NEt₃.3HF (3.0 g, 18.9 mmol) at 0° C. The mixture was stirred at RT for 4 h., and checked by LCMS. After the reaction was complete, the reaction was quenched with sat. Na₂SO₃ solution and sat. NaHCO₃ solution. The solution was extracted with EA (3×100 mL). The organic layer was washed with brine, dried over anhydrous Na₂SO₄, and evaporated at low pressure. The residue was purified by silica gel column chromatography (EA in PE from 12% to 50%) to give 16-4 (11.0 g, 79.9%).

To a solution of 16-4 (10.0 g, 13.7 mmol) in dry DMF (100 mL) was added NaOBz (19.8 g, 137 mmol) and 15-crown-5 (30.2 g, 137 mmol). The reaction was stirred for 48 h at 90° C., and diluted with EA. The solution was washed with water and brine, and dried over MgSO₄. The organic layer was evaporated at low pressure, and the residue was purified by silica gel column chromatography (EA in PE from 12% to 50%) to give 16-5 (8.0 g, 80.0%).

Compound 16-5 (6.0 g, 8.3 mmol) was co-evaporated with anhydrous toluene 3 times, and treated with NH₃ in MeOH (4N, 50 mL) at RT. The reaction was stirred for 18 h at RT. The reaction was monitored by LCMS. After the reaction was complete, the mixture was concentrated at low pressure. The residue was purified by silica gel column chromatography (EA in PE from 20% to 50%) to give 16-6 (4.5 g, 87.8%). ESI-MS: m/z 617.9 [M+H]⁺.

To an ice cooled mixture of 16-6 (25 mg, 0.07 mmol) and NMI (46 µL, 8 eq.) in acetonitrile (0.7 mL) was added the phosphorochloridate reagent (73 mg, 3 eq.) and stirred overnight at RT. Additional amounts of NMI (46 uL) and the phosphorochloridate reagent (73 mg) were added and stirring continued for 1 d. The reaction was quenched with sat. aq. NH₄Cl, diluted with EtOAc and water. The organic layer was separated and washed with aq. NaHCO₃, water, and brine, and then dried (Na₂SO₄). The residue was purified on silica gel (10 g column) with CH₂Cl₂/i-PrOH (4-10% gradient) to yield compound 16 (18 mg, 40%). MS: m/z=655 [M+1].

Example 15

Compound 18

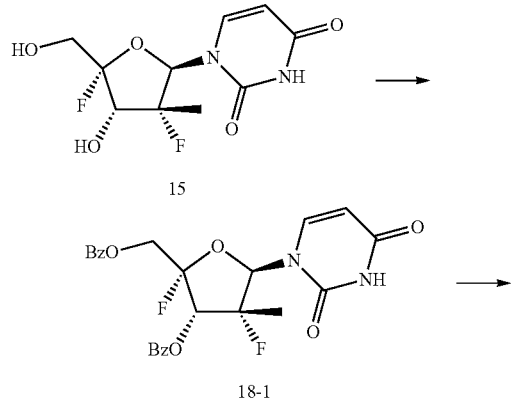

15

18-1

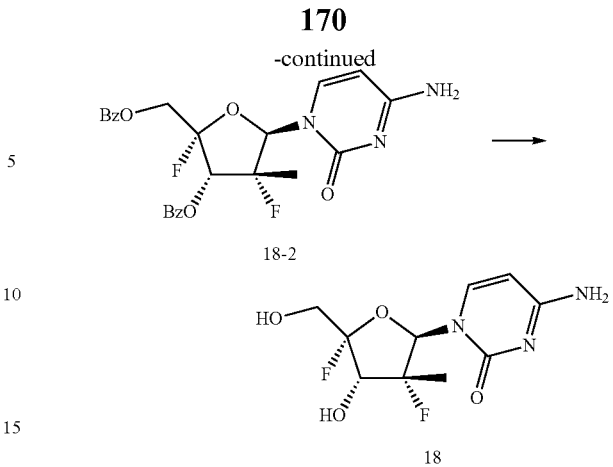

18-2

18

To a solution of compound 15 (139 mg, 0.5 mmol) in pyridine (5 mL) was added BzCl (92 mg, 0.55 mmol) at 0° C. The mixture was stirred at RT for 5 h, diluted with EtOAc and washed with 1N HCl solution. The organic layer was dried over anhydrous Na₂SO₄, and concentrated at low pressure. The residue was purified by silica gel column (20% EA in PE) to give 18-1 (274 mg, 79%) as a white solid.

To a solution of 18-1 (490 mg, 1 mmol), DMAP (244 mg, 2 mmol) and TEA (205 mg, 2.1 mmol) in MeCN (10 mL) were added TPSCl (604 mg, 2 mmol) at 0° C. The mixture was stirred at RT for 2 h., and then NH₄OH aq. was added at RT. The mixture was stirred for 0.5 h, diluted with EtOAc and washed with sat. aq. NaHCO₃ and brine. The organic layer was dried over anhydrous Na₂SO₄, and concentrated at low pressure. The residue was purified by silica gel column (30% EA in PE) to give 18-2 (250 mg, 41%) as a white solid.

Compound 18-2 (250 mg, 0.51 mmol) was dissolved in NH₃/MeOH (15 mL). The mixture was stirred at RT for 5 h. and then concentrated at low pressure. The residue was purified by silica gel column (5% DCM in DCM) to give compound 18 (95 mg, 66%) as a white powder. ESI-MS: m/z 278.1 [M+H]⁺.

Example 16

Compound 20

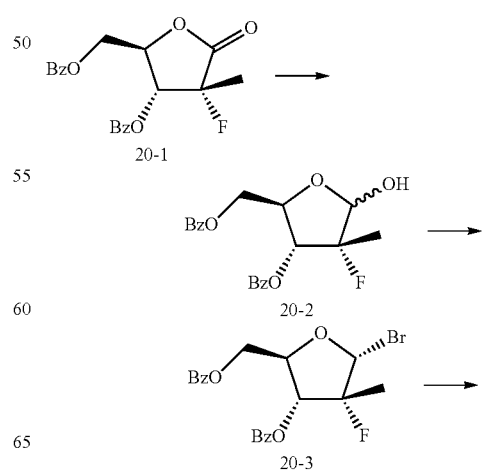

20-1

20-2

20-3

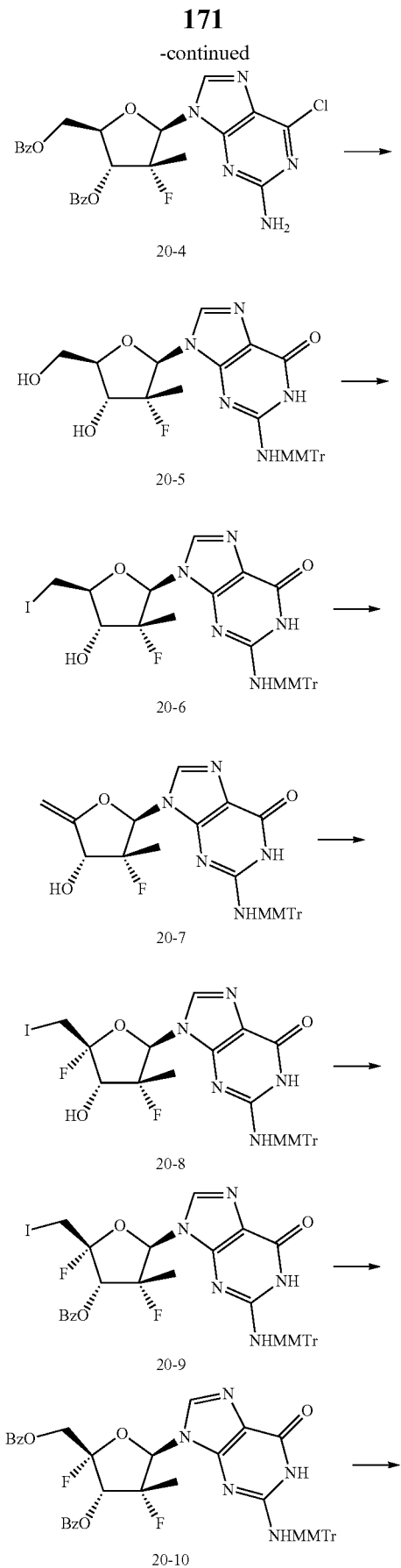
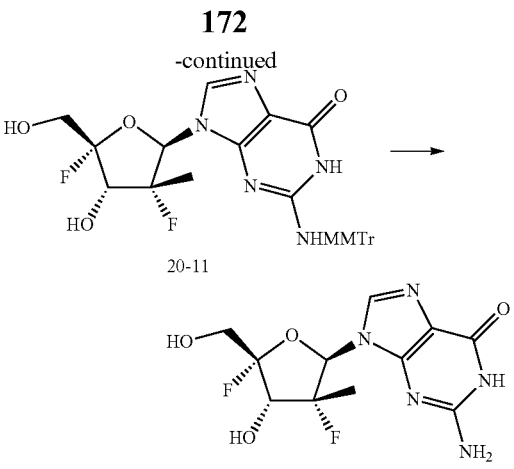

To a solution of compound 20-1 (30 g, 0.08 mol) in anhydrous THF (300 mL) was added a solution of lithium tri-tert-butoxyaluminohydride (120 mL, 0.12 mol) dropwise at −78° C. under $N_2$. The mixture was stirred at −20° C. for 1 h. The reaction was quenched with sat. aq. $NH_4Cl$ and then filtered. The filtrate was extracted with EA (3×300 mL). The organic layer was dried over anhydrous $Na_2SO_4$, and concentrated at low pressure. The residue was purified by silica gel column (10% EA in PE) to give 20-2 (26 g, 86%) as a colorless oil.

To a stirred solution of $PPh_3$ (37.7 g, 0.144 mol) in DCM (100 mL) was added compound 20-2 (27 g, 0.072 mol) at −20° C. under $N_2$. After the mixture was stirred at RT for 15 mins, $CBr_4$ (42 g, 0.129 mol) was added while maintaining the reaction temperature between −25 and −20° C. under $N_2$. The mixture was then stirred below −17° C. for 20 mins. Silica gel was added into the solution, and then purified by flash silica gel column separation to give the crude oil product. The crude was purified by silica gel column (EA in PE from 2% to 20%) to give 20-3 (α-isomer, 17 g, 55%) as a colorless oil.

A mixture of 6-Cl-guanine (11.6 g, 68.8 mmol) and t-BuOK (8.2 g, 73 mmol) in t-BuOH (200 mL) and MeCN (150 mL) was stirred at 35° C. for 30 mins, and then 20-3 (10 g, 22.9 mmol) in MeCN 100 mL) was added at RT. The mixture was heated at 50° C. overnight. The reaction was quenched with a solution of $NH_4Cl$ (5 g) in water (40 mL), and the mixture was filtered. The filtrate was evaporated at low pressure. The residue was purified by silica gel column (20% EA in PE) to give 20-4 (6 g, 42%) as a yellow solid.

To a solution of 20-4 (12.5 g, 23.8 mol) in DCM (50 mL) was added $AgNO_3$ (8.1 g, 47.6 mmol), collidine (5.77 g, 47.6 mmol) and MMTrCl (11 g, 35.7 mmol). The mixture was stirred at RT overnight. The reaction was quenched with MeOH (5 mL), filtered and concentrated at low pressure. The residue was purified by silica gel column (5% MeOH in DCM) to give the intermediate (16 g, 86%) as a yellow solid. To a solution of $HOCH_2CH_2CN$ (4.7 g, 66 mmol) in THF (200 mL) was added NaH (3.7 g, 92 mmol) at 0° C. The mixture was stirred at RT for 30 mins. A solution of the intermediate (10.5 g, 13 mmol) in THF (50 mL) was added, and the reaction mixture was stirred at RT for 12 h. The reaction was quenched with MeOH (2 mL), diluted with EA (100 mL), and washed with brine. The organic layer was dried over anhydrous $Na_2SO_4$, and concentrated at low pressure. The residue was purified by silica gel column (5% MeOH in DCM) to give 20-5 (5.8 g, 77%) as a yellow solid.

To a solution of PPh₃ (7.0 g, 26.6 mmol) in anhydrous pyridine (100 mL) was added I₂ (6.3 g, 24.9 mmol), and stirred at RT for 30 mins. The mixture was treated with a solution of 20-5 (9.5 g, 16.6 mmol) in pyridine (40 mL). The mixture was stirred at RT overnight. The reaction was quenched with sat. Na₂S₂O₃ solution, and the mixture was extracted with EA. The organic layer was washed with brine, dried over anhydrous Na₂SO₄, and concentrated at low pressure. The residue was purified by silica gel column (30% EA in PE) to give 20-6 (7 g, 66%) as a yellow solid.

To a solution of 20-6 (7.5 g, 11 mmol) in dry THF (50 mL) was added DBU (5.4 g, 33 mmol), and the mixture was heated to reflux for 4 h. The mixture was diluted with EA (3×100 mL), and washed with brine. The organic layer was dried over anhydrous Na₂SO₄, and concentrated at low pressure. The residue was purified by silica gel column (30% EA in PE) to give 20-7 (4.0 g, 67%) as a white solid.

To an ice-cooled solution of 20-7 (3.0 g, 5.4 mmol) in anhydrous MeCN (20 mL) was added TEA.3HF (0.65 g, 4.1 mmol) and NIS (1.53 g, 6.78 mmol) at RT, and the reaction mixture was stirred at RT for 2 h. The mixture was diluted with EA (50 mL), and washed with sat. Na₂S₂O₃ solution and NaHCO₃ aq. The organic layer was dried over anhydrous Na₂SO₄, and concentrated to dryness at low pressure. The residue was purified by prep-HPLC (0.1% HCOOH in water and MeCN) to separate the two isomers (about 1:1). NOE showed the polar one was 20-8 (0.6 g, 16%) as a white solid.

To a solution of 20-8 (0.7 g, 1 mmol) in dry pyridine (10 mL) was added BzCl (147 mg, 1.05 mmol) at 0° C. The mixture was stirred at RT for 3 h. The mixture was then diluted with EA, and washed with sat. NaHCO₃ aq. and brine. The organic layer was dried over Na₂SO₄, and evaporated at low pressure. The residue was purified by silica gel column (20% EA in PE) to give 20-9 (0.65 g, 81%) as a white solid.

To a solution of 20-9 (0.65 g, 0.8 mmol) in dry DMF (40 mL) was added NaOBz (1.15 g, 8 mmol) and 15-crown-5 (1.77 g, 8 mmol). The mixture was stirred at 100° C. for 48 h. The solvent was evaporated at low pressure, and the residue was dissolved in EA (30 mL), and washed with water and brine. The organic layer was dried over Na₂SO₄ and concentrated at low pressure. The residue was purified by silica gel column (20% EA in PE) to give 20-10 (500 mg, 78%) as a white solid.

Compound 20-10 (400 mg, 0.5 mmol) in NH₃/MeOH (7N, 100 mL) was stirred at RT for 18 h. The mixture was concentrated at low pressure, and the residue was purified by silica gel column (5% MeOH in DCM) to give 20-11 (220 mg, 63%) as a white solid. ESI-MS: m/z 590.3 [M+H]⁺.

Compound 20-11 (59 mg, 0.1 mmol) was dissolved in 50% TFA in methanol (10 mL), and the mixture was kept at RT for 2 h. The solvent was evaporated and co-evaporated with a methanol/toluene mixture to remove traces of the acid. The residue was suspended in CH₃CN (1 mL) and centrifuged. The precipitate was washed with CH₃CN (1 mL) and dried. Compound 20 was obtained as a colorless solid (21 mg, 65%. MS: m/z 316.2 [M−1].

Example 17

Compound 21

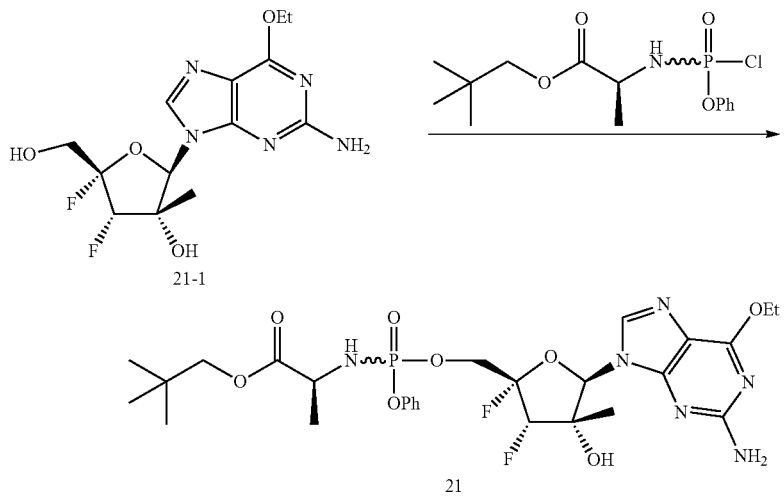

Compound 21 (15 mg, 16%) was prepared from 21-1 (50 mg) in acetonitrile (2 mL) with the phosphorochloridate reagent (0.14 g) and NMI (0.1 mL) in the same manner as compound 7. MS: m/z=643 [M+1].

Example 18

Compound 22

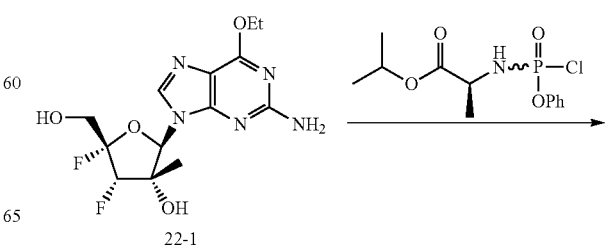

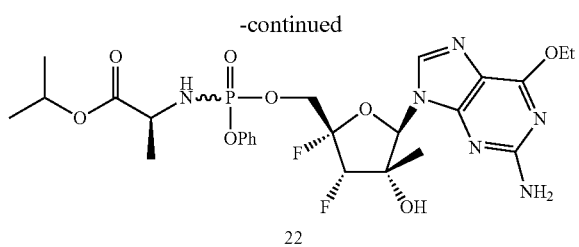

22

Compound 22 (30 mg, 32%) was prepared from 22-1 (50 mg) in acetonitrile (2 mL) with the phosphorochloridate reagent (0.14 g) and NMI (0.1 mL) in the same manner as compound 7. MS: m/z=615 [M+1].

Example 19

Compound 23

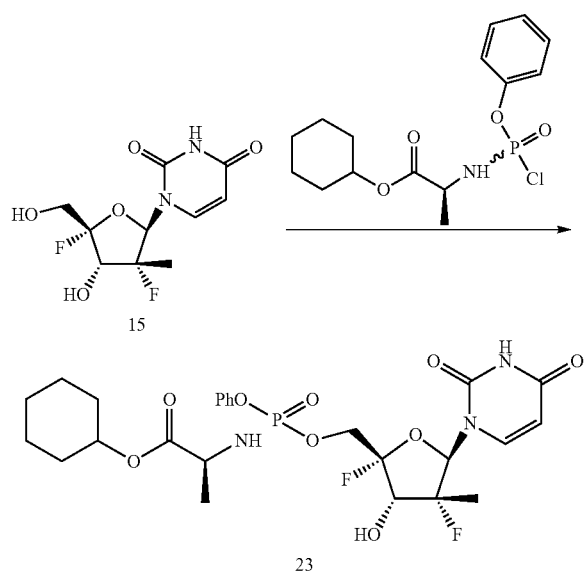

To a stirred solution of compound 15 (60 mg, 0.22 mmol) in anhydrous THF (2.0 mL) was added N-methylimidazole (0.142 mL, 1.73 mmol) at 0° C. (dry ice/acetone bath) followed by solution of phenyl (cyclohexanoxy-L-alaninyl) phosphorochloridate (235 mg, 0.68 mmol, dissolved in THF (2 mL). The resulting solution was stirred at 0° C. for 1 h, and the temperature was raised up-to 10° C. over the next 1 h. The reaction left at 10° C. for 3 h. The mixture was cooled to 0 to 5° C., diluted with EA, and water (5 mL) was added. The solution was washed with H₂O and brine. The organic layer was separated, dried over anhydrous Na₂SO₄ and filtered. The filtrate was concentrated in vacuum to give a residue, which dissolved in 25% CH₃CN/H₂O. The compound was purified on a reverse-phase HPLC (C18) using acetonitrile and water, followed by lyophilization gave a white foam. The produce was re-dissolved in EtOAc, washed with 50% aqueous citric acid solution, dried over anhydrous MgSO₄ and filtered. The filtrate was concentrated in vacuum, and lyophilized to give two isomers (Rp/Sp) of compound 23 (6.3 mg). MS m/z 586.05 (M−H).

Example 20

Compound 24

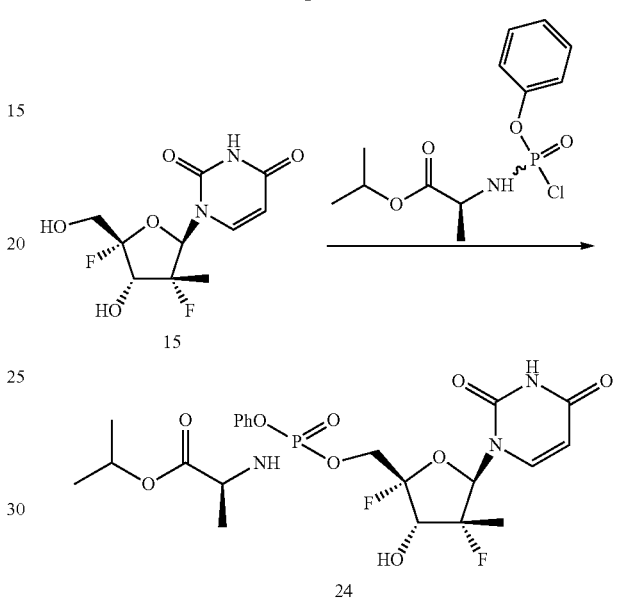

24

To a stirred solution of compound 15 (100 mg, 0.36 mmol) in anhydrous THF (3.0 mL) was added N-methylimidazole (236 μL, 2.87 mmol) at 0° C. (dry ice/acetone bath) followed by a solution of the phosphorochloridate (329 mg, 1.08 mmol, dissolved in 2 mL of THF). The solution was stirred at 0° C. for 1 h, the reaction temperature was raised up-to 10° C. during the next 1 h, and the solution was left at 10° C. for the next 4 h. The mixture was cooled to 0 to 5° C., diluted with EA, and water was added (15 mL). The solution was washed H₂O, 50% aqueous citric acid solution and brine. The organic layer was separated, dried over anhydrous MgSO₄ and filtered. The filtrate was concentrated in vacuum to give a residue, which dissolved in 25% CH₃CN/H₂O. The residue was purified on a reverse-phase HPLC (C18) using acetonitrile and water, followed by lyophilization to give a mixture of two isomers of compound 24 (17.5 mg). MS m/z 546.05 (M−H).

Example 21

Compounds 25 and 26

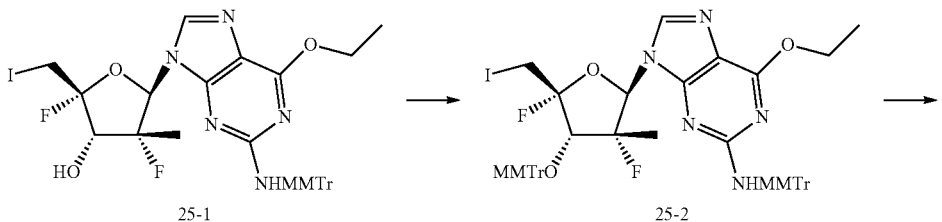

-continued

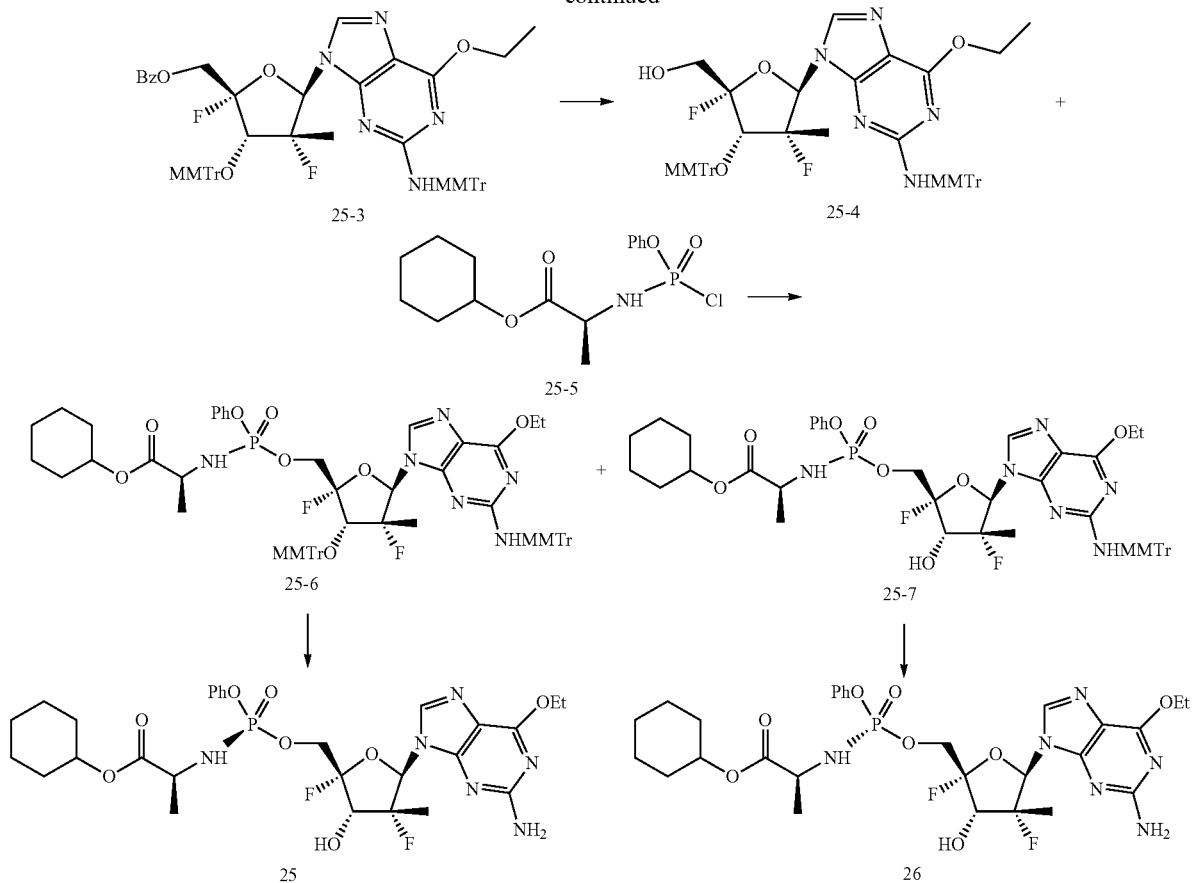

To a solution of 25-1 (0.47 g, 0.65 mol) in DCM (3 mL) was added AgNO$_3$ (0.22 g, 1.29 mmol), collidine (0.15 g, 1.29 mmol) and MMTrCl (0.3 g, 0.974 mmol) at 0° C. The mixture was stirred at RT overnight. The mixture was filtered, and the filter was washed with sat. aq. NaHCO$_3$ solution and brine. The organic layer was separated, dried over anhydrous Na$_2$SO$_4$ and concentrated at low pressure. The residue was purified by silica gel column to give 25-2 (0.55, 85%) as a white solid.

To a solution of 25-2 (0.5 g, 0.5 mmol) in dry DMF (10 mL) was added NaOBz (0.72 g, 5 mmol) and 15-crown-5 (0.9 mL). The mixture was stirred at 95° C. for 72 h. The mixture was diluted with EA, and washed with water and brine. The organic phase was dried over MgSO$_4$ and concentrated at low pressure. The residue was purified by silica gel column (10% EA in PE) to give 25-3 (0.3 g, 60%) as a white solid.

Compound 25-3 (0.3 g, 0.3 mmol) in NH$_3$/MeOH (30 mL) was stirred at RT for 18 h. The mixture was concentrated at low pressure, and the residue was purified by silica gel column (20% EA in PE) to give 25-4 (145 mg, 56%) as a white solid. ESI-LCMS: m/z 890.5 [M+H]$^+$.

To a stirred solution of 25-4 (161 mg, 0.16 mmol) in anhydrous CH$_3$CN (2.0 mL) was added N-methylimidazole (118 μL, 2.87 mmol) at 0 to 5° C. (ice/water bath) followed by solution of 25-5 (186 mg, 0.54 mmol, dissolved in 2 mL of CH$_3$CN). The solution was stirred at 0 to 5° C. for 4 h. The mixture was diluted with EA, and water was added (15 mL). The solution was washed H$_2$O, 50% aqueous citric acid solution and brine. The organic layer was separated, dried over anhydrous MgSO$_4$ and filtered. The filtrate was concentrated in vacuum to give a residue, which was purified on silica gel with 0 to 40% EA/hexanes to give as 25-6 (82.6 mg) as the faster eluting isomer and 25-7 (106 mg) as the slower eluting isomer.

Compound 25-6 (82.6 mg, 0.07 mmol) was dissolved in anhydrous CH$_3$CN (0.5 mL), and 4N HCl in dioxane (35 μL) was added at 0 to 5° C. The mixture was stirred at RT for 1 h, and anhydrous EtOH (100 μL) was added. The solvents were evaporated at RT and co-evaporated with toluene 3 times. The residue was dissolved in 50% CH$_3$CN/H$_2$O, and purified on a reverse-phase HPLC (C18) using acetonitrile and water, followed by lyophilization to give compound 25 (19.4 mg). $^1$H NMR (CD$_3$OD-d$_4$, 400 MHz) δ 7.9 (s, 1H), 7.32-7.28 (t, J=8.0 Hz, 2H), 7.2-7.12 (m, 3H), 6.43 (d, J=17.6 Hz, 1H), 4.70-4.63 (m, 2H), 4.55-4.4 (m, 3H), 3.94-3.9 (m, 1H), 1.79-1.67 (m, 4H), 1.53-1.49 (m, 1H), 1.45-1.22 (m, 15H); $^{31}$P NMR (CD$_3$OD-d$_4$) δ 4.06 (s); ESI-LCMS: m/z=655.2 [M+H]$^+$, 653.15 [M−H]$^−$.

Compound 25-7 (100 mg, 0.083 mmol) was dissolved in anhydrous CH$_3$CN (0.5 mL), and 4N HCl in dioxane (50 μL) was added at 0 to 5° C. Following the procedure for obtaining compound 25, compound 26 (31.8 mg) was obtained. $^1$H NMR (CD$_3$OD-d$_4$, 400 MHz) δ 7.93 (s, 1H), 7.33-7.29 (m, 2H), 7.24-7.14 (m, 3H), 6.41 (d, J=17.6 Hz, 1H), 4.70-4.60 (m, 2H), 4.54-4.49 (m, 2H), 4.44-4.39 (m, 1H), 3.92-3.89 (m, 1H), 1.77-1.66 (m, 4H), 1.54-1.24 (m, 16H); $^{31}$P NMR (CD$_3$OD-d$_4$) δ 3.91 (s); ESI-LCMS: m/z=655.2 [M+H]$^+$, 653.1 [M−H]$^−$.

Example 22
Compounds 27 and 28
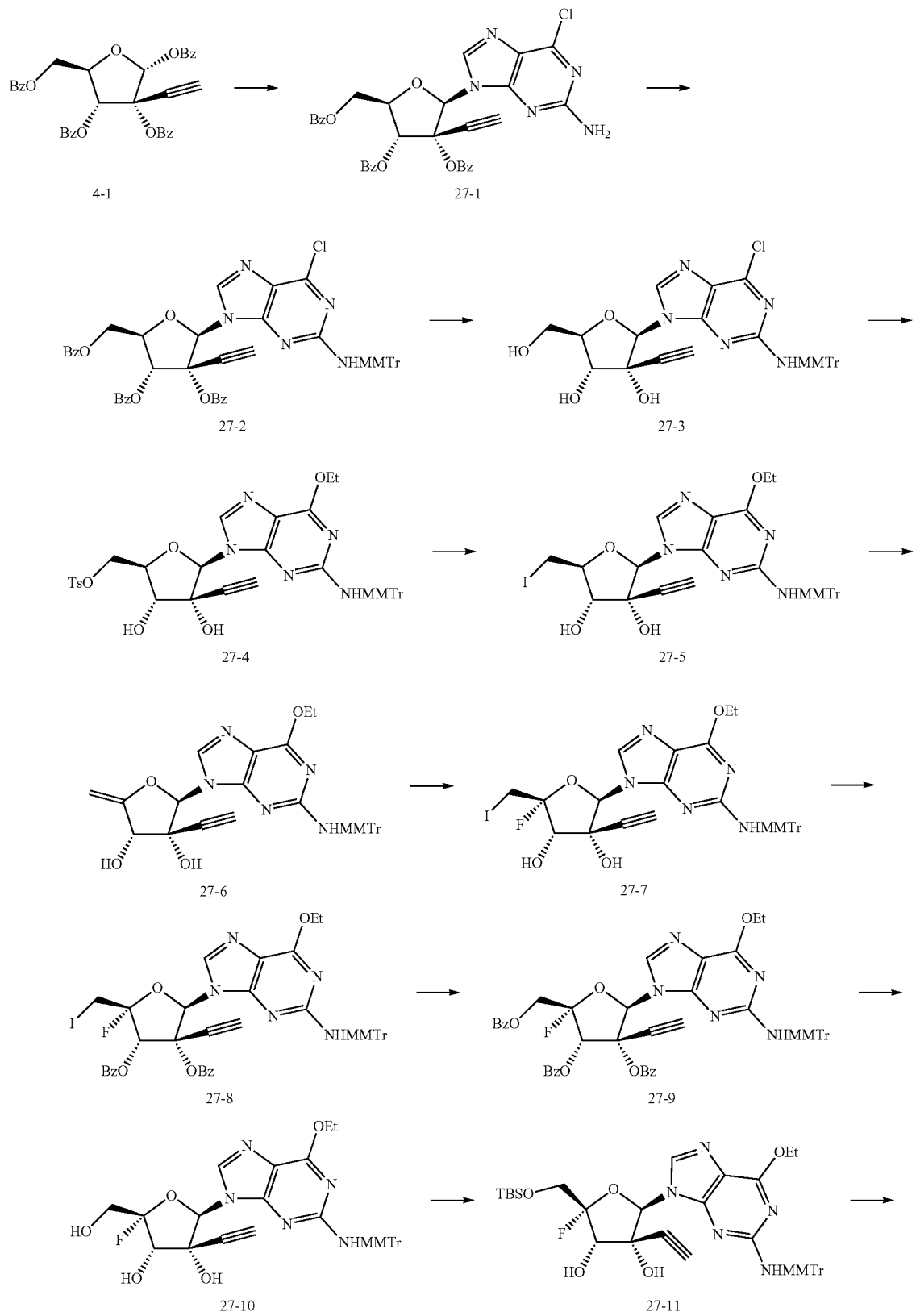

-continued

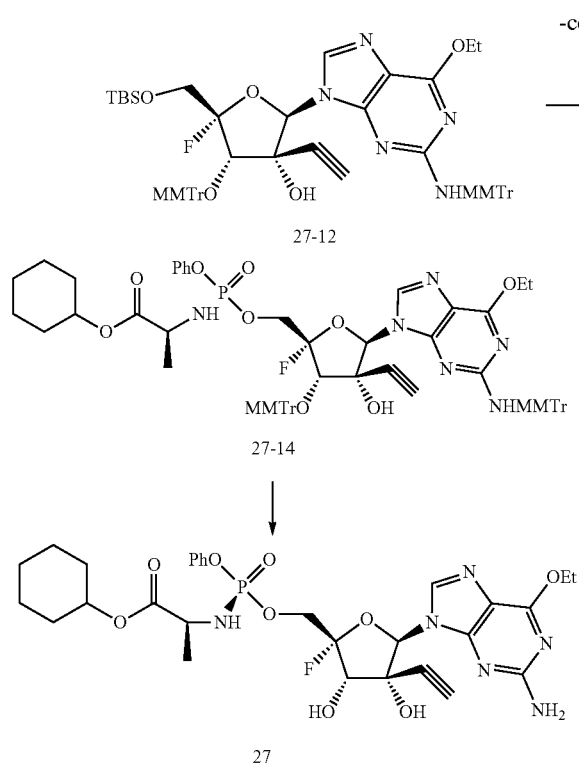

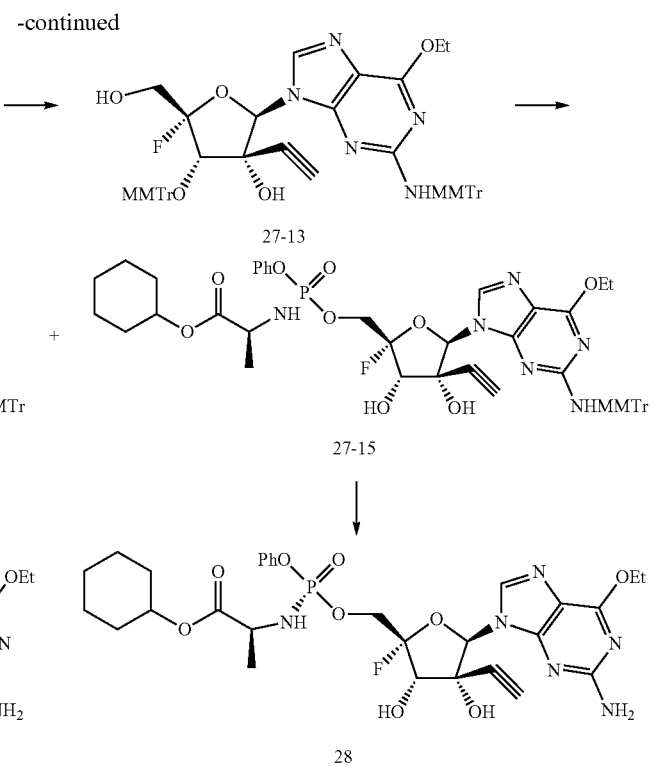

To a stirred suspension of 4-1 (50 g, 84.8 mmol) and 2-amino-6-chloropurine (28.6 g, 169.2 mmol) in anhydrous MeCN (500 mL) was added DBU (77.8 g, 508 mmol) at 0° C. The mixture was stirred at 0° C. for 30 mins, and TMSOTf (150.5 g, 678 mmol) was added dropwise at 0° C. The mixture was stirred at RT for 20 mins until a clear solution was formed. The mixture was stirred at 90-110° C. overnight. The mixture was cooled to RT, and diluted with EA. The solution was washed with sat. NaHCO$_3$ solution and brine. The organic layer was dried over Na$_2$SO$_4$ and then concentrated at low pressure. The residue was purified by silica gel column (PE/EA=2/1) to give 27-1 (30 g, 55.5%) as a white solid.

To a solution of 27-1 (30 g, 47.1 mmol) in anhydrous DCM (300 mL) was added collidine (30 mL), AgNO$_3$ (24 g, 141.4 mmol) and MMTrCl (43.6 g, 141.4 mmol). The mixture was stirred at RT overnight. The mixture was filtered, and the filtrate was washed with water and brine. The organic layer was dried over anhydrous Na$_2$SO$_4$, and concentrated at low pressure. The residue was purified by silica gel column (PE/EA=4/1) to give 27-2 (35 g, 82%) as a white solid.

To a stirred solution of 27-2 (35 g, 38.5 mmol) in anhydrous EtOH (150 mL) was added a solution of EtONa in EtOH (2N, 150 mL). The mixture was stirred at RT overnight, and then concentrated at low pressure. The residue was dissolved in EA (200 mL) and the solution was washed with water and brine. The organic layer was dried over Na$_2$SO$_4$, and concentrated at low pressure. The residue was purified by silica gel column (DCM/MeOH=100/2) to give 27-3 (19 g, 81%) as a white solid.

Compound 27-3 (19 g, 31.3 mmol) was co-concentrated with anhydrous pyridine for 3 times. To an ice cooled solution of 27-3 in anhydrous pyridine (120 mL) was added a solution of TsCl (6.6 g, 34.6 mmol) in pyridine (40 mL) dropwise at 0° C. The mixture was stirred at 0° C. for 16 h. The mixture was quenched with water, and the reaction mixture was concentrated. The residue was re-dissolved in EA (200 mL). The solution was washed with sat. aq. NaHCO$_3$ and brine. The organic layer was dried over anhydrous Na$_2$SO$_4$ and filtered, and the filtrate was concentrated. The residue was purified by silica gel column (DCM/MeOH=100/1) to give 27-4 (16 g, 67%) as a yellow solid.

To a solution of 27-4 (15 g, 19.7 mmol) in acetone (100 mL) was added NaI (30 g, 197 mmol). The mixture was refluxed overnight, and then concentrated at low pressure. The residue was purified by silica gel column (DCM/MeOH=100/1) to give 27-5 (9 g, 63.7%) as a white solid.

To a solution of 27-5 (8 g, 11.2 mmol) in anhydrous THF (60 mL) was added DBU (5.12 g, 33.5 mmol), and the mixture was heated at 60° C. overnight. The mixture was diluted with EA, and washed with water and brine. The organic layer was dried over anhydrous Na$_2$SO$_4$ and filtered, and the filtrate was concentrated. The residue was purified by silica gel column (PE/acetone=4/1) to give 27-6 (5.7 g, 86%) as a white solid. $^1$H-NMR (CD$_3$OH, 400 MHz) δ=8.18 (s, 1H), 7.17-7.33 (m, 12H), 6.80 (d, J=8.8 Hz, 2H), 5.98 (s, 1H), 5.40 (d, J=8.6 Hz, 1H), 3.87 (m, 5H), 3.75 (s, 3H), 2.69 (s, 1H), 1.05 (s, 3H).

To an ice cooled solution of 27-6 (4.44 g, 7.5 mmol) in anhydrous MeCN (45 mL) was added TEA.3HF (1.23 g, 7.6 mmol) and NIS (2.16 g, 9.5 mmol). The mixture was stirred at RT for 2-3 h. The reaction was quenched with sat. Na$_2$SO$_3$ and NaHCO$_3$ solution. The mixture was extracted with EA (3×100 mL). The organic layer was separated, dried over anhydrous Na$_2$SO$_4$ and concentrated at low pressure. The residue was purified by silica gel column (DCM/acetone=100/2) to give 27-7 (4.4 g, 79.8%) as a white solid.

To a solution of 27-7 (5.36 g, 7.3 mmol) in anhydrous DCM (50 mL) was added DMAP (3.6 g, 29.8 mmol) and BzCl (3.1 g, 22.1 mmol) at 0° C. The mixture was stirred at RT overnight. The mixture was washed with sat. aq. NaHCO₃ and brine. The organic layer was concentrated, and the residue was purified by silica gel column (PE/EA=5/1) to give 27-8 (5.6 g, 81.3%) as a white solid.

To a solution of 27-8 (5.0 g, 5.3 mmol) in anhydrous DMF (150 mL) was added NaOBz (7.64 g, 53 mmol) and 15-crown-5 (14 g, 68 mmol). The mixture was stirred at 90-100° C. for 48 h. The mixture was diluted with EA, and washed with water and brine. The organic layer was concentrated, and the residue was purified by silica gel column (PE/EA=5/1) to give 27-9 (3.9 g, 78.5%) as a white solid.

Compound 27-9 in NH₃ in MeOH (7N, 60 mL) was stirred at RT for 18 h. The mixture was concentrated at low pressure. The residue was purified by silica gel column (DCM/acetone=50/1) to give 27-10 (500 mg, 74.7%) as a white solid. ESI-MS: m/z 626.3 [M+H]⁺.

To a solution of 27-10 (350 mg, 0.56 mmol) in anhydrous pyridine (4 mL) was added imidazole (50 mg, 0.72 mmol) and TBSCl (108 mg, 0.72 mmol) at 0 to 5° C., and stirred at RT for 15 h. The reaction was quenched with absolute EtOH (0.5 mL). The solution was concentrated to dryness under reduced pressure. The residue was dissolved in EA (150 mL), and washed with water, sat. NaHCO₃ and brine. The combined organic layers were dried over Na₂SO₄, filtered and evaporated at low pressure. The residue was purified by silica gel column (10-30% EA in hexanes) to give 27-11 (338 mg, 81.8%) as a white solid.

To a solution of compound 27-11 (328 mg, 0.44 mmol), AgNO₃ (226 mg, 1.33 mmol) and collidine (0.59 mL, 4.84 mmol) in anhydrous DCM (4 mL) was added MMTrCl (410 mg, 1.33 mmol) under N₂. The mixture was stirred at RT overnight under N₂, and monitored by TLC to completion. The mixture was filtered through pre-packed Celite filter, and the filtrate was washed with water, 50% aqueous citric acid, and brine. The organic layer was separated, dried over anhydrous Na₂SO₄, filtered and concentrated at low pressure. The residue was purified by silica gel column (EA in hexanes from 0% to 30%) to give 27-12 (337 mg).

To a solution of 27-12 (337 mg, 0.33 mmol) in anhydrous THF (4 mL) was added 1.0 M solution of TBAF (0.66 ML, 0.66 mmol) at 0 to 5° C. The reaction was slowly warmed to RT, and stirred for 1 h. The mixture was quenched with silica gel, and filtered. The solvents were evaporated to give the crude product, which was purified by silica gel column (EA in hexanes from 0% to 50%) to give 27-13 (188 mg).

To a stirred solution of 27-13 (180 mg, 0.16 mmol) in anhydrous CH₃CN (2.5 mL) was added N-methylimidazole (132 µL, 1.6 mmol) at 0-5° C. (ice/water bath) followed by solution of phenyl (cyclohexanoxy-L-alaninyl) phosphorochloridate (207 mg, 0.6 mmol, dissolved in 2 mL of CH₃CN). The solution was stirred at RT for 2.5 h, and the mixture was diluted with EA followed by addition of water (15 mL). The solution was washed H₂O, 50% aqueous citric acid solution and brine. The organic layer was separated, dried over anhydrous MgSO₄ and filtered. The filtrate was concentrated in vacuum to give a residue, which was purified on silica gel with 0 to 40% EA/hexanes to give 27-14 (75.8 mg) and 27-15 (108 mg) as a slower eluting isomer.

Compound 27-14 (76 mg, 0.063 mmol) was dissolved in anhydrous CH₃CN (0.5 mL), and 4N HCl in dioxane (47 µL) was added at 0 to 5° C. (ice/water bath). The mixture was stirred at RT for 40 mins, and anhydrous EtOH (200 µL) was added. The solvents were evaporated at RT and co-evaporated with toluene 3 times. The residue was dissolved in 50% CH₃CN/H₂O, purified on a reverse-phase HPLC (C18) using acetonitrile and water, and lyophilized to give compound 27 (26.6 mg). ESI-LCMS: m/z=663.3 [M+H]⁺.

Compound 27-15 (108 mg, 0.089 mmol) was dissolved in anhydrous CH₃CN (0.7 mL), and 4N HCl in dioxane (67 µL) was added at 0 to 5° C. (ice/water bath). The mixture was stirred at RT for 60 mins, and anhydrous EtOH (200 µL) was added. The solvents were evaporated at RT and co-evaporated with toluene 3 times. The residue was dissolved in 50% CH₃CN/H₂O, purified on a reverse-phase HPLC (C18) using acetonitrile and water, and lyophilized to give compound 28 (40.3 mg). ESI-LCMS: m/z=663.2 [M+H]⁺.

Example 23

Compounds 30 and 31

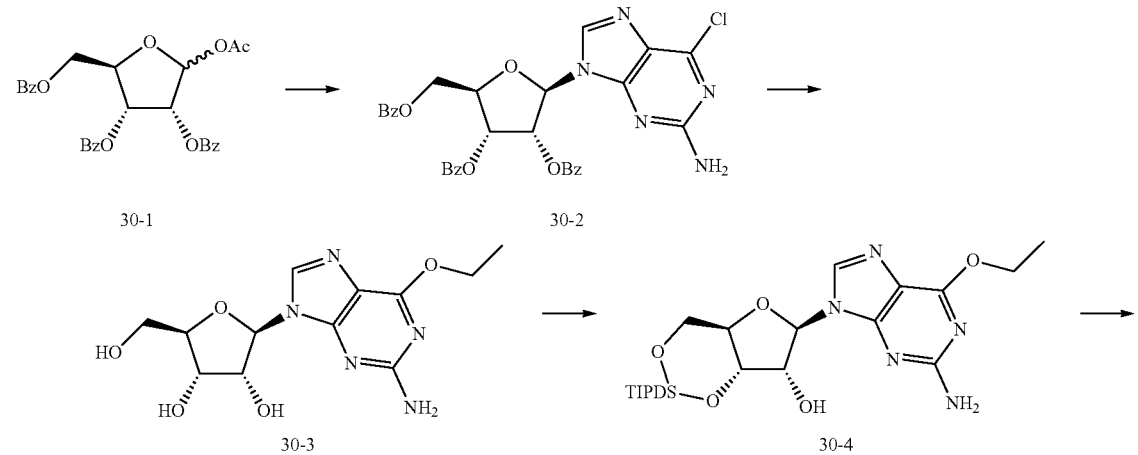

-continued
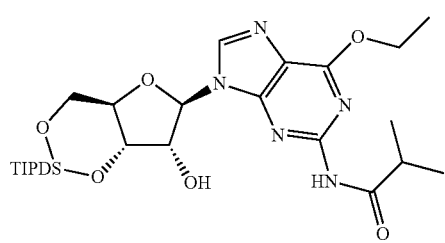
30-5
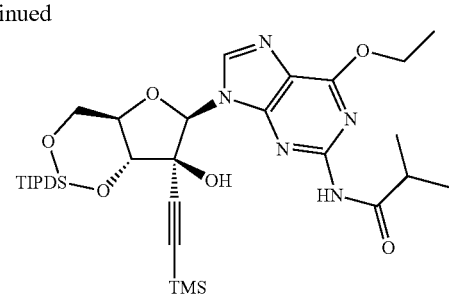
30-6
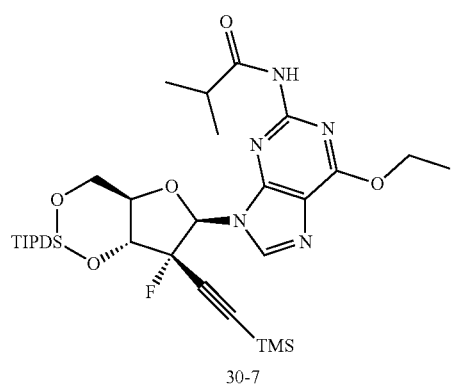
30-7
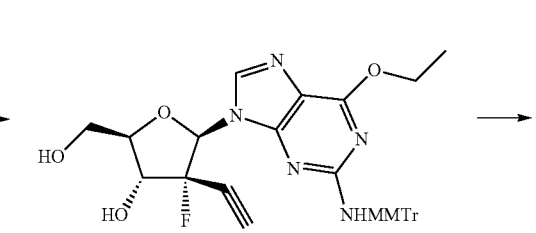
30-8
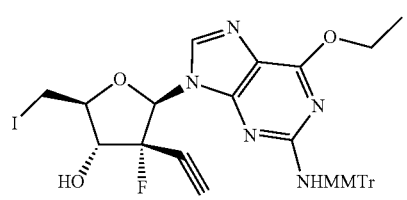
30-9
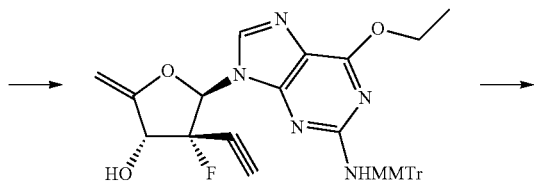
30-10
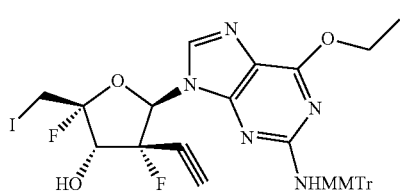
30-11
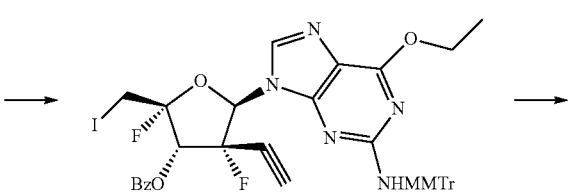
30-12
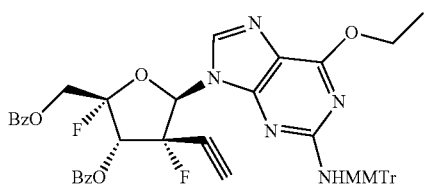
30-13
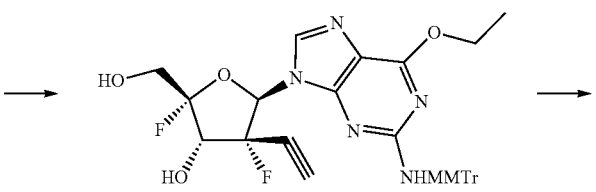
30-14
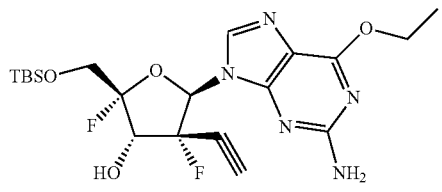
30-15
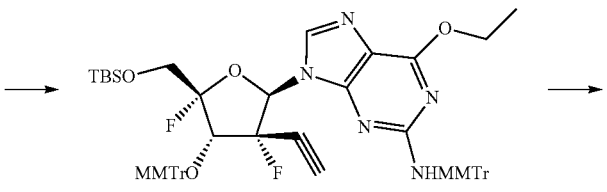
30-16

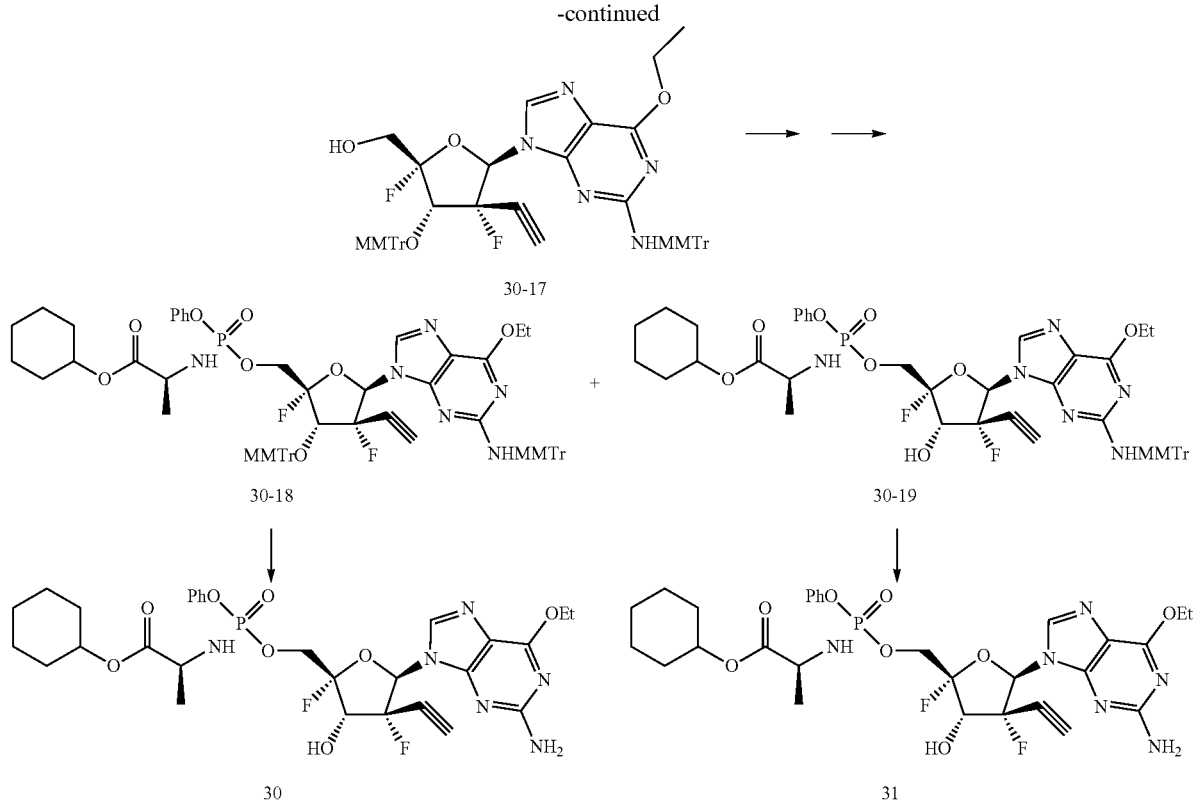

To a mixture of pre-silylated 6-Cl-guanine (using HMDS and (NH$_4$)$_2$SO$_4$) (25.2 g, 150 mmol) in DCE (300 mL) was added 30-1 (50 g, 100 mmol) and TMSOTf (33.3 g, 150 mmol) at 0° C. The mixture was stirred at 70° C. for 16 h, and then concentrated at low pressure. The residue was re-dissolved in EA, and washed with sat. aq. NaHCO$_3$ and brine. The organic layer was dried over anhydrous Na$_2$SO$_4$, and concentrated at low pressure. The residue was purified on silica gel column (PE/EA=2/1) to give pure 30-2 (45 g, 73%) as a white solid.

To a solution of 30-2 (45 g, 73.4 mmol) in EtOH (73 mL) was added with EtONa (1N in EtOH, 360 mL). The mixture was stirred at RT for 16 h. The mixture was then concentrated to give a residue, which was purified by silica gel column (DCM/MeOH=10/1) to give pure 30-3 (19 g, 83%) as a white solid.

To a solution of 30-3 (19 g, 61.1 mmol) in pyridine (120 mL) was added with TIPDSCl$_2$ (19.2 g, 61 mmol) dropwise at 0° C. The mixture was stirred at RT for 16 h, and then concentrated at low pressure. The residue was re-dissolved in EA, and washed with sat. aq. NaHCO$_3$. The organic layer was dried over anhydrous Na$_2$SO$_4$, and concentrated at low pressure. The residue was purified by silica gel column (DCM/MeOH=20/1) to give pure 30-4 (22 g, 65%) as a white solid.

To a solution of 30-4 (22 g, 39.8 mmol) in DMF/pyridine (5/1, 100 mL) was added TMSCl (12.9 g, 119 mmol) dropwise at 0° C. The mixture was stirred at RT for 1 h and then treated with isobutyryl chloride (5.4 g, 50 mmol). The mixture was stirred at RT for 3 h and then quenched by NH$_4$OH. The mixture was concentrated at low pressure. The residue was dissolved in EA (200 mL). The solution was washed with sat. aq. NaHCO$_3$, and then the organic layer was dried and concentrated at low pressure. The residue was purified by silica gel column (DCM/MeOH=50/1) to give pure 30-5 (15 g, 60%) as a white solid.

To a solution of 30-5 (15 g, 24.1 mmol) in DCM (100 mL) was added PDC (13.5 g, 26 mmol) and Ac$_2$O (9.8 g, 96 mmol) at 0° C. The mixture was stirred at RT for 16 h. The reaction was quenched by sat. aq. NaHCO$_3$, and then extracted with EA. The organic layer was dried over anhydrous Na2SO4, and concentrated at low pressure. The residue was dissolved in anhydrous THF (100 mL). To a solution of TMSCCH (12 g, 112 mmol) in THF (200 mL) was added n-BuLi (2.5 N, 44 mL) at −78° C. The mixture was stirred at −78° C. for 15 mins and 0° C. for 15 mins. The mixture was treated with a solution of crude ketone in THF at −78° C. and stirred at −30° C. for 2 h. The reaction was quenched by sat. aq. NH$_4$Cl, and then extracted by EA. The combined organic layer was dried over anhydrous Na$_2$SO$_4$, and concentrated at low pressure. The residue was purified by silica gel column (PE/EA=10/1) to give pure 30-6 (3.1 g, 18%) as a white solid.

To a solution of 30-6 (7 g, 7.5 mmol) and pyridine (1.4 g, 17 mmol) in DCM (35 mL) was added with DAST (5.6 g, 35 mmol) at −78° C. The mixture was stirred at −78° C. for 3 h. The reaction was quenched by sat. aq. NaHCO$_3$, and then extracted with EA. The combined organic layer was dried over anhydrous, and concentrated at low pressure. The residue was purified by silica gel column (PE/EA=10/1) to give pure 30-7 (3.1 g, 18%) as a white solid.

Compound 30-7 (4.1 g, 5.7 mmol) in sat. NH$_3$/MeOH (100 mL) was stirred at RT for 16 h, and concentrated at low pressure. The residue was re-dissolved in anhydrous DCM (300 mL), and was treated with AgNO$_3$ (27.0 g, 160 mmol), collidine (22 mL) and MMTrCl (23.0 g, 75.9 mmol) in small portions under N$_2$. The mixture was stirred at RT for 16 h. The mixture was filtered, and the filtrate was washed with sat. NaHCO₃ solution and brine. The organic layer was separated, dried over anhydrous Na₂SO₄, and concentrated at low pressure. The residue was purified by silica gel column (PE/EA=10/1) to give the pure intermediate. The intermediate was dissolved in a solution of TBAF/THF (1N, 20 mL). The mixture was stirred at RT for 2 h and then concentrated at low pressure. The residue was purified by silica gel column (DCM/MeOH=50/1) to give pure 30-8 (3.0 g, 86%) as a white solid.

To a solution of 30-8 (3.0 g, 4.9 mmol) in THF (50 mL) was added imidazole (840 mg, 12 mmol), PPh₃ (3.2 g, 12 mmol), and I₂ (2.4 g, 9.2 mmol) at 0° C. The mixture was stirred at RT for 16 h. The reaction was quenched by sat. aq. Na₂S₂O₃, and then extracted with EA. The combined organic layer was dried over anhydrous Na₂SO₄, and concentrated at low pressure. The residue was purified by silica gel column (PE/EA=2/1) to give crude 30-9 (4.2 g, >100%, containing TPPO) as a white solid.

To a solution of crude 30-9 in anhydrous THF (30 mL) was added DBU (2.7 g, 18 mmol), and heated to 80° C. The mixture was stirred for 1 h and checked by LCMS. The mixture was quenched by water, and extracted with EA. The organic layer was dried over anhydrous Na₂SO₄ and filtered, and the filtrate was concentrated at low pressure. The residue was purified by silica gel column (PE/EA=2/1) to give 30-10 (2.0 g, 69%) as a white solid.

To an ice cooled solution of 30-10 (2.0 g, 3.38 mmol) in anhydrous MeCN (15 mL) was added NIS (777 mg, 3.5 mmol) and NEt₃.3HF (536 g, 3.3 mmol) at 0° C. The mixture was stirred at RT for 16 h and checked by LCMS. After completion, the mixture was quenched by sat. Na₂SO₃ and sat. NaHCO₃ solution, and extracted with EA. The organic layer was separated, dried over anhydrous Na₂SO₄ and concentrated at low pressure. The residue was purified by silica gel column chromatography (PE/EA=10/1 to 3/1) to give 30-11 (2.1 g, 84.0%) as a white solid.

To a solution of crude 30-11 (2.1 g, 2.85 mmol) in anhydrous DCM (100 mL) was added DMAP (490 mg, 4 mmol), and BzCl (580 mg, 4 mmol) at 0° C. The mixture was stirred overnight and checked by LCMS. The reaction was washed with sat. NaHCO₃ solution. The organic layer was dried over anhydrous Na₂SO₄, and concentrated at low pressure. The residue was purified by silica gel column chromatography (PE/EA=8/1 to 3/1) to give 30-12 (2.0 g, 83.4%) as a white solid.

To a solution of 30-12 (2.0 g, 2.4 mmol) in anhydrous DMF (60 mL) was added NaOBz (3.3 g, 23.0 mmol) and 15-crown-5 (5.11 g, 23 mmol). The mixture was stirred at 110° C. for 36 h. The reaction was quenched by water, and the mixture was extracted with EA. The organic layer was dried over anhydrous Na₂SO₄, and concentrated at low pressure. The residue was purified by silica gel column (PE/EA=5/1 to 3/1) to give 30-13 (830 mg, 42.0%) as a white solid. ESI-MS: m/z 836.11 [M+H]⁺.

A solution of 30-13 (831 mg, 1.0 mmol) in anhydrous n-butylamine (4 mL) was stirred at RT for 3 h under N₂ atmosphere. The reaction was monitored by TLC. The solvent was evaporated in vacuo, and the residue was purified by silica gel column (MeOH in DCM from 0% to 10%) to give the crude product, which as re-purified using silica gel column to give 30-14 as a light pink solid (563 mg).

To a solution of 30-14 (560 mg, 0.89 mmol) in anhydrous pyridine (5 mL) was added imidazole (78.6 mg, 1.16 mmol) and TBSCl (202 mg, 1.34 mmol) at 0 to 5° C. The mixture was stirred for 15 h. The reaction was quenched by adding absolute EtOH (0.3 mL). The solution was concentrated to dryness under reduced pressure, and co-evaporated with toluene 3 times. The residue was dissolved in EA (150 mL), and washed with water, sat. NaHCO₃, and brine. The combined organic layer was dried over Na₂SO₄, filtered and evaporated at low pressure. The residue was purified by silica gel column (0-20% EA in hexanes) to give 30-15 (303 mg) as a white solid.

To a solution of 30-15 (303 mg, 0.41 mmol), AgNO₃ (208 mg, 1.23 mmol) and collidine (0.55 mL, 4.51 mmol) in anhydrous DCM (4 mL) was added MMTrCl (378 mg, 1.3 mmol) under N₂. The mixture was stirred at RT overnight under N₂, and monitored by TLC. The mixture was filtered through pre-packed celite filter, and the filtrate was washed with water and, 50% aqueous citric acid, and brine. The organic layer was separated, dried over anhydrous Na₂SO₄, filtered and concentrated at low pressure. The residue was purified by silica gel column (EA in hexanes from 0% to 30%) to give 30-16 (374 mg, 90%).

To a solution of 30-16 (374 mg, 0.37 mmol) in anhydrous THF (4 mL) was added 1.0 M solution of TBAF (0.74 mL, 0.74 mmol) at 0 to 5° C. The mixture was stirred at RT for 1 h. The mixture was quenched with silica gel, and filtered. The solvents were evaporated to give the crude product, which was purified by silica gel column (EA in hexanes from 0% to 50%) to give 30-17 (265 mg).

To a stirred solution of 30-17 (187.5 mg, 0.16 mmol) in anhydrous CH₃CN (2.5 mL) was added N-methylimidazole (136 μL, 1.66 mmol) at 0-5° C. (ice/water bath) followed by solution of phenyl (cyclohexanoxy-L-alaninyl) phosphorochloridate (214 mg, 0.62 mmol, dissolved in 0.5 mL of CH₃CN). The solution was stirred at RT for 3 h, and then diluted with EA followed by the addition of water (15 mL). The solution was washed with H₂O, 50% aqueous citric acid solution and brine. The organic layer was separated, dried over anhydrous MgSO₄ and filtered. The filtrate was concentrated in vacuum to give a residue, which was purified on silica gel with 0 to 40% EA/hexanes to give (single isomers) of 30-18 (108 mg) Elution of the latter fraction gave (single isomers) of 30-19 (120 mg) as glassy solid.

Compound 30-18 (108 mg, 0.089 mmol) was dissolved in anhydrous CH₃CN (0.5 mL), and 4N HCl in dioxane (67 μL) was added at 0 to 5° C. (ice/water bath). The mixture was stirred at RT for 40 mins, and anhydrous EtOH (200 μL) was added. The solvents were evaporated at RT and co-evaporated with toluene 3 times. The residue was dissolved in 50% CH₃CN/H₂O, was purified on a reverse-phase HPLC (C18) using acetonitrile and water, followed by lyophilization to give compound 30 (26.6 mg) as a white foam. ¹H NMR (CD₃OD-d₄, 400 MHz) δ 7.89 (s, 1H), 7.33-7.29 (m, 2H), 7.20-7.13 (m, 3H), 7.17 (m, 1H), 6.62 (d, J=15.6 Hz, 1H), 5.39 (t, J=25.2 Hz, 1H), 4.75-4.42 (m, 6H), 3.92 (t, J=8.8 Hz, 1H), 3.24 (d, J=5.6 Hz, 1H), 1.76-1.51 (m, 5H), 1.45-1.25 (m, 12H); ³¹P NMR (CD₃OD-d₄) δ4.04 (s); ESI-LCMS: m/z=665.2 [M+H]⁺.

Compound 31 (44.4 mg, single isomer) was obtained according to the procedure described for compound 30 using 30-19. ¹H NMR (CD₃OD-d₄, 400 MHz) δ 7.93 (s, 1H), ), 7.32 (t, J=8.0 Hz, 1H), 7.24 (d, J=7.6 Hz, 2H), 7.16 (t, J=7.6 Hz, 1H), 6.61 (d, J=16.0 Hz, 1H), 4.68-4.60 (m, 2H), 4.54-4.39 (m, 3H), 3.93-3.89 (m, 1H), 3.24 (d, J=5.6 Hz, 1H), 1.75-1.5 (m, 5H), 1.48-1.23 (m, 12H); ¹⁹F NMR (CD₃OD-d₄) δ−122.95 (s), −155.84-155.99 (m); ³¹P NMR (CD₃OD-d₄) δ3.94 (s); ESI-LCMS: m/z=665.15 [M+H]⁺.

Example 24

Compound 32

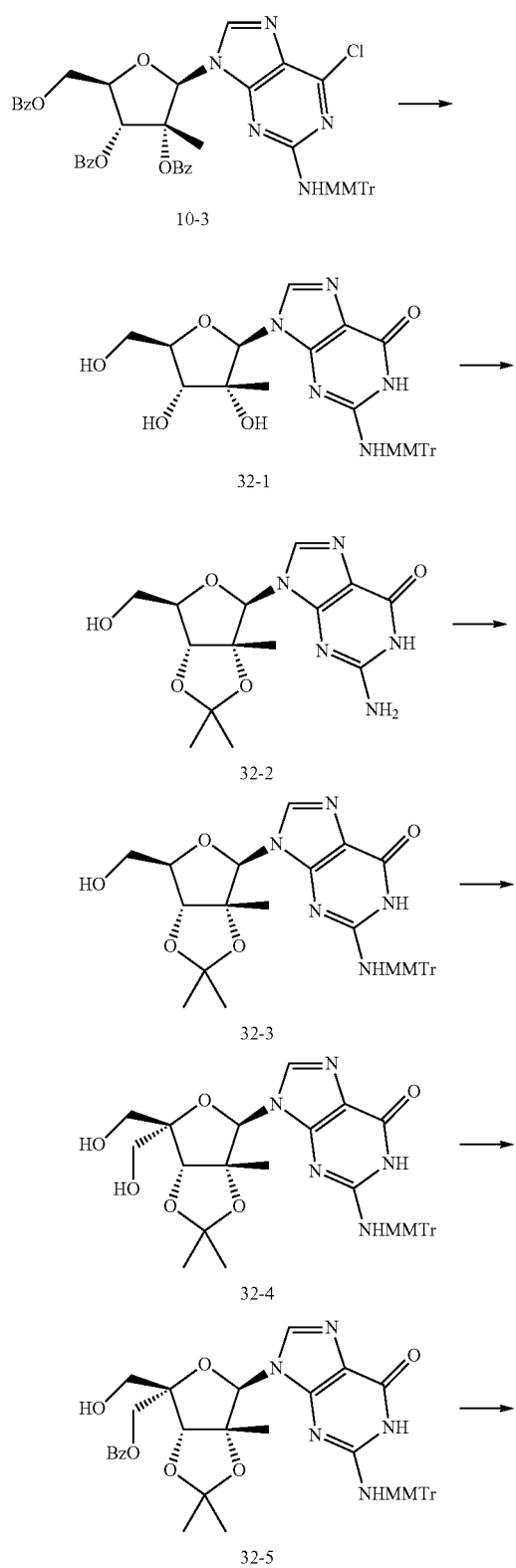

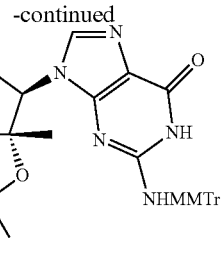

32-6

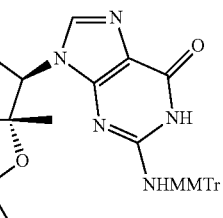

32-7

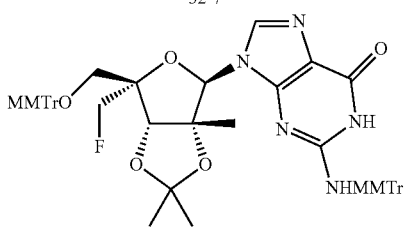

32-8

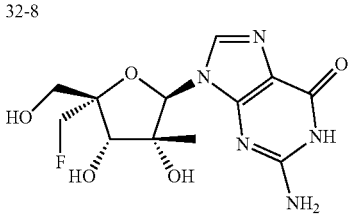

32

To a solution of 3-hydroxypropanenitrile (27 g, 0.15 mol) in THF (150 mL) was added NaH (8.4 g, 0.21 mol) at 0° C., and the mixture was stirred for 1 h. at RT. Compound 10-3 (27 g, 0.03 mol) in THF (100 mL) was treated with this mixture at 0° C. The combined mixture was stirred for 6 h. at RT. The reaction was quenched with H$_2$O, and extracted with EA. The organic layer was dried over anhydrous Na$_2$SO$_4$, and concentrated at low pressure. The residue was purified by column chromatography to give 32-1 (9.38 g, 55%).

To a solution of 32-1 (1 g, 1.76 mmol) and TsOH (1 g, 5.28 mmol) in DMF (4 mL) and acetone (8 mL) was added 2,2-dimethoxypropane (1.8 g, 17.6 mmol) at RT. The mixture was heated to 50° C. for 3 h. The reaction was quenched with H$_2$O (50 mL), and extracted with EA (3×50 mL). The organic layer was dried over anhydrous Na$_2$SO$_4$, and concentrated at low pressure. The residue was purified by column chromatography to give 32-2 (520 mg, 87%).

To a stirred solution of 32-2 (10.0 g, 29.6 mmol) in pyridine (100 mL) was added TBSCl (53.4 g, 35.6 mmol) at RT, and the mixture was stirred for 5 h. The mixture was concentrated at low pressure, and the residue was dissolved in EA (100 mL). The solution was washed with water and brine. The organic layer was dried over anhydrous Na$_2$SO$_4$, and concentrated at low pressure. The crude product was co-evaporated with toluene 3 times. To a solution of anhydrous crude product (2.0 g, 4.43 mmol) in DCM (30 mL)

was added DMTrCl (2.24 g, 6.65 mmol), 2,4,6-trimethylpyridine (1.07 g, 8.86 mmol) and AgNO$_3$ (1.5 g, 8.86 mmol). The mixture was stirred for 1.5 h. The mixture was filtered, and the filtrate was washed with 0.5 N HCl solution. The solution was washed with brine, dried over anhydrous Na$_2$SO$_4$, and concentrated at low pressure to give the crude yellow solid. The crude yellow solid (7.2 g, 10 mmol) was treated with a solution of NH$_4$F (7.2 g, 200 mmol) in MeOH (50 mL), and the mixture was heated to 50° C. for 8 h. The mixture was concentrated at low pressure. The residue was purified by silica gel column to give 32-3 (4.8 g, 80%).

To a solution of 32-3 (200 mg, 0.33 mmol) in DCM (5 mL) was added TFA.Py (40 mg, 0.328 mmol), DMSO (0.15 mL), and DCC (191 mg, 0.99 mmol) at RT. The mixture was stirred for 6 h, and concentrated at low pressure. The residue was purified by silica gel column to give the product. To a solution of the product (0.2 g, 0.328 mmol) and HCHO (0.2 mL) in 1,4-dioxane (2 mL) was added NaOH (0.4 mL, 2 M) at RT. The mixture was stirred for 5 h. The mixture was then treated with NaBH$_4$ (24 mg, 0.66 mmol), and stirred for 3 h. The mixture was diluted with EA (20 mL), and washed with brine. The organic phase was dried over anhydrous Na$_2$SO$_4$, and concentrated at low pressure. The residue was purified by silica gel column to give 32-4 (125 mg, 60%).

To a solution of 32-4 (4 g, 6.25 mmol) in DCM (40 mL) was added pyridine (10 mL) and BzCl (920 mg, 15.6 mmol) at −78° C. The mixture was slowly warmed up to RT. The reaction was monitored by LCMS. The mixture was quenched with H$_2$O (40 mL), and extracted with DCM (3×50 mL). The organic layer was washed brine, dried over anhydrous Na$_2$SO$_4$, and concentrated at low pressure. The residue was purified by silica gel column to give 32-5 (3.25 g, 70%).

To a solution of 32-5 (5.75 g, 7.7 mmol) in DCM (20 mL) was added DMTrCl (3.58 g, 11.1 mmol), 2,4,6-trimethylpyridine (1.87 g, 15.4 mmol) and AgNO$_3$ (2.63 g, 15.4 mmol), and stirred for 3 h. The mixture was filtered, and the filtrate was washed with 0.5 N HCl solution. The organic phase was washed with brine, dried over anhydrous Na$_2$SO$_4$, and concentrated at low pressure. The residue was purified by silica gel column to give 32-6 (6.25 g, 80%).

To a solution of 32-6 (4.3 g, 4.23 mmol) in MeOH (40 mL) was added NaOMe (0.82 g, 12.6 mmol) at RT, and stirred for 3 h. The mixture was concentrated at low pressure. The residue was dissolved in EA (30 mL), and washed with brine. The organic layer was dried over anhydrous Na$_2$SO$_4$, and concentrated at low pressure. The residue was purified by silica gel column to give 32-7 (2.89 g, 75%).

To a solution of 32-7 (0.5 g, 0.54 mmol) and pyridine (0.478 g, 5.4 mmol) in DCM (4 mL) was slowly added a solution of Tf$_2$O (0.201 g, 0.713 mmol) in DCM (3 mL) at −35° C. The mixture was warmed up to −5° C. slowly. The reaction was monitored by LCMS. The reaction was quenched with sat. NaHCO$_3$ solution, and extracted with DCM (3×20 mL). The organic phase was washed with brine, dried over anhydrous Na$_2$SO$_4$, and concentrated at low pressure. The residue was purified by silica gel column to give the product. To a solution of the product was added TBAF in THF (25 mL, 1N), and the mixture was stirred for 5 h at RT. The reaction was monitored by LCMS. The mixture was concentrated at low pressure, and the residue was purified by prep-HPLC to give 32-8 (221 mg, 45%). ESI-MS: m/z 914.4 [M+H]$^+$.

Compound 32-8 (2.14 g) was dissolved in 80% HCOOH (10 mL) and was at RT overnight. The solvent was evaporated to dryness, and the residue crystallized from methanol twice. The crystals were dissolved in a mixture of THF and 36% HCl 4:1 v:v and left overnight. The solvent was evaporated, and the nucleoside was isolated by RP HPLC on Synergy 4 micron Hydro-RP column (Phenominex). A linear gradient of methanol from 0 to 60% with 0.1% HCOOH was used for elution. Compound 32 was obtained (370 mg, 48%). MS: m/z 316.2 [M−1].

Example 25

Compound 17

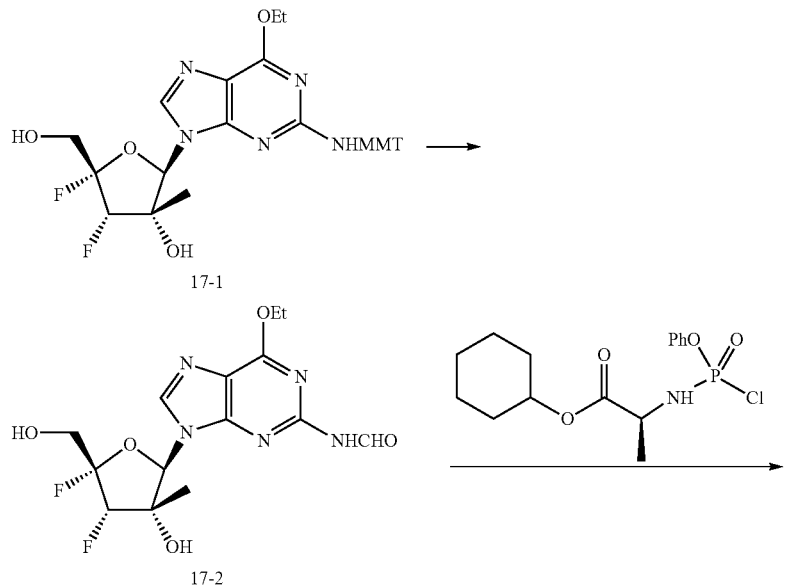

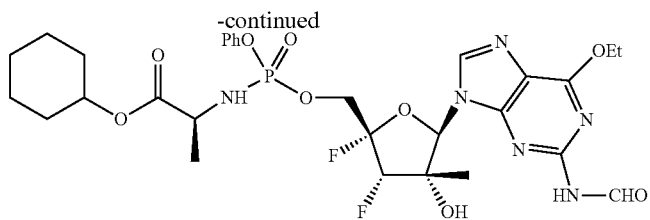

17

A solution of 17-1 (25 mg, 0.04 mmol) in 80% aq. HCOOH was kept at RT for 3 h. The mixture was concentrated and coevaporated with toluene. The crude residue was purified on silica gel (10 g column) with CH$_2$Cl$_2$/MeOH (4-10% gradient) to yield 17-2 (8 mg, 54%).

A mixture of 17-2 (8 mg, 0.02 mmol) in acetonitrile (0.4 mL) was stirred with NMI (15 mL, 8 eq.) and the phosphorochloridate reagent overnight at RT. The reaction was quenched with sat. aq. NH$_4$Cl, diluted with EtOAc and water. The organic layer was separated, washed with aq. NaHCO$_3$, water and brine, and dried (Na$_2$SO$_4$). The residue was purified on silica gel (10 g column) with CH$_2$Cl$_2$/i-PrOH (4-10% gradient) to yield compound 17 (9 mg, 66%). MS: m/z=683 [M+1].

Example 26

Compound 35

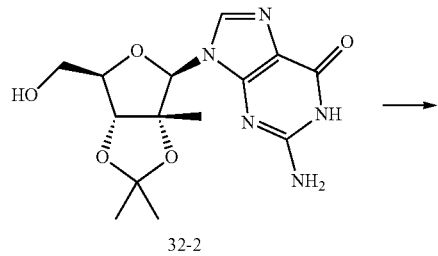
32-2

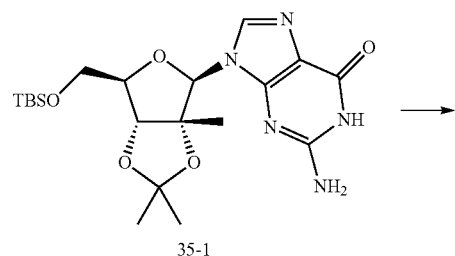
35-1

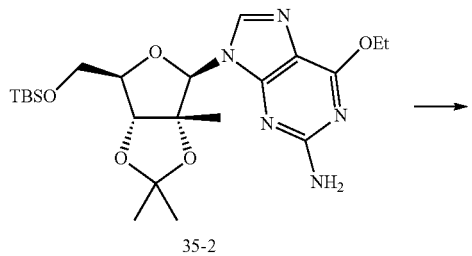
35-2

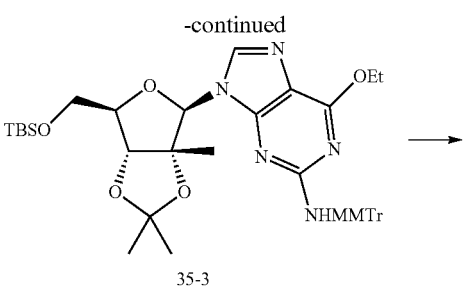
35-3

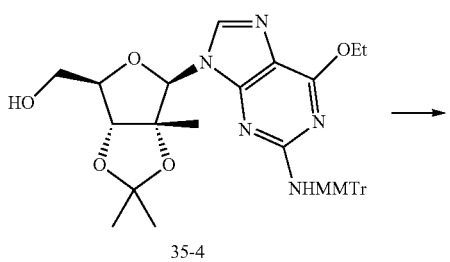
35-4

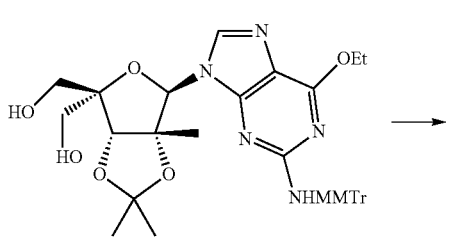
35-5

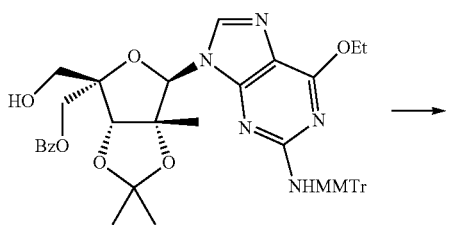
35-6

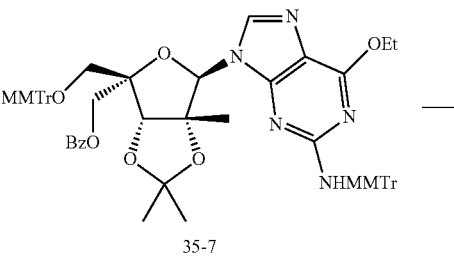
35-7

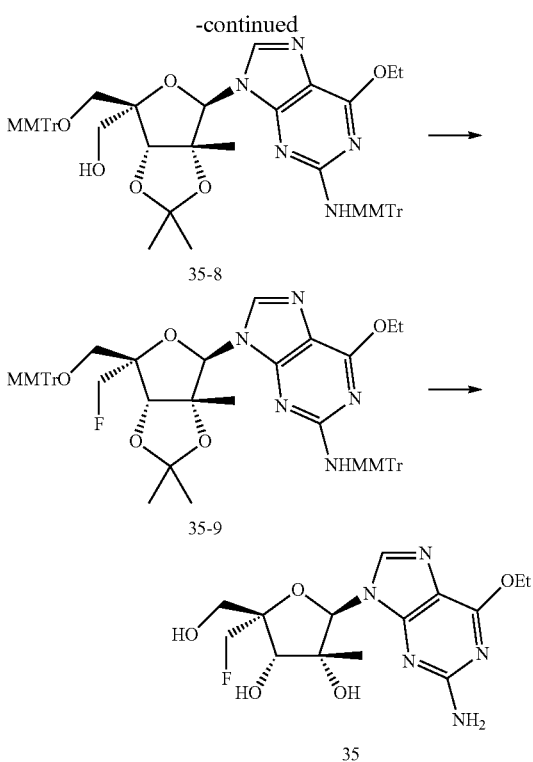

To a stirred solution of 32-2 (5.0 g, 14.83 mmol) in anhydrous pyridine (50 mL) was added TBSCl (3.33 g, 22.24 mmol) at RT under $N_2$. The mixture was stirred at RT for 12 h and concentrated at low pressure. The residue was purified by silica gel column chromatography to give 35-1 (5.69 g, 85.1%).

To a solution of $PPh_3$ (2.76 g, 10.6 mmol) and DIAD (2.15 g, 10.6 mmol) in dioxane (20 mL) was added EtOH (0.49 g, 10.6 mmol) at RT. After stirring for 30 mins, a solution of 35-1 (2.4 g, 5.3 mmol) in dioxane (10 mL) was added. The solution was stirred overnight at RT. After the reaction was complete, the reaction was quenched with sat. $NaHCO_3$ solution. The solution was extracted with EA (3×40 mL). The organic layer was washed with brine, dried over anhydrous $Na_2SO_4$, and concentrated at low pressure. The residue was purified by silica gel column (10% EA in PE) to give 35-2 (2 g, 78.4%) as a white solid.

To a solution of 35-2 (8 g, 16.9 mmol) in dichloromethane (60 mL) was added $AgNO_3$ (5.67 g, 33.4 mmol), collidine (4.03 g, 33.4 mmol) and MMTrCl (7.7 g, 25 mmol) in small portions under $N_2$ at 0° C. The mixture was stirred at RT overnight. The reaction was monitored by TLC. After completion, the mixture was filtered. The filtrate was washed with sat. aq. $NaHCO_3$ and brine. The organic layer was dried over anhydrous $Na_2SO_4$, and concentrated at low pressure. The residue was purified by silica gel column to give 35-3 (10 g, 80%) as a white solid.

To a solution of 35-3 (10 g, 13.3 mmol) in methanol (100 mL) was added $NH_4F$ (10 g, 270 mmol), and heated to reflux overnight. The mixture was concentrated at low pressure. The residue was purified by silica gel chromatography (50% PE in EA) to give 35-4 as a white solid (5 g, 59%).

To a solution of 35-4 (4 g, 6.27 mmol) and DCC (3.65 g, 18.8 mmol) in anhydrous DMSO (40 mL) was added TFA.Py (1.21 g, 6.27 mmol) at RT under $N_2$. The mixture was stirred at RT overnight. The reaction was quenched with water (100 mL), and diluted with EA (200 mL). After filtration, the filter was washed with sat. $NaHCO_3$ solution. The organic phase was washed with brine, dried over anhydrous $Na_2SO_4$, and concentrated at low pressure. The residue (4 g, 6.27 mmol) was dissolved in dioxane (40 mL), and 37% formaldehyde (4 mL) followed by addition of 2N NaOH solution (8 mL) at RT. The mixture was stirred at 30° C. overnight. $NaBH_4$ (0.7 g, 18.9 mmol) was added in portions at 5° C., and the mixture was stirred at RT for 30 mins. The reaction was quenched with water, and the mixture was extracted with EA (3×50 mL). The organic layer was dried over anhydrous $Na_2SO_4$, and concentrated at low pressure. The residue was purified on a silica gel column (20% EA in PE) to give 35-5 (2.5 g, 60%) as a white solid.

To a solution of 35-5 (2.29 g, 3.43 mmol) in pyridine (5 mL) and DCM (20 mL) was added BzCl (0.53 g, 3.77 mmol) at −78° C., and stirred overnight at RT. The mixture was quenched with water, and extracted with DCM (3×40 mL). The organic layer was dried over anhydrous $Na_2SO_4$, and concentrated at low pressure. The residue was purified by silica gel column to give the 35-6 (1.62 mg, 62%).

To a solution of 35-6 (1.62 g, 2.1 mmol) in dichloromethane (20 mL) was added $AgNO_3$ (714 mg, 4.2 mmol), collidine (508 mg, 4.2 mmol) and MMTrCl (970 mg, 3.2 mmol) in small portions under $N_2$ at 0° C. The mixture was stirred at RT overnight. The reaction was monitored by TLC. After filtration, the filter was washed with sat. aq. $NaHCO_3$ and brine. The combined organic layer was dried over anhydrous $Na_2SO_4$, and concentrated at low pressure. The residue was purified by silica gel column to give 35-7 (2 g, 91.3%) as a white solid.

To a solution of 35-7 (2.1 g, 2 mmol) in MeOH (30 mL) was added NaOMe (220 mg, 4 mmol) at RT and stirred for 1 h. After all starting material disappeared as indicated by TLC, the reaction was quenched with dry ice, and evaporated at low pressure. The residue was purified by silica gel column chromatography to give 35-8 (1.3 g, 69%) as a white solid.

To a solution of 35-8 (1.3 g, 1.38 mmol) in anhydrous DCM (15 mL) and pyridine (1 mL) was added dropwise $Tf_2O$ (585 mg, 2.07 mmol) at −20° C. The mixture was stirred at RT for 3 h, and diluted with DCM (150 mL). The solution was washed successively with water and brine. The organic solution was dried over $Na_2SO_4$ and concentrated at low pressure. The residue (1.48 g) was dissolved in anhydrous THF (15 mL), and treated with TBAF (3 mL, 1M in THF) at RT. The mixture was stirred overnight. The reaction was quenched with sat. aq. $NaHCO_3$, and extracted with EA (3×60 mL). The combined organic layer was dried over $Na_2SO_4$, and evaporated at low pressure. The residue was purified by silica gel column (30% EA in PE) to give 35-9 (1.25 g, 96%) as a white solid. ESI-LCMS: m/z 942.4 $[M+H]^+$.

Compound 35-9 (0.55 g, 0.58 mmol) was added into ice cooled 80% aq. TFA (5 mL) and kept overnight at 5° C. The mixture was concentrated under reduced pressure at 5° C. Thick oily residue was coevaporated several times with toluene and purified on silica gel (10 g column) with $CH_2Cl_2$/MeOH (4-15% gradient) to yield compound 35 (75 mg, 36%). MS: m/z=358 [M+1].

Example 27
Compound 36
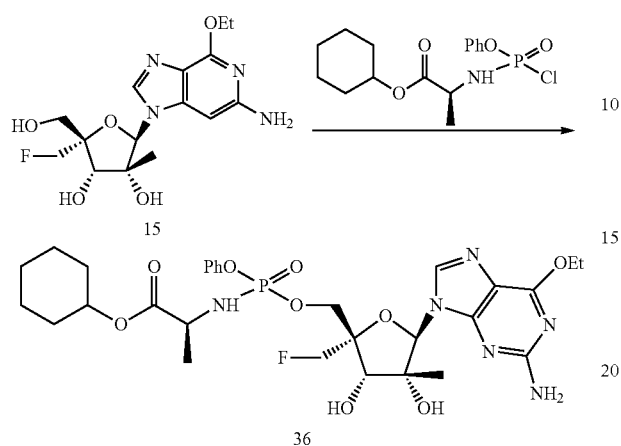
Compound 36 (8 mg, 10%) was prepared from compound 15 (48 mg) in acetonitrile (1.5 mL) with the phosphorochloridate reagent (0.14 g) and NMI (0.17 mL) in the same manner as compound 7. Purification was done by RP-HPLC (30-100% B, A: 50 mM TEAA in water, B: 50 mM TEAA in MeCN). MS: m/z=665 [M−1].
Example 28
Compound 38
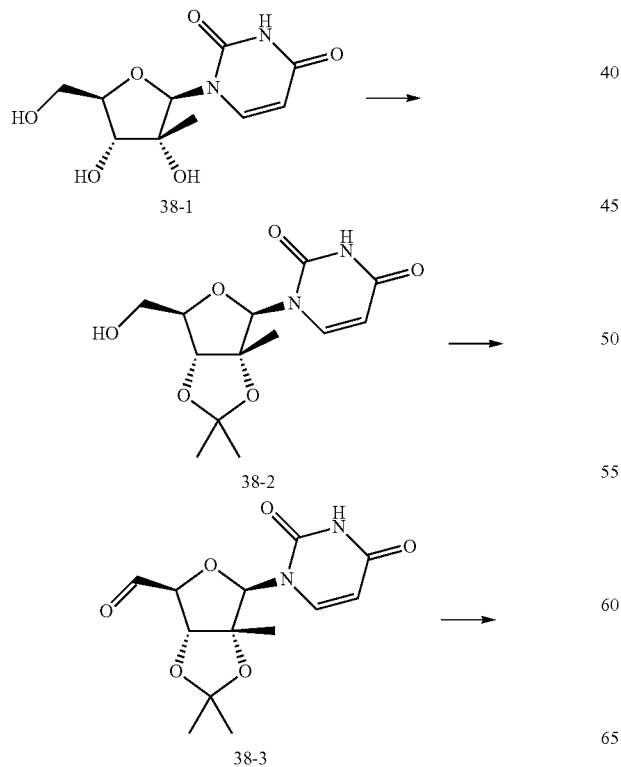
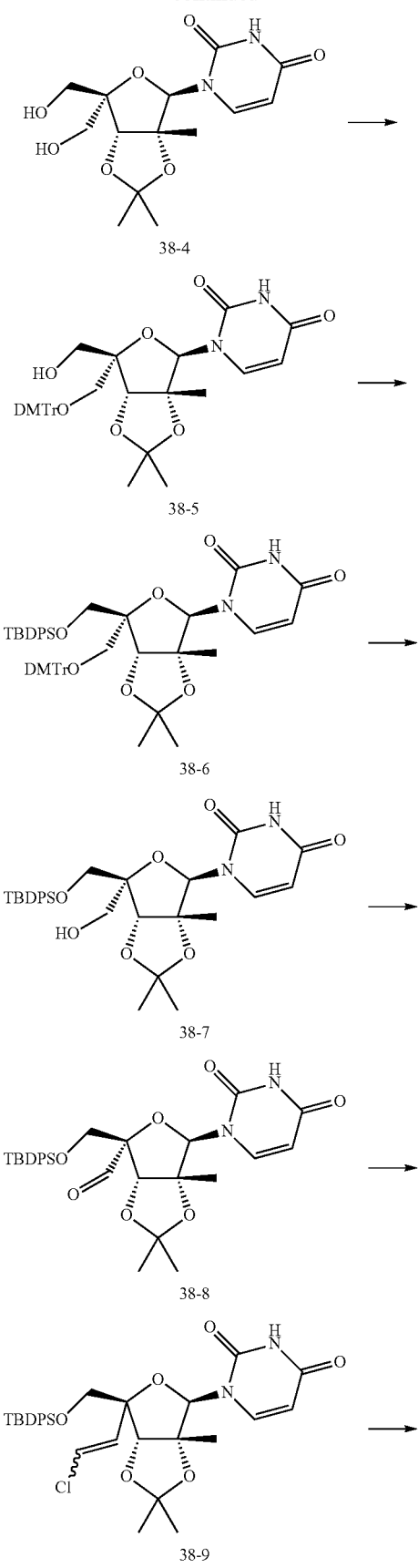

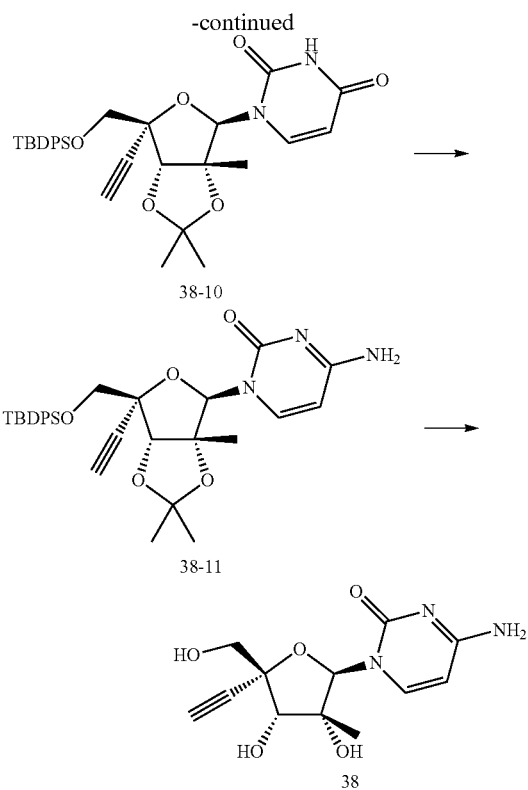

To a solution of 38-1 (17 g, 65.9 mmol) and 2,2-dimethoxypropane (34.27 g, 329.5 mmol, 5 eq.) in acetone (200 mL) was added p-toluenesulfonic acid monohydrate (11.89 g, 62.6 mmol, 0.95 eq.). The =mixture was allowed to stir overnight at RT. The reaction was quenched with sat. aq. NaHCO$_3$. The mixture was filtered, and dried over anhydrous Na$_2$SO$_4$. The filtrate was concentrated to give 38-2 (19 g, 97%).

To a solution of 38-2 (6 g, 20.1 mmol) in anhydrous CH$_3$CN (80 mL) was added IBX (7.05 g, 25.2 mmol, 1.25 eq.) at RT. The mixture was refluxed for 1 h., and cooled to 0° C. The precipitate was filtered, and the filtrate was concentrated to give crude 38-3 (6 g 100%) as a yellow solid.

Compound 38-3 (6 g 20.1 mmol) was dissolved in 1,4-dioxane (60 mL). 37% HCHO (6 mL, 69 mol) and 2M NaOH aqueous solution (12 mL, 24 mmol, 1.2 eq.) were added at 10° C. The mixture was stirred at RT overnight and neutralized with AcOH to pH=7. The mixture was treated with NaBH$_4$ (1.53 g, 40.2 mmol, 2 eq.) at 10° C. The mixture was stirred at RT for 30 mins, and then quenched with sat. aq. NH$_4$Cl. The mixture was extracted with EA. The organic layer was dried over anhydrous Na$_2$SO$_4$, and concentrated to dryness. The residue was purified on silica gel column (1-3% MeOH in DCM) to give 38-4 (3.5 g, 53%) as a white solid.

To a solution of 38-4 (3.5 g, 10.7 mmol) in anhydrous pyridine (60 mL) was added DMTrCl (3.6 g, 10.7 mmol, 1 eq.) in anhydrous DCM (8 mL) dropwise at −30° C. The mixture was stirred at RT overnight. The solution was treated with MeOH, and concentrated to dryness at low pressure. The residue was purified by column chromatography (0.5-2% MeOH in DCM) to give 38-5 (3 g, 45%) as a yellow solid.

To a solution of 38-5 (2.5 g, 4 mmol) in anhydrous CH$_2$Cl$_2$ (30 mL) was added AgNO$_3$ (0.816 g, 4.8 mmol, 1.2 eq.), imidazole (0.54 g, 8 mmol, 2 eq.) and TBDPSCl (1.18 g, 4.8 mmol, 1.2 eq.) under N$_2$ atmosphere. The mixture was stirred at RT for 14 h. The precipitate removed via filtration, and the filtrate was washed with brine and dried over Na$_2$SO$_4$. The solvent was removed under reduced pressure to give crude 38-6 (3.4 g, 100%) as a yellow solid.

Compound 38-6 (4 g, 4.6 mmol) was dissolved in 80% HOAc aqueous solution (50 mL). The mixture was stirred at RT for 3 h. The solution was treated with MeOH, and concentrated to dryness. The residue was purified by column chromatography (1-2% MeOH in DCM) to give 38-7 (1.2 g, 45%) as a white solid.

To a solution of 38-7 (1 g, 1.77 mmol) in anhydrous DCM (15 mL) was added Dess-Martin periodinane reagent (1.12 g, 2.65 mmol, 1.5 eq.) at 0° C. under nitrogen atmosphere. The reaction was stirred at RT for 2.5 h. The solution was quenched by addition of 4% Na$_2$S$_2$O$_3$ and washed with 4% sodium bicarbonate aqueous solution (50 mL). The mixture was stirred for another 15 mins. The organic layer was washed with brine, and concentrated under reduced pressure. The residue was purified by silica gel column chromatography (20% EtOAc in hexane) to give 38-8 (0.7 g, 70%) as a white solid.

To a solution of methyltriphenylphosphonium chloride (2.95 g, 8.51 mmol, 4 eq.) in anhydrous THF (20 mL) was added n-BuLi (3.2 mL, 8.1 mmol, 3.8 eq.) dropwise at −70° C. under nitrogen atmosphere. The mixture was stirred at 0° C. for 1 h. A solution of 38-8 (1.2 g, 2.13 mmol) in anhydrous THF (3 mL) was added dropwise at 0° C. under nitrogen atmosphere. The solution was stirred 0° C. for 2 h. The reaction was quenched with NH$_4$Cl and extracted with EtOAc. The organic layer was washed with brine and concentrated under reduced pressure. The crude product was purified by silica gel column chromatography (20% EtOAc in hexane) to give 38-9 (0.9 g, 75%) as a white solid.

To a solution of 38-9 (0.85 g, 1.43 mmol) in anhydrous THF (50 mL) was added n-BuLi (5.7 mL, 14.3 mmol, 10 eq.) at −70° C. under nitrogen atmosphere. The mixture was stirred at −70° C. for 2 h. The reaction was quenched with NH$_4$Cl and extracted with EtOAc. The organic layer was washed with brine and concentrated under reduced pressure. The crude product was purified by silica gel column chromatography (20% EtOAc in hexane) to give 38-10 (0.4 g, 50%) as a white solid.

To a solution of 38-10 (0.4 g, 0.714 mmol) in anhydrous CH$_3$CN (30 mL) were added TPSCl (0.433 g, 1.43 mmol, 2 eq.), DMAP (0.174 g, 1.43 mmol, 2 eq.) and TEA (1.5 mL) at RT. The mixture was stirred at RT for 3 h. NH$_4$OH (3 mL) was added, and the mixture was stirred for 1 h. The mixture was diluted with EA (150 mL), and washed with water, 0.1 M HCl and saturated aqueous NaHCO$_3$. The organic layer was washed with brine and concentrated under reduced pressure. The crude product was purified by silica gel column chromatography (2% MeOH in DCM) to give 38-11 (0.2 g, 50%) as a yellow solid.

Compound 38-11 (1.35 g, 1.5 mmol) was dissolved in 80% HOAc aqueous solution (40 mL). The mixture was stirred at 60° C. for 2 h and concentrated to dryness. The crude was purified on silica gel column (5% MeOH in DCM) to give compound 38 (180 mg, 35%) as a white solid. ESI-MS: m/z 282.1 [M+H]$^+$.

Example 29
Compound 39
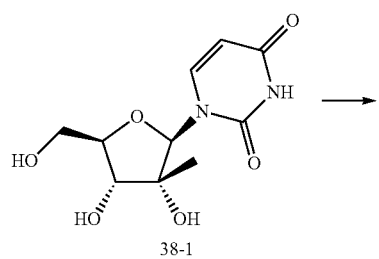
38-1
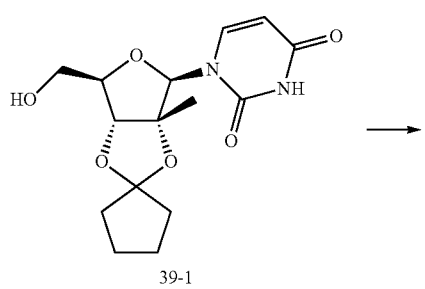
39-1
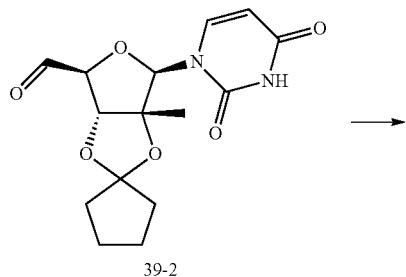
39-2
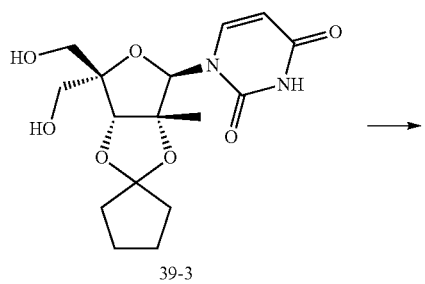
39-3
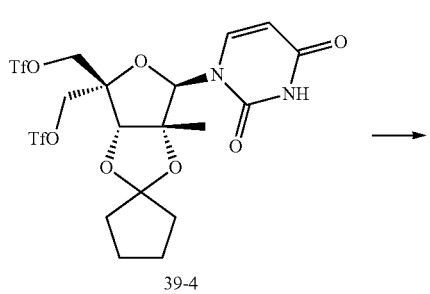
39-4
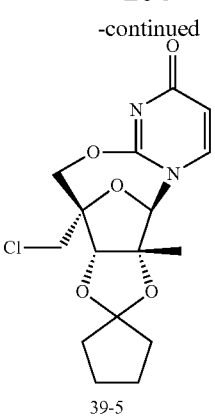
39-5
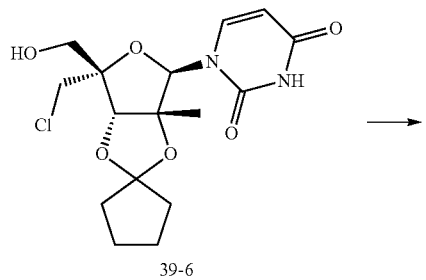
39-6
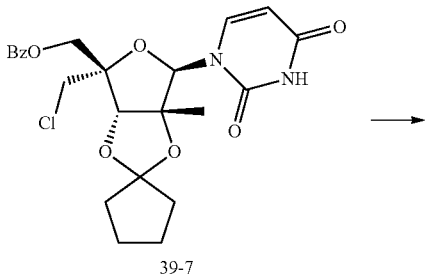
39-7
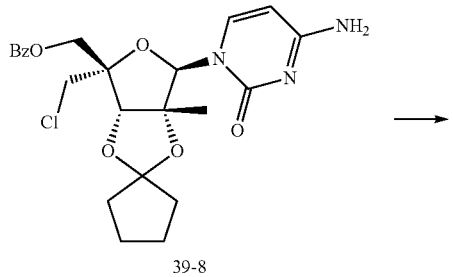
39-8
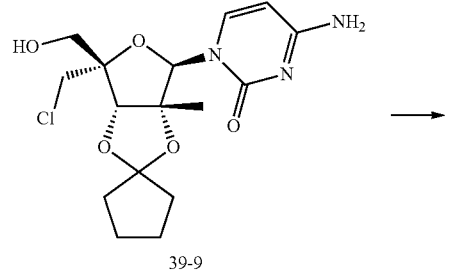
39-9
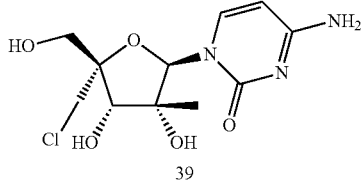
39

To a solution of cyclopentanone (6.0 g, 71 mmol) in MeOH (60 mL) was added TsOH.H₂O (1.35 g, 7.1 mmol) and trimethoxymethane (8 mL) at RT. The solution was stirred at RT for 2 h. The reaction was quenched with NaOMe, and the mixture was extracted with hexane (30 mL). The organic layer was dried and concentrated to give crude 1,1-dimethoxycyclopentane (9.2 g), which was dissolved in 1,2-dichloroethane (50 mL). To the above solution was added 38-1 (5.0 g, 19.38 mmol) and TsOH.H₂O (0.36 g, 1.9 mmol) at RT. The mixture was stirred at 60° C. for 4 h. The reaction was quenched with TEA and concentrated at low pressure. The residue was purified on silica gel column (1% MeOH in DCM) to give 39-1 (4.77 g, 76%) as a white solid.

To a solution of 39-1 (4.77 g, 14.73 mmol) in anhydrous DCM (50 mL) was added DMP (6.56 g, 15.6 mmol) at 0° C. The solution was stirred at RT for 10 h and concentrated to dryness. The residue was suspended in PE (30 mL) and DCM (5 mL), and the solid was precipitated. After filtration, the filtrate was concentrated to give the crude 39-2 (4.78 g, 100%) as a foam.

Crude 39-2 (4.77 g, 14.73 mmol) was re-dissolved in anhydrous 1,4-dioxane (50 mL). To the solution was added CH₂O aq. (37%, 3.6 mL) and NaOH aq. (2M, 11.3 mL) at 0° C. The mixture was stirred at RT for 16 h. The mixture was treated with NaBH₄ (1.48 g, 40 mmol) at 0° C. and stirred for 0.5 h. The reaction was quenched with water, and the mixture was extracted with EA. The organic layer was dried over anhydrous Na₂SO₄, and concentrated to dryness. The residue was purified on silica gel column (40% EA in PE) to give 39-3 (2.6 g, 49.9%) as a white solid.

To a stirred solution of 39-3 (5.0 g, 14.1 mmol) in pyridine (5.6 g, 71 mmol) and DCM (100 mL) was added Tf₂O (8.7 g, 31.2 mmol) dropwise at −35° C. The mixture was allowed to warm to 0° C. slowly and stirred for 2 h. The mixture was quenched with 0.5M aq. HCl and the DCM layer was separated. The organic phase was dried over anhydrous Na₂SO₄, and concentrated to dryness. The crude was purified on silica gel column (20% EA in PE) to give 39-4 (4.5 g, 52%).

39-4 (4.5 g, 7.28 mmol) was dissolved in anhydrous THF (50 mL) at 0° C. The solution was treated with NaH (60% in mineral oil, 0.32 g, 8 mmol, 1.1 eq.) in portions, and the mixture was stirred at RT for 8 h. The reaction was quenched with water, and extracted with EA (3×60 mL). The organic layer was washed with brine, dried over anhydrous Na₂SO₄, and concentrated at low pressure to give the crude product used directly for next step. To a solution of the crude product (2.0 g, 3.6 mmol) in MeCN (10 mL) was added LiCl (4.0 g, 13 mmol). The reaction was allowed to proceed overnight. Aqueous NaOH (1N, ~2 eq.) was added, and the mixture was stirred for 1 h. The mixture was partitioned between sat. NH₄Cl solution and EA. The organic layer was concentrated under reduced pressure, and the crude was purified on silica gel column (20% EA in PE) to give 39-6 (0.6 g, 46%) as a white solid. ESI-MS: m/z 395.0 [M+Na]⁺.

Compound 39-6 (3.0 g, 8.06 mmol) was co-evaporated with toluene (30 mL). To a solution of 39-6 (3.0 g, 8.06 mmol), DMAP (98 mg, 0.80 mmol) and TEA (2.3 mL, 2 eq.) in DCM (30 mL) was added Bz₂O (1.82 g, 8.06 mmol) at 0° C. and stirred for 3 h. The reaction was quenched with 1.0 M HCl and extracted with DCM. The DCM layer was dried over high vacuum pump to give crude 39-7 (3.3 g, 80.9%).

To a solution of 39-7 (400 mg, 0.84 mmol) in anhydrous CH₃CN (3 mL) was added TPSCl (507 mg, 1.68 mmol), TEA (169 mg, 1.68 mmol) and DMAP (207 mg, 1.68 mmol), and the mixture was stirred for 2 h. at RT. Completion of the reaction was determined by TLC. Ammonium solution (3.0 mL) was added at RT, and the solution was stirred for 2 h. The mixture was washed with 1.0 M HCl solution and extracted with DCM. The DCM layer was dried over Na₂SO₄ and concentrated to dryness. The crude was purified by column chromatography to provide 39-8 (250 mg, 63%).

Compound 39-8 (250 mg, 0.53 mmol) in 80% formic acid (3 mL) was stirred at RT for 3 h. Completion of the reaction was determined by TLC. The mixture was concentrated at a low pressure. The crude was purified by column chromatography to give 39-9 (130 mg, 66%).

Compound 39-9 (270 mg, 0.73 mmol) was dissolved in MeOH/NH₃ (10 mL), and the solution was stirred for 6 h. The mixture was concentrated at low pressure. The crude product was washed with DCM, and the solution was lyophilized to give compound 39 (118 mg, 52%). ESI-MS: m/z 328.3 [M+H+Na]⁺.

Example 30

Compound 40

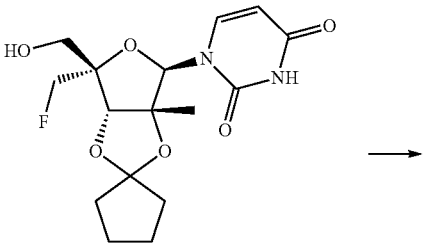

40-1

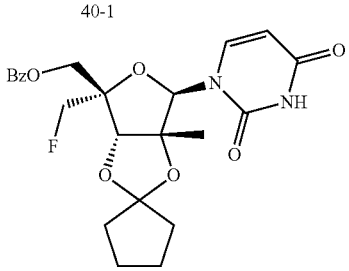

40-2

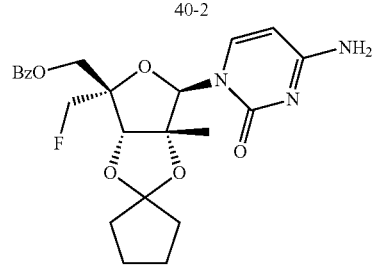

40-3

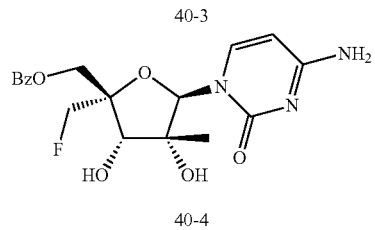

40-4

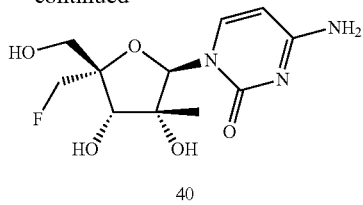

40

Compound 40-1 (3.0 g, 8.42 mmol) was co-evaporated with toluene (30 mL). To a solution of 40-1 (3.0 g, 8.42 mmol), DMAP (103 mg, 0.84 mmol) and TEA (2.5 mL, 2 eq.) in DCM (30 mL) was added Bz$_2$O (2.01 g, 8.42 mmol) at 0° C. and stirred for 3 h. The solution was quenched with 1.0 M HCl and extracted with DCM. The DCM layer was dried over high vacuum pump to give crude 40-2 (3.3 g, 85%).

To a solution of 40-2 (200 mg, 0.43 mmol) in anhydrous CH$_3$CN (2 mL) was added TPSCl (260 mg, 0.86 mmol), TEA (95 mg, 0.94 mmol) and DMAP (106.4 mg, 0.86 mmol), and the mixture was stirred for 2 h at RT. Completion of the reaction was determined by TLC. Ammonium solution (1.33 mL) was added at RT, and left to stir for 2 h. The mixture was washed with 1.0 M HCl solution, and extracted with DCM. The DCM layer was dried over anhydrous Na$_2$SO$_4$, and concentrated to dryness at low pressure. The residue was purified by column chromatography to provide 40-3 (150 mg, 75%).

Compound 40-3 (100 mg, 0.21 mmol) in 80% formic acid (2 mL) was stirred at RT for 3 h. Completion of the reaction was determined by TLC. The mixture was concentrated at low pressure, and the residue was purified by column chromatography to give 40-4 (50 mg, 58%).

Compound 40-4 (270 mg, 0.68 mmol) was dissolved in MeOH/NH$_3$ (10 mL), and the resulting solution was stirred for 6 h. The mixture was concentrated at low pressure. The crude product was washed with DCM, and the solution was lyophilized to give compound 40 (105 mg, 53.8%). ESI-MS: m/z 290.4 [M+H]$^+$.

Example 31

Compound 41

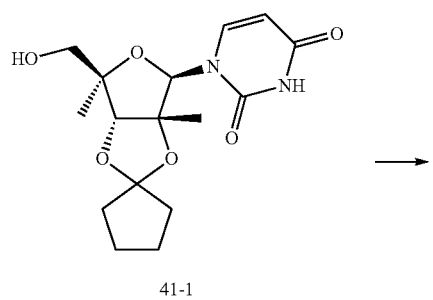

41-1

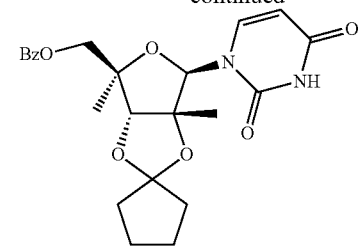

41-2

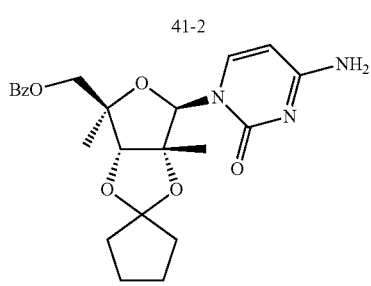

41-3

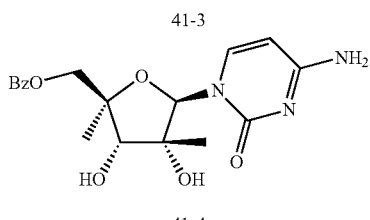

41-4

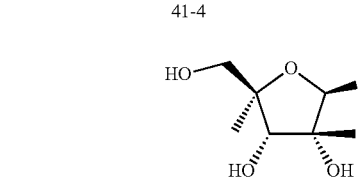

41

Compound 41-1 (3.0 g, 8.87 mmol) was co-evaporated with toluene (30 mL). To a solution of 41-1 (3.0 g, 8.87 mmol), DMAP (108 mg, 0.88 mmol) and TEA (2.5 mL, 2 eq.) in DCM (30 mL) was added Bz$_2$O (2.01 g, 8.87 mmol) at 0° C. The solution was stirred for 3 h. The reaction was quenched with 1.0 M HCl solution, and extracted with DCM. The DCM layer was dried over high vacuum pump to give crude 41-2 (3.5 g, 85%) as a solid.

To a solution of 41-2 (200 mg, 0.45 mmol) in anhydrous CH$_3$CN (2 mL) was added TPSCl (260 mg, 0.90 mmol), TEA (99 mg, 0.99 mmol) and DMAP (106.4 mg, 0.90 mmol). The mixture was stirred at RT for 2 h. Completion of the reaction was determined by TLC. An ammonium solution (1.33 mL) was added at RT, and the mixture was stirred for 2 h. The mixture was washed with 1.0 M HCl solution, and extracted with DCM. The DCM layer was dried over anhydrous Na$_2$SO$_4$, and concentrated to dryness at low pressure. The crude product was purified by column chromatography to provide 41-3 (150 mg, 75%).

Compound 41-3 (100 mg, 0.23 mmol) in 80% formic acid (2 mL) was stirred at RT for 3 h. Completion of the reaction was determined by TLC. The mixture was concentrated at a low pressure. The crude product was purified by column chromatography to give 41-4 (50 mg, 58%).

Compound 41-4 (270 mg, 0.72 mmol) was dissolved in MeOH/NH$_3$ (10 mL), and the solution was stirred for 6 h. The mixture was concentrated at low pressure. The crude product was washed with DCM, and the solution was lyophilized to give compound 41 (105 mg, 53.8%). ESI-MS: m/z 675.4 [2M+H]$^+$.

Example 32

Compound 42

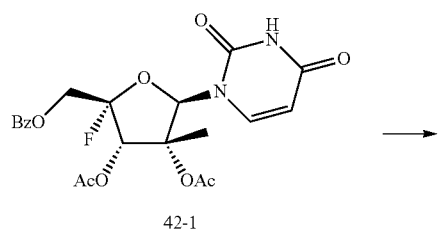
42-1

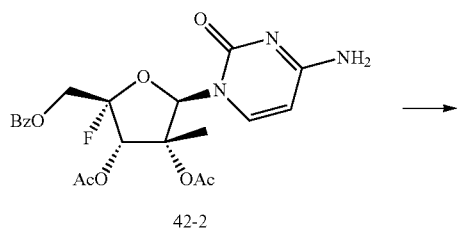
42-2

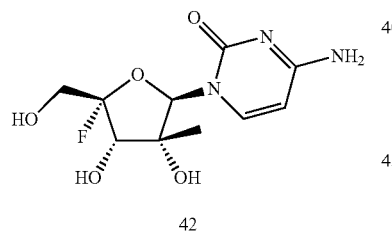
42

To a solution of 42-1 (600 mg, 1.29 mmol) in anhydrous CH$_3$CN (4 mL) was added DMAP (315 mg, 2.59 mmol), TEA (391 mg, 3.87 mmol) and TPSCl (782 mg, 2.58 mmol). The mixture was stirred for 3 h. under N$_2$. A solution of NH$_3$ in THF (2 mL) was added, and stirred for 1 h. The reaction was quenched with sat. NH$_4$Cl solution, and extracted with EA. The organic layer was dried over anhydrous Na$_2$SO$_4$, and concentrated to dryness at low pressure. The residue was purified by column chromatography to provide 42-2 (370 mg, 62%) as a white foam solid.

Compound 42-2 (370 mg, 1.48 mmol) in methanolic ammonium was stirred at RT for 4 h. The solution was concentrated to dryness to give compound 42 (200 mg, 91%) as a white solid. ESI-MS: m/z 275.9 [M+H]$^+$.

Example 33

Compound 43

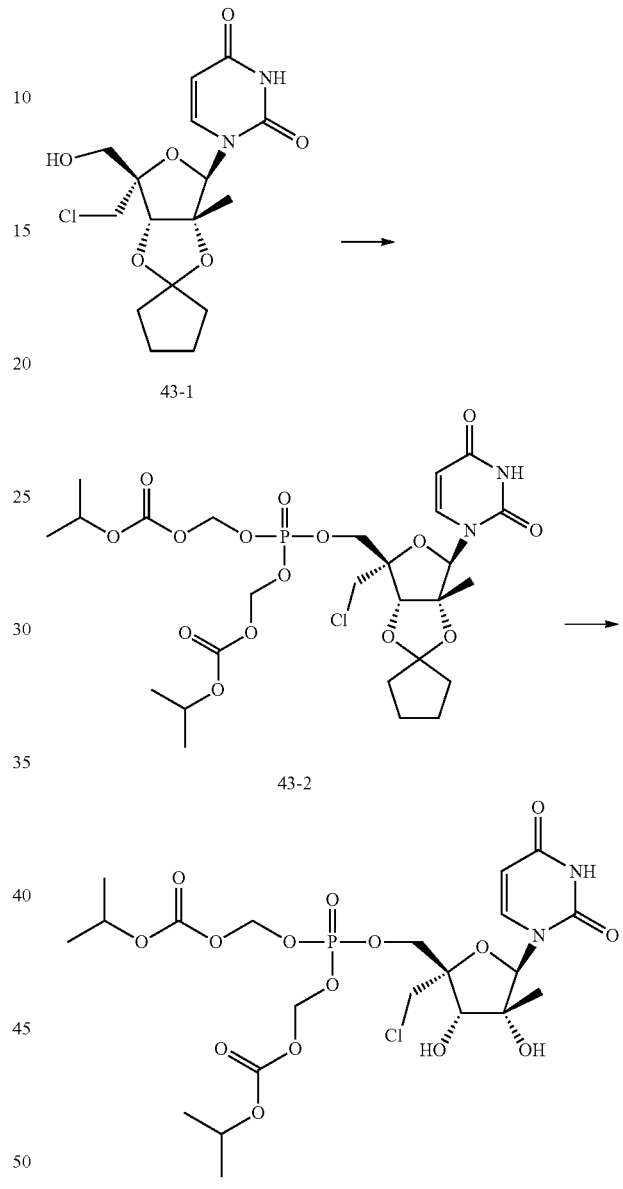

To a solution of triethylammonium bis(isopropyloxycarbonyloxymethyl)phosphate (0.6 mmol, prepared from bis(POC)phosphate (0.2 g) and Et$_3$N (83 μL)) in THF was added 43-1 (74 mg, 0.2 mmol). The mixture evaporated and rendered anhydrous by co-evaporating with pyridine follow by toluene. The residue was dissolved in anhydrous THF (2 mL). Diisopropylethylamine (0.35 mL; 10 eq.) was added, followed by BOP-Cl (0.25 g; 5 eq.) and 3-nitro-1,2,4-triazole (0.11 g; 5 eq.). The mixture was stirred at RT for 90 mins, diluted with EtOAc, washed with sat. aq. NaHCO$_3$ and brine, and dried with Na$_2$SO$_4$. The residue was purified on silica (10 g column) with CH$_2$Cl$_2$/i-PrOH (4-10% gradient) to yield 50 mg (37%) of give 43-2.

A solution of 43-2 (40 mg; 0.06 mmol) in 80% aq. HCOOH was heated at 45° C. for 8 h. The mixture was evaporated, co-evaporated with toluene and purified on silica (10 g column) with CH₂Cl₂/MeOH (4-10% gradient) to yield compound 43 (35 mg, 91%). MS: m/z=619 [M+1].

Example 34

Compound 44

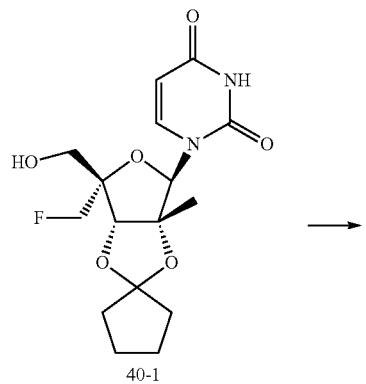

40-1

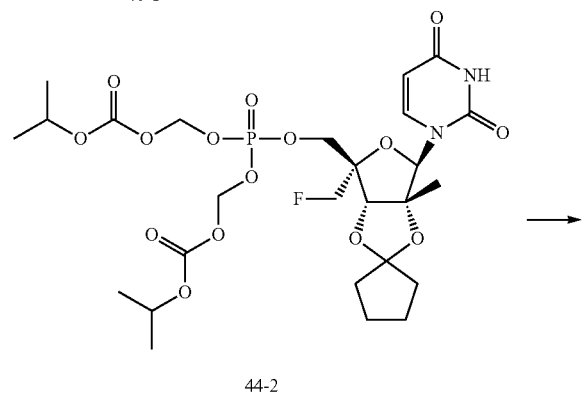

44-2

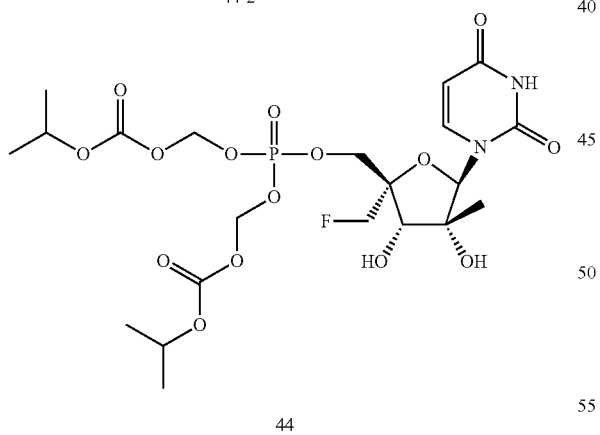

44

Compound 44-2 was prepared from 40-1 following a similar procedure for the preparation of 43-2. The residue was purified on silica (10 g column) with hexanes/EtOAc (35-100% gradient) to yield 44-2 (0.45 g, 75%).

A solution of 44-2 (0.40 g; 0.6 mmol) in 80% aq. HCOOH (15 mL) was heated at 45° C. for 8 h. The mixture was evaporated, co-evaporated with toluene and purified on silica (10 g column) with CH₂Cl₂/MeOH (4-10% gradient) to yield compound 44 (0.27 g, 75%). MS: m/z=603 [M+1].

Example 35

Compound 45

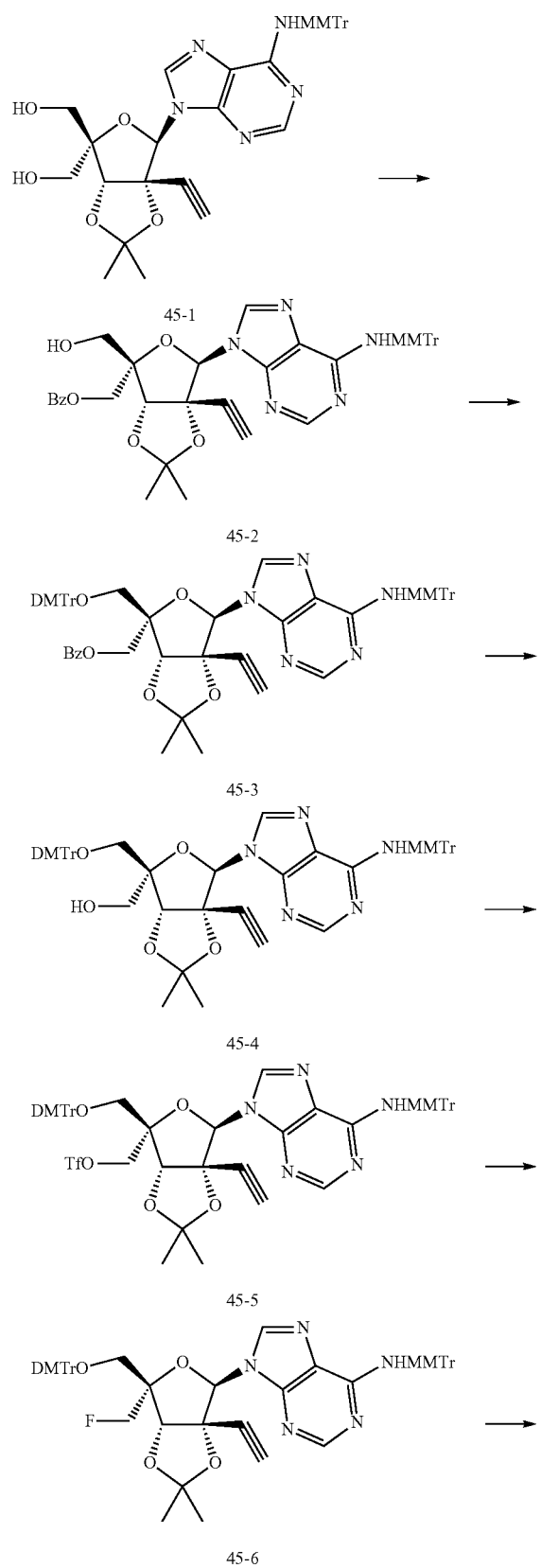

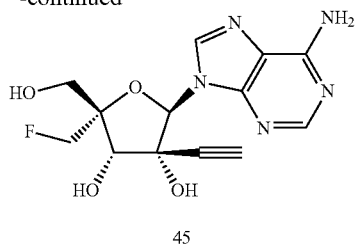

45

To a solution of 45-1 (3.0 g, 4.7 mmol) in CH₃CN/pyridine (15 mL/20 mL) was added BzCl (0.67 g, 4.7 mmol) at 0° C. slowly. The mixture was stirred at 10° C. for 12 h. The reaction was quenched with sat. NaHCO₃ solution, and extracted with DCM. The solution was washed with brine, dried over anhydrous Na₂S O₄, and concentrated at low pressure. The residue was purified on silica gel column (EA in PE from 2% to 50%) to afford 45-2 (2.6 g, 72%) as a solid.

To a solution of 45-2 (1.0 g, 1.35 mmol) in pyridine (8 mL) was added DMTrCl (0.64 g, 1.9 mmol). The mixture was stirred at 20-35° C. overnight. The reaction was monitored by LCMS and TLC. The reaction was quenched with MeOH, and concentrated at low pressure. The residue was purified by silica gel column to give 45-3 (1.5 g), which was used without further purification.

To a solution of 45-3 (1.5 g, 1.35 mmol) in MeOH/THF (1/1, 10 mL) was added NaOMe (0.11 g, 2.0 mmol), and stirred at 40° C. for 3 h. The reaction was monitored by TLC. The reaction was quenched with dry ice, and concentrated to dryness at low pressure. The residue was dissolved in DCM (100 mL). The solution was washed with brine, dried over anhydrous Na₂SO₄, and concentrated at low pressure. The residue was purified on silica gel column (EA in PE from 2% to 50%) to provide 45-4 (1.0 g, 79%).

To a solution of 45-4 (950 mg, 1.02 mmol) in DCM (5 mL) was added pyridine (241 mg, 3.05 mmol) and Tf₂O (344 mg, 1.22 mmol) at 0° C. slowly. The mixture was stirred at RT for 12 h. Completion of the reaction was determined by TLC and LCMS. The reaction was quenched with sat. NaHCO₃ solution, and extracted with DCM (3×60 mL). The organic phase was dried over anhydrous Na₂SO₄, and concentrated at low pressure to give crude 45-5 (1.08 g, 1.02 mmol), which was used without further purification.

To a solution of 45-5 (1.08 g, 1.02 mmol) in THF (6 mL) was added TBAF (0.8 g, 3 mmol), and stirred at 30-40° C. for 12 h. The reaction was quenched with sat. NaHCO₃ solution, and extracted with EA (3×60 mL). The solution was dried over anhydrous Na₂SO₄, and concentrated at low pressure. The residue was purified by silica gel column (EA in PE from 2% to 50%) to afford 45-6 (0.62 g, 65%).

A mixture of 45-6 (0.55 g, 0.59 mmol) in TFA (90%, 5 mL) was stirred at 50-60° C. for 16 h. The mixture was treated with MeOH, and concentrated at low pressure. The residue was purified by prep-HPLC to afford compound 45 (60 mg, 31%). ESI-MS: m/z 324.0 [M+H]⁺.

Example 36

Compound 46

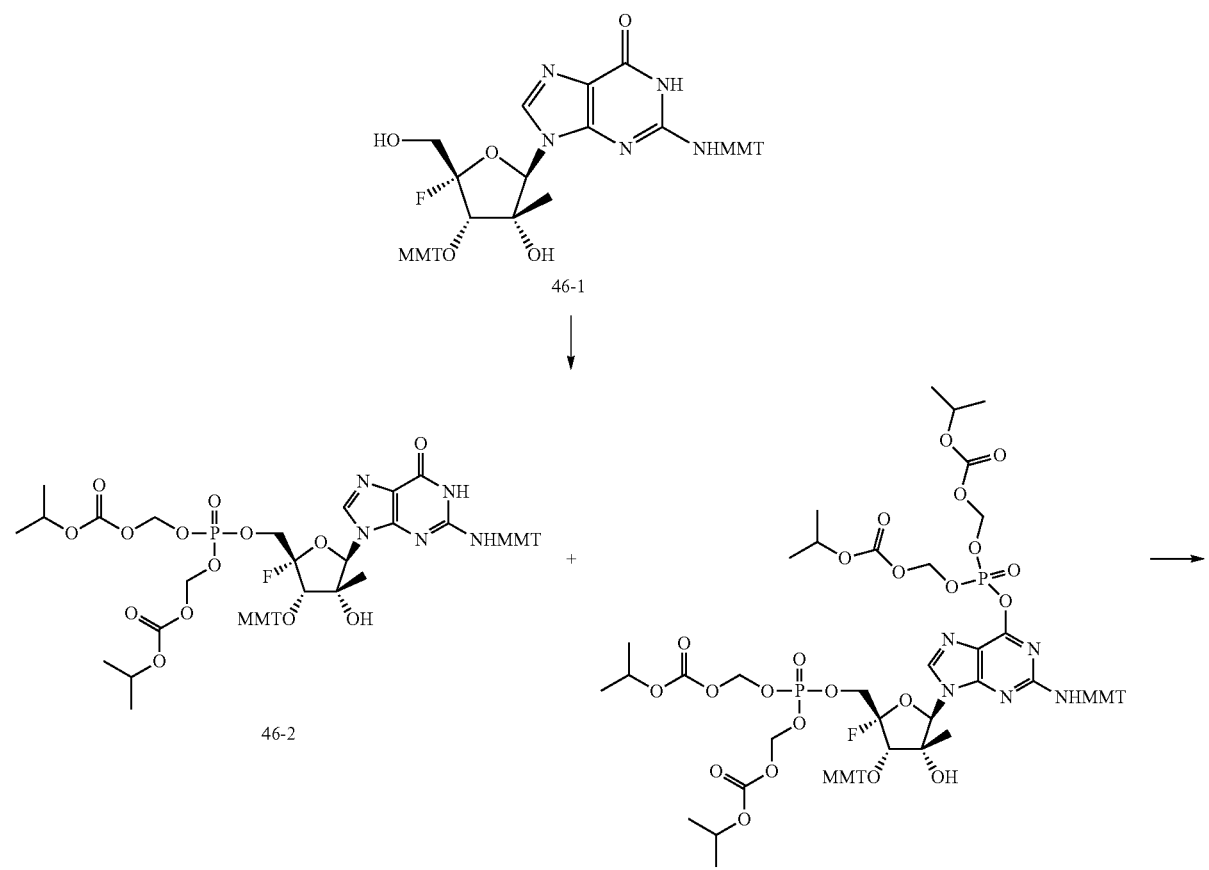

-continued

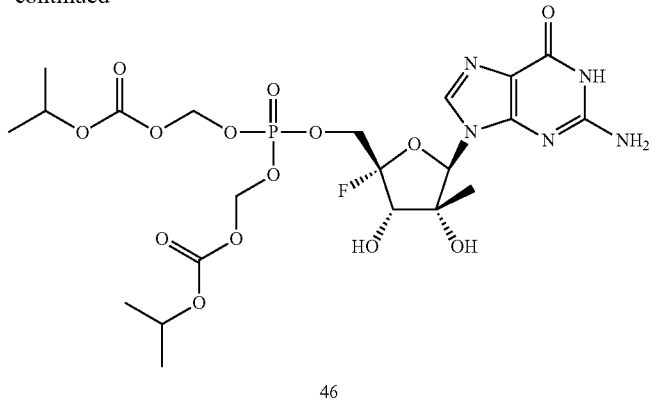

46

To a solution of triethylammonium bis(isopropyloxycarbonyloxymethyl)phosphate (0.33 mmol, prepared from 110 mg of bis(POC)phosphate and 46 μL of Et₃N) in THF was added 46-1 (91 mg, 0.11 mmol). The mixture evaporated and rendered anhydrous by co-evaporating with pyridine follow by toluene. The residue was dissolved in anhydrous THF (1.5 mL) and cooled in an ice-bath. Diisopropylethylamine (0.19 mL, 10 eq.) was added, followed by BOP-Cl (0.14 g, 5 eq.), and 3-nitro-1,2,4-triazole (63 mg, 5 eq.). The mixture was stirred 0° C. for 90 mins, diluted with EtOAc (30 mL), washed with sat. aq. NaHCO₃, brine, and dried (Na₂SO₄). The residue was purified on silica (10 g column) with CH₂Cl₂/i-PrOH solvent system (2-10% gradient) to obtain 46-2 (13 mg, 10%) and 46-3 (95 mg, 58%).

A solution of 46-2 and 46-3 (13 mg and 95 mg, respectively) in 80% aq. HCOOH (3 mL) was stirred at RT for 3 h, then evaporated and co-evaporated with toluene. The residue was purified on silica (10 g column) with CH₂Cl₂/MeOH (4-10% gradient) to obtain compound 46 in (42 mg, 94%) yield. MS: m/z=628 [M+1].

Example 37

Compound 47

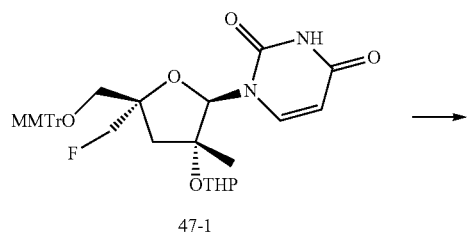

47-1

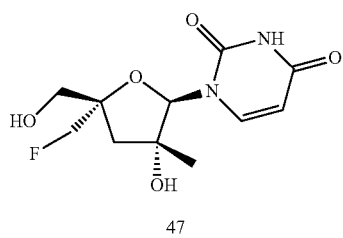

47

Compound 47-1 (320 mg, 0.51 mmol) was dissolved in a mixture of CH₃COOH/THF/H₂O (4/2/1) (7 mL), and the mixture was stirred at 50° C. for 2 h. The solution was concentrated to dryness, and the residue was purified by prep-HPLC to give compound 47 (38 mg, 31%) as a white solid. ESI-MS: m/z 296.9 [M+H+Na]⁺.

Example 38

Compound 48

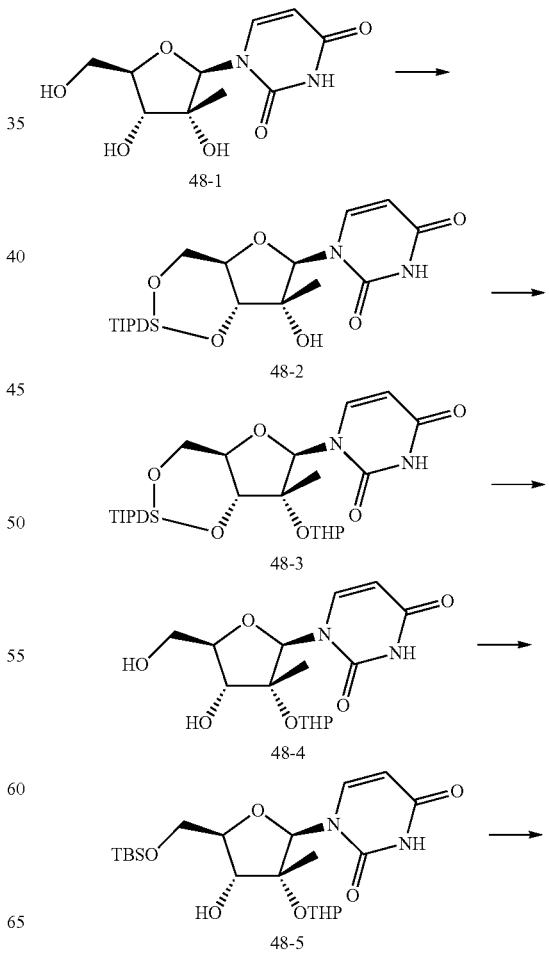

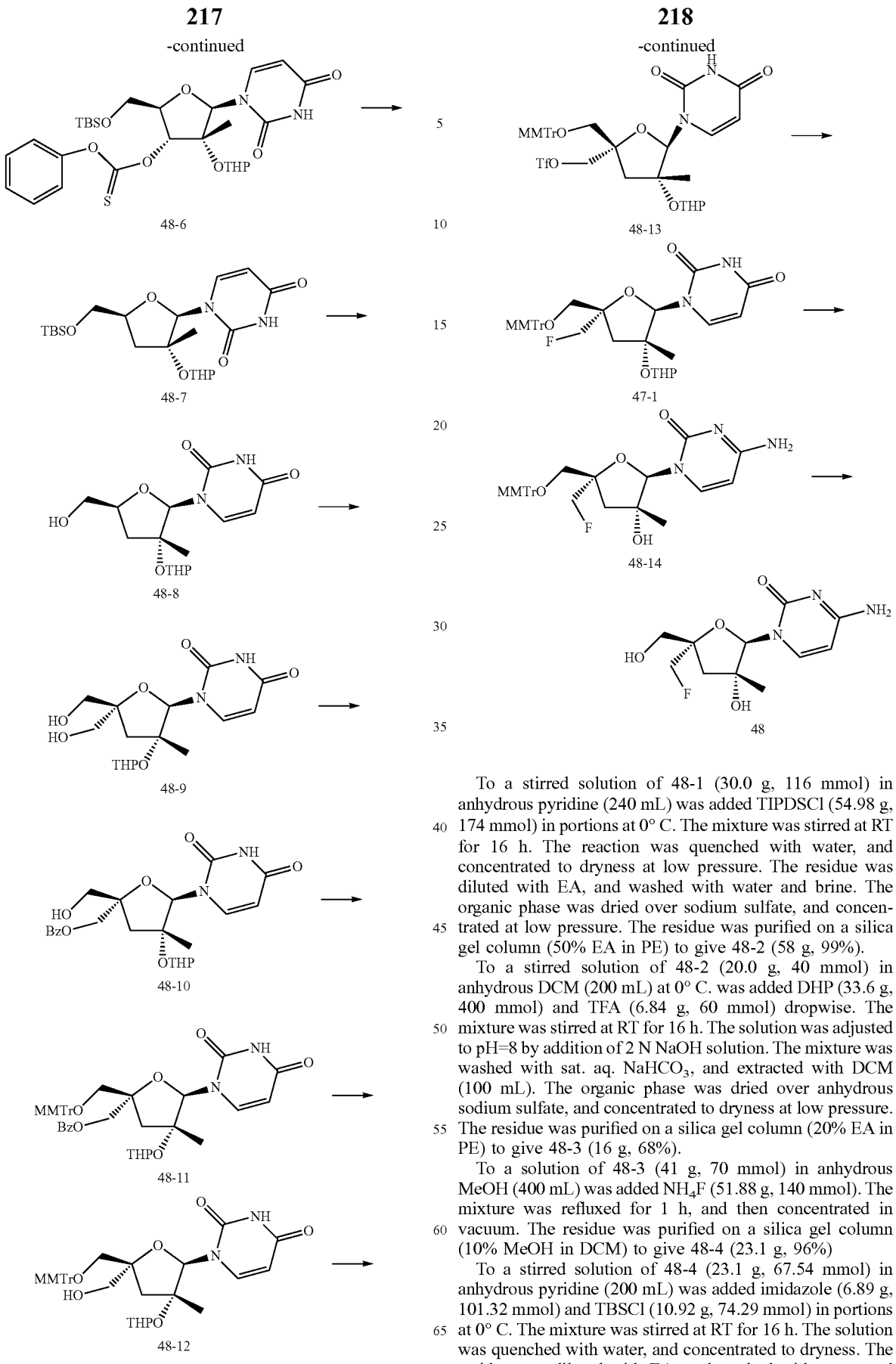

To a stirred solution of 48-1 (30.0 g, 116 mmol) in anhydrous pyridine (240 mL) was added TIPDSCl (54.98 g, 174 mmol) in portions at 0° C. The mixture was stirred at RT for 16 h. The reaction was quenched with water, and concentrated to dryness at low pressure. The residue was diluted with EA, and washed with water and brine. The organic phase was dried over sodium sulfate, and concentrated at low pressure. The residue was purified on a silica gel column (50% EA in PE) to give 48-2 (58 g, 99%).

To a stirred solution of 48-2 (20.0 g, 40 mmol) in anhydrous DCM (200 mL) at 0° C. was added DHP (33.6 g, 400 mmol) and TFA (6.84 g, 60 mmol) dropwise. The mixture was stirred at RT for 16 h. The solution was adjusted to pH=8 by addition of 2 N NaOH solution. The mixture was washed with sat. aq. NaHCO$_3$, and extracted with DCM (100 mL). The organic phase was dried over anhydrous sodium sulfate, and concentrated to dryness at low pressure. The residue was purified on a silica gel column (20% EA in PE) to give 48-3 (16 g, 68%).

To a solution of 48-3 (41 g, 70 mmol) in anhydrous MeOH (400 mL) was added NH$_4$F (51.88 g, 140 mmol). The mixture was refluxed for 1 h, and then concentrated in vacuum. The residue was purified on a silica gel column (10% MeOH in DCM) to give 48-4 (23.1 g, 96%)

To a stirred solution of 48-4 (23.1 g, 67.54 mmol) in anhydrous pyridine (200 mL) was added imidazole (6.89 g, 101.32 mmol) and TBSCl (10.92 g, 74.29 mmol) in portions at 0° C. The mixture was stirred at RT for 16 h. The solution was quenched with water, and concentrated to dryness. The residue was diluted with EA, and washed with water and brine. The organic phase was dried over anhydrous sodium sulfate, and concentrated at low pressure. The residue was purified on a silica gel column to give 48-5 (23 g, 74%).

To a solution of 48-5 (27.56 g, 60.44 mmol) in anhydrous MeCN (560 mL) was added DMAP (18.43 g, 151.1 mol) and PhOCSCl (14.55 g, 84.61 mmol) at 0° C. under $N_2$. The mixture was stirred at RT overnight, and the reaction was quenched with water. The mixture was extracted with EA. The organic phase was dried with anhydrous $Na_2SO_4$, and concentrated at low pressure. The residue was purified on a silica gel column eluted with 30% EA in PE to provide 48-6 (23 g, 64%).

To a solution of 48-6 (14.5 g, 24.5 mmol) in anhydrous toluene (700 mL) was added AIBN (1.21 g, 7.3 mmol) and $Bu_3SnH$ (10.73 g, 36.74 mmol) in toluene (10 mL). $N_2$ was bubbled into the solution for 30 mins. The mixture was warmed to 135° C. for 2 h. Saturated aqueous CsF was added, and the mixture was stirred for 1 h. The mixture was diluted with EA (150 mL), and washed successively with water, sat. aq. $NaHCO_3$ and brine. The organic layer was removed at low pressure. The residue was purified on a silica gel column (30% EA in PE) to provide 48-7 (10.5 g, 97%).

To a solution of 48-7 (21 g, 47.73 mmol) in anhydrous MeOH (200 mL) was added $NH_4F$ (35.32 g, 950 mmol). The mixture was refluxed for 1 h and concentrated in vacuum. The residue was purified on a silica gel column (20% MeOH in DCM) to give 48-8 (14 g, 90%).

TFA.Py (2.37 g, 12.27 mmol) was added to a mixture of 48-8 (4 g, 12.27 mmol) and DCC (7.58 g, 36.81 mmol) in anhydrous DMSO (40 mL) at RT under $N_2$ atmosphere. The mixture was stirred at RT for 2 h. 37% formaldehyde (10 mL, 115 mmol) was added at RT, and stirred for 15 mins, followed by treatment with 2N NaOH (20 mL, 40 mmol). The mixture was stirred at 30° C. overnight and neutralized with AcOH to pH=7. $NaBH_4$ (1.87 g, 49.08 mmol) was added in portions at 5° C., and the mixture was stirred at RT for 30 mins. The mixture was extracted with EtOAc (3×100 mL). The organic layer was dried over anhydrous $Na_2SO_4$ and concentrated at low pressure. The residue was purified on a silica gel column (5% MeOH in DCM) to give 48-9 (2 g, 46%) as a white solid.

To a solution of 48-9 (2 g, 5.62 mmol) in anhydrous $CH_3CN$ (8 mL) was added pyridine (10 mL) and BzCl (0.79 g, 5.62 mmol) in a solution of DCM (2 mL) at 0° C. under $N_2$. The mixture was stirred at RT overnight. The reaction was quenched with water, and concentrated at low pressure. The residue was diluted with EA (50 mL), and washed successively with water and brine. The organic layer was dried over anhydrous $Na_2SO_4$, and concentrated at a low pressure. The residue was purified on a silica gel column (3% MeOH in DCM) to provide 48-10 (1.6 g, 62%)

To a solution of 48-10 (1.6 g, 3.48 mmol) in anhydrous pyridine (16 mL) was added MMTrCl (1.61 g, 5.22 mmol) at 0° C. under $N_2$. The mixture was stirred at RT overnight. The reaction was quenched with water, and concentrated in vacuo. The residue was diluted with EA (50 mL) and washed successively with water and brine. The organic layer was dried over $Na_2SO_4$ and concentrated at a low pressure to give crude 48-11 (2.55 g, 100%), which used without further purification.

To a solution of 48-11 (2.55 g, 3.48 mmol) in anhydrous MeOH (50 mL) was added $NaOCH_3$ (0.28 g, 5.23 mmol). The mixture was stirred at 45° C. for 2 h, bubbled to pH=7 by using dry ice and concentrated to dryness. The residue was purified on a silica gel column (2% MeOH in DCM) to give 48-12 (0.93 g, 42%).

To a solution of 48-12 (0.93 g, 1.48 mmol) in anhydrous DCM (10 mL) was added pyridine (1.17 g, 14.8 mmol) at −30° C. $Tf_2O$ (0.63 g, 2.22 mmol) in DCM (3 mL) was added dropwise. The mixture was stirred at −30° C.-0° C. for 20 mins and at 0° C. for 10 mins. The reaction was quenched with water, and the mixture was extracted with DCM (3×100 mL). The organic layer was dried over anhydrous $Na_2SO_4$, and concentrated at low pressure to provide crude 48-13 (1.13 g, 100%), which was used without further purification.

To a solution of 48-13 (1.13 g, 1.48 mmol) in anhydrous THF (10 mL) was added TBAF (3.86 g, 14.8 mmol). The mixture was stirred at 30° C. for 2 h. The reaction was quenched with water, and the mixture was extracted with EtOAc (3×100 mL). The organic layer was dried over anhydrous $Na_2SO_4$, and concentrated to dryness at low pressure. The residue was purified on a silica gel column (3% MeOH in DCM) to give 47-1 (0.42 g, 45%).

To a solution of 47-1 (50 mg, 0.079 mmol) in anhydrous $CH_3CN$ (1 mL) was added TPSCl (48.07 mg, 0.16 mmol), DMAP (19.36 mg, 0.16 mmol) and $NEt_3$ (0.2 mL) at RT. The mixture was stirred at RT for 3 h. 28% aqueous ammonia (0.4 mL) was added, and the mixture was stirred for 1 h. The mixture was diluted with EA (150 mL), and washed successively with water, sat. aq. $NaHCO_3$ and brine. The organic layer was dried over anhydrous $Na_2SO_4$, and concentrated at a low pressure. The residue was purified on a silica gel column (5% MeOH in DCM) to give 48-14 (40 mg, 80%).

Compound 48-14 (320 mg, 0.51 mmol) was dissolved in 80% HCOOH (6 mL), and the mixture was stirred at 10° C. for 1 h. The mixture was concentrated at low pressure, and the residue was purified by prep-HPLC to give compound 48 (43 mg, 31%) as a white solid. ESI-MS: m/z 273.9 [M+H]$^+$, 547.1 [2M+H]$^+$.

Example 39

Compound 49

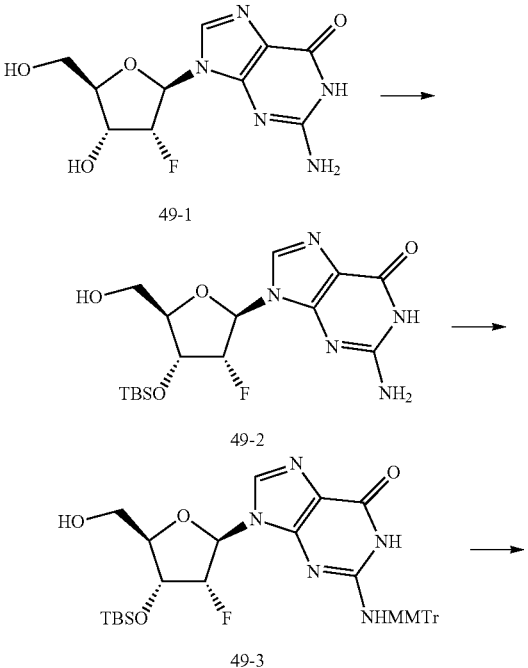

49-1

49-2

49-3

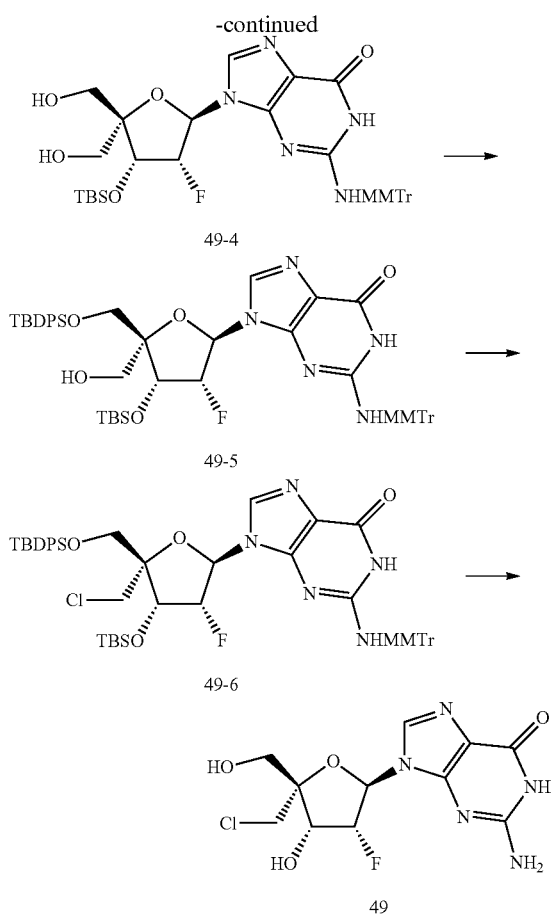

To a solution of 49-1 (20.0 g, 70.2 mmol) in anhydrous pyridine (200 mL) was added imidazole (19.1 g, 280 mmol) and TBSCl (42.1 g, 281 mmol) at 25° C. The solution was stirred at 25° C. for 15 h, and then concentrated to dryness under reduced pressure. The residue was dissolved in EtOAc and then filtered. The filtrate was concentrated to dryness to give the TBS protected derivative (36.4 g, 99%). The TBS protected derivative (36.5 g, 71.1 mmol) was dissolved in THF (150 mL). $H_2O$ (100 mL), and then AcOH (300 mL) were added. The solution was stirred at 80° C. for 13 h. The reaction was cooled to RT, and then concentrated to dryness under reduced pressure to give 49-2 (31.2 g, 61%) as a white solid.

To a solution of 49-2 (31.2 g, 78.2 mmol) in anhydrous pyridine (300 mL) was added $Ac_2O$ (11.9 g, 117.3 mmol). The mixture was stirred at 25° C. for 18 h. MMTrCl (72.3 g, 234.6 mmol) and $AgNO_3$ (39.9 g, 234.6 mmol) were added, and the solution was stirred at 25° C. for 15 h. $H_2O$ was added to quench the reaction and the solution was concentrated to dryness under reduced pressure. The residue was dissolved in EtOAc and washed with water. The organic layer was dried over $Na_2SO_4$ and filtered. The filtrate was concentrated in vacuum to give a residue, which was purified by silica gel (DCM:MeOH=200:1 to 50:1) to give the MMTr protected amine derivative (35.2 g, 63%). The MMTr protected amine derivative (35.2 g, 49.3 mmol) was dissolved in $NH_3$/MeOH (300 mL). The mixture was stirred at 25° C. for 20 h. The solution was evaporated to dryness, and purified by a silica gel column (DCM:MeOH=100:1 to 50:1) to give 49-3 as a yellow solid (28.6 g, 87%).

To a solution of 49-3 (12.0 g, 17.9 mmol) in anhydrous DCM (200 mL) was added Dess-Martin periodinane (11.3 g, 26.8 mmol) at 0° C. The mixture was stirred at 0° C. for 2 h, and then at RT for 2 h. The mixture was quenched with a saturated $NaHCO_3$ and $Na_2S_2O_3$ solution. The organic layer was washed with brine (2x) and dried over anhydrous $Na_2SO_4$. The solvent was evaporated to give the aldehyde (12.6 g), which was used directly in the next step. To a solution of the aldehyde (12.6 g, 18.0 mmol) in 1,4-dioxane (120 mL) was added 37% HCHO (11.6 g, 144 mmol) and 2N NaOH aqueous solution (13.5 mL, 27 mmol). The mixture was stirred at 25° C. overnight. EtOH (60 mL) and $NaBH_4$ (10.9 g, 288 mmol) were added, and the reaction was stirred for 30 mins. The mixture was quenched with saturated aqueous $NH_4Cl$, and then extracted with EA. The organic layer was dried over $Na_2SO_4$, and purified by silica gel column chromatography (DCM:MeOH=200:1 to 50:1) to give 49-4 (7.5 g, 59%) as a yellow solid.

To a solution of 49-4 (3.8 g, 5.4 mmol) in DCM (40 mL) was added pyridine (10 mL) and DMTrCl (1.8 g, 5.4 mmol) at 0° C. The solution was stirred at 25° C. for 1 h. MeOH (15 mL) was added, and the solution was concentrated. The residue was purified by silica gel column chromatography (DCM:MeOH=200:1 to 50:1) to give the MMTr protected derivative (3.6 g, 66%) as a yellow solid. To a solution of the MMTr protected derivative (3.6 g, 3.6 mmol) in anhydrous pyridine (30 mL) was added TBDPSCl (2.96 g, 10.8 mmol) and $AgNO_3$ (1.84 g, 10.8 mmol). The mixture was stirred at 25° C. for 15 h. The mixture was filtered and concentrated. The mixture was dissolved in EtOAc and washed with brine. The organic layer was dried over $Na_2SO_4$, and then purified by silica gel column chromatography (DCM:MeOH=200:1 to 50:1) to give the TBDPS protected derivative (3.8 g, 85.1%) as a solid. To a solution of the TBDPS protected derivative (3.6 g, 2.9 mmol) in anhydrous DCM (50 mL) was added $Cl_2CHCOOH$ (1.8 mL) in anhydrous DCM (18 mL). The mixture was stirred at −78° C. for 1 h. $Cl_2CHCOOH$ (3.6 mL) was added at −78° C. The mixture was stirred at −10° C. for 30 mins. The reaction was quenched with saturated aqueous $NaHCO_3$ and extracted with DCM. The organic layer was dried over $Na_2SO_4$, and then purified by silica gel column chromatography (DCM:MeOH=200:1 to 50:1) to give 49-5 (2.2 g, 80%).

To an ice cooled solution of 49-5 (800 mg, 0.85 mmol) in anhydrous DCM (20 mL) was added pyridine (336 mg, 4.25 mmol) and $Tf_2O$ (360 mg, 1.28 mmol) dropwise. The reaction mixture was stirred at 0° C. for 15 mins. The reaction was quenched by ice water and stirred for 30 mins. The mixture was extracted with EtOAc, washed with brine (50 mL) and dried over $MgSO_4$. The solvent was evaporated to give the crude bis(triflate) derivative. To the bis(triflate) derivative (790 mg, 0.73 mmol) in anhydrous DMF (35 mL) was added LiCl (302 mg, 7.19 mmol). The mixture was heated to 40° C. and stirred overnight. Completion of the reaction was determined by LCMS. The solution was washed with brine and extracted with EtOAc. The combined organic layers were dried over $MgSO_4$, and the residue was purified on a silica gel column (DCM/MeOH=100:1) to give 49-6 (430 mg, 61%).

To 49-6 (470 mg, 0.49 mmol) in MeOH (85 mL) was added $NH_4F$ (8.1 g, 5.92 mmol), and the solution was heated to reflux overnight. The mixture was filtered, and the filtrate was concentrated to dryness. The residue was purified on a silica gel column (DCM/MeOH=20:1) to give the diol (250 mg, 84%) as a white solid. The diol (130 mg, 0.21 mmol) in formic acid (5 mL) was stirred at 25° C. overnight. The solution was concentration to dryness, and the residue in MeOH (30 mL) was stirred at 70° C. overnight. Completion of the reaction was determined by LCMS and HPLC. The solvent was removed, and the crude product was washed with EtOAc to give compound 49 (58 mg, 81%) as a white solid. $^1$H NMR (DMSO-d$_6$, 400 MHz) δ 10.73 (br, 1H), 7.98 (s, 1H), 6.58 (br, 2H), 6.08 (q, J=4.8, 9.2 Hz, 2H), 5.64 (dt, J=5.6, 52.8 Hz, 1H), 5.40 (m, 1H), 4.52 (m, 1H), 3.80-3.82 (m, 2H), 3.64 (q, 2H). ESI-MS: m/z 333.8 [M+H]$^+$, 666.6 [2M+H]$^+$.
Example 40
Compound 50
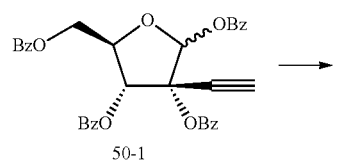
50-1
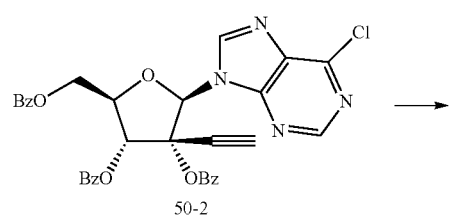
50-2
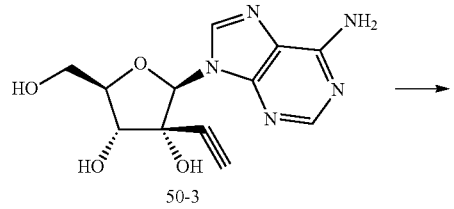
50-3
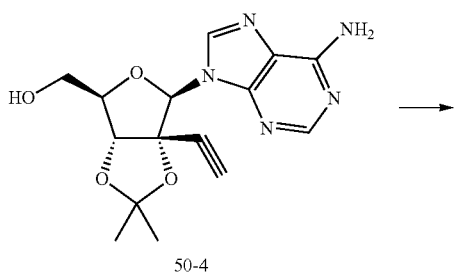
50-4
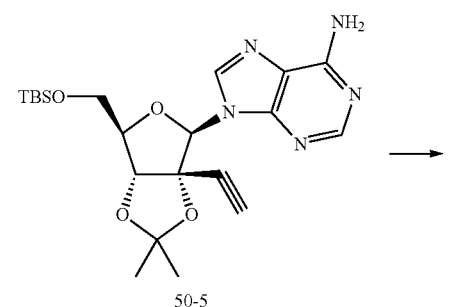
50-5
-continued
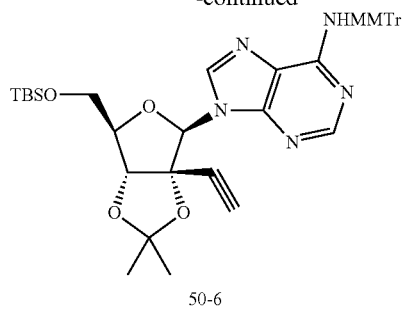
50-6
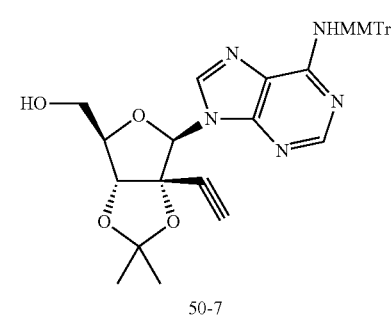
50-7
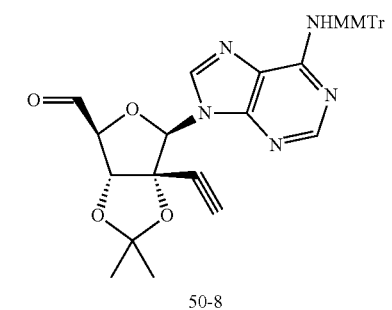
50-8
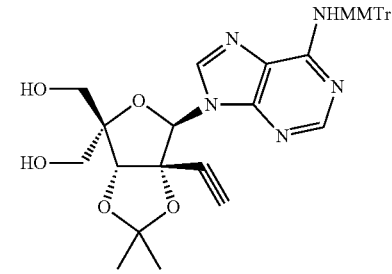
45-1
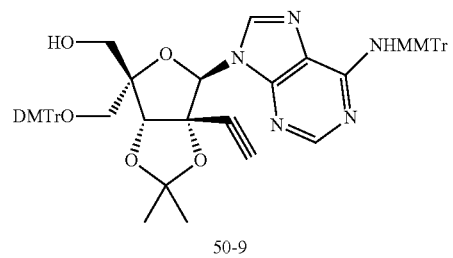
50-9

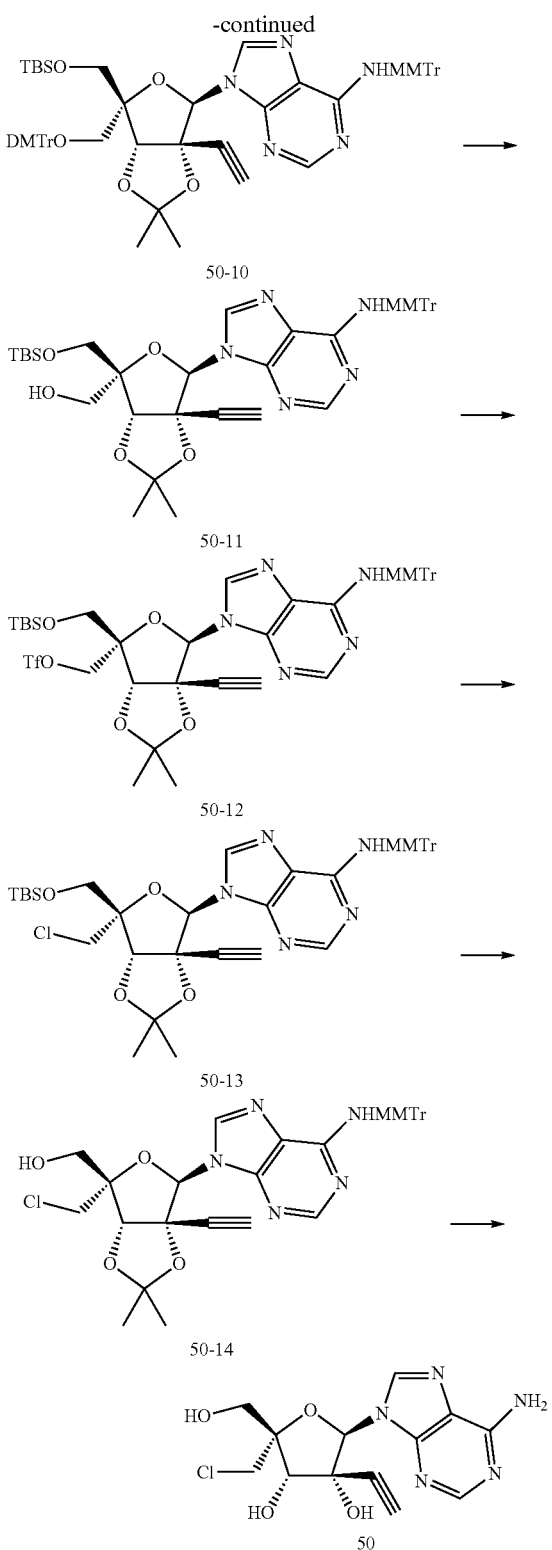

50-10

50-11

50-12

50-13

50-14

50

Compound 50-1 (5.0 g, 8.5 mmol) and 6-chloropurine (3.0 g, 17.7 mmol) were co-evaporated with anhydrous toluene 3 times. To a stirred suspension of 50-1 and 6-chloropurine in anhydrous MeCN (50 mL) was added DBU (7.5 g, 49 mmol) at 0° C. The mixture was stirred at 0° C. for 15 mins, and TMSOTf (15 g, 67.6 mmol) was added dropwise at 0° C. The mixture was stirred at 0° C. for 15 mins until a clear solution formed. The mixture was heated to 70° C., and stirred overnight. The reaction was monitored by LCMS. The mixture was cooled to RT, and diluted with EA (100 mL). The solution was washed with sat. NaHCO$_3$ solution and brine. The organic layer was dried over anhydrous Na$_2$SO$_4$, and concentrated at low pressure. The residue was purified on silica gel column (EA in PE from 6% to 50%) to afford 50-2 (2.5 g, 46.3%) as a white foam.

Compound 50-2 (3.0 g, 4.8 mmol) was treated with NH$_3$ in MeOH (8 N, 20 mL) in autoclave at 40-60° C. for 12 h. The mixture was evaporated at low pressure, and the residue was purified on silica gel column (MeOH in EA from 0 to 10%) to give 50-3 (1.0 g, 71%) as a white foam.

To a solution of 50-3 (4.3 g, 14.8 mmol) in acetone/DMF (4/1, 40 mL) was added TsOH.H$_2$O (8.4 g, 0.044 mol) and 2,2-dimethoxypropane (30 g, 0.296 mol), and the mixture stirred at 60-70° C. for 12 h. The mixture was concentrated at low pressure, and the residue was purified on silica gel column (EA in PE from 50% to 100%) to give 50-4 (5.0 g, 83%).

To a solution of 50-4 (10.5 g, 31.7 mmol) in pyridine (50 mL) was added TBSCl (5.3 g, 34.9 mmol), and the mixture stirred at RT for 12 h. The solvent was removed at low pressure, and the residue was dissolved in DCM (100 mL). The solution was washed with brine, dried over anhydrous Na$_2$SO$_4$, and concentrated at low pressure. The residue was purified by silica gel column to provide 50-5 (8.4 g, 60%), which used without further purification.

Compound 50-5 (8.4 g, 18.8 mmol) was co-evaporated with pyridine. To a stirred solution of 50-5 (8.4 g, 18.8 mmol) in pyridine (35 mL) was added MMTrCl (8.1 g, 26.4 mmol). The mixture was stirred at 30-40° C. for 12 h under N$_2$. The mixture was concentrated at a low pressure, and the residue was dissolved in DCM (150 mL). The solution was washed with saturated NaHCO$_3$ solution, dried over anhydrous Na$_2$SO$_4$, and concentrated at low pressure. The residue was purified on silica gel column (EA in PE from 10% to 20%) to provide 50-6 (10.8 g, 80%) as a solid To a solution of 50-6 (11.5 g, 0.016 mol) in THF (100 mL) was added TBAF (4.62 g, 0.018 mol) at RT, and the mixture stirred for 4 h. The solvent was evaporated at low pressure, and the mixture was dissolved in DCM (150 mL). The solution was washed with brine, dried over anhydrous Na$_2$SO$_4$, and concentrated at low pressure. The residue was purified on silica gel column (EA in PE from 50% to 100%) to afford 50-7 (8.8 g, 91%). ESI-MS: m/z 604.4 [M+H]$^+$.

To a solution of 50-7 (4.4 g, 7.3 mmol) in dioxane (50 mL) was added DCC (4.5 g, 21.9 mmol), DMSO (2.5 mL), TFA.Py (1.48 g, 7.65 mmol) at 0° C. The mixture was slowly warm to RT and stirred for 4 h. Completion of the reaction was determined by LCMS. The mixture was concentrated at low pressure. The residue was purified on silica gel column to give 50-8 (4.4 g, 7.3 mmol), which was used without further purification.

To a solution of 50-8 in dioxane (40 mL) was added water (20 mL), HCHO (37%, 7 mL) and NaOH (1N, 15 mL). The solution was stirred at RT overnight. The mixture was treated with NaBH$_4$ (1.1 g, 29.2 mmol) slowly, and stirred for 30 mins. The mixture was adjusted to pH=7-8 by slow addition of HCl (1M) solution, and extracted with EA (150 mL). The solution was washed with brine, dried over anhydrous Na$_2$SO$_4$, and concentrated at low pressure. The residue was purified on silica gel column to give 45-1 (3.0 g, 65%). ESI-MS: m/z 633.9 [M+H]$^+$.

To a solution of 45-1 (1.5 g, 2.37 mmol) in anhydrous pyridine (30 mL) was added DMTrCl (3.6 g, 10.7 mmol) at −30° C. The mixture was stirred at RT overnight. The solution was quenched with MeOH, and concentrated at low pressure. The residue was purified by column chromatography to give 50-9 (3 g, 45%) as a yellow solid To a solution of 50-9 (1.1 g, 1.18 mmol) in pyridine (10 mL) was added imidazole (0.24 g, 3.53 mmol) and TBSCl (0.35 g, 2.35 mmol). The mixture was stirred at RT for 12 h. The solvent was evaporated at low pressure, and the residue was dissolved in EA (50 mL). The solution was washed with brine, dried over anhydrous $Na_2SO_4$, and concentrated at low pressure. The residue was purified on silica gel column (30% EA in PE) to afford 50-10 (0.83 g, 67%)

To a solution of 50-10 (1.1 g, 1.05 mmol) in DCM (12 mL) was added $Cl_2CHCOOH$ (0.5 mL) at −70° C., and stirred for 1 h. The solution was treated with $Cl_2CHCOOH$ (1 mL) in DCM (10 mL) at −70° C., and the mixture was stirred at −70~−10° C. for 20 mins. Completion of the reaction was determined by LCMS. The reaction was quenched with sat. $NaHCO_3$ solution, and extracted with DCM (3×40 mL). The organic phase was dried over anhydrous $Na_2SO_4$, and concentrated at low pressure. The residue was purified on silica gel column (EA in PE from 15% to 30%) to afford 50-11 (0.58 g, 74%).

To a solution of 50-11 (200 mg, 0.268 mmol) and pyridine (53 mg, 0.67 mmol) in anhydrous DCM (5 mL) was added $Tf_2O$ (90 mg, 0.32 mmol) at −30° C. The mixture was stirred for 1 h, and slowly warmed to RT. Completion of the reaction was determined by TLC. The reaction was quenched with sat. $NaHCO_3$ solution, and extracted with DCM (3×30 mL). The organic phase was dried over anhydrous $Na_2SO_4$, and concentrated to dryness at low pressure. Crude 50-12 (200 mg, 0.27 mmol) was used without further purification.

To a solution of 50-12 (200 mg, 0.27 mmol) in DMF (5 mL) was added LiCl (45 mg, 1.07 mmol), and stirred at 30-40° C. for 12 h. The solvent was evaporated at low pressure, and the residue was dissolved in DCM (10 mL). The solution was washed with brine, dried over anhydrous $Na_2SO_4$, and concentrated at low pressure. Crude 50-13 was used without further purification.

A mixture of 50-13 (245 mg, 0.32 mmol) and TBAF (200 mg, 0.7 mmol) in THF was stirred at 30° C. for 1 h. The mixture was concentrated at a low pressure, and the residue was dissolved in DCM (15 mL). The solution was washed with brine, dried over anhydrous $Na_2SO_4$, and concentrated at low pressure. The residue was purified on silica gel column (EA in PE from 2% to 50%) to provide 50-14 (150 mg, 72%). ESI-MS: m/z 652.3 [M+H]$^+$.

Compound 50-14 (0.2 mmol) was dissolved in 50% TFA (10 mL) in methanol, and the mixture was kept at RT overnight. The solvent was evaporated and co-evaporated with methanol/toluene mixture to remove traces of acid. The residue was dissolved in 20% triethylamine in methanol, kept for 15 mins and evaporated. The product was isolated by RP HPLC on Synergy 4 micron Hydro-RP column (Phenominex). A linear gradient of methanol from 0 to 60% in 50 mM triethylammonium acetate buffer (pH 7.5) was used for elution. The corresponding fractions were combined, concentrated and lyophilized 3 times to remove excess buffer. Compound 50 was obtained (45 mg, 67%). MS: m/z 338.0 [M−1].

Example 41

Compound 51

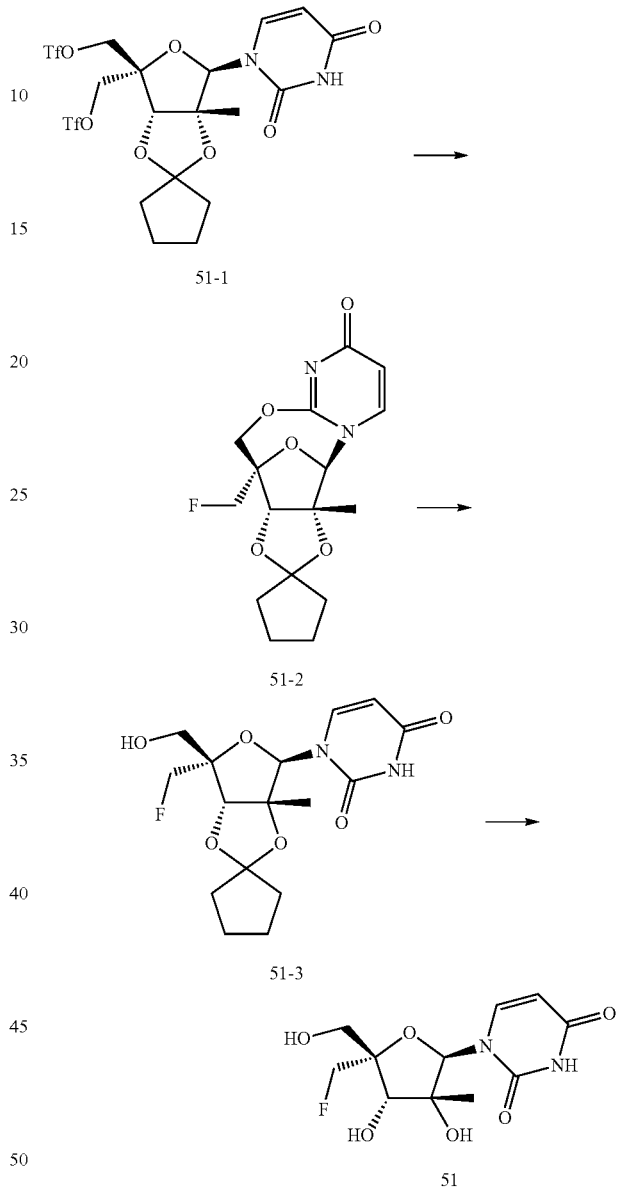

To a solution of 51-1 (12.3 g, 19.9 mmol) in DMF (50 mL) was added NaH (800 mg, 20 mmol) at 0° C. The mixture was stirred at RT for 3 h. The mixture was treated with CsF (30.4 g, 200 mmol), and then stirred at RT for 3 h. The reaction was quenched with water, and extracted with EA. The organic layer was dried over anhydrous $Na_2SO_4$, and concentrated to dryness at low pressure. The residue was purified on silica gel column (20% EA in PE) to give 51-2 (4.1 g, 61%) as a white solid.

To a solution of 51-2 (4.1 g, 12.1 mmol) in THF (120 mL) was added NaOH solution (1N, 13 mL) at 0° C. The mixture was stirred at RT for 3 h. The solution was neutralized with 0.5 M HCl aq. to pH~7. The mixture was partitioned between EA and water. The organic layer was dried over anhydrous Na$_2$SO$_4$, and concentrated to dryness at low pressure. The residue was purified on silica gel column (30% EA in PE) to give 51-3 (3.1 g, 72%) as a white solid. ESI-MS:m/z 379.1 [M+Na]$^+$.

Compound 51-3 (0.2 mmol) was dissolved in 80% HCOOH (10 mL), and the mixture was heated at 45° C. for 24 h. The solvent was evaporated and co-evaporated with methanol/toluene mixture to remove traces of acid. The residue was dissolved in 20% triethylamine in methanol, kept for 15 mins and evaporated. Compound 51 (68%) was isolated by silica gel chromatography in gradient of methanol in DCM from 5% to 20%. MS: m/z 289.0 [M−1].

Example 42

Compound 52

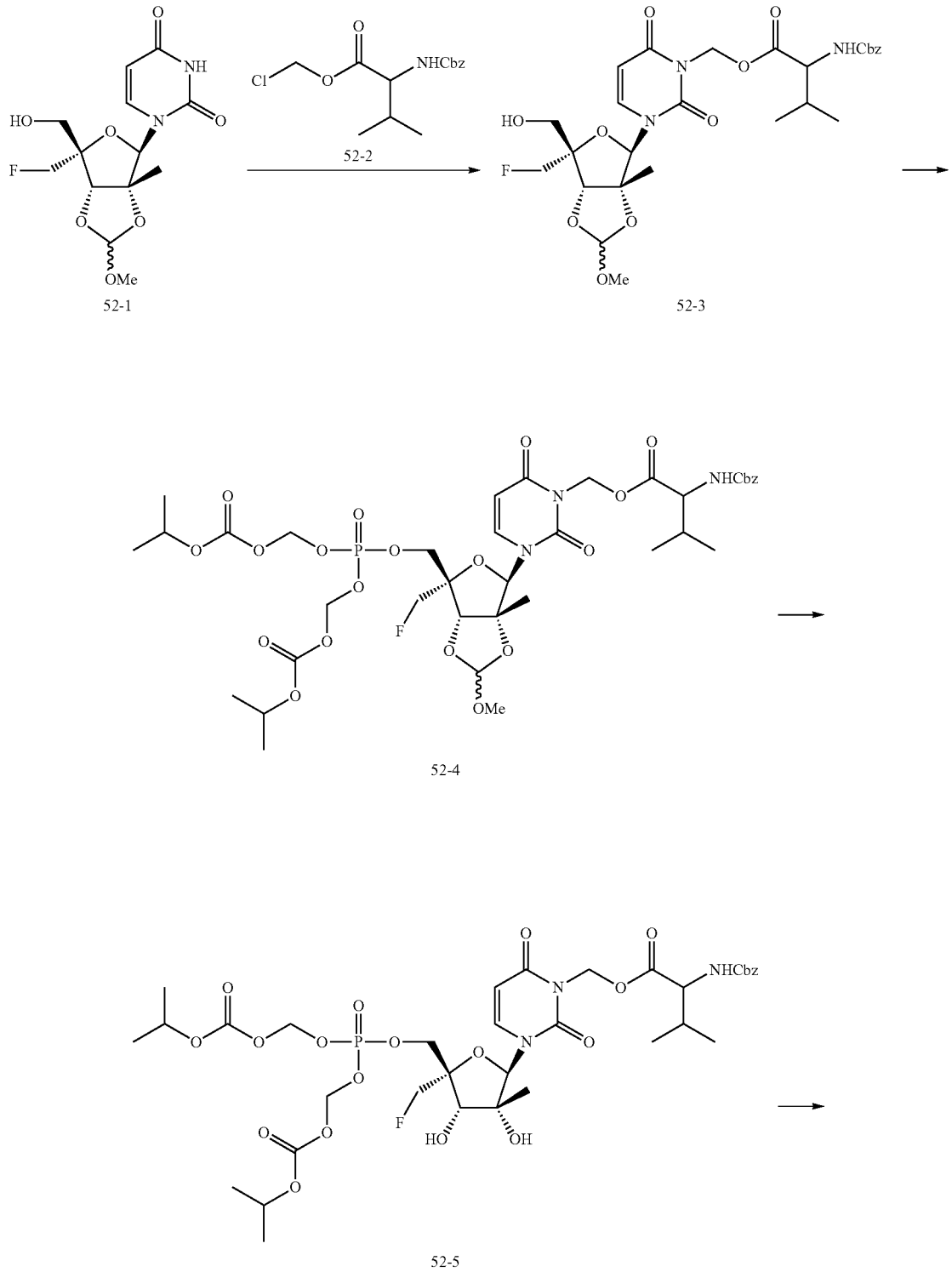

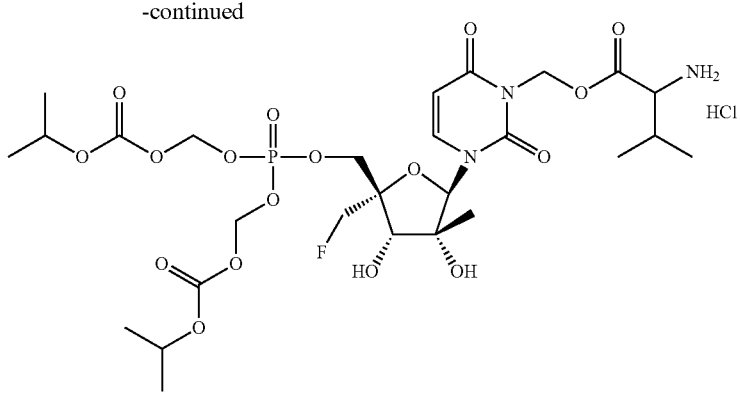

52

A mixture of 52-2 (1.2 g; 4 mmol) and NaI (0.6 g; 4 mmol) in acetone (13 mL) was stirred at RT for 1 h. Compound 52-1 (1 g; 3 mmol) and $K_2CO_3$ (2.07 g; 45 mmol) were added. The mixture was stirred at RT for 24 h. The precipitate was filtered, and the filtrate was evaporated. Purification of the residue on silica (25 g column) with hexanes/EtOAc (30-100% gradient) yielded 52-3 as a colorless foam (1.14 g; 64%).

To a solution of triethylammonium bis(isopropyloxycarbonyloxymethyl)phosphate (2.3 mmol, prepared from of bis(POC)phosphate (0.75 g) and $Et_3N$ (0.32 mL)) in THF was added 52-3 (1.14 g; 1.9 mmol). The mixture evaporated and rendered anhydrous by co-evaporating with pyridine follow by toluene. The residue was dissolved in anhydrous THF (20 mL) and cooled down in an ice-bath. Diisopropylethylamine (1.0 mL; 2 eq.) was added, followed by BOP-Cl (0.72 g; 1.5 eq.) and 3-nitro-1,2,4-triazole (0.32 g; 1.5 eq.). The n mixture was stirred at 0° C. for 90 mins, diluted with EtOAc, washed with sat. aq. $NaHCO_3$ and brine, and dried ($Na_2SO_4$). The residue was purified on silica (25 g column) with $CH_2Cl_2$/i-PrOH (3-10% gradient) to yield (1.2 g, 70%) of 52-4.

A solution of 52-4 (1.2 g; 1.3 mmol) in 80% aq. HCOOH was stirred at RT for 2 h, and then concentrated. The residue was co-evaporated with toluene and then with MeOH containing small amount of $Et_3N$ (2 drops). Purification on silica (25 g column) with $CH_2Cl_2$/i-PrOH (4-10% gradient) yielded 52-5 (0.96 g, 85%).

To a solution of 52-5 (0.52 g; 0.57 mmol) in EtOH (25 mL) were added HCl (4 N/dioxane; 0.29 mL, 2 eq.) and 10% Pd/C (25 mg). The mixture was stirred under $H_2$ (normal pressure) for 1 h. The catalyst was removed by filtration through a Celite pad, and the filtrate was evaporated to yield compound 52 as its HCl salt (4.2 g; 96%). MS: m/z=732 [M+1].

Example 43

Compound 53

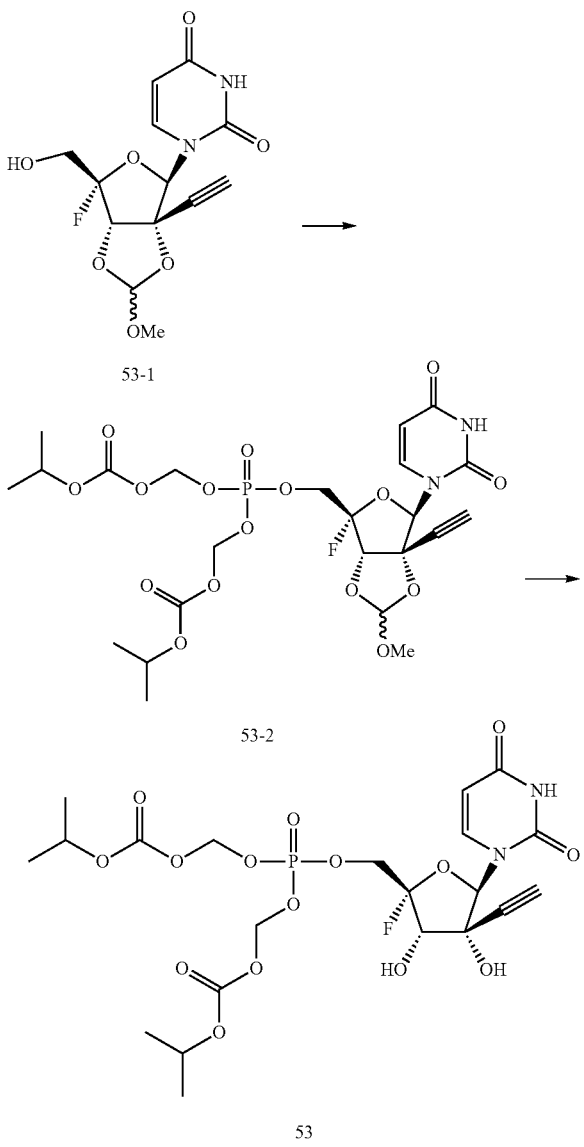

Compound 53-2 (0.20 g, 64%) was prepared in the same manner from 53-1 (0.16 g; 0.49 mmol) and triethylammonium bis(isopropyloxycarbonyloxymethyl)phosphate (0.74 mmol) with DIPEA (0.34 mL), BopCl (250 mg), and 3-nitro-1,2,4-triazole (112 mg) in THF (5 mL) following the procedure for the preparation of 52-4.

A solution of 53-2 (0.20 g; 0.31 mmol) in 80% aq. HCOOH was stirred at RT for 2 h, and then concentrated. The residue was co-evaporated with toluene and then with MeOH containing small amount of Et₃N (2 drops). Purification on silica gel (10 g column) with CH₂Cl₂/MeOH (4-10% gradient) was followed by RP-HPLC purification in 5 runs on a Synergi Hydro RP column 250×30 mm (Phenomenex P/N 00G-4375-U0-AX) using H₂O and ACN both 50 mM TEAA. Gradient was 25-75% ACN in 20 mins at 24 mL/mins, 254 nM detection. The product eluted at 16.0 mins. Pure fractions were pooled and lyophilized. TEAA was removed by dissolving the product in DMSO (2 mL) and injecting the product on the same column using only H₂O and ACN. Pure fractions were pooled and lyophilized to produce compound 53 (18 mg). MS: m/z=1197 (2M+1).

Example 44

Compound 54

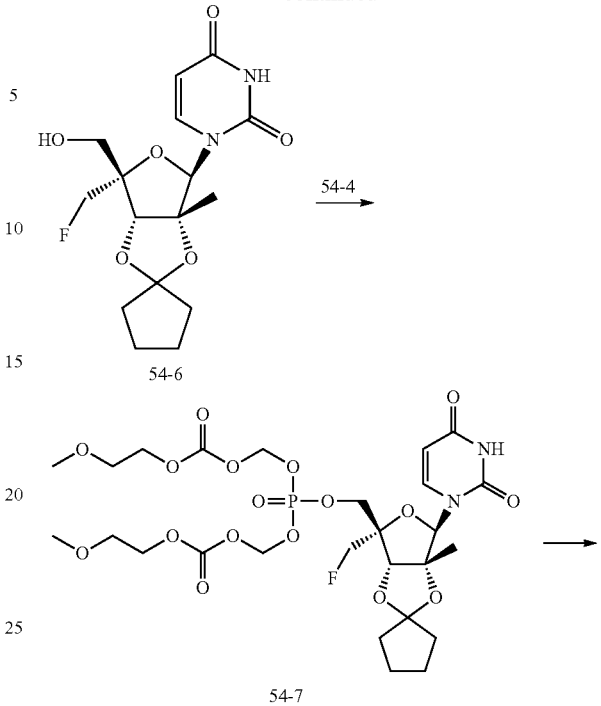

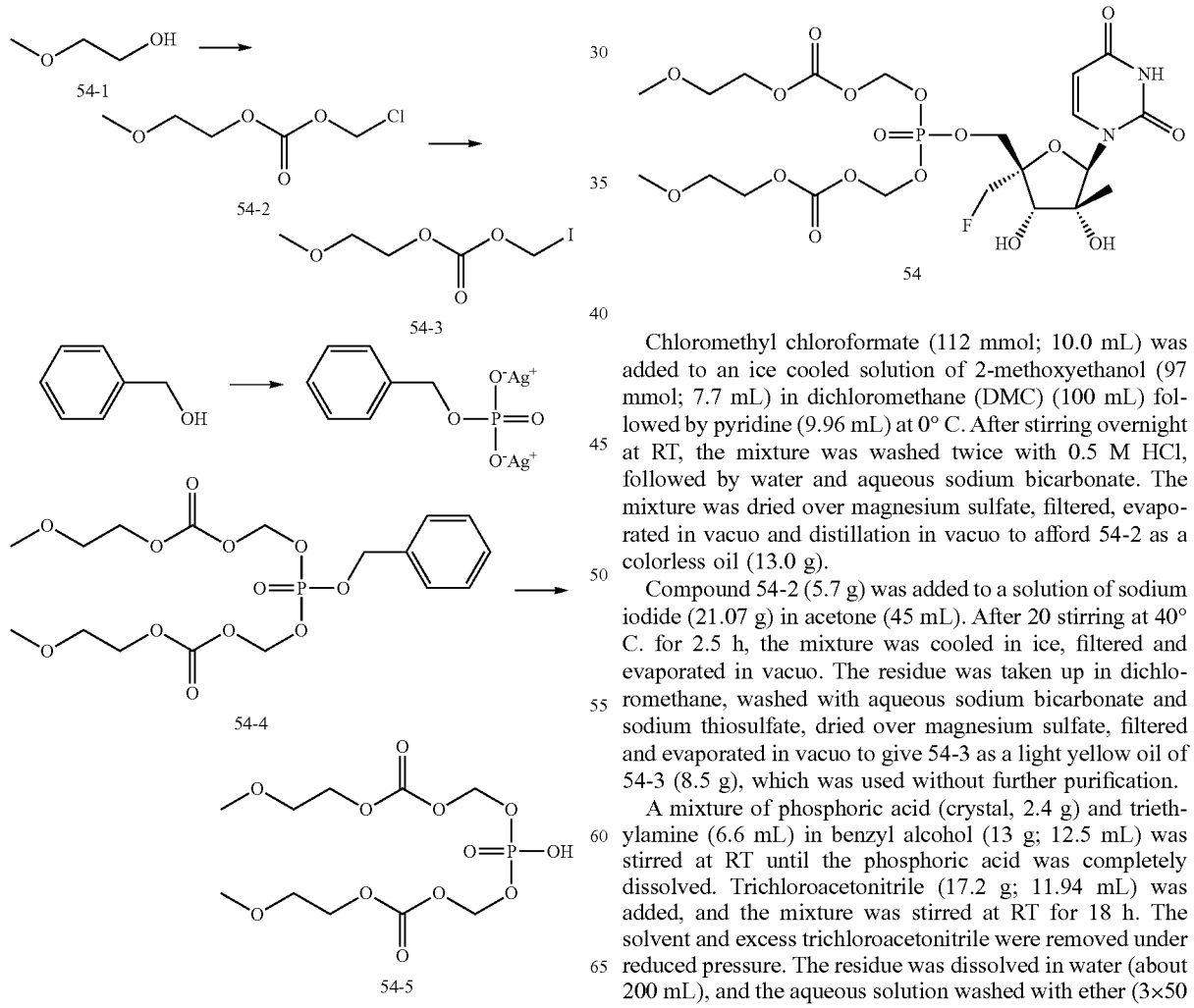

Chloromethyl chloroformate (112 mmol; 10.0 mL) was added to an ice cooled solution of 2-methoxyethanol (97 mmol; 7.7 mL) in dichloromethane (DMC) (100 mL) followed by pyridine (9.96 mL) at 0° C. After stirring overnight at RT, the mixture was washed twice with 0.5 M HCl, followed by water and aqueous sodium bicarbonate. The mixture was dried over magnesium sulfate, filtered, evaporated in vacuo and distillation in vacuo to afford 54-2 as a colorless oil (13.0 g).

Compound 54-2 (5.7 g) was added to a solution of sodium iodide (21.07 g) in acetone (45 mL). After 20 stirring at 40° C. for 2.5 h, the mixture was cooled in ice, filtered and evaporated in vacuo. The residue was taken up in dichloromethane, washed with aqueous sodium bicarbonate and sodium thiosulfate, dried over magnesium sulfate, filtered and evaporated in vacuo to give 54-3 as a light yellow oil of 54-3 (8.5 g), which was used without further purification.

A mixture of phosphoric acid (crystal, 2.4 g) and triethylamine (6.6 mL) in benzyl alcohol (13 g; 12.5 mL) was stirred at RT until the phosphoric acid was completely dissolved. Trichloroacetonitrile (17.2 g; 11.94 mL) was added, and the mixture was stirred at RT for 18 h. The solvent and excess trichloroacetonitrile were removed under reduced pressure. The residue was dissolved in water (about 200 mL), and the aqueous solution washed with ether (3×50 mL). Benzylphosphoric acid (triethylamine salt) was obtained after lyophilization as a yellowish semi-solid (7.15 g). A solution of benzylphosphoric acid (TEA salt, 1.6 g) in MeOH (90 mL) and water (30 mL) was treated with Dowex 50WX2-400 ("153 mL" settled resin) at RT for 18 h. The resin was removed by filtration, and silver carbonate powder (1.25 g) was added to the filtrate. After the suspension was heated at 80° C. for 1 h, all solvent was removed under reduced pressure to dryness. The solid was used without further purification.

Dry acetonitrile (25 mL) was added to benzylphosphoric acid (silver salt) followed by addition of 54-3 (3.12 g; 12 mmol). The suspension was stirred at RT overnight. After the solid was removed by filtration, the product was purified by silica gel chromatography using hexane/ethyl acetate (3:1 v:v) as the eluent to give 54-4 as a colorless liquid (860 mg, 50%).

Compound 54-4 (750 mg; 1.65 mmol) was dissolved in methanol (10 mL). Pd-on-carbon (85 mg) and TEA (1 eq.) were added. The flask was charged with hydrogen gas for 1 h. The catalyst was filtered, and the solvent removed in vacuo to give 54-5 (triethylammonium salt) (510 mg) which was used immediately without further purification.

Compound 54-6 (320 mg; 0.9 mmol) and 54-5 (510 mg, 1.35 mmol; 1.5×) were co-evaporated twice with pyridine and twice with toluene. Compounds 54-5 and 54-6 were dissolved in THF (8 mL) at 0° C. Diisopropylethylamine (DIPEA) (0.62 mL; 4 eq.), bis(2-oxo-3-oxazolidinyl) phosphinic chloride (Bop-Cl) (0.45 g; 2 eq.), nitrotriazole (0.2 g, 2 eq.) were added. The mixture was kept at 0° C. for 2 h and then diluted with EA (50 mL). The mixture was then extracted with sat. sodium bicarbonate (2×50 mL) and dried over sodium sulfate. The solvents were removed in vacuo. The residue was purified by flash chromatography using a 10 to 100% gradient of EA in hexane to give purified 54-7 (430 mg, 0.6 mmol).

Purified 54-7 was dissolved in 80% aq. HCOOH (20 mL) and kept at 45° C. for 18 h. After cooling to RT, the solvent was removed in vacuo. The residue co-evaporated with toluene (3×25 mL). The residue was purified by flash chromatography using a 0 to 20% gradient of methanol in DCM to give purified compound 54 (200 mg, 0.3 mmol). $^1$H-NMR (CDCl$_3$): δ 9.28 (s, 1H), 7.54 (d, 1H), 5.95 (s, 1H), 5.65-5.81 (m, 5H), (d, 2H), 4.76 (dd, 2H), 4.44-4.46 (m, 1H), 4.35-4.40 (m, 5H), 4.22 (2H), 4.04 (1H), 3.65 (t, 4H), 3.39 (6H), 1.8 (s, 1H), 1.24 (s, 3H). $^{31}$P-NMR (CDCl$_3$): δ −4.09 ppm.

Example 45

Compound 55

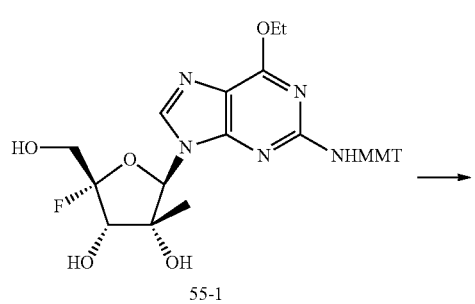

55-1

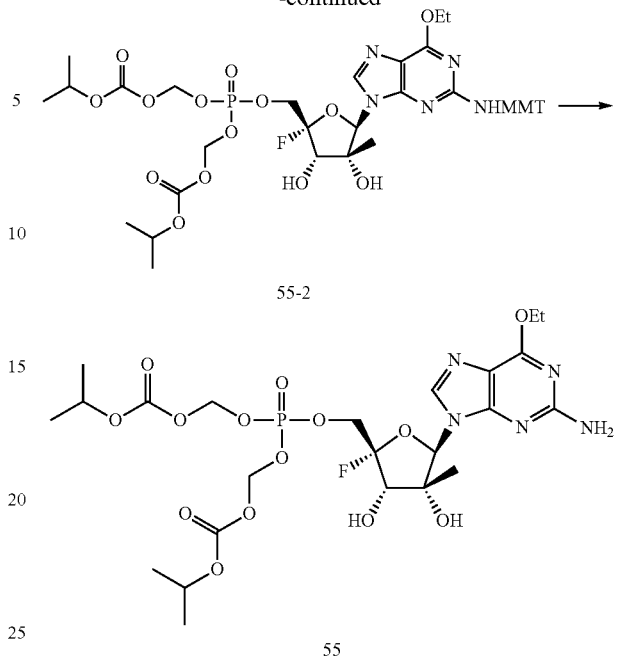

Compound 55-2 (158 mg, 50%) was prepared from 55-1 (0.21 g; 0.35 mmol) and triethylammonium bis(isopropyloxycarbonyloxymethyl)phosphate (0.54 mmol) with DIPEA (0.18 mL), BopCl (178 mg), and 3-nitro-1,2,4-triazole (80 mg) in THF (4 mL).

A solution of 55-2 (158 mg) in acetonitrile (1 mL) and HCl (4 N/dioxane; 85 μL) was stirred at RT for 30 mins. The reaction was quenched with MeOH and concentrated. The residue was purified on silica gel (10 g column) with CH$_2$Cl$_2$/i-PrOH (3-10% gradient) to give compound 55 (85 mg, 76%). MS: m/z=656 [M+1].

Example 46

Compound 56

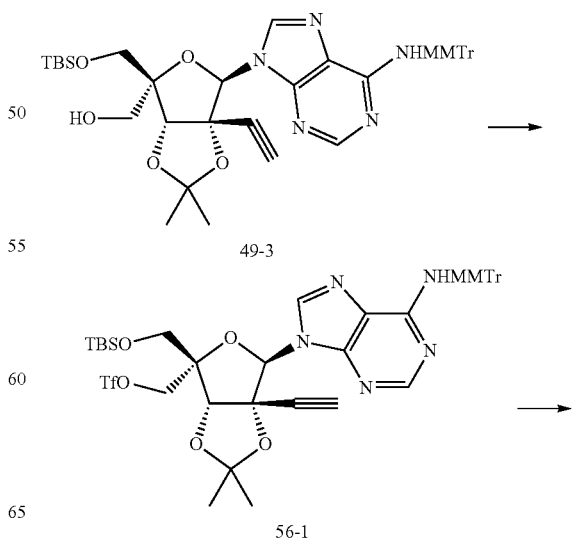

-continued

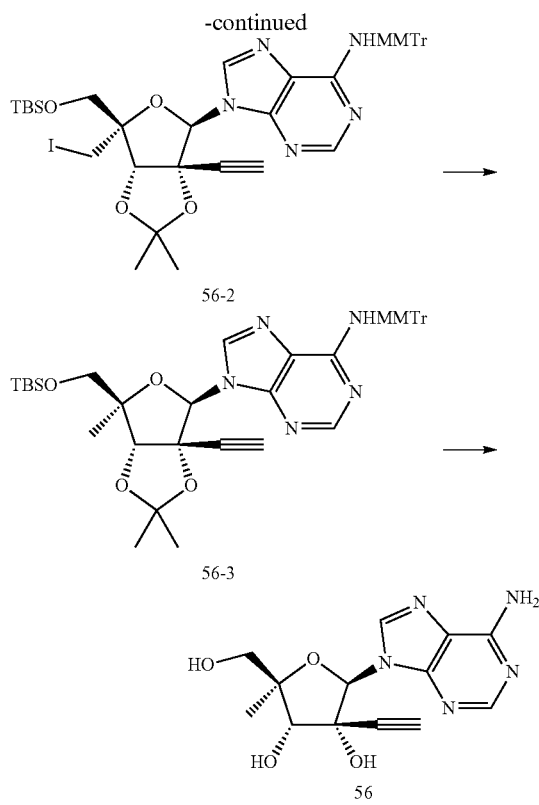

56-2

56-3

56

To a solution of 49-3 (300 mg, 0.4 mmol) and pyridine (80 mg, 1.0 mmol) in DCM (5 mL) was added Tf$_2$O (136 mg, 0.48 mol) in a solution of DCM (1 mL) dropwise at −30° C. The mixture was stirred at −30° C. to 0° C. for 20 mins. The reaction was quenched with water, and extracted with DCM (20 mL). The organic phase was dried over anhydrous Na$_2$SO$_4$, and evaporated to give crude 56-1 (352.8 mg, 0.4 mmol), which was used without further purification.

To a solution of 56-1 (352.8 mg, 0.4 mmol) in DMF (5 mL) was added NaI (480 mg, 3.2 mmol). The mixture was stirred at 30° C. for 10 h. The reaction was quenched with water, and extracted with DCM (20 mL). The organic phase was dried over anhydrous Na$_2$SO$_4$, and concentrated to dryness at low pressure. The residue was purified by prep-TLC (30% EA in PE) to give 56-2 (270 mg, 31%).

To a solution of 56-2 (600 mg, 0.7 mmol) in anhydrous toluene (30 mL) was added AIBN (34 mg, 0.21 mmol) and Bu$_3$SnH (307.7 mg, 1.05 mmol) in toluene (10 mL). The mixture was bubbled with N$_2$ for 30 mins, and heated to 135° C. for 2 h. The mixture was treated with sat. aq. CsF, and then stirred for 2 h. The mixture was diluted with EA (100 mL). The organic phase was washed with brine, dried over anhydrous Na$_2$SO$_4$ and concentrated at low pressure. The residue was purified on a silica gel column (10% EA in PE) to give 56-3 and a by-product (400 mg, 72%).

A mixture of 56-3 (400 mg, 0.55 mmol) in 90% TFA (10 mL) was stirred at 50° C. for 4 h. The reaction was monitored by LCMS. The mixture was treated with MeOH (5 mL), and concentrated under reducing pressure. The residue was purified by prep-HPLC to give compound 56 (46 mg, 27%). ESI-MS: m/z 306.1 [M+H]$^+$.

Example 47

Compound 57

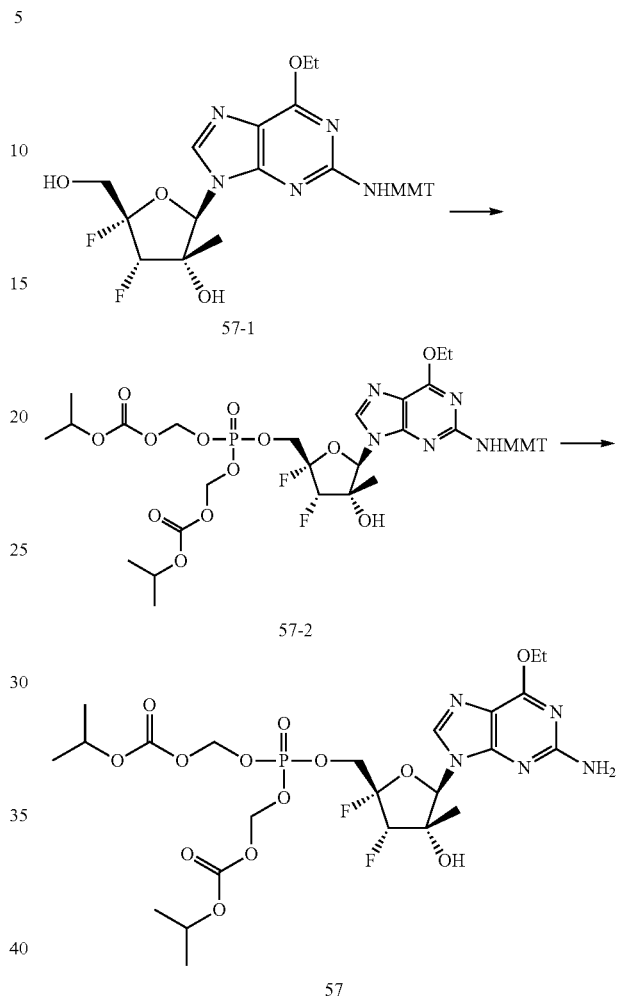

57-1

57-2

57

Compound 57-2 (120 mg, 72%) was prepared in the same manner from 57-1 (0.11 g; 0.18 mmol) and triethylammonium bis(isopropyloxycarbonyloxymethyl)phosphate (0.35 mmol) with DIPEA (0.15 mL), BopCl (114 mg), and 3-nitro-1,2,4-triazole (51 mg) in THF (2.5 mL) using the method as described for 52-4 from 52-3.

Compound 57 (14 mg, 77%) was prepared from 57-2 (25 mg) in acetonitrile (0.1 mL) and 4 N HCl/dioxane (8 μL) using the method as described for compound 55. MS: m/z=658 [M+1].

Example 48

Compound 60

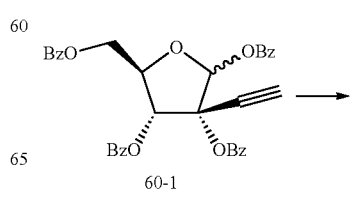

60-1

-continued

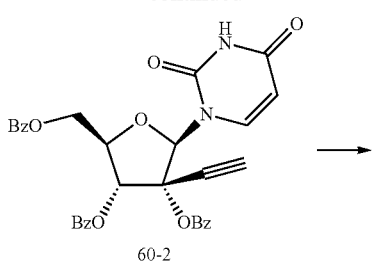
60-2

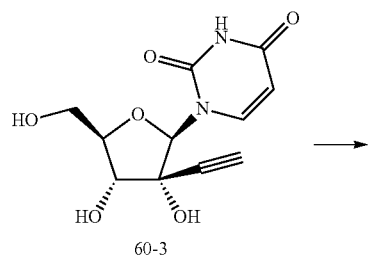
60-3

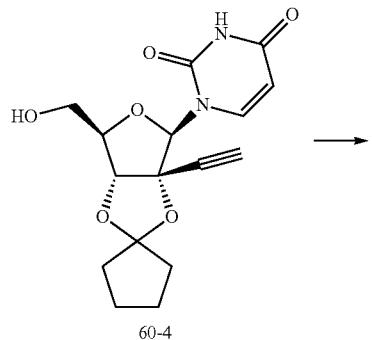
60-4

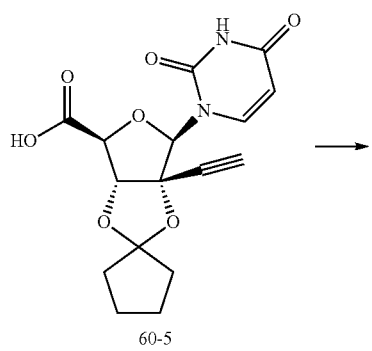
60-5

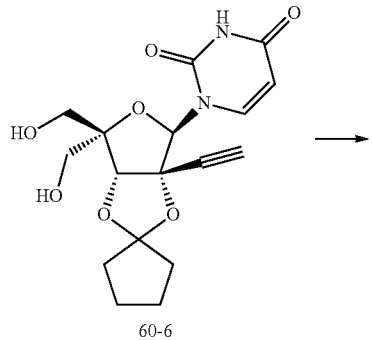
60-6

-continued

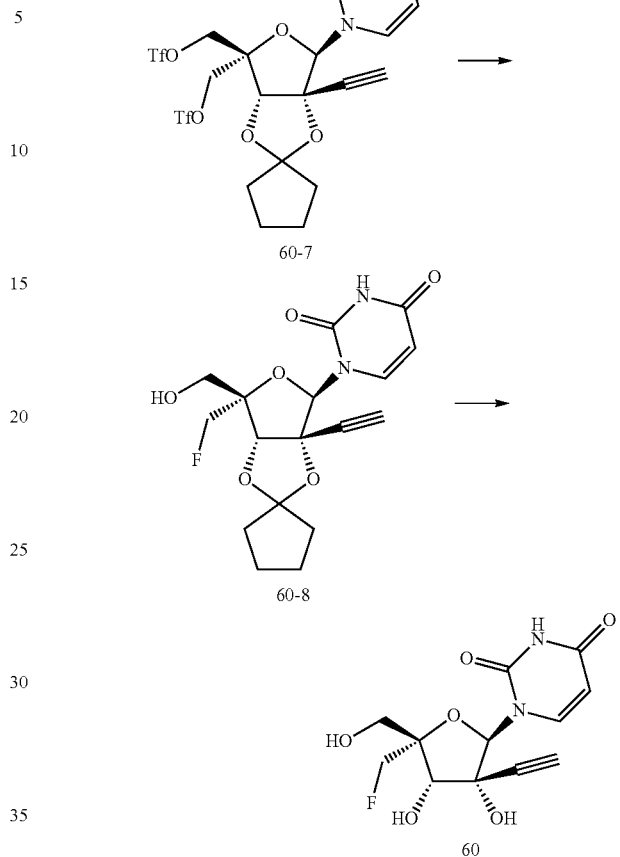

To a stirred solution of uracil (21 g, 188 mmol) in anhydrous MeCN (200 mL) was added BSA (110 g, 541 mmol), and the mixture was refluxed for 2 h. The mixture was then cooled to RT and treated with 60-1 (55 g, 93.2 mmol) and TMSOTf (145 g, 653 mmol). The mixture was refluxed overnight. After the starting material disappeared, the reaction was quenched with sat. $NaHCO_3$ solution, and extracted with EA. The organic layer was dried over anhydrous $Na_2SO_4$, and concentrated to dryness at low pressure. The residue was purified on silica column gel (20% EA in PE) to give 60-2 (38 g, 70%) as a white sold.

Compound 60-2 (35 g, 0.06 mol) was treated with $NH_3$ in MeOH (7N, 200 mL) at RT. The mixture was stirred for 24 h at RT. Completion of the reaction was determined by LCMS. The mixture was concentrated at a low pressure, and the residue was washed with DCM to give 60-3 (13 g, 81%) as a white solid.

To a solution of cyclopentanone (6 g, 8.33 mmol), and trimethoxymethane (8 mL) in MeOH (60 mL) was added TsOH (1.35 g, 7.1 mmol) at RT, and the mixture was stirred 2 h. The resulting was quenched with NaOMe (0.385 g, 7.12 mmol), and extracted with n-hexane (30 mL). The organic layer was dried over anhydrous $Na_2SO_4$, and concentrated at low pressure to give 1,1-dimethoxycyclopentane. To a solution of 60-3 (30 g, 0.11 mol) and 1,1-dimethoxy cyclopentane (57 g, 0.44 mol) in 1,2-dichloroethane (200 mL) was added TsOH (2.1 g, 0.011 mol), and the mixture was heated to 60° C. overnight. The reaction was quenched with triethylamine, and concentrated to dryness at low pressure. The residue was washed with MeOH to give 60-4 (30 g, 82%).

To a solution of 60-4 (10 g, 30 mmol) in anhydrous CH₃CN (100 mL) was added IBX (8.4 g, 30 mmol, 1.05 eq.) at RT. The mixture was refluxed for 12 h., and then cooled to 0° C. The precipitate was removed by filtration, and the filtrate was concentrated to give crude 60-5 (10 g, 100%) as a yellow solid.

Crude 60-5 (10 g, 30 mmol) was dissolved in 1,4-dioxane (100 mL). 37% HCHO (10 mL) and 2N NaOH aqueous solution (20 mL) were added at RT. The mixture was stirred at RT overnight, and adjusted to pH=7. The mixture was treated with NaBH₄ (4.44 g, 120 mmol) at 0° C. The reaction was stirred at RT for 30 mins and then quenched with sat. aq. NH₄Cl. The mixture was extracted with EA. The organic layer was dried over Na₂SO₄, and concentrated to dryness at low pressure. The residue was purified by silica gel column chromatography (1-3% MeOH in DCM) to give 60-6 (5.5 g, 50%) as a white solid.

To a stirred solution of 60-6 (5.0 g, 13.8 mmol) and pyridine (5 mL) in DCM (20 mL) was added Tf₂O (8.5 g, 30.3 mmol) dropwise at −70° C. The solution was warmed to 0° C. slowly, stirred at 0° C. for 0.5 h, and washed with HCl (0.5 M). The DCM layer was concentrated to dryness at low pressure, and the residue was purified on silica gel column to give 60-7 (4.5 g, 52%) as a white solid.

To a solution of 60-7 (3.0 g, 4.8 mmol) in MeCN (10 mL) was added TBAF (5.0 g, 19.2 mmol). The reaction was allowed to proceed overnight. The reaction was monitored by HPLC and LCMS. Aqueous sodium hydroxide (1N~2 eq.) was added, and the solution was stirred for 1 h. The mixture was partitioned between sat. ammonium chloride solution and EA. The organic layer was separated, and concentrated under reduced pressure. The crude product was purified on silica gel column to give 60-8 (0.8 g, 46%) as a white solid. ESI-MS: m/z 367.0 [M+H]⁺, 389.0 [M+Na]⁺.

Compound 60-8 (0.2 mmol) was dissolved in 80% HCOOH (10 mL), and the mixture was heated at 45° C. for 24 h. The solvent was evaporated and co-evaporated with methanol/toluene mixture to remove traces of acid. The residue was dissolved in 20% triethylamine in methanol, kept for 15 mins and evaporated. Compound 60 (65-68%) was isolated by silica gel chromatography in gradient of methanol in DCM from 5% to 20%. MS: m/z 321.0 [M−1].

Example 49

Compound 63

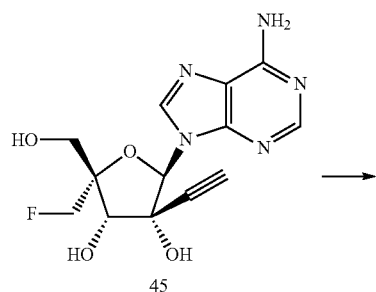

45

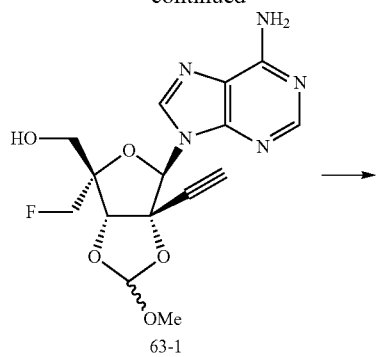

63-1

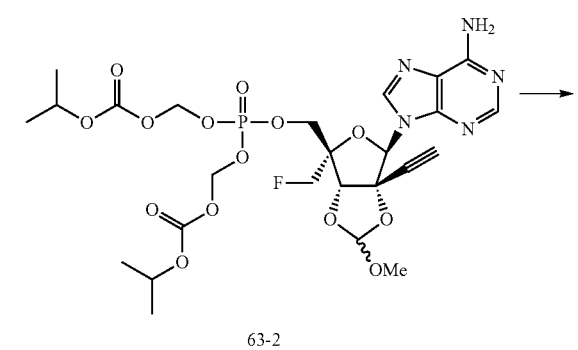

63-2

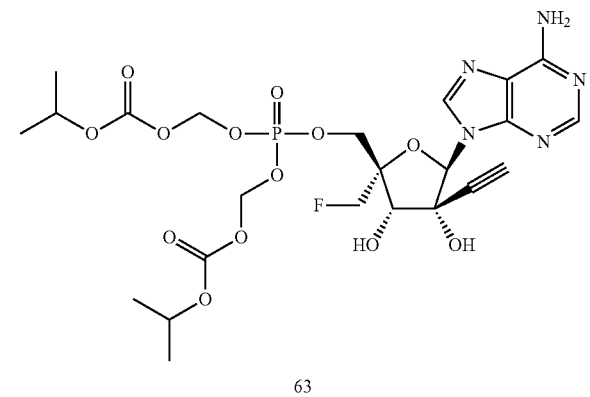

63

A mixture of compound 45 (30 mg, 0.09 mmol), PTSA monohydrate (18 mg, 1 eq.), and trimethyl orthoformate (0.3 mL; 30 eq.) in dioxane (1 mL) was stirred 1 d at RT. The reaction was neutralized with NH₃/MeOH and then filtered. The filtrate was dissolved in a mixture of THF (0.5 mL) and 80% aq. AcOH (0.25 mL). The solution kept for 1 h at RT, and then evaporated. The residue was purified on silica gel (10 g column) with CH₂Cl₂/MeOH (4-15% gradient) to yield 63-1 (30 mg, 91%).

Compound 63-2 (28 mg, 52%) was prepared in the same manner from 63-1 (30 mg, 0.08 mmol) and triethylammonium bis(isopropyloxycarbonyloxymethyl)phosphate (0.12 mmol) with DIPEA (56 μL), BopCl (40 mg), and 3-nitro-1,2,4-triazole (18 mg) in THF (1 mL) using the method for preparing 52-4 from 52-3. Purification was done with CH₂Cl₂/MeOH (4-10% gradient).

Compound 63 (15 mg, 67%) was prepared from 63-2 (24 mg) using the method for preparing 52-5. Purification was done with CH₂Cl₂/MeOH (4-10% gradient). MS: m/z=636 [M+1].

Example 50

Compound 64

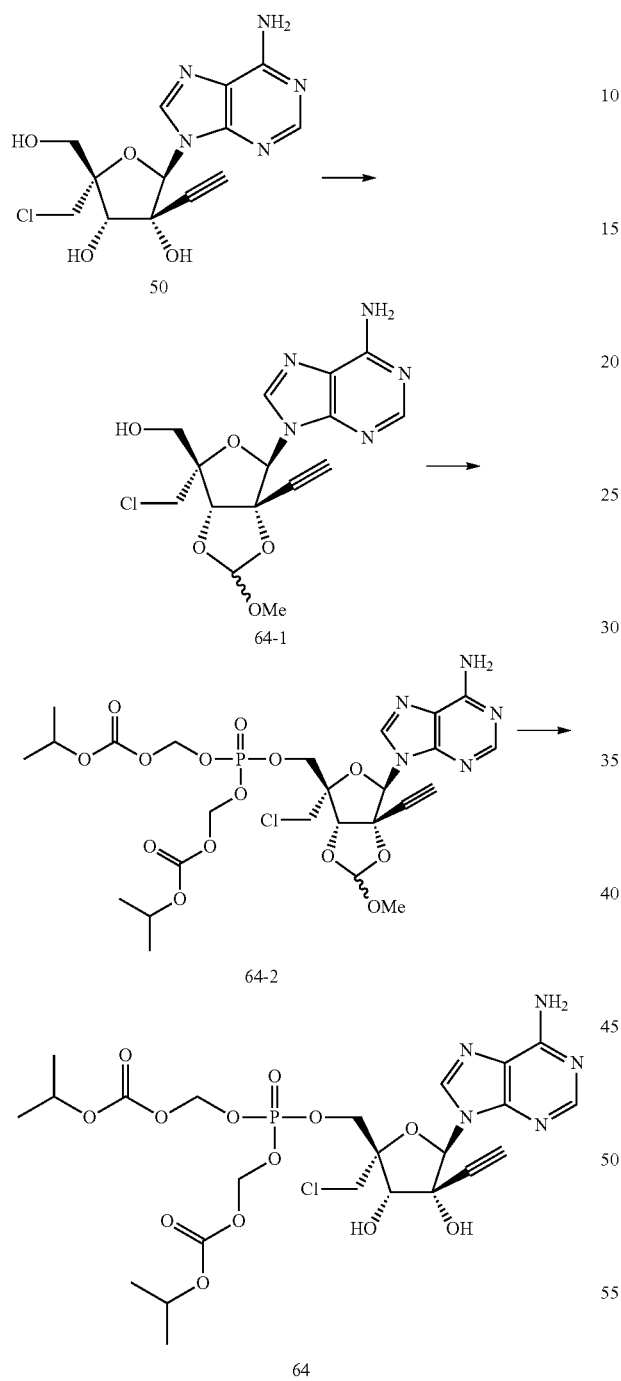

Compound 64-1 (8 mg, 40%) was prepared from compound 50 (17 mg) and trimethylorthoformate (0.15 mL) with PTSA monohydrate (9 mg) in dioxane (0.5 mL) in the same manner as 63-1.

Compound 64-2 (10 mg, 72%) was prepared in the same manner from 64-1 (8 mg, 0.02 mmol) and triethylammonium bis(isopropyloxycarbonyloxymethyl)phosphate (0.036 mmol) with DIPEA (14 μL), BopCl (10 mg), and 3-nitro-1,2,4-triazole (5 mg) in THF (0.4 mL) in the same manner as 63-2.

Compound 64 (15 mg, 67%) was prepared from 64-2 (24 mg) in the same manner as 63. MS: m/z=652 [M+1].

Example 51

Compound 65

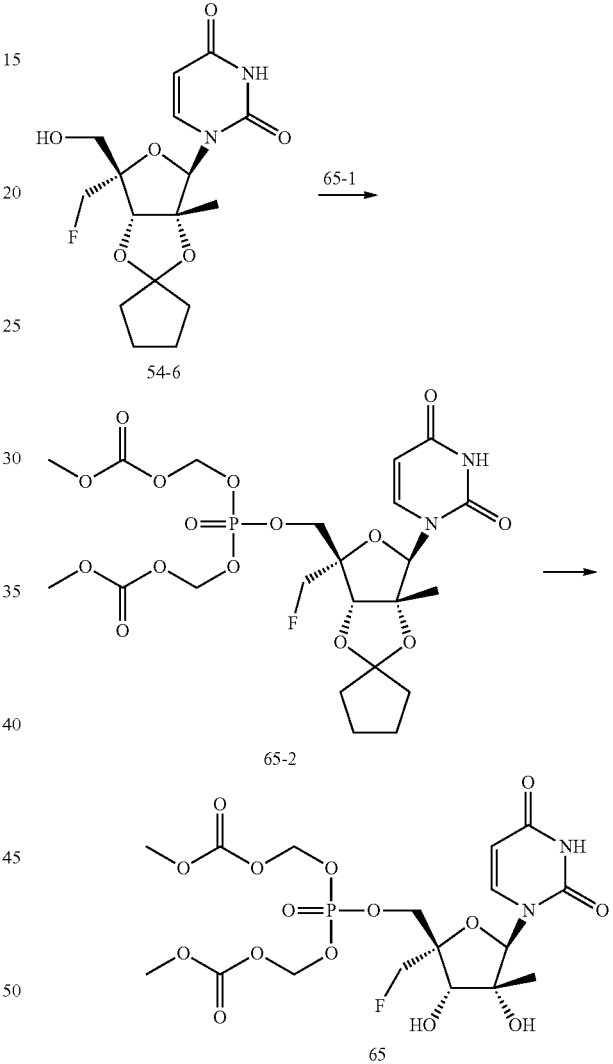

Commercially available chloromethyl methyl carbonate (5.0 g) was treated with NaI to give 65a (5.38 g). Benzylphosphate (silver salt) and 65a were reacted to yield purified 65b (1.5 g) as described for compound 54. $^1$H-NMR (CD$_3$CN): δ 7.39-7.42 (m, 5H), 5.60 (d, 4H), 5.11 (d, 2H), 3.8 (s, 6H). $^{31}$P-NMR (CD$_3$CN): δ −4.47 ppm. Compound 65b (415 mg; 1.7 mmol) was deprotected to give 65-1 (triethylammonium salt) (510 mg), which was used immediately without further purification. Compound 54-6 (320 mg; 0.9 mmol) and 65-1 (510 mg) were reacted to purified 65-2 (400 mg). Compound 65-2 (230 mg) was deprotected to give purified compound 65 (250 mg). The aforementioned reactions were conducted using a method described in the preparation of compound 54. $^1$H-NMR (CDCl$_3$): δ 9.00 (s, 1H), 7.55 (d, 1H), 5.93 (s, 1H), 5.81 (d, 1H), 5.66-5.75 (m, 4H), 4.76 (dd, 2H), 4.37-4.46 (m, 2H), 4.15 (d, 2H), 3.86 (t, 6H), 3.70 (d, 6H), 1.65 (s, 6H), 1.25 (s, 3H). $^{31}$P-NMR (CDCl$_3$): δ −4.13 ppm.

Example 52

Compound 66

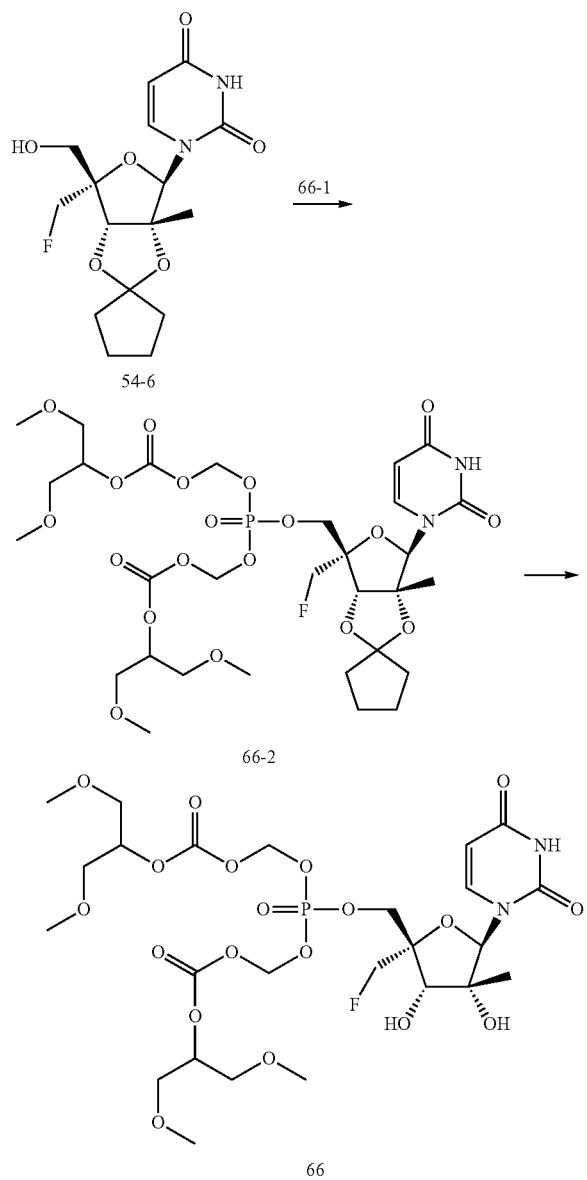

Compound 66a was prepared from 1,3-dimethoxypropan-2-ol. $^1$H-NMR (CDCl$_3$) δ 5.73 (s, 2H), 5.03-5.06 (m, 1H), 3.59 (d, 4H), 3.38 (s, 6H). Dry ACN (25 mL) was added to benzylphosphate (silver salt) (5 mmol) followed by addition of 66a (3.12 g; 12 mmol). The suspension was heated at 60° C. for 18 h. After the solid was removed by filtration, the product was purified by silica gel chromatography using hexane/EA (3:1) as the eluent to provide 66b as a colorless liquid (540 mg, 50%). $^1$H-NMR (CD$_3$CN): δ 7.39-7.42 (m, 5H), 5.61 (d, 4H), 5.10 (d, 2H), 4.97-5.01 (m, 2H), 3.50-3.52 (m, 8H), 3.30 (s, 6H), 3.28 (s, 6H). $^{31}$P-NMR (CD$_3$CN): δ −4.42 ppm. Compound 66b (540 mg; 1.0 mmol) was deprotected to give 66-1 (triethylammonium salt), which was used immediately without further purification. Compound 54-6 (285 mg; 0.8 mmol) and 66-1 were reacted to give purified 66-2 (300 mg). Compound 66-2 (300 mg) was deprotected to give purified compound 66 (290 mg). The aforementioned reactions were conducted using a method described in the preparation of compound 54. $^1$H-NMR (CDCl$_3$): δ 9.35 (s, 1H), 7.56 (d, 1H), 6.1 (s, 1H), 5.66-5.82 (m, 5H), 5.04 (s, 1H), 4.76 (dd, 2H), 4.60 (d, 1/2H), 4.37-4.48 (m, 2H), 4.22 (d, 2H), 4.06 (s, 1H), 3.58 (s, 8H), 3.57 (s, 12H), 1.93 (s, 1H), 1.23 (s, 3H). $^{31}$P-NMR (CDCl$_3$): δ −4.08 ppm.

Example 53

Compound 67

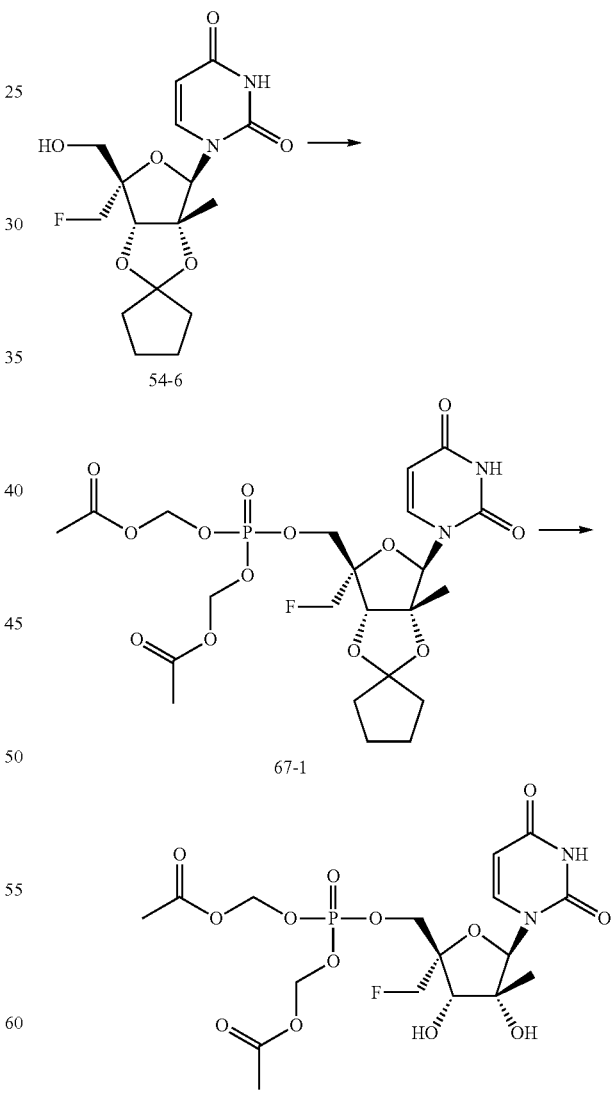

Compound 67-1 (180 mg, 62%) was prepared in the same manner from 54-6 (0.18 g, 0.5 mmol) and triethylammonium bis(acetyloxymethyl)phosphate (1.0 mmol) with DIPEA (0.35 mL), BopCl (0.25 g), and 3-nitro-1,2,4-triazole (0.11 g) in THF (1 mL) using a method as described for compound 44. Purification was done with CH$_2$Cl$_2$/i-PrOH (4-10% gradient).
Compound 67 (60 mg, 78%) was prepared from 67-1 (85 mg) using a method as described for compound 44. MS: m/z=1027 (2M−1).
Example 54
Compound 68
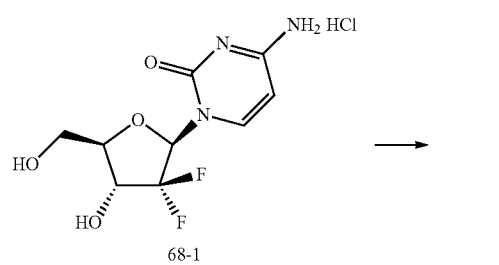
68-1
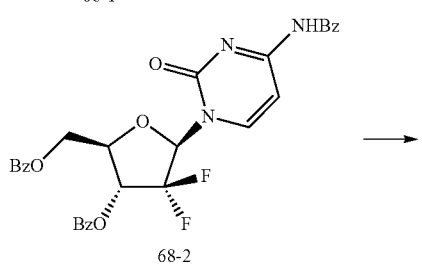
68-2
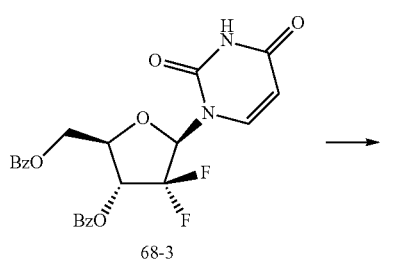
68-3
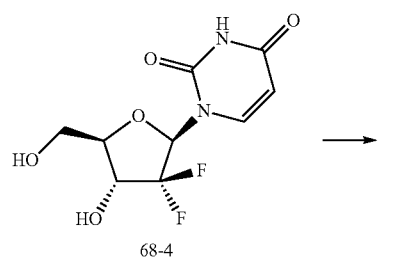
68-4
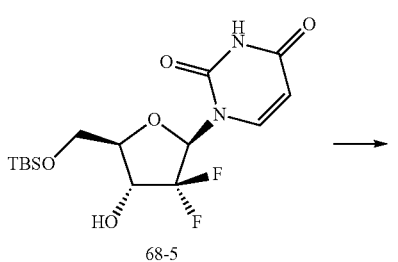
68-5
-continued
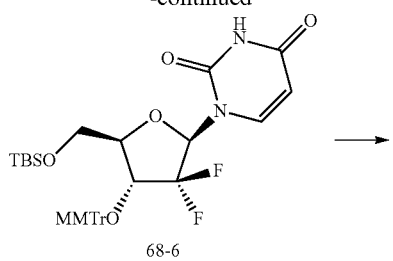
68-6
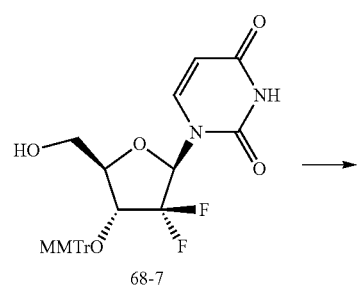
68-7
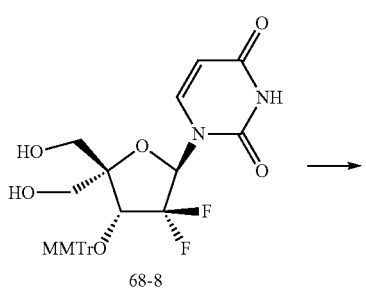
68-8
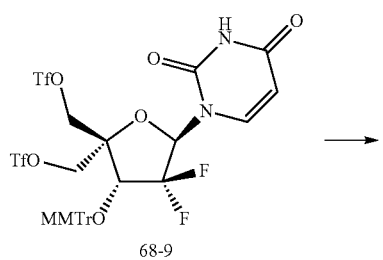
68-9
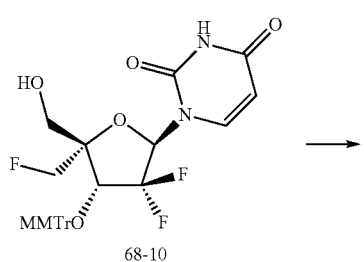
68-10
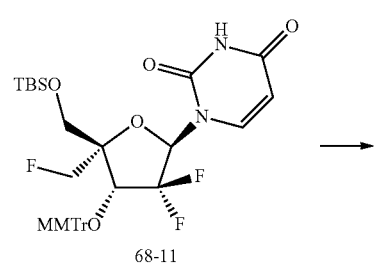
68-11

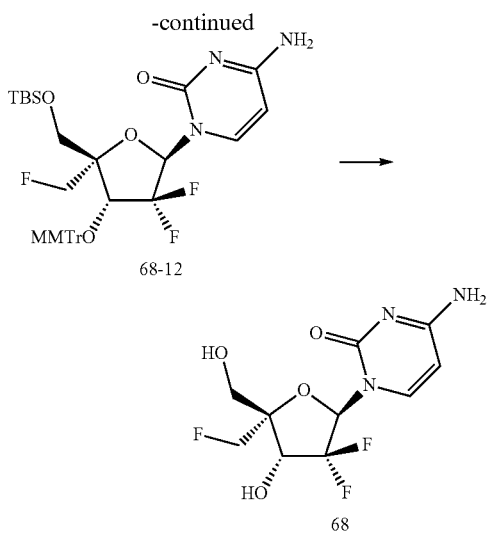

To a solution of 68-1 (15 g, 50.2 mmol) in anhydrous pyridine (180 mL) was added BzCl (23.3 g, 165.5 mmol) at 0° C. under nitrogen. The mixture was stirred overnight at RT. The mixture was diluted with EA and washed with NaHCO$_3$ aq. solution. The organic layer was dried with anhydrous Na$_2$SO$_4$, and concentrated to dryness. The organic layer was dried and concentrated to give a residue, which was purified by silica gel column chromatography (15% EtOAc in PE) to give 68-2 (27 g, 93.5%) as a white solid.

Compound 68-2 (27 g, 47 mmol) was dissolved in 90% HOAc (250 mL) and heated to 110° C. The mixture was stirred overnight at 110° C. The solvent was removed and diluted with EA. The mixture was washed with NaHCO$_3$ aq. solution and brine. The organic layer was dried and concentrated to give crude 68-3.

Compound 68-3 was dissolved in NH$_3$/MeOH (600 mL) and stirred overnight. The solvent was concentrated to give the residue, which was purified by silica gel column chromatography (5% MeOH in DCM) to give 68-4 (12 g, 99%) as a white solid.

To a solution of 68-4 (15 g, 56.8 mmol) in anhydrous pyridine (200 mL) was added imidazole (7.7 g, 113.6 mmol) and TBSCl (9.4 g, 62.5 mmol) at RT. The mixture was stirred overnight. And the solvent was removed and diluted with EA. The mixture was washed with NaHCO$_3$ aq. solution and brine. The organic layer was dried and concentrated to give crude 68-5.

To a solution of 68-5 in anhydrous DCM (200 mL) was added collidine (6.8 g, 56.8 mmol), MMTrCl (17.8 g, 56.8 mmol) and AgNO$_3$ (9.6 g, 56.8 mmol) at RT. The mixture was stirred overnight. The mixture was filtered, and the filtrate was washed with NaHCO$_3$ aq. solution and brine. The organic layer was dried over Na$_2$SO$_4$, and concentrated at low pressure to give the residue, which was purified by silica gel column chromatography (5% EA in PE) to give 68-6 (32 g, 87%).

Compound 68-6 (32 g, 49.2 mmol) was dissolved in a solution of TBAF in THF (1M, 4 eq.) at RT. The mixture was stirred overnight, and the solvent was removed. The mixture was diluted with EA and washed with water. The organic layer was dried and concentrated to give the crude product, which was purified by silica gel column chromatography (33% EA in PE) to give 68-7 (21 g, 79%).

To a solution of 68-7 (21 g, 38.8 mmol) in DCM (200 mL) was added pyridine (9.2 mL, 116.4 mmol). The solution was cooled to 0° C. and Dess-Martin periodinane (49 g, 116.4 mmol) was added in a single portion. The mixture was stirred for 4 h at RT. The reaction was quenched with Na$_2$S$_2$O$_3$ solution and sodium bicarbonate aqueous solution. The mixture was stirred for 15 mins. The organic layer was separated, washed with diluted brine and concentrated under reduced pressure. The residue was dissolved in dioxane (200 mL), and the solution was treated with 37% aqueous formaldehyde (20 mL, 194 mmol) and 2 N aqueous sodium hydroxide (37.5 mL, 77.6 mmol). The mixture was stirred at RT overnight and NaBH$_4$ (8.8 g, 232.8 mmol) was added. After stirring for 0.5 h at RT, the excess of aqueous sodium hydroxide was removed with ice water. The mixture was diluted with EA. The organic phase was washed with brine, dried over magnesium sulfate and concentrated at low pressure. The residue was purified by column chromatography (4% MeOH in DCM) to give 68-8 (10 g, 50.5%) as a white foam.

Compound 68-8 (4.8 g, 8.5 mmol) was co-evaporated with toluene twice. The residue was dissolved in anhydrous DCM (45 mL) and pyridine (6.7 g, 85 mmol). The solution was cooled to 0° C. and triflic anhydride (4.8 g, 18.7 mmol) was added dropwise over 10 mins. At this temperature, the reaction was stirred for 40 mins. TLC (50% EA in PE) showed that the reaction was complete. The mixture was purified by column chromatography (EA in PE from 0 to 20%) to give 68-9 (6.1 g, 86.4%) as a brown foam.

Compound 68-9 (6.1 g, 7.3 mmol) was dissolved in MeCN (25 mL). The mixture was treated with a solution of TBAF in THF (1M, 25 mL) at RT. The mixture was stirred overnight. TBAF in THF (1M, 15 mL) was added and stirred for 4 h. The mixture was treated with aqueous sodium hydroxide (1N, 14.6 mmol) and stirred for 1 h. The reaction was quenched with water (50 mL) at 0° C. and extracted with EA. The organic layer was dried and concentrated to give the crude product, which was purified by silica gel column chromatography (50% EA in PE) to give 68-10 (2.1 g, 50.6%).

To a solution of 68-10 (1.5 g, 2.6 mmol) in anhydrous pyridine (15 mL) was added imidazole (530 mg, 7.8 mmol) and TBSCl (585 mg, 3.9 mmol) at RT. The mixture was stirred for 2 h. The solvent was removed and diluted with EA. The mixture was washed with NaHCO$_3$ aq. solution and brine. The organic layer was dried and concentrated to give the residue, which was purified by silica gel column chromatography (10% EA in PE) to give 68-11 (1.5 g, 84.5%).

To a solution of 68-11 (1.5 g, 2.2 mmol) in anhydrous CH$_3$CN (11 mL) were added DMAP (671 mg, 5.5 mmol), TEA (555 mg, 5.5 mmol) and TPSCl (1.66 g, 5.5 mmol) at RT. The reaction was stirred overnight at RT. NH$_4$OH (10 mL) was added, and the mixture was stirred for 2 h. The mixture was diluted with EA and washed with NaHCO$_3$ solution. The organic layer was dried and concentrated at low pressure. The residue was purified by silica gel column chromatography (2% MeOH in DCM) to give crude 68-12, which was purified by prep-TLC to give 68-12 (1.2 g, 80%) as a white solid.

A solution of 68-12 (1.2 g, 1.76 mmol) in 80% HCOOH (60 mL) was stirred for 4 h. The solvent was removed at low pressure. The crude product was dissolved in MeOH (40 mL) and stirred overnight. The solvent was concentrated to give the crude product, which was purified by column chromatography on silica gel (MeOH in DCM 10%) to give compound 68 (480 mg, 92%) as a white solid. ESI-MS: m/z 591 [2M+H]$^+$.

Example 55

Compound 69

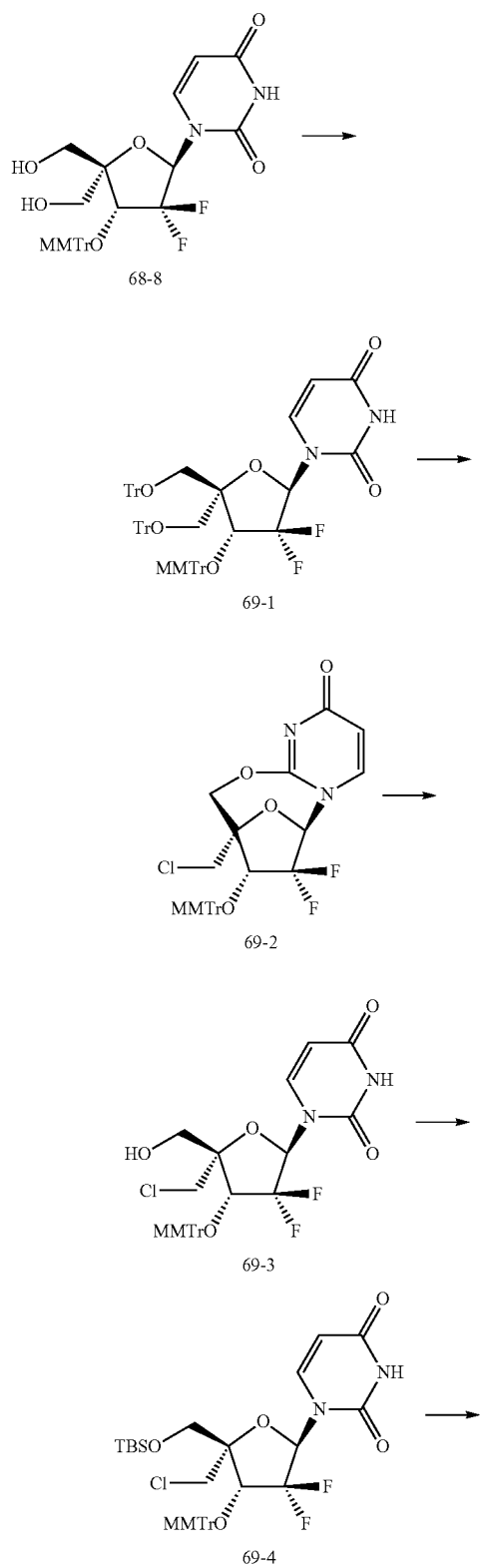

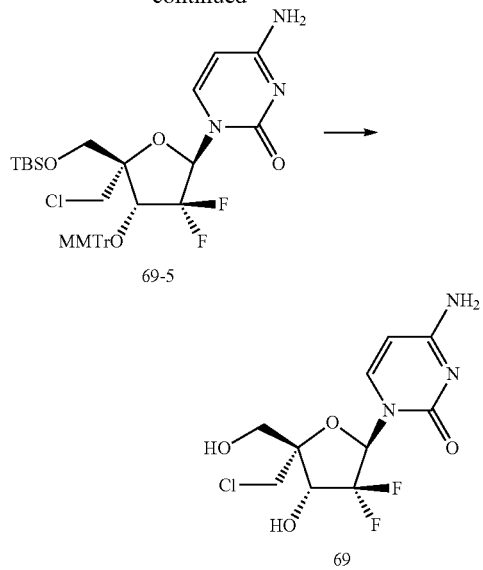

A solution of 68-8 (2.63 g, 4.64 mmol) in anhydrous pyridine/DCM at 0° C. was added Tf₂O (3.27 g, 11.59 mmol). The mixture was stirred at RT for 40 mins. The solvent was removed at reduced pressure, and the residue was purified by column chromatography to give 69-1 (2.60 g, 67%).

A solution of 69-1 (2.65 g, 3.19 mmol) in anhydrous DMF was added sodium hydride (153 mg, 3.82 mmol) at 0° C. for 1 h. The solution was used for the next step without purification. The solution was treated with LiCl (402 mg, 9.57 mmol) at RT. The mixture was stirred at RT for 12 h. The reaction was quenched with saturated ammonium chloride solution, and extracted with EA. The organic layers were dried over Na₂SO₄, and concentrated at low pressure to give crude 69-2.

To a solution 69-2 (1.81 g, 3.19 mmol) in anhydrous THF (20 mL) was added 1 N NaOH (4 mL, 3.83 mmol) at RT. The mixture was stirred at RT for 2 h. The reaction was quenched with saturated sodium bicarbonate solution, and extracted with EA. The organic phase was dried over anhydrous Na₂SO₄, and concentrated at low pressure. The residue was purified by column chromatography to give 69-3. (1.34 g, 72%).

A solution of 69-3 (925 mg, 1.58 mmol) in dichloromethane (10 mL) was added TBSCl (713 mg, 4.75 mmol) and imidazole (323 mg, 4.74 mmol), and stirred at RT overnight. The mixture was diluted with EA (20 mL), and washed with brine. The organic phase was concentrated at low pressure to give the crude product. The residue was purified by column chromatography to give 69-4 (1.0 g, 90%).

A solution of 69-4 (1.24 g, 1.78 mmol) in anhydrous acetonitrile (10 mL) was added TPSCl (1.34 g, 4.45 mmol), DMAP (543 mg, 4.45 mmol) and TEA (450 mg, 4.45 mmol), and the mixture was stirred at RT for 3 h. The solvent was removed under reduced pressure, and the residue was dissolved in EA (30 mL). The solution was washed with brine, dried with anhydrous Na₂SO₄, and concentrated at low pressure. The residue was purified on silica gel to give 69-5 (1.0 g, 81%) as a white solid.

Compound 69-5 (1.0 g, 1.43 mmol) was treated with 80% HCOOH (10 mL), and stirred at RT overnight. The solvent was removed under reduced pressure, and the residue was purified on silica gel using 5% MeOH in CH$_2$Cl$_2$ to give compound 69 (264 mg, 60%). ESI-MS: m/z 311.9 [M+H]$^+$.

Example 56

Compound 70

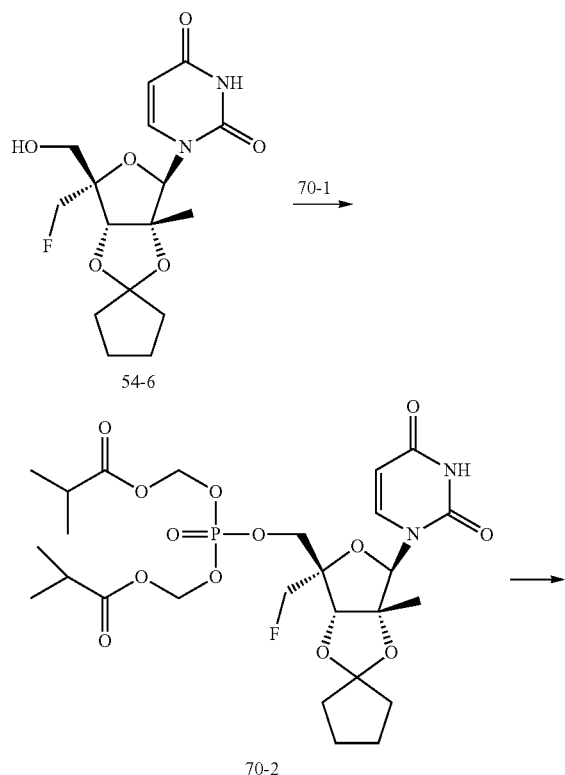

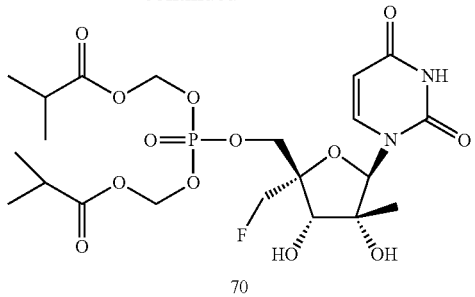

Benzylphosphate (silver salt) and commercially available chloromethyl isobutylrate (5.0 g) yielded purified 70a (3.84 g). $^1$H-NMR (CD$_3$CN): δ 7.39-7.42 (m, 5H), 5.60 (d, 4H), 5.09 (d, 2H), 1.94-1.96 (m, 2H), 1.12-1.17 (m, 12H). $^{31}$P-NMR (CD$_3$CN): δ −4.03 ppm. Compound 70a (780 mg; 2.0 mmol) was deprotected to give 70-1 (triethylammonium salt), which was used immediately without further purification. Compound 54-6 (356 mg; 1.0 mmol) and 70-1 were reacted to give purified 70-2 (230 mg). Compound 70-2 (230 mg) was deprotected to yield purified compound 70 (80 mg, 0.14 mmol). The aforementioned reactions were conducted using a method described in the preparation of compounds 54 and 66. $^1$H-NMR (CDCl$_3$): δ 8.25 (s, 1H), 7.55 (d, 1H), 5.93 (s, 1H), 5.81 (d, 1H), 5.66-5.75 (m, 4H), 4.76 (dd, 2H), 4.37-4.46 (m, 2H), 4.15 (d, 2H), 3.86 (t, 6H), 3.70 (d, 6H), 1.65 (s, 6H), 1.25 (s, 3H). $^{31}$P-NMR (CDCl$_3$): δ −4.41 ppm.

Example 57

Compound 71

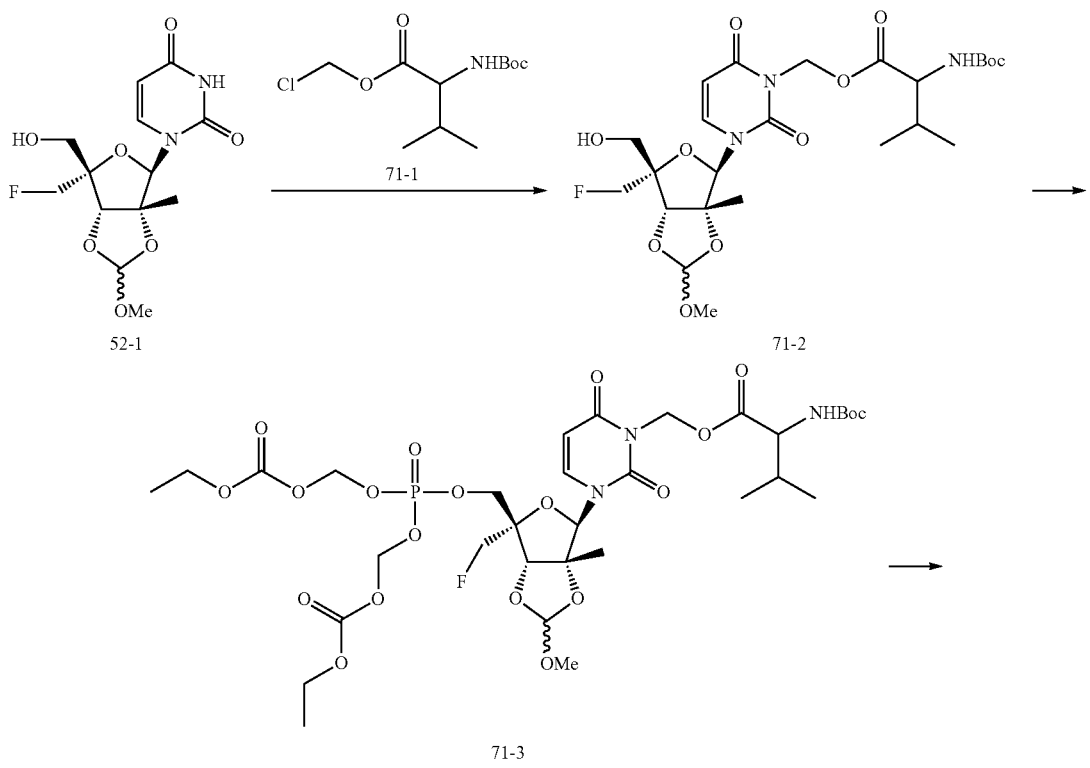

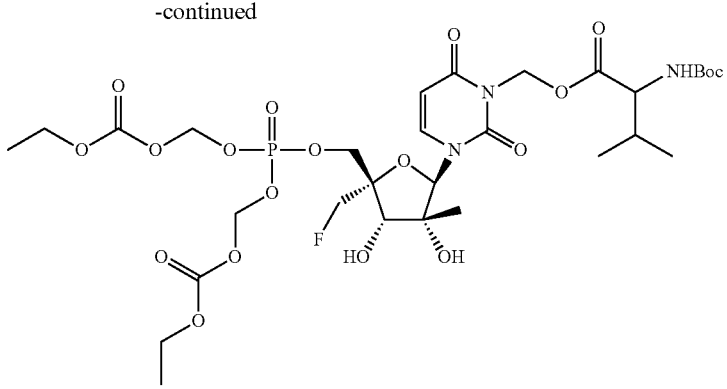

71-4

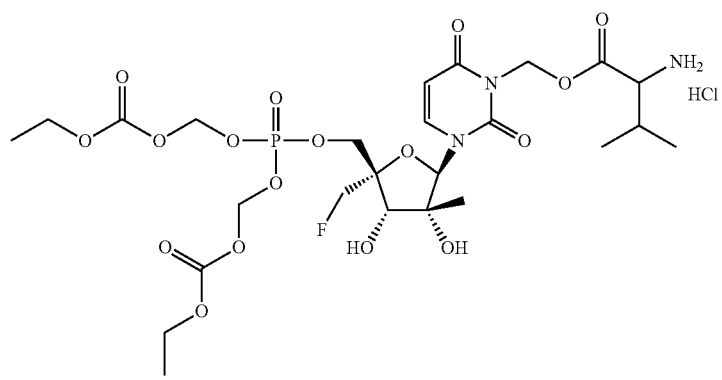

71

Compound 71-2 (0.34 g, 60%) was prepared from 52-1 (0.33 g) and 71-1 (0.34 g) in acetone (6 mL) with NaI (0.19 g) and K₂CO₃ (0.69 g).

Compound 71-3 (0.28 g, 74%) was prepared in the same manner from 71-2 (0.25 g, 0.45 mmol) and triethylammonium bis(ethoxycarbonyloxymethyl)phosphate (0.9 mmol) with DIPEA (0.35 mL), BopCl (0.25 g), and 3-nitro-1,2,4-triazole (0.11 g) in THF (5 mL). Purification was done with hexanes/EtOAc (30-100% gradient).

A solution of 71-3 (0.28 g, 0.33 mmol) in 80% aq. AcOH was heated at 45° C. for 4 h and then concentrated. The residue was coevaporated with toluene and then with MeOH containing small amount of Et₃N (2 drops). Purification on silica gel (10 g column) with CH₂Cl₂/i-PrOH (4-10% gradient) yielded 71-4 (0.22 g, 84%).

To a solution of 71-4 (148 mg, 0.18 mmol) in EtOAc (0.6 mL) at 0° C. was added 4 N HCl/dioxane (0.5 mL), and the mixture kept at RT for 1 h. Ether was added and compound 71 precipitated. The mixture was filtered and washed with ether to give compound 71 (100 mg, 75%). The aforementioned reactions were conducted using a method described in the preparation of compound 52. MS: m/z=704 [M+1].

Example 58

Compound 33

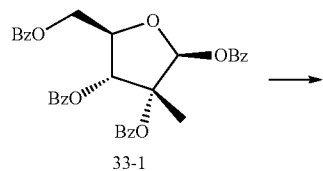

33-1

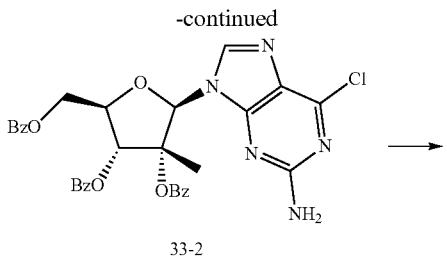

33-2

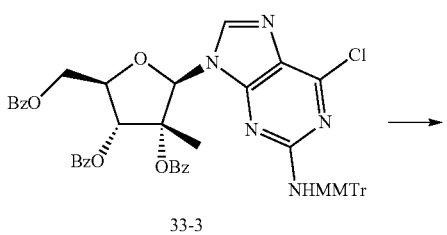

33-3

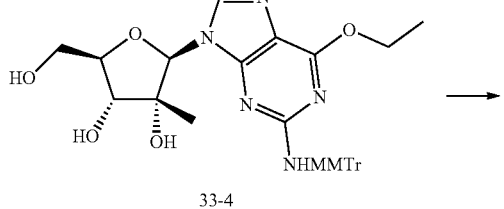

33-4

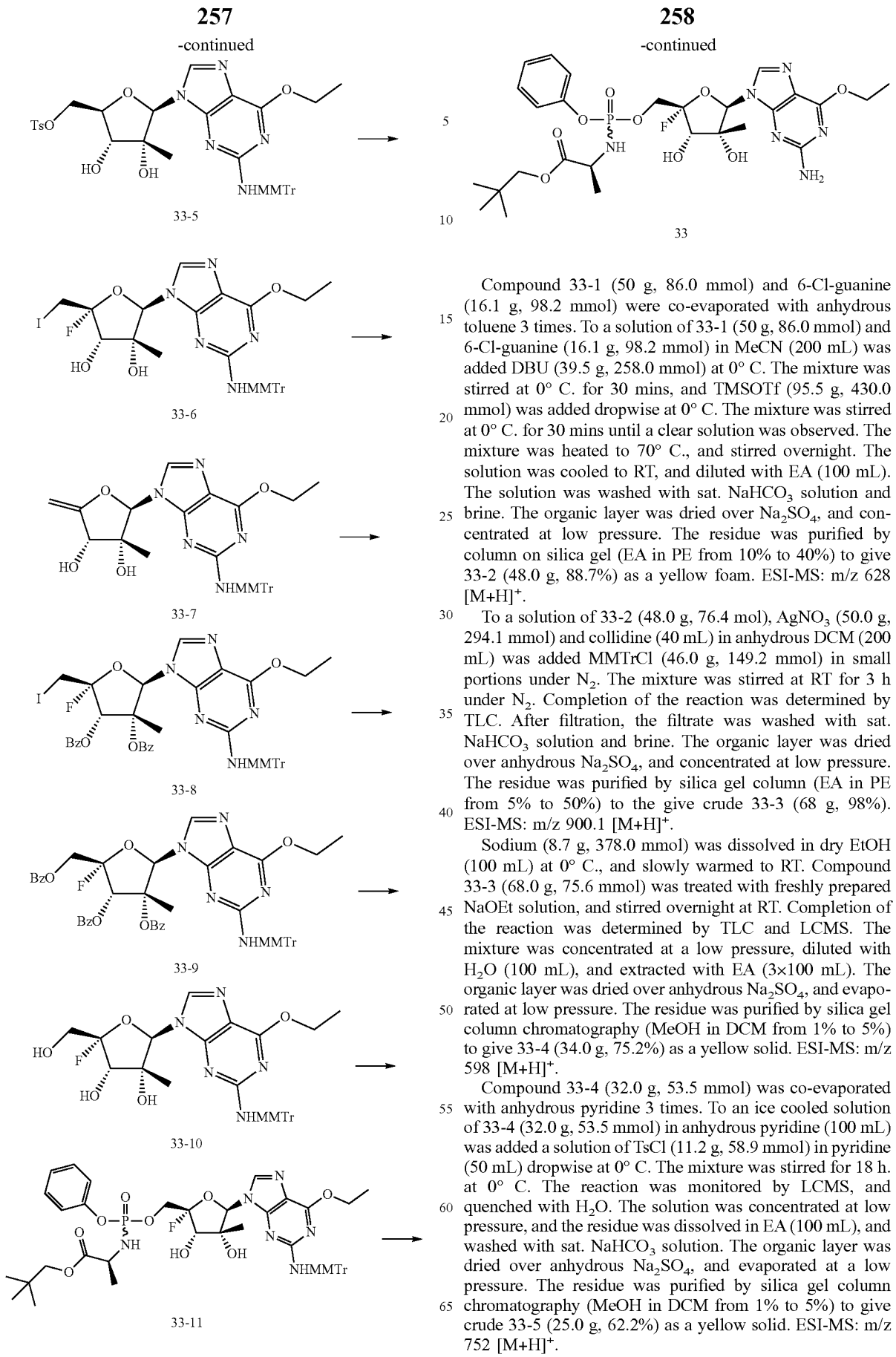

Compound 33-1 (50 g, 86.0 mmol) and 6-Cl-guanine (16.1 g, 98.2 mmol) were co-evaporated with anhydrous toluene 3 times. To a solution of 33-1 (50 g, 86.0 mmol) and 6-Cl-guanine (16.1 g, 98.2 mmol) in MeCN (200 mL) was added DBU (39.5 g, 258.0 mmol) at 0° C. The mixture was stirred at 0° C. for 30 mins, and TMSOTf (95.5 g, 430.0 mmol) was added dropwise at 0° C. The mixture was stirred at 0° C. for 30 mins until a clear solution was observed. The mixture was heated to 70° C., and stirred overnight. The solution was cooled to RT, and diluted with EA (100 mL). The solution was washed with sat. NaHCO$_3$ solution and brine. The organic layer was dried over Na$_2$SO$_4$, and concentrated at low pressure. The residue was purified by column on silica gel (EA in PE from 10% to 40%) to give 33-2 (48.0 g, 88.7%) as a yellow foam. ESI-MS: m/z 628 [M+H]$^+$.

To a solution of 33-2 (48.0 g, 76.4 mol), AgNO$_3$ (50.0 g, 294.1 mmol) and collidine (40 mL) in anhydrous DCM (200 mL) was added MMTrCl (46.0 g, 149.2 mmol) in small portions under N$_2$. The mixture was stirred at RT for 3 h under N$_2$. Completion of the reaction was determined by TLC. After filtration, the filtrate was washed with sat. NaHCO$_3$ solution and brine. The organic layer was dried over anhydrous Na$_2$SO$_4$, and concentrated at low pressure. The residue was purified by silica gel column (EA in PE from 5% to 50%) to the give crude 33-3 (68 g, 98%). ESI-MS: m/z 900.1 [M+H]$^+$.

Sodium (8.7 g, 378.0 mmol) was dissolved in dry EtOH (100 mL) at 0° C., and slowly warmed to RT. Compound 33-3 (68.0 g, 75.6 mmol) was treated with freshly prepared NaOEt solution, and stirred overnight at RT. Completion of the reaction was determined by TLC and LCMS. The mixture was concentrated at a low pressure, diluted with H$_2$O (100 mL), and extracted with EA (3×100 mL). The organic layer was dried over anhydrous Na$_2$SO$_4$, and evaporated at low pressure. The residue was purified by silica gel column chromatography (MeOH in DCM from 1% to 5%) to give 33-4 (34.0 g, 75.2%) as a yellow solid. ESI-MS: m/z 598 [M+H]$^+$.

Compound 33-4 (32.0 g, 53.5 mmol) was co-evaporated with anhydrous pyridine 3 times. To an ice cooled solution of 33-4 (32.0 g, 53.5 mmol) in anhydrous pyridine (100 mL) was added a solution of TsCl (11.2 g, 58.9 mmol) in pyridine (50 mL) dropwise at 0° C. The mixture was stirred for 18 h. at 0° C. The reaction was monitored by LCMS, and quenched with H$_2$O. The solution was concentrated at low pressure, and the residue was dissolved in EA (100 mL), and washed with sat. NaHCO$_3$ solution. The organic layer was dried over anhydrous Na$_2$SO$_4$, and evaporated at a low pressure. The residue was purified by silica gel column chromatography (MeOH in DCM from 1% to 5%) to give crude 33-5 (25.0 g, 62.2%) as a yellow solid. ESI-MS: m/z 752 [M+H]$^+$.

To a solution of 33-5 (23.0 g, 30.6 mmol) in acetone (150 mL) was added NaI (45.9 g, 306.0 mmol) and TBAI (2.0 g), and the mixture was refluxed overnight. Completion of the reaction was determined by LCMS. The mixture was concentrated at low pressure, and the residue was dissolved in EA (100 mL). The solution was washed with brine, and dried over anhydrous Na$_2$SO$_4$. The organic solution was evaporated at low pressure, and the residue was purified by silica gel column chromatography (DCM:MeOH=100:1 to 20:1) to give a crude product. To a solution of the crude product in dry THF (200 mL) was added DBU (14.0 g, 91.8 mmol), and the mixture was heated to 60° C. and stirred overnight. The reaction was monitored by LCMS. The reaction was quenched with sat. NaHCO$_3$ solution, and the solution was extracted with EA (100 mL). The organic layer was dried over anhydrous Na$_2$SO$_4$, and evaporated at low pressure. The residue was purified by silica gel column chromatography (MeOH in DCM from 1% to 5%) to give 33-6 (12.0 g, 67.4%) as a yellow solid. ESI-MS: m/z 580 [M+H]$^+$.

To an ice cooled solution of 33-6 (8.0 g, 13.8 mmol) in anhydrous MeCN (100 mL) was added NIS (3.9 g, 17.2 mmol) and TEA.3HF (3.3 g, 20.7 mmol) at 0° C. The mixture was stirred at RT for 18 h, and the reaction was checked by LCMS. After the reaction was completed, the reaction was quenched with sat. Na$_2$SO$_3$ solution and sat. NaHCO$_3$ solution. The solution was extracted with EA (3×100 mL). The organic layer was dried over anhydrous Na$_2$SO$_4$, and evaporated at low pressure. The residue was purified by silica gel column chromatography (EA in PE from 10% to 50%) to give 33-7 (7.2 g, 72.0%) as a solid. ESI-MS: m/z 726 [M+H]$^+$.

To a solution of 33-7 (7.2 g, 9.9 mmol) in dry DCM (100 mL) was added DMAP (3.6 g, 29.8 mmol), and BzCl (2.8 g, 19.8 mmol) at 0° C. The mixture was stirred overnight, and checked by LCMS. The mixture was washed with sat. NaHCO$_3$ solution. The organic layer was dried over anhydrous Na$_2$SO$_4$, and evaporated at low pressure. The residue was purified by silica gel column chromatography (EA in PE from 10% to 30%) to give 33-8 (8.0 g, 86.4%) as a solid. ESI-MS: m/z 934 [M+H]$^+$.

To a solution of 33-8 (7.5 g, 8.0 mmol) in dry DMF (100 mL) was added NaOBz (11.5 g, 80.0 mmol) and 15-crown-5 (15.6 mL). The mixture was stirred for 36 h. at 90° C. The mixture was diluted with H$_2$O (100 mL), and extracted with EA (3×150 mL). The organic layer was dried over anhydrous Na$_2$SO$_4$, and evaporated at low pressure. The residue was purified by silica gel column chromatography (EA in PE from 10% to 30%) to give crude 33-9 (6.0 g, 80.0%) as a solid. ESI-MS: m/z 928 [M+H]$^+$.

Compound 33-9 (4.0 g, 4.3 mmol) was co-evaporated with anhydrous toluene 3 times, and treated with NH$_3$/MeOH (50 mL, 4N) at RT. The mixture was stirred for 18 h. at RT. Completion of the reaction was determined by LCMS. The mixture was concentrated at low pressure, and the residue was purified by silica gel column chromatography (EA in PE from 30% to 50%) to give product 33-10 (1.9 g, 71.7%) as a solid. ESI-MS: m/z 616 [M+H]$^+$.

Compound 33-10 (300.0 mg, 0.49 mmol) was co-evaporated with anhydrous toluene 3 times, and was dissolved in MeCN (2 mL). The mixture was treated with NMI (120.5 mg, 1.47 mmol) and the phosphorochloridate reagent (326.3 mg, 0.98 mmol) in MeCN (1 mL) at 0° C. The mixture was stirred for 18 h at RT and monitored by LCMS. The mixture was diluted with 10% NaHCO$_3$ solution, and extracted with EA (3×30 mL). The residue was purified by silica gel column chromatography (EA in PE from 30% to 50%) to give 33-11 (210 mg, 47.5%) as a solid. ESI-MS: m/z 913.0 [M+H]$^+$.

Compound 33-11 (210 mg, 0.26 mmol) was treated with 80% of AcOH (15 mL), and the mixture was stirred for 18 h at RT. Completion of the reaction was determined by LCMS. The mixture was concentrated at low pressure, and the residue was purified by silica gel column chromatography (MeOH in DCM from 1% to 3%) to give compound 33 (71.8 mg, 48.7%) as a solid. ESI-MS: m/z 641.3 [M+H]$^+$.

Example 59

Compound 75

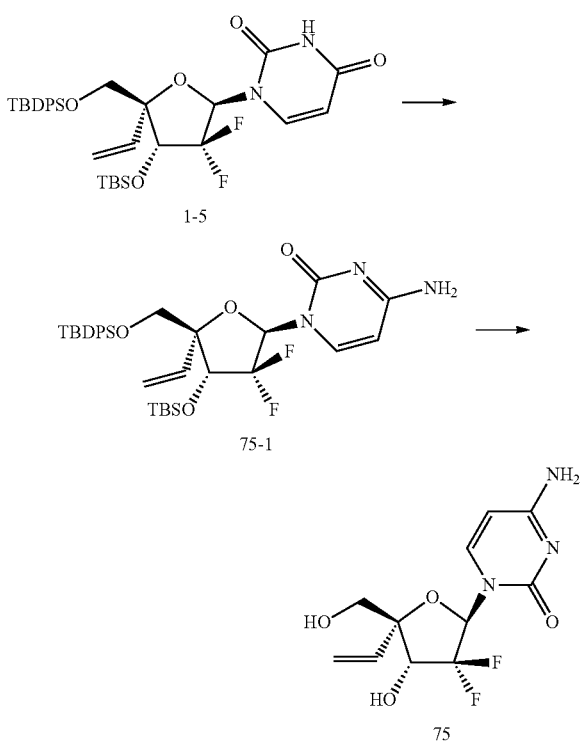

A mixture solution of 1-5 (317 mg, 0.49 mmol), TPSCl (373 mg, 1.23 mmol), DMAP (150 mg, 1.23 mmol) and TEA (124 mg, 1.23 mmol) in anhydrous MeCN was stirred at RT overnight. The mixture was treated with ammonium solution, and then stirred at RT for 3 h. The solvent was removed under reduced pressure, and the residue was purified by column chromatography to give 75-1 (200 mg, 63%).

A solution of 75-1 (286 mg, 0.45 mmol) and ammonium fluoride (500 mg, 13.5 mmol) in methanol (10 mL) was refluxed overnight. The solvent was removed under reduced pressure and the residue was purified on silica gel to give compound 75 (75 mg, 57%). ESI-MS: m/z 289.9 [M+H]$^+$.

Example 60
Compound 76
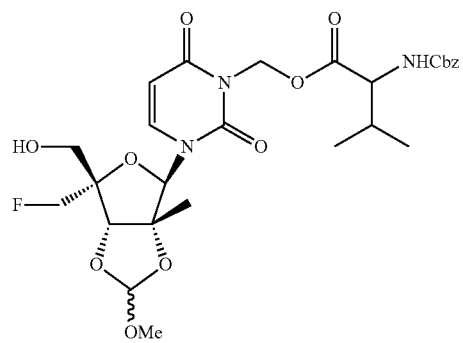
52-3
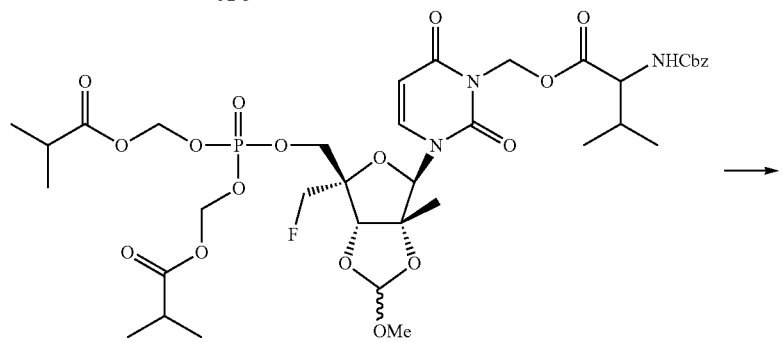
76-1
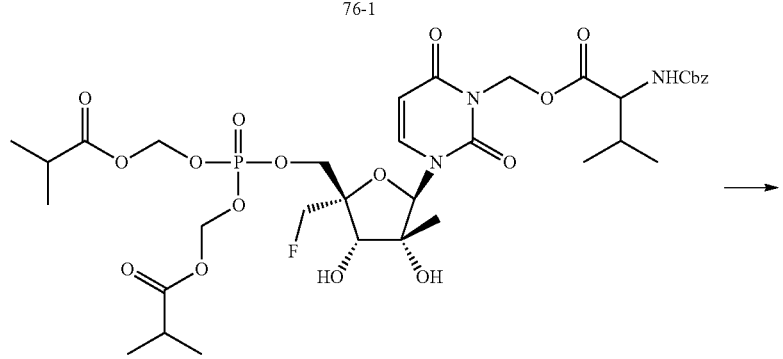
76-2
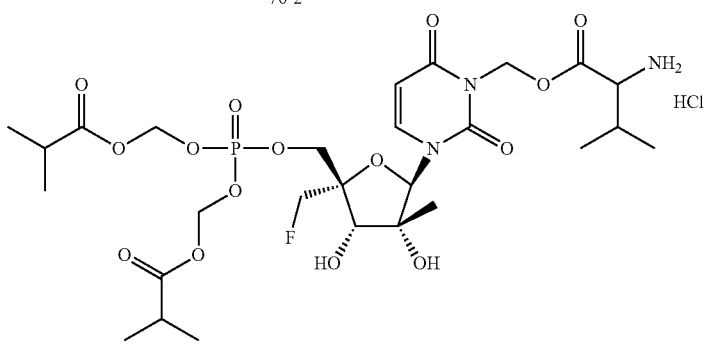
76
Compound 76-1 (0.44 g, 34%) was prepared from 52-3 (0.88 g, 1.48 mmol) and triethylammonium bis(isobutyryloxymethyl)phosphate (3 mmol) with DIPEA (1.05 mL), BopCl (0.76 g), and 3-nitro-1,2,4-triazole (0.34 g) in THF (10 mL). Purification was done with hexanes/EtOAc (5-100% gradient). Compound 76-2 (0.43 g, 85%) was prepared from 76-1 (0.44 g); and compound 76 (0.19 g, 98%) was prepared from 76-2 (0.22 g) in EtOH (10 mL) with 10% Pd/C (10 mg), 4 N HCl/dioxane (132 μL), and under the H₂ atmosphere. The aforementioned reactions were conducted using a method described in the preparation of compound 52. MS: m/z=700 [M+1].
Example 61
Compound 77
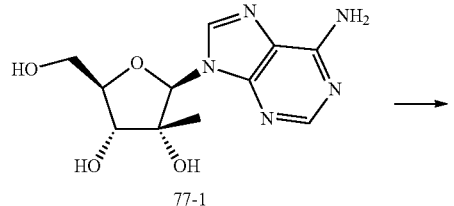
77-1
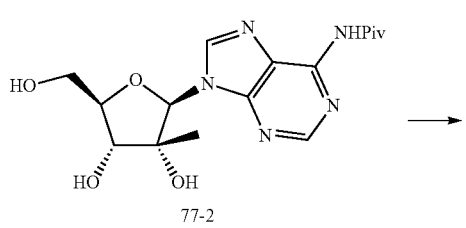
77-2
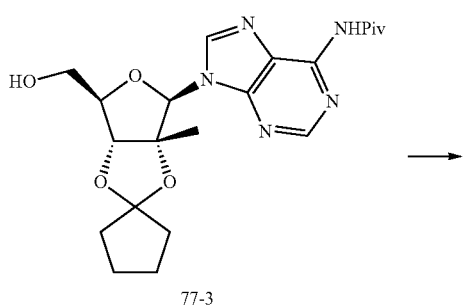
77-3
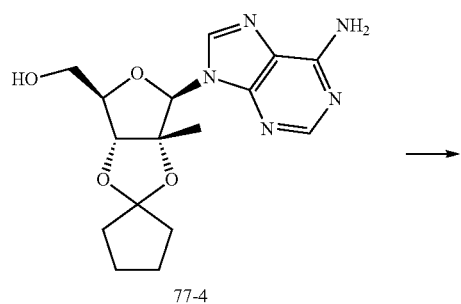
77-4
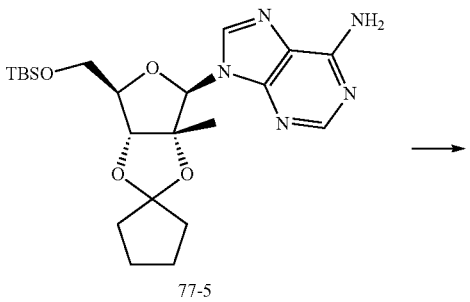
77-5
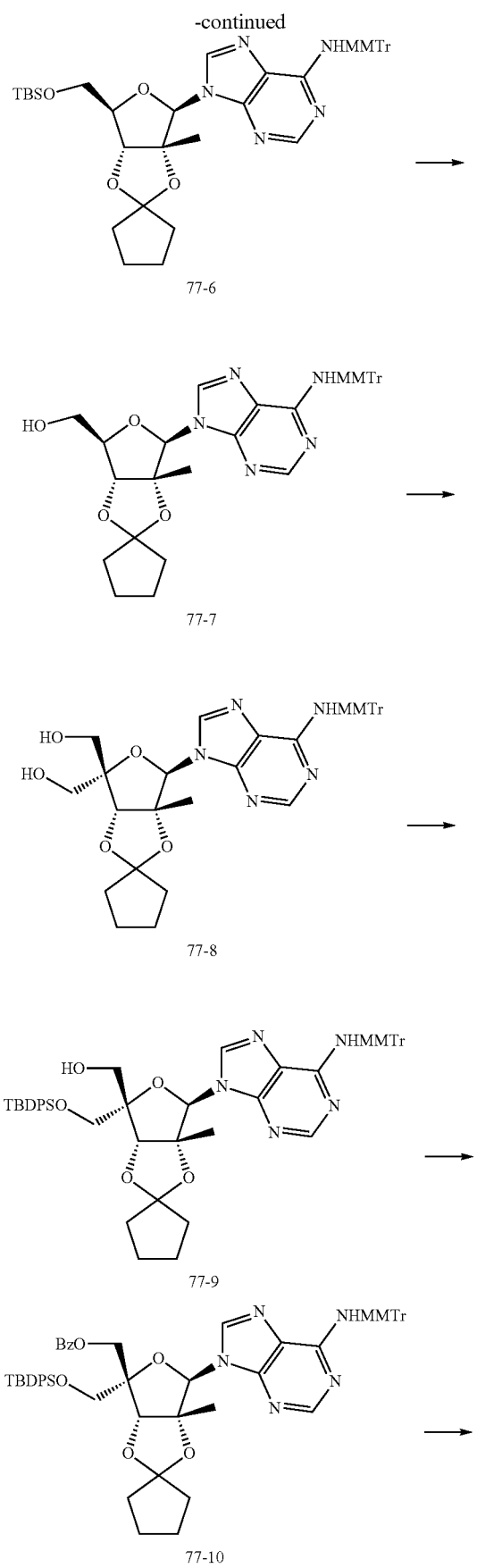

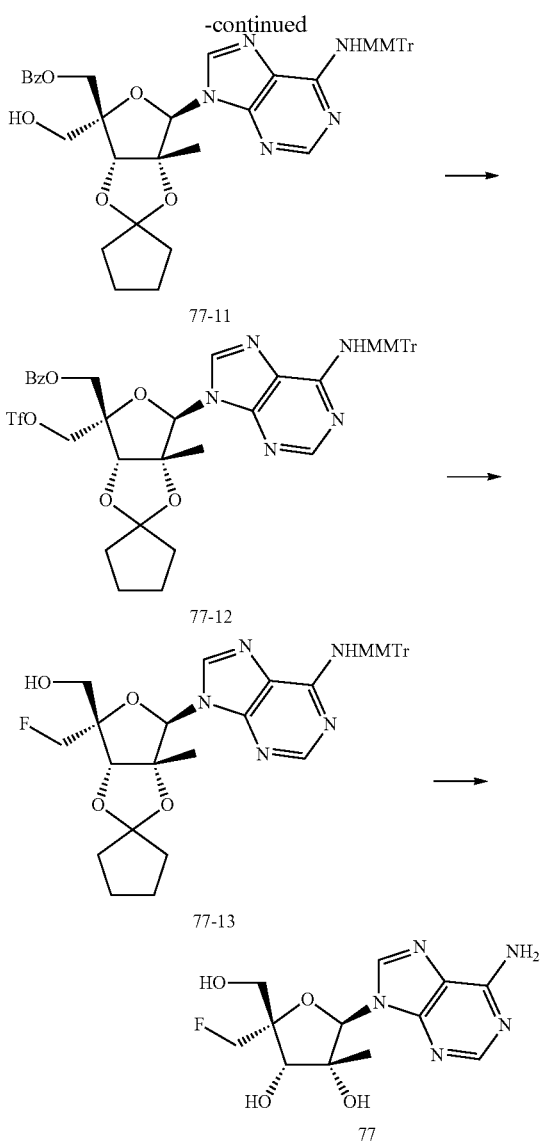

To a stirred solution of 77-1 (2.0 g, 7.12 mmol) in pyridine (20 mL) was added TMSCl (3.86 g, 35.58 mmol) at 0° C. under N₂. The mixture was slowly warmed to RT and stirred for 2 h. PivCl (1.71 g, 14.23 mmol) was added, and the mixture was stirred for 24 h. The solvent was evaporated at low pressure, and the residue was dissolved in EA (50 mL). The solution was washed with brine, dried over anhydrous Na₂SO₄, and concentrated at low pressure to give the crude product. The crude product was dissolved in MeOH (20 mL) and NH₄F (1.4 g, 37.86 mmol) was added. The mixture was refluxed for 2 h. The solvent was removed, and the residue was purified by column chromatography to give 77-2 (2.2 g, 85%).

To a solution of 77-2 (8.5 g, 23.28 mmol) and 1,1-dimethoxycyclopentane (2 mL) in a mixture of DMF (15 mL) and cyclopentanone (6 mL) was added TsOH (6.63 g, 34.93 mmol). The mixture was stirred at RT for 12 h. The reaction was quenched with triethylamine, and concentrated at low pressure. The residue was purified by column chromatography to give 77-3 (6.5 g, 65%).

To a stirred solution of 77-3 (6.0 g, 13.92 mmol) in anhydrous MeOH (60 mL) was added MeONa (2.25 g, 41.76 mmol) at RT. The mixture was stirred for 12 h and then neutralized with HOAc. The mixture was concentrated at low pressure, and the residue was purified by column chromatography to give 77-4 (4.4 g, 92%).

To a stirred solution of 77-4 (5.0 g, 14.40 mmol) in anhydrous pyridine (50 mL) was added TBSCl (3.24 g, 21.61 mmol) at RT under N₂, and the mixture was stirred overnight. The mixture was concentrated at low pressure, and the residue was purified by column chromatography to give 77-5 (5.44 g, 82%).

To a stirred solution of 77-5 (5.0 g, 10.84 mmol) in anhydrous DCM (50 mL) was added MMTrCl (5.01 g, 16.26 mmol), collidine (5 mL), and AgNO₃ (2.76 g, 16.26 mmol) at RT under N₂, and the mixture was stirred for 2 h. The precipitate was removed by filtration, and the filtrate was concentrated at low pressure. The residue was purified by column chromatography to give 77-6 (7.1 g, 89%).

To a stirred solution of 77-6 (7.1 g, 9.68 mmol) in anhydrous THF (70 mL) was added TBAF (5.05 g, 19.37 mmol) at RT under N₂, and the mixture was stirred for 4 h. The mixture was concentrated at low pressure, and the residue was purified by column chromatography to give 77-7 (5.1 g, 87%).

To a stirred solution of 77-7 (3.2 g, 5.17 mmol) and pyridine (2.04 g, 25.85 mmol) in anhydrous DCM (30 mL) was added DMP (3.28 g, 7.75 mmol) at RT under N₂. The mixture was stirred at RT for 3 h. The reaction was quenched with sat. Na₂S₂O₃ solution, and washed with sat. NaHCO₃ solution and brine. The organic phase was dried over anhydrous Na₂SO₄, and concentrated at low pressure. The residue was purified by column chromatography to give the aldehyde (1.8 g). To a stirred solution of the aldehyde (1.8 g, 2.92 mmol) in dioxane (29.2 mL) was added 37% HCHO (2.36 g, 29.17 mmol) and 1N LiOH (1.6 mL, 2.34 mmol) at RT. The mixture was stirred at RT for 1.5 h. The solution was neutralized with HOAc. The mixture was treated with EtOH (15 mL) and NaBH₄ (1.66 g, 43.8 mmol), and stirred at RT for 2 h. The mixture was quenched with water, and concentrated at low pressure. The residue was purified by column chromatography to give 77-8 (2.01 g, 61%).

To a stirred solution of 77-8 (200 mg, 0.31 mmol) in anhydrous DCM (2 mL) was added TBDPSCl (170 mg, 0.62 mmol) and imidazole (42 mg, 0.62 mmol) at RT under N₂. The mixture was stirred at RT for 2 h. The mixture was diluted with DCM (10 mL), and washed with brine. The organic phase was concentrated at low pressure, and the residue was purified by column chromatography to give 77-9 (175 mg, 64%).

To a stirred solution of 77-9 (270 mg, 0.304 mmol) in anhydrous DCM (2 mL) was added BzCl (63 mg, 0.61 mmol), DMAP (74 mg, 0.61 mmol) and TEA (61 mg, 0.61 mmol) at RT under N₂. The mixture was stirred at RT until the starting material disappeared. The =mixture was evaporated at low pressure, and the residue was purified by column chromatography to give 77-10 (250 mg, 83.3%).

Compound 77-10 (300 mg, 0.302 mmol) in THF (5 mL) was treated with a solution of TBAF (0.61 mL, 0.61 mmol, 1M in THF) and HOAc (0.2 mL) at RT. The mixture was stirred at RT for 12 h. The mixture was concentrated at low pressure, and the residue was purified by column chromatography to give 77-11 (170 mg, 75%).

To a stirred solution of 77-11 (400 mg, 0.531 mmol) in anhydrous DCM (4 mL) was added Tf₂O (299 mg, 1.06 mmol) and pyridine (84 mg, 1.06 mmol) at RT under N₂. The mixture was stirred at RT until the starting material disappeared. The mixture was concentrated at low pressure, and the residue was purified by column chromatography to give 77-12 (401 mg, 85%).

Compound 77-12 (500 mg, 0.564 mmol) was treated with TBAF in THF (1.0 M, 2 mL) at RT under $N_2$. The mixture was diluted with water (20 mL), and extracted with DCM. The solution was washed with brine, dried over anhydrous $Na_2SO_4$, and concentrated at low pressure. The residue was purified by column chromatography to give 77-13 (150 mg, 40.8%) as a white solid. ESI-MS: m/z 652.1 [M+H]$^+$.

Compound 77-13 (50 mg) was dissolved in 80% HCOOH (10 mL), and the mixture was heated at 45° C. for 24 h. The solvent was evaporated and co-evaporated with methanol/toluene to remove traces of acid. The residue was dissolved in 20% triethylamine in methanol, kept for 15 mins and then evaporated. Compound 77 (18 mg, 75%) was isolated by silica gel chromatography in a gradient of methanol in DCM from 0% to 15%. MS: m/z 312.5 [M−1].

Example 62

Compound 78

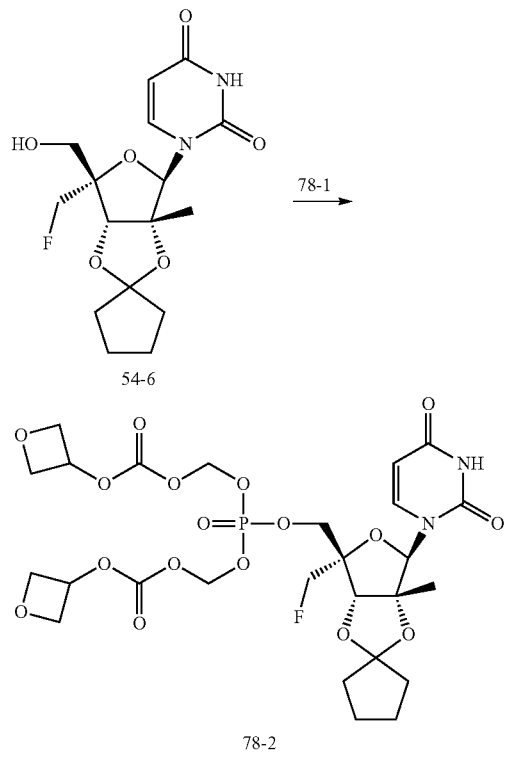

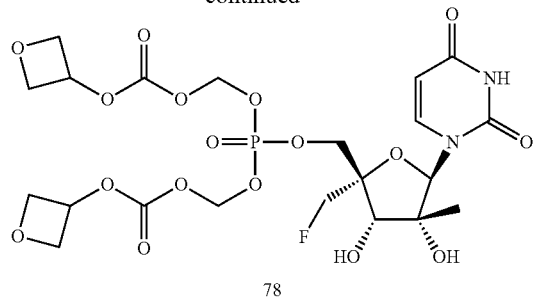

78

Compound 78a was prepared from commercially available 3-hydroxyoxetane (5.0 g). $^1$H-NMR (CDCl$_3$) δ 5.73 (s, 2H), 5.48-5.51 (m, 1H), 4.90 (d, 2H), 4.72 (d, 2H). Compound 78b (8.0 g) was prepared from 78a. $^1$H-NMR (CDCl$_3$) δ 5.95 (s, 2H), 5.48-5.51 (m, 1H), 4.90 (d, 2H), 4.72 (d, 2H). Benzylphosphate (silver salt) and 78b (8.0 g) were reacted to yield purified 78c (1.92 g). $^1$H-NMR (CD$_3$CN): δ 7.39-7.42 (m, 5H), 5.62 (d, 4H), 5.39-5.42 (m, 2H), 5.15 (d, 2H), 4.80-4.83 (m, 4H), 4.56-4.60 (m, 4H). $^{31}$P-NMR (CD$_3$CN): δ −4.55 ppm. Compound 78c was deprotected to give 78-1 (triethylammonium salt), which was used immediately without further purification. Compound 54-6 (356 mg; 1.0 mmol) and 78-1 were reacted to give purified 78-2 (230 mg). Compound 78-2 (230 mg) was deprotected to yield purified compound 78 (12.5 mg, 0.02 mmol). The aforementioned reactions were conducted using a method described in the preparation of compound 54. $^1$H-NMR (CDCl$_3$): δ 8.25 (s, 1H), 7.54 (d, 1H), 5.90 (s, 1H), 5.81 (d, 1H), 5.66-5.75 (m, 4H), 5.44-5.49 (m, 2H), 4.88-4.92 (m, 5H), 4.61-4.78 (m, 5H), 4.37-4.46 (m, 2H), 4.21 (s, 1H), 3.49 (s, 1H), 1.25 (s, 3H). $^{31}$P-NMR (CDCl$_3$): δ −4.28 ppm.

Example 63

Compound 83

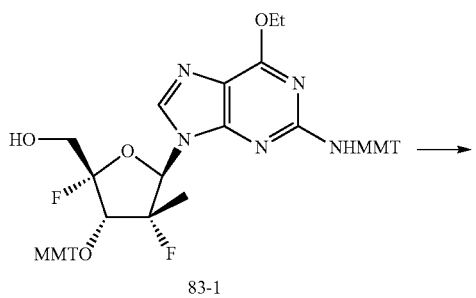

83-1

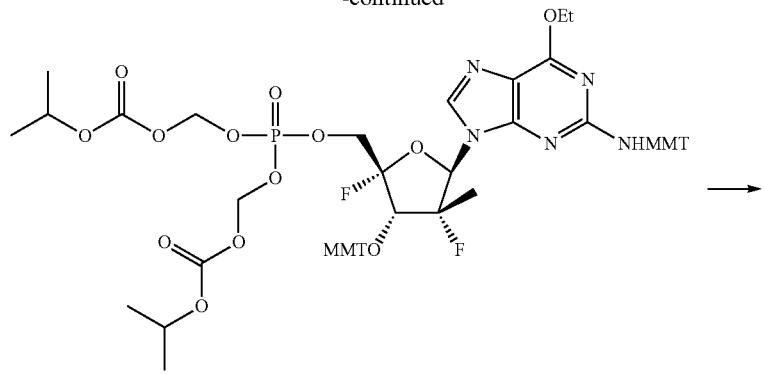

83-2

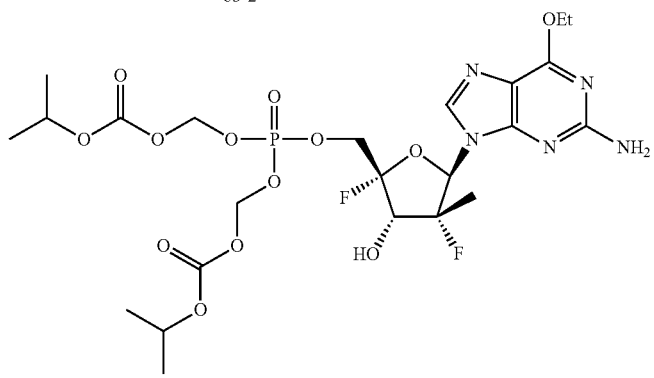

83

Compound 83-2 (70 mg, 58%) was prepared in the same manner from compound 83-1 (90 mg; 0.1 mmol) and triethylammonium bis(isopropyloxycarbonyloxymethyl) phosphate (0.2 mmol) with DIPEA (87 µL), BopCl (44 mg), and 3-nitro-1,2,4-triazole (29 mg) in THF (2 mL) as described in the preparation of compound 44. Purification was done with hexanes/EtOAc with a 20-80% gradient.

Compound 83 (25 mg, 64%) was prepared from 83-2 (70 mg) in acetonitrile (0.6 mL) and 4 N HCl/dioxane (50 µL) as described in the preparation of compound 55. MS: m/z=658 [M+1].

Example 64

Compound 84

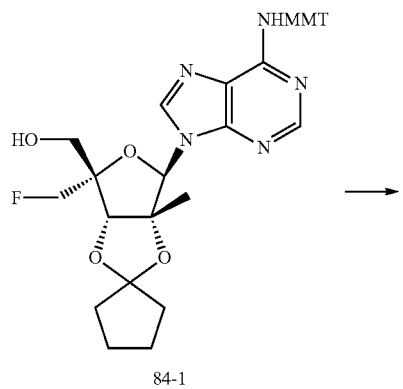

84-1

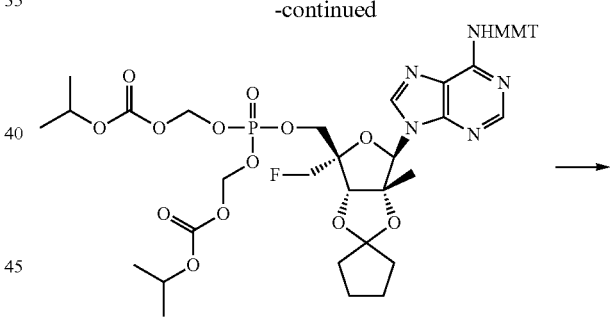

84-2

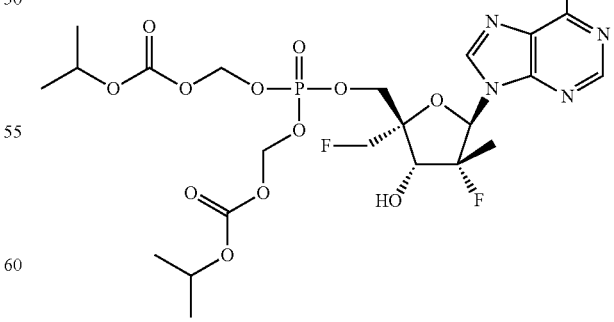

84

Compound 84-2 (69 mg, 90%) was prepared from 84-1 (52 mg; 0.08 mmol) and triethylammonium bis(isopropyloxycarbonyloxymethyl)phosphate (0.16 mmol) with DIPEA (74 μL), BopCl (51 mg), and 3-nitro-1,2,4-triazole (23 mg) in THF (1 mL) as described in the preparation of compound 44. Purification was done with hexanes/EtOAc with a 20-100% gradient.

Compound 84 (27 mg, 62%) was prepared from 84-2 (65 mg) as described in the preparation of compound 44. MS: m/z=626 [M+1].

Example 65

Compound 85

A mixture of 76-2 and acetic anhydride in pyridine was stirred overnight at RT, then concentrated and purified on silica gel (10 g column) with CH$_2$Cl$_2$/i-PrOH (4-10% gradient) to yield 85-1 (12 mg, 69%).

Compound 85 (10 mg, 92%) was prepared from 85-1 (12 mg) in EtOH (0.5 mL) with 10% Pd/C (1 mg), 4 N HCl/dioxane (7 μL), and under the H$_2$ atmosphere in the same manner compound 52. MS: m/z=742 [M+1].

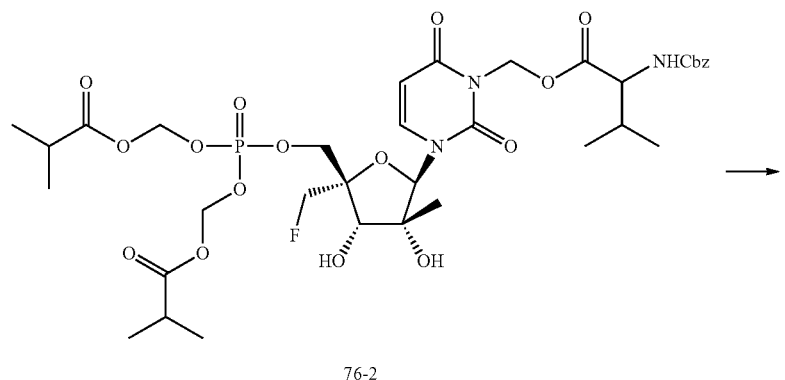

76-2

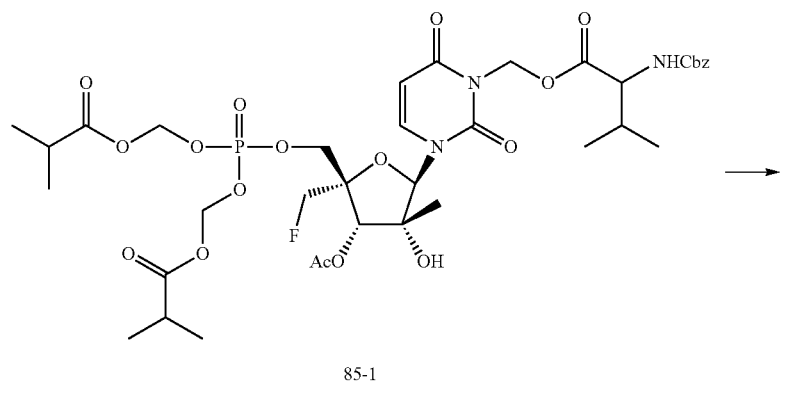

85-1

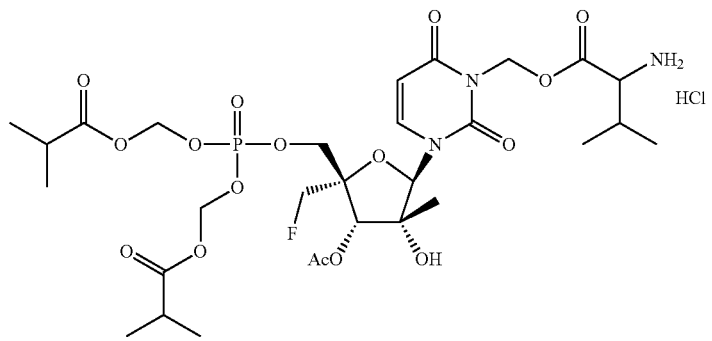

85

Example 66

Compounds 86 and 87

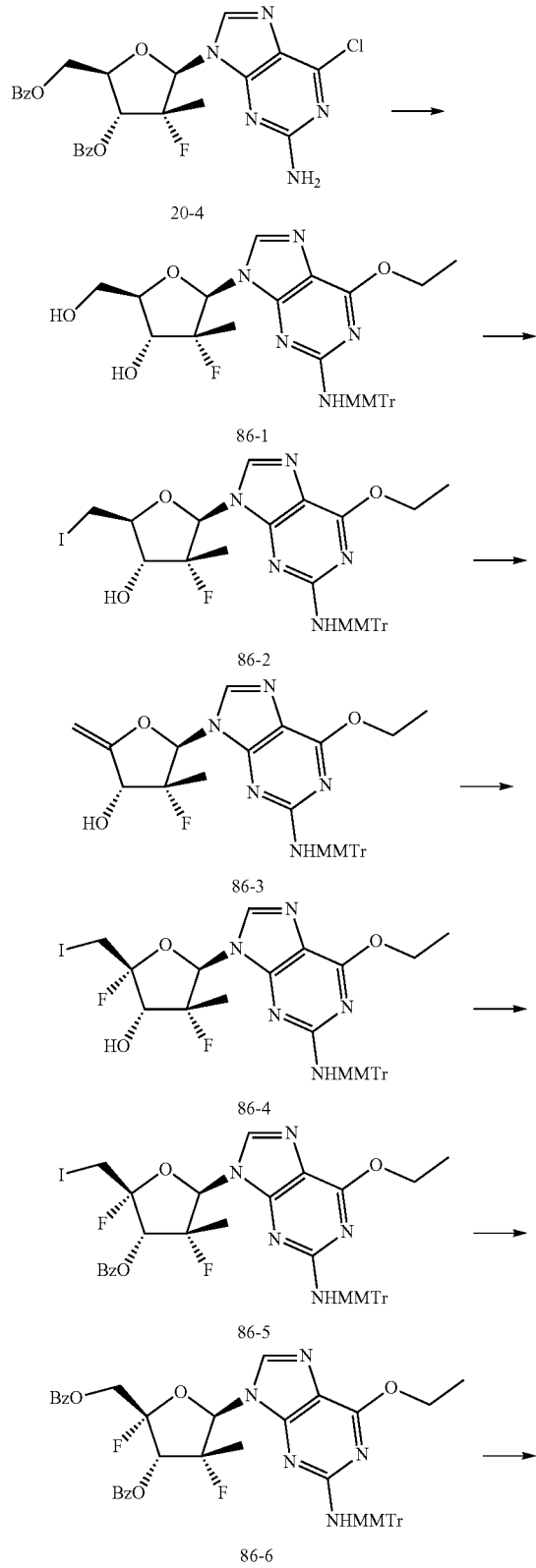

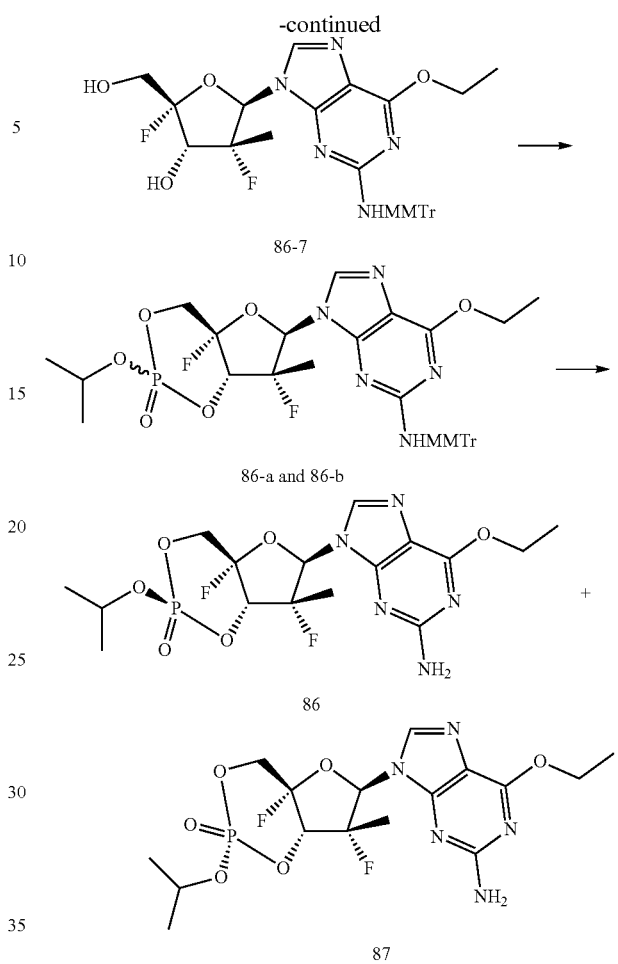

A freshly prepared EtONa in dry EtOH (2N, 150 mL) was added to a solution of 20-4 (13.67 g, 17.15 mmol) in EtOH (50 mL) at 0° C. The mixture was stirred at RT for 1 h, and then concentrated at low pressure. The residue was purified by silica gel column (5% MeOH in DCM) to give 86-1 (10 g, 98%) as a yellow solid.

To a solution of $PPh_3$ (2.73 g, 10.4 mol) in anhydrous pyridine (60 mL) was added $I_2$ (2.48 g, 9.76 mmol) at RT, and the reaction mixture was stirred RT for 30 mins. A solution of 86-1 (3.9 g, 6.51 mmol) in pyridine (10 mL) was added. The mixture was stirred at RT overnight. The reaction was quenched with sat. $Na_2S_2O_3$ solution and $NaHCO_3$ aq., and then extracted with EA (100 mL). The organic layer was dried over anhydrous $Na_2SO_4$, and evaporated at low pressure. The residue was purified by silica gel column (2% MeOH in DCM) to give 86-2 (3.0 g, 75%) as a yellowed solid.

To a solution of 86-2 in dry THF (300 mL) was added DBU (14.0 g, 91.8 mmol), and the mixture was heated to reflux for 3 h. The mixture was concentrated at low pressure. The residue was dissolved in EA (100 mL), and washed with brine. The organic layer was dried over anhydrous $Na_2SO_4$, and evaporated at low pressure. The residue was purified by silica gel column (20% EA in PE) to give 86-3 (0.6 g, 37.5%) as a white solid.

To an ice-cooled solution of 86-3 (2.0 g, 3.44 mmol) in anhydrous MeCN (20 mL) was added NIS (0.975 g, 4.3 mmol) and TEA.3HF (0.82 g, 5.16 mmol) at 0° C. The mixture was stirred at RT for 2 h. The reaction was quenched with sat. Na$_2$SO$_3$ and NaHCO$_3$ aqueous solution, and then concentrated at low pressure. The residue was dissolved in EA (50 mL), washed with brine, dried over anhydrous Na$_2$SO$_4$, and evaporated at low pressure. The residue was purified by silica gel column (20% EA in PE) to give 86-4 (1.5 g, 60%) as a white solid.

To a solution of 86-4 (1 g, 1.37 mmol) in dry pyridine (100 mL) was added BzCl (0.23 g, 1.65 mmol) at 0° C. The reaction was stirred for 30 mins and checked by LCMS. The mixture was concentrated at low pressure, and the residue was dissolved in EA (50 mL). The solution was washed with brine. The organic layer was dried over MgSO$_4$, and evaporated at low pressure. The residue was purified by silica gel column chromatography (10% EA in PE) to give 86-5 (0.9 g, 78%) as a white solid.

To a solution of 86-5 (2 g, 2.4 mmol) in dry DMF (40 mL) was added NaOBz (3.46 g, 24 mmol) and 15-crown-5 (4.5 mL). The mixture was stirred at 95° C. for 72 h. The mixture was then diluted with EA (100 mL), and washed with water and brine. The organic phase was dried over MgSO$_4$, and concentrated at low pressure. The residue was purified by silica gel column (15% EA in PE) to give 86-6 (1.5 g, 75%) as a white solid.

A mixture of 86-a and 86-b (61.5 mg, 0.085 mmol) was dissolved in anhydrous CH$_3$CN (0.5 mL), and 4N HCl in dioxane (64 μL) was added at 0 to 5° C. (ice/water bath). The mixture was stirred at RT for 40 mins, and anhydrous EtOH (200 μL) was added. The solvents were evaporated at RT and co-evaporated with toluene 3 times. The residue was dissolved in 50% CH$_3$CN/H$_2$O, was purified on a reverse-phase HPLC (C18) using acetonitrile and water, followed by lyophilization to give compound 86 (1.8 mg) and compound 87 (14.5 mg).

Compound 86: $^1$H NMR (CD$_3$OD-d$_4$, 400 MHz) δ 8.0 (s, 1H), 6.69 (d, J=16.0 Hz, 1H), 5.9-5.6 (br s, 1H), 4.94-4.85 (m, 1H), 4.68-4.52 (m, 3H), 1.49-1.3 (m, 12H); $^{19}$F NMR (CD$_3$OD-d$_4$) δ −122.8 (s), −160.06 (s); $^{31}$P NMR (CD$_3$OD-d$_4$) δ −7.97 (s). ESI-LCMS: m/z=450.1 [M+H]$^+$; Compound 87: $^1$H NMR (CD$_3$OD-d$_4$, 400 MHz) δ 7.96 (s, 1H), 6.68 (s, 1H), 6.69 (d, J=16.8 Hz, 1H), 6.28-6.1 (br s, 1H), 4.81-4.5 (m, 4H), 1.45-1.39 (m, 12H); $^{31}$P NMR (CD$_3$OD-d$_4$) δ −5.84 (s). ESI-LCMS: m/z=450. [M+H]$^+$.

Example 67

Compounds 88 and 89

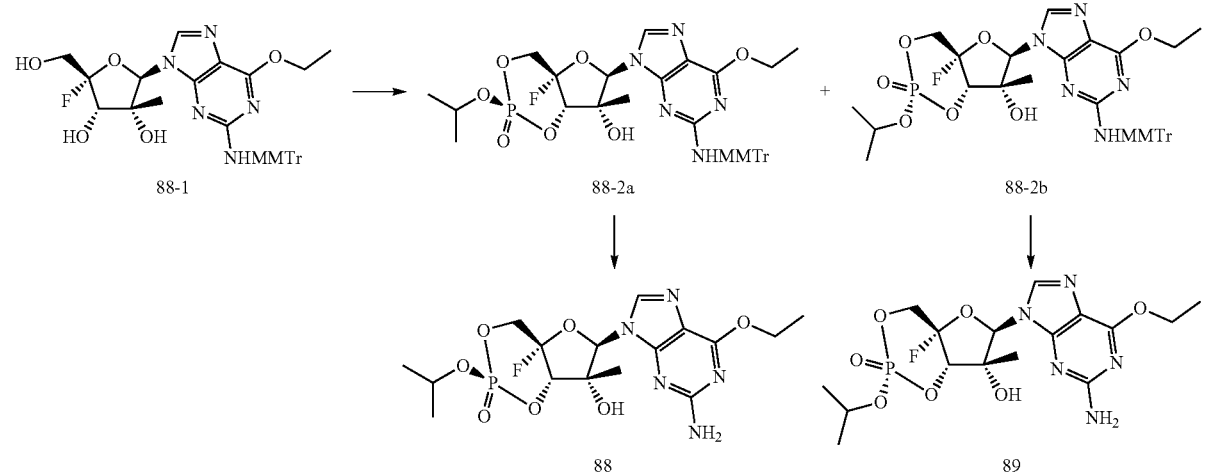

Compound 86-6 (1.35 g, 1.64 mmol) in NH$_3$/MeOH (150 mL) was stirred at RT for 18 h. The mixture was concentrated at low pressure, and the residue was purified by silica gel column (5% MeOH in DCM) to give 86-7 (0.9 g, 90%) as a white solid. ESI-MS: m/z 618.3 [M+H]$^+$.

To a solution of 86-7 (99 mg, 0.16 mmol) in DCM (1.0 mL), triethylamine (92.7 μL, 0.64 mmol) was added at RT. The mixture was cooled to 0 to 5° C. (ice/water bath), and freshly prepared and distilled isopropyl phosphorodichloridate (36.6 μL, 0.2 mmol, prepared according to a procedure, Reddy et al., J. Org. Chem. (2011) 76 (10):3782-3790) was added to the mixture. The mixture was stirred 0 to 5° C. (ice/water bath) for 15 mins, followed by addition of N-methylimidazole (26.3 μL, 0.32 mmol). The mixture was then stirred for 1 h at 0 to 5° C. TLC showed absence of 86-7. EA (100 mL) was added, followed by water. The organic layer was washed H$_2$O, saturated aqueous NH$_4$Cl solution and brine. The organic layer was separated, dried over anhydrous MgSO$_4$ and filtered. The filtrate was concentrated in vacuum to give a residue, which was purified on silica gel with 0 to 10% iPrOH/DCM to give a mixture of 86-a and 86-b (61.5 mg).

To a solution of 88-1 (150 mg, 0.24 mmol) in DCM (2.0 mL), triethylamine (141 μL, 2.0 mmol) was added at RT. The mixture was cooled to 0 to 5° C. (ice/water bath), and freshly prepared and distilled isopropyl phosphorodichloridate (45 μL, 0.26 mmol, prepared according to a procedure, Reddy et al., J. Org. Chem. (2011) 76 (10):3782-3790) was added. The mixture was stirred at 0 to 5° C. (ice/water bath) for 15 mins, followed by N-methylimidazole (40 μL, 0.49 mmol). The mixture was stirred for 1 h at 0 to 5° C. TLC showed the absence of starting material 88-1. EA (100 mL) was added, followed by water. The organic layer was washed with H$_2$O, sat. aq. NH$_4$Cl solution and brine. The organic layer was separated, dried over anhydrous MgSO$_4$ and filtered. The filtrate was concentrated in vacuum to give a residue, which was purified on silica gel with 0 to 10% iPrOH/DCM to give 88-2a (16.9 mg, faster eluting isomer) and 88-2b (72.7 mg, slower eluting isomer).

Compounds 88-2a and 88-2b were deprotected using a procedure described herein. Compound 88 (7.3 mg, single isomers from 88-2a (16.5 mg, 0.0235 mmol)) and compound 89 (29.0 mg. single isomers from 88-2b (72.7 mg, 0.1 mmol)) were obtained.

Compound 88: $^1$H NMR (CD$_3$OD-d$_4$, 400 MHz) δ 7.94 (s, 1H), 6.32 (s, 1H), 6.00-5.9 (br s, 1H), 4.9-4.487 (m, 1H), 4.83-4.77 (m, 1H), 4.65-4.50 (m, 3H), 1.45-1.39 (s, 9H), 1.2 (s, 3H); $^{19}$F NMR (CD$_3$OD-d$_4$) δ−120.3 (s); $^{31}$P NMR (CD$_3$OD-d$_4$) δ−5.19 (s); ESI-LCMS: m/z=448.05 [M+H]$^+$.

Compound 89: $^1$H NMR (CD$_3$OD-d$_4$, 400 MHz) δ 7.98 (s, 1H), 6.34 (s, 1H), 5.78-5.64 (br s, 1H), 4.95-4.48 (m, 2H), 4.62-4.52 (m, 3H), 1.48-1.42 (s, 9H), 1.1 (s, 3H); $^{19}$F NMR (CD$_3$OD-d$_4$) δ−121.3 (s); $^{31}$P NMR (CD$_3$OD-d$_4$) δ−7.38 (s); ESI-LCMS: m/z=448.05 [M+H]$^+$.

Example 68

Compound 90

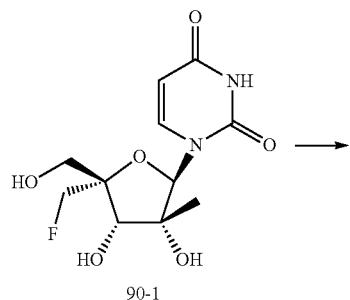

90-1

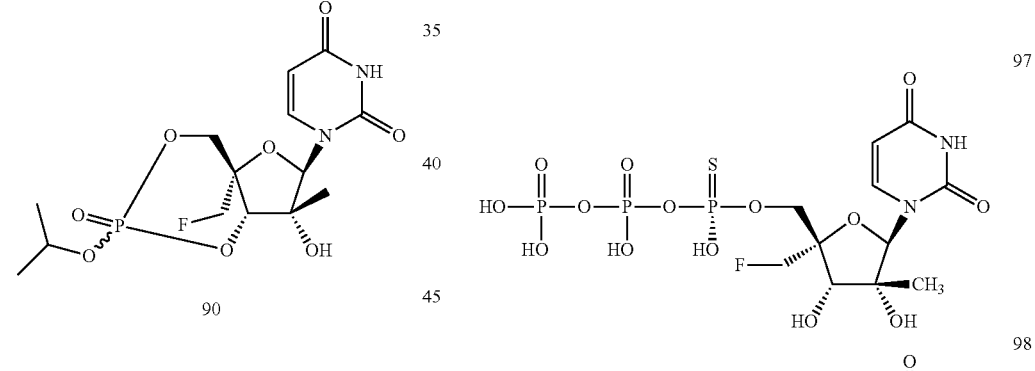

90

To a stirred solution of 90-1 (532 mg, 1.84 mmol) in anhydrous CH$_3$CN (8.0 mL) was added N-methylimidazole (2.0 mL, 24.36 mmol) at 0 to 5° C. (ice/water bath) followed by a solution of freshly prepared and distilled isopropyl phosphorodichloridate (0.5 mL, 2.84 mmol). The solution was stirred at RT for 15 h. The mixture was diluted with EA, followed by water (15 mL). The solution was washed with H$_2$O, 50% aqueous citric acid solution and brine. The organic layer was separated, dried over anhydrous MgSO$_4$ and filtered. The filtrate was concentrated in vacuum to give a residue, which was purified on silica gel with 0 to 8% MeOH/DCM to give the crude product (72 mg). The crude product was re-purified purified on a reverse-phase HPLC (C18) using acetonitrile and water, followed by lyophilization to give compound 90 (43.6 mg). MS: m/z=395.05 [M+H]$^+$, 393.0 [M−H]$^−$, 787.05.0 [2M−H]$^−$.

Example 69

Compound 96

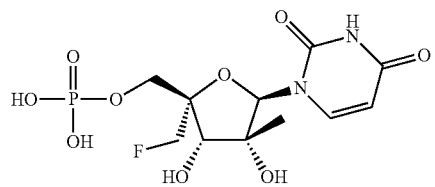 [SMILES: C[C@@]1(O)[C@H](O)[C@@](CF)(COP(=O)(O)O)O[C@H]1n1ccc(=O)[nH]c1=O]

Dry 51 (0.05 mmol) was dissolved in the mixture of PO(OMe)$_3$ (0.7 mL) and pyridine (0.3 mL). The mixture was evaporated in vacuum for 15 mins at bath temperature 42° C., and then cooled to RT. N-Methylimidazole (0.009 mL, 0.11 mmol) was added followed by POCl$_3$ (9 ul, 0.11 mmol), and the mixture was kept at RT for 20-40 mins. The reaction was controlled by LCMS and monitored by the appearance of 96. Isolation was performed by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer to yield compound 96. MS: m/z 369.0 [M−1].

Example 70

Compounds 97 and 98

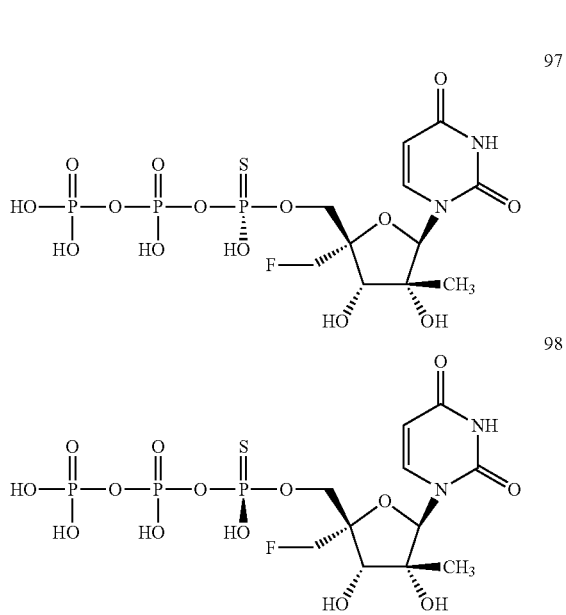

Dry 51 (0.05 mmol) was dissolved in the mixture of PO(OMe)$_3$ (0.7 mL) and pyridine (0.3 mL). The mixture was evaporated in vacuum for 15 mins at bath temperature 42° C., than cooled to RT. N-Methylimidazole (0.009 mL, 0.11 mmol) was added followed by PSCl$_3$ (9 uL, 0.11 mmol), and the mixture was kept at RT for 20-40 mins. The reaction was controlled by LCMS and monitored by the appearance of the nucleoside 5'-thiophosphate. After completion of the reaction, tetrabutylammonium salt of pyrophosphate (150 mg)

was added, followed by DMF (0.5 mL) to get a homogeneous solution. After 1.5 hours at ambient temperature, the reaction was quenched with water (10 mL). The 5′-triphosphate as mixture of diastereomers was isolated by IE chromatography on AKTA Explorer using column HiLoad 16/10 with Q Sepharose High Performance. Separation was done in linear gradient of NaCl from 0 to 1N in 50 mM TRIS-buffer (pH 7.5). Fractions containing thiotriphosphate were combined, concentrated and desalted by RP HPLC on Synergy 4 micron Hydro-RP column (Phenominex). Linear gradient of methanol from 0 to 30% in 50 mM triethylammonium buffer was used for elution over 20 mins, flow 10 mL/mins. Compounds 97 and 98 were collected. Analytical RP HPLC was done in 50 mM triethylammonium acetate buffer, pH 7.5 containing linear gradient of acetonitrile from 0% to 25% in 7 mins on Synergy 4 micron Hydro-RP column (Phenominex). Compound 97: RT 5.50 mins. $^{31}$P NMR: δ +42.45 (1P, d), −6.80 (1P, d), −23.36 (1P, q). MS: m/z 544.9 [M−1]. Compound 98: RT 6.01 mins. $^{31}$P NMR: δ +41.80 (1P, d), −6.57 (1P, d), −23.45 (1P, q). MS: m/z 544.9 [M−1].

Example 71

Compound 99

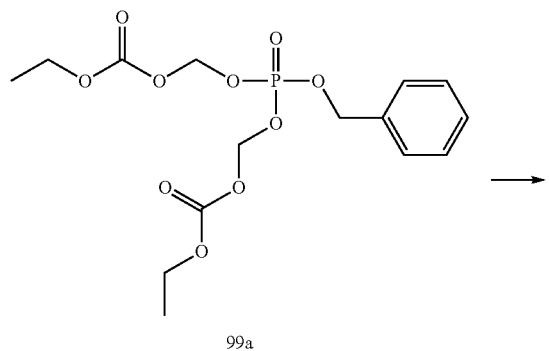

99a

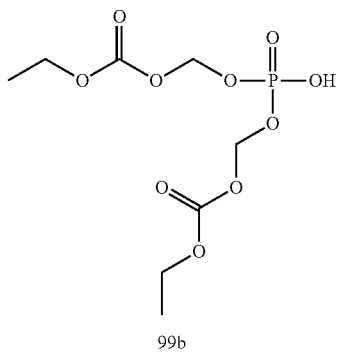

99b

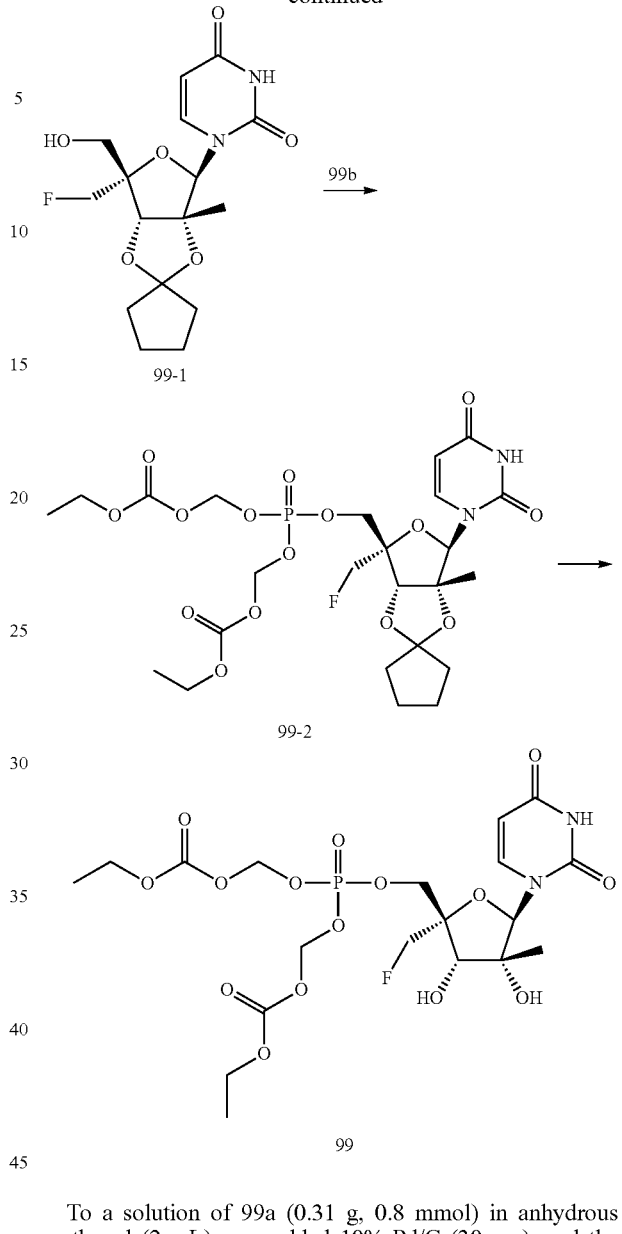

To a solution of 99a (0.31 g, 0.8 mmol) in anhydrous methanol (2 mL), was added 10% Pd/C (30 mg), and the mixture was stirred under H$_2$ atmosphere for 1 h. After completion, the mixture was filtered, and the catalyst cake was washed with methanol. The washing and filtrate were combined. The solvent was removed under vacuum to give 99b as a semi-solid (252 mg), which was used without further purification. $^1$H NMR (CDCl$_3$, 400 MHz) δ5.57 (d, J=13.6 Hz, 4H), 4.23 (q, J=7.2 Hz, 4H), 1.30 (t, J=7.2 Hz, 6H), $^{31}$P NMR (CDCl$_3$) δ−4.64 (s).

To a solution of triethylammonium bis (EOC) phosphate (0.7 mmol, prepared from 213 mg of 99b and 0.2 mL of TEA) in THF (3 mL) was added 99-1 (160 mg, 0.45 mmol) followed by diisopropylethylamine (0.33 mL, 1.8 mmol), BOP-Cl (229 mg, 0.9 mmol), and 3-nitro-1,2,4-triazole (103 mg, 0.9 mmol). The mixture was stirred at RT for 90 mins. The mixture was diluted with EtOAc, and washed with water and brine. The organic layer was separated, dried over anhydrous Na$_2$SO$_4$ and filtered. The filtrate was concentrated in vacuum to a white solid, which was purified on silica gel column (CH$_3$OH:DCM; 9.5:0.5) to give 99-2 (189 mg, 66%).

To a solution of 99-2 (180 mg, 0.28 mmol) in 80% HCOOH (7 mL), was heated for 6 h at 45° C. The solvents were evaporated, and then co-evaporated with toluene 3 times. The residue was purified on silica gel column using 0 to 10% MeOH in DCM to obtain compound 99 (97.3 mg) as a white foam after lypholization. MS: m/z=575.1 [M+H]$^+$.

Example 72

Compound 100

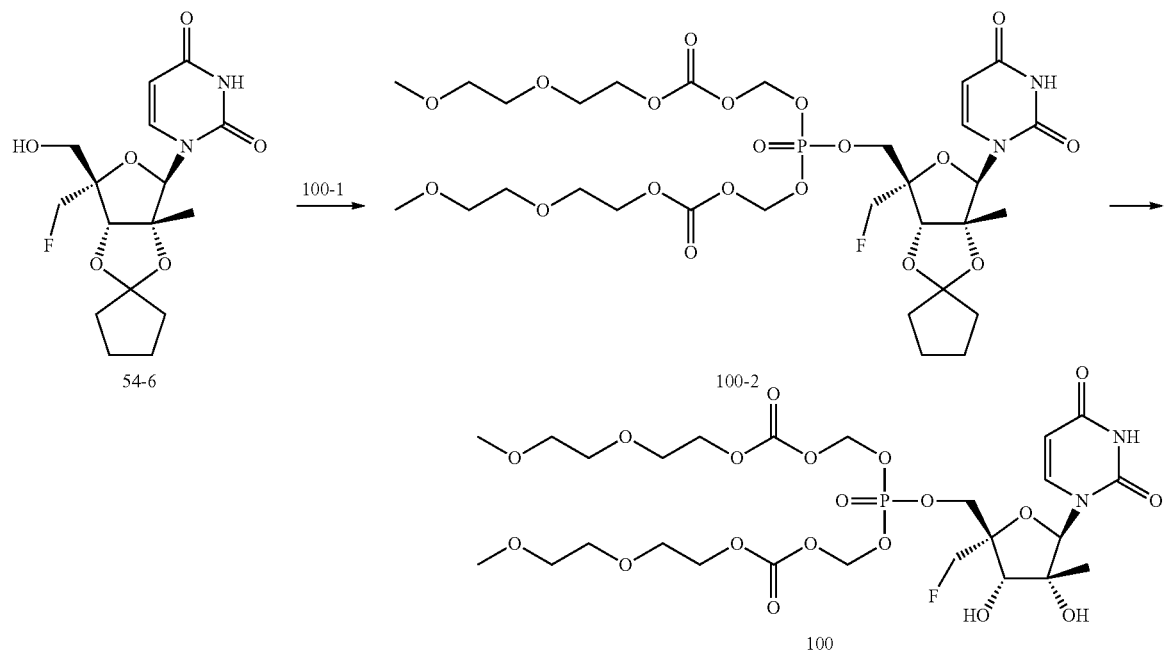

Compound 100a was prepared from commercially available 2-(2-methoxyethoxy)-ethanol (11.56 mL). Compound 100a (13.5 g) was obtained as a clear colorless oil. $^1$H-NMR (CDCl$_3$) δ 5.73 (s, 2H), 4.38-4.40 (m, 2H), 3.74-3.77 (m, 2H), 3.64-3.67 (m, 2H), 3.54-3.57 (m, 2H), 3.39 (s, 3H). Compound 100b (9.6 g) was prepared from 100a, and was obtained as a clear, slightly colored oil. $^1$H-NMR (CDCl$_3$) δ 5.96 (s, 2H), 4.38-4.40 (m, 2H), 3.74-3.77 (m, 2H), 3.64-3.67 (m, 2H), 3.54-3.57 (m, 2H), 3.39 (s, 3H). Benzylphosphate (silver salt) and 100b (2.4 g) were reacted and yielded purified 100c (1.02 g). $^1$H-NMR (CD$_3$CN): δ 7.39-7.42 (m, 5H), 5.60 (d, 4H), 5.11 (d, 2H), 4.27-4.29 (m, 4H), 3.65-3.67 (m, 4H), 3.56 (t, 4H), 3.46 (t, 4H), 3.30 (s, 6H). $^{31}$P-NMR (CD$_3$CN): δ −4.55 ppm. Compound 100c (620 mg; 1.15 mmol) was deprotected to give 100-1 (triethylammonium salt), which was used immediately without further purification. Compound 54-6 (356 mg; 1.0 mmol) and 100-1 were reacted to give purified 100-2 (250 mg). Compound 100-2 (250 mg) was deprotected to yield purified compound 100 (110 mg, 0.14 mmol). The aforementioned reactions were conducted using a method described in the preparation of compound 54. $^1$H-NMR (CDCl$_3$): δ 8.62 (s, 1H), 7.54 (d, 1H), 5.96 (s, 1H), 5.64-5.79 (m, 5H), 4.76 (dd, 2H), 4.37-4.46 (m, 6H), 4.25 (d, 2H), 3.86 (s, 1H), 3.75 (t, 4H), 3.70 (t, 4H), 3.58 (t, 4H), 3.38 (s, 6H), 1.65 (s, 6H), 1.25 (s, 3H). $^{31}$P-NMR (CDCl$_3$): δ −3.90 ppm.

Example 73

Compound 104

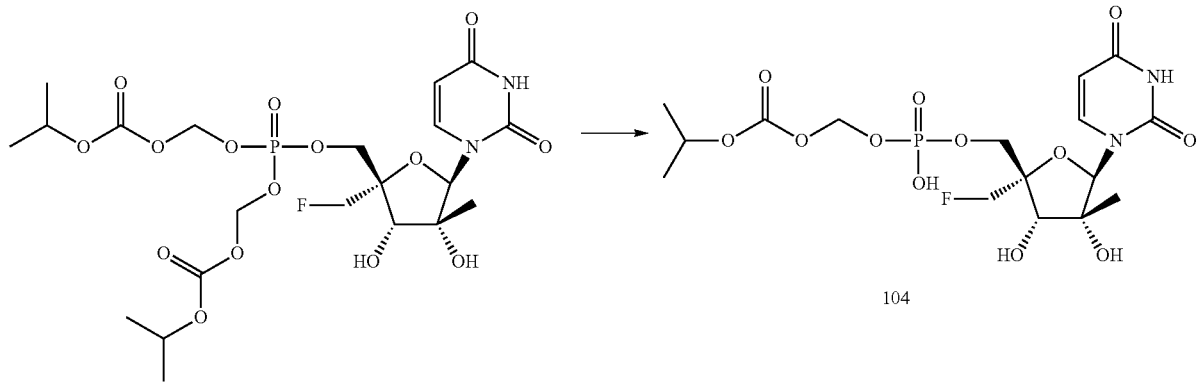

Compound 44 (0.010 g, 0.016 mmol) was added to normal saline solution (3 mL, pH 7.3), and stored in a heat block at 37° C. for 6 days. The mixture was purified by preparative HPLC using a Synergi 4u Hydro-RP column (Phenomenex, 00G-4375-U0-AX), with H₂O (0.1% formic acid) and ACN (0.1% formic acid) solvents (0-65% gradient in 20 minutes). The compound eluted at 13.0 mins. Pure fractions were pooled and lyophilized to yield compound 104 (0.005 g, 63%). MS: m/z=487 [M+1].

Example 74

Compound 102

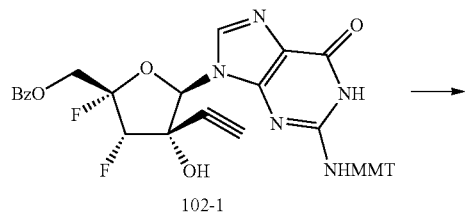
102-1

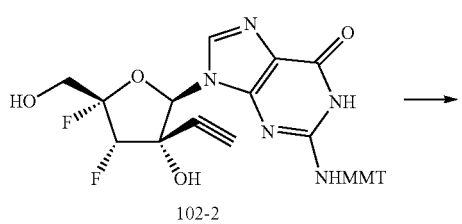
102-2

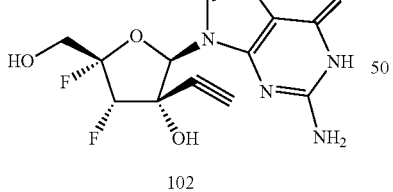
102

A mixture of 102-1 (45 mg, 0.06 mmol) and butylamine (0.4 mL) was kept overnight at RT and then evaporated. The crude residue was purified on silica gel (10 g column) with CH₂Cl₂/MeOH (4-12% gradient) to yield 102-2 as a colorless glass (20 mg, 56%).

To a solution of 102-2 (20 mg, 0.03 mmol) in ACN (0.5 mL) was added 4N HCl in dioxane (35 μL). The mixture was stirred at RT for 4 h and then quenched with MeOH. The residue was treated with ACN to yield compound 102 as an off-white solid (9 mg, 80%). MS m/z=328 [M+1].

Example 75

Compound 105

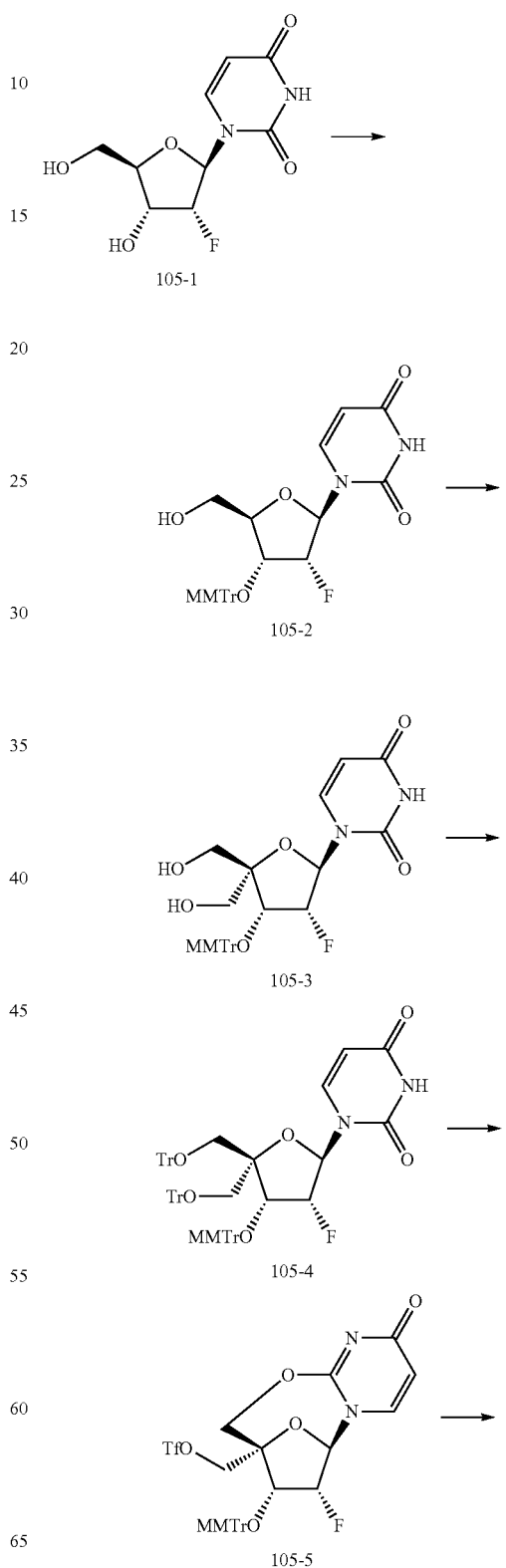

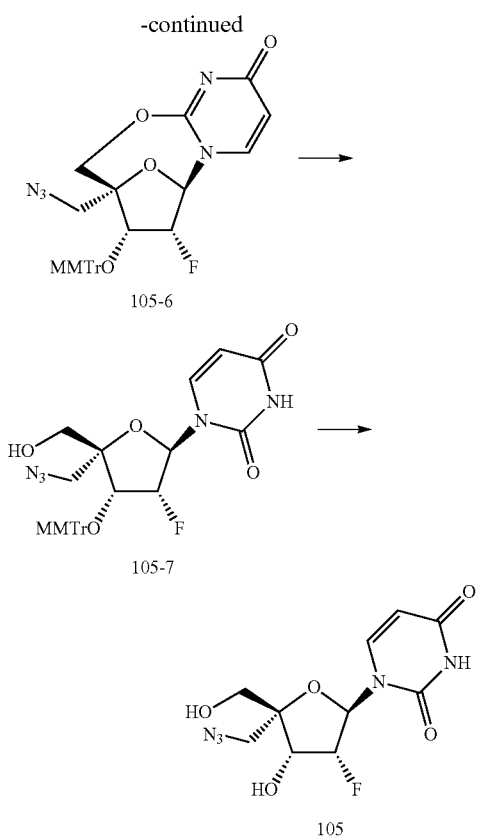

To a solution of 105-1 (50 g, 203 mmol) in anhydrous pyridine (200 mL) was added TBDPS-Cl (83.7 g, 304 mmol). The reaction was allowed to proceed overnight at RT. The solution was concentrated under low pressure to give a residue, which was partitioned between ethyl acetate and water. The organic layer was separated, washed with brine, dried over magnesium sulfate and concentrated under reduced pressure to give 5'-OTBDPS ether as a white foam (94 g).

To a solution of the 5'-OTBDPS ether (94.0 g, 194.2 mmol) in anhydrous DCM (300 mL) were added silver nitrate (66.03 g, 388.4 mmol) and collidine (235 mL, 1.94 mol). The mixture was stirred at RT. After 15 mins, the mixture was cooled to 0° C., and monomethoxytrityl chloride (239.3 g, 776.8 mmol) was added as a single portion. After being stirred overnight at RT., the mixture was filtered through Celite and the filtrate was diluted with TBME. The solution was washed successively with 1M citric acid, diluted brine and 5% sodium bicarbonate. The organic solution was dried over sodium sulfate and concentrated under vacuum to give the fully protected intermediate as a yellow foam.

This fully protected intermediate was dissolved in toluene (100 mL) and the solution was concentrated under reduced pressure. The residue was dissolved in anhydrous THF (250 mL) and treated with TBAF (60 g, 233 mmol). The mixture was stirred for 2 h at RT., and the solvent was removed under reduced pressure. The residue was taken into ethyl acetate and the solution was washed first with saturated sodium bicarbonate and then with brine. After being dried over magnesium sulfate, the solvent was removed in vacuum and the residue was purified by column chromatography (50% EA in PE) to give 105-2 (91 g, 86.4%) as a white foam.

To a solution of 105-2 (13.5 g, 26 mmol) in DCM (100 mL) was added pyridine (6.17 mL, 78 mmol). The solution was cooled to 0° C., and Dess-Martin periodinane (33.8 g, 78 mmol) was added as a single portion. The reaction mixture was stirred for 4 h at RT., and quenched by the addition of $Na_2S_2O_3$ solution (4%) and sodium bicarbonate aqueous solution (4%) (the solution was adjusted to pH 6, ~150 mL). The mixture was stirred for 15 mins. The organic layer was separated, washed with diluted brine and concentrated under reduced pressure. The residue was dissolved in dioxane (100 mL) and the solution was treated with 37% aqueous formaldehyde (21.2 g, 10 eq.) and 2N aqueous sodium hydroxide (10 eq.). The reaction mixture was stirred at RT., overnight. After stirring for 0.5 h at RT., the excess of aqueous sodium hydroxide was removed with saturated $NH_4Cl$ (~150 mL). The mixture was concentrated under reduced pressure, and the residue was partitioned between ethyl acetate and 5% sodium bicarbonate. The organic phase was separated, washed with brine, dried over magnesium sulfate and concentrated. The residue was purified by column chromatography (2% MeOH in DCM) to give 105-3 (9.2 g, 83.6%) as a white foam.

Compound 105-3 (23 g, 42.0 mmol) was co-evaporated with toluene twice. The residue was dissolved in anhydrous DCM (250 mL) and pyridine (20 mL). The solution was cooled to 0° C., and triflic anhydride (24.9 g, 88.1 mmol) was added dropwise over 10 mins. At this temperature, the reaction was stirred for 40 mins. The reaction was monitored by TLC (PE:EA=2:1 and DCM:MeOH=15:1). After completion, the reaction mixture was quenched with water (50 mL) at 0° C. The mixture was stirred for 30 mins, and extracted with EA. The organic phase was dried over $Na_2SO_4$ and filtered through a silica gel pad. The filtrate was concentrated under reduced pressure, and the residue was purified by column chromatography (50% EA in PE) to give 105-4 (30.0 g, 88.3%) as a brown foam.

To a stirred solution of 105-4 (4.4 g, 5.42 mmol) in anhydrous DMF (50 mL) was added NaH (260 mg, 6.5 mmol) at 0° C. under nitrogen atmosphere. The solution was stirred at RT., for 1.5 h. The solution was used for the next step without any further workup.

To the stirred solution was added $NaN_3$ (1.5 g, 21.68 mmol) at 0° C. under nitrogen atmosphere, and the resulting solution was stirred at RT. for 1.5 h. The reaction was quenched with water, extracted with EA, washed with brine, and dried over $MgSO_4$. The concentrated organic phase was used for the next step without further purification.

To a solution of 105-6 (3.0 g, 5.4 mmol) in anhydrous 1,4-dioxane (18 mL) was added NaOH (5.4 mL, 2M in water) at RT. The reaction mixture was stirred at RT. for 3 h. The reaction was diluted with EA, washed with brine, and dried over $MgSO_4$. The concentrated organic phase was purified on a silica gel column (30% EA in PE) to give 105-7 (2.9 g, 93%) as a white foam.

Compound 105-7 (520 mg, 0.90 mmol) was dissolved in 80% of HCOOH (20 mL) at RT. The mixture was stirred for 3 h, and monitored by TLC. The solvent was removed and the residue was treated with MeOH and toluene for 3 times. $NH_3$/MeOH was added, and the reaction mixture was stirred at RT., for 5 mins. The solvent was concentrated to dryness and the residue was purified by column chromatography to give compound 105 (120 mg, 44.4%) as a white solid. ESI-LCMS: m/z 302.0 [M+H]$^+$, 324.0[M+Na]$^+$.

Example 76

Compound 106

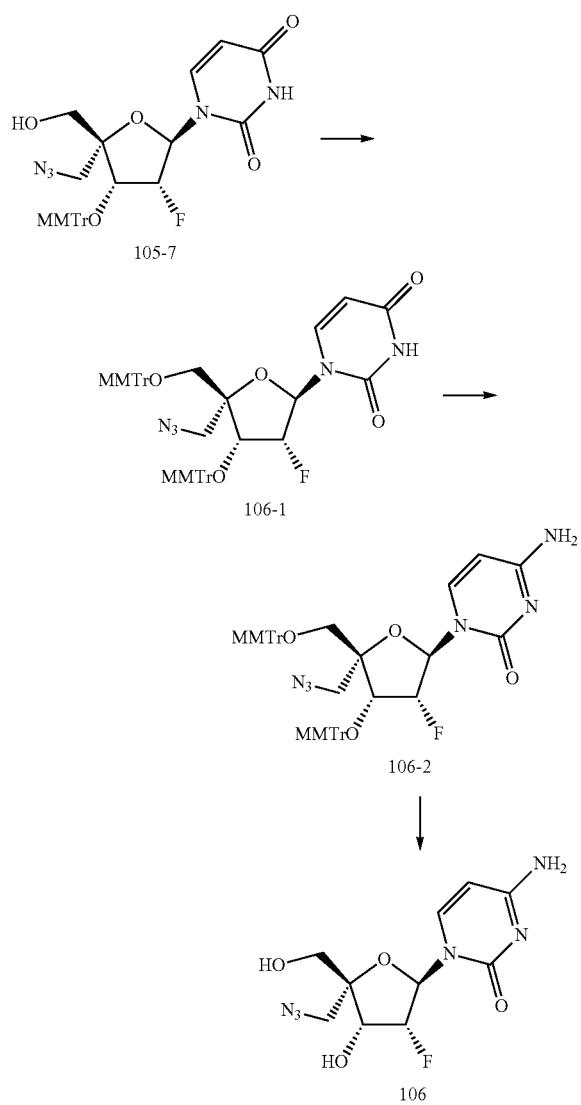

To a stirred solution of 105-7 (1.1 g, 2.88 mmol) in anhydrous DCM (10 mL) was added MMTrCl (1.77 g, 5.76 mmol), AgNO$_3$ (1.47 g, 8.64 mmol) and collidine (1.05 g, 8.64 mmol) at 25° C. under a N$_2$ atmosphere. The reaction was refluxed for 12 h. MeOH (20 mL) was added and the solvent was removed to dryness. The residue was purified on a silica gel column (20% EA in PE) to give 106-1 (1.6 g, 85.1%) as a white foam.

To a stirred solution of 106-1 (800 mg, 0.947 mmol) in anhydrous MeCN (10 mL) were added TPSCl (570 mg, 1.89 mmol), DMAP (230 mg, 1.89 mmol) and TEA (190 mg, 1.89 mmol) at RT. The mixture was stirred for 12 h. NH$_4$OH (25 mL) was added and the mixture was stirred for 2 h. The solvent was removed, and the residue was purified on a silica gel column as a yellow foam. Further purification by prep-TLC gave 106-2 (700 mg, 87.1%) as a white solid.

Compound 106-2 (300 mg, 0.355 mmol) was dissolved in 80% of HCOOH (5 mL) at RT. The mixture was stirred for 3 h, and monitored by TLC. The solvent was then removed and the residue was treated with MeOH and toluene (3 times). NH$_3$/MeOH was added and the mixture was stirred at RT, for 5 mins. The solvent was removed and the residue was purified by column chromatography to give compound 106 (124 mg, 82.6%) as a white solid. ESI-LCMS: m/z 301.0 [M+H]$^+$, 601.0 [2M+H]$^+$.

Example 77

Compound 108

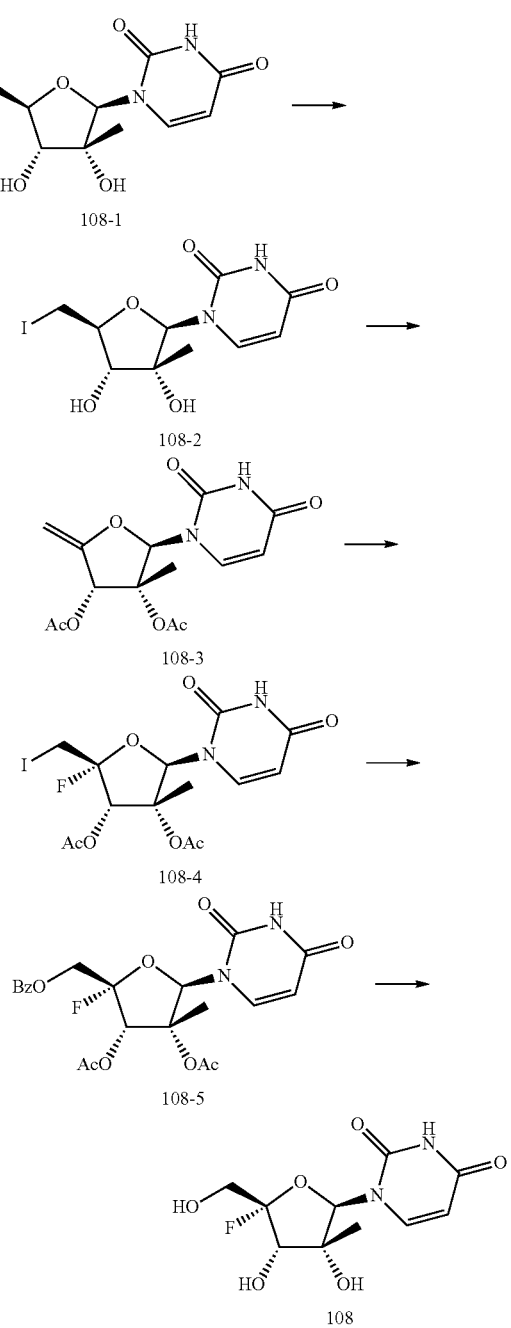

To a stirred suspension of 108-1 (20 g, 77.5 mmol), PPh$_3$ (30 g, 114.5 mmol), imidazole (10 g, 147 mmol) and pyridine (90 mL) in anhydrous THF (300 mL) was added a solution of I$_2$ (25 g, 98.4 mmol) in THF (100 mL) dropwise at 0° C. The mixture was warmed to room temperature (RT) and stirred at RT for 10 h. The reaction was quenched by MeOH (100 mL). The solvent was removed, and the residue was re-dissolved in a mixture ethyl acetate (EA) and THF (2 L, 10:1). The organic phase was washed with saturated Na$_2$S$_2$O$_3$ aq., and the aqueous phase was extracted with a mixture of EA and THF (2 L, 10:1). The organic layer was combined and concentrated to give a residue, which was purified on a silica gel column (0-10% MeOH in DCM) to give 108-2 (22.5 g, 78.9%) as a white solid. $^1$H NMR: (DMSO-d$_6$, 400 MHz) δ 11.42 (s, 1H), 7.59 (d, J=8.4 Hz, 1H), 5.82 (s, 1H), 5.63 (d, J=8.0 Hz, 1H), 5.50 (s, 1H), 5.23 (s, 1H), 3.77-3.79 (m, 1H), 3.40-3.62 (m, 3H), 0.97 (s, 3H).

To a stirred solution of 108-2 (24.3 g, 66.03 mmol) in anhydrous MeOH (240 mL) was added NaOMe (10.69 g, 198.09 mmol) at RT under N$_2$. The mixture was refluxed for 3 h. The solvent was removed, and the residue was re-dissolved in anhydrous pyridine (200 mL). To the mixture was added Ac$_2$O (84.9 g, 833.3 mmol) at 0° C. The mixture was warmed to 60° C. and stirred for 10 h. The solvent was removed, and the residue was diluted with DCM, washed with saturated NaHCO$_3$ and brine. The organic layer was concentrated and purified on a silica gel column (10-50% EA in PE) to give 108-3 (15 g, 70.1%) as a white solid. $^1$H NMR: (CDCl$_3$, 400 MHz) δ 8.82 (s, 1H), 7.23 (d, J=2.0 Hz, 1H), 6.54 (s, 1H), 5.85 (s, 1H), 5.77 (dd, J=8.0, 2.0 Hz, 1H), 4.69 (d, J=2.4 Hz, 1H), 4.58 (d, J=2.8 Hz, 1H), 2.07 (d, J=5.2 Hz, 6H), 1.45 (s, 3H).

To an ice cooled solution of 108-3 (15 g, 46.29 mmol) in anhydrous DCM (300 mL) was added AgF (29.39 g, 231.4 mmol). I$_2$ (23.51 g, 92.58 mmol) in anhydrous DCM (1.0 L) was added dropwise to the solution. The reaction mixture was stirred at RT for 5 h. The reaction was quenched with saturated Na$_2$S$_2$O$_3$ and NaHCO$_3$, and extracted with DCM. The organic layer was separated, dried and evaporated to dryness. The residue was purified on a silica gel column (10-30% EA in PE) to give 108-4 (9.5 g, 43.6%) as a white solid. $^1$H NMR: (Methanol-d$_4$, 400 MHz) δ 7.52 (d, J=8.0 Hz, 1H), 6.21 (s, 1H), 5.80 (d, J=17.2 Hz, 1H), 5.73 (d, J=8.0 Hz, 1H), 3.58 (s, 1H), 3.54 (d, J=6.8 Hz, 1H), 2.17 (s, 3H), 2.09 (s, 3H), 1.58 (s, 3H).

To a solution of 108-4 (7.0 g, 14.89 mmol) in anhydrous DMF (400 mL) were added NaOBz (21.44 g, 148.9 mmol) and 15-crown-5 (32.75 g, 148.9 mmol). The reaction mixture was stirred at 130° C. for 6 h. The solvent was removed, diluted with EA and washed with water and brine. The organic layer was evaporated and purified on a silica gel column (10-30% EA in PE) to give 108-5 (2.8 g, 40.5%). ESI-MS: m/z 444.9 [M−F+H]$^+$.

A mixture of 108-5 (4.0 g; 8.6 mmol) and liquid ammonia was kept overnight at RT in a high-pressure stainless-steel vessel. Ammonia was then evaporated, and the residue purified on silica (50 g column) with a CH$_2$Cl$_2$/MeOH solvent mixture (4-12% gradient) to yield compound 108 as a colorless foam (2.0 g; 84% yield). ESI-MS: m/z 275.1 [M−H]$^−$.

Example 78

Compounds 109 and 110

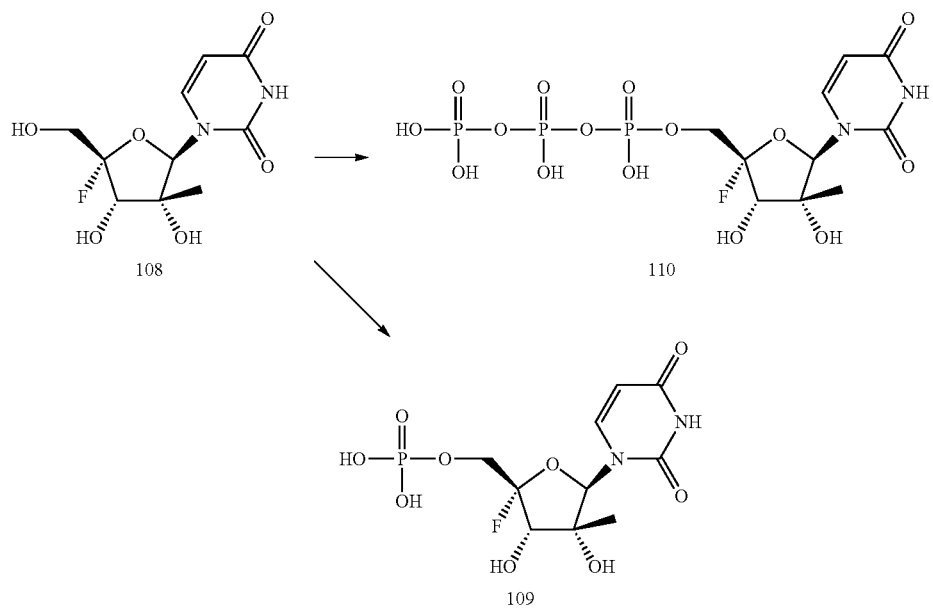

Dry compound 108 (14 mg, 0.05 mmol) was dissolved in the mixture of PO(OMe)$_3$ (0.750 mL) and pyridine (0.5 mL). The mixture was evaporated in vacuum for 15 mins at bath temperature 42° C., and then cooled down to RT. N-Methylimidazole (0.009 mL, 0.11 mmol) was added followed by POCl$_3$ (0.009 mL, 0.1 mmol). The mixture was kept at RT for 45 mins. Tributylamine (0.065 mL, 0.3 mmol) and N-tetrabutyl ammonium salt of pyrophosphate (100 mg) was added. Dry DMF (about 1 mL) was added to get a homogeneous solution. In 1 h, the reaction was quenched with 2M ammonium acetate buffer (1 mL, pH=7.5), diluted water (10 mL) and loaded on a column HiLoad 16/10 with Q Sepharose High Performance. The separation was done in linear gradient of NaCl from 0 to 1N in 50 mM TRIS-buffer (pH7.5). The fractions eluted at 60% buffer B contained Compound 109 and at 80% buffer B contained Compound 110. The corresponding fractions were concentrated, and the residue purified by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer. Compound 109: $P^{31}$-NMR ($D_2O$): −3.76 (s); MS: 378.2 [M−1]. Compound 110: $P^{31}$-NMR ($D_2O$): −9.28 (d, 1H, Pα), −12.31 (d, 1H, Pγ), −22.95 (t, 1H, Pβ); MS 515.0 [M−1].

Example 79

Compound 112

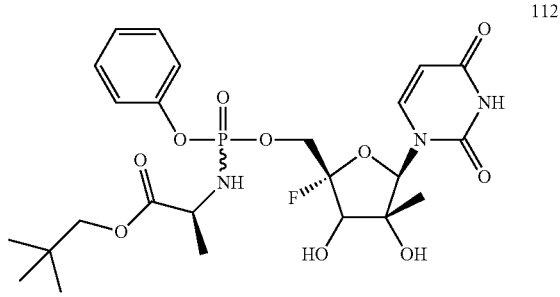 [SMILES: C[C@H](NP(=O)(OC[C@@]1(F)O[C@@H](n2ccc(=O)[nH]c2=O)[C@](C)(O)C1O)Oc1ccccc1)C(=O)OCC(C)(C)C]

Compound 112 (36 mg, 63%) was synthesized as described for compound 2 using a neopentyl ester phosphorochloridate reagent. MS: 572.6 [M−1].

Example 80

Compounds 116 and 117

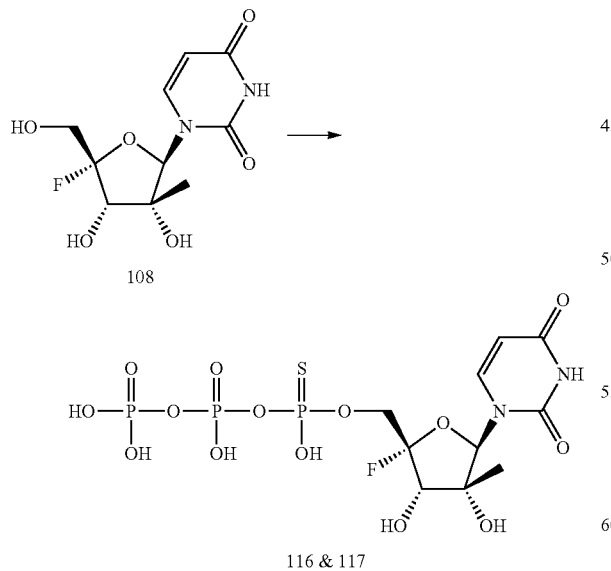

Dry compound 108 (14 mg, 0.05 mmol) was dissolved in the mixture of PO(OMe)$_3$ (0.750 mL) and pyridine (0.5 mL). The mixture was evaporated in vacuum for 15 mins at bath temperature 42° C., and then cooled down to RT. N-Methylimidazole (0.009 mL, 0.11 mmol) was added followed by PSCl$_3$ (0.01 mL, 0.1 mmol). The mixture was kept at RT for 1 h. Tributylamine (0.065 mL, 0.3 mmol) and N-tetrabutyl ammonium salt of pyrophosphate (200 mg) was added. Dry DMF (about 1 mL) was added to get a homogeneous solution. In 2 h, the reaction was quenched with 2M ammonium acetate buffer (1 mL, pH=7.5), diluted with water (10 mL) and loaded on a column HiLoad 16/10 with Q Sepharose High Performance. Separation was done in linear gradient of NaCl from 0 to 1N in 50 mM TRIS-buffer (pH7.5). The fractions eluted at 80% buffer B contained compounds 116 and 117. The corresponding fractions were concentrated, and the residue purified by RP HPLC on Synergy 4 micron Hydro-RP column (Phenominex). A linear gradient of methanol from 0 to 20% in 50 mM triethylammonium acetate buffer (pH 7.5) was used for elution. Two peaks were collected. The corresponding fractions were combined, concentrated and lyophilized 3 times to remove excess of buffer. Peak 1 (more polar): $^{31}$P-NMR ($D_2O$): +42.68 (d, 1H, Pα), −9.05 (d, 1H, Pγ), −22.95 (t, 1H, Pβ); MS 530.9.0 [M−1]. Peak 2 (less polar): $^{31}$P-NMR ($D_2O$): +42.78 (d, 1H, Pα), −10.12 (bs, 1H, Pγ), −23.94 (t, 1H, Pβ); and MS 530.9.0 [M−1].

Example 81

Compounds 118 and 121

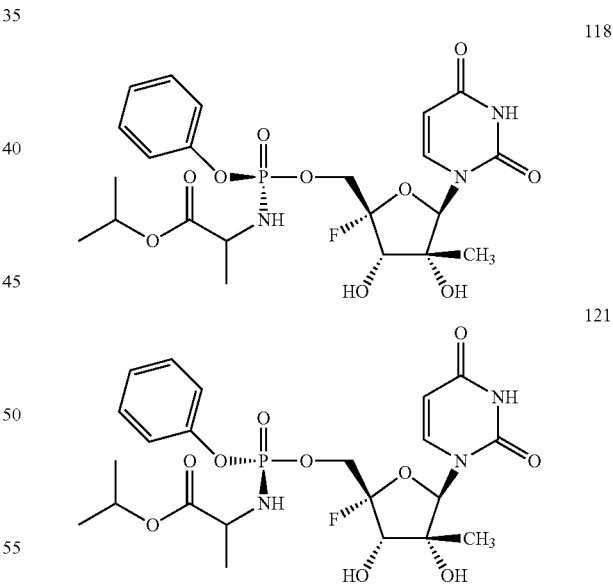

The diastereomers of compound 5 were separated by RP-HPLC. A gradient of 10-43% ACN in $H_2O$ over 26 mins on a Synergi Hydro RP 30×250 m 4u particle column (Phenomenex PN 00G-4375-U0-AX) eluted compound 121 (29.5 mins) and compound 118 (30.1 mins). Pure fractions were lyophilized to produce a white powder. Compound 121: $^{31}$P-NMR (DMSO-d6) 3.448 ppm; MS: m/z: 544 M−1; Compound 118: $^{31}$P-NMR (DMSO-d6) 3.538 ppm; MS: m/z: 544 M−1.

Example 82

Compounds 120 and 119

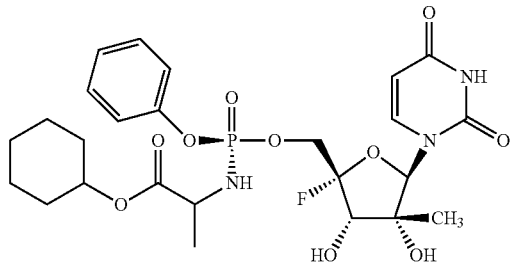

120

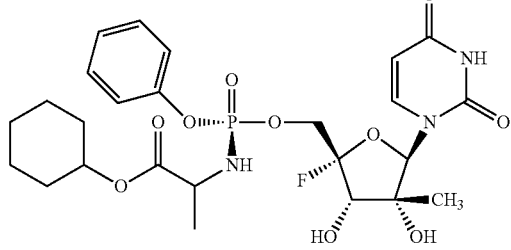

119

The diastereomers of compound 8 were separated by RP-HPLC. A gradient of 25-52% ACN in H$_2$O over 26 minutes on a Synergi Hydro RP 30×250 m 4u particle column (Phenomenex PN 00G-4375-U0-AX) eluted compound 119 (24.8 mins) and compound 120 (25.3 mins). Pure fractions were lyophilized to produce a white powder. Compound 119: $^{31}$P-NMR (DMSO-d6) 3.492 ppm; MS: m/z: 584 M−1. Compound 120: $^{31}$P-NMR (DMSO-d6) 3.528 ppm; MS: m/z: 584 M−1.

Example 83

Compound 122, Bis-lithium Salt

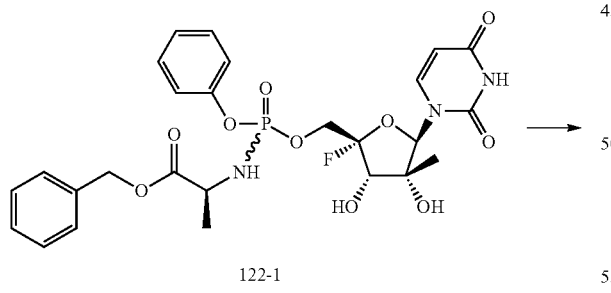

122-1

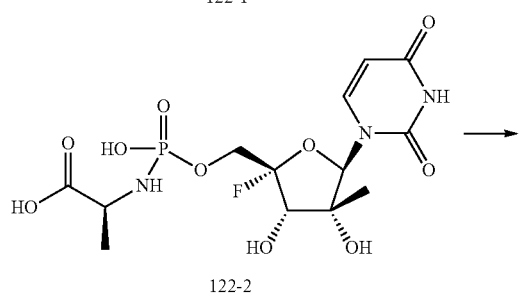

122-2

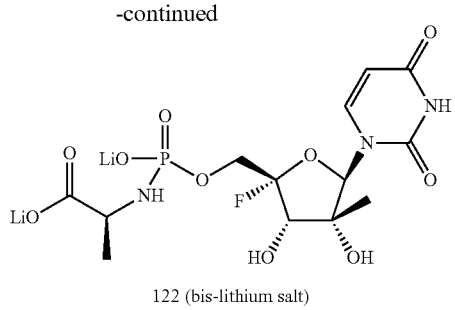

122 (bis-lithium salt)

Compound 122-1 was synthesized using a procedure similar for preparing compound 2 using alanine benzyl ester hydrochloride. LCMS: m/z 592 [M−1]$^-$.

To a solution of 122-1 (1.1 g, 1.85 mmol) in dioxane (15 mL) and water (3 mL) was added aqueous triethylammonium acetate (2M, 2 mL, 4 mmol) followed by Pd—C (10%, 100 mg). The mixture was hydrogenated (balloon) for 2 h, and monitored by HPLC. The catalyst was filtered off, and the filtrate was concentrated to dryness. The residue was suspended in 3% solution of lithium perchlorate in acetone (25 mL). The solid was isolated by filtration, rinsed with acetone and dried under vacuum to give compound 122 (bis-lithium salt) (731 mg, 90%). LCMS: m/z 426 [M−1]$^-$.

Example 84

Compound 151

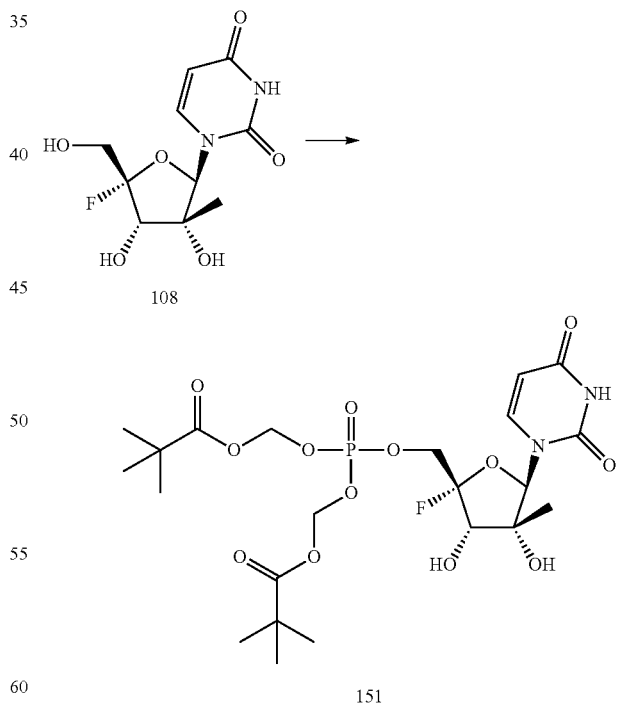

108

151

Compound 108 (40 mg, 0.14 mmol) and triethylammonium bis(pivaloyloxymethyl)phosphate (0.21 mmol, prepared from 80 mg of bis(pivaloyloxymethyl)phosphate and 30 µL of Et$_3$N) were rendered anhydrous by coevaporating with pyridine, followed by toluene. The evaporated residue was dissolved in anhydrous THF (2 mL) and cooled in an ice-bath. Diisopropylethyl amine (73 µL, 3 eq.), BopCl (71 mg, 2 eq.), and 3-nitro-1,2,4-triazole (32 mg, 2 eq.) were added. The mixture was stirred at 0° C. for 90 mins. The mixture was then diluted with EtOAc, washed with sat. aq. NaHCO$_3$ and brine, and dried (Na$_2$SO$_4$). Purification on silica gel column with CH$_2$Cl$_2$/i-PrOH (4-10% gradient) followed by RP-HPLC purification (A: water, B: MeCN) yielded compound 151 (13 mg, 16%). MS: m/z=1167 (2M−1).

Example 85

Compound 159

To a solution of triethylammonium bis(isopropyloxycarbonyloxyethyl-1)phosphate (0.28 mmol, prepared from 100 mg of bis(isopropyloxycarbonyloxyethyl-1)phosphate and 40 µL of Et$_3$N) in THF was added 159-1 (60 mg, 0.18 mmol). The mixture was evaporated and rendered anhydrous by coevaporating with pyridine follow by toluene. The evaporated residue was dissolved in anhydrous THF (2.5 mL) and cooled in an ice-bath. Diisopropylethyl amine (94 µL, 3 eq.) was added, followed by BOP-Cl (92 mg, 2 eq.) and 3-nitro-1,2,4-triazole (41 mg, 2 eq.). The mixture was stirred at 0° C. for 90 mins., diluted with EtOAc and washed with sat. aq. NaHCO$_3$ and brine, and dried (Na$_2$SO$_4$). The residue was purified on a silica gel column with CH$_2$Cl$_2$/i-PrOH (3-10% gradient) to yield 159-2 (19 mg, 17%).

A solution of 159-2 (19 mg, 0.03 mmol) in 80% aq. HCOOH was stirred at RT for 90 mins., and then concentrated. The residue was coevaporated with toluene and then with MeOH containing small amount of Et$_3$N (1 drop). Purification on a silica gel column with CH$_2$Cl$_2$/MeOH (4-10% gradient) yielded compound 159 (5 mg, 26%). MS: m/z=629 [M−1].

Example 86

Compound 160

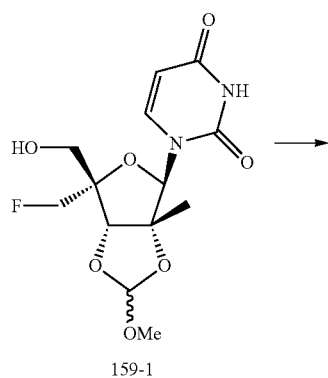
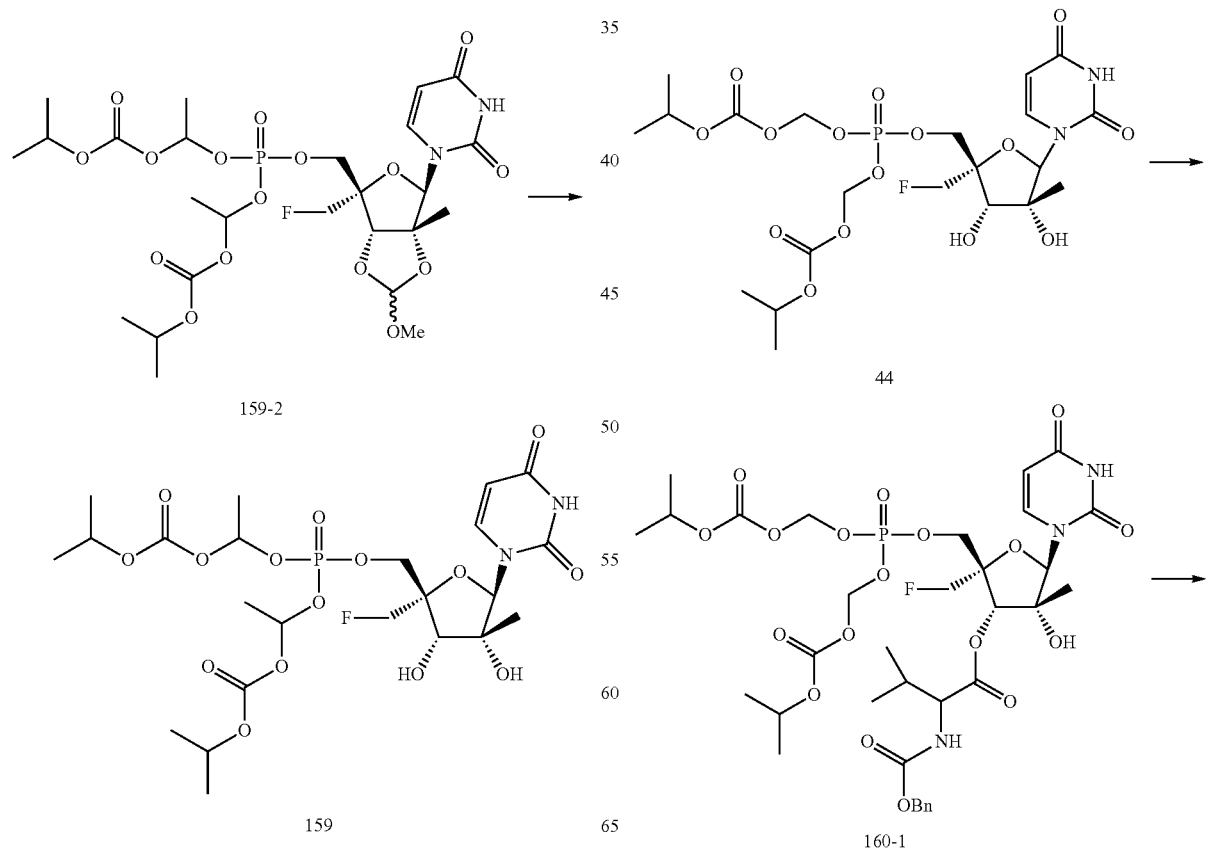

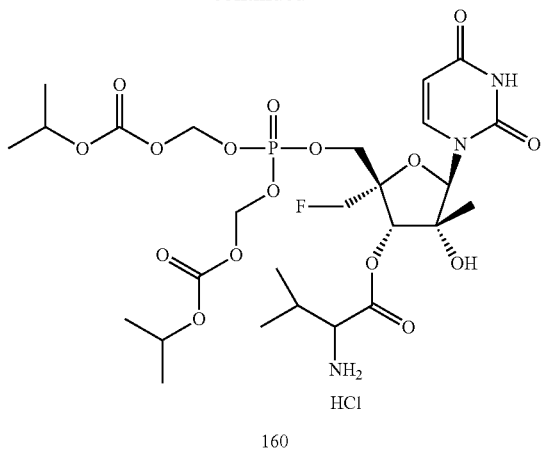

160

A mixture of benzyloxycarbonyl-L-valine (55 mg, 0.22 mmol) in THF (1 mL) and CDI (36 mg, 0.22 mmol) was stirred at RT for 1.5 h and then at 40° C. for 20 mins. The solution was added to a mixture of compound 44 (122 mg, 0.2 mmol) and DMAP (3 mg, 0.03 mmol) in DMF (1.5 mL) and TEA (0.75 mL) at 80° C. The mixture was stirred at 80° C. for 1 h. After cooling, the mixture was concentrated, and the residue partitioned between tert-butyl methyl ether and water. The organic layer was washed with 0.1 N citric acid, sat. aq. NaHCO$_3$ and brine, and dried (Na$_2$SO$_4$). The residue was purified on a silica gel column with CH$_2$Cl$_2$/i-PrOH (4-10% gradient) to yield 160-1 (83 mg, 50%) as a colorless foam.

To a solution of 160-1 (83 mg, 0.1 mmol) in EtOH were added HCl (4 N in dioxane; 50 µL, 2 eq.) and 10% Pd/C (5 mg). The mixture was stirred under H$_2$ atmosphere (normal pressure) for 1 h. The catalyst was removed by filtration through a Celite pad, and the filtrate evaporated to yield compound 160 (50 mg) as a white solid. MS: m/z=702 [M+1].

Example 87

Compound 113

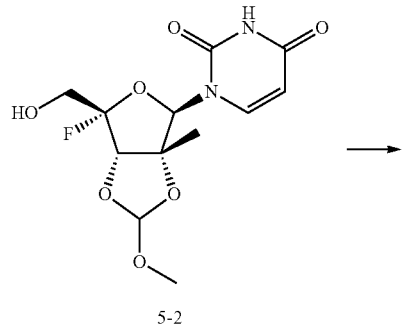

5-2

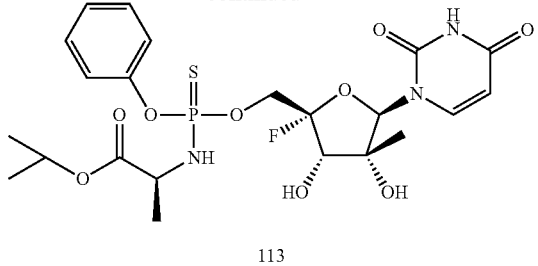

113

Compound 5-2 (32 mg, 0.1 mmol) was dissolved in dry THF (3 mL) and 2M solution of isopropylmagnesium bromide in THF (0.1 mL) was added at 0° C. The reaction was left for 1 h at RT, and phenyl(isopropyl-L-alaninyl) thiophosphorochloridate was added (0.3 mmol). The mixture was left overnight at RT. LSMS analysis showed about 20% of unreacted starting material. The same amount of Grignard reagent and thiophosphorochloridate were added, and the mixture was heated at 37° C. for 4 h. The reaction was quenched with NH$_4$Cl. The product was extracted with EA, washed with brine, dried over Na$_2$SO$_4$, and evaporated. The resulting oil was dissolved in 80% formic acid (4 mL) and in 1 h evaporated. Compound 113 was purified by RP HPLC in gradient of methanol in water from 30% to 95% on Synergy 4u Hydro-RP column (Phenominex) yielding a colorless solid. Compound 113 (7 mg, yield 12.5%). MS 560.0 (M−H).

Example 88

Compound 125

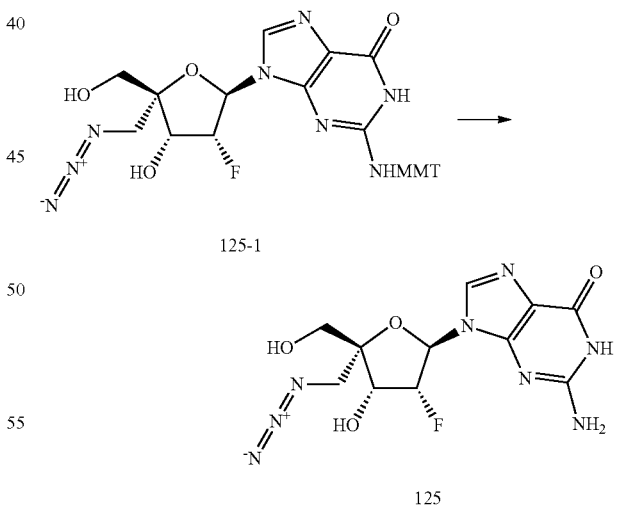

Compound 125-1 (109 mg) was dissolved in 80% HCOOH (15 mL) and kept for 3 h at RT, then evaporated. The residue was treated with NH$_3$/MeOH for 1 h at RT to remove formyl-containing side-products. After evaporation compound 125 was purified by crystallization using methanol to yield compound 125 (52 mg, 86%). MS: 339.6 [M−1], 679.7 (2M−1).

Example 89

Compound 148

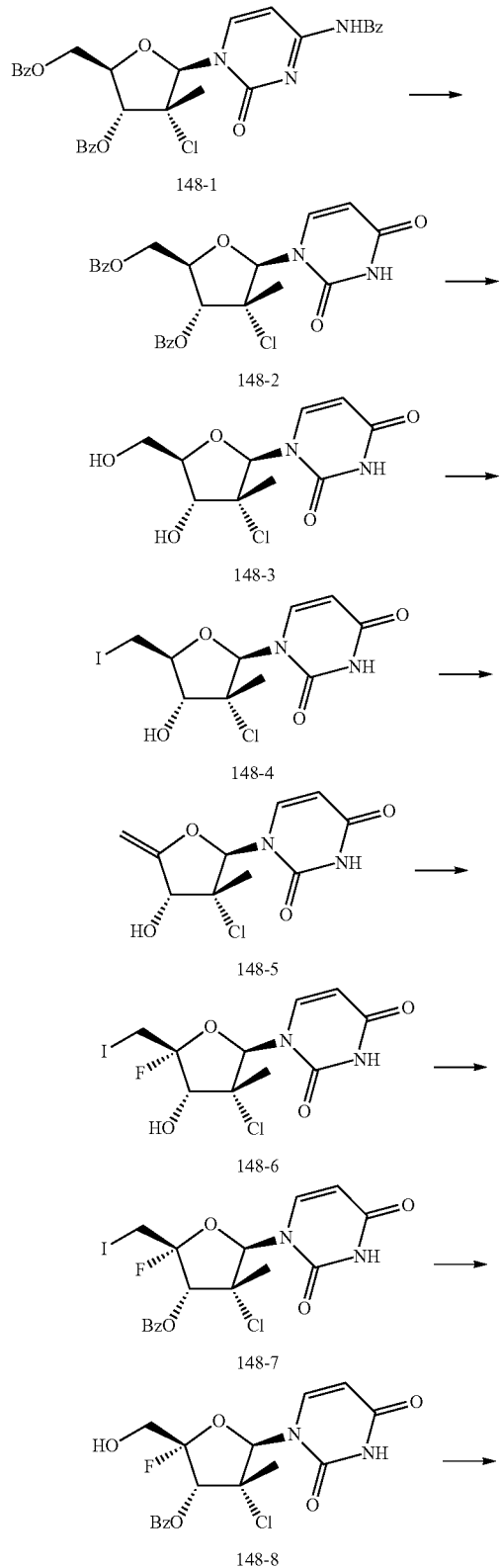

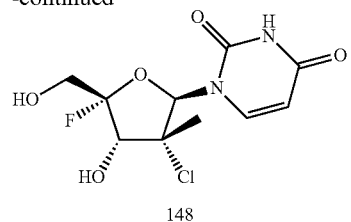

Compound 148-1 (15.0 g, 25.55 mmol) was treated with 90% HOAc (150 mL) at RT. The mixture was stirred at 110° C. for 12 h, and then concentrated at a low pressure. The residue was dissolved in DCM, and the solution was washed with brine. The organic phase was dried over anhydrous $Na_2SO_4$, and then concentrated at a low pressure. The residue was purified by column chromatography (5% MeOH in DCM) to give 148-2 (11.0 g, 88.9%) as a white solid.

Compound 148-2 (12.0 g, 24.79 mmol) was treated with $NH_3$ in MeOH (200 mL, 7 M) at RT. The solution was stirred at RT for 12 h, and then concentrated at a low pressure. The residue was purified by column chromatography (10% MeOH in DCM) to give 148-3 (6.5 g, 95.0%) as a white solid.

To a stirred suspension of 148-3 (4.3 g, 15.58 mmol), $PPh_3$ (8.16 g, 31.15 mmol), imidazole (2.11 g, 31.15 mmol) and pyridine (15 mL) in anhydrous THF (45 mL) was added a solution of $I_2$ (7.91 g, 31.15 mmol) in THF (100 mL) dropwise at 0° C. The mixture was slowly warmed to RT and stirred overnight. The mixture was quenched with MeOH (100 mL). The solvent was removed at a low pressure, and the residue was re-dissolved in a mixture of EA and THF (0.2 L, 10:1). The organic phase was washed with sat. $Na_2S_2O_3$ aq. (2×). The aqueous phase was extracted with a mixture of EA and THF (0.2 L, 10:1, 2×). The concentrated organic phase was dried over anhydrous $Na_2SO_4$. The residue was purified on a silica gel column (0-10% MeOH in DCM) to afford 148-4 (5.1 g, 85.0%) as a white solid.

Compound 148-4 (800 mg, 2.07 mmol) was dissolved in a mixture of DBU (4 mL) and THF (4 mL) at RT under $N_2$. The solution was stirred at RT for 1 h. The mixture was neutralized with HOAc, and extracted with a mixture of EA and THF (10:1, 40 mL). The organic phase was washed with brine, and dried over anhydrous $Na_2SO_4$. The concentrated organic phase was purified by column chromatography (0-10% MeOH in DCM) to give 148-5 (240 mg, 44.9%) as a white solid.

To an ice-cooled solution of 148-5 (1.20 g, 4.65 mmol) in anhydrous MeCN (12 mL) was added NIS (1.57 g, 6.97 mmol) and TEA.3HF (1.12 g, 6.97 mmol) under $N_2$. The mixture was stirred at RT for 5 h. The reaction was quenched with sat. $NaHCO_3$ solution, and extracted with EA (3×100 mL). The organic phase was dried over anhydrous $Na_2SO_4$, and evaporated to dryness at low pressure. The residue was purified on a silica gel column (0-5% MeOH in DCM) to give 148-6 (0.91 g, 48.6%) as a white solid.

To a stirred solution of 148-6 (1.2 g, 2.97 mmol) in anhydrous DCM (12 mL) was added BzCl (0.83 g, 5.94 mmol), TEA (0.6 g, 5.94 mmol) and DMAP (0.72 g, 5.94 mmol) successively at RT. The mixture was stirred at RT for 12 h. The reaction was quenched with water, and extracted with EA (3×60 mL). The organic phase was concentrated at low pressure. The residue was purified by column chromatography (0-5% MeOH in DCM) to give 148-7 (1.2 g, 66.2%) as a white solid.

Tetra-butyl ammonium hydroxide (25.78 mL, 51.78 mmol) was neutralized with TFA (4.3 mL) to pH=4, and the solution was added to a solution of 148-7 (1.09 g, 2.14 mmol) in DCM (30 mL). m-CPBA (1.85 g, 10.74 mmol) was added portionwise under vigorous stirring, and the mixture was stirred for 12 h. The mixture was diluted with EA (100 mL), and washed with sat. sodium bicarbonate. The organic phase was concentrated at low pressure. The residue was purified by column chromatography (50% EA in PE) to give 148-8 (350 mg, 41.1%) as a white solid.

Compound 148-8 (280 mg, 0.704 mmol) was treated with NH$_3$ in MeOH (10 mL, 7 M) at RT. The mixture was stirred at RT for 2 h. The mixture was concentrated at a low pressure. The residue was purified by column chromatography (0-10% MeOH in DCM) to give compound 148 (110 mg, 53.1%) as a white solid. ESI-LCMS: m/z 295.1 [M+H]$^+$.

Example 90

Compound 150

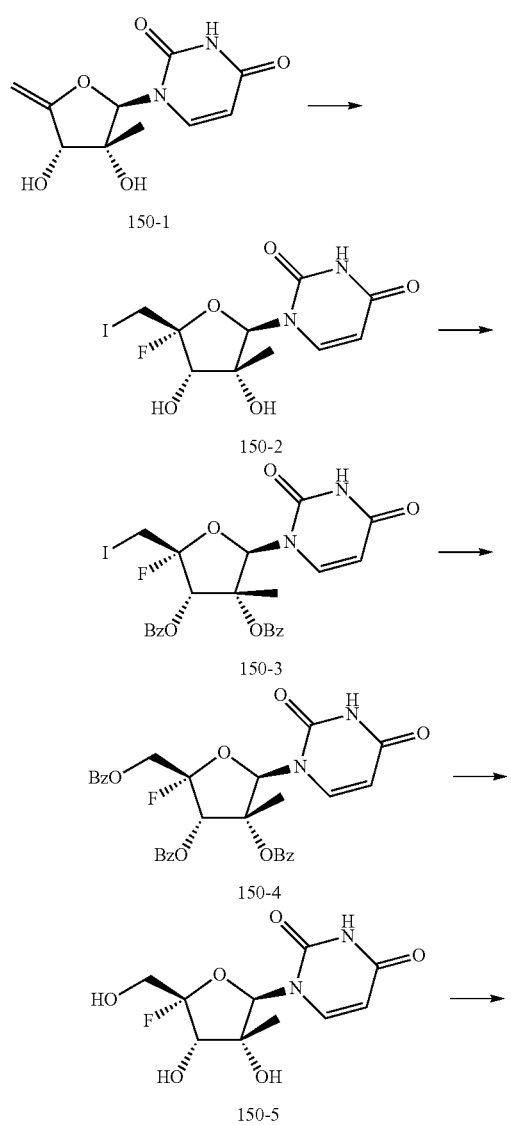

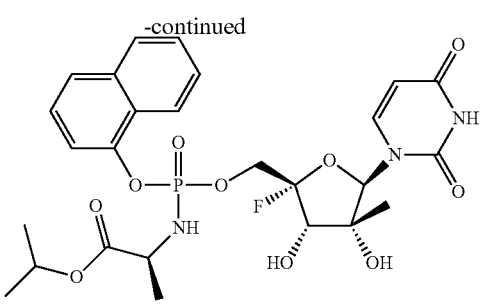

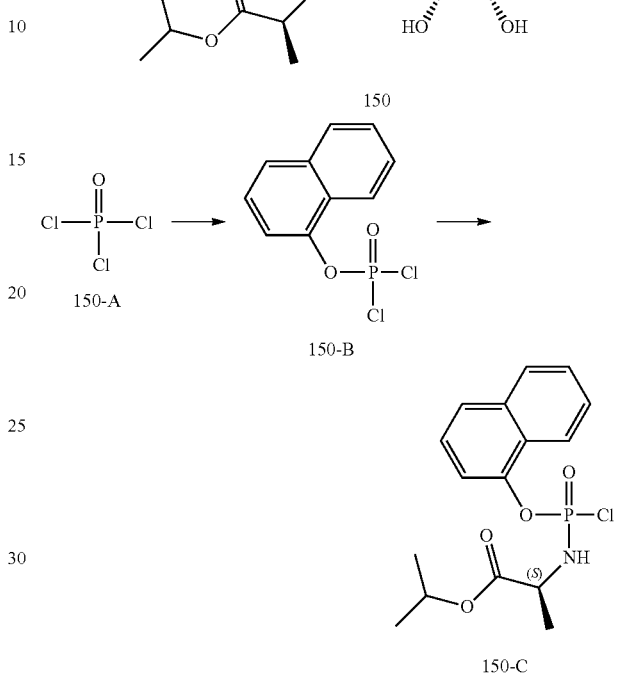

To an ice-cooled solution of 150-1 (10 g, 42 mmol) in anhydrous MeCN (200 mL) was added TEA.3HF (10 g, 62.5 mmol) and NIS (28 g, 126 mmol). The mixture was stirred at RT for 1.5 h, and monitored by LCMS. After the reaction was completed, the mixture was concentrated at a low pressure. The residue was purified by silica gel column chromatography (15% MeCN in DCM) to give 150-2 (12 g, 74%) as a yellow solid.

To a solution of 150-2 (22 g, 57 mmol) in anhydrous DCM (200 mL) was added DMAP (21 g, 171 mmol) and BzCl (17.6 g, 125 mol). The mixture was stirred for 5 h at RT, and monitored by LCMS. The solution was washed with sat. NaHCO$_3$ solution and brine, and extracted with EA. The organic phase was dried over anhydrous Na$_2$SO$_4$ and filtered. The filtrate was concentrated at low pressure. The residue was purified by silica gel column chromatography (20% EA in PE) to give 150-3 (30 g, 88%) as a white foam.

To a solution of 150-3 (6.5 g, 11 mmol) in anhydrous DMF (270 mL) was added NaOBz (15.8 g, 110 mmol) and 15-crown-5 (29 g, 132 mmol). The mixture was stirred at 95° C. for 48 h. The precipitate was removed by filtration, and the organic solvent was removed at low pressure. The residue was dissolved in EA (200 mL), and the solution was washed with sat. NaHCO$_3$ solution, and brine. The organic layer was dried over anhydrous Na$_2$SO$_4$ and filtered. The filtrate was concentrated at low pressure. The residue was purified by silica gel column chromatography (20% EA in PE) to give 150-4 (3 g crude, 46.1%) as an oil.

Compound 150-4 (3 g, crude) was treated with NH$_3$ in MeOH (120 mL, 7 M). The mixture was stirred for 3 h and monitored by TLC. The solution was concentrated at low pressure. The residue was purified by silica gel column chromatography (10% isopropanol in DCM) to give 150-5 (1.0 g, 67%) as a white solid. $^1$H-NMR (CD$_3$OD, 400 mHz) δ=1.19 (s, 3H), 3.76-3.82 (m, 2H), 4.02 (d, J=19.8 Hz, 1H), 5.70 (d, J=8.07 Hz, 1H), 6.27 (s, 1H), 7.89 (d, J=8.07 Hz, 1H).

Compound 150-5 (100 mg, 0.36 mmol) was co-evaporated with toluene 3 times. To a stirred solution of 150-5 (100 mg, 0.36 mmol) in a mixture of MeCN (1.0 mL) and NMI (295 mg, 3.6 mmol) was added a solution of 150-C (255.6 mg, 0.72 mmol, preparation described below) in MeCN (0.5 mL) at 0° C. The mixture was stirred at RT overnight. The reaction was quenched with water, and diluted with EA (20 mL). The organic layer was washed with water and brine. The organic layer was dried over anhydrous Na$_2$SO$_4$. The organic phase was concentrated at low pressure. The residue was purified on a silica gel column (5% i-PrOH in DCM) to give the crude product. The product was purified by prep-HPLC (0.1% HCOOH in water and MeCN) to give compound 150 (46.7 mg, 23.3%) as a white solid. ESI-LCMS: m/z 618 [M+Na]$^+$.

To a stirred solution of 150-A (2.0 g, 13.16 mmol) and naphthalen-1-ol (1.89 g, 13.16 mmol) in anhydrous DCM (100 mL) was added a solution of TEA (1.33 g, 13.16 mmol) in DCM (20 mL) dropwise at −78° C. After addition, the mixture was gradually warmed to RT, and stirred for 2 h. The solution was cooled to −78° C., and (S)-isopropyl 2-aminopropanoate hydrochloride (2.20 g, 13.16 mmol) in DCM (20 mL) was added, followed by TEA (2.66 g, 26.29 mmol) in DCM (20 mL) dropwise. The mixture was gradually warmed to RT, and stirred for 2 h. The organic solvent was removed at low pressure. The residue was dissolved in methyl-butyl ether. The precipitate was filtered, and the filtrate was concentrated at low pressure. The residue was purified on a silica gel column (anhydrous DCM) to give 150-C (1.0 g, 24.8%) as a colorless oil.

Example 91

Compounds 152 and 153

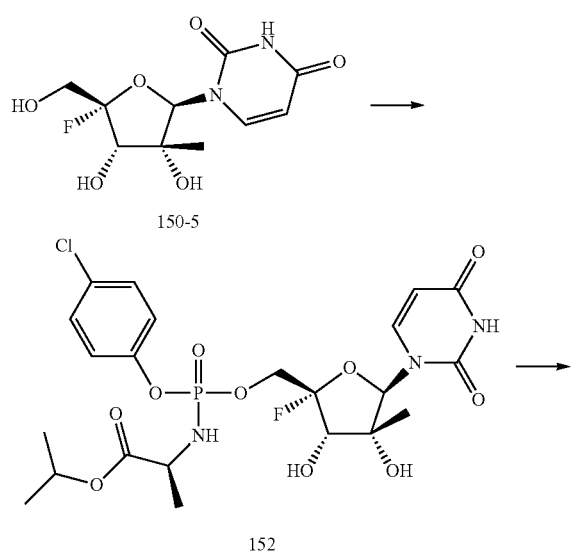

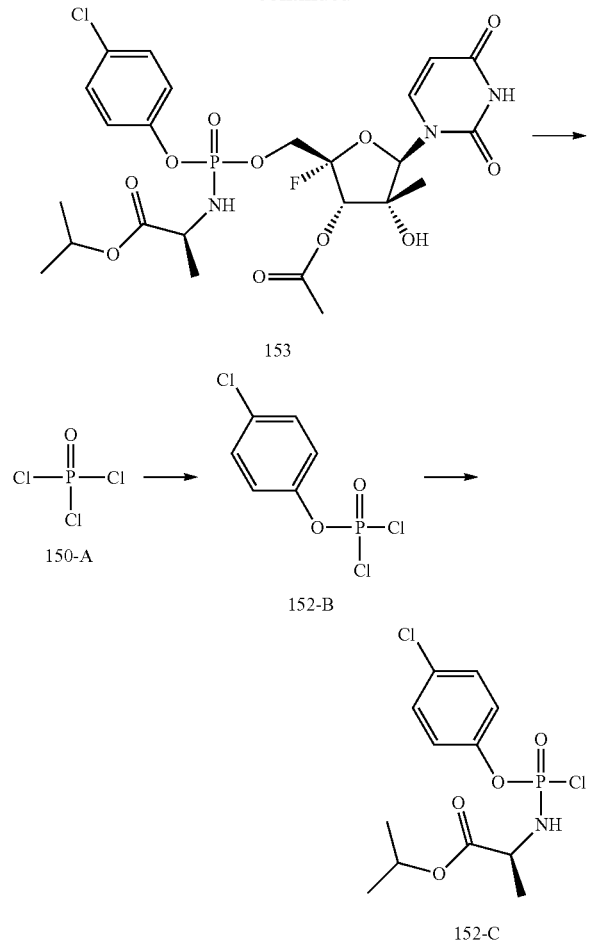

To a solution of 150-5 (300 mg, 1.08 mmol) and NMI (892 mg, 10 mmol) in anhydrous MeCN (4 mL) was added a solution of 152-C (736 mg, 2.17 mmol, preparation described below) in anhydrous MeCN (1 mL) dropwise at 0° C. The mixture was stirred at RT overnight. The reaction was quenched with water, and diluted with EA (30 mL). The organic layer was washed with water and brine. The organic phase was dried over anhydrous Na$_2$SO$_4$ and concentrated at low pressure. The residue was purified by a silica gel column (iPrOH in DCM from 1% to 5%) to give crude compound 152 (276 mg, crude). Crude compound 152 (96 mg) was purified by prep-HPLC (0.1% HCOOH in water and MeCN) to give pure compound 152 (46 mg, 47.9%) as a white solid. ESI-LCMS: m/z 560 [M−F]$^+$.

To a solution of compound 152 (180 mg, 0.31 mmol) in anhydrous pyridine (6 mL) was added acetic anhydride (158 mg, 1.54 mmol) dropwise at 0° C. The mixture was stirred at RT overnight. The solution was quenched with water and concentrated at a low pressure. The residue was dissolved in EA (10 mL), and washed with brine. The organic layer was dried over anhydrous Na$_2$SO$_4$. The organic phase was concentrated at low pressure. The residue was purified by silica gel column (i-PrOH in DCM from 1% to 3%) to give crude compound 153 (172 mg). Crude compound 153 was purified by prep-HPLC (0.1% HCOOH in water and MeCN) to give pure compound 153 (46 mg, 23.8%) as a white solid. ESI-LCMS: m/z 602.3 [M−F]$^+$.

Compound 152-C (1.02 g, 23%, a colorless oil) was prepared using a procedure similar to the preparation of 150-C using 150-A (2.00 g, 13.16 mmol) and 4-chlorophenol (1.68 g, 13.16 mmol).
Example 92
Compound 165
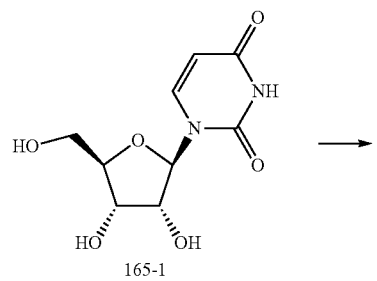
165-1
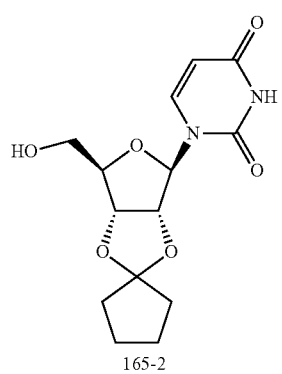
165-2
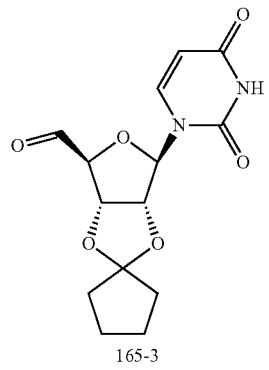
165-3
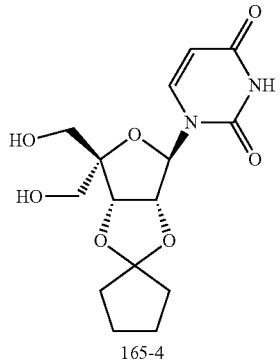
165-4
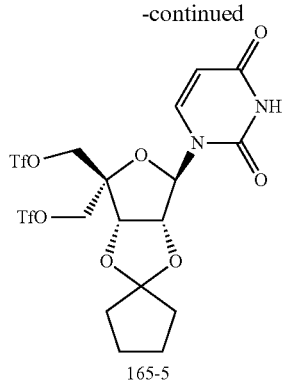
165-5
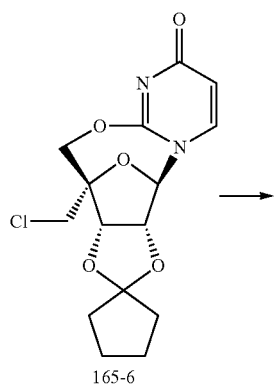
165-6
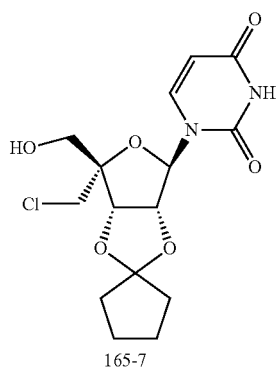
165-7
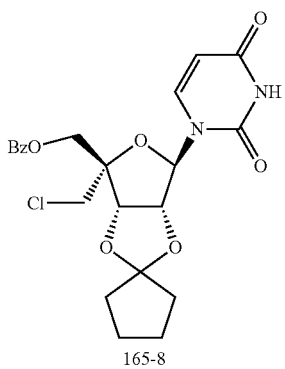
165-8

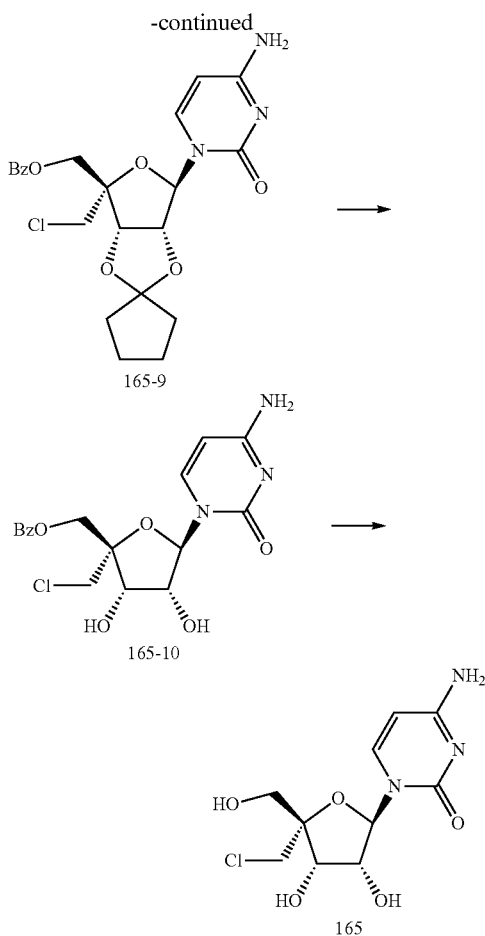

To a solution of 165-1 (5 g, 0.02 mol), cyclopentanone (5.25 g, 0.06 mol, 4.5 eq.) and trimethoxymethane (6.52 g, 0.06 mol, 3 eq.) in MeCN (80 mL) was added TSOH.H$_2$O (1.95 g, 0.01 mol). The mixture was heated at 80° C. overnight. The mixture was concentrated at low pressure. The residue was purified by column chromatography (20% EA in PE) to give 165-2 (3.8 g, 60%) as a white oil.

To a solution of 165-2 (5 g, 0.16 mol) in MeCN (50 mL, anhydrous) was added IBX (5.33 g, 0.019 mol, 1.11 eq.) at RT. The mixture was heated at 80° C. for 5 h. The mixture was cooled to RT and filtered. The filtrate was concentrated to give 165-3 (4.5 g, purity: 90%).

To a solution of 165-3 (5 g, 0.016 mol) and CH$_2$O (3.6 mL) in 1,4-dioxane (50 mL) was added NaOH solution (11.3 mL, 2 N) at RT. The mixture was stirred for 5 h at RT. NaBH$_4$ (1.48 g, 0.038 mol) was added at 0° C., and stirred for 1 h. The reaction was quenched with H$_2$O (30 mL) and extracted with EA (3×30 mL). The organic layer was washed by brine, dried over anhydrous Na$_2$SO$_4$, and concentrated at low pressure. The residue was purified by column chromatograph (50% EA in PE) to give 165-4 (2.1 g, 38%) as a white oil.

To a stirred solution of 165-4 (3 g, 0.0088 mol) and pyridine (3.51 mL, 5 eq.) in DCM (27 mL) was added Tf$_2$O (3.27 mL, 0.019 mol) at −35° C. The mixture was slowly warmed to 0° C. and stirred for 2 h at 0° C. The mixture was washed with sat. NaHCO$_3$ solution and extracted with DCM (3×30 mL). The organic layer was separated and washed by brine, dried over anhydrous Na$_2$SO$_4$, and concentrated at low pressure. The residue was purified by column chromatography (5% EA in PE) to give 165-5 (2.65 g, 39%) as a white oil.

To a solution of 165-5 (12.3 g, 0.02 mol) in DMF (20 mL) was added NaH (0.977 g, 0.024 mol) at 0° C. The mixture was stirred for 3 h at RT. The mixture was treated with LiCl (2.6 g, 0.062 mol), and then stirred for 2 h. The reaction was quenched with H$_2$O (20 mL) and extracted with EA (3×30 mL). The organic layer was washed with brine, dried over anhydrous Na$_2$SO$_4$, and concentrated at low pressure. The residue was purified by column chromatography (20% EA in PE) to give 165-6 (3.11 g, 45%) as a white oil.

To a solution of 165-6 (12 g, 0.035 mol) in THF (120 mL) was added NaOH solution (38.8 mL, 0.038 mol) at 0° C., and stirred for 3 h. at RT. The mixture was adjusted to pH=7 with HCl (1.0 N) solution, and extracted with EA (3×80 mL). The organic layer was washed with brine, dried over anhydrous Na$_2$SO$_4$, and concentrated at low pressure. The residue was purified by column chromatography to give 165-7 (7.58 g, 60%) as a white solid.

165-7 (3 g, 8.0 mmol) was co-evaporated with toluene (30 mL). To a solution of 165-7 (3 g), DMAP (100 mg) and TEA (2.5 mL, 2 eq.) in DCM (30 mL) was added Bz$_2$O (2.01 g, 1 eq.) at 0° C. The mixture was stirred for 3 h at RT. The reaction was quenched with H$_2$O, and extracted with DCM (3×30 mL). The DCM layer was dried over anhydrous Na$_2$SO$_4$, and concentrated at low pressure. The residue was purified by column chromatography (5% EA in PE) to give 165-8 (3.1 g, 80%) as a white solid.

To a solution of 165-8 (200 mg, 0.43 mmol) in CH$_3$CN (2 mL, anhydrous) was added TPSCl (260 mg, 2 eq.), TEA (0.13 mL) and DMAP (106.4 mg, 2 eq.). The mixture was stirred for 2 h at RT.

The mixture was treated with NH$_3$.H$_2$O (33%, 1.33 mL), and stirred for 2 h at RT. The reaction was quenched with 1 N HCl (30 mL), and extracted with DCM (3×30 mL). The DCM layer was dried over anhydrous Na$_2$SO$_4$ and concentrated at low pressure. The residue was purified by column chromatography to give 165-9 (85 mg, 50%) as a white solid.

165-9 (100 mg, 0.216 mmol) was treated with HCOOH (7 mL, 80%), and stirred for 3 h at RT. The mixture was concentrated at low pressure. The residue was purified by column chromatography (90% EA in PE) to give 165-10 (51 mg, 60%) as a white solid.

165-10 (270 mg, 0.68 mmol) was treated with NH$_3$ in MeOH (10 mL) at −60° C. The mixture was warmed to RT. The mixture was stirred for 6 h. at RT. The mixture was concentrated at low pressure. The residue was purified by reverse HPLC to give 165 (60 mg, 30%) as a white solid.

Example 93

Compound 169

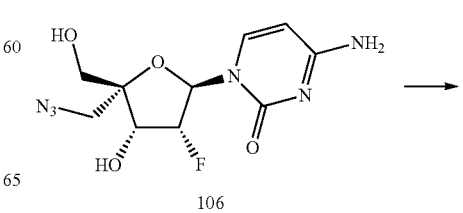

106

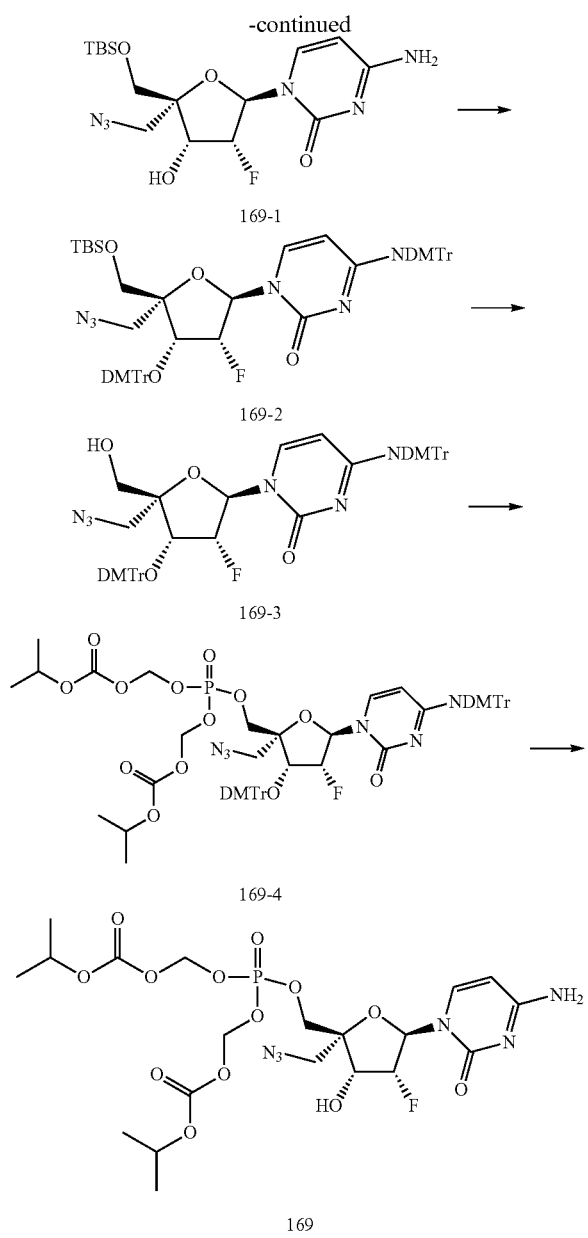

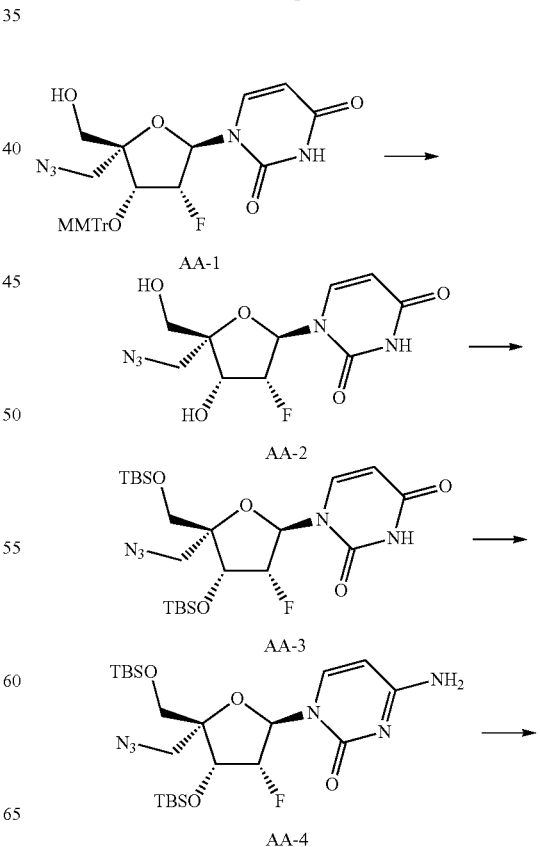

To a solution of 169-2 (83 mg, 0.081 mmol) in THF (1 mL), was added a 1M solution of TBAF in THF (0.122 mL, 0.122 mmol) at ice bath temperature. The mixture was stirred for 1.5 h. The mixture was diluted with EA, and washed with water and brine. The organic layer was dried and concentrated to give the crude product, which was purified by silica gel column chromatography (DCM to 5% MeOH in DCM) to give 169-3 (66.6 mg, 91%) as a white foam.

169-3 (66.6 mg, 0.074 mmol) was co-evaporated with toluene and THF (3×). Bis(POC)phosphate (33 mg, 0.96 mmol) was added, and then co-evaporated with toluene (3×). The mixture was dissolved in anhydrous THF (1.5 mL) and cooled in an ice bath (0 to 5° C.). 3-nitro-1,2,4-triazole (13 mg, 0.11 mmol), diisopropylethyl amine (54 µL, 0.3 mmol), and BOP-Cl (28 mg, 0.11 mmol) were added successively. The mixture was stirred 2 h at 0 to 5° C., diluted with EtOAc, washed with 1.0M citric acid, sat. aq. NaHCO₃ and brine, and dried with Na₂SO₄. The residue was purified on silica (10 g column) with CH₂Cl₂:i-PrOH (4-10% gradient) to give 169-4 (68 mg, 76%) as a white solid.

169-4 (68 mg, 0.07 mmol) was dissolved in 80% HCOOH. The mixture was stirred at RT for 2 h. The solvents were evaporated at RT and co-evaporated with toluene (3×). The residue was dissolved in 50% CH₃CN/H₂O, was purified on a reverse-phase HPLC (C18) using CH₃CN and H₂O. The product was lyophilization to give 169 (4.8 mg, 14%) as a white foam. ESI-LCMS: m/z=613.1 [M+H]⁺, 1225.2 [2M+H]⁺.

Example 94

Compound 145

To a solution of 106 (200 mg, 0.67 mmol) in anhydrous pyridine (5 mL) was added TBSCl (120 mg, 0.8 mmol) at RT. The mixture was stirred overnight, and the reaction mixture was diluted with EA. The mixture was washed with NaHCO₃ aq. solution and brine. The organic layer was dried, filtered and concentrated to give residue, which was purified by silica gel column chromatography (5% MeOH in DCM to 25% MeOH in DCM to give 169-1 (153 mg, 55%) as a white solid.

To a solution of 169-1 (54 mg, 0.13 mmol) in anhydrous DCM (2 mL) was added collidine (95 µL, 0.78 mmol), DMTrCl (262 mg, 0.78 mmol) and AgNO₃ (66 mg, 0.39 mmol) at RT. The mixture was stirred overnight, and then diluted with DCM (5 mL). The mixture was filtered through a pre-packed celite funnel, and the filtrate was washed with NaHCO₃ aq. solution, 1.0 M citric acid solution and then brine. The organic layer was dried over Na₂SO₄, and concentrated at low pressure to give a residue. The residue was purified by silica gel column chromatography (25% EA in PE to 100% EA) to give 169-2 (83.5 mg, 63.6%).

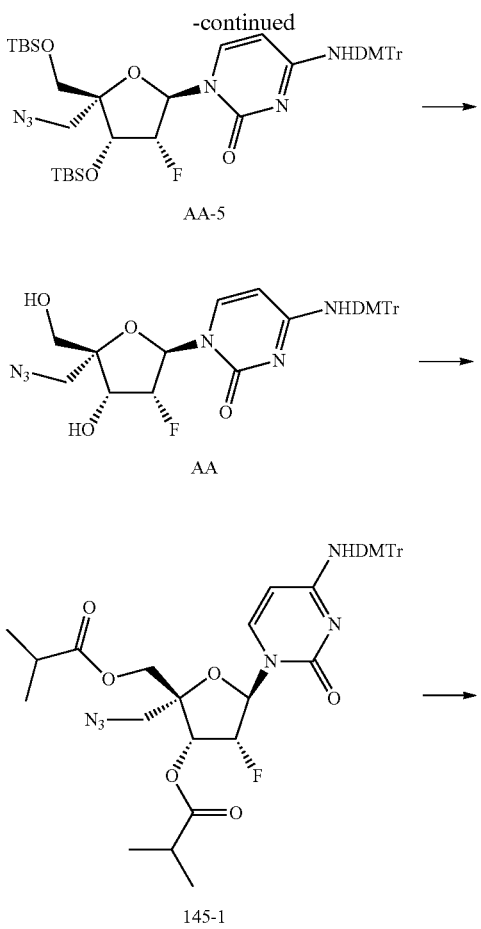

purified on a silica gel column using 20% EA in Hexane to give AA-3 (1.4 g, 79.5%) as a white solid.

To a stirred solution of AA-3 (1.50 g, 2.83 mmol, 1.00 eq.) in anhydrous $CH_3CN$ (28 mL) was added TPSCl (1.71 g, 5.80 mmol, 2.05 eq.), DMAP (691.70 mg, 5.66 mmol, 2.00 eq.) and TEA (573.00 mg, 5.66 mmol, 2.00 eq.) at RT (15° C.). The mixture was stirred for 2 h. $NH_3.H_2O$ (20 mL) was added, and the mixture was stirred for 3 h. The mixture was extracted with EA (3×60 mL). The organic phase was washed with brine, dried over anhydrous $Na_2SO_4$ and concentrated at low pressure. The residue was purified on a silica gel column (30% EA in PE) to give AA-4 (2.3 g, crude) as a yellow foam.

To a stirred solution of AA-4 (1.90 g, 2.34 mmol) in anhydrous DCM (20 mL) was added DMTrCl (1.82 g, 3.49 mmol) and 2,4,6-trimethylpyridine (1.00 g, 8.25 mmol) at RT (15° C.) under $N_2$ atmosphere. The mixture was stirred at RT for 12 h. MeOH (20 mL) was added. The mixture was filtered, and the filtrate was concentrated to dryness. The residue was dissolved in EA (80 mL). The solution was washed with brine, dried over anhydrous $Na_2SO_4$ and concentrated at low pressure. The residue was purified on a silica gel column (5% MeOH in DCM) to give AA-5 (1.4 g, crude) as a white solid.

AA-5 (2.40 g, 2.60 mmol) was dissolved in TBAF (10 mL, 1M in THF). The mixture was stirred at RT (15° C.) for 30 mins. The mixture was concentrated to dryness, and the residue was dissolved in EA (60 mL). The solution was washed with brine, dried over $MgSO_4$ and concentrated under reduced pressure. The residue was purified on a silica gel column (5% MeOH in DCM) to give AA (1.50 g, 95.8%) as a white solid. ESI-MS: m/z 625.3 $[M+Na]^+$.

To a solution of AA (60.0 mg, 99.57 μmol, 1.00 eq.) in pyridine (1 mL) was added isobutyric anhydride (31.50 mg, 199.13 μmol, 2.00 eq.) in 1 portion at RT (15° C.) under $N_2$ atmosphere. The mixture was stirred at RT for 12 h. The mixture was concentrated, and the residue was partitioned between EA and water. The combined organic phases were washed with water and brine, and dried over anhydrous $Na_2SO_4$. The mixture was filtered, and the filtrate was concentrated to dryness. The residue was purified by silica gel chromatography (30% EA in PE) to afford 145-1 (59.00 mg, 79.77%) as a white solid.

145-1 (57.00 mg, 76.74 μmol, 1.00 eq.) was dissolved in 80% $CH_3COOH$ (8 mL). The solution was stirred at RT (15° C.) for 12 h. The mixture was concentrated to dryness. The residue was purified on a silica gel column (2.5% MeOH in DCM) to give 145 (23.00 mg, 68.05%) as a white foam. ESI-MS: m/z 441.2 $[M+H]^+$, 463.2 $[M+Na]^+$.

Example 95

Compound 170

AA-1 (2.20 g, 3.84 mmol) was dissolved in 80% HCOOH (40 mL) at RT (18° C.). The mixture was stirred at RT for 12 h. The solvent was removed at low pressure. The residue was purified by column chromatography using 50% EA in Hexane to give AA-2 (1.05 g, 91.3%) as a white solid.

To a stirred solution of AA-2 (1 g, 3.32 mmol) in anhydrous pyridine (20 mL) was added TBSCl (747 mg, 4.98 mmol) and imidazole (451 mg, 6.64 mmol) at RT (16° C.) under $N_2$ atmosphere. The mixture was stirred at RT for 4 h. The resulting solution was concentrated to dryness under reduced pressure, and the residue was dissolved in EA (100 mL). The solution was washed with sat. $NaHCO_3$ solution and brine, and dried over anhydrous $MgSO_4$. The solution was concentrated to dryness, and the residue was

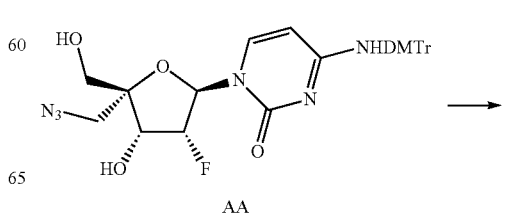

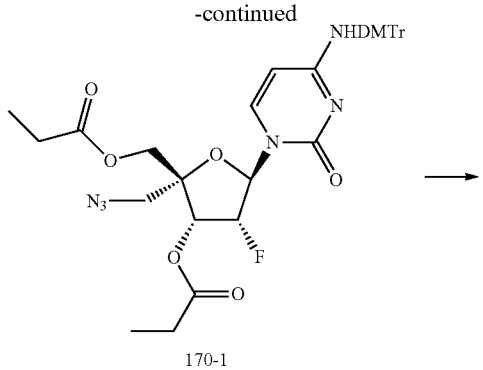

170-1

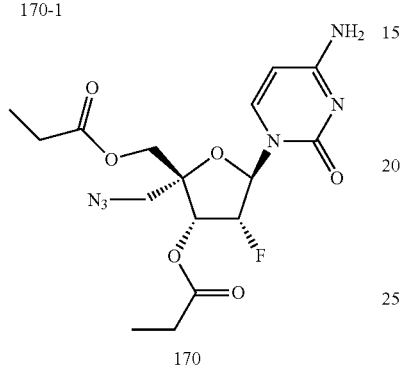

170

170-1 was prepared in similar manner as 145-1 using AA (60.00 mg, 99.57 μmol, 1.00 eq.) in pyridine (1 mL) and propionic anhydride (25.92 mg, 199.13 μmol, 2.00 eq.). 170-1 (white solid, 56.00 mg, 78.69%).

170 was prepared in similar manner as 145 using 170-1 (54.00 mg, 75.55 μmol, 1.00 eq.) 170 (white foam, 18.00 mg, 57.78%). ESI-MS: m/z 413.1 [M+H]$^+$.

Example 96

Compound 171

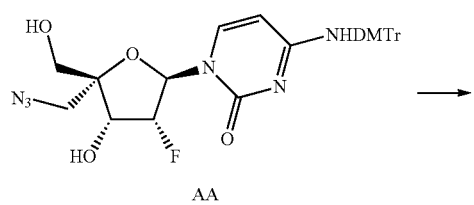

AA

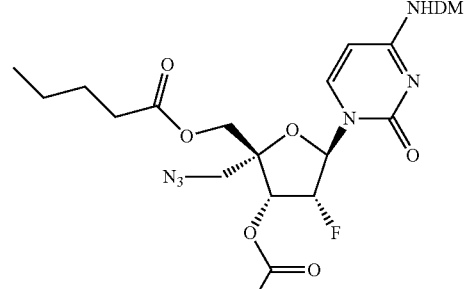

171-1

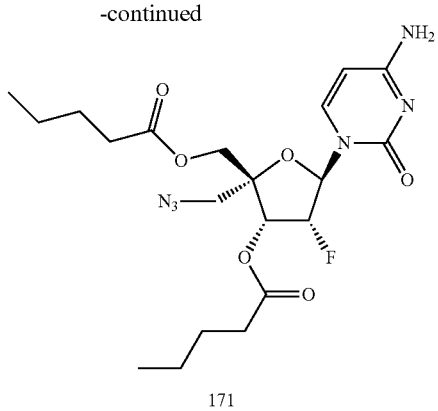

171

171-1 was prepared in similar manner as 145-1 using AA (62.00 mg, 102.89 μmol, 1.00 eq.) in pyridine (1 mL) and pentanoic anhydride (38.32 mg, 205.77 μmol, 2.00 eq.). 171-1 (white solid, 60.00 mg, 75.65%).

171 was prepared in similar manner as 145 using 171-1 (75.00 mg, 97.30 mol, 1.00 eq.) 171 (white foam, 28.00 mg, 61.43%). ESI-MS: m/z 469.2 [M+H]$^+$.

Example 97

Compound 146

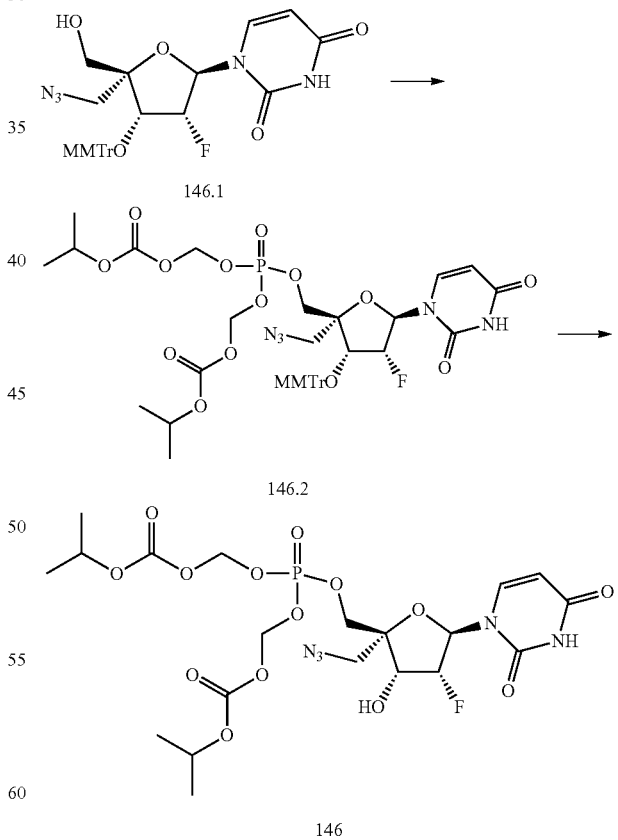

146-2 (40.7 mg, 53%) was prepared in the same manner from 146-1 (50 mg, 0.087 mmol) and bis(isopropyloxycarbonyloxymethyl)phosphate (58 mg, 0.175 mmol) with DIPEA (75 μL, 0.52 mmol), BOP-Cl (66.2 mg, 0.26 mmol), and 3-nitro-1,2,4-triazole (30 mg, 0.26 mmol) in THF (0.4 mL) in a similar manner as 169-4.

146-2 (40 mg, 0.045 mmol) was dissolved in anhydrous CH₃CN (0.5 mL), and 4N HCl in dioxane (34 μL, 0.135 mmol) was added at 0 to 5° C. The mixture was stirred at RT for 3 h. Anhydrous EtOH (200 μL) was added. The solvents were evaporated at RT and co-evaporated with toluene (3×). The residue was purified on silica (10 g column) with MeOH/CH₂Cl₂ (5-7% gradient) and lyophilized give 146 (15.4 mg, 76%) as a white foam. ESI-LCMS: m/z=614.15 [M+H]⁺, 1227.2 [2M+H]⁺.

Example 98

Compound 172

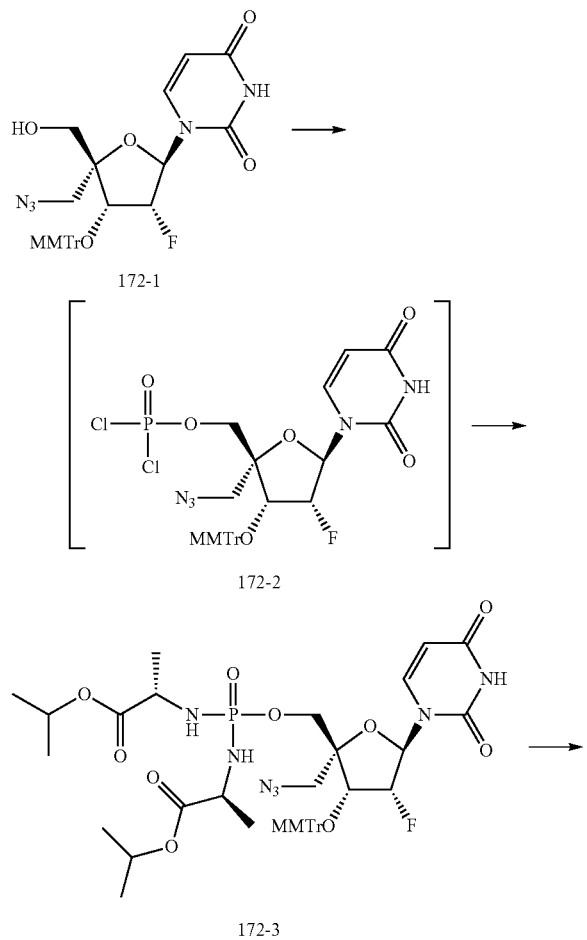

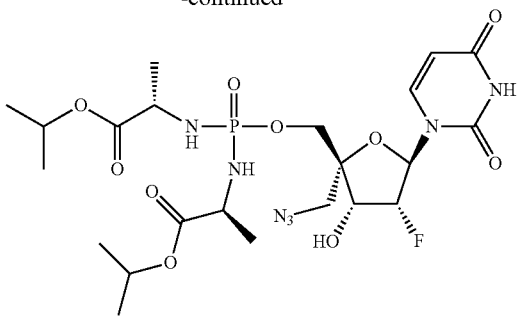

172-1 (100 mg, 0.174 mmol) was co-evaporated with anhydrous pyridine (3×), toluene (3×) and CH₃CN (3×), and dried under high vacuum overnight. 172-1 was dissolved in CH₃CN (2 mL). A proton sponge (112 mg, 0.52 mmol), POCl₃ (49 μL, 0.52 mmol) were added at 0 to 5° C. The mixture was stirred for 3 h at 0 to 5° C. to give intermediate 172-2. To this solution, L-alanine isopropyl ester hydrochloride (146 mg, 0.87 mmol), and TEA (114 μL, 1.74 mmol) were added. The mixture was stirred for 4 h at 0 to 5° C. The mixture was stirred 2 h at 0 to 5° C., then diluted with EtOAc. The mixture was washed with 1.0M citric acid, sat. aq. NaHCO₃ and brine, and dried with Na₂SO₄. The residue was purified on silica (10 g column) with CH₂Cl₂/MeOH (0-7% gradient) to give 172-3 (67 mg, 43.7%) as a white solid.

172-3 (65 mg, 0.074 mmol) was dissolved in anhydrous CH₃CN (0.5 mL), and 4N HCl in dioxane (55 μL, 0.22 mmol) was added at 0 to 5° C. The mixture was stirred at RT for 1.5 h. A second portion of 4N HCl in dioxane (15 μL) was added, and the mixture stirred at RT for 2 h. Anhydrous EtOH (300 μL) was added. The solvents were evaporated at RT and co-evaporated with toluene (3×). The residue was dissolved in 50% CH₃CN/H₂O, was purified on a reverse-phase HPLC (C18) with CH₃CN and water, and lyophilized to give 172 (9 mg, 20%) as a white foam. ESI-LCMS: m/z=608.15 [M+H]⁺, 1215.3 [2M+H]⁺.

Example 99

Compound 173

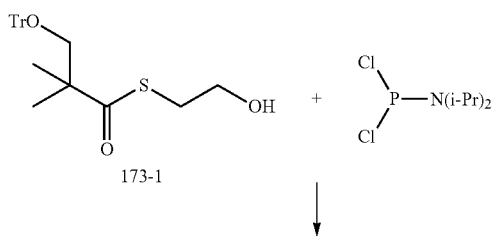

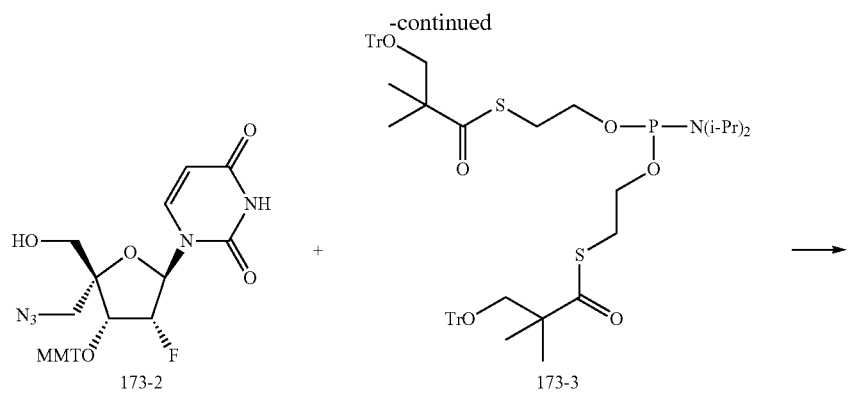

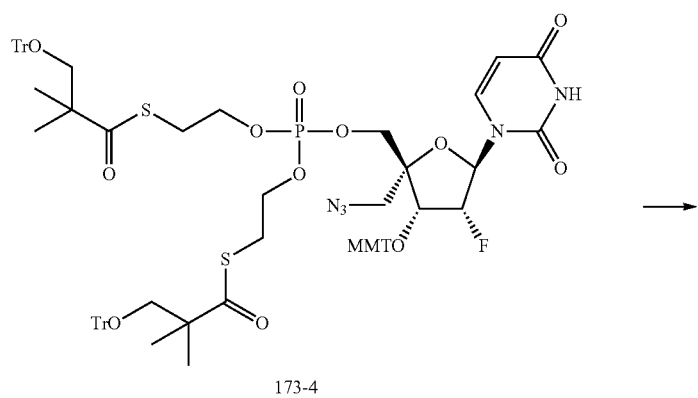

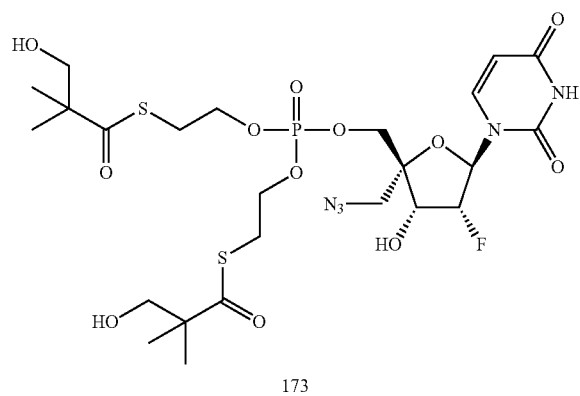

A solution of 173-1 (4.7 g, 11.2 mmol; prepared according to the procedure Villard et al., *Bioorg. Med. Chem.* (2008) 16:7321-7329) and Et$_3$N (3.4 mL, 24.2 mmol) in THF (25 mL) was added dropwise over 1 h to a stirred solution of N,N-diisopropylphosphorodichloridite (1.0 mL, 5.5 mmol) in THF (35 mL) at −75° C. The mixture was stirred at RT for 4 h. The mixture was filtered, and the filtrate concentrated. The oily residue was purified on silica gel column with EtOAc/hexanes (2-20% gradient) to give 173-3 (1.4 g, 26%).

To a solution of 173-2 (50 mg, 0.08 mmol) and 173-3 (110 mg, 0.11 mmol) in CH$_3$CN (1.0 mL) was added 5-(ethylthio) tetrazole (0.75 mL, 0.16 mmol; 0.25 M in CH$_3$CN). The mixture was stirred at RT for 1 h. The mixture was cooled to −40° C., and a solution of 3-chloroperoxybenzoic acid (37 mg, 0.16 mmol) in CH$_2$Cl$_2$ (0.3 mL) was added. The mixture was warmed to RT over 1 h. The reaction was quenched with 7% Na$_2$S$_2$O$_3$ solution in sat aq. NaHCO$_3$. The mixture was diluted with EtOAc, and the layers were separated. The organic layer was washed with brine and dried with Na$_2$SO$_4$. The solvent was evaporated, and the residue was purified on a silica gel column with EtOAc/hexanes (30-100% gradient) to give 173-4 (52 mg, 45%).

A solution of 173-4 (52 mg, 0.036 mmol) in MeCN (0.5 mL) and HCl (45 μL; 4 N in dioxane) was stirred 20 h at RT. The reaction was quenched with MeOH, and the solvents were evaporated. The residue was co-evaporated with toluene and purified on a silica gel column with MeOH/CH$_2$Cl$_2$ (4-10% gradient) to give 173 (14 mg, 51%). ESI-LCMS: m/z=702 [M+H]$^+$.

Example 100

Compound 174

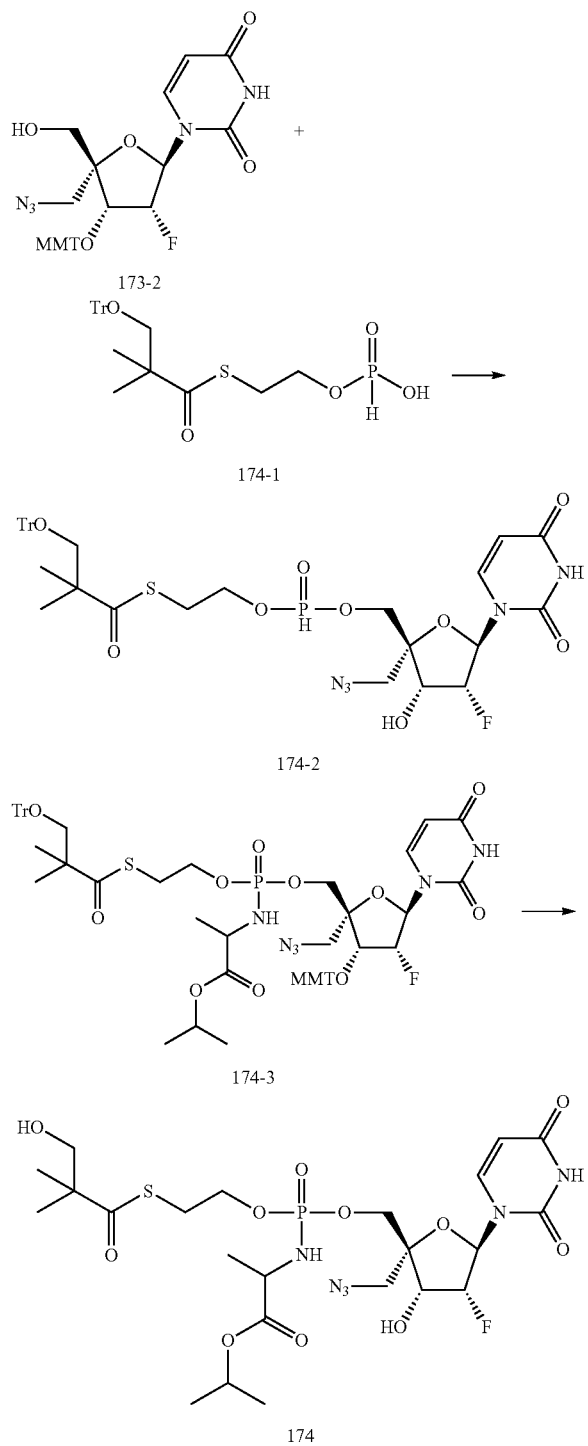

A mixture of 174-1 (0.14 g, 0.24 mmol; prepared according to the procedure described in WO 2008/082601, filed Dec. 28, 2007) and 173-2 (120 mg, 0.2 mmol) was rendered anhydrous by evaporating with pyridine and then dissolved in pyridine (3 mL). Pivaloyl chloride (48 μL) was added dropwise at −15° C. The mixture was stirred at −15° C. for 2 h. The reaction was quenched with sat. aq. NH$_4$Cl solution and diluted with CH$_2$Cl$_2$. The organic layer was washed with brine and dried with Na$_2$SO$_4$. The solvents were evaporated, and the residue was purified on a silica gel column with EtOAc/hexanes (30-100% gradient) to give 174-2 (50 mg, 24%).

A mixture of 174-2 (43 mg; 0.04 mmol) in CCl$_4$ (0.8 mL), L-valine isopropyl ester hydrochloride (20 mg, 0.12 mmol) and Et$_3$N (33 μl, 0.24 mmol) was stirred at RT for 2 h. The mixture was diluted with EtOAc. The mixture was washed with sat. aq. NaHCO$_3$ and brine, and dried with Na$_2$SO$_4$. The solvents were evaporated, and the residue was purified on a silica gel column with i-PrOH/CH$_2$Cl$_2$ (2-10% gradient) to 174-3 (35 mg, 75%).

A solution of 174-3 (35 mg, 0.03 mmol) in MeCN (0.4 mL) and HCl (40 μL; 4 N in dioxane) was stirred 4 h at RT. The reaction was quenched with the addition of MeOH, and the solvents were evaporated. The residue was co-evaporated with toluene and purified on a silica gel column with MeOH/CH$_2$Cl$_2$ (4-10% gradient) to give 174 (11 mg, 56%). ESI-LCMS: m/z=655 [M+H]$^+$.

Example 101

Compound 175

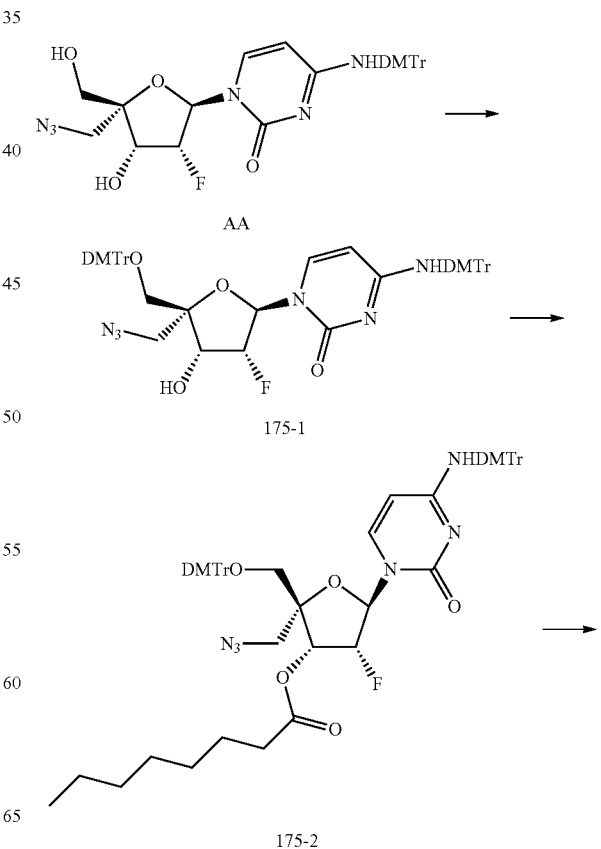

321

-continued

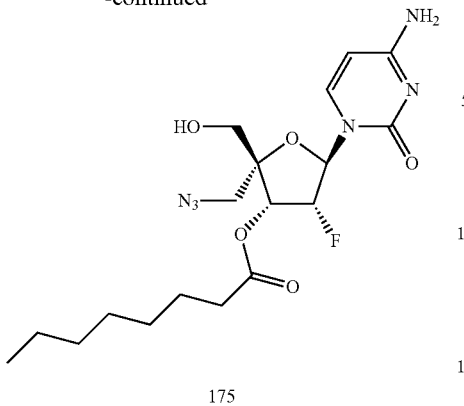

175

To a stirred solution of AA (300.0 mg, 497.83 μmol) in anhydrous pyridine (0.5 mL) was added DMTrCl (337.36 mg, 995.66 μmol) at RT (17° C.) under $N_2$ atmosphere. The solution was stirred at 50° C.-60° C. for 12 h. The mixture was concentrated to dryness under reduced pressure, and the residue was dissolved in EA (40 mL). The solution was washed with brine, dried over anhydrous $MgSO_4$, and concentrated to dryness at low pressure. The residue was purified on a silica gel column using 20% EA in PE to give 175-1 (300 mg, 66.59%) as a white solid.

To a stirred solution of 175-1 (100.00 mg, 110.50 μmol) in anhydrous pyridine (0.5 mL) was added DMAP (6.75 mg, 55.25 μmol), DCC (22.80 mg, 110.50 μmol) and n-octanoic acid (31.87 mg, 221.00 μmol) at RT (18° C.) under $N_2$ atmosphere. The solution was stirred at RT for 12 h. The solution was concentrated to dryness under reduced pressure. The residue was purified on a silica gel column using 15% EA in PE to give 175-2 (98.00 mg, 86.0%) as a white foam.

175-2 (90.00 mg, 87.28 μmol) was dissolved in 80% $CH_3COOH$ (20 mL) at RT (16° C.). The mixture was stirred RT for 12 h. The reaction was quenched with MeOH, and the mixture was concentrated to dryness. The residue was purified on a silica gel column (5% MeOH in DCM) to give 175 (33.00 mg, 88.7%) as a white solid. ESI-MS: m/z 427.2 $[M+H]^+$.

Example 102

Compound 176

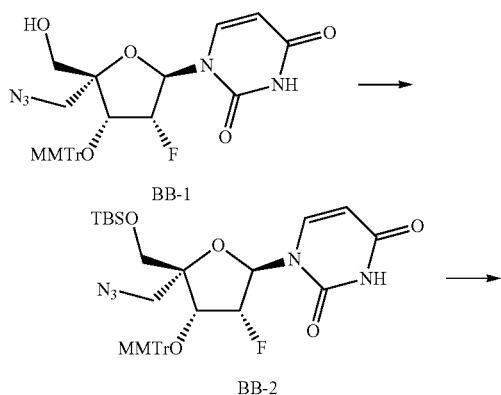

322

-continued

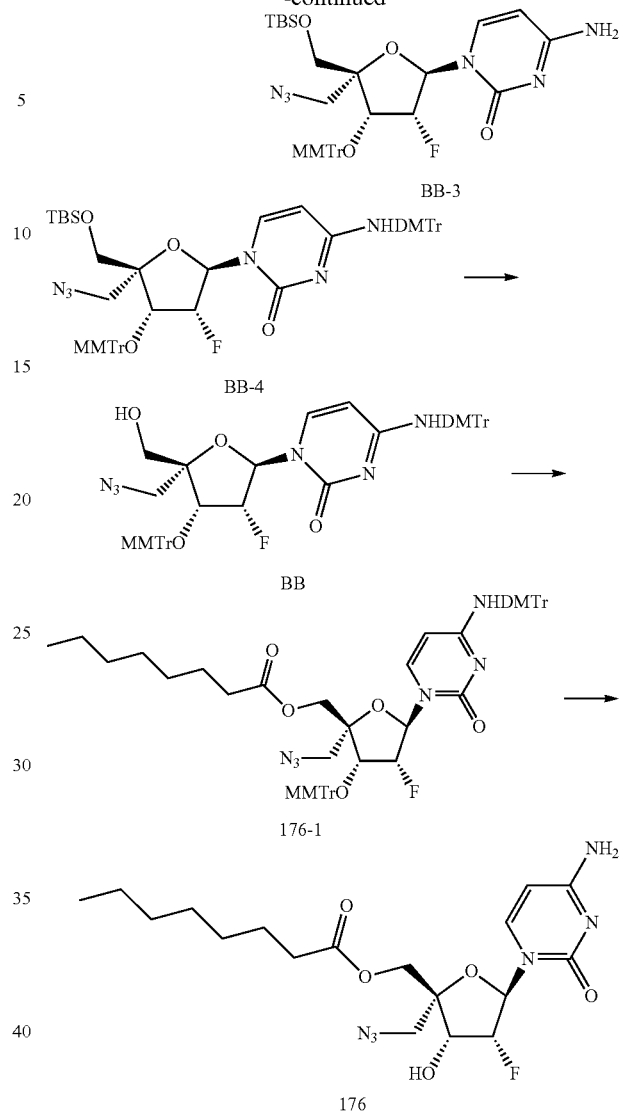

To a stirred solution of BB-1 (500.00 mg, 0.87 mmol) in anhydrous pyridine (1 mL) was added TBSCl (236.5 mg, 1.57 mmol) at 20° C. under $N_2$. The solution was stirred at 50° C.-60° C. for 12 h. The solution was concentrated to dryness under reduced pressure. The residue was dissolved in EA (50 mL). The solution was washed with sat. $NaHCO_3$ solution and brine, and dried over anhydrous $MgSO_4$. The solution was filtered, and the filtrate was concentrated to dryness. The residue was purified on a silica gel column to give BB-2 (510.00 mg, 85.06%) as a white solid.

To a stirred solution of BB-2 (430.00 mg, 625.15 mmol) in anhydrous MeCN (6 mL) was added TPSCl (368.65 mg, 1.25 mmol), DMAP (152.75 mg, 1.25 mmol) and TEA (126.52 mg, 1.25 mmol) at RT. The mixture was stirred for 2 h. $NH_4OH$ (8 mL) was added, and the mixture stirred for 3 h. The mixture was extracted with EA (3×40 mL). The organic phase was washed with brine, dried over anhydrous $Na_2SO_4$ and concentrated at low pressure. The residue was purified on a silica gel column (25% EA in PE) to give BB-3 (500 mg of crude) as a yellow foam.

To a stirred solution of BB-3 (500 mg of crude, 0.72 mmol) in anhydrous DCM (7 mL) was added DMTrCl (365 mg, 1.0 mmol) and collidine (305 mg, 2.5 mmol) and AgNO₃ (184 mg, 1.08 mmol) at RT (15° C.) under N₂ atmosphere. The mixture was stirred at RT for 12 h. MeOH (5 mL) was added. The mixture was filtered, and the filtrate was concentrated to dryness. The residue was dissolved in EA (50 mL). The solution was washed with brine, dried over anhydrous Na₂SO₄ and concentrated at low pressure. The residue was purified on a silica gel column (5% MeOH in DCM) to give BB-4 (500 mg, 70.3%) as a white solid.

BB-4 (1.00 g, 1.01 mmol) was dissolved in TBAF (5 mL, 1M in THF) and stirred at RT for 30 mins. The mixture was diluted with EA (100 mL). The mixture was washed with water and brine, and dried over anhydrous MgSO₄. The organic phase was concentrated to dryness. The residue was purified on the silica gel column (30% EA in PE) to give BB (0.80 g, 91.5%) as a white solid. ESI-MS: m/z 873.7 [M+1]⁺.

To a solution of BB (100.00 mg, 114.29 μmol) in anhydrous pyridine (1.5 mL) was added DMAP (2.79 mg, 22.86 μmol), DCC (70.75 mg, 342.88 μmol) and n-octanoic acid (49.45 mg, 342.88 μmol) at RT (18° C.) under N₂ atmosphere. The solution was stirred at RT for 12 h. The solution was concentrated to dryness under reduced pressure. The residue was purified on a silica gel column using 15% EA in PE to give 176-1 (95.00 mg, 83.03%) as a white foam.

176-1 (110.00 mg, 109.87 μmol) was dissolved in 80% CH₃COOH (25 mL) at RT (15° C.). The mixture was stirred for 12 h. The reaction was quenched with MeOH, and the solution was concentrated to dryness. The residue was purified on a silica gel column (5% MeOH in DCM) to give 176 (30.00 mg, 64.03%) as a white solid. ESI-MS: m/z 427.2 [M+H]⁺.

Example 103

Compound 177

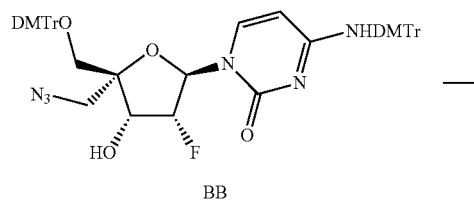

BB

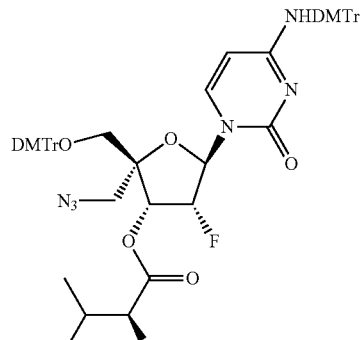

177-1

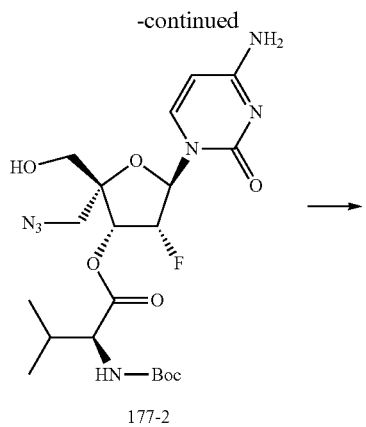

177-2

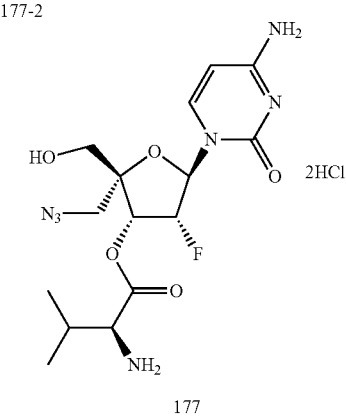

177

177-1 was prepared in similar manner as 143-1 using BB (250.0 mg, 276.25 μmol), (2S)-2-(tert-butoxycarbonylamino)-3-methyl-butanoic acid (360.11 mg, 1.66 mmol) and TEA (83.86 mg, 828.75 μmol). 177-1 (white foam, 220.0 mg, 72.12%).

177-2 was prepared in similar manner as 143-2 using 177-1 (230.00 mg, 208.29 μmol, 1.00 eq.). 177-2 (white foam, 80.00 mg, 77.66%).

177 was prepared in similar manner as 143 using 177-2 (100.00 mg, 200.20 μmol, 1.00 eq.). 177 (white solid, 56 mg, 59.57%). ESI-MS: m/z 400.0 [M+H]⁺, 422.1 [M+Na]⁺; 799.1 [2M+H]⁺, 821.2 [2M+Na]⁺.

Example 104

Compound 178

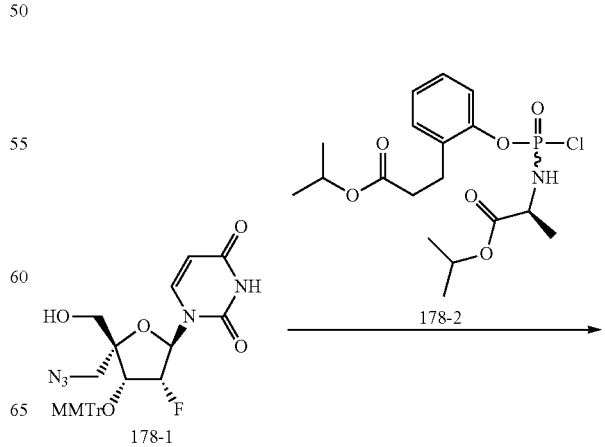

178-1

-continued

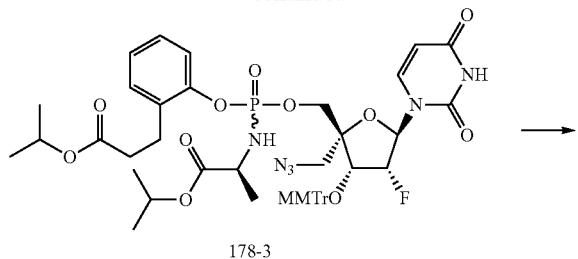
178-3

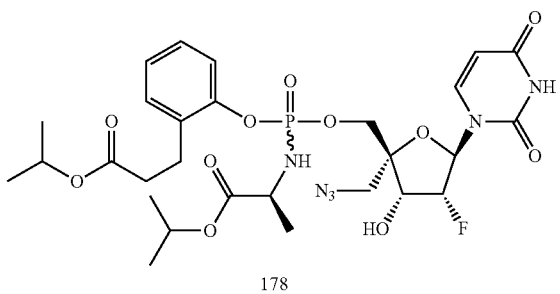
178

To a stirred solution of 178-1 (100 mg, 0.175 mmol) in anhydrous CH₃CN (2.0 mL) was added N-methylimidazole (0.14 mL, 1.4 mmol) at 0° C. (ice/water bath). A solution of 178-2 (220 mg, 0.53 mmol, dissolved in 0.5 mL of CH₃CN), (prepared according to a general procedure described in Bondada, L. et al., *ACS Medicinal Chemistry Letters* (2013) 4(8):747-751) was added. The solution was stirred at 0 to 5° C. for 1 h and then stirred at RT for 16 h. The mixture was cooled to 0 to 5° C., diluted with EA followed by addition of water (5 mL). The solution was washed with 1.0M citric acid, sat. aq. NaHCO₃ and brine, and dried with MgSO₄. The residue was purified on silica (10 g column) with EA/hexanes (25-100% gradient) to give 178-3 (56.4 mg, 33.7%) as a white foam.

178-3 (56 mg, 0.0585 mmol) was dissolved in anhydrous CH₃CN (0.7 mL), and 4N HCl in dioxane (44 µL, 0.176 mmol) was added at 0 to 5° C. The mixture was stirred at RT for 2 h. 4N HCl in dioxane (20 µL) was added. The mixture was stirred at RT for 2 h. Anhydrous EtOH (100 µL) was added. The solvents were evaporated at RT and co-evaporated with toluene (3×). The residue was purified on silica (10 g column) with MeOH/CH₂Cl₂ (1-7% gradient) and lyophilized to give 178 (27.6 mg, 69%) as a white foam. ESI-LCMS: m/z=685.2[M+H]⁺.

Example 105

Compound 179

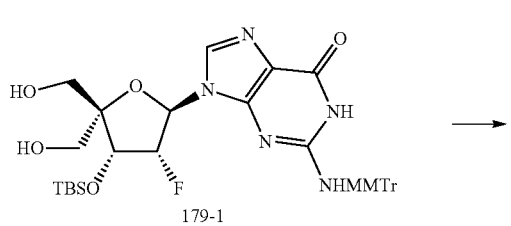
179-1

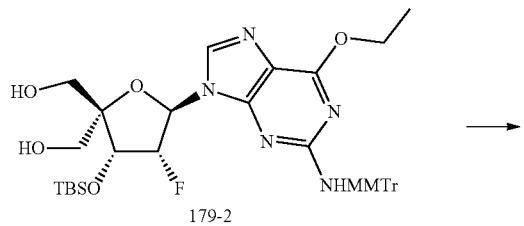
179-2

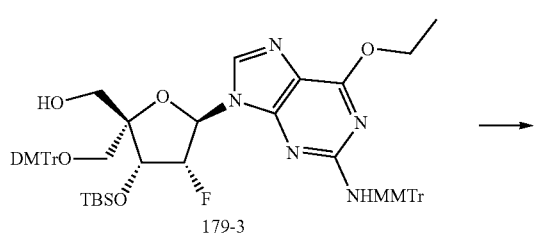
179-3

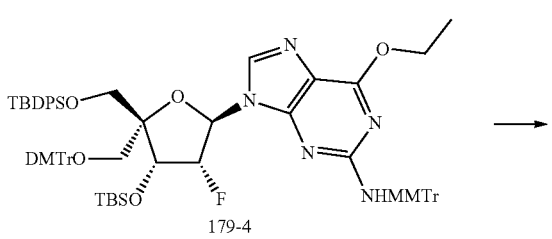
179-4

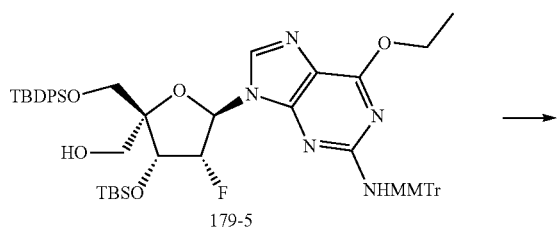
179-5

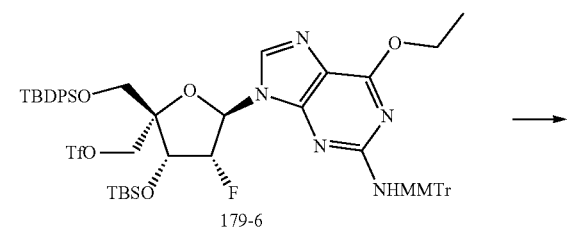
179-6

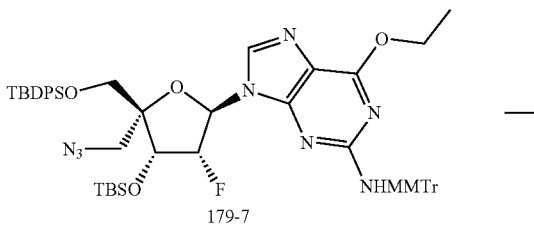
179-7

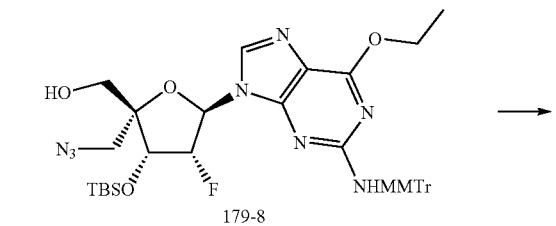
179-8

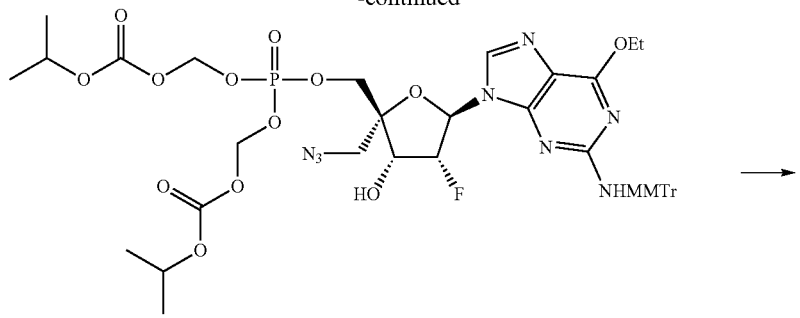

179-9

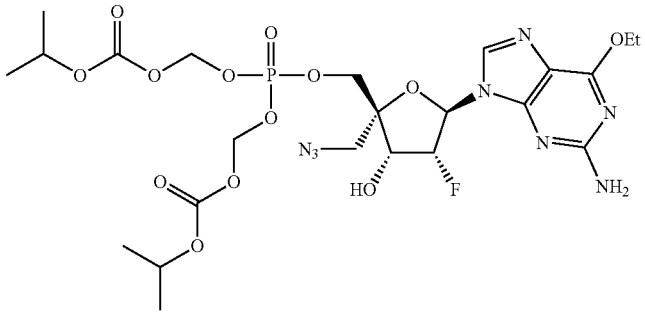

179

To a stirred solution of 179-1 (1.92 g, 27.3 mmol), PPh₃ (1.43 g, 54.7 mmol), EtOH (0.25 g, 54.7 mmol) in anhydrous dioxane (20 mL) was added DIAD (1.11 g, 54.7 mmol) dropwise at 0° C. The solution was stirred at 25° C. for 15 h. The reaction was quenched with water and extracted with EA. The mixture was washed with water and brine. The organic layer was dried over Na₂SO₄ and filtered. The filtrate was concentrated in vacuum to dryness, and the residue was purified on a silica gel column (2% to 5% MeOH in DCM) to give 179-2 (1.43 g, 71%) as a white foam.

To a stirred solution of 179-2 (1.43 g, 19.6 mmol) in DMF (15 mL) was added TEA (0.59 g, 58.8 mmol) and DMTrCl (0.99 g, 29.4 mmol) at 0° C. The solution was stirred at 25° C. for 12 h. The mixture was treated with MeOH (1 mL), and diluted with EA. The solution was washed with water and brine. The organic layer was dried over anhydrous NaSO₄, and concentrated to dryness. The residue was purified on a silica gel column (2% MeOH in DCM) to give 179-3 (1.13 g, 56%) as a yellow solid.

To a stirred solution of 179-3 (1.13 g, 1.1 mmol) in anhydrous pyridine (10 mL) was added TBDPSCl (0.91 g, 3.3 mmol) and AgNO₃ (0.61 g, 3.3 mmol). The mixture was stirred at 25° C. for 15 h. The solid was removed by filtration, and the filtrate was diluted with EA (50 mL). The solution was washed with brine. The organic layer was dried over anhydrous Na₂SO₄, and concentrated at low pressure. The residue was purified on a silica gel column (2% MeOH in DCM) to give 179-4 (1.22 g, 88%) as a white foam.

To a stirred solution of 179-4 (1.22 g, 1.0 mmol) in anhydrous DCM (15 mL) was added Cl₂CHCOOH (0.6 mL) at −78° C. The mixture was stirred at −20° C. for 1 h. The reaction was quenched with sat. aq. NaHCO₃ and extracted with DCM. The organic layer was dried over anhydrous Na₂SO₄, and concentrated at low pressure. The residue was purified by column chromatography (2% MeOH in DCM) to give 179-5 (0.52 g, 56%) as a white foam.

To a stirred solution of 179-5 (0.52 g, 0.5 mmol) in anhydrous DCM (15 mL) and pyridine (0.21 g, 2.5 mmol) was added Tf₂O (0.30 g, 1.0 mmol) in DCM (1 mL) dropwise at 0° C. The mixture was stirred at 0° C. for 15 mins. The reaction was quenched with ice water. The organic layer was separated and washed with water. The organic layer was dried over anhydrous Na₂SO₄ and concentrated at low pressure to give 179-6 (442 mg crude) as a yellow foam.

To a stirred solution of 179-6 (442 mg, 0.4 mmol) in anhydrous DMF (5 mL) was added NaN₃ (131 mg, 2.0 mmol). The mixture was stirred at RT for 12 h. The reaction was quenched with water and extracted by EA (20 mL, (2×)). The organic layer was washed with water and dried over Na₂SO₄. The organic phase was evaporated to dryness under reduced pressure. The residue was purified on a silica gel column (1% MeOH in DCM) to give 179-7 (352 mg, 88%) as a white foam.

A mixture of 179-7 (352 mg, 0.35 mmol) and NH₄F (392 mg, 10.6 mmol) in MeOH (10 mL) was stirred at 80° C. for 12 h. The mixture was cooled to RT. The solid was removed by filtration. The solvent was concentrated under reduced pressure. The residue was purified on a silica gel column (2% to 5% MeOH in DCM) to give crude 179-8 (151 mg). The crude product was purified by prep-HPLC (0.1% NH₄HCO₃ in water and CH₃CN) to give 179-8 (71.5 mg, 32%) as a white solid. MS: m/z 641[M+H]⁺.

A mixture of 179-8 (64 mg, 0.1 mmol) and bis(pivaloyloxymethyl)phosphate, after rendered anhydrous by evaporating with toluene, was dissolved in CH₃CN (1 mL) and cooled to 0° C. BopCl (40 mg, 0.15 mmol) and NMI (40 μL, 0.5 mmol) were added. The mixture was stirred at 0° C. for 2 h. EtOAc was added, and the mixture was washed with 0.5 N aq. citric acid, sat. aq. NaHCO₃ and brine, and then dried with Na₂SO₄. The solvents were removed, and the residue was purified on a silica gel column with 3% i-PrOH in CH₂Cl₂ to 179-9 (38 mg, 40%).

A solution of 179-9 (30 mg, 0.03 mmol) in CH₃CN (0.3 mL) and HCl (30 µL; 4 N dioxane) was stirred at RT for 100 mins. The reaction was quenched with EtOH, and the mixture was evaporated. The crude residue was purified on a silica gel column with i-PrOH/CH₂Cl₂ (3-10% gradient) to yield 179 (10 mg, 50%). ESI-LCMS: m/z=681 [M+H]⁺.

Example 106

Compound 180

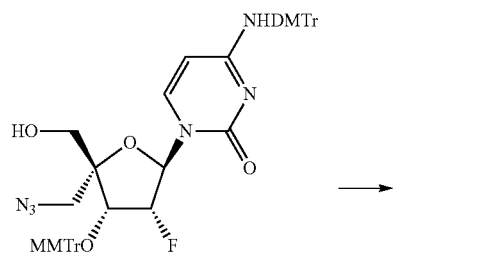

BB


180-1

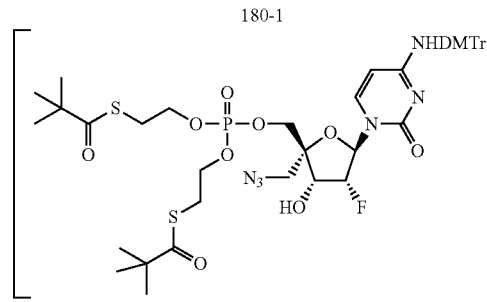

180-2

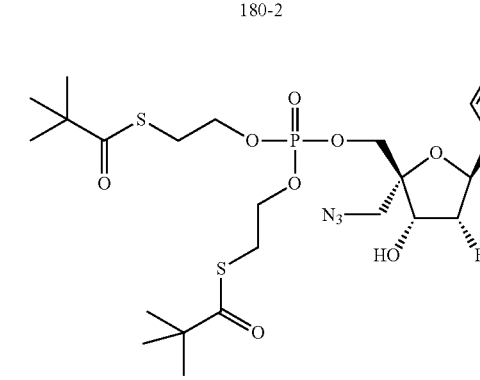

180

To a solution of BB (100 mg, 0.114 mmol) in anhydrous CH₃CN (2 mL) were added a solution of bis-SATE-phosphoroamidate (62.2 mg, 0.14 mmol) in CH₃CN (1 mL) followed by 5-ethylthio-1H-tetrazole in CH₃CN (0.25M; 0.56 mL, 0.14 mmol) at 0 to 5° C. dropwise. The mixture was stirred 2 h at 0 to 5° C. under Ar. A solution of 77% m-CPBA (49 mg, 0.22 mmol) in DCM (1 mL) was added, and the mixture was stirred 2 h at 0 to 5° C. under Ar. The mixture was diluted with EtOAc (50 mL), washed with 1.0M citric acid, sat. NaHCO₃, and brine, and dried with MgSO₄. The mixture was filtered and the solvents were evaporated in vacuo. The residue was purified on silica (10 g column) with EA/hexanes (10-100% gradient) to give 180-1 (72 mg, 50.8%) as a white solid.

180-1 (72 mg, 0.056 mmol) was dissolved in anhydrous CH₃CN (1.0 mL), and 4N HCl in dioxane (87 µL, 0.35 mmol) was added at 0 to 5° C. The mixture was stirred at RT for 2 h. Intermediate 180-2 was observed by LCMS. The solvents were evaporated at RT and co-evaporated with toluene (3×). The residue obtained was re-dissolved in 80% HCOOH (2 mL). The mixture was stirred at RT for 4.5 h. The solvents were evaporated at RT and co-evaporated with toluene (3×). Anhydrous EtOH (3×5 mL) was added. The residue was dissolved in 50% CH₃CN/H₂O, purified on a reverse-phase HPLC (C18) using CH₃CN and H₂O, and lyophilized to give 180 (19.2 mg) as a white foam. ESI-LCMS: m/z=669.2 [M+H]⁺, 1337.25 [2M+H]⁺.

Example 107

Compound 181

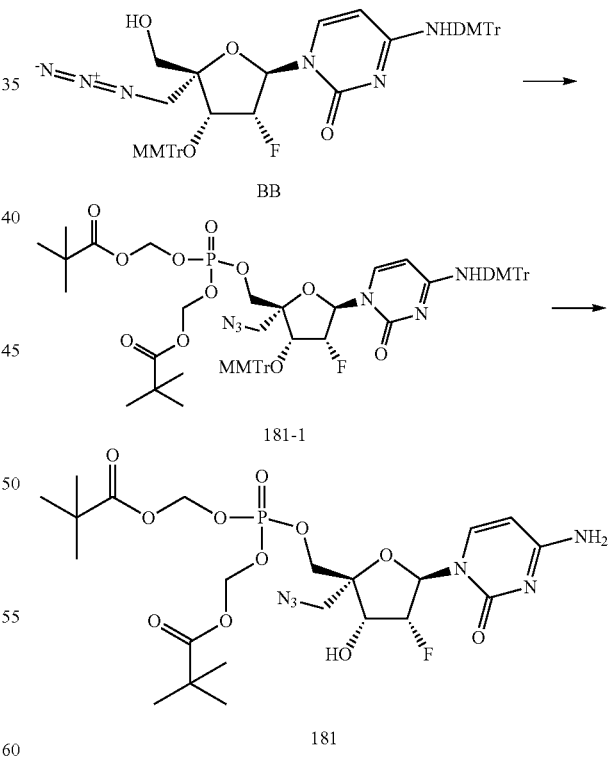

181-1 (98 mg, 72.6%) was prepared in the same manner from BB (100 mg, 0.114 mmol) and bis(tert-butoxycarbonyloxymethyl)phosphate (83 mg, 0.35 mmol) with DIPEA (126 µL, 0.69 mmol), BOP-Cl (87 mg, 0.34 mmol), and 3-nitro-1,2,4-triazole (39 mg, 0.34 mmol) in THF (1.5 mL) in the same manner as 169-4.

181 (30.2 mg, 60%) was prepared from 181-1 (98 mg, 0.083 mmol) in the same manner as 146. ESI-LCMS: m/z=609.15 [M+H]⁺, 1217.3 [2M+H]⁺.
Example 108
Compounds 182 and 183
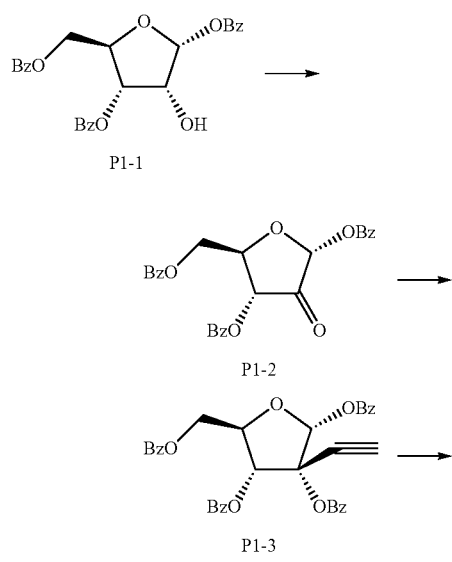
-continued
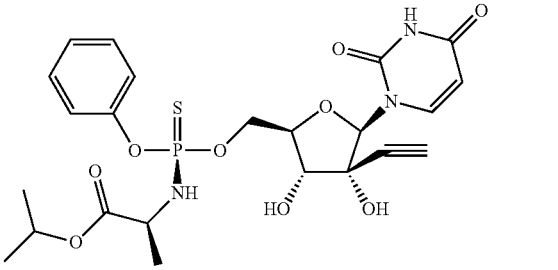
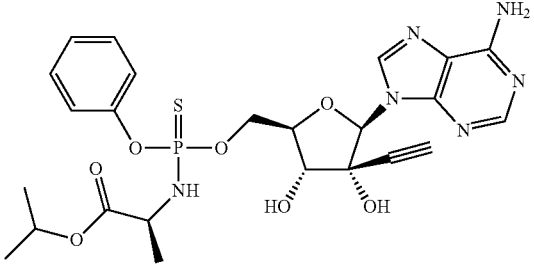
Compounds 182, 182aa, 182ab and 183 were prepared as described in PCT Publication No. WO 2014/96680, published Jun. 27, 2014. 182: ESI-LCMS: m/z 554.0 [M+H]⁺; 182aa and 182ab: Faster eluting diastereomer—$^{31}$P NMR 67.1, LC/MS 552 [M−1]⁻ Slower eluting diastereomer—$^{31}$P NMR 67.9, LC/MS 552 [M−1]. 183: ESI-MS: m/z 576.9 [M+H]⁺.
Example 109
Compounds 186-201
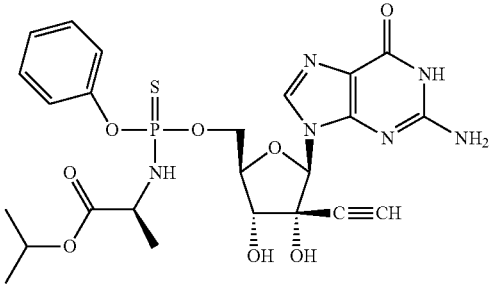
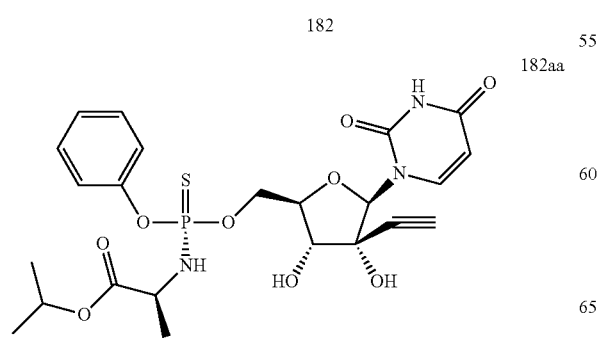
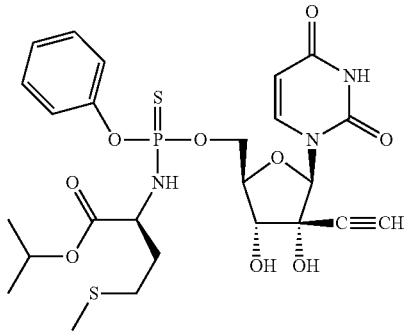

333
-continued
188
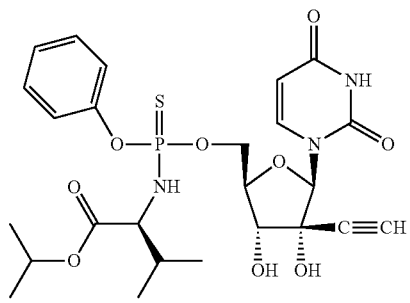
189
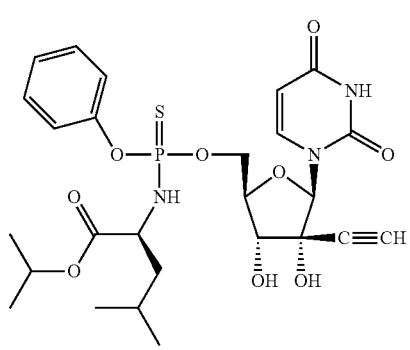
190
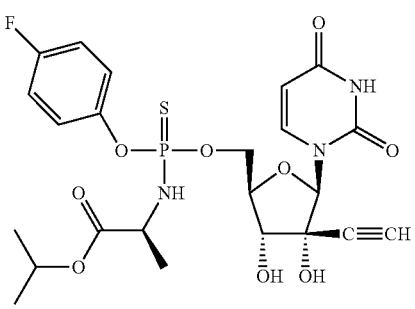
191
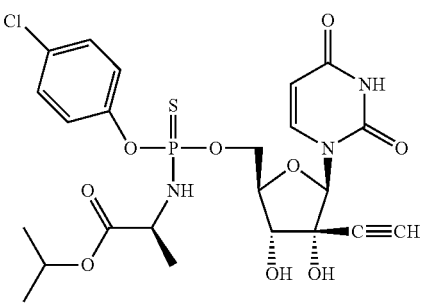
192
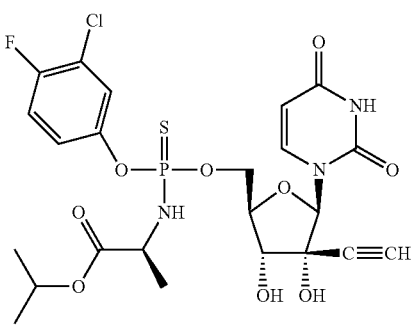
334
-continued
193
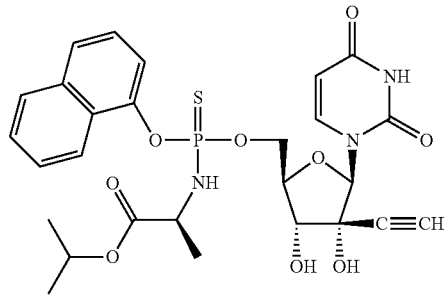
194
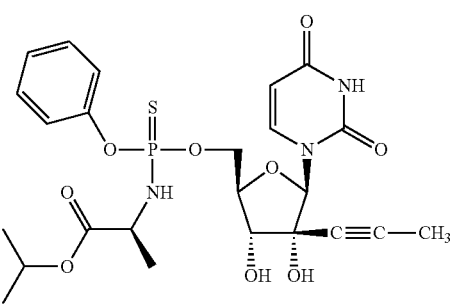
195
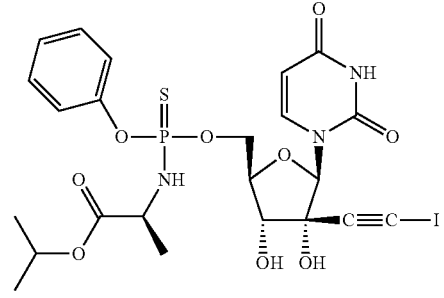
196
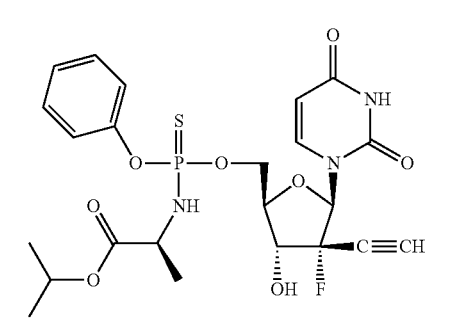
197
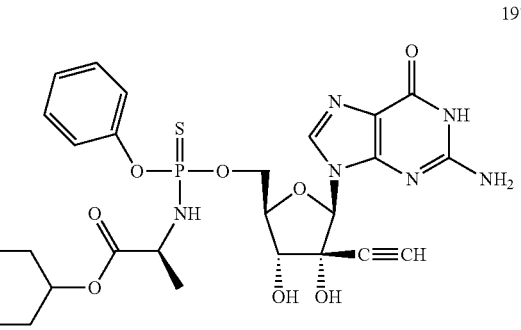

335
-continued

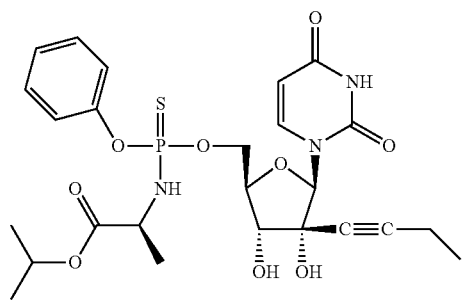
198

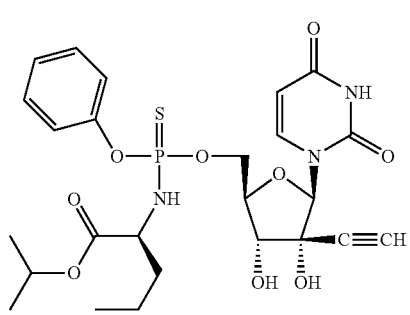
199

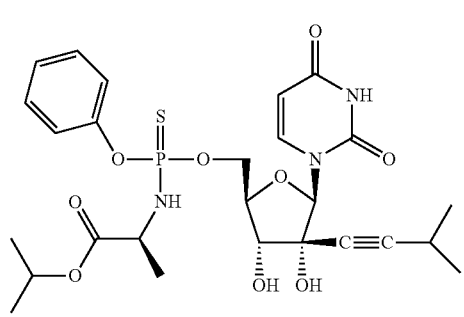
200

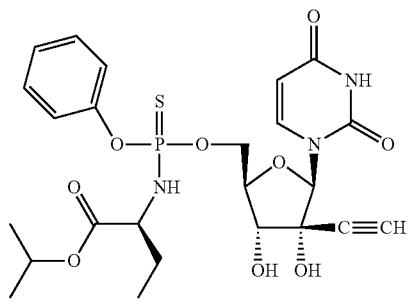
201

Compounds 186-201 were prepared as described in PCT Publication No. WO 2014/96680, published Jun. 27, 2014. 186: ESI-LCMS: m/z 593.0 [M+H]+. 187: ESI-LCMS: m/z 614.1 [M+H]+. 188: ESI-LCMS: m/z 582.1 [M+H]+. 189: ESI-LCMS: m/z 596.1 [M+H]+. 190: ESI-LCMS: m/z 672.0 [M+H]+. 191: ESI-LCMS: m/z 589.0 [M+H]+. 192: ESI-LCMS: m/z 606.0 [M+H]+. 193: ESI-LCMS: m/z 604.1 [M+H]+. 194: ESI-LCMS: m/z 568 [M+H]+, 590 [M+Na]+. 195: ESI-LCMS: m/z 680 [M+H]+. 196: ESI-LCMS: m/z 578.0 [M+Na]+. 197: ESI-MS: m/z 633.1 [M+H]+. 198: ESI-LCMS: m/z 604 [M+Na]+, 582 [M+H]+. 199: ESI-LCMS: m/z 582.0 [M+H]+. 200: ESI-LCMS: m/z 618 [M+Na]+. 201: ESI-LCMS: m/z 568.1 [M+H]+.

336

Example 110

Compound 204

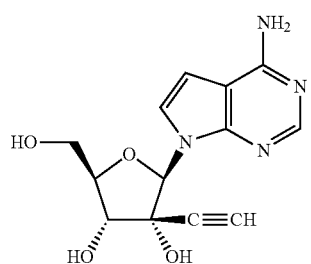
204

A method for preparing compound 204 is provided in WO 2010/015643, filed Aug. 4, 2009.

Example 111

Compound 206

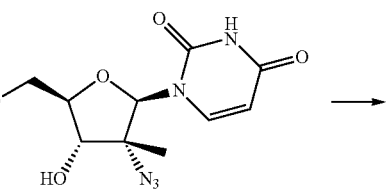
206-1

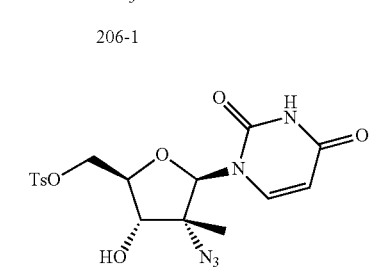
206-2

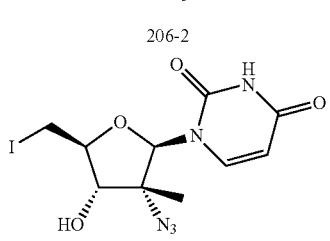
206-3

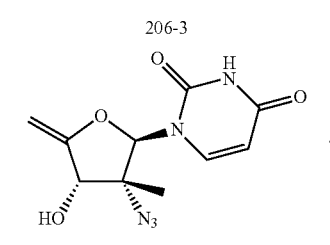
206-4

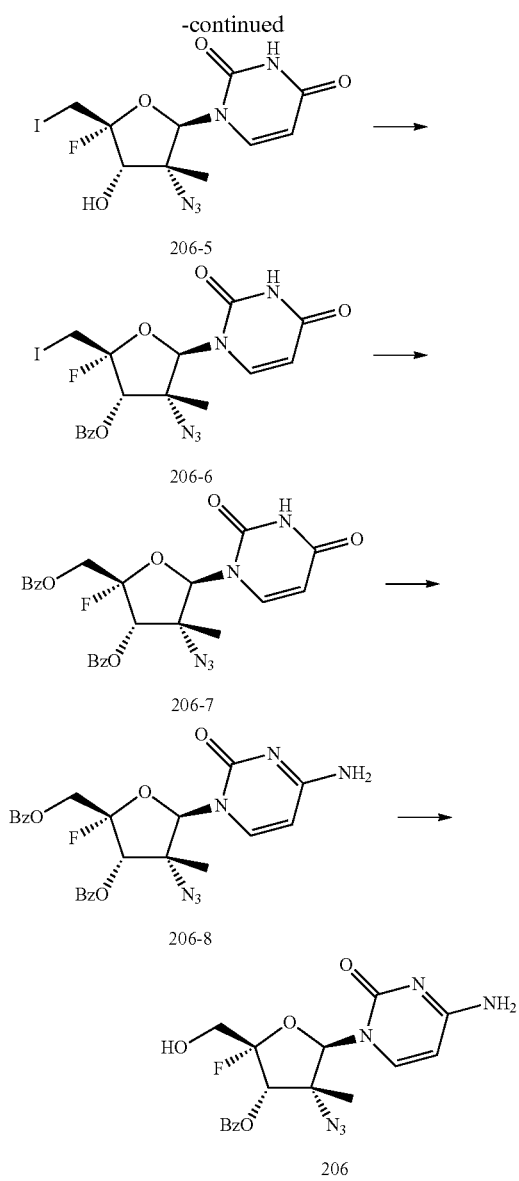

206-1 (1.0 g, 3.53 mmol) was coevaporated with anhydrous pyridine 3 times to remove H₂O. To an ice-cold solution of 206-1 in anhydrous pyridine (9 mL) was added TsCl (808 mg, 4.24 mmol) in pyridine (3 mL) drop-wise at 0° C., and the mixture was stirred for 18 h. at 0° C. The reaction was monitored by LCMS, and then quenched with H₂O. After concentration at low pressure, the residue was dissolved in EA (50 mL). The solution was washed with sat. NaHCO₃ solution and brine. The organic layer was dried over anhydrous Na₂SO₄ and filtered. The filtrate was evaporated at low pressure, and the residue was purified by silica gel column chromatography (1% MeOH in DCM) to give 206-2 (980 mg, 63%) as a white solid.

To a solution of 206-2 (980 mg, 2.24 mmol) in acetone (10 mL) was added NaI (1.01 g, 6.73 mmol), and the mixture was heated to reflux overnight. The reaction was monitored by LCMS. After the reaction was completed, the mixture was concentrated at low pressure. The residue was dissolved in EA (50 mL). The solution was washed with brine, and dried over anhydrous Na₂SO₄. The solution was evaporated at low pressure, and the residue was purified by silica gel column chromatography (1% MeOH in DCM) to give 206-3 (700 mg, 79%) as a solid.

To a solution of 206-3 (700 mg, 1.78 mmol) in dry THF (9 mL) was added DBU (817 mg, 5.34 mmol), and the mixture was heated to 60° C. The mixture was stirred overnight, and monitored by LCMS. The reaction was quenched with sat. NaHCO₃ and extracted with EA (3×50 mL). The organic phase was dried over anhydrous Na₂SO₄, and filtered. The filtrate was evaporated at low pressure, and the residue was purified by silica gel column chromatography (1% MeOH in DCM) to give 206-4 (250 mg, 53%) as a white solid.

To an ice-clod solution of 206-4 (250 mg, 0.94 mmol) in dry MeCN (5 mL) was added NEt₃-3HF (151 mg, 0.94 mmol) and NIS (255 mg, 1.13 mmol). The mixture was stirred at RT for 3 h., and checked by LCMS. The reaction was quenched with sat Na₂S₂O₃ and sat. NaHCO₃ solution, and extracted with EA (3×50 mL). The organic layer was separated, dried over anhydrous Na₂SO₄, and evaporated at low pressure. The residue was purified by silica gel column chromatography (2% acetone in DCM) to give 206-5 (170 mg, 44%).

To a solution of 206-5 (270 mg, 0.65 mmol) in dry DCM (4 mL) was added DMAP (158.6 mg, 1.3 mmol), and BzCl (137 mg, 0.98 mmol). The mixture was stirred for 4-5 h. at RT and checked by LCMS. The mixture was diluted with CH₂Cl₂, and washed with sat. NaHCO₃ solution and brine. The organic layer was evaporated at low pressure, and the residue was purified by silica gel column chromatography (20% EA in PE) to give 206-6 (290 mg, 86%) as a solid.

To a solution of 206-6 (900 mg, 1.74 mmol) in dry DMF (45 mL) was added NaOBz (2.5 g, 17.4 mmol) and 15-crown-5 (4.5 g, 20.9 mmol). The mixture was stirred for 48 h at 90-100° C. The mixture was diluted with EA (100 mL), and washed with brine. The organic layer was evaporated at low pressure, and the residue was purified by silica gel column chromatography (20% EA in PE) to give 206-7 (500 mg, 56%) as a solid.

To a solution of 206-7 (500 mg, 0.98 mmol) in anhydrous CH₃CN (5 mL) was added TPSCl (741 mg, 2.45 mmol), DMAP (299.6 mg, 2.45 mmol) and NEt₃ (248 mg, 2.45 mmol) at RT, and the mixture was stirred overnight. The mixture was then treated with NH₃ in THF (5 mL) and then stirred for another 30 mins. The mixture was diluted with EA (100 mL). The solution was washed with 0.5% AcOH solution. The organic solvent was dried over anhydrous MgSO4, and concentrated at low pressure. The crude product was purified by silica gel column chromatography (2% Acetone in DCM) to give 206-8 (257 mg, 51.6%) as a white solid. ESI-MS: m/z 509 [M+H]⁺.

206-8 (80 mg, 0.16 mmol) was dissolved in n-butylamine (3 mL). The mixture was kept overnight at RT and evaporated. The residue was crystallized from methanol to give 206 (30 mg). The mother liquor was purified by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer to yield additional 206 (13 mg). 206 (total yield 43 mg, 73%). MS: m/z 299.7 [M−1]⁻.

Example 112

Compound 207

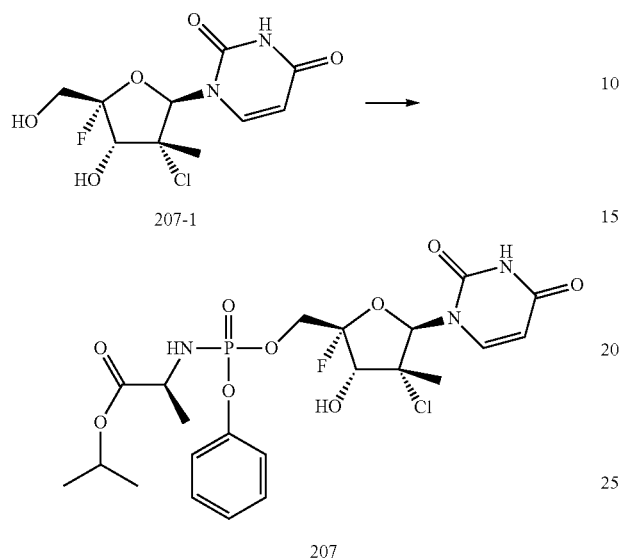

207-1 (30 mg, 0.1 mmol) was dissolved in a mixture of CH$_3$CN (2 mL) and N-methylimidazole (200 µL). Phosphorochloridate (100 mg, 0.3 mmol) was added, and the mixture was kept for 5 d at RT. The mixture was distributed between water and EA. The organic layer was separated, washed with brine, dried and evaporated. The phosphoroamidate was isolated by silica gel chromatography in a gradient of methanol in DCM from 3% to 10%. The corresponding fractions were concentrated and re-purified by RP HPLC on Synergy 4 micron Hydro-RP column (Phenominex). A linear gradient of methanol in DCM from 3% to 95% containing 0.1% formic acid was used for elution. 207 was obtained as a mixture Rp and Rs isomers (9 mg, 16%). MS: m/z 562.1[M−1]⁻.

Example 113

Compound 211

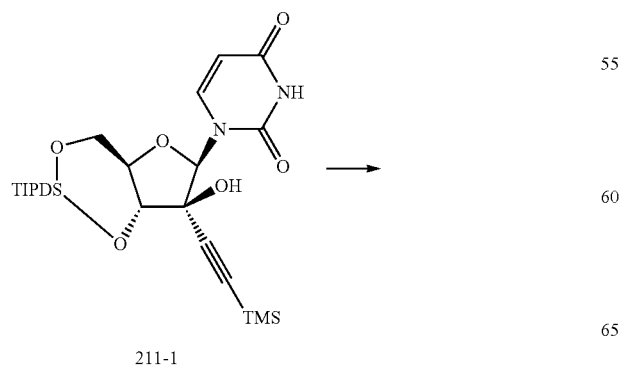

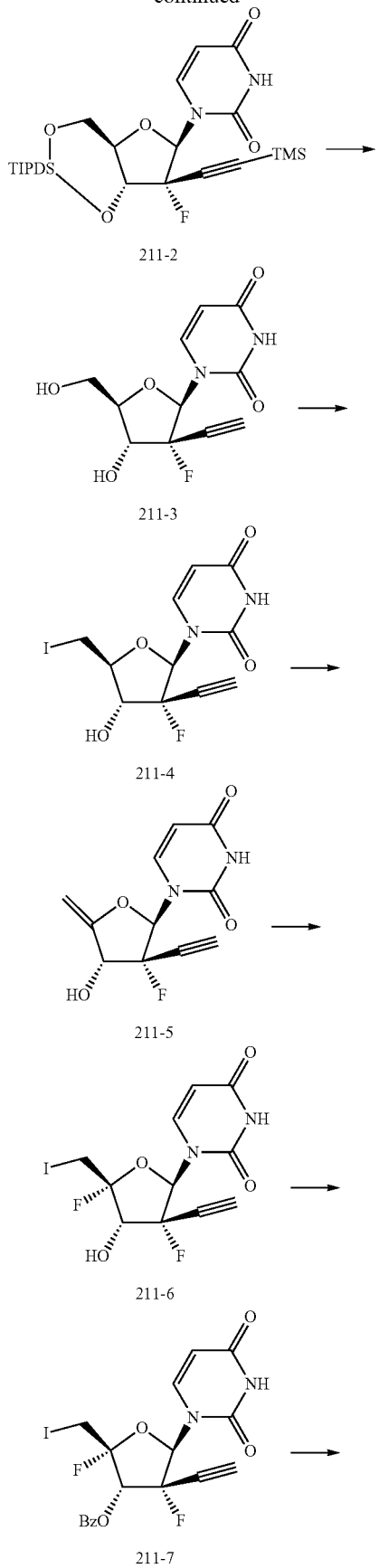

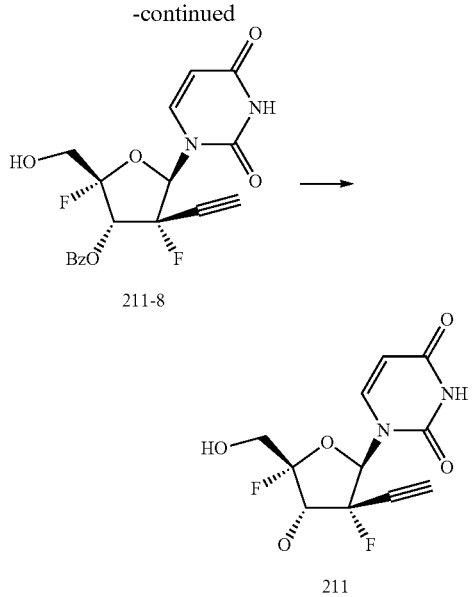

To a solution of 211-1 (23.0 g, 39.5 mmol) in anhydrous toluene (200 mL) was added DAST (31.9 g, 198 mmol) dropwise at −78° C., and the solution was stirred at −78° C. for 3 h. The mixture was quenched with sat. NaHCO$_3$, extracted with EA (2×200 mL) and dried over with anhydrous Na$_2$SO$_4$. The solution was concentrated to dryness under low pressure. The residue was purified on a silica gel column (50% EA in PE) to give 211-2 (16.5 g, 71%) as a yellow foam.

A mixture of 211-2 (16.0 g, 27.4 mmol) and NH$_4$F (3.0 g, 82.2 mmol) in methanol (100 mL) was stirred at 70° C. for 12 h. The reaction was cooled, and the salt was removed by filtration. The filtrate was concentrated to dryness at low pressure. The residue was purified on a silica gel column (3% MeOH in DCM) to give 211-3 (5.1 g, 69.0%) as a white foam.

To a stirred suspension of 211-3 (4.1 g, 15.2 mmol), PPh$_3$ (8.0 g, 30.4 mmol), imidazole (2.1 g, 30.4 mmol) and pyridine (18.2 mL) in anhydrous THF (40 mL) was added dropwise a solution of I$_2$ (5.8 g, 22.8 mmol) in THF (20 mL) at 0° C. The mixture was stirred at RT for 12 h. The reaction was quenched with MeOH (100 mL), and the solvent was removed under reduced pressure. The residue was purified on a silica gel column (4% MeOH in DCM) to give pure 211-4 (4.4 g, 77%) as a white solid. ESI-MS: m/z 381.1 [M+1]$^+$.

To a stirred solution of 211-4 (2.5 g, 0.7 mmol) in anhydrous THF (3 mL) was added DBU (2.1 g, 14 mmol) at RT, and the mixture was stirred at RT for 1 h. The reaction was quenched with HOAc, and diluted with 2-Me-tetrahydrofuran. The solution was washed with brine, dried over with anhydrous Na$_2$SO$_4$ and concentrated to dryness at low pressure. The residue was purified on a silica gel column (MeOH 5% in DCM) to give 211-5 (1.1 g, 68.9%) as a white foam.

To a stirred solution of 211-5 (800 mg, 3.17 mmol) in anhydrous CH$_3$CN (10 mL) was added TEA.3HF (510 mg, 3.17 mmol) and NIS (785 mg, 3.49 mmol) at 0° C. The mixture was stirred for 30 mins, gradually warmed to RT and stirred for 1 h. The mixture was quenched with sat. NaHCO$_3$ solution and Na$_2$S$_2$O$_3$ solution, and extracted with EA (2×20 mL). The organic layer was dried over with anhydrous Na$_2$SO$_4$, and concentrated to dryness at low pressure. The residue was purified on a silica gel column to give pure 211-6 (695 mg, 57.9%) as a yellow solid.

To a stirred solution of 211-6 (650 mg, 1.63 mmol) in pyridine (3 mL) was added BzCl (507 mg, 3.59 mmol) at 0° C., and stirred at RT for 12 h. The mixture was quenched with water, and concentrated to dryness under reducing pressure. The residue was purified on a silica gel column (EA 50% in PE) to yield 211-7 (550 mg, 67%) as a white foam.

Tetra-butylammonium hydroxide (9 mL as 54-56% aqueous solution, 72 mmol) was neutralized with TFA to pH~4 (1.5 mL), and the mixture was added to a solution of 211-7 (375 mg, 0.75 mmol) in DCM (9 mL). m-Chloroperbenzoic acid (924 mg, 60-70%, 3.75 mmol) was added in portions with vigorous stirring, and the mixture was stirred overnight. The mixture was washed with brine, dried over magnesium sulfate and concentrated under reduced pressure. The residue was purified by column chromatography (EA 50% in PE) to give 211-8 (230 mg, 78.8%) as a white foam. ESI-MS: m/z 393.1 [M+1]$^+$.

211-8 (120 mg, 0.24 mmol) was treated with 7N NH$_3$.MeOH (20 mL), and stirred for 5 h. The mixture was concentrated to dryness at low pressure. The residue was purified on a silica gel column (propan-2-ol 15% in DCM) to yield 211 (53 mg, 60.2%) as a white solid. ESI-MS: m/z 288.8 [M+1]$^+$.

Example 114

Compounds 212a and 212b

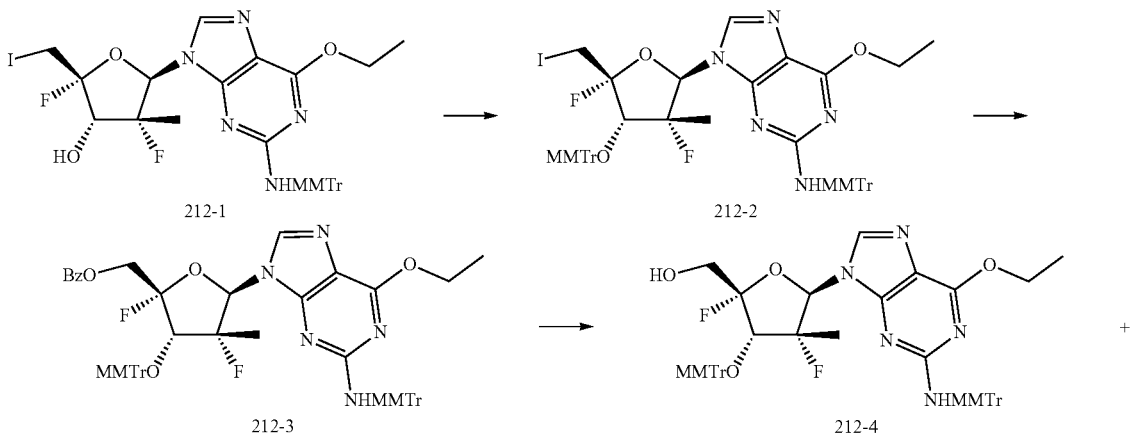

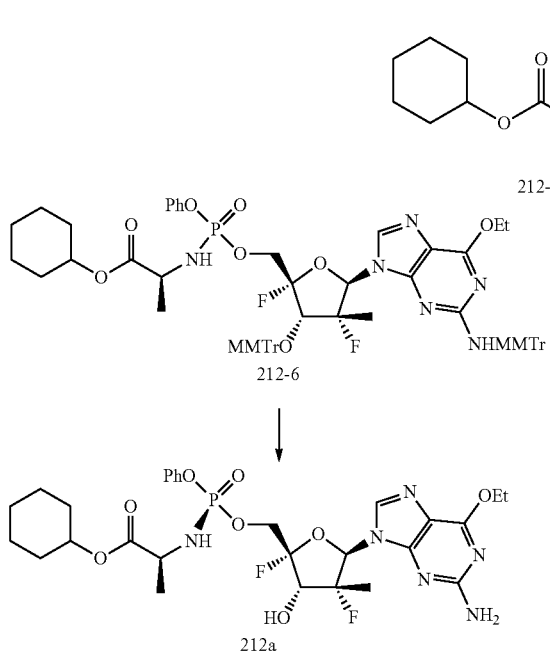
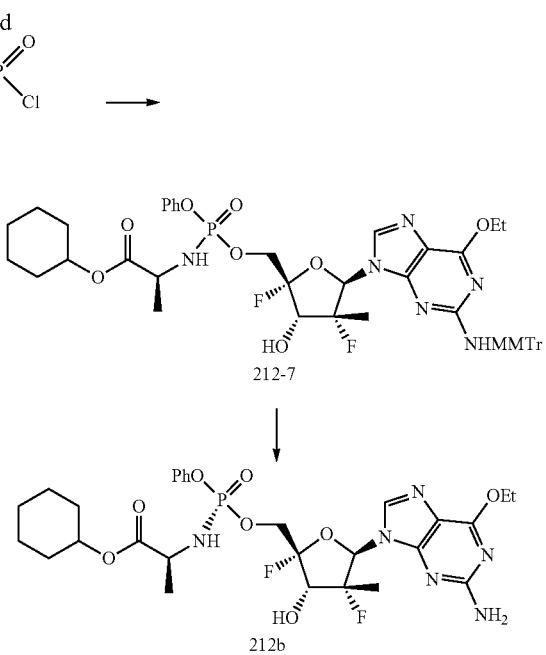

To a solution of 212-1 (0.47 g, 0.65 mol) in DCM (3 mL) was added AgNO$_3$ (0.22 g, 1.29 mmol), collidine (0.15 g, 1.29 mmol) and MMTrCl (0.3 g, 0.974 mmol) at 0° C. The mixture was stirred at RT overnight. The mixture was filtered, and the filter was washed with sat. aq. NaHCO$_3$ solution and brine. The organic layer was separated, dried over anhydrous Na$_2$SO$_4$ and concentrated at low pressure. The residue was purified by silica gel column to give 212-2 (0.55, 85%) as a white solid.

To a solution of 212-2 (0.5 g, 0.5 mmol) in dry DMF (10 mL) was added NaOBz (0.72 g, 5 mmol) and 15-crown-5 (0.9 mL). The mixture was stirred at 95° C. for 72 h. The mixture was diluted with EA, and washed with water and brine. The organic phase was dried over MgSO$_4$ and concentrated at low pressure. The residue was purified by silica gel column (10% EA in PE) to give 212-3 (0.3 g, 60%) as a white solid.

212-3 (0.3 g, 0.3 mmol) in NH$_3$/MeOH (30 mL) was stirred at RT for 18 h. The mixture was concentrated at low pressure, and the residue was purified by silica gel column (20% EA in PE) to give 212-4 (145 mg, 56%) as a white solid. ESI-LCMS: m/z 890.5 [M+H]$^+$.

To a stirred solution of 212-4 (161 mg, 0.16 mmol) in anhydrous CH$_3$CN (2.0 mL) was added N-methylimidazole (118 μL, 2.87 mmol) at 0 to 5° C. (ice/water bath) followed by solution of 212-5 (186 mg, 0.54 mmol, dissolved in 2 mL of CH$_3$CN). The solution was stirred at 0 to 5° C. for 4 h. The mixture was diluted with EA, and water was added (15 mL). The solution was washed H$_2$O, 50% aqueous citric acid solution and brine. The organic layer was separated, dried over anhydrous MgSO$_4$ and filtered. The filtrate was concentrated in vacuum to give a residue, which was purified on silica gel with 0 to 40% EA/hexanes to give as 212-6 (82.6 mg) as the faster eluting isomer and 212-7 (106 mg) as the slower eluting isomer.

212-6 (82.6 mg, 0.07 mmol) was dissolved in anhydrous CH$_3$CN (0.5 mL), and 4N HCl in dioxane (35 μL) was added at 0 to 5° C. The mixture was stirred at RT for 1 h, and anhydrous EtOH (100 μL) was added. The solvents were evaporated at RT and co-evaporated with toluene 3 times. The residue was dissolved in 50% CH$_3$CN/H$_2$O, and purified on a reverse-phase HPLC (C18) using acetonitrile and water, followed by lyophilization to give 212a (19.4 mg). ESI-LCMS: m/z=655.2 [M+H]$^+$, 653.15 [M−H]$^-$.

212-7 (100 mg, 0.083 mmol) was dissolved in anhydrous CH$_3$CN (0.5 mL), and 4N HCl in dioxane (50 μL) was added at 0 to 5° C. Following the procedure for obtaining 212a, 212b (31.8 mg) was obtained. ESI-LCMS: m/z=655.2 [M+H]$^+$, 653.1 [M−H]$^-$.

Example 115

Compound 213

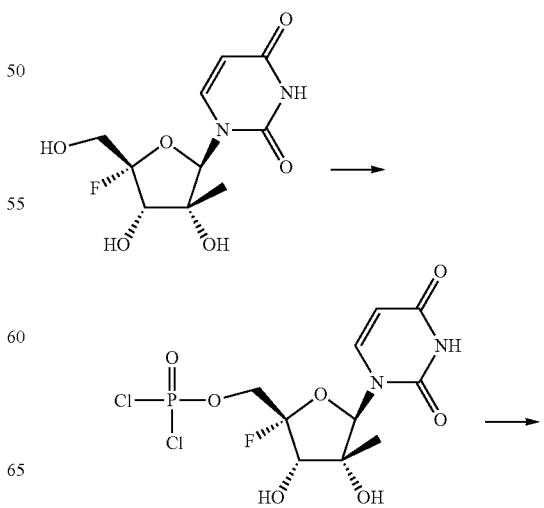

345

-continued

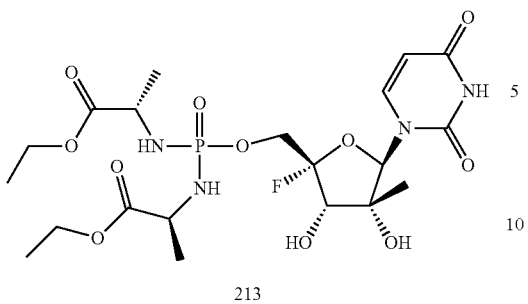

213

To a solution of the nucleoside (300 mg, 1.09 mmol) and proton-sponge (467 mg, 2.18 mmol) in anhydrous CH₃CN (5 mL) at 0° C. under N₂ was added dropwise a solution of phosphorus oxychloride (330 mg, 2.18 mmol) in anhydrous CH₃CN (1 mL). The mixture was stirred at 0° C. for 30 mins, and the hydrogen chloride salt of (S)-ethyl 2-aminopropanoate (998 mg, 6.52 mmol) and triethylamine (1.5 mL, 10.87 mmol) at 0° C. were added. The mixture was stirred overnight at 30° C. The reaction was quenched with water, and extracted with EA (3×20 mL). The organic layer was concentrated at low pressure, and the residue was purified by reverse phase HPLC to give 213 (20 mg, 3%) as a white solid. ESI-LCMS: m/z 535 [M-F]⁺.

Example 116

Compound 214

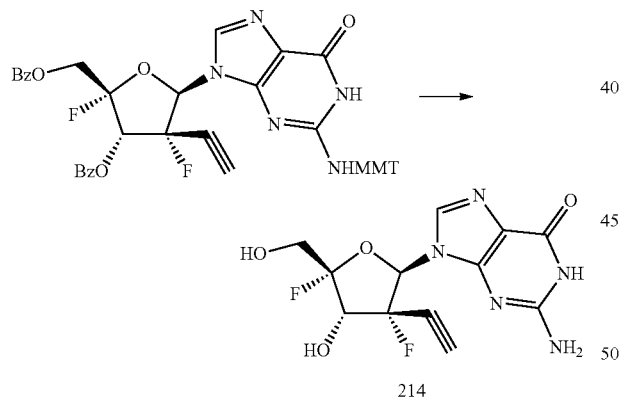

214

The nucleoside (140 mg, 0.42 mmol) was dissolved in n-butylamine (0.5 mL). The mixture was kept for 2 h at RT, and the amine was then evaporated. The residue was dissolved in EtOAc, and the organic layer was washed twice with 10% citric acid, dried over Na₂SO₄, and evaporated. The residue purified by column chromatography on silica gel in linear gradient of methanol in DCM from 0% to 12% over 10 column volumes. The fractions containing the product were concentrated and treated with 80% HCOOH for 1 h at RT. The mixture was evaporated to dryness, and suspended in CH₃CN. The precipitate was separated, washed with CH₃CN (1 mL) and dried to yield 214 (27 mg, 50%). MS: m/z 326.5 [M-1]⁻.

346

Example 117

Compound 216

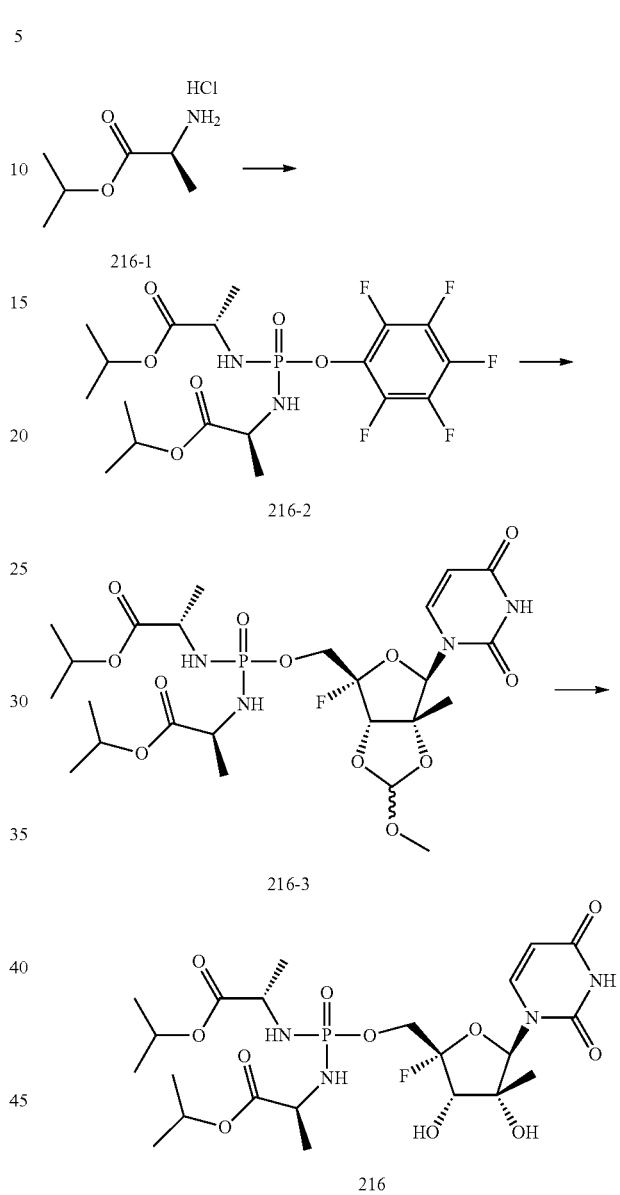

To a solution of 216-1 (3.0 g, 18.0 mmol) and POCl₃ (1.35 g, 9.0 mmol) in DCM (80 mL) was added TEA (3.6 g, 36.0 mmol) in DCM (20 mL) dropwise at 0° C. The mixture was stirred at 0° C. for 2 h. A solution of pentafluorophenol (1.65 g, 9.0 mmol) and TEA (0.9 g, 9.0 mmol) in DCM (20 mL) was added dropwise at 0° C., and the mixture was stirred at 0° C. for 15 h. After the reaction was completed, the mixture was concentrated under reduced pressure. The residue was washed by TBME and filtered. The filtrate was concentrated under reduced pressure, and the residue was purified by silica gel chromatography (20% EA in PE) to give 216-2 (2.7 g, 62.7%) as a white solid. ESI-MS: m/z 491.1 [M+1]⁺.

To a stirred solution of 1-((3aR,4R,6S,6aS)-6-fluoro-6-(hydroxymethyl)-2-methoxy-3a-methyltetrahydrofuro[3,4-d][1,3]dioxol-4-yl)pyrimidine-2,4(1H,3H)-dione (150 mg, 0.47 mmol) in anhydrous THF (2 mL) was added a solution of t-BuMgCl (0.46 mL, 1M in THF) dropwise at 0° C. The mixture was stirred at RT for 40 mins, and re-cooled to 0° C. A solution of 216-2 (462 mg, 0.94 mmol) was added, and the mixture was stirred at RT for 4 h. The mixture was quenched with H$_2$O, and extracted with EA. The organic layer was dried over Na$_2$SO$_4$ and concentrated under reducing pressure. The residue was purified on a silica gel column (50% EA in PE) to give 216-3 as a white foam (230 mg, 78%).

216-3 (230 mg, 0.37 mmol) was dissolved in 80% HCOOH aqueous solution (20 mL), and the mixture was stirred at RT for 24 h. The solvent was removed at low pressure. The residue was purified on a silica gel column to give the crude product, which was purified by RP HPLC (HCOOH system) to give 216 as a mixture of two P-isomers (75 mg, 33%). ESI-TOF-MS: m/z 583.0 [M+H]$^+$.

Example 118

Compound 218 washed with brine, dried and evaporated. The azido-phosphoroamidate was purified by RP HPLC on Synergy 4 micron Hydro-RP column (Phenominex). A linear gradient of methanol from 30% to 100% in 50 mM triethylammonium acetate buffer (pH 7.5) was used for elution. The azido-phosphoroamidate (8 mg) was dissolved in pyridine/Et$_3$N (3 mL, 8:1 v:v) and cooled to 0° C. H$_2$S gas was bubbled through the solution for 10 mins, and the reaction was kept for 1 h at RT. The solvents were evaporated, and the residue isolated by RP HPLC. The corresponding fractions were combined, concentrated and lyophilized 3 times to remove excess of buffer, to provide 218 (1.2 mg) as mixture Rp and Rs isomers. MS: m/z 544.1 [M+1]$^+$.

Example 119

Compound 219

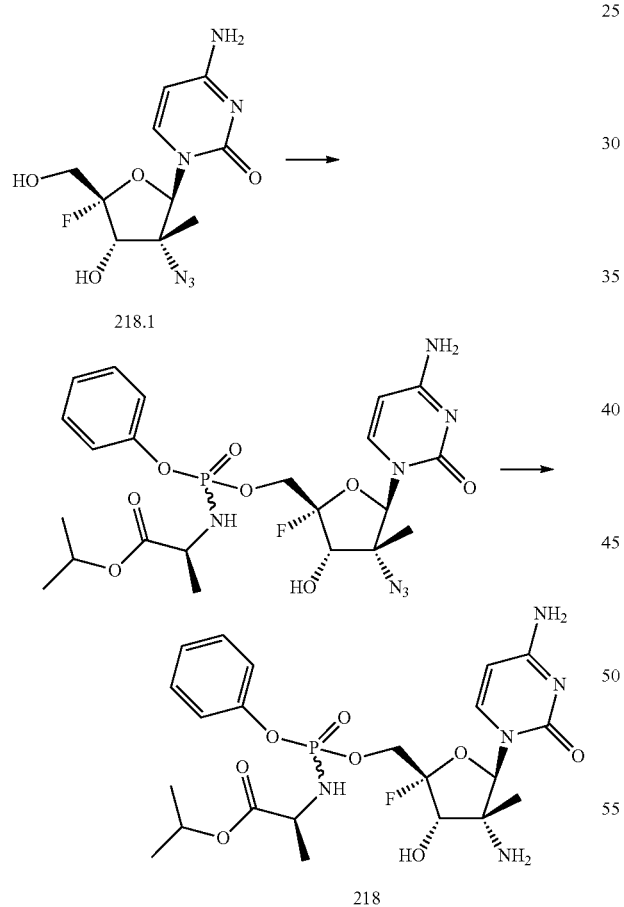

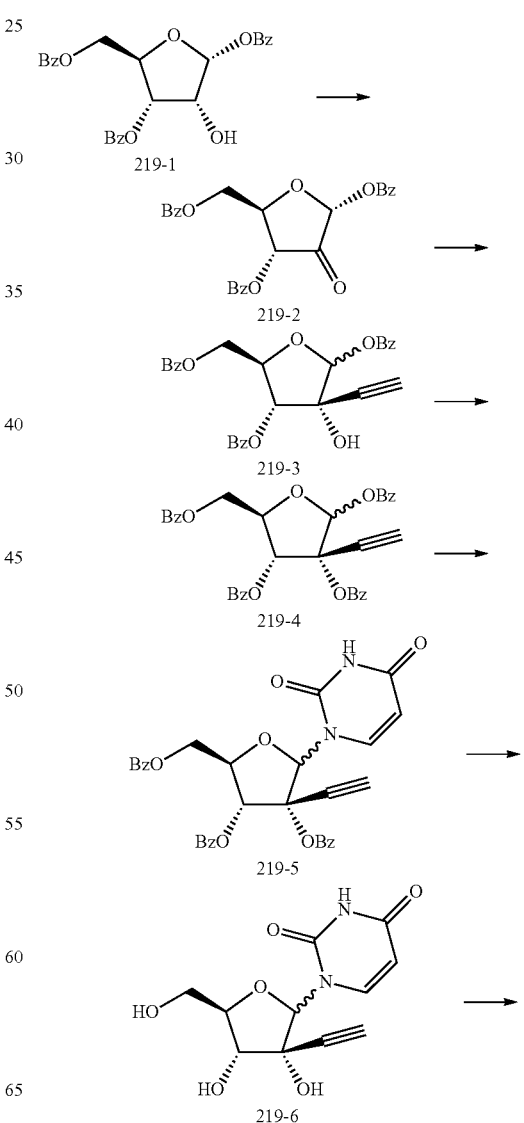

218-1 (30 mg, 0.1 mmol) was dissolved in a mixture of CH$_3$CN (2 mL) and N-methylimidazole (200 uL). Phosphorochloridate (100 mg, 0.3 mmol) was added, and the mixture was kept overnight at 40° C. The temperature was increased to 65° C. and heated for 1 h. The mixture was distributed between water and EA. The organic layer was separated,

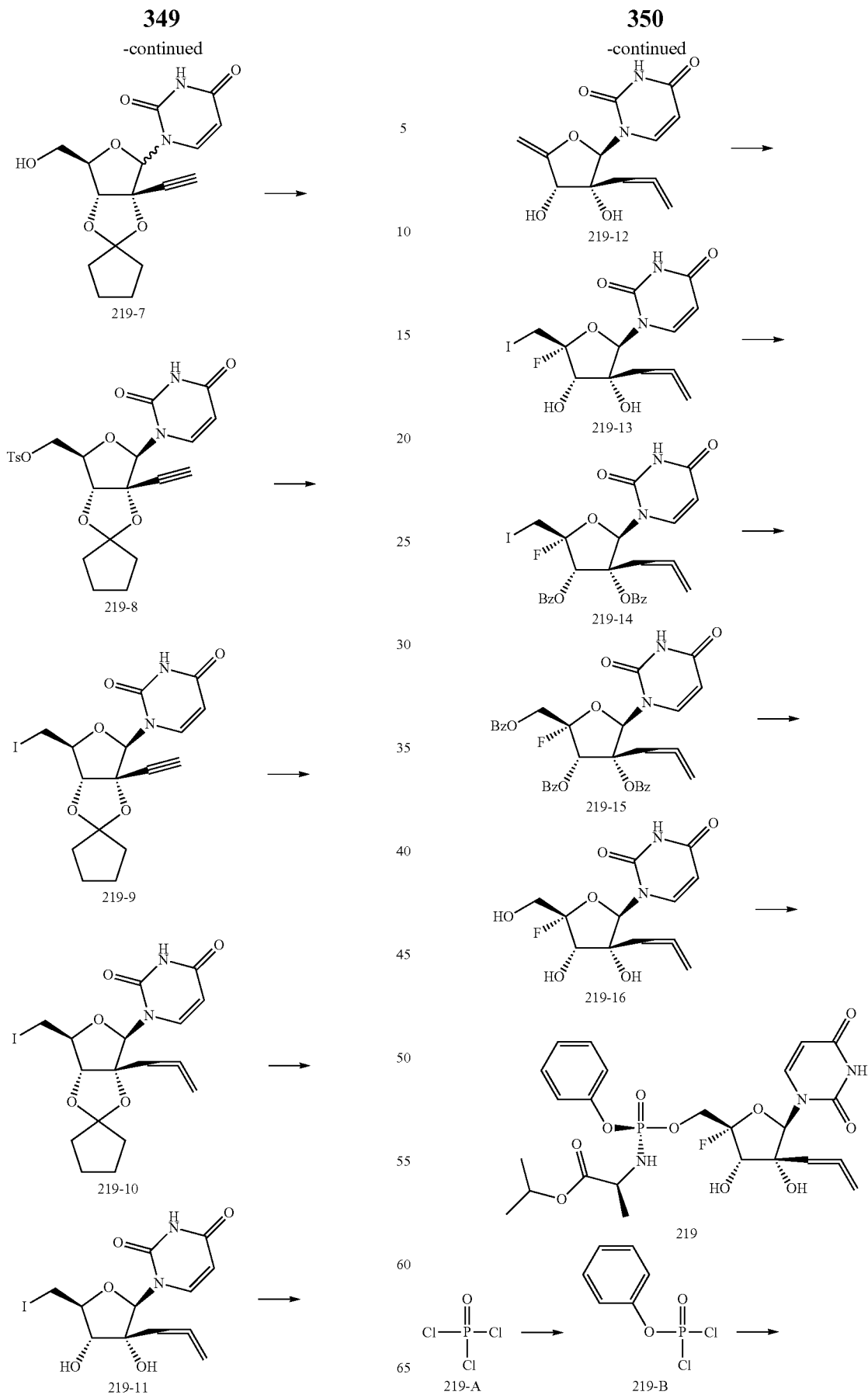

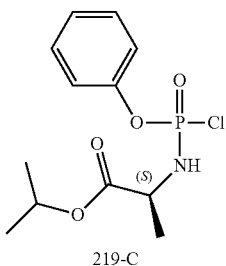

219-C

To a solution of IBX (133.33 g, 476 mmol) in dry $CH_3CN$ (2 L) was added 219-1 (100.0 g, 216 mol) at RT. The mixture was refluxed and stirred for 12 h. The mixture was filtered, and the filtrate was concentrated at low pressure to give 219-2 as a yellow oil (90.0 g, 90.4%).

219-2 (50.0 g, 108.70 mmol) was coevaporated with anhydrous toluene twice to remove $H_2O$. Ethynyl magnesium bromide, (800 mL, 400.0 mmol) was added dropwise into a solution of 73-2 in THF (500 mL) over 20 mins at −78° C. The mixture was stirred for about 10 mins at −78° C. When the starting material was consumed, the ice-acetone cooling bath was removed. The mixture was quenched with a sat. $NH_4Cl$ solution with stirring, and then warmed to RT. The mixture was extracted with EA, filtered through Celite and washed with brine. The combined organic phase was dried over anhydrous $Na_2SO_4$, filtered and concentrated at low pressure to give crude 219-3 as a deep yellow oil (48.0 g, yield: 90.8%).

219-3 (200.0 g, 411.52 mmol) was dissolved in anhydrous $CH_2Cl_2$ (2000 mL) and then DMAP (100.41 g, 823.05 mmol) and $Et_3N$ (124.94 g, 1.23 mol) were added at RT. The mixture was treated with benzoyl chloride (173.46 g, 1.23 mol) at 0° C. After stirring for 12 h at RT, the reaction was quenched with $H_2O$. The combined aq. phase was extracted with DCM. The combined organic phase was dried over anhydrous $Na_2SO_4$, filtered and evaporated to dryness under reduced pressure to give a black oil. The oil was purified by column chromatography using 7%-20% EA in PE as the eluent to give a yellow oil. The residue triturated with $CH_3OH$ and filtered. The filter cake was concentrated in vacuo to give 219-4 as a white solid (30.0 g, 36.4%).

Uracil (34.17 g, 305.08 mmol) were coevaporated with anhydrous toluene twice to remove $H_2O$. To a stirred suspension of uracil in anhydrous MeCN (150 mL) was added N,O-BSA (123.86 g, 610.17 mmol) at RT. The mixture was refluxed for 1.5 h and then cooled to RT. 219-4 (90 g, 152.54 mmol, which were coevaporated with anhydrous toluene twice to remove $H_2O$) was added. TMSOTf (237.05 g, 1.07 mol) was then added at RT. The mixture was heated to 70° C., and then stirred overnight and then monitored by LCMS. The mixture was cooled to RT and quenched with a sat. $NaHCO_3$ solution. The solution was extracted with EA. The organic layer was dried over $Na_2SO_4$, and then concentrated at low pressure. The residue was purified using a silica gel column eluted with 10%-50% EA in PE to give 219-5 as a white solid (45 g, 50.9%).

219-5 (50 g, 86.21 mmol) was treated with $NH_3$ in MeOH (1 L) at RT, and then stirred for 48 h. The mixture was concentrated at low pressure, and the residue was purified by column chromatography (10% MeOH in DCM) to give 219-6 (12.6 g, 54.55%) as a white solid.

To a solution of cyclopentanone (100 g, 1.189 mmol) and trimethyl orthoformate (150 mL) in MeOH (600 mL) was added $TsOH.H_2O$ (1.13 g, 5.9 mmol), and the mixture was stirred at RT for 30 mins. The reaction was quenched with NaOMe (0.32 g, 5.9 mmol) and $H_2O$, and the solution was extracted by n-hexane. The organic layer was dried over anhydrous $Na_2SO_4$, and then concentrated at low pressure. The cyclopentyl dimethoxy acetal and 219-6 (20 g, 74.63 mmol) was dissolved in DCE (200 mL), and then treated with $TsOH.H_2O$ (0.71 g, 3.73 mmol). The mixture was stirred at 50° C. for 12 h, and then concentrated at low pressure. The residue was purified by silica gel column chromatography (1-10% MeOH in DCM) to give 219-7 (15.4 g, 61.8%) as a white solid.

219-7 (20.0 g, 0.06 mol) was coevaporated with anhydrous pyridine three times to remove $H_2O$. To an ice-cold solution of 219-7 in anhydrous pyridine (100 mL) was added TsCl (22.8 g, 0.12 mol) at 0° C., and the mixture was stirred overnight and monitored by LCMS and TLC. The reaction was quenched with $H_2O$ and extracted with EA. The organic phase was dried over anhydrous $NaSO_4$ and evaporated at low pressure. The residue was purified by silica gel column chromatography (DCM:MeOH=100:1 to 15:1) to give 219-8 (20.0 g, 69.0%) as a white solid.

To a solution of 219-8 (20.0 g, 0.04 mol) in acetone (200 mL) was added NaI (31.0 g, 0.2 mol) and heated to reflux overnight and monitored by LCMS. The mixture was quenched with a sat. $Na_2S_2O_3$ solution, and extracted with EA. The organic phase was dried over anhydrous $Na_2SO_4$ and evaporated at low pressure. The residue was purified by silica gel column chromatography (DCM:MeOH=100:1 to 15:1) to give 219-9 (15.0 g, 83.3%) as a white solid.

To 219-9 (30.0 g, 0.068 mol) in dioxane (60 mL) in sealed tube was added CuBr (4.9 g, 0.034 mol), $i-Pr_2NH$ (13.6 g, 0.135 mol) and $(CH_2O)_n$ (5.1 g, 0.17 mol) under $N_2$. The mixture was heated at reflux for 16 h. The mixture was diluted with EtOAc, and washed with a sat. $NH_4Cl$ solution and brine. The solution was dried over anhydrous $MgSO_4$, and concentrated under reduced pressure. The residue was purified by column chromatography (DCM:MeOH=100:1 to 15:1) to give 219-10 (10.0 g, 32.3%) as a white solid.

219-10 (10 g, 21.83 mmol) was treated with HCOOH (80%) in $H_2O$ at RT. The solution was stirred at 60° C. for 2 h, and then concentrated at a low pressure. The residue was purified by column chromatography (1%-10% MeOH in DCM) to give 219-11 (5.1 g, 58.55%) as a white solid.

219-11 (5 g, 12.79 mmol) was dissolved in anhydrous MeOH (100 mL) and treated with NaOMe (4.83 g, 89.5 mmol) at RT. The solution was stirred at 60° C. for 36 h. The mixture was quenched with $CO_2$ and then concentrated at low pressure. The residue was purified by column chromatography (0-10% MeOH in DCM) to give 219-12 (2.3 g, 68.05%) as a yellow solid. $^1$H-NMR (CDCl$_3$, 400 MHz) δ=7.29 (d, J=8 Hz 1H), 6.10 (s, 1H), 5.71 (d, J=8.0 Hz 1H), 5.18 (t, J=6.4 Hz, 1H), 4.79-4.84 (m, 1H), 4.61 (d, J=8.0 Hz, 2H), 4.39 (s, 1H), 3.45 (s, 1H).

To an ice-cold solution of 219-12 (1.5 g, 5.68 mmol) in anhydrous MeCN (15 mL) was added NIS (1.66 g, 7.39 mmol) and TEA.3HF (0.73 g, 4.55 mmol) under $N_2$. The mixture was stirred at RT for 1 h. The reaction was quenched with sat. $NaHCO_3$ and sat. $Na_2SO_3$ solution, and extracted with EA (3×100 mL). The organic phase was dried over anhydrous $Na_2SO_4$, and evaporated to dryness at low pressure. The residue was purified on a silica gel column (0-5% MeOH in DCM) to give 219-13 (1.08 g, 46.2%) as a yellow solid.

To a stirred solution of 219-13 (1 g, 2.44 mmol) in anhydrous DCM (10 mL) was added DMAP (0.60 g, 4.88 mmol) and $Et_3N$ (0.74 g, 7.32 mmol) at RT. The mixture was treated with benzoyl chloride (0.79 g, 5.61 mmol) at 0° C.

and then stirred at RT for 3 h. The reaction was quenched with water, and extracted with EA (3×60 mL). The organic phase was concentrated at low pressure, and the residue was purified by column chromatography (0-10% MeOH in DCM) to give 219-14 (0.9 g, 59.6%) as a white solid.

Bu$_4$NOH (55% in H$_2$O, 13.74 mL) was treated with TFA (to adjust pH=3-4). The mixture was cooled to RT. To a solution of 219-14 (0.9 g, 1.46 mmol) in DCM (9 mL) was added m-CPBA (80%, 1.57 g, 7.28 mmol) at RT. The mixture was stirred at 25° C. for 48 h. The mixture was washed with sat. aq. NaHCO$_3$. The organic layer was passed through an anhydrous Al$_2$O$_3$ column, and the solution was concentrated at low pressure. The residue was purified by a silica gel column (30% EA in PE) to give 219-15 (0.26 g, 35.1%) as a yellow solid.

219-15 (0.25 g, 0.49 mmol) was dissolved in NH$_3$/MeOH (5 mL, 7 M), and the mixture was stirred at RT for 24 h under N$_2$. The mixture was concentrated at low pressure at RT, and the residue was purified by a silica gel column (5% MeOH in DCM) to give 219-16 (100 g, 67.75%) as a white solid. $^1$H-NMR (CD$_3$OD, 400 MHz) δ=7.83 (d, J=8 Hz 1H), 6.29 (s, 1H), 5.67 (d, J=6.0 Hz 1H), 5.12 (t, J=6.8 Hz, 1H), 4.99-5.01 (m, 1H), 4.38 (d, J=19.6 Hz 1H), 3.74-3.81 (m, 2H), 3.35 (s, 1H).

219-16 (100 mg, 0.33 mmol) was co-evaporated with toluene three times to remove H$_2$O. To a stirred solution of 219-16 (100 mg, 0.33 mmol) in a mixture of MeCN (1.0 mL) and NMI (271 mg, 3.3 mmol) was added a solution of 219-C (216.5 mg, 0.66 mmol) in MeCN (0.5 mL) at 0° C. The mixture was stirred at RT overnight and then reaction was quenched with water. The mixture was diluted with EA (20 mL), and the organic layer was washed with water and brine, and dried over anhydrous Na$_2$SO$_4$. The organic phase was concentrated at low pressure, and the residue was purified on a silica gel column (5% i-PrOH in DCM) to give the crude product. The crude product was purified by prep-HPLC (0.1% HCOOH in water and MeCN) to give 219 (35.6 mg, 19.0%) as a white solid. ESI-LCMS: m/z 592 [M+Na]$^+$.

To a stirred solution of 219-A (2.0 g, 13.16 mmol) and phenol (1.22 g, 13.16 mmol) in anhydrous DCM (100 mL) was added a solution of TEA (1.33 g, 13.16 mmol) in DCM (20 mL) dropwise at −78° C. The mixture was warmed gradually to RT, and then stirred for 2 h. The solution was re-cooled to −78° C., and (S)-isopropyl 2-aminopropanoate hydrochloride (2.20 g, 13.16 mmol) in DCM (20 mL) was added, followed by the dropwise addition of TEA (2.66 g, 26.29 mmol) in DCM (20 mL). The mixture was warmed gradually to RT, and then stirred for 2 h. The organic solvent was removed at low pressure, and the residue was dissolved in methyl-butyl ether. The precipitate was filtered, and the filtrate was concentrated at low pressure. The residue was purified on a silica gel column (anhydrous DCM) to give 219-C (0.9 g, 22.3%) as a colorless oil.

Example 120

Compound 220

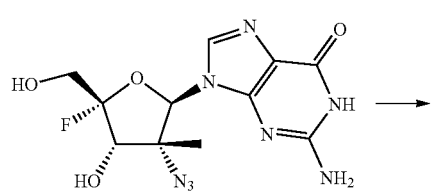

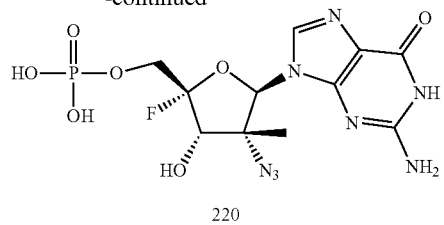

220

Dry nucleoside (0.05 mmol) was dissolved in a mixture of PO(OMe)$_3$ (0.7 mL) and pyridine (0.3 mL). The mixture was evaporated in vacuum for 15 mins. at 42° C., then cooled to RT. N-Methylimidazole (0.009 mL, 0.11 mmol) was added followed by POCl$_3$ (0.009 mL, 0.11 mmol). The mixture was kept at RT for 20-40 mins and monitored for the formation of 220 by LCMS. The reaction was quenched with water and isolated by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer. MS: m/z 396.5 [M−1]$^-$.

Example 121

Compound 223

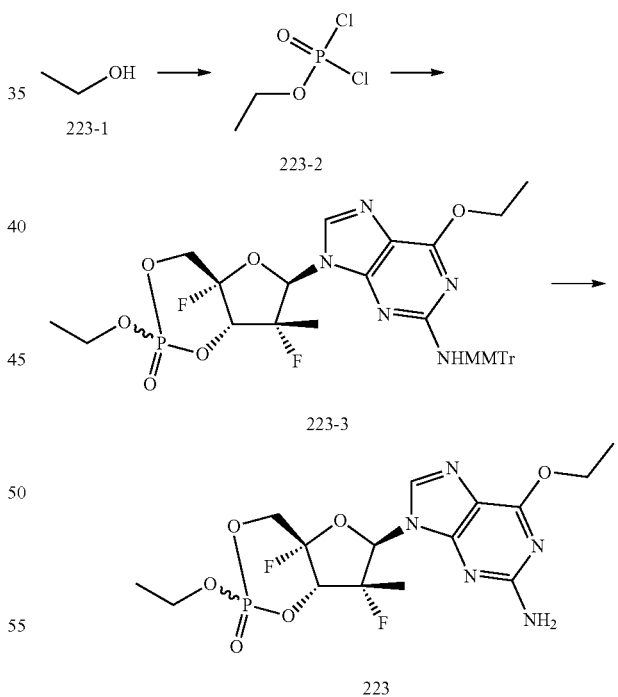

A solution of 223-1 (16.70 g, 0.363 mol) and TEA (36.66 g, 0.363 mol) in CH$_2$Cl$_2$ (150 mL) was added dropwise to a stirred solution of POCl$_3$ (55.65 g, 0.363 mol) in DCM (100 mL) over 25 mins at −78° C. After the mixture was stirred for 2 h. at RT, the triethylamine hydrochloride salt was filtered, and washed with CH$_2$Cl$_2$ (100 mL). The filtrate was concentrated at low pressure, and the residue was distilled under high vacuum (~10 mm Hg) with a cow-head fraction collector. 223-2 was collected between 45° C. (distillation head temperature) as a colorless liquid (30.5 g, 50% yield). $^1$H-NMR (400 MHz, CDCl$_3$) δ=4.44 (dq, J=10.85, 7.17 Hz, 2H), 1.44-1.57 (m, 3H); $^{31}$P-NMR (162 MHz, CDCl$_3$) δ=6.75 (br. s., 1P).

To a stirred suspension of 227-A (93 mg, 0.15 mmol) in CH$_2$Cl$_2$ (1 mL) was added TEA (61 mg, 0.15 mmol) at RT. The mixture was cooled to −20° C., and then was treated with a 223-2 (35 mg, 0.21 mmol) solution dropwise over a period of 10 mins. The mixture was stirred at this temperature for 15 mins., and then was treated with NMI (27 mg, 0.33 mmol). The mixture was stirred at −20° C., and then slowly warmed to RT. The mixture was stirred overnight. The mixture was suspended in EA (15 mL), washed with brine (10 mL) and dried over anhydrous sodium sulfate. The solution was concentrated at low pressure, and the residue was purified by chromatography (DCM:MeOH=100:1) to give 223-3 (60 mg, yield: 56%) as a solid.

A solution of 223-3 (60 mg, 0.085 mmol) in 80% AcOH aqueous (2 mL) was stirred at RT for 2 h. The mixture was concentrated under reduced pressure, and the residue was purified by a silica gel column eluting DCM/MeOH=50/1and prep-HPLC to give 223 (23 mg, 62%) as a white solid. ESI-MS: m/z 436.3 [M+H]$^+$.

Example 122

Compound 224

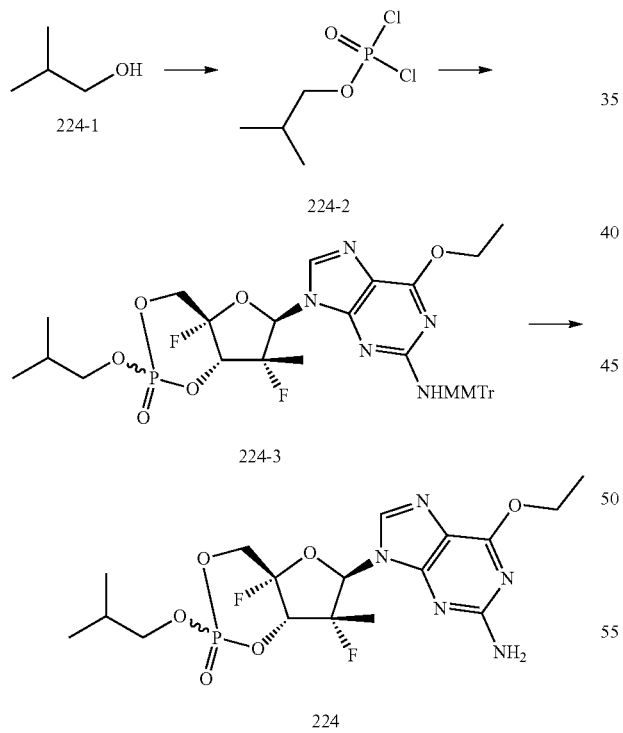

224-2 was prepared using a similar procedure as for the preparation of 223-2 using a solution of iso-butanol (23.9 g, 322.98 mmol) and POCl$_3$ (49.5 g, 322.98 mmol). 224-2 (26 g, 42% yield) was obtained as a colorless liquid. $^1$H-NMR (400 MHz, CDCl$_3$) δ=4.10 (dd, J=9.04, 6.39 Hz, 2H), 2.09 (dq, J=13.24, 6.67, 6.67, 6.67, 6.67 Hz, 1H), 1.01 (d, J=6.62 Hz, 6H); $^{31}$P-NMR (162 MHz, CDCl$_3$) δ=7.06 (br. s., 1P).

To a stirred suspension of 227-A (310 mg, 0.5 mmol) in CH$_2$Cl$_2$ (3 mL) was added TEA (202 mg, 2 mmol) at RT. The mixture was cooled to −20° C., and then was treated with 224-2 (134 mg, 0.7 mmol). The mixture was stirred at this temperature for 15 mins and then was treated with NMI (90 mg, 1.1 mmol). The mixture was stirred at −20° C. for 1 h., and then slowly warmed to RT overnight. The mixture was suspended in EA (15 mL), washed with brine (10 mL), and dried over anhydrous sodium sulfate. The organic phase was concentrated at low pressure, and the residue was purified by silica column gel (DCM:MeOH=100:1) to give 224-3 (310 mg, yield: 84%) as a solid.

A solution of 224-3 (310 mg, 0.43 mmol) in 80% AcOH aqueous (4 mL) was stirred at RT for 2 h. The mixture was concentrated at low pressure, and the residue was purified by a silica gel column eluting DCM/MeOH=50/1 and prep-HPLC to give 224 (79 mg, 50%) as a white solid. ESI-MS: m/z 464.0 [M+H]$^+$.

Example 123

Compound 225

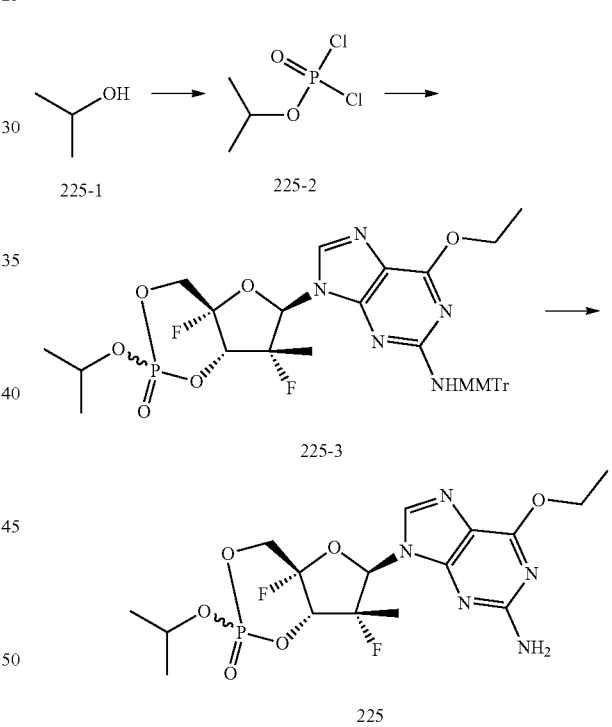

225-2 was prepared using a similar procedure as for the preparation of 223-2 using a solution of isopropyl alcohol (21 g, 350 mmol) and POCl$_3$ (53.6 g, 350 mmol). 225-2 (40.5 g, 65% yield) was obtained as a colorless liquid. $^1$H-NMR (400 MHz, CDCl$_3$) δ=4.94-5.10 (m, 1H), 1.48 (d, J=6.17 Hz, 6H); $^{31}$P-NMR (162 MHz, CDCl$_3$) δ=5.58 (br. s., 1P).

225-3 was prepared using a similar procedure as for the preparation of 224-3 using 225-2 (124 mg, 0.7 mmol) and 227-A (310 mg, 0.5 mmol). 225-3 (300 mg, 83%) was obtained as a solid.

225 was prepared using a similar procedure as for the preparation of 224 using 225-3 (300 mg, 0.41 mmol) in 80%

AcOH aqueous (4 mL). 225 (80 mg, 43%) was obtained as a white solid. ESI-MS: m/z 450.0 [M+H]⁺.

Example 124

Compound 227

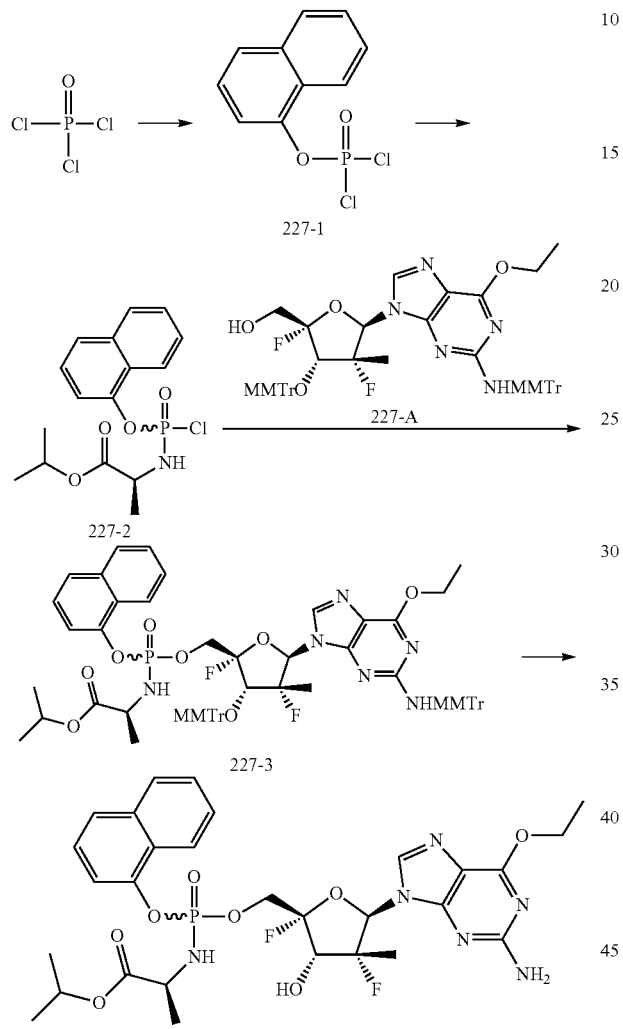

To a stirred solution of POCl₃ (2.0 g, 13 mmol) in anhydrous DCM (10 mL) was added 1-naphthol (1.88 g, 13 mmol) at −70° C., and TEA (1.31 g, 13 mmol) in DCM (3 mL) dropwise at −70° C. The mixture was gradually warmed to RT and stirred for 1 h. Crude 227-1 was obtained.

To a stirred solution of (S)-isopropyl 2-aminopropanoate hydrochloride (2.17 g, 13 mmol) in DCM (10 mL) was added crude 227-1 at −70° C. TEA (2.63 g, 26 mmol) was added to the stirred solution dropwise at −70° C. The mixture was gradually warmed to RT and stirred for 2 h. The reaction was monitored by LCMS and quenched with n-propylamine. The mixture was concentrated at low pressure, and the residue was purified by a silica gel column (PE: MTBE=5:1~1:1) to give pure 227-2 (1.6 g, 35%).

To a solution of 227-A (300 mg, 0.337 mmol) and NMI (276 mg, 3.37 mmol) in anhydrous CH₃CN (4 mL) was added 227-2 (240 mg, 0.674 mol, in DCM (5 mL)) at 0° C. The mixture was stirred at RT for 10 h. The reaction was monitored by LCMS. The reaction was quenched with water, and extracted with CH₂Cl₂ (3×20 mL). The organic phase was dried over anhydrous MgSO4, and concentrated at low pressure. The residue was purified by sil-gel (PE: EA=5:1-2:1) to give 227-3 (380 mg, 93%).

227-3 (380 mg, 0.314 mmol) was dissolved in CH₃COOH (80%, 8 mL), and stirred at 40-50° C. for 2.5 h. The reaction was monitored by LCMS. The mixture was concentrated at low pressure, and the residue was purified by chromatography (PE:EA=1:1~EA) to give crude 227. The crude product was purified by prep-HPLC (neutral system, NH₄HCO₃) to give pure 227 (70 mg, 80%) as a white solid. ESI-MS: m/z 665.1 [M+H]⁺.

Example 125

Compound 228

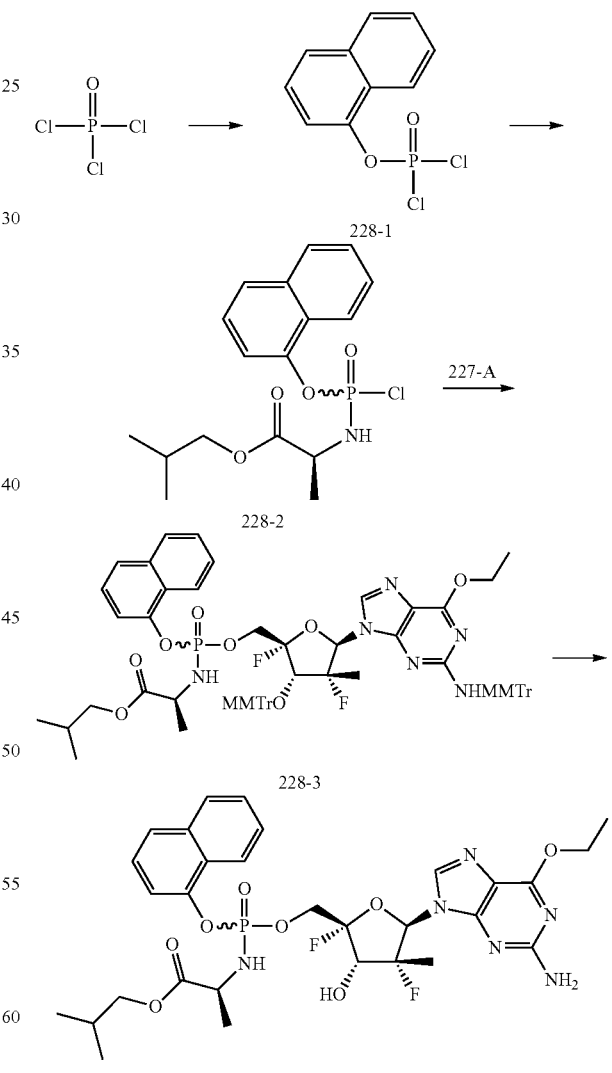

To a stirred solution of POCl₃ (2.0 g, 13 mmol) in anhydrous DCM (10 mL) was added 1-naphthol (1.88 g, 13 mmol) at −70° C. and TEA (1.31 g, 13 mmol) in DCM (3 mL) dropwise at −70° C. The mixture was gradually warmed to RT, and stirred for 1 h. A crude solution of 228-1 was obtained.

To a stirred solution of (S)-isobutyl 2-aminopropanoate hydrochloride (2.35 g, 13 mmol) in DCM (20 mL) was added TEA (2.63 g, 26 mmol) and a crude solution of 228-1 at −70° C. The mixture was gradually warmed to RT, and stirred for 2 h. The reaction was monitored by LCMS and quenched with n-propylamine. The solvent was evaporated at low pressure, and the residue was purified by chromatography (PE:MTBE=5:1-1:1) to give pure 228-2 (1.8 g, 37%).

To a solution of 227-A (300 mg, 0.337 mmol) and NMI (276 mg, 3.37 mmol) in anhydrous CH₃CN (4 mL) was added 228-2 (249 mg, 0.674 mol, in DCM (5 mL)) at 0° C. The mixture was stirred at RT for 10 h. The reaction was monitored by LCMS, and then quenched with H₂O. The mixture was extracted with CH₂Cl₂ (3×20 mL). The organic phase was dried over anhydrous MgSO4, and concentrated at low pressure. The residue was purified by chromatography using PE:EA=5:1~2:1 as the eluent to give 228-3 (360 mg, 87%).

228-3 (360 mg, 0.294 mmol) was dissolved in CH₃COOH (80%, 8 mL), and stirred at 40-50° C. for 2.5 h. The reaction was monitored by LCMS and then quenched with MeO. The mixture was concentrated at low pressure, and the residue was purified by chromatography using PE:EA=1:1 as the eluent to generate crude 228. The product purified by prep-HPLC (neutral system, NH₄HCO₃) to give 228 (70 mg, 75%) as a white solid. ESI-MS: m/z 679.2 [M+H]⁺.

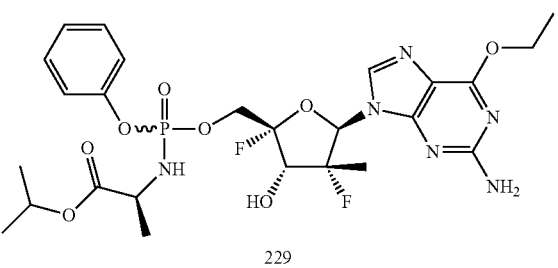

229

To a stirred solution of POCl₃ (2.0 g, 13 mmol) in anhydrous DCM (10 mL) was added phenol (1.22 g, 13 mmol) at −70° C. and TEA (1.31 g, 13 mmol) in DCM (3 mL) dropwise at −70° C. The mixture was gradually warmed to RT, and stirred for 1 h. A crude solution of 229-1 was obtained.

229 was prepared using a similar procedure as for the preparation of 228 using 229-2 (205 mg, 0.674 mol, in DCM (5 mL) obtained from (S)-isopropyl 2-aminopropanoate hydrochloride and 229-1) and 227-A (300 mg, 0.337 mmol). 229 (50 mg, 74%) was obtained as a white solid. ESI-MS: m/z 615.2 [M+H]⁺.

Example 127

Compound 230

Example 126

Compound 229

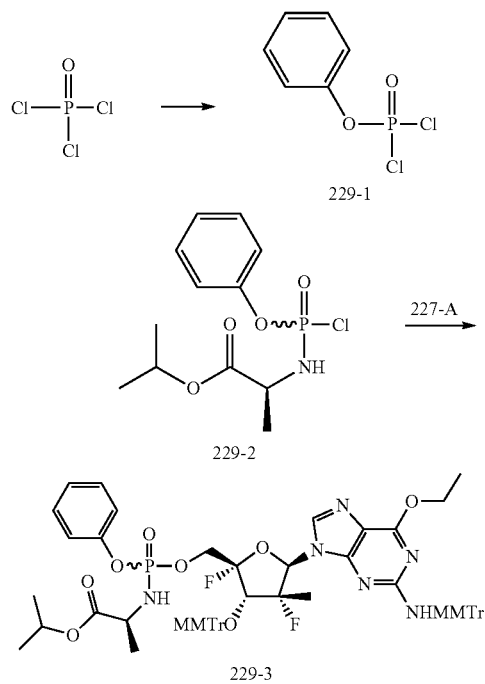

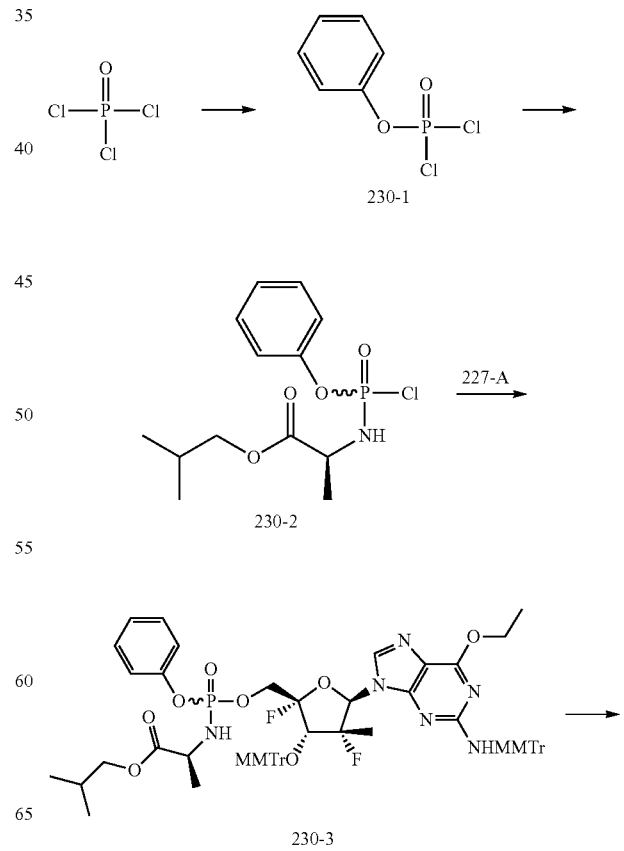

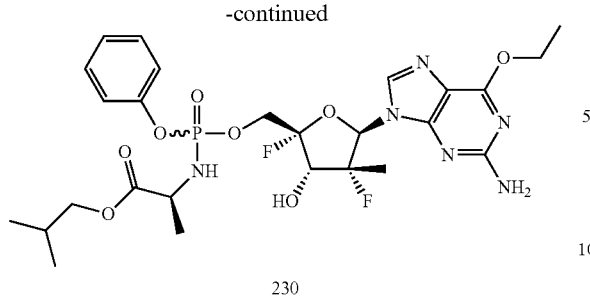

230 was prepared using a similar procedure as for the preparation of 228 using 230-2 (214 mg, 0.674 mol, in DCM (5 mL) obtained from (S)-isobutyl 2-aminopropanoate hydrochloride and 230-1) and 227-A (300 mg, 0.337 mmol). 230 (70 mg, 87%) was obtained as a white solid. ESI-MS: m/z 629.2 [M+H]$^+$.

Example 128

Compound 231

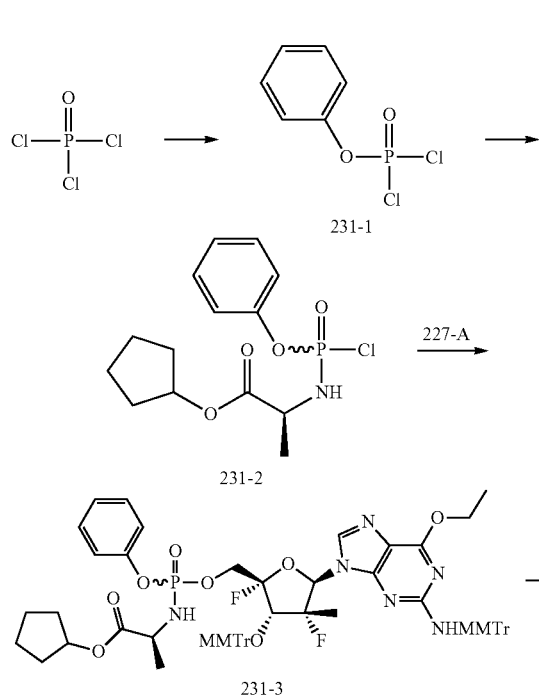

231 was prepared using a similar procedure as for the preparation of 228 using 231-2 (223 mg, 0.674 mol, DCM (5 mL) obtained from (S)-cyclopentyl 2-aminopropanoate hydrochloride and 231-1) and 227-A (300 mg, 0.337 mmol). 231 (62 mg, 71%) was obtained as a white solid. ESI-MS: m/z 641.2 [M+H]$^+$.

Example 129

Compound 232

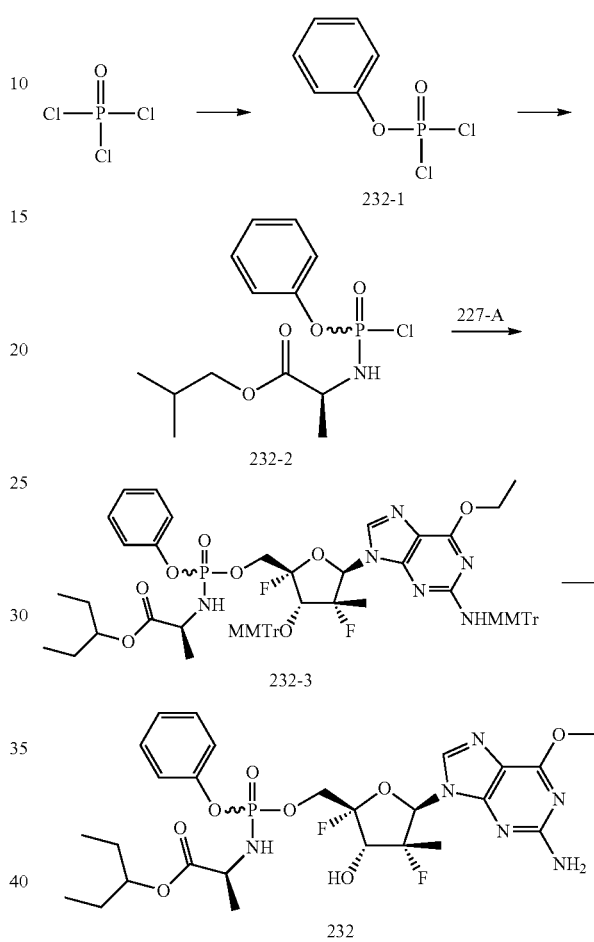

232 was prepared using a similar procedure as for the preparation of 228 using 232-2 (223 mg, 0.674 mol, DCM (5 mL), obtained from (S)-3-pentyl 2-aminopropanoate hydrochloride and 232-1) and 227-A (300 mg, 0.337 mmol). 232 (42 mg, 60%) was obtained as a white solid. ESI-MS: m/z 643.2 [M+H]$^+$.

Example 130

Compound 233

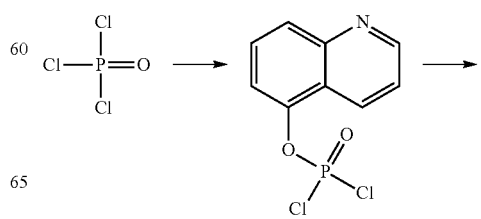

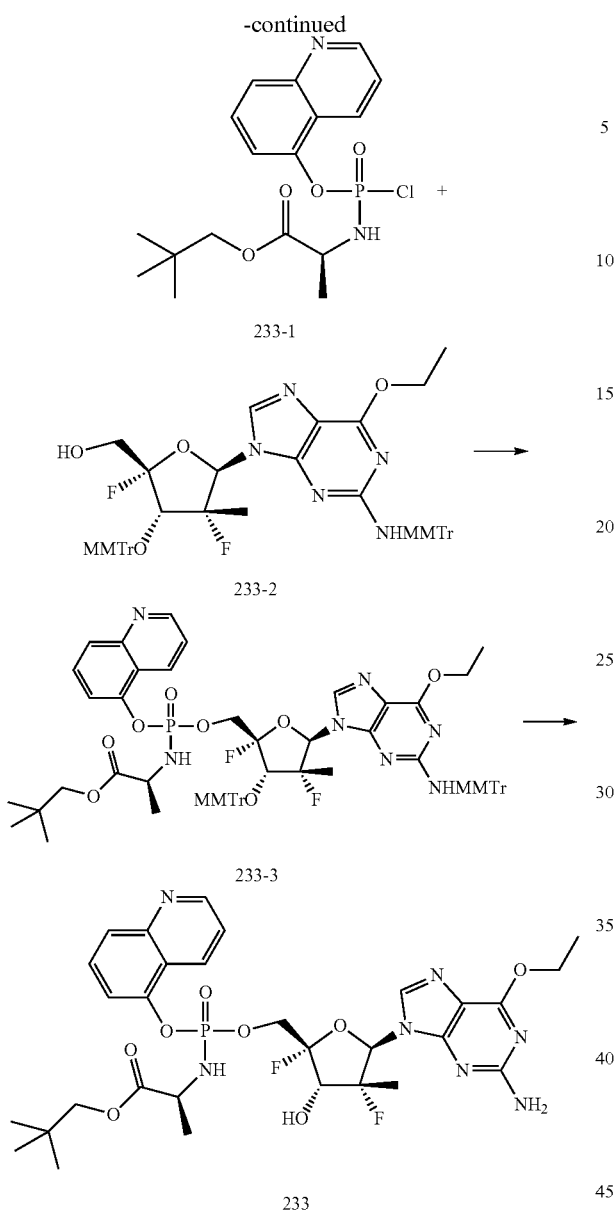

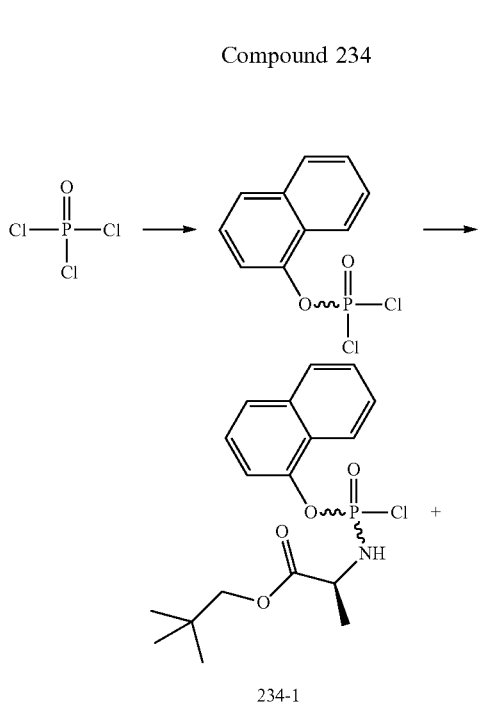

AcOEt. The organic phase was washed with brine, dried over anhydrous sodium sulfate, and concentrated at low pressure. The residue was purified by silica gel column (33% EA in PE) to give 233-3 as a yellow powder (300 mg, 71.9%).

233-3 (300 mg, 0.243 mmol) was dissolved in 80% CH$_3$COOH (3 mL), and the mixture was stirred at 60° C. for 2.5 h. The mixture was partitioned between AcOEt and water. The organic layer phase was washed by brine, dried over sodium sulfate and concentrated at low pressure. The residue was purified by silica gel column (50% EA in PE) to give 233 as a yellow powder (81 mg, crude product). The crude product (81 mg) was purified by RP HPLC to give 233 as a white solid. (28.7 mg, 17.1%). ESI-LCMS: m/z 694.1 [M+H]$^+$.

Example 131

Compound 234

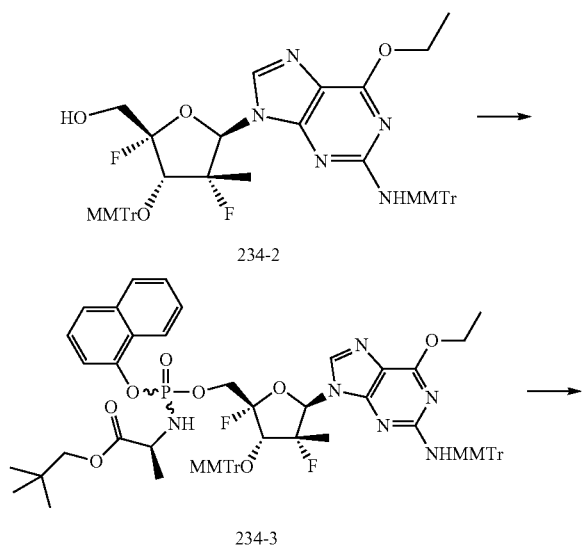

A stirred solution of phosphoryl trichloride (1.00 g, 6.58 mmol) and 5-quinoline (955 mg, 6.58 mmol) in anhydrous DCM (50 mL) was treated with a solution of TEA (665 mg, 6.58 mmol) in DCM (10 mL) at −78° C. The mixture was gradually warmed to RT, and stirred for 2 h. The solution was cooled to −78° C. and then treated with (S)-neopentyl 2-aminopropanoate hydrochloride (1.28 g, 6.58 mmol). TEA (1.33 g, 13.16 mmol) was added dropwise at −78° C. The mixture was gradually warmed to RT, and stirred for 2 h. The mixture was concentrated at low pressure, and the residue was dissolved in methyl-butyl ether. The precipitate was filtered off, and the filtrate was concentrated at low pressure. The residue was purified by a silica gel column (pure AcOEt) to give 233-1 as colorless oil (500 mg, 20%).

To a solution of 233-2 (300 mg, 0.337 mmol) and NMI (276.6 mg, 3.37 mmol) in anhydrous CH$_3$CN (0.9 mL) was added 233-1 (388 mg, 1.011 mmol) in CH$_3$CN (0.3 mL) dropwise at 0° C. The mixture was stirred at RT overnight. The reaction was quenched with water, and extracted with -continued

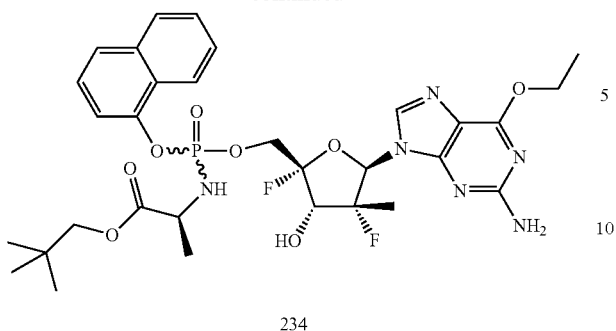

234

234-1 was prepared using a similar procedure as for the preparation of 233-1 using phosphoryl trichloride (2.00 g, 13.16 mmol), 1-naphthol (1.882 g, 13.16 mmol) and (S)-neopentyl 2-aminopropanoate hydrochloride (2.549 g, 13.16 mmol). 234-1 (600 mg, 12%) was obtained as a colorless oil.

A solution of 234-2 (230 mg 0.26 mmol) and NMI (212 mg 2.60 mmol) in anhydrous CH$_3$CN (1 mL) was treated with a solution of 234-1 (300 mg 0.78 mmol) in anhydrous CH$_3$CN (0.5 mL) at RT. The mixture was stirred at RT overnight. The reaction was quenched with water, and extracted with EA (3×20 mL). The organic layer was washed with brine, dried by anhydrous sodium sulfate, and concentrated at low pressure. The residue was purified by a silica gel column (CH$_3$OH in CH$_2$Cl$_2$ from 1% to 5%) to give 234-3 (300 mg, 93%) as a white solid.

234-3 (300 mg, 0.24 mmol) was dissolved in CH$_3$COOH (80%, 5 mL). The mixture was stirred at 60° C. for 2.5 h. The mixture was diluted with EA (30 mL) and washed with brine. The organic phase was dried over anhydrous sodium sulfate, and concentrated at low pressure. The residue was purified by a silica gel column (CH$_3$OH in CH$_2$Cl$_2$ from 1% to 5%) to give crude 234 (105 mg). The crude product was purified by HPLC (0.1% NH$_4$HCO$_3$ in water and CH$_3$CN) to give 234 (45 mg, 26%) as a white solid. ESI-LCMS: m/z 693.2 [M+H]$^+$.

Example 132

Compound 235

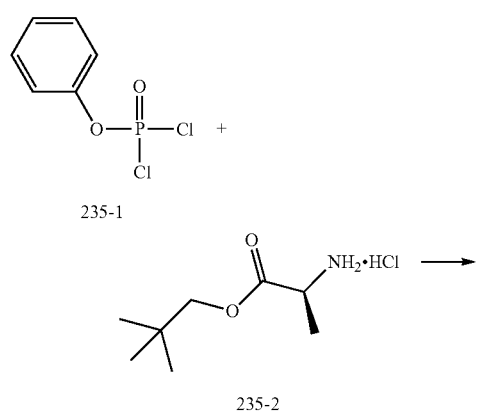

-continued

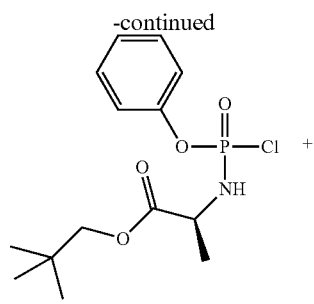

235-3

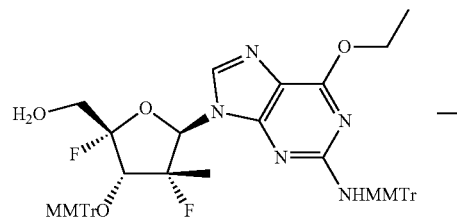

235-4

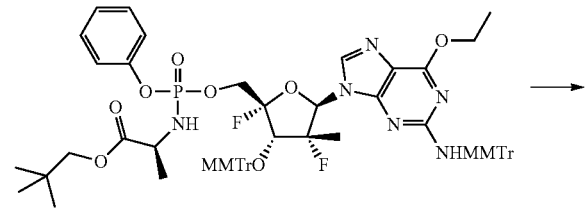

235-5

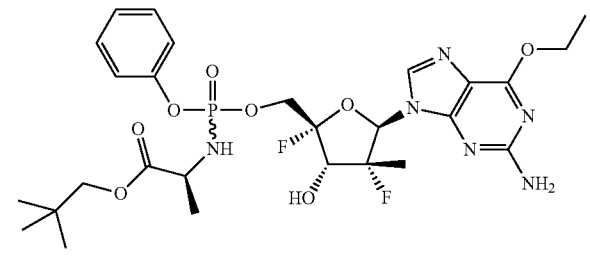

235

A stirred solution of 235-1 (2.00 g, 13.99 mmol) and 235-2 (2.00 g, 13.99 mmol) in anhydrous DCM (8 mL) was treated with a solution of TEA (3.11 g, 30.8 mmol) in DCM (20 mL) dropwise at −78° C. The mixture was stirred for 2 h. at −78° C. and then gradually warmed to RT. The organic solvent was removed at low pressure, and the residue was dissolved in methyl-butyl ether. The precipitate was filtered off, and the filtrate was concentrated at low pressure. The residue was purified on a silica gel column (dry DCM) to give 235-3 as colorless oil (1 g, 20.96%).

235-4 (260 mg, 0.29 mmol) was coevaporated with toluene 3 times to remove H$_2$O. Dried 235-4 was treated with MeCN (0.8 mL) and NMI (240 mg, 2.9 mmol) and then stirred for 10 mins. The mixture was treated with a solution of 235-3 (291 mg, 0.87 mmol) in MeCN (0.4 mL), and then concentrated at low pressure. The residue was purified on a silica gel column (75% EA in PE)) to give 235-5 (300 mg, 86%) as a white solid.

235-5 (300 mg, 0.25 mmol) was treated with CH$_3$COOH (5 mL, 80%), and stirred at 50° C. for 3 h. The mixture was diluted with EA. The solution was washed with brine, dried over anhydrous Na$_2$SO$_4$, and concentrated at low pressure.

367

The residue was purified by silica gel column chromatography (67% EA in PE) to give crude 235, which was purified by HPLC. The product was dried by lyophilization to give 235 (30 mg, 18.5%) as a white solid. ESI-LCMS: m/z 643 [M+H]$^+$.

Example 133

Compound 247

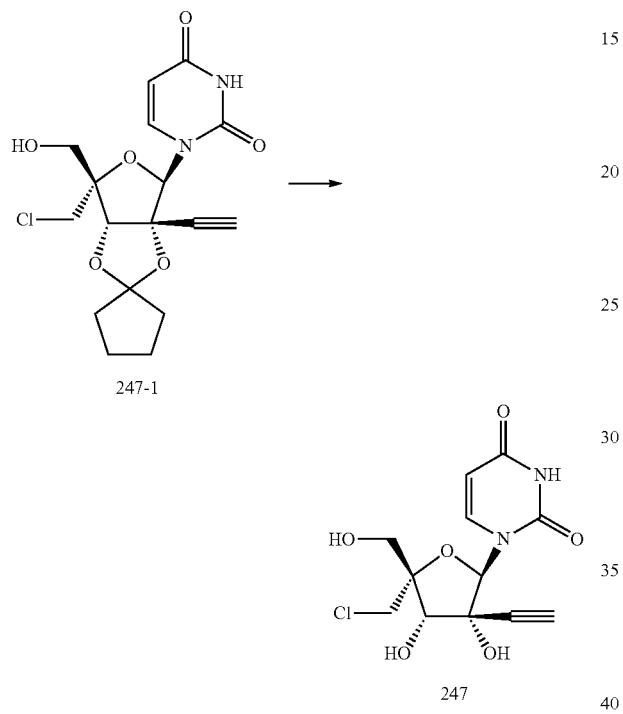

247-1 (50 mg, 0.13 mmol) was dissolved in 80% formic acid (3 mL) and heated at 50° C. overnight. The solvent was evaporated, co-evaporated with water to remove the acid. The residue was dissolved in a mixture of methanol and triethylamine (3 mL, 4:1 v:v). After 0.5 h, the solvent was evaporated. The nucleoside was lyophilized from water to yield 247 (40 mg, 97%). MS: m/z 315.5 [M−1].

Example 134

Compound 248

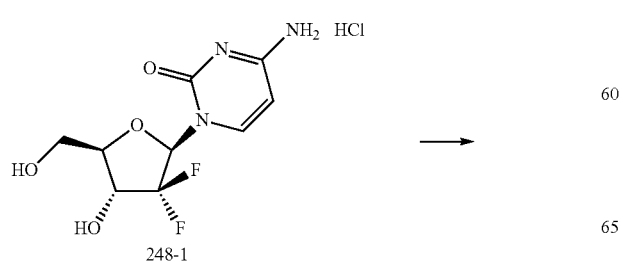

368

-continued

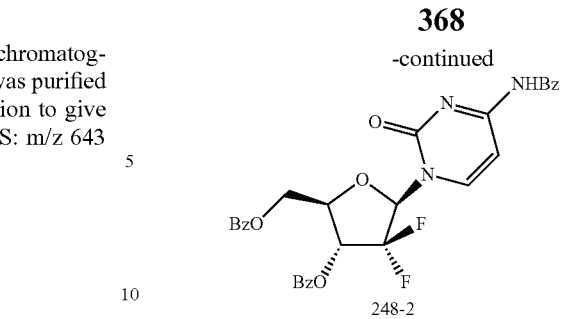

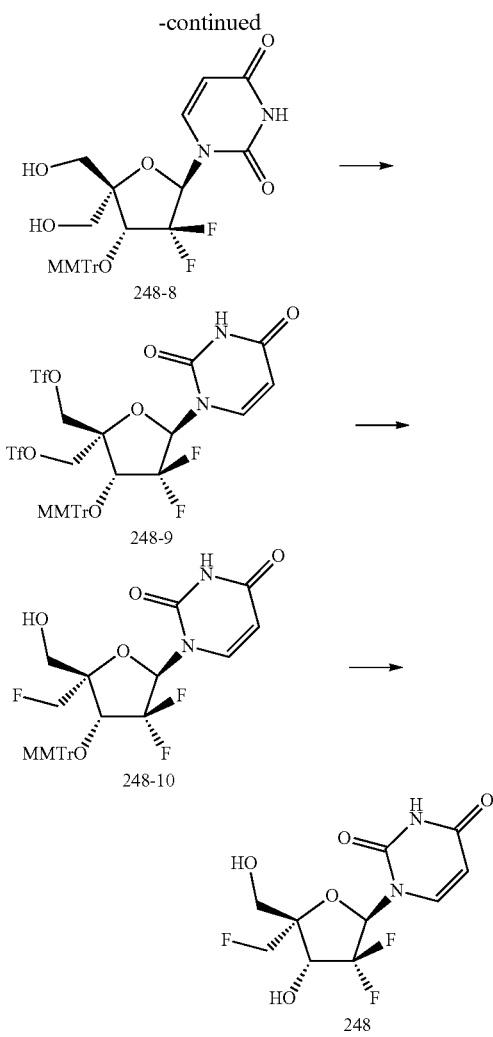

To a stirred solution of 248-1 (15.0 g, 50.2 mmol) in anhydrous pyridine (180 mL) was added BzCl (23.3 g, 165.5 mmol) at 0° C. under N₂ atmosphere. The mixture was stirred for 12 h at RT. The mixture was diluted with EA and washed with sat.NaHCO₃ aq. solution and brine. The organic layer was dried with anhydrous Na₂SO₄ and filtered. The organic phase was concentrated to dryness at low pressure. The residue was purified by column chromatography (15% EtOAc in PE) to give 248-2 (27 g, 93.5%) as a white solid.

248-2 (27.0 g, 47 mmol) was dissolved in 90% HOAc (250 mL). The mixture was stirred at 110° C. for 12 h. The solvent was removed under reduced pressure. The residue was diluted with EA and washed with sat. NaHCO₃ aq. solution and brine. The organic layer was dried over anhydrous Na₂SO₄ and filtered. The organic phase was concentrated at low pressure to give crude 248-3 (21.7 g, crude) as a light yellow solid.

248-3 (21.7 g, 45.9 mmol) was treated with NH₃/MeOH (600 mL) and stirred at RT for 12 h. The solvent was concentrated under reduced pressure to give the crude product. The crude product was purified by column chromatography (5% MeOH in DCM) to give 248-4 (12 g, 99%) as a white solid.

To a stirred solution of 248-4 (15.0 g, 56.8 mmol) in anhydrous pyridine (200 mL) was added imidazole (7.7 g, 113.6 mmol) and TBSCl (9.4 g, 62.5 mmol) at RT. The mixture was stirred at RT for 12 h. The solvent was removed under reduced pressure. The residue was diluted with EA and washed with sat. NaHCO₃ aq. solution and brine. The organic phase was dried over anhydrous Na₂SO₄ and filtered. The organic phase was concentrated at a low pressure to give crude 248-5 (21.3 g, crude) as a light yellow solid.

To a stirred solution of 248-5 (21.3 g, crude) in anhydrous DCM (200 mL) was added collidine (6.8 g, 56.8 mmol), MMTrCl (17.8 g, 56.8 mmol) and AgNO₃ (9.6 g, 56.8 mmol) at RT. The mixture was stirred at RT for 12 h. The solid was removed by filtration, and the filtrate was washed with sat.NaHCO₃ aq. solution and brine. The organic layer was dried over anhydrous Na₂SO₄ and concentrated at low pressure. The residue was purified by column chromatography (5% EA in PE) to give 248-6 (32 g, 87%) as a light yellow solid.

248-6 (32 g, 49.2 mmol) was dissolved in a solution of TBAF in THF (1M, 4.0 eq.) at RT. The mixture was stirred at RT for 12 h. The solvent was removed under reduced pressure. The residue was diluted with EA and washed with brine. The organic layer was dried over anhydrous Na₂SO₄ and concentrated at low procedure. The residue was purified by column chromatography (33% EA in PE) to give 248-7 (21.0 g, 79%) as a white solid.

To a stirred solution of 248-7 (21.0 g, 38.8 mmol) in anhydrous DCM (200 mL) was added pyridine (9.2 mL, 116.4 mmol) and Dess-Martin periodinane (49 g, 116.4 mmol) at 0° C. The mixture was stirred at RT for 4 h. The reaction was quenched with sat. Na₂S₂O₃ solution and sat. NaHCO₃ aq. solution. The organic layer was washed with brine, dried over anhydrous Na₂SO₄ and concentrated under reduced pressure to give a crude product (21.0 g).

The crude product (21.0 g, crude) was dissolved in dioxane (200 mL) and treated with 37% aqueous formaldehyde (20 mL, 194 mmol) and 2.0 N aqueous sodium hydroxide (37.5 mL, 77.6 mmol). The mixture was stirred at RT for 12 h. The solution was treated with NaBH₄ (8.8 g, 232.8 mmol). After stirring for 0.5 h at RT, the reaction was quenched with ice water. The mixture was diluted with EA and washed with brine. The organic phase was dried over anhydrous Na₂SO₄ and concentrated at low pressure. The residue was purified by column chromatography (4% MeOH in DCM) to give 248-8 (10.0 g, 50.5%) as a white foam.

248-8 (4.8 g, 8.5 mmol) was co-evaporated with toluene (2×). The residue was dissolved in anhydrous DCM (45 mL) and pyridine (6.7 g, 85 mmol). The solution was cooled to 0° C. Triflic anhydride (4.8 g, 18.7 mmol) was added dropwise over 10 mins. At 0° C., the mixture was stirred over 40 mins and monitored by TLC (PE:EA=1:1). The mixture was diluted with CH₂Cl₂ (50 mL). The solution was washed with sat. NaHCO₃ solution. The organic phase was washed with brine, dried over anhydrous Na₂SO₄, and concentrated at low pressure. The residue was purified by column chromatography (PE:EA=100:0-4:1) to give 248-9 (6.1 g, 86.4%) as a brown foam.

248-9 (6.1 g, 7.3 mmol) was dissolved in MeCN (25 mL). A solution of TBAF in THF (1M, 25 mL) was added at RT. The mixture was stirred at RT for 12 h. A solution of TBAF in THF (1M, 15 mL) was added, and the mixture was stirred for 4 h. The mixture was treated with aq. NaOH (1N, 14.6 mmol) and the mixture was stirred for 1 h. The reaction was quenched with water and extracted with EA. The organic phase was washed with brine, dried over anhydrous Na₂SO₄ and concentrated at low pressure. The residue was purified by column chromatography (50% EA in PE) to give 248-10 (2.1 g, 50.6%) as a white solid.

248-10 (700 mg, 1.23 mmol) was dissolved in 80% HCOOH (40 mL) at RT. The mixture was stirred at RT for 2 h. The reaction was quenched with MeOH (40 mL) and stirred for 12 h. The solvent was concentrated at low pressure, and the residue was purified by column chromatography (5% MeOH in DCM) to give 248 (210 mg, 57.7%) as a white solid. ESI-MS: m/z 296.9 [M+H]$^+$.
Example 135
Compound 250
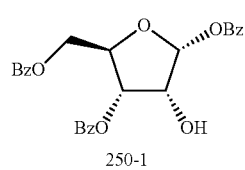
250-1
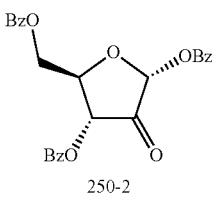
250-2
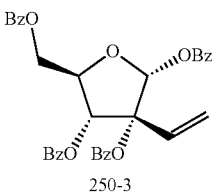
250-3
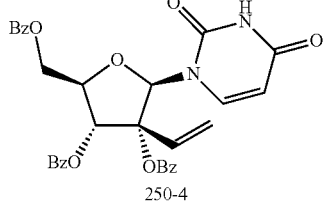
250-4
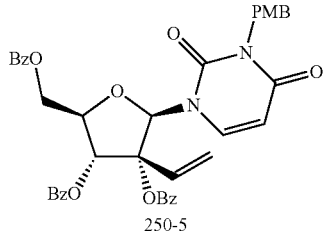
250-5
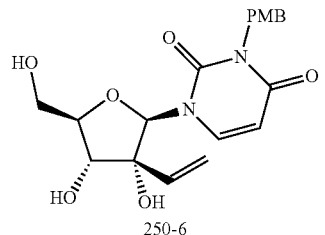
250-6
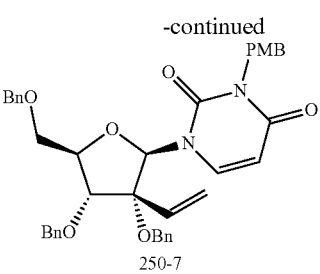
250-7
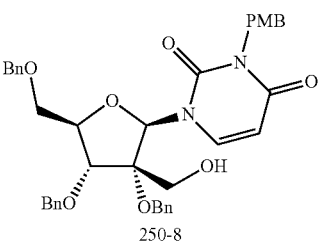
250-8
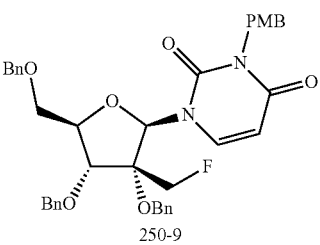
250-9
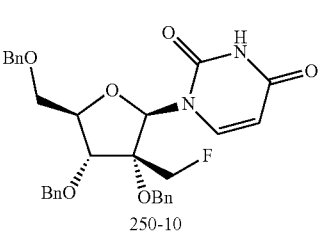
250-10
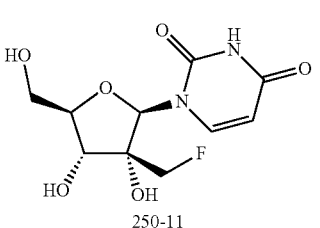
250-11
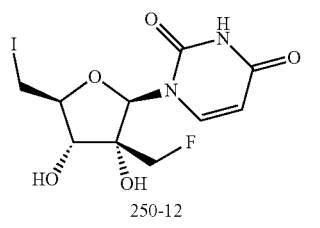
250-12
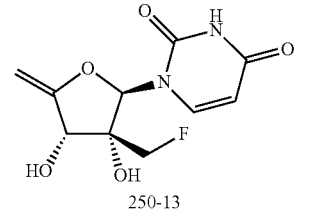
250-13

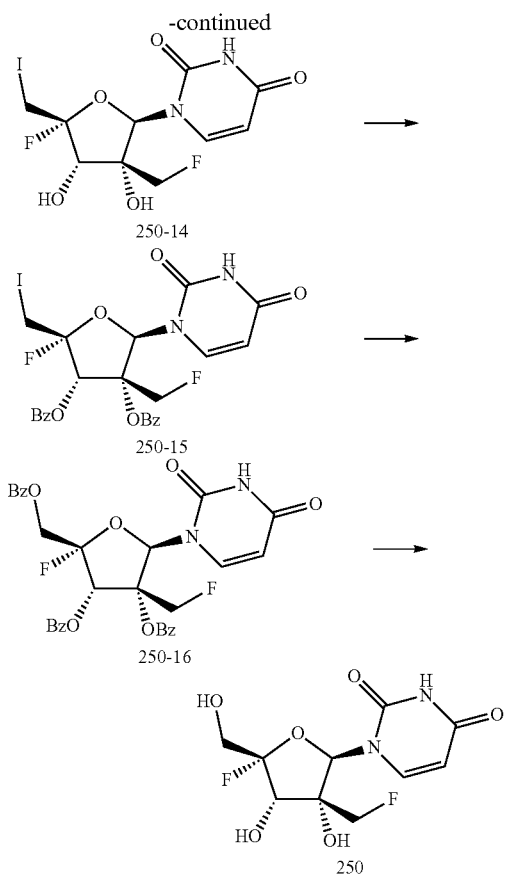

A mixture of 250-1 (120 g, 0.26 mol) and IBX (109 g, 0.39 mol) in CH$_3$CN (2.0 L) was heated to refluxed and stirred for 12 h. After cooling down to RT, the mixture was filtered. The filtrate was concentrated to dryness at low pressure.

250-2 (130 g, crude, 0.26 mol) was co-evaporated with anhydrous toluene (3×). Vinyl magnesium bromide (700 mL, 0.78 mol, 1.0 N in THF) was added dropwise into a solution of 250-2 in THF (300 mL) over 30 mins at −78° C., and the mixture was stirred for about 1 h at RT. When the starting material was consumed as determined by TLC, the mixture was poured into a sat. NH$_4$Cl solution. The organic layer was washed with brine, dried over anhydrous Na$_2$SO$_4$, and concentrated at low pressure.

To a solution of the above residue (170 g, crude, 0.346 mol) in anhydrous CH$_2$Cl$_2$ was added TEA (105 g, 1.04 mol), DMAP (84 g, 0.69 mol), and benzoyl chloride (146 g, 1.04 mol), and stirred for 12 h at RT. The mixture was diluted with CH$_2$Cl$_2$ and washed with sat. aq. NaHCO$_3$. The combined aq. phase was extracted with DCM (100 mL). The combined organic phase was dried over anhydrous Na$_2$SO$_4$, filtered and evaporated to dryness under reduced pressure. The residue was purified by column chromatography using EA in PE (10% to 50%) to get 250-3 (107 g, 52%).

A mixture of uracil (co-evaporated with toluene (2×)) and NOBSA (81.4 g, 0.4 mol) and CH$_3$CN (150 mL) was stirred to reflux for 1.5 h. After cooling to RT, the mixture was treated with 250-3 (59 g, 0.1 mol) and TMSOTf (155 g, 0.7 mol). The mixture was heated to 60-70° C., and stirred for 12 h. After cooling to RT, the mixture was poured into a sat. NaHCO$_3$ solution, and a solid precipitated. After filtration, pure 250-4 was obtained as a white solid (40 g, 69%) was obtained.

To a solution of 250-4 (50 g, 0.086 mol), K$_2$CO$_3$ (17.8 g, 0.13 mol) in DMF (50 mL) was added PMBCl (16 g, 0.1 mol) at 0° C., and stirred at RT for 12 h. The reaction was quenched with water, and extracted with EA (3×100 mL). The organic phase was washed with brine, dried over anhydrous Na$_2$SO$_4$, and concentrated at low pressure to give 250-5 (65 g).

A mixture of 250-5 (65 g, 0.086 mol) and NaOMe (16.8 g, 0.3 mol) in MeOH:DCM (500 mL, v:v=4:1) was stirred at RT for 2.5 h. The reaction was quenched with CO$_2$ (solid) and concentrated at low pressure. The residue was dissolved in EA (200 mL). The solution was washed with water, dried over anhydrous Na$_2$SO$_4$, and concentrated at low pressure. The residue was purified by column chromatography (4% MeOH in DCM) to give 250-6 as a yellow foam (25 g, 75%).

To a mixture of 250-6 (25.5 g, 0.065 mol) in DMF (60 mL) was added NaH (10.5 g, 0.26 mol, 60% in coal oil) BnBr (36.3 g, 0.21 mol) in an ice bath, and stirred at RT for 12 h. The reaction was quenched with NH$_4$Cl (aq.), and the mixture was diluted with EA (150 mL). The solution was washed with brine, dried over anhydride Na$_2$SO$_4$, and concentrated at low pressure. The residue was purified by sil-gel (15% EA in PE) to give 250-7 (20 g, 46%).

To a solution of 250-7 (20 g, 0.03 mol) and NMMO (7 g, 0.06 mol) in THF:H$_2$O (100 mL, v:v=5:1) was added OsO$_4$ (2.6 g, 0.01 mol) at RT, and stirred at RT for 24 h. The reaction was quenched with sat. Na$_2$S$_2$O$_3$ solution, and extracted with EA (3×80 mL). The organic layer was washed with brine, dried over anhydrous Na$_2$SO$_4$, and concentrated at low pressure.

To a solution of diol-product (0.03 mol) in MeOH:H$_2$O: THF (v:v:v=170 mL:30 mL:50 mL) was added NaIO$_4$ (9.6 g, 0.045 mol) at RT, and stirred at RT for 2 h. After filtration, the filter was used directly for the next step.

The previous solution was treated with NaBH$_4$ (1.8 g, 0.048 mol) at 0° C., and stirred at RT for 30 mins. The reaction was quenched with HCl (1 N) solution. The mixture was extracted with EA (3×60 mL). The organic phase was washed with brine, dried over anhydrous Na$_2$SO$_4$, and concentrated at low pressure. The residue was purified by sil-gel (25% EA in PE, TLC: PE:EA=2:1, Rf=0.6) to give 250-8 (12 g, 61% over 3 steps).

To a solution of 250-8 (14 g, 21 mmol) and DMAP (5.1 g, 42 mmol) in DCM (60 mL) was added MsCl (3.1 g, 27 mmol) at 0° C., and stirred at RT for 40 mins. The reaction was quenched with sat. NaHCO$_3$ solution. The organic phase was washed with HCl (0.2 N) solution, dried over anhydrous Na$_2$SO$_4$, and concentrated at low pressure. The residue was purified by sil-gel (25% EA in PE) to give the Ms-product (14 g, 90%) as a white solid.

Ms-product (41 g, 55 mmol) was treated with TBAF (Alfa, 1 N in THF, 500 mL), and stirred at 70-80° C. for 3 days. The mixture was concentrated at low pressure. The residue was dissolved in EA (200 mL). The solution was washed with brine, dried over anhydrous Na$_2$SO$_4$, and concentrated at low pressure. The residue was purified by sil-gel column (25% EA in PE) to give 250-9 (9.9 g, 27%).

To a solution of 250-9 (6.3 g, 9.45 mmol) in CAN:H$_2$O (v:v=3:1, 52 mL) was added CAN (15.5 g, 28.3 mmol), and stirred at RT overnight. The reaction was quenched with water, and extracted with EA (3×80 mL). The organic phase was washed with brine, dried over anhydrous Na$_2$SO$_4$, and concentrated at low pressure. The residue was purified by column chromatography (25% EA in PE) to give 250-10 (3.6 g, 71%) as a yellow oil.

To a solution of 250-10 (2.4 g, 4.4 mmol) in anhydrous DCM (10 mL) was added BCl$_3$ (1 N, 30 mL) at −70° C., and stirred for 2 h at −70° C. The reaction was quenched with MeOH at −70° C. The mixture was concentrated directly under 35° C. at low pressure. The residue was purified by column chromatography (50% EA in PE to 100% EA) to give 250-11 (1.2 g, 86%). ESI-MS: m/z 277.1 [M+H]⁺.

To a solution of PPh₃ (3.37 g, 12.8 mmol) in pyridine (15 mL) was added I₂ (3.06 g, 12 mmol) at 0° C., and stirred at RT for 30 mins until the orange color appeared. The mixture was cooled to 0° C., and treated with 250-11 (2.2 g, 8 mmol) in pyridine (5 mL), and stirred at RT under N₂ for 12 h. The reaction was quenched with Na₂S₂O₃ (sat., 30 mL), and extracted with EA (3×60 mL). The organic phase was washed with brine, dried over anhydrous Na₂SO₄, and concentrated at low pressure. The residue was purified by column chromatography (1% to 2% MeOH in DCM) to give 250-12 (1.8 g, 58%) as a light yellow foam.

A mixture of 250-12 (1.35 g, 3.5 mmol) and DBU (1.06 g, 7 mmol) in THF:CH₃CN (v:v=10 mL:5 mL) was stirred at 60-70° C. for 2 h. The mixture was diluted with EA (50 mL), and adjusted to pH=7-8 with HCl (0.2 N) solution. The organic phase was washed with brine, dried over anhydrous Na₂SO₄, and concentrated at low pressure. The residue was purified by column chromatography to give 250-13 (0.5 g, 55%).

To a solution of 250-13 (670 mg, 2.6 mmol) in CH₃CN (6 mL) was added NIS (730 mg, 3.25 mmol) and 3HF-TEA (335 mg, 2.1 mmol) at 0° C., and stirred at RT for 2 h. The reaction was quenched with NaHCO₃ (sat.) solution and Na₂S₂O₃ (sat.) solution, and extracted with EA (3×30 mL). The organic phase was washed with brine, dried over anhydrous Na₂SO₄, and concentrated at low pressure. The residue was purified by column chromatography (50% EA in PE and 2% MeOH in DCM) to give 250-14 (1.2 g, 80%) as a brown oil.

To a solution of 250-14 (1.0 g, 2.47 mmol), DMAP (0.75 g, 6.2 mmol) and TEA (0.75 g, 7.42 mmol) in DCM (10 mL) was added BzCl (1.15 g, 8.16 mmol) in DCM (1 mL) at 0° C., and stirred at RT for 12 h. The reaction was quenched with NaHCO₃ (aq.) solution. The organic phase was washed with brine, dried over anhydrous Na₂SO₄, and concentrated at low pressure. The residue was purified by column chromatography (30% EA in PE) to give 250-15 (850 mg, 85%).

A mixture of 250-15 (600 mg, 1 mmol), BzONa (1.45 g, 10 mmol), and 15-crown-5 (2.2 g, 10 mmol) in DMF (25 mL) was stirred at 90-100° C. for 24 h. The mixture was diluted with EA (20 mL). The solution was washed with brine, dried over anhydrous Na₂SO₄, and concentrated at low pressure. The residue was purified by column chromatography (30% EA in PE) to give 250-16 (275 mg, 37%) as a light yellow foam.

A mixture of 250-16 (250 mg, 0.41 mmol) in NH₃.MeOH (7 N, 5 mL) was stirred at RT for 15 h. The mixture was concentrated at low pressure directly. The residue was purified by column chromatography (50% EA in PE) and re-purified by prep-HPLC to give 250 (33 mg, 25%) as a white solid. ESI-MS: m/z 295.1 [M+H]⁺.

Example 136

Compound 126

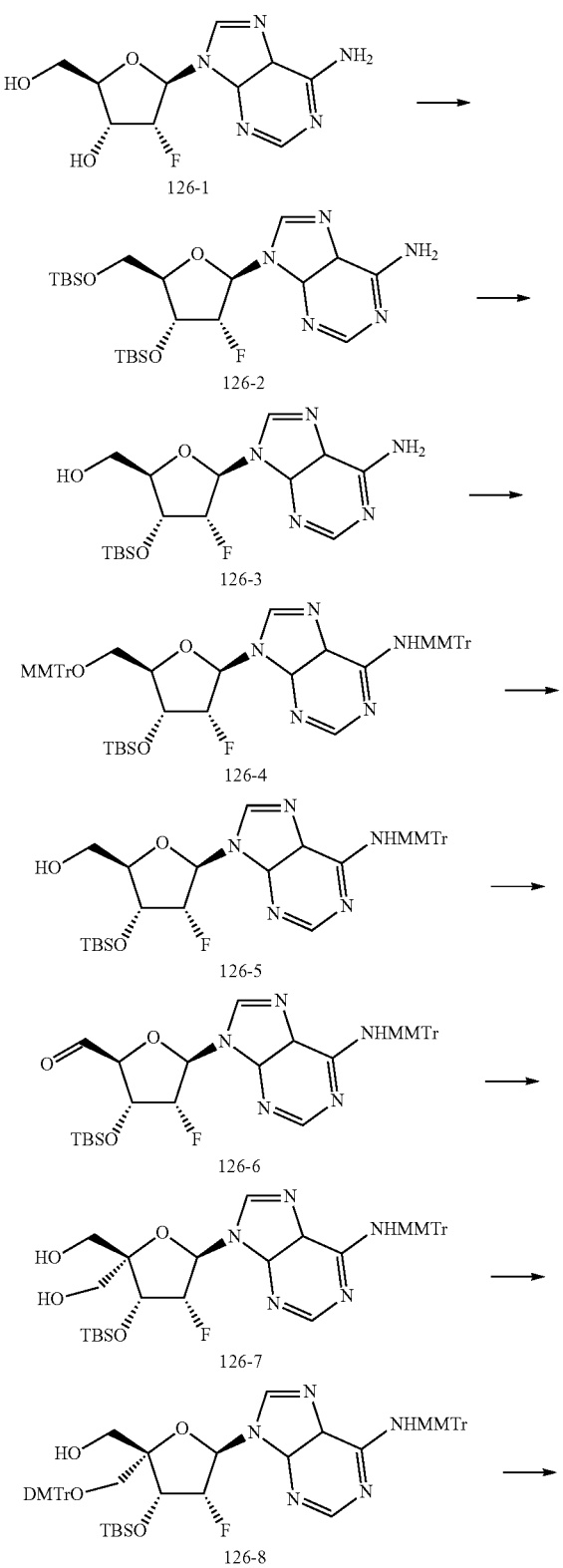

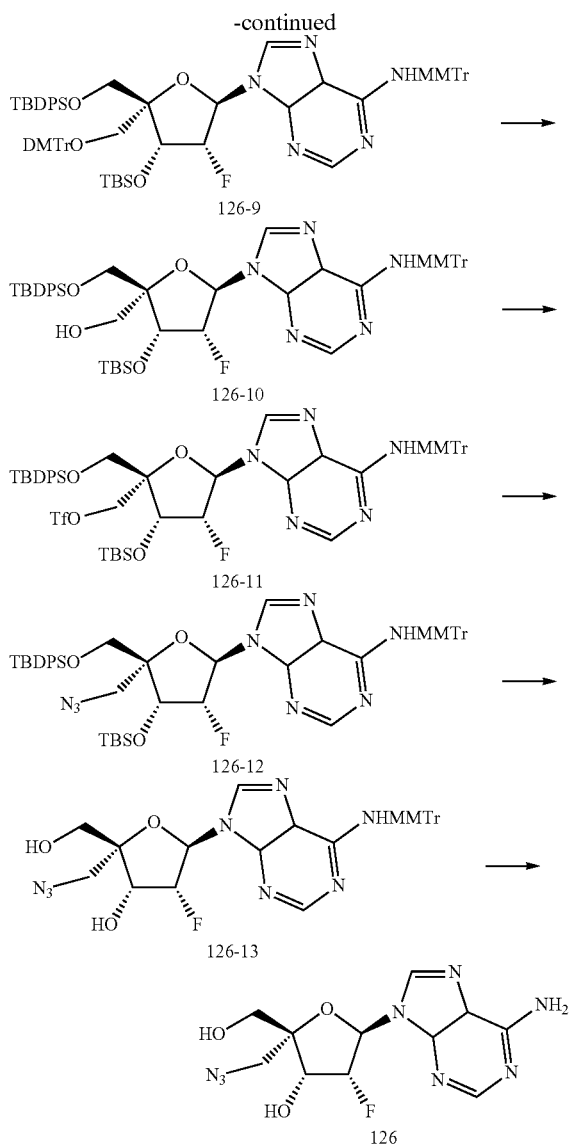

To a solution of 126-1 (3.0 g, 11.15 mmol) in anhydrous pyridine (90 mL) was added imidazole (3.03 g, 44.59 mmol) and TBSCl (6.69 g, 44.59 mmol) at 25° C. under $N_2$ atmosphere. The solution was stirred at 25° C. for 15 h. The solution was concentrated to dryness under reduced pressure. The residue was dissolved in EA. The solution was washed with sat. $NaHCO_3$ and brine, and dried over anhydrous $MgSO_4$. The solvent was removed at low pressure to give crude 126-2 (4.49 g, 90%) as a white solid.

To a stirred solution of 126-2 (3.5 g, 7.04 mmol) in a mixture of EA and EtOH (1:1, 55 mL) was added TsOH (10.7 g, 56.34 mmol) at 0° C. The mixture was stirred at 30° C. for 8 h. Water (30 mL) was added, and the solution was removed to dryness. The residue was purified on a silica gel column (10% MeOH in DCM) to give 126-3 (1.75 g, 65%) as a white foam.

To a solution of 126-3 (3.4 g, 8.88 mmol) in anhydrous pyridine (17 mL) was added collidine (4.3 g, 35.51 mmol), $AgNO_3$ (5.50 g, 35.51 mmol) and MMTrCl (8.02 g, 26.63 mmol) at 25° C. under $N_2$. The mixture was stirred at 25° C. for 12 h. MeOH (20 mL) was added, and the solvent was removed to dryness at low pressure. The residue was purified on a silica gel column (10% EA in PE) to give 126-4 (5.76 g, 70%) as a white foam.

To a solution of 126-4 (2.0 g, 2.16 mmol) in anhydrous DCM (10 mL) was added $Cl_2CHCOOH$ (2.8 g, 21.57 mmol) dropwise at −78° C. The mixture was warmed to −10° C. and stirred at this temperature for 20 mins. The reaction was quenched with sat.$NaHCO_3$ at −10° C. The mixture was extracted with DCM, washed with brine, and dried over anhydrous $MgSO_4$. The solution was concentrated at low pressure. The residue was purified on silica gel column (10% EA in PE) to give 126-5 (0.99 g, 70%) as a white foam.

To a stirred solution of 126-5 (3.5 g, 5.34 mmol) in anhydrous DMSO (35 mL) was added DCC (3.30 g, 16.03 mmol) and Py.TFA (1.03 g, 5.34 mmol). The mixture was stirred at 30° C. for 1 h. The reaction was quenched with cold water at 0° C., and extracted with EA (3×60 mL). The precipitate was filtered. The organic layers were washed with brine (3×) and dried over anhydrous $MgSO_4$. The organic phase was concentrated at low pressure to give crude 126-6 (3.5 g) as a yellow oil.

To a stirred solution of 126-6 (3.5 g, 5.34 mmol) in MeCN (35 mL) was added 37% HCHO (11.1 mL) and TEA (4.33 g, 42.7 mmol). The mixture was stirred at 25° C. for 12 h. The mixture was treated with EtOH (26 mL) and $NaBH_4$ (3.25 g, 85.5 mmol) and then stirred for 30 mins. The reaction was quenched with sat. aq. $NH_4Cl$ and extracted with EA (3×60 mL). The organic layer was dried over anhydrous $MgSO_4$, and concentrated at low pressure. The residue was purified by column chromatography (from 10% EA in PE to 50% DCM in PE) to give 126-7 (1.46 g, 40%) as a white solid.

To a stirred solution of 126-7 (1.85 g, 2.7 mmol) in pyridine (24 mL) and DCM (9.6 mL) was added DMTrCl (1.3 g, 3.9 mmol) at −35° C. under $N_2$ atmosphere. The solution was stirred at 25° C. for 16 h. The mixture was treated with MeOH (15 mL) and concentrated at low pressure. The residue was purified by column chromatography (EA in PE from 10% to 30%) to give 126-8 (1.60 g, 60%) as a white solid.

To a solution of 126-8 (1.07 g, 1.08 mmol) in anhydrous pyridine (5 mL) was added $AgNO_3$ (0.65 g, 3.79 mmol) and TBDPSCl (1.04 g, 3.79 mmol). The mixture was stirred at 25° C. for 16 h. The solvent was removed under reduced pressure. The residue was dissolved in EA (50 mL). The resulting solution was washed with brine. The organic layer was dried over anhydrous $MgSO_4$, and concentrated at low pressure. The residue was purified on a silica gel column (10% EA in PE) to give 126-9 (0.93 g, 70%) as a white foam.

To a stirred solution of 126-9 (1 g, 0.82 mmol) in anhydrous DCM (13.43 mL) was added $Cl_2CHCOOH$ (2.69 mL) at −78° C. The mixture was stirred at −10° C. for 20 mins. The reaction was quenched with sat. aq. $NaHCO_3$ and extracted with DCM. The organic layer was dried over anhydrous $Na_2SO_4$, and concentrated at low pressure. The organic phase was purified by column chromatography (MeOH in DCM form 0.5% to 2%) to give 126-10 (0.48 g, 65%) as a solid.

To an ice cold solution of 126-10 (0.4 g, 0.433 mmol) in anhydrous DCM (2.7 mL) was added pyridine (171 mg, 2.17 mmol) and $Tf_2O$ (183 mg, 0.65 mmol) by dropwise at −35° C. The mixture was stirred at −10° C. for 20 mins. The reaction was quenched with ice water and stirred for 30 mins. The mixture was extracted with DCM (3×20 mL). The organic phase was washed with brine (100 mL), dried over anhydrous $Na_2SO_4$, and concentrated at low pressure to give crude 126-11 (0.46 g), which was used for next step without further purification.

To a solution of 126-11 (0.46 g, 0.43 mmol) in anhydrous DMF (2.5 mL) was added NaN$_3$ (42 mg, 0.65 mmol). The mixture was stirred at 30° C. for 16 h. The solution was diluted with water and extracted with EA (3×30 mL). The combined organic layers were dried over anhydrous Na$_2$SO$_4$, and concentrated at low pressure. The residue was purified on a silica gel column (EA in PE from 5% to 15%) to give 126-12 (0.31 g, 70%) as a solid.

To a solution of 126-12 (0.31 g, 0.33 mmol) in MeOH (5 mL) was added NH$_4$F (0.36 g, 9.81 mmol) at 70° C. The mixture was stirred at this temperature for 24 h. The mixture was evaporated to dryness. The residue was purified on silica gel column (MeOH in DCM from 0.5% to 2.5%) to give 126-13 (117 mg, 60%) as a white solid.

126-13 (300 mg, 0.50 mmol) was dissolved in 80% of HOAc (20 mL). The mixture was stirred at 55° C. for 1 h. The reaction was quenched with MeOH and concentrated at low pressure. The residue was purified by prep-HPLC to give 126 (100 mg, 61.3%) as a white solid. ESI-LCMS: m/z 325.1 [M+H]$^+$.

Example 137

Compound 137

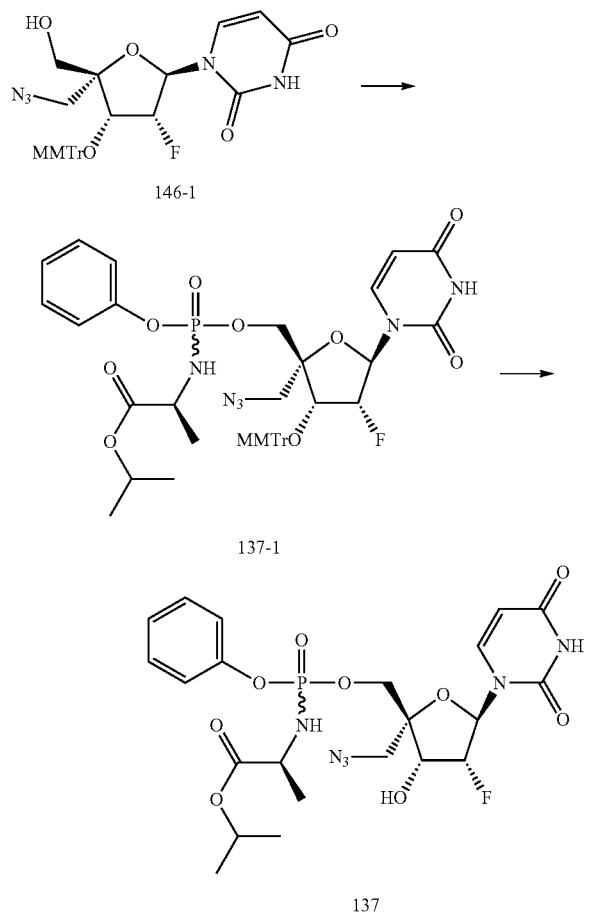

To a stirred solution of 146-1 (80 mg, 0.14 mmol) in anhydrous CH$_3$CN (2.0 mL) was added N-methylimidazole (0.092 mL, 1.12 mmol) at 0° C. (ice/water bath). A solution of phenyl (isopropoxy-L-alaninyl) phosphorochloridate (128 mg, 0.42 mmol, dissolved in CH$_3$CN (0.5 mL)) was then added (prepared according to a general procedure as described in McGuigan et al., *J. Med. Chem.* (2008) 51:5807-5812). The solution was stirred at 0 to 5° C. for h and then stirred at RT for 16 h. The mixture was cooled to 0 to 5° C., diluted with EA followed by the addition of water (5 mL). The solution was washed with 1.0M citric acid, sat. aq. NaHCO$_3$ and brine, and dried with MgSO$_4$. The residue was purified on silica (10 g column) with EA/hexanes (25-100% gradient) to give 137-1 (57.3 mg, 49%) as a foam.

137-1 (57.3 mg, 0.07 mmol) was dissolved in anhydrous CH$_3$CN (0.5 mL), and 4N HCl in dioxane (68 μL, 0.27 mmol) was added at 0 to 5° C. The mixture was stirred at RT for 2 h, and anhydrous EtOH (100 μL) was added. The solvents were evaporated at RT and co-evaporated with toluene (3×). The residue was purified on silica (10 g column) with MeOH/CH$_2$Cl$_2$ (1-7% gradient) and lyophilized to give 137 (27.8 mg, 72%) as a white foam. ESI-LCMS: m/z=571.1 [M+H]$^+$, 1141.2 [2M+H]$^+$.

Example 138

Compound 138

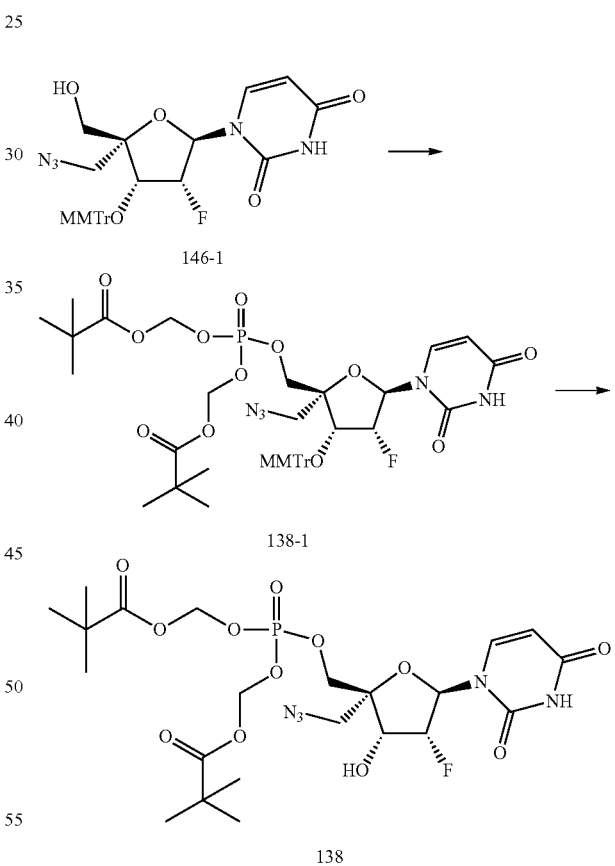

138-1 (68.4 mg, 44.7%) was prepared from 146-1 (100 mg, 0.174 mmol) and bis(tert-butoxycarbonyloxymethyl) phosphate (126 mg, 0.35 mmol) with DIPEA (192 μL, 1.04 mmol), BOP-Cl (133 mg, 0.52 mmol), and 3-nitro-1,2,4-triazole (59 mg, 0.52 mmol) in THF (1.5 mL) in the same manner as 169-4.

138 (31.4 mg, 67%) was prepared from 138-1 (68 mg, 0.077 mmol) in the same manner as 146. ESI-LCMS: m/z=627.15 [M+Na]$^+$, 1219.25 [2M+H]$^+$.

Example 139

Compound 139

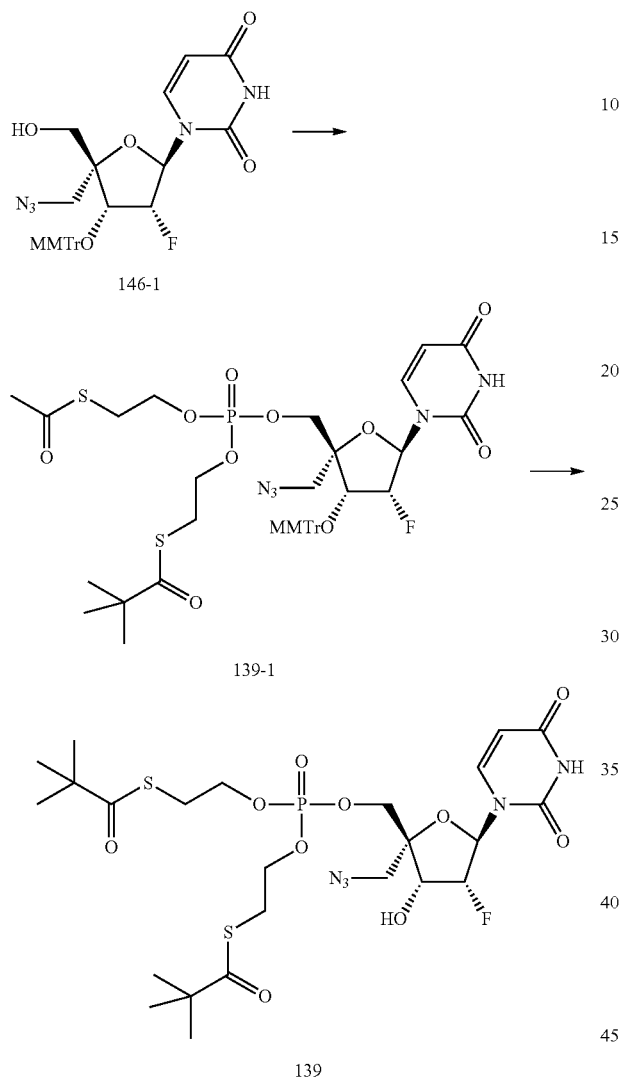

Example 140

Compound 143

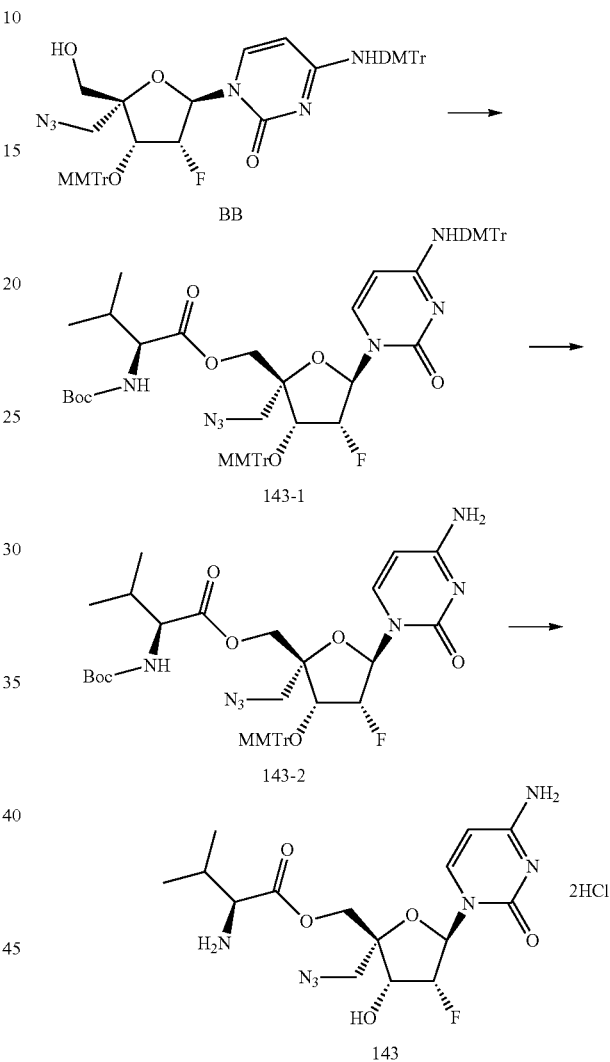

To a solution of 146-1 (100 mg, 0.175 mmol) in anhydrous CH₃CN (2 mL) was added 5-ethylthio-1H-tetrazole in CH₃CN (0.25M; 0.84 mL, 0.21 mmol). Bis-SATE-phosphoroamidate (95 mg, 0.21 mmol) in CH₃CN (1 mL) was added at 0 to 5° C. dropwise. The mixture was stirred 2 h at 0 to 5° C. under Ar. A solution of 77% m-CPBA (78 mg, 0.35 mmol) in DCM (1 mL) was added, and the mixture stirred 2 h at 0 to 5° C. under Ar. The mixture was diluted with EtOAc (50 mL), washed with 1.0M citric acid, sat. NaHCO₃ and brine, and dried with MgSO₄. The mixture was filtered, and the solvents were evaporated in vacuo. The residue was purified on silica (10 g column) with EA/hexanes (20-100% gradient) to give 139-1 (105 mg, 63.6%) as a white foam.

139-1 (105 mg, 0.112 mmol) was dissolved in anhydrous CH₃CN (0.8 mL), and 4N HCl in dioxane (84 μL, 0.334 mmol) was added at 0 to 5° C. The mixture was stirred at RT for 2 h. Anhydrous EtOH (100 μL) was added. The solvents were evaporated at RT, and co-evaporated with toluene (3×). The residue was purified on silica (10 g column) with MeOH/CH₂Cl₂ (1-7% gradient) and lypholized to give 139 (42.7 mg, 57%) as a white foam. ESI-LCMS: m/z=692.15 [M+Na]⁺, 1339.30 [2M+H]⁺.

To a solution of N-Boc-L-Valine (620.78 mg, 2.86 mmol) and TEA (144.57 mg, 1.43 mmol) in anhydrous THF (2.5 mL) was added BB (250.00 mg, 285.73 μmol). The mixture was co-evaporated with pyridine and toluene to remove water. The residue was dissolved in THF (2.5 mL). DIPEA (369.28 mg, 2.86 mmol) was added, followed by addition of BOP-Cl (363.68 mg, 1.43 mmol) and 3-nitro-1H-1,2,4-triazole (162.95 mg, 1.43 mmol) at RT (18° C.). The mixture was stirred at RT for 12 h and then diluted with EA (40 mL). The solution was washed with brine, dried over anhydrous Na₂SO₄ and concentrated to dryness at low pressure. The residue was purified on a silica gel column (30% EA in PE) to give 143-1 (220 mg, crude) as a white foam.

143-1 (250.0 mg, 232.73 μmol) was dissolved in 80% CH₃COOH (30 mL). The solution was heated to 50° C. and stirred for 12 h. The reaction was quenched with MeOH, and the solution was concentrated to dryness. The residue was purified on a silica gel column (5% MeOH in DCM) to give 143-2 (80.00 mg, 68.82%) as a white foam.

143-2 (78.00 mg, 156.16 μmol) was dissolved in HCl/dioxane (1.5 mL) and EA (1.5 mL) at RT (19° C.). The mixture was stirred at RT for 30 mins. The solution was concentrated to dryness at low pressure. The residue was purified by prep-HPLC to give 143 (23 mg, 31.25%) as a white solid. ESI-MS: m/z 400.20 [M+H]$^+$, 799.36 [2M+H]$^+$.

Example 141

Compound 154

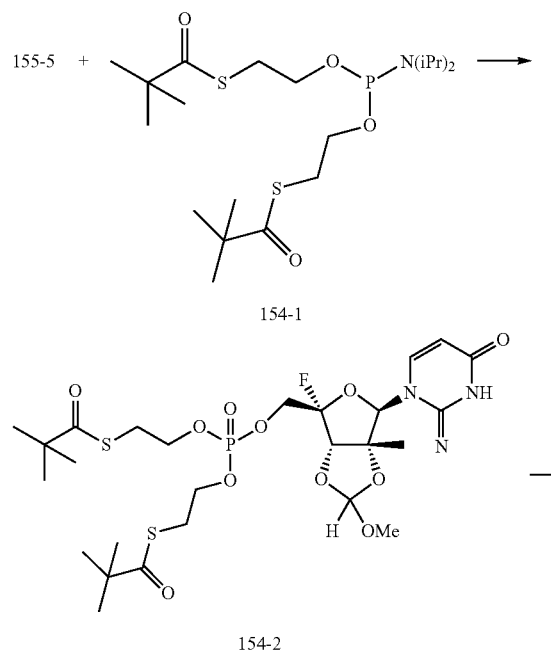

154-1

154-2

154

154-1 was prepared according to the procedure described in Lefebre et al., *J. Med. Chem.* (1995) 38:3941-3950, which is hereby incorporated by reference for the limited purpose of its description of the preparation of 154-1.

154-2 (0.33 g, 0.5 mmol) was prepared using a similar procedure to the one used to prepare 155-6 using 155-5 and 154-1. 154-2 was obtained as a white solid. Using a similar procedure to the one used to prepare 155, 154-2 was used to prepare 154 (130 mg). $^1$H-NMR (CDCl$_3$): 7.40 (d, 1H), 6.1 (s, 1H), 5.83 (d, 1H), 4.3 (t, 2H), 4.1-4.2 (m, 6H), 3.2 (t, 4H), 1.69 (s, 4H), 1.3 (s, 3H), 1.23 (s, 18H); $^{31}$P-NMR (CDCl$_3$): −2.4 ppm.

Example 142

Compound 155

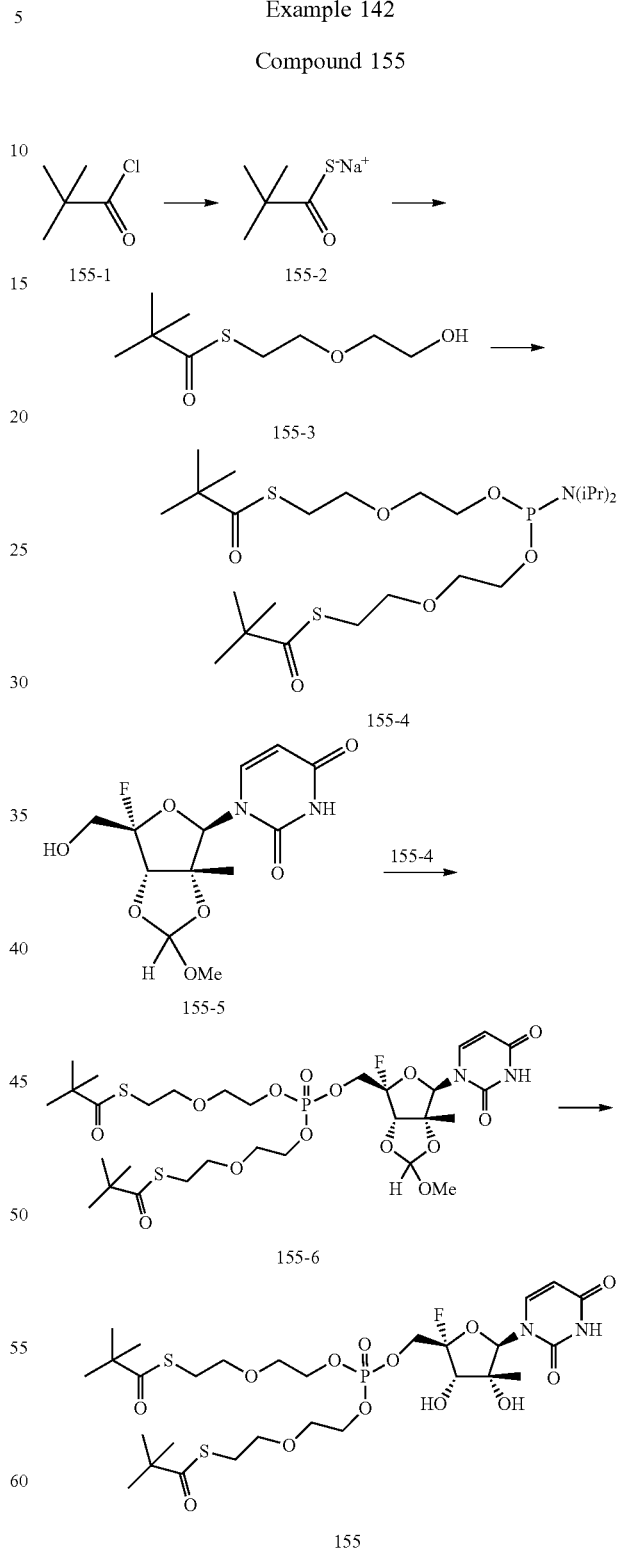

155

To a solution of sodium hydrosulfide (4.26 g, 76.0 mmol) in EtOH (100 mL) was added t-butyryl chloride (76.2 mmol; 9.35 mL) dropwise at 0° C., and the mixture was stirred at RT for 1 h. A solution of 2-(2-chloroethoxy)ethanol (57 mmol; 6.0 mL) and TEA (21 mL, 120 mmol) was added, and the mixture was heated at reflux for 60 h. The mixture was filtered, and then concentrated to a small volume. The residue was dissolved in EA, and then washed with water, sat. aq. NaHCO$_3$ and brine. The organic phase was dried over Na$_2$SO$_4$, filtered and concentrated in vacuo. The crude product (10.0 g) was isolated and 5 grams were purified by silica gel flash column chromatography using a gradient of 0 to 100% EA in hexane to give 155-3 (4.5 g, 22 mmol) as a clear, colorless oil. $^1$H-NMR (CDCl$_3$): 3.70-3.74 (m, 2H), 3.5-3.65 (m, 4H), 3.1 (t, 2H), 1.25 (s, 9H).

A solution 155-3 (4.5 g; 21.8 mmol) and triethylamine (6.7 mL, 87.2 mmol) in tetrahydrofuran (50 mL) was added dropwise over 1 h to a stirred solution of N,N-diisopropylphosphorodichloridite (2.0 mL, 10.9 mmol) in THF (50 mL) under argon at −78° C. The mixture was stirred at RT for 2 h, and then diluted with EA (200 mL). The mixture was washed with sat. aq. NaCl and dried over Na$_2$SO$_4$. After filtration, the filtrate was evaporated under reduced pressure to give a pale yellow oil. Purification by flash column chromatography using a gradient of EA (0-5%) in hexane containing 5% triethylamine afforded 155-4 (2.5 g, 4.25 mmol) as a clear, colorless oil. $^1$H-NMR (CDCl$_3$): 3.70-3.82 (m, 4H), 3.57-3.65 (m, 10H), 3.1 (t, 4H), 1.25 (s, 18H), 1.17 (t, 12H); $^{31}$P-NMR (CDCl$_3$): 148.0 ppm.

155-5 (285 mg, 0.9 mmol) and DCI (175 mg, 1.5 mmol) were coevaporated twice with ACN and then dissolved in ACN (5 mL). 155-4 (790 mg, 1.35 mmol) in ACN (4 mL) was added, and the reaction was monitored by TLC. After 15 mins, tert-butylhydroperoxide (0.5 mL of 5.5M solution in decane) was added, and the mixture was stirred for 10 mins. The mixture was diluted with EA (25 mL), washed with sat. aq. NaHCO$_3$ and sat. aq. NaCl solution, dried over Na$_2$SO$_4$, filtered and concentrated. Purification by flash column chromatography using a gradient of EA (0-100%) in hexane afforded 155-6 (0.17 g, 0.22 mmol) as a white solid. 155-6 was dissolved in 80% aq. HCOOH (5 mL). After 30 mins at RT, the solvent was removed and coevaporated twice with toluene. The residue was dissolved in methanol (10 mL) and TEA (0.2 mL) was added. After 2 mins at RT, the solvent was removed in vacuo. Purification by flash column chromatography using a gradient of methanol (0-15%) in DCM afforded 155 (90 mg). $^1$H-NMR (CDCl$_3$): 7.40 (d, 1H), 6.1 (s, 1H), 5.83 (d, 1H), 4.3 (t, 2H), 4.1-4.2 (m, 6H), 3.70-3.82 (m, 4H), 3.57-3.65 (m, 4H), 3.1 (t, 4H) 1.61 (s, 8H), 1.3 (s, 3H), 1.23 (s, 18H). $^{31}$P-NMR (CDCl$_3$): −1.55 ppm.

Example 143

Compound 156

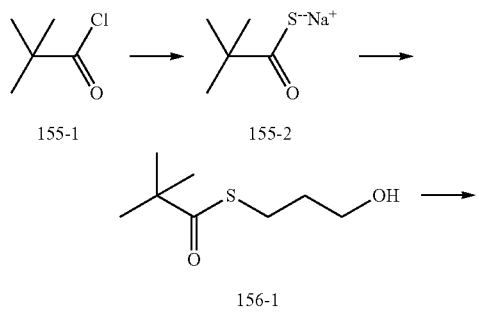

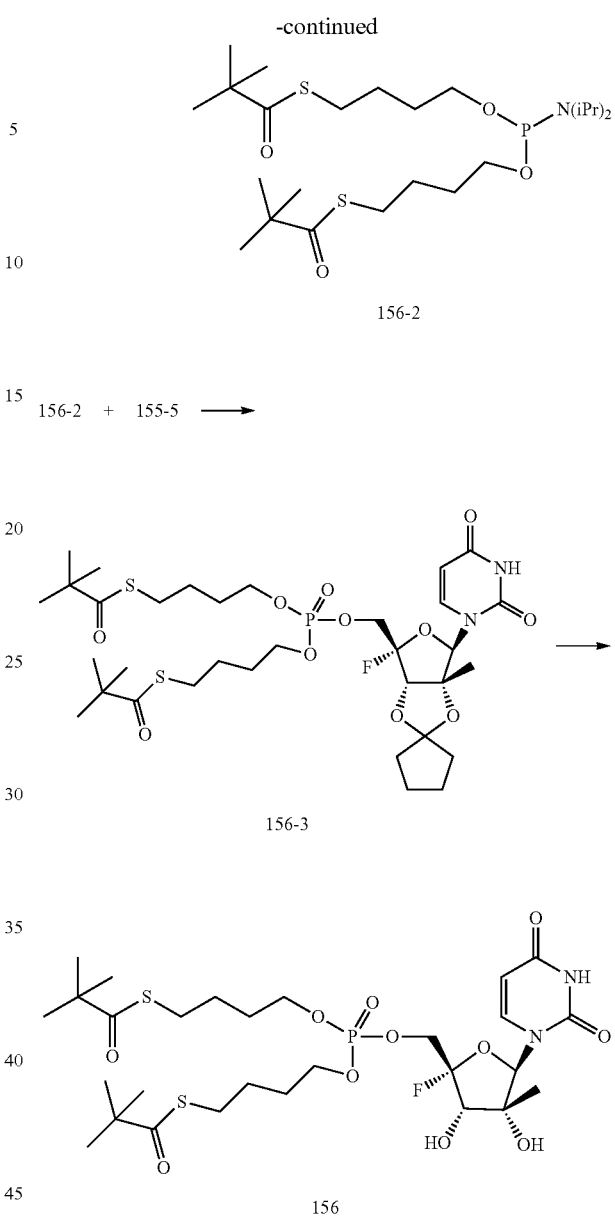

156-1 (6.0 g, 31.6 mmol) was prepared using a similar procedure to the one used to prepare 155-3 using 4-chlorobutanol. 156-1 was obtained as a clear, colorless oil. $^1$H-NMR (CDCl$_3$): 3.67 (s, 2H), 2.86 (m, 2H), 1.65 (m, 4H), 1.25 (s, 9H).

156-2 (2.14 g, 4.0 mmol) was prepared using a similar procedure to the one used to prepare 155-4. 156-2 was obtained as a clear, colorless oil. $^1$H-NMR (CDCl$_3$): 3.67 (m, 6H), 2.86 (t, 4H), 1.65 (m, 8H), 1.25 (s, 18H), 1.17 (t, 12H). $^{31}$P-NMR (CDCl$_3$): 143.7 ppm.

156-3 (0.23 g, 0.22 mmol) was prepared using a similar procedure to the one used to prepare 155-6 using 155-5 and 156-2. 156-3 was obtained as a white solid. Using a similar procedure to the one used to prepare 155, 156-3 was used to prepare 156 (170 mg). $^1$H-NMR (CDCl$_3$): 7.40 (d, 1H), 6.1 (s, 1H), 5.83 (d, 1H), 4.3 (t, 2H), 4.1-4.2 (m, 6H), 2.8 (t, 4H), 1.78 (m, 4H), 1.69 (s, 8H), 1.3 (s, 3H), 1.23 (s, 18H). $^{31}$P-NMR (CDCl$_3$): −1.56 ppm.

Example 144

Compound 161

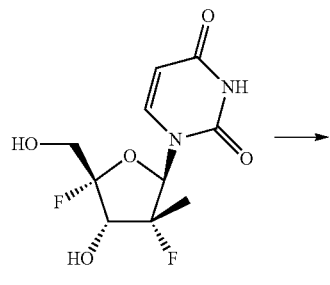

161-1

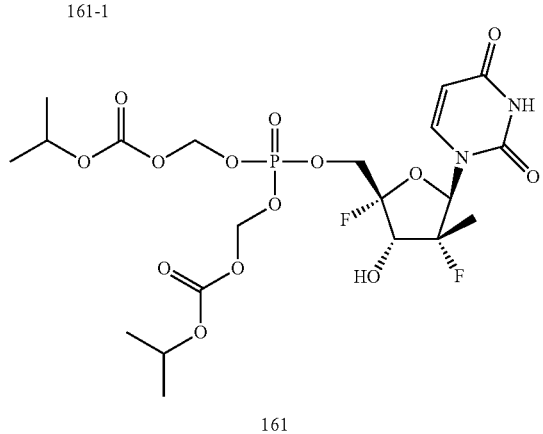

161

161-1 (109 mg, 0.39 mmol) and triethylammonium bis(isopropyloxycarbonyloxymethyl)phosphate (0.6 mmol, prepared from 195 mg of bis(isopropyloxycarbonyloxymethyl)phosphate and 85 µL of Et$_3$N) were rendered anhydrous by coevaporating with pyridine, followed by toluene. The residue was dissolved in anhydrous THF (3 mL) and cooled in an ice-bath. Diisopropylethyl amine (0.2 mL, 3 eq.), BopCl (190 mg, 2 eq.), and 3-nitro-1,2,4-triazole (81 mg, 2 eq.) were added, and the mixture was stirred at 0° C. for 90 mins. The mixture was diluted with EtOAc, washed with sat. aq. NaHCO$_3$ and brine, and dried (Na$_2$SO$_4$). Purification on silica gel column with CH$_2$Cl$_2$/i-PrOH (4-10% gradient) followed by RP-HPLC purification (A: 0.1% HCOOH in water, B: 0.1% HCOOH in MeCN) yielded 161 (28 mg, 12%). $^1$H-NMR (CDCl$_3$): δ 7.24 (d, 1H), 6.6 (br, 1H), 5.84 (d, 1H), 5.65-5.73 (m, 4H), 4.94 (m, 2H), 4.38 (m, 2H), 4.1 (b, 1H), 2.88 (d, 1H), 1.47 (d, 3H), 1.33 (m, 12H).

Example 145

Compound 269

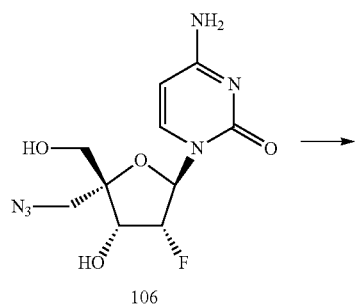

106

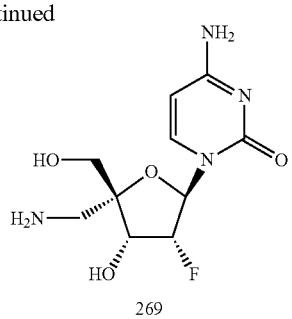

269

106 (30 mg, 0.1 mmol) was hydrogenated in MeOH over 10% Pd/C at normal pressure. The catalyst was filtered off, and the filtrate was purified by RP HPLC on Synergy 4 micron Hydro-RP column (Phenominex). A linear gradient of MeOH from 0 to 20% in 50 mM triethylammonium acetate buffer (pH 7.5) was used for elution. The corresponding fractions were combined, concentrated and lyophilized (3×) to remove excess of buffer to yield 269 (17 mg, 63%). ESI-LCMS: m/z=275.2 [M+H]$^+$, 297.1 [M+Na]$^+$.

Example 146

Compound 275

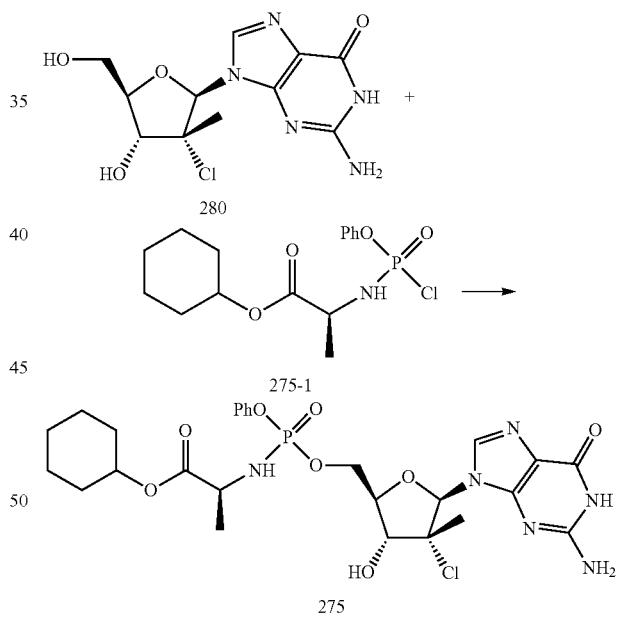

To an ice cold solution of 280 (50 mg, 0.16 mmol) and N-methylimidazole (50 µL, 0.64 mmol) in acetonitrile (1.5 mL) was added a solution of 275-1 (0.1 g, 0.28 mmol) in acetonitrile (0.15 mL). The mixture stirred at 5° C. for 1 h. The reaction was quenched with EtOH, and the mixture concentrated. The evaporated residue was partitioned between EtOAc and citric acid (0.5 N). The organic layer was washed with sat. aq. NaHCO$_3$ and brine, and then dried with Na$_2$SO$_4$. Purification by RP-HPLC (A: water, B: MeCN) yielded 275 (30 mg, 30%) as a white powder. MS: m/z 625 [M+1].

Example 147

Compound 157

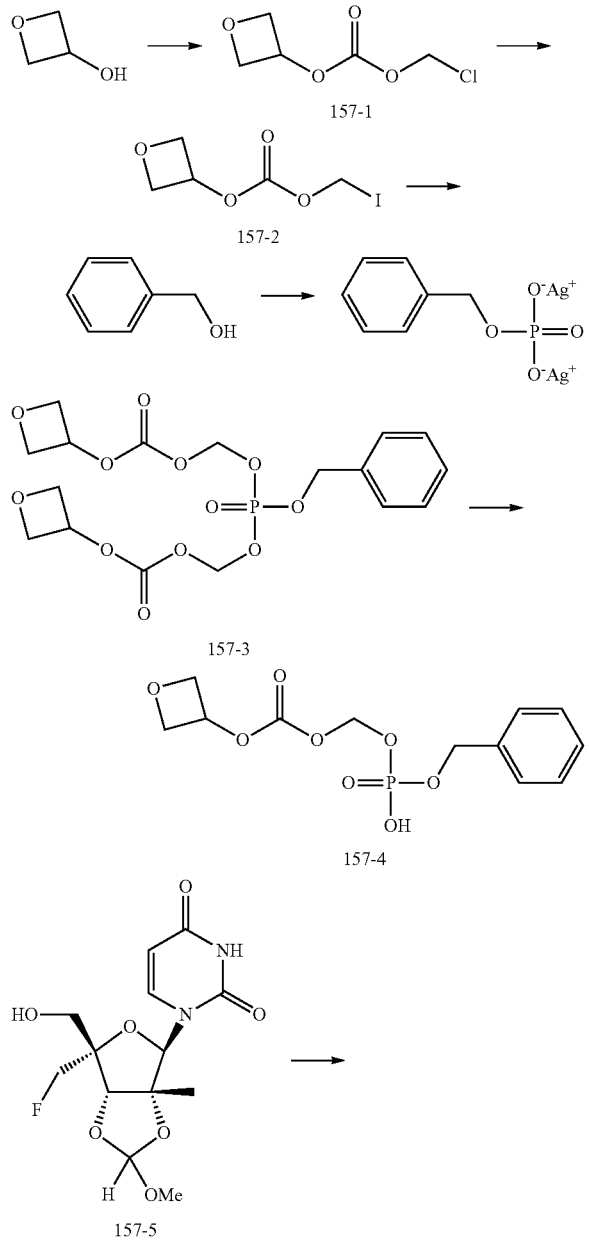

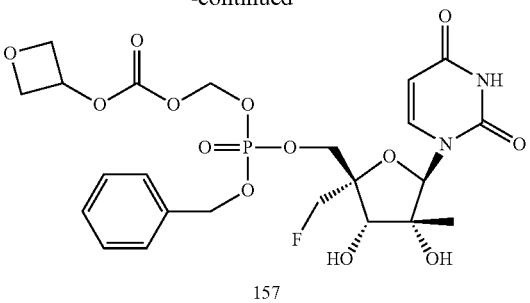

Compound 157-1 was prepared from commercially available 3-hydroxyoxetane (5.0 g) using the procedure described for preparing 54-2 (5.6 g). $^1$H-NMR (CDCl$_3$) δ 5.73 (s, 2H), 5.48-5.51 (m, 1H), 4.90 (d, 2H), 4.72 (d, 2H).

Compound 157-2 was prepared from 157-1 using the procedure described for preparing 54-3 (8.0 g). $^1$H-NMR (CDCl$_3$) δ 5.95 (s, 2H), 5.48-5.51 (m, 1H), 4.90 (d, 2H), 4.72 (d, 2H).

Benzylphosphate (silver salt) and 157-2 (8.0 g) were reacted as described for preparing 54-4 to yield purified 157-3 (1.92 g). $^1$H-NMR (CD$_3$CN): δ 7.39-7.42 (m, 5H), 5.62 (d, 4H), 5.39-5.42 (m, 2H), 5.15 (d, 2H), 4.80-4.83 (m, 4H), 4.56-4.60 (m, 4H). $^{31}$P-NMR (CD$_3$CN): δ −4.55 ppm.

Compound 157-3 (970 mg, 2.16 mmol) was dissolved in methanol containing triethylamine (0.3 mL, 2.16 mmol). After 3 h at R.T, the solvents were removed in vacuo to give crude 157-4 that was used without further purification.

Compound 157-5 (400 mg; 1.2 mmol) and 157-4 (900 mg, 2.16 mmol; 1.5×) were coevaporated with pyridine (2×) and toluene (2×), and then dissolved in THF (8 mL) at 0° C. Diisopropylethylamine (DIPEA) (0.82 mL; 4 eq.), bis(2-oxo-3-oxazolidinyl) phosphinic chloride (Bop-Cl) (0.6 g; 2 eq.), nitrotriazole (0.266 g, 2 eq.) were added. The mixture kept at 0° C. for 2 h. The mixture was diluted with EA (50 mL) and extracted with saturated sodium bicarbonate (2×50 mL) and dried over sodium sulfate. The solvents were removed in vacuo. The residue was purified by flash chromatography using a 10 to 100% gradient of EA in hexane to give purified 157-6 (175 mg, 0.6 mmol).

Purified 157-6 was dissolved in 80% aq. HCOOH (20 mL) and kept at 20° C. for 1 h. After cooling to RT, the solvent was removed in vacuo, and the residue coevaporated with toluene (3×25 mL). The residue was purified by flash chromatography using a 0 to 20% gradient of MeOH in DCM to give purified 157 (26 mg). ESI-LCMS: m/z 589.6 [M−H]$^-$.

Example 148

Compound 158

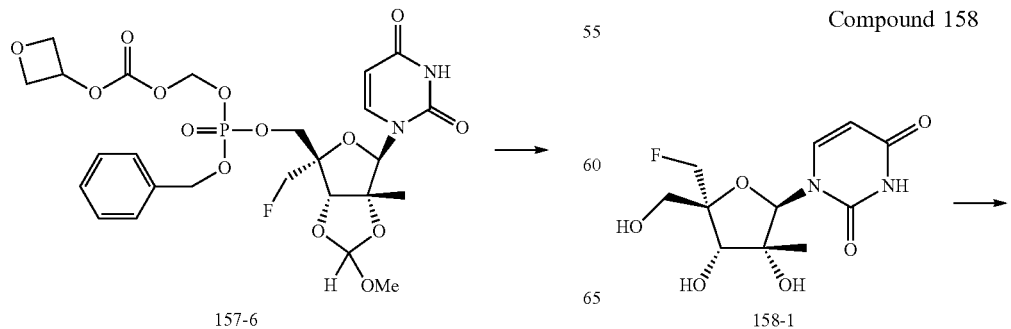

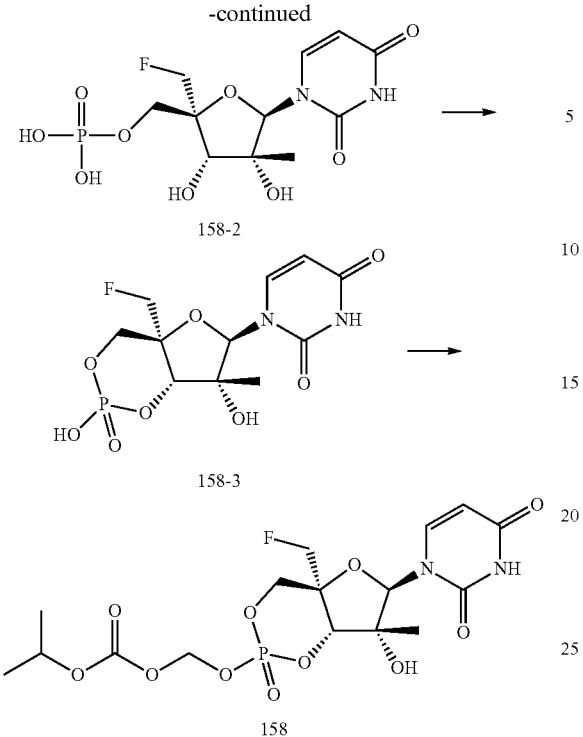

Nucleoside 158-1 (from Wuxi) (44 mg, 0.15 mmol) was dissolved in a mixture of trimethyl phosphate (2 mL) and dry pyridine (0.5 mL). The mixture was evaporated in vacuum for 15 mins at 42° C., than cooled to RT. N-Methylimidazole (0.027 mL, 0.33 mmol) was added followed by POCl$_3$ (0.027 mL, 0.3 mmol). The mixture was kept at RT. The reaction was monitored by LC/MS in 0-50% gradient. After 4 h, the reaction was complete. The reaction was quenched with 2M triethylammonium acetate buffer (2 mL), pH7.5 (TEAA). 158-2 was isolated on prep-HPLC (Phenomenex Synergi 4u Hydro-RP 250×21.2 mm) using a gradient of 0-30% ACN in 50 mM TEAA.

Compound 158-2 (triethylammonium salt; 45 mg, 0.1 mmol) was dried by repeated co-evaporation with dry pyridine (3×). 158-2 was dissolved in dry pyridine (1 mL) and the solution added dropwise into a boiling solution of diisopropylcarbodiimide (63 mg, 0.5 mmol) in pyridine (4 mL) over 2.5 h. The mixture was heated under reflux for 1 h. After being cooled to 25° C., the reaction was quenched with 2M TEAA buffer (2 mL) and kept at 25° C. for 1 h. The solution was concentrated to dryness, and the residual pyridine removed by coevaporated with toluene (3×2 mL). 158-3 was isolated on prep-HPLC (Phenomenex Synergi 4u Hydro-RP 250×21.2 mm) using a gradient of 0-30% ACN in 50 mM TEAA.

Compound 158-3 (triethylammonium salt; 26 mg, 0.045 mmol) was dissolved in dry DMF (0.5 mL) at RT under argon. To the stirred solution was added N,N-diisopropylethylamine (40 uL, 0.22 mmol) followed by chloromethyl isopropyl carbonate (35 mg, 0.22 mmol). The mixture was stirred at 65° C. for 18 h. The mixture was evaporated to dryness, and the residue was purified by silica column using a 0-15% gradient of MeOH in CH$_2$Cl$_2$. The fractions having 158 were pooled, and the mixture was concentrated to dryness to give 158 (2.3 mg). ESI-LCMS: m/z 467.5 [M−H]$^−$.

Example 149

Compound 276

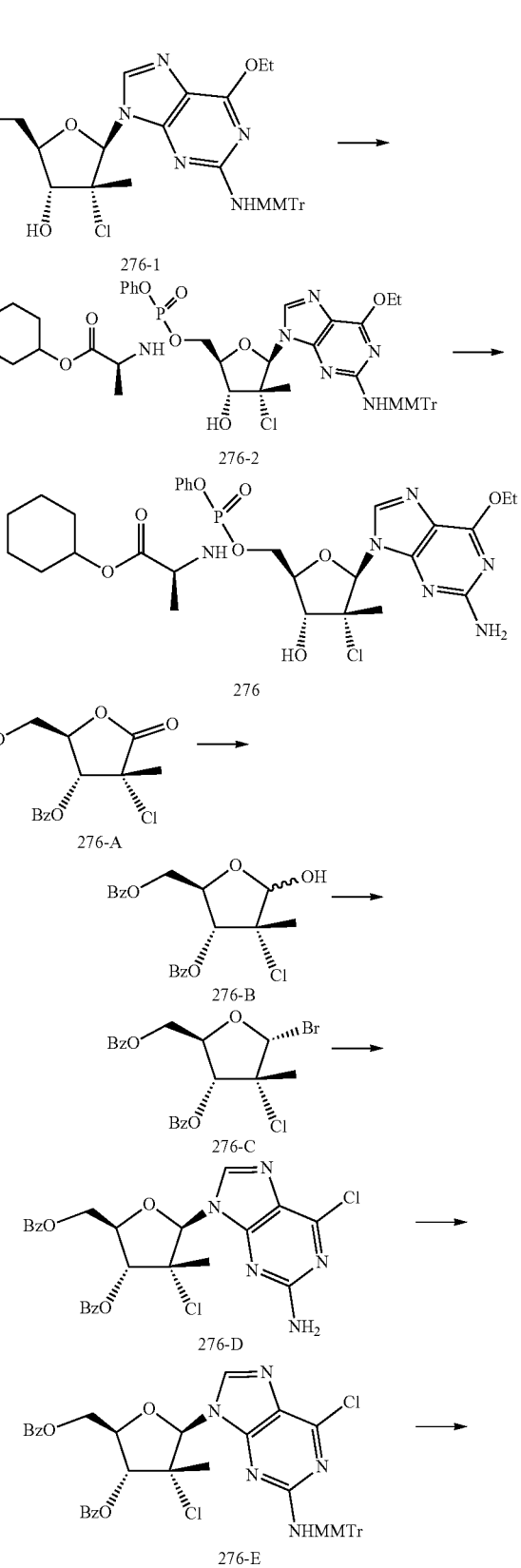

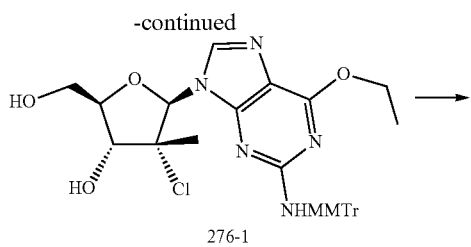

276-1

To a stirred solution of 276-1 (180 mg, 0.16 mmol) in anhydrous CH₃CN (2.0 mL) was added N-methylimidazole (53.4 μL, 0.65 mmol) at 0° C. (ice/water bath). A solution of phenyl (cyclohexyloxy-L-alaninyl) phosphorochloridate (101 mg, 0.29 mmol) dissolved in CH₃CN (0.5 mL), prepared according to a general procedure (McGuigan et al., *J. Med. Chem.* (2008) 51:5807-5812), was added. The solution was stirred at 0 to 5° C. for 3 h. N-methylimidazole (50 μL) at 0° C. (ice/water bath) followed by solution of phenyl (cyclohexyloxy-L-alaninyl) phosphorochloridate (52 mg, dissolved in 0.5 mL of CH₃CN) were added. The mixture was stirred at RT for 16 h. The mixture was cooled to 0 to 5° C. and diluted with EA. Water (5 mL) was added. The solution was washed with 1.0M citric acid, sat. aq. NaHCO₃ and brine, and dried with MgSO₄. The residue was purified on silica (10 g column) with DCM/MeOH (0-10% gradient) to give 276-2 (96.8 mg, 64%) as foam.

Compound 276-2 (95 mg, 0.11 mmol) was dissolved in anhydrous CH₃CN (0.5 mL), and 4N HCl in dioxane (77 μL, 0.3 mmol) was added at 0 to 5° C. The mixture was stirred at RT for 30 mins, and anhydrous EtOH (100 μL) was added. The solvents were evaporated at RT and co-evaporated with toluene (3×). The residue was purified on RP-HPLC with H₂O/CH₃CN (50-100% gradient) and lypholized to give 276 (37.7 mg, 52.5%) as a white foam. ESI-LCMS: m/z=653.2 [M+H]⁺, 1305.4 [2M+H]⁺.

To a solution of 276-A (56 g, 0.144 mol) in anhydrous THF (600 mL) was added a solution of lithium tri-tert-butoxyaluminohydride (216 mL, 1M, 0.216 mol) dropwise at −78° C. under N₂ for 30 mins. The solution was stirred between −78° C. to 0° C. for 1 h. The reaction was quenched with sat.NH₄Cl solution and extracted with EA (3×200 mL). The combined organic layers were dried over anhydrous Na₂SO₄, filtrated and concentrated to give 276-B (52 g, 92%) as a colorless oil.

To a stirred solution of PPh₃ (45.7 g, 0.174 mol) in CH₂Cl₂ (200 mL) was added 276-B (34 g, 0.087 mol) at −20° C. under N₂. The mixture was stirred for 15 mins. CBr₄ (58 g, 0.174 mol) was added dropwise while maintaining the temperature between −25° C. and −20° C. under N₂ flow. The mixture was then stirred below −17° C. for 20 mins. The mixture was treated with silica gel. The solution was filtered through cold silica column gel and washed with cold elute (PE:EA=50:1 to 4:1). The combined filtrates were concentrated under reduced pressure at RT to give the crude oil product. The residue was purified by silica column gel (PE:EA=50:1 to 4:1) to give 276-C (α-isomer, 24 g, 61%) as a colorless oil. ¹H-NMR (CDCl₃, 400 MHz), δ=8.16 (d, J=6.8 Hz, 2H), 8.01 (d, J=7.6 Hz, 2H), 7.42-7.62 (m, 6H), 6.43 (s, 1H), 5.37 (d, J=4.4 Hz, 1H), 4.68-4.86 (m, 3H), 1.88 (s, 3H).

A mixture of 6-Cl-guanosine (80.8 g, 0.478 mol) and t-BuOK (57 g, 0.509 mol) in t-BuOH (1 L) was stirred at 30-35° C. for 30 mins. 276-C (72 g, 0.159 mol, in MeCN 500 mL) was added at RT and the mixture was heated to 70° C. and stirred for 3 h. The reaction was quenched with sat. NH₄Cl solution, and extracted with EA (3×300 mL). The combined organic layers were dried over anhydrous Na₂SO₄ and evaporated at low pressure. The residue was purified by silica gel column (PE:EA=4:1 to 2:1) to give 276-D (14 g, 16%). ¹H-NMR (CDCl₃, 400 MHz) δ 7.93-8.04 (m, 4H), 7.90 (s, 1H), 7.30-7.50 (m, 6H), 6.53 (d, J=8.8 Hz, 1H), 6.36 (s, 1H), 5.35 (s, 2H), 5.06-5.10 (m, 1H), 4.81-4.83 (m, 1H), 4.60-4.64 (m, 1H), 1.48 (s, 3H).

To a solution of 276-D (14 g, 25.9 mmol) in DCM (15 mL) was added AgNO₃ (8.8 g, 51.8 mmol) and collidine (6.3 g, 51.8 mmol) and MMTrCl (12.1 g, 38.9 mmol). The mixture was stirred at RT for 1 h. The reaction was quenched with MeOH (5 mL). After filtration, the filter was washed with brine, dried over anhydrous Na₂SO₄, and concentrated at low pressure. The residue was purified by silica gel column (PE:EA=10:1 to 3:1) to give 276-E (16 g, 80%). ¹H-NMR (CDCl₃, 400 MHz) δ=8.05-8.07 (m, 4H), 7.93 (s, 1H), 7.18-7.57 (m, 18H), 6.77 (d, J=8.8 Hz, 2H), 6.71 (s, 1H), 5.86 (s, 1H), 5.6 (s, 1H), 4.77 (d, J=10.0 Hz, 1H), 4.67-4.76 (m, 1H), 4.55-4.59 (m, 1H), 3.75 (s, 1H), 1.06 (s, 3H).

Sodium (170 mg, 7.38 mmol) was dissolved in dry EtOH (5 mL) at 70° C., and the solution was cooled to 0° C. 276-E (1 g, 1.23 mmol) was added in portions at 0° C. The mixture was stirred for 8 h at RT. The mixture was neutralized with CO₂ to pH 7.0, and concentrated at low pressure. The residue was purified by prep-HPLC (10% CH₃CN/H₂O) to give 276-1 (0.4 g, 53%) as a yellow solid. ESI-MS: m/z 616 [M+H]⁺.

Example 150

Compound 222

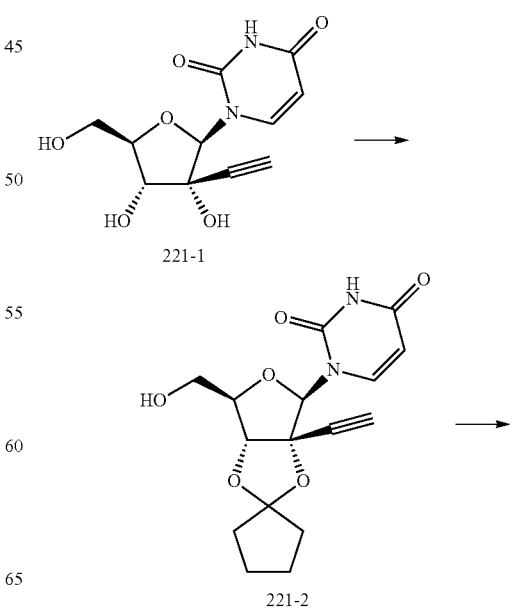

221-1

221-2

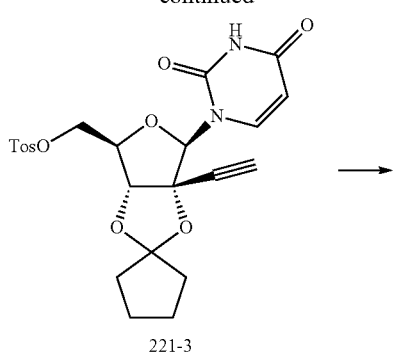

221-3

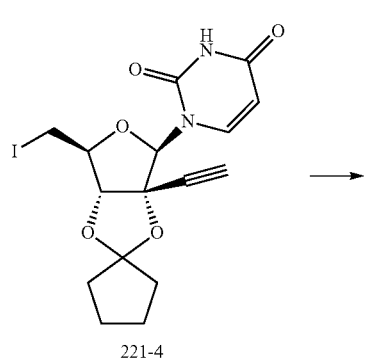

221-4

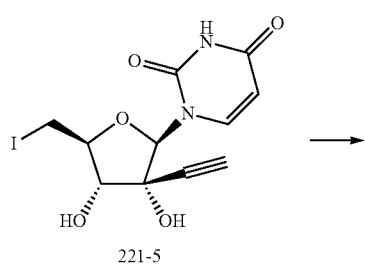

221-5

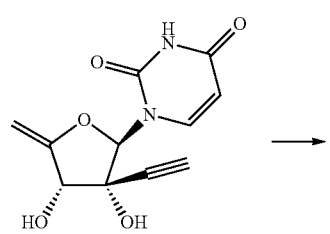

221-6

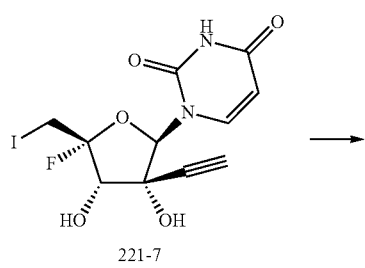

221-7

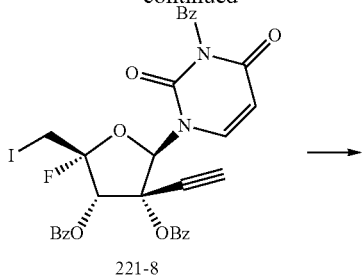

221-8

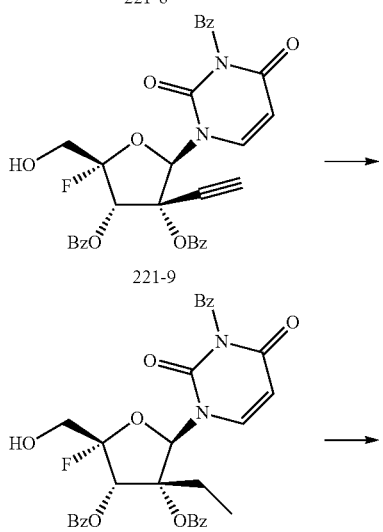

221-9

222-1

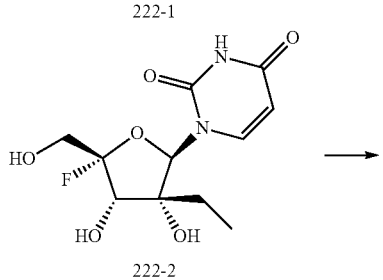

222-2

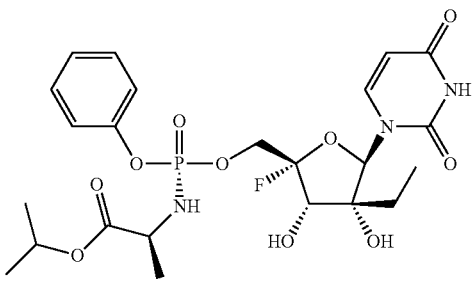

222

To a solution of 221-9 (300 mg, 0.50 mmol) in MeOH (30 mL) was added wet Pd/C (300 mg, 10%) under $N_2$. The mixture was stirred under $H_2$ (1 atm) at 25° C. for 1.5 h. The suspension was filtered, and then concentrated at low pressure to give crude 222-1 (307 mg) as a white solid.

Compound 222-1 (307 mg, 0.48 mmol) was dissolved in $NH_3$/MeOH (30 mL, 7 M). The mixture was stirred at RT for 24 h under $N_2$ then concentrated at low pressure. The residue was purified by prep-HPLC (0.1% HCOOH in water and MeCN) to give 222-2 (30 mg, 21% over two steps) as a white solid.

Compound 222-2 (91 mg, 0.31 mmol) was co-evaporated with toluene 3 times to remove H₂O. To a stirred solution of 222-2 (91 mg, 0.31 mmol) in a mixture of MeCN (0.5 mL) and NMI (254 mg, 3.90 mmol) was added a solution 222-C (203 mg, 0.66 mmol) in MeCN (0.5 mL) at 0° C. The mixture was stirred at RT overnight and then concentrated at low pressure. The residue was purified on a silica gel column (5% MeOH in DCM) to the crude 222, which purified by prep-HPLC (0.1% HCOOH in water and MeCN) to give 222 (30 mg, 17%) as a white solid. ESI-MS: m/z 540.1 [M−F]⁺.

Example 151

Compound 226

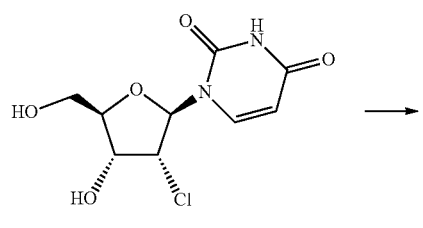

226-1

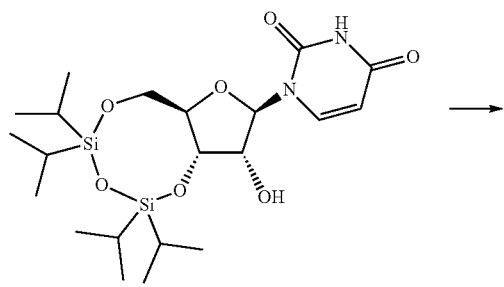

226-2

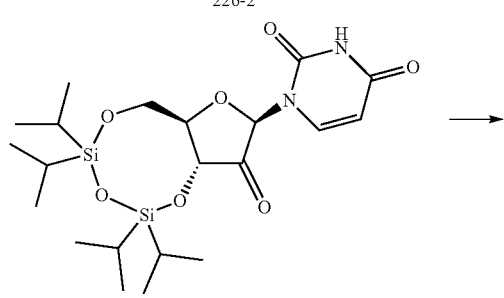

226-3

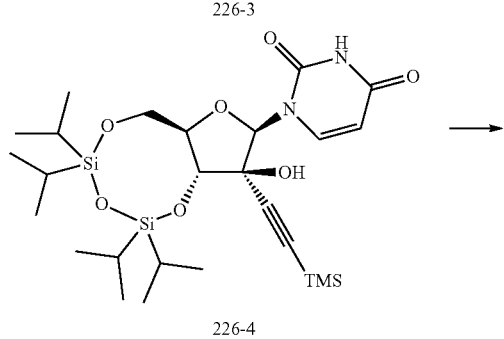

226-4

-continued

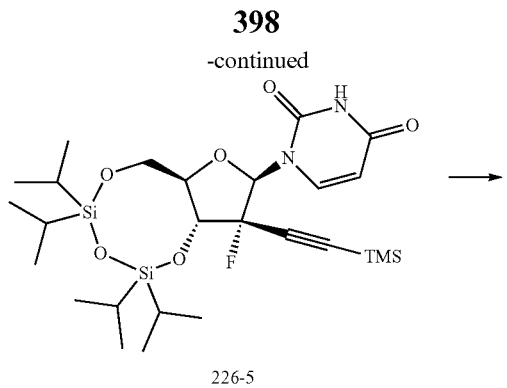

226-5

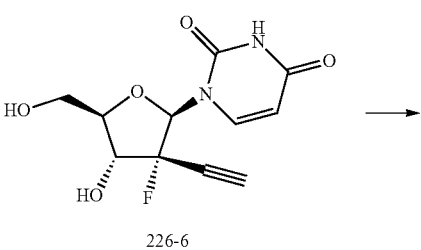

226-6

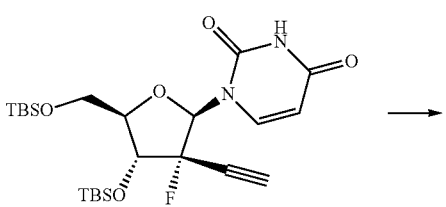

226-7

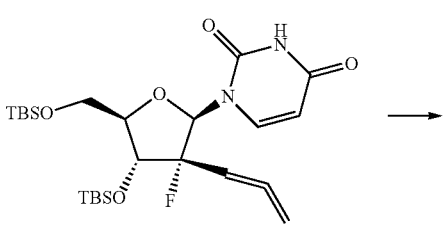

226-8

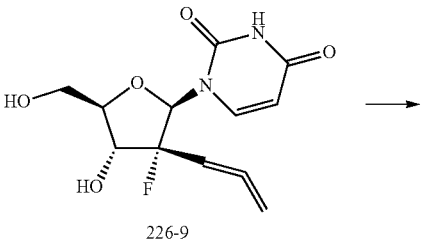

226-9

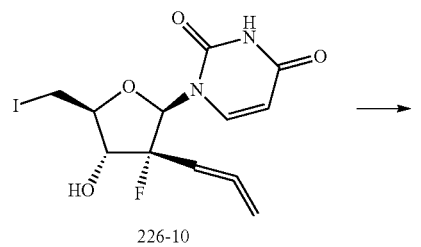

226-10

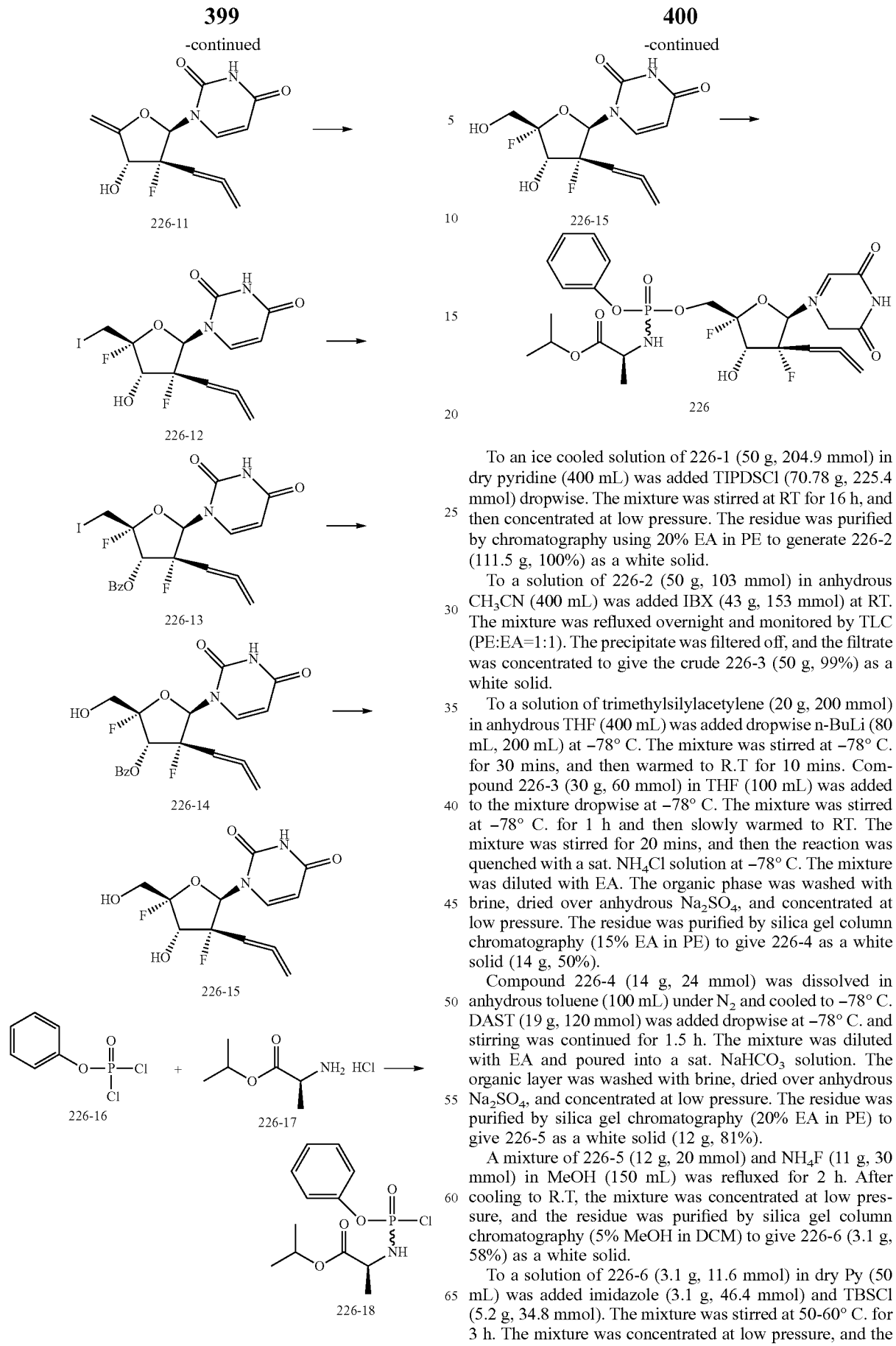

To an ice cooled solution of 226-1 (50 g, 204.9 mmol) in dry pyridine (400 mL) was added TIPDSCl (70.78 g, 225.4 mmol) dropwise. The mixture was stirred at RT for 16 h, and then concentrated at low pressure. The residue was purified by chromatography using 20% EA in PE to generate 226-2 (111.5 g, 100%) as a white solid.

To a solution of 226-2 (50 g, 103 mmol) in anhydrous $CH_3CN$ (400 mL) was added IBX (43 g, 153 mmol) at RT. The mixture was refluxed overnight and monitored by TLC (PE:EA=1:1). The precipitate was filtered off, and the filtrate was concentrated to give the crude 226-3 (50 g, 99%) as a white solid.

To a solution of trimethylsilylacetylene (20 g, 200 mmol) in anhydrous THF (400 mL) was added dropwise n-BuLi (80 mL, 200 mL) at −78° C. The mixture was stirred at −78° C. for 30 mins, and then warmed to R.T for 10 mins. Compound 226-3 (30 g, 60 mmol) in THF (100 mL) was added to the mixture dropwise at −78° C. The mixture was stirred at −78° C. for 1 h and then slowly warmed to RT. The mixture was stirred for 20 mins, and then the reaction was quenched with a sat. $NH_4Cl$ solution at −78° C. The mixture was diluted with EA. The organic phase was washed with brine, dried over anhydrous $Na_2SO_4$, and concentrated at low pressure. The residue was purified by silica gel column chromatography (15% EA in PE) to give 226-4 as a white solid (14 g, 50%).

Compound 226-4 (14 g, 24 mmol) was dissolved in anhydrous toluene (100 mL) under $N_2$ and cooled to −78° C. DAST (19 g, 120 mmol) was added dropwise at −78° C. and stirring was continued for 1.5 h. The mixture was diluted with EA and poured into a sat. $NaHCO_3$ solution. The organic layer was washed with brine, dried over anhydrous $Na_2SO_4$, and concentrated at low pressure. The residue was purified by silica gel chromatography (20% EA in PE) to give 226-5 as a white solid (12 g, 81%).

A mixture of 226-5 (12 g, 20 mmol) and $NH_4F$ (11 g, 30 mmol) in MeOH (150 mL) was refluxed for 2 h. After cooling to R.T, the mixture was concentrated at low pressure, and the residue was purified by silica gel column chromatography (5% MeOH in DCM) to give 226-6 (3.1 g, 58%) as a white solid.

To a solution of 226-6 (3.1 g, 11.6 mmol) in dry Py (50 mL) was added imidazole (3.1 g, 46.4 mmol) and TBSCl (5.2 g, 34.8 mmol). The mixture was stirred at 50-60° C. for 3 h. The mixture was concentrated at low pressure, and the residue was dissolved in EA (100 mL). The solution was washed with brine, dried over anhydrous Na$_2$SO$_4$, and concentrated at low pressure. The residue was purified by silica gel chromatography (20% EA in PE) to give 226-7 as a white solid (5 g, 86%).

To a solution of 226-7 (4.5 g, 9 mmol) in 1,4-dioxane (45 mL) was added CuBr (643 mg, 4.5 mmol), dicyclohexylamine (3.3 g, 18 mmol) and paraformaldehyde (675 mg, 22.5 mmol). The mixture was refluxed for 24 h and then cooled to RT. The reaction was quenched with a sat. NH$_4$Cl solution. The mixture was extracted with EA (3×100 mL). The organic layer was washed with brine, dried over anhydrous Na$_2$SO$_4$, and concentrated at low pressure. The residue was purified by silica gel column chromatography (15% EA in PE) to give 226-8 as a white solid (2.0 g, 43%).

A mixture of 226-8 (2 g, 4 mmol) and NH$_4$F (2.2 g, 60 mmol) in MeOH (20 mL) was refluxed overnight. After cooling to RT, the mixture was concentrated at low pressure, and the residue was purified by silica gel column chromatography (5% MeOH in DCM) to give 226-9 (946 mg, 83%) as a white solid.

To a stirred suspension of 226-9 (946 mg, 3.33 mmol), PPh$_3$ (1.3 g, 5 mmol), imidazole (453 mg, 6.66 mmol) and pyridine (3 mL) in anhydrous THF (12 mL) was added a solution of I$_2$ (1 g, 4.33 mmol) in THF (4 mL) dropwise at 0° C. The mixture was warmed to RT and stirred for 16 h. The reaction was quenched with a sat. Na$_2$S$_2$O$_3$ aq. solution and extracted with EA (3×60 mL). The organic layer was dried over Na$_2$SO$_4$ and concentrated at low pressure. The residue was purified on a silica gel column (2% MeOH in DCM to 5% MeOH in DCM) to afford 226-10 (2.1 g, crude) as a white solid.

To a solution of 226-10 (2.1 g, 5.3 mmol) in THF (15 mL) was added DBU (15 g, 100 mmol) and the mixture stirred for 30 mins. The mixture was diluted with EA and neutralized with acetic acid. The solution was washed with brine, dried over anhydrous Na$_2$SO$_4$, and concentrated at low pressure. The residue was purified by silica gel column chromatography (1.5% MeOH in DCM) to give 226-11 as a white solid (800 mg, 90%).

To an ice-cooled solution of 226-11 (800 mg, 3 mmol) in dry MeCN (1.5 mL) was added NEt$_3$.3HF (484 mg, 3 mmol) and NIS (1.68 g, 7.5 mmol). The mixture was stirred at RT for 30 mins., and the reaction was monitored by LCMS. The reaction was quenched with sat. Na$_2$S$_2$O$_3$ and sat. NaHCO$_3$ solution, and extracted with EA (3×50 mL). The organic layer was dried over anhydrous Na$_2$SO$_4$, and concentrated at low pressure. The residue was purified by a silica gel column (25% EA in PE) to afford 226-12 (850 mg, 68%) as a white solid.

To a solution of 226-12 (850 mg, 2 mmol) in dry DCM (10 mL) was added DMAP (488 mg, 4 mmol) and BzCl (422 mg, 3 mol). The mixture was stirred for 4-5 h at RT, and the reaction was monitored by LCMS. The mixture was diluted with CH$_2$Cl$_2$ (40 mL), and washed with a sat. NaHCO$_3$ solution. The organic layer was dried over anhydrous Na$_2$SO$_4$, and filtered. The filtrate was evaporated at low pressure, and the residue was purified by silica gel column chromatography (20% EA in PE) to give 226-13 (900 mg, 87%) as a white foam.

Tetra-butylammonium hydroxide (21 mL as 54-56% aqueous solution, ~42 mmol, 24 eq.) was adjusted with TFA to pH~4 (~3.5 mL), and the solution was treated with a solution of 226-13 (900 mg, 1.7 mmol) in DCM (21 mL). m-Chloroperbenzoic acid (2.1 g, 60-70%, ~8.75 mmol, ~5 eq.) was added portionwise under vigorous stirring, and the mixture was stirred overnight. The mixture was diluted with CH$_2$Cl$_2$ (30 mL), and washed with a saturated NaHCO$_3$ solution. The organic layer was washed with brine, dried over anhydrous magnesium sulfate and concentrated under reduced pressure. The residue was purified by column chromatography in (40-70% EA in PE) to give 226-14 as an oil. The residue was purified by TLC (50% EA in PE) to give pure 226-14 (350 mg 50%).

Compound 226-14 (350 mg, 0.86 mg) was treated with 7N NH$_3$ in MeOH (15 mL). The mixture was stirred for 2-3 h and monitored by TLC. The mixture was concentrated at low pressure, and the residue was purified by silica gel column chromatography (5% isopropanol in DCM) to give 226-15 (250 mg, 96%) as a white solid. $^1$H NMR (CD$_3$OD, 400 M Hz) δ=7.75 (d, J=7.9 Hz, 1H), 6.60-6.35 (m, 1H), 5.72 (d, J=8.2 Hz, 1H), 5.37-5.25 (m, 1H), 5.17-5.06 (m, 1H), 5.04-4.94 (m, 1H), 4.59-4.29 (m, 1H), 3.87-3.70 (m, 2H).

To a stirred solution of 226-16 (3.79 g, 18 mmol) and 226-17 (3 g, 18 mmol) in anhydrous DCM (60 mL) was added with a solution of TEA (4 g, 39 mmol) in DCM (40 mL) dropwise at −78° C., and the mixture was stirred for 2 h. The mixture was concentrated at low pressure, and the residue was dissolved in methyl-butyl ether. The precipitate was removed by filtration, and the filtrate was concentrated to give the crude product. The residue was purified by dry column chromatography (anhydrous DCM) to give pure 226-18 as a colorless oil (3 g, 54%).

Compound 226-15 (200 mg, 0.66 mmol) was coevaporated with toluene 3 times to remove H$_2$O. Compound 226-15 was treated with MeCN (1.5 mL) and NMI (541 mg, 6.6 mmol). The mixture was stirred at RT, and then 226-18 (403 mg, 1.32 mmol) in MeCN (0.5 mL) was added. The residue was purified by a silica gel column (5% iPrOH in DCM) to give the crude product, which was purified by HPLC (0.1% HCOOH in water and MeCN) to give 226 (33 mg, 9%). ESI-LCMS: m/z 594 [M+Na]$^+$.

Example 152

Compounds 277 and 278

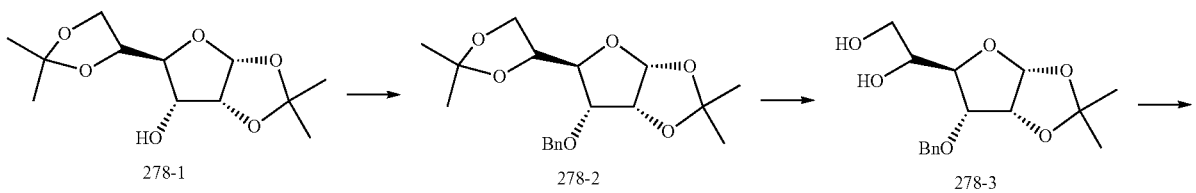

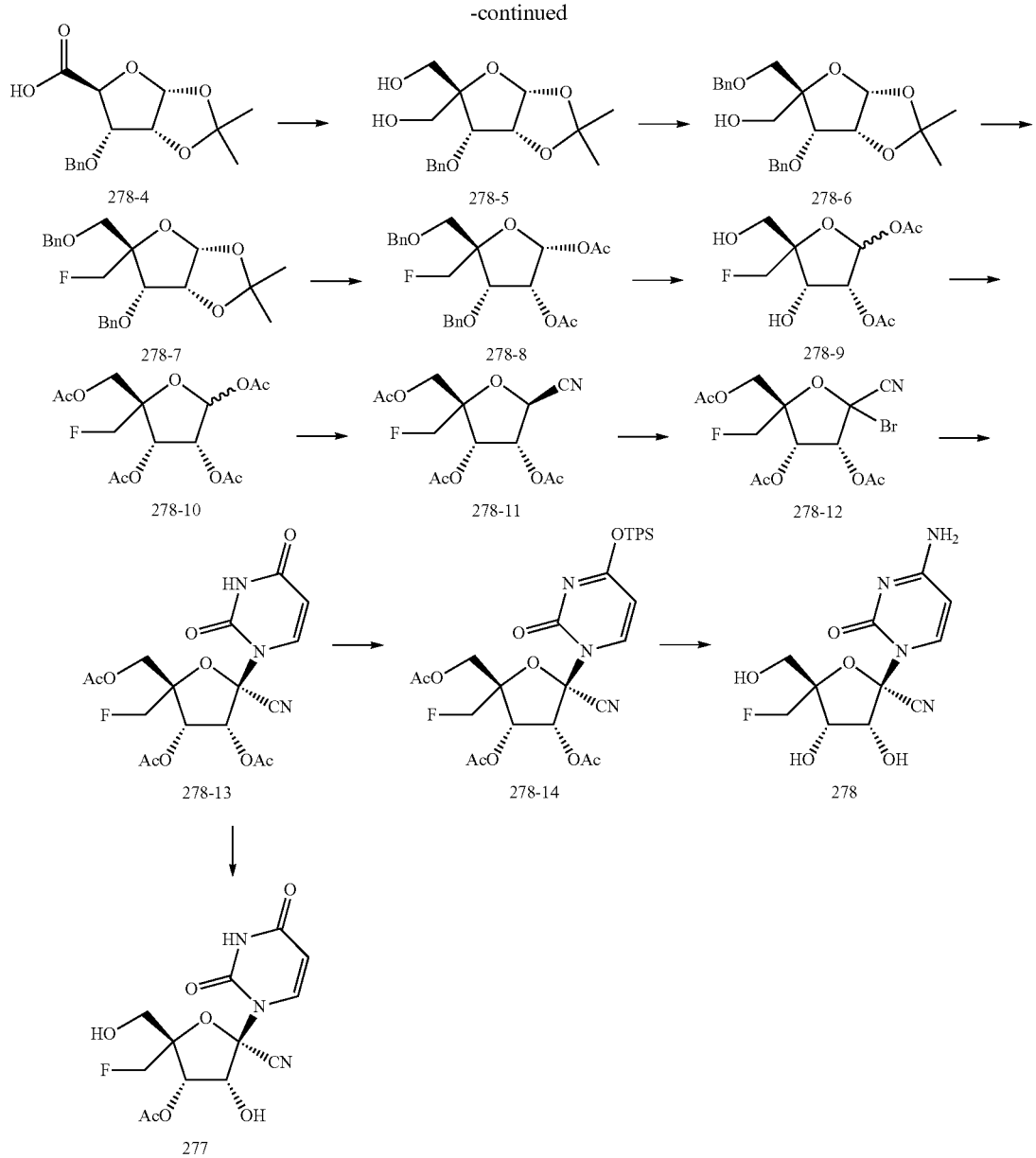

Into a 2000-mL round-bottom flask, was placed a solution of 278-1 (100 g, 384.20 mmol, 1.00 eq.) in N,N-dimethylformamide (1000 mL) at RT. NaH (11.8 g, 491.67 mmol, 1.20 eq.) was added in several batches and the mixture was stirred at 0° C. for 0.5 h. (bromomethyl)benzene (78.92 g, 461.44 mmol, 1.20 eq.) was added at 0° C. and the solution was stirred overnight at RT. The reaction was quenched with water. The solution was diluted with EA (2000 mL), washed with aq. NaCl (3×500 mL), dried over anhydrous sodium sulfate, filtered and concentrated under reduced pressure. The crude product was purified by a silica gel column with EA:PE (1:10) to yield 278-2 (105 g, 78%).

Into a 1000-mL round-bottom flask, was placed 278-2 (100 g, 285.38 mmol, 1.00 eq.), acetic acid (300 mL) and water (100 mL). The solution was stirred overnight at RT. The mixture was then diluted with EA (2000 mL), washed with aq. NaCl (2×500 mL) and aq. sodium bicarbonate (3×500 mL), dried over anhydrous sodium sulfate, filtered and concentrated under reduced pressure. Crude 278-3 (64 g) was obtained as light yellow oil. ESI MS m/z: 333 [M+Na]$^+$.

Into a 5000-mL round-bottom flask, was placed a solution of 278-3 (140 g, 451.11 mmol, 1.00 eq.) in MeOH (500 mL). A solution of sodium periodate (135.2 g, 632.10 mmol, 1.40 eq.) in water (1000 mL) was added. The solution was stirred at RT for 1 h, then diluted with EA (2000 mL), washed with sat. NaCl solution (3×500 mL), dried over anhydrous sodium sulfate, filtered and concentrated under reduced pressure. The solid was dried in an oven under reduced pressure to yield crude 278-4 (97 g) as yellow oil Into a 3000-mL round-bottom flask, was placed a solution of 278-4 (100 g, 359.32 mmol, 1.00 eq.) in tetrahydrofuran (500 mL) at RT. Water (500 mL) was added. To the mixture was added a NaOH solution (600 mL, 2 N in water) at 0° C. followed by aq. formaldehyde (240 mL, 37%). The solution was stirred overnight at RT. The mixture was diluted with EA (1500 mL), washed with sat. NaCl solution (3×500 mL), dried over anhydrous sodium sulfate, filtered and concentrated under reduced pressure. The crude product was purified by a silica gel column with EA:PE (1:1) to give 278-5 (52.5 g, 47%) as a white solid. ESI MS m/z: 333 [M+Na]$^+$.

Into a 3000-mL round-bottom flask, was placed a solution of 278-5 (76 g, 244.89 mmol, 1.00 eq.) in acetonitrile (1500 mL) at RT. NaH (6.76 g, 281.67 mmol, 1.15 eq.) was added in several batches at 0° C. The solution was stirred at 0° C. for 15 mins, then (bromomethyl)benzene (48.2 g, 281.82 mmol, 1.15 eq.) was added. The solution was stirred overnight at RT. The reaction was quenched with water, diluted with EA (3000 mL), washed with aq. NH$_4$Cl (3×500 mL), dried over anhydrous sodium sulfate, filtered and concentrated under reduced pressure. The crude product was purified by a silica gel column with EA:PE (1:5) to yield 278-6 (50 g, 51%) as a yellow oil. ESI MS m/z: 423 [M+Na]$^+$.

Into a 250-mL round-bottom flask, was placed a solution of diethylaminosulfur trifluoride (6.6 mL, 2.00 eq.) in toluene (10 mL) at RT. 278-6 (10 g, 24.97 mmol, 1.00 eq.) in toluene (120 mL) was added at 0° C. The solution was stirred for 3 h at 60° C. in an oil bath. The mixture was cooled to 0° C., diluted with EA (300 mL), washed with sat. NaCl solution (3×50 mL), dried over anhydrous sodium sulfate, filtered and concentrated under reduce pressure. The crude product was purified by a silica gel column with EA:PE (1:5) to give 278-7 (5000 mg, 50%) as a yellow oil. ESI MS m/z: 425 [M+Na]$^+$.

Into a 250-mL 3-necked round-bottom flask purged and maintained with an inert atmosphere of N$_2$, was placed 278-7 (10 g, 23.61 mmol, 1.00 eq., 95%) in acetic acid (80 mL). Acetic anhydride (6 mL) and sulfuric acid (0.05 mL) were added. The solution was stirred for 2 h at RT. The mixture was then diluted with EA (500 mL), washed with water (3×200 mL) and aq. sodium bicarbonate (3×200 mL), dried over anhydrous sodium sulfate, filtered and concentrated under reduced pressure. The crude product was purified by a silica gel column with EA:PE (1:10-1:5) to yield 278-8 (6 g, 54%) as a yellow oil. ESI MS m/z: 469 [M+Na]$^+$.

Into a 50-mL round-bottom flask purged, was placed a solution of 278-8 (4 g, 8.96 mmol, 1.00 eq.), 10% Pd—C catalyst (4 g) in MeOH/DCM (25 mL/25 mL). To this mixture was introduced H$_2$ (gas) in, ~3 atmospheric pressure. The solution was stirred for 48 h at RT. The solids were collected by filtration, and the solution was concentrated under reduced pressure to give 278-9 (0.7 g, 29%) of as a colorless oil.

Into a 25-mL round-bottom flask, was placed 278-9 (2000 mg, 7.51 mmol, 1.00 eq.), Ac$_2$O (8 mL), 4-dimethylaminopyridine (183.2 mg, 0.20 eq.) in pyridine (8 mL). The solution was stirred for 3 h at RT. The reaction was a sat. sodium bicarbonate solution. The solution was diluted with EA (200 mL), washed with sat. NaCl solution (3×50 mL), dried over anhydrous sodium sulfate, filtered and concentrated under reduced pressure. The crude product was purified by a silica gel column with EA:PE (1:7) to yield (1500 mg, 57%) of 278-10 as a white solid. ESI MS m/z: 373 [M+Na]$^+$.

Into a 25-mL round-bottom flask, was placed a solution of 278-10 (300 mg, 0.86 mmol, 1.00 eq.) in dichloromethane (3 mL) at RT. Trimethylsilanecarbonitrile (169 mg, 1.70 mmol, 2.00 eq.) was added at RT, followed by tetrachlorostannane (223 mg, 0.86 mmol, 1.00 eq.) at 0° C. The solution was stirred at 0° C. for 3 h. The reaction was quenched with sat. sodium bicarbonate solution. The solution was diluted with DCM (50 mL), washed with sat. NaCl solution (2×10 mL), dried over sodium sulfate, filtered and concentrated under reduced pressure. The crude product was purified by a silica gel column with PE:EA (5:1) to give 278-11 (110 mg, 40%) as a yellow oil. $^1$H-NMR (400 MHz, CDCl$_3$): δ ppm 5.67~5.75 (m, 2H), 4.25~4.78 (m, 5H), 2.19 (s, 3H), 2.14 (s, 3H), 2.10 (s, 3H]

Into a 25-mL round-bottom flask, was placed 278-11 (200 mg, 0.63 mmol, 1.00 eq.), NBS (223 mg, 1.25 mmol, 2.00 eq.) in tetrachloromethane (5 mL). The solution was heated under reflux for 3 h over a 250 W tungsten lamp, and then cooled to RT. The reaction was quenched sat. sodium bicarbonate solution. The solution was EA (100 mL), washed with sat. NaCl solution (3×20 mL), dried over sodium sulfate, filtered and concentrated under reduced pressure. The crude product was purified by a silica gel column with PE:EA (7:1) to give 278-12 (120 mg, 48%) as a yellow oil. $^1$H-NMR (400 MHz, CDCl$_3$): δ ppm 6.03 (d, J=4.8 Hz, 1H), 5.90 (d, J=4.8 Hz, 1H), 4.29-4.30 (m, 4H), 2.25 (s, 3H), 2.15 (s, 3H), 2.25 (s, 3H).

Into a 25-mL round-bottom flask purged and maintained with an inert atmosphere of argon, was placed a solution of N-(2-oxo-1,2-dihydropyrimidin-4-yl)benzamide (54.3 mg, 2.00 eq.) and (NH$_4$)$_2$SO$_4$ (5 mg) in HMDS (3 mL). The solution was stirred overnight at 120° C. in an oil bath. The solution was concentrated under vacuum, and the residue was dissolved DCE (1 mL) under Ar. A solution of 278-12 (50 mg, 0.13 mmol, 1.00 eq.) in MeCN (1 mL) was added followed by AgOTf (32.5 mg, 1.00 eq.). The solution was stirred for 3 h at 80° C. in a 10-mL sealed tube. After cooling to RT, the solution was diluted with EA (50 mL), washed with sat. sodium bicarbonate solution (3×10 mL) and sat. NaCl (2×10 mL) solution, dried over anhydrous sodium sulfate, filtered and concentrated under reduced pressure. The crude product was purified by a silica gel column with DCM:MeOH (15:1) to yield 278-13 (30 mg, 45%) as a yellow oil. ESI MS m/z: 428 [M+H]$^+$.

Into a 25-mL round-bottom flask, was placed a solution of 278-13 (100 mg, 0.23 mmol, 1.00 eq.) in ACN (3 mL). 4-dimethylaminopyridine (28.5 mg, 0.23 mmol, 1.00 eq.) and TEA (71 mg, 0.70 mmol, 3.00 eq.) was added followed by TPSCl (212.8 mg, 0.70 mmol, 3.00 eq.). The solution was stirred for 3 h at RT, and then concentrated under vacuum. Crude 278-14 (200 mg) was obtained as a yellow oil.

Into a 25-mL round-bottom flask, was placed a solution of 278-14 (140 mg, 0.10 mmol, 1.00 eq.) in ACN (3 mL) and ammonium oxidanide (3 mL). The solution was stirred for 4 h at 35° C. in an oil bath. The mixture was concentrated under vacuum. The crude product was purified by Prep-HPLC (Prep-HPLC-020): Column, XBridge Prep C18 OBD Column, 19*150 mm 5 um 13 nm; mobile phase, WATER WITH 0.05% TFA and ACN (35.0% ACN up to 48.0% in 8 mins); Detector, nm to yield 278 (21.3 mg, 25%) as a white solid. ESI MS m/z: 301.1 [M+1]$^+$.

Into a 25-mL round-bottom flask, was placed a solution of 278-13 (50 mg, 0.12 mmol, 1.00 eq.), sat. NH$_4$OH (2 mL) and 1,4-dioxane (2 mL). The solution was stirred for 2 h at RT. After concentrated under reduced pressure, the crude product was purified by Prep-HPLC [(Prep-HPLC-020): Column, XBridge Prep C18 OBD Column, 19*150 mm 5 um 13 nm; mobile phase, WATER WITH 0.05% TFA and ACN (35.0% ACN up to 48.0% in 8 mins); Detector, nm] to yield 277 (13.6 mg, 39%) as a white solid ESI MS m/z: 299.9 [M−1]$^−$.

Example 153

Compound 279

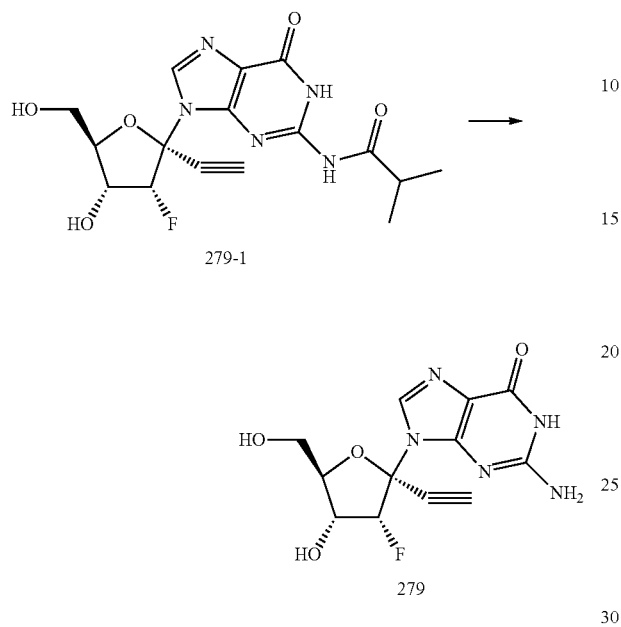

Nucleoside 279-1 (100 mg, 0.26 mmol) was dissolved in n-butylamine (2 mL) and left for 2 h at RT. The solvent was evaporated, and the residue was purified by RP HPLC on Synergy 4 micron Hydro-RP column (Phenominex). A linear gradient of MeOH from 10 to 60% in 50 mM triethylammonium acetate buffer (pH 7.5) was used for elution. The corresponding fractions were combined, concentrated and lyophilized (3×) to remove excess of buffer and yield 279 (20 mg, 25%). MS: m/z 308 [M−1].

Example 154

Compound 280

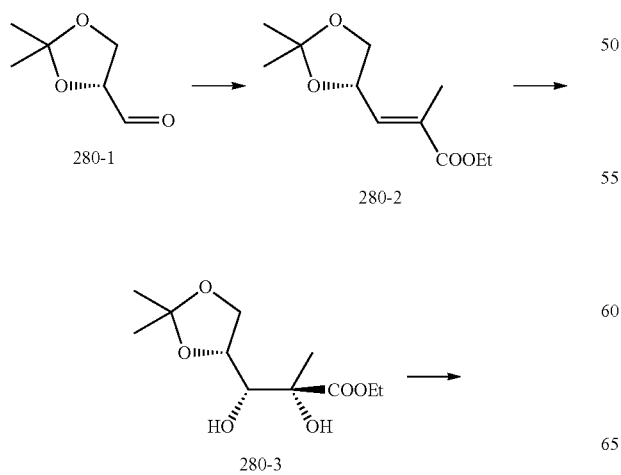

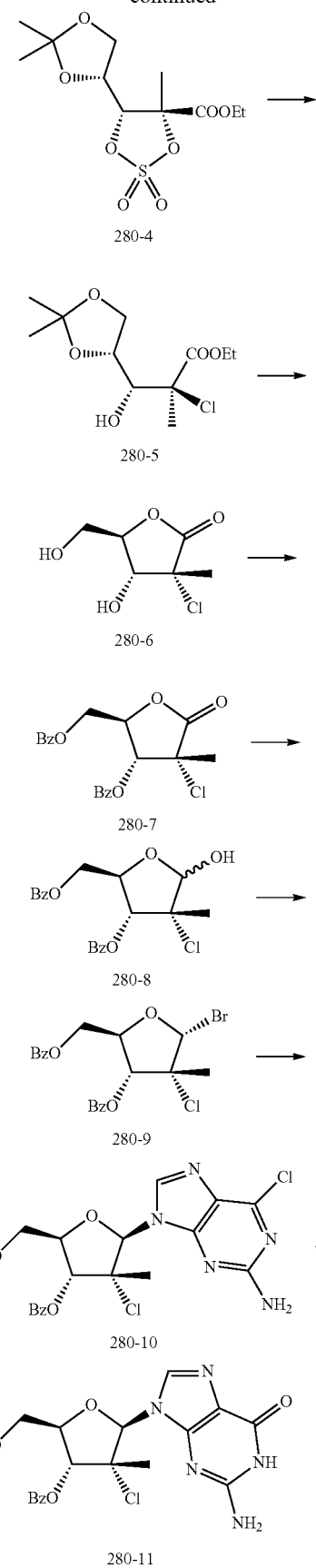

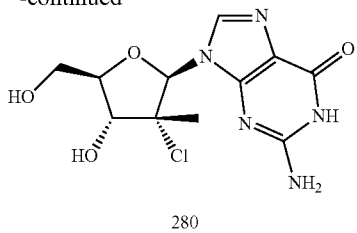

280

To a stirred solution of 280-1 (43.6% in dichloromethane, 345.87 g, 1.16 mol) in anhydrous DCM (1.0 L) was added ethyl-2-(triphenylphosphoranylidene) propanoate (400 g, 1.100 mol) dropwise over a period of 30 mins at −40° C. The mixture was allowed to warm to 25° C. and stirred for 12 h. The mixture was concentrated under reduced pressure. The residue was suspended in TMBE (2.0 L). The solid was removed by filtration. The filtrate was concentrated under reduced pressure. The residue was purified on silica gel column (1.2% EA in PE) to give 280-2 (191.3 g, 80.26%) as a white foam. $^1$H-NMR (400 Hz, CDCl$_3$), δ=6.66 (dd, J=6.8, 8.0 Hz, 1H), 4.81-4.86 (m, 1H), 4.11-4.21 (m, 3H), 3.60 (t, J=8.4 Hz, 1H), 1.87 (d, J=1.2 Hz, 3H), 1.43 (s, 3H), 1.38 (s, 3H), 1.27 (t, J=6.8 Hz, 3H).

To a stirred solution of 280-2 (100 g, 0.47 mol) in acetone (2.0 L) was added KMnO$_4$ (90 g, 0.57 mol) in portions at 0-5° C. The mixture was stirred at 0-5° C. for 2 h. The reaction was quenched using sat. sodium sulfite solution (600 mL). After 2 h, a colorless suspension was formed. The solid was removed by filtration. The filter cake was washed with EA (300 mL). The filtrate was extracted with EA (3×300 mL). The organic phase was dried over anhydrous Na$_2$SO$_4$. The organic phase was concentrated under reduced pressure to give crude 280-3 (50 g, 43.4%) as a solid.

To a stirred solution of 280-3 (50.0 g, 0.20 mol) and triethylamine (64.0 g, 0.63 mol) in anhydrous DCM (1.0 L) was added thionyl chloride (36.0 g, 0.31 mol) at 0° C. After 30 mins, the mixture was diluted with dichloromethane (500 mL) and washed with cold water (1.0 L) and brine (600 mL). The organic phase was dried over anhydrous Na$_2$SO$_4$. The organic phase was concentrated under reduced pressure to give the crude as a brown oil. To crude in anhydrous acetonitrile were added TEMPO catalyst (500 mg) and NaHCO$_3$ (33.87 g, 0.40 mol) at 0° C. A sodium hypochlorite solution (10-13%, 500 mL) was added dropwise at 0° C. for 20 mins. The solution was stirred at 25° C. for 1 h. The organic phase was concentrated, and the aqueous phase was extracted with dichloromethane (3×). The organic phase was dried over anhydrous Na$_2$SO$_4$. The solvent was removed under reduced pressure to give 280-4 (53.0 g, 85.48%) as a yellow oil.

To a stirred solution of 280-4 (62.0 g, 0.20 mol) in anhydrous dioxane (1.5 L) was added TBACl (155.4 g, 0.50 mol) at 25° C. The solution was stirred at 100° C. for 10 h. The mixture was cooled to 25° C., and treated with 2,2-dimethoxypropane (700 mL), followed by conc. HCl (12 N, 42 mL). The mixture was stirred at 25° C. for 3 h and then concentrated under reduced pressure to give crude 280-5 as a brown oil (45.5 g, crude), which was used for next step without further purification.

Crude 280-5 (45.5 g, 171 mmol) was dissolved in a mixture of EtOH (500 mL) and conc. HCl (12 N, 3.0 mL). The mixture was stirred at 25° C. for 16 h. The solvent was removed under reduced pressure. The residue was co-evaporated with toluene (3×) to give crude 280-6 (24.6 g, crude) as a brown oil, which was used for the next step.

To a stirred solution of crude 280-6 (24.6 g, crude) and DMAP (4.8 g, 40.0 mmol) in anhydrous pyridine (800 mL) was added benzoyl chloride (84.0 g, 0.60 mol) dropwise over a period of 40 mins at 0° C. The mixture was stirred at 25° C. for 12 h and then concentrated at low pressure. The residue was dissolved in EA (1.5 L). The solution was washed with 1.0 M HCl solution (400 mL) and brine (800 mL). The organic phase was dried over anhydrous Na$_2$SO$_4$. The solvent was removed under reduced pressure to give a brown solid. The solid was suspended in MeOH (600 mL). After filtration, the filter cake was washed with MeOH. The filter cake was dried under reduced pressure to give 280-7 (40.0 g, 75.0%) as a white solid.

To a stirred solution of 280-7 (7.0 g, 18.04 mmol) in anhydrous THF (70 mL) was added a solution of lithium tri-tert-butoxyaluminohydride (27 mL, 1.0 M, 27.06 mmol) dropwise over a period of 30 mins at −78° C. under N$_2$. The mixture was stirred at −20° C. for 1 h. The reaction was quenched with sat. NH$_4$Cl aq. and diluted with EA. After filtration, the filtrate was extracted with EA. The organic phase was dried over anhydrous Na$_2$SO$_4$, and concentrated at low pressure. The residue was purified by silica column gel (5% EA in PE) to give 280-8 (6.8 g, 96.7%) as a colorless oil.

To a stirred solution of PPh$_3$ (1.34 g, 5.12 mmol) in CH$_2$Cl$_2$ (5 mL) was added 280-8 (1.0 g, 2.56 mmol) at −20° C. under N$_2$. After the mixture was stirred for 15 mins, CBr$_4$ (1.96 g, 5.89 mmol) was added in portions while maintaining the reaction temperature between −25 and −20° C. under N$_2$ flow. After completion of the addition, the mixture was stirred below −17° C. for 20 mins. The reaction was treated with silica gel. After filtration, the pad of silica gel was washed with CH$_2$Cl$_2$. The combined filtrates were purified by silica column gel (EA in PE from 2% to 25%) to give 280-9 (α-isomer, 0.5 g, 43.4%) as a colorless oil.

A 0.25 L three-neck round-bottomed flask was charged with 6-chloro-9H-purin-2-amine (5.5 g, 34.75 mmol) followed by anhydrous t-BuOH (45 mL) with stirring. To this solution was added potassium tert-butoxide (3.89 g, 32.58 mmol) in portions at RT under N$_2$ flow. After 30 mins, a solution of 280-9 (4.92 g, 10.86 mmol) in anhydrous acetonitrile (30 mL) was added over a period of 5 mins at 25° C. The mixture was slowly heated to 50° C. and stirred for 12 h. The mixture was treated with solid NH$_4$Cl and water, and then filtered through a short pad of Celite. The pad was washed with EA, and the filtrates were neutralized with aqueous 1.0 M HCl. The combined organic layers were dried over anhydrous Na$_2$SO$_4$. The organic phase was concentrated under reduced pressure. The residue was purified by silica column gel (EA in PE from 2% to 20%) to give 280-10 (1.7 g, 28.9%) as a white foam. $^1$H-NMR (400 MHz, DMSO-d$_6$) δ=8.37 (s, 1H), 8.07-8.01 (m, 2H), 7.93-7.87 (m, 2H), 7.75-7.69 (m, 1H), 7.65-7.53 (m, 3H), 7.41 (t, J=7.8 Hz, 2H), 7.13 (s, 2H), 6.37 (d, J=19.3 Hz, 1H), 6.26-6.13 (m, 1H), 4.86-4.77 (m, 1H), 4.76-4.68 (m, 2H), 1.3 (d, J=20 Hz, 3H).

Compound 280-10 (700 mg, 1.29 mmol) was dissolved in 4% HCl in MeOH (25 mL) at 25° C. The mixture was stirred at 50° C. for 12 h. The solvent was removed under reduced pressure. The residue was purified by column chromatography to give 280-11 (401 mg, 59.2%) as a white solid.

Compound 280-11 (250 mg, 0.477 mmol) was treated with 7.0 M NH$_3$ in MeOH (25 mL) at 25° C. and stirred for 18 h. The solvent was removed at low pressure. The residue was purified by prep-HPLC (NH$_4$HCO$_3$ system) to give 280 (85 mg, 56.4%) as a white solid. MS: m/z 315.7 [M+H]$^+$, 630.5 [2M+H]$^+$.

Example 155

Compound 281

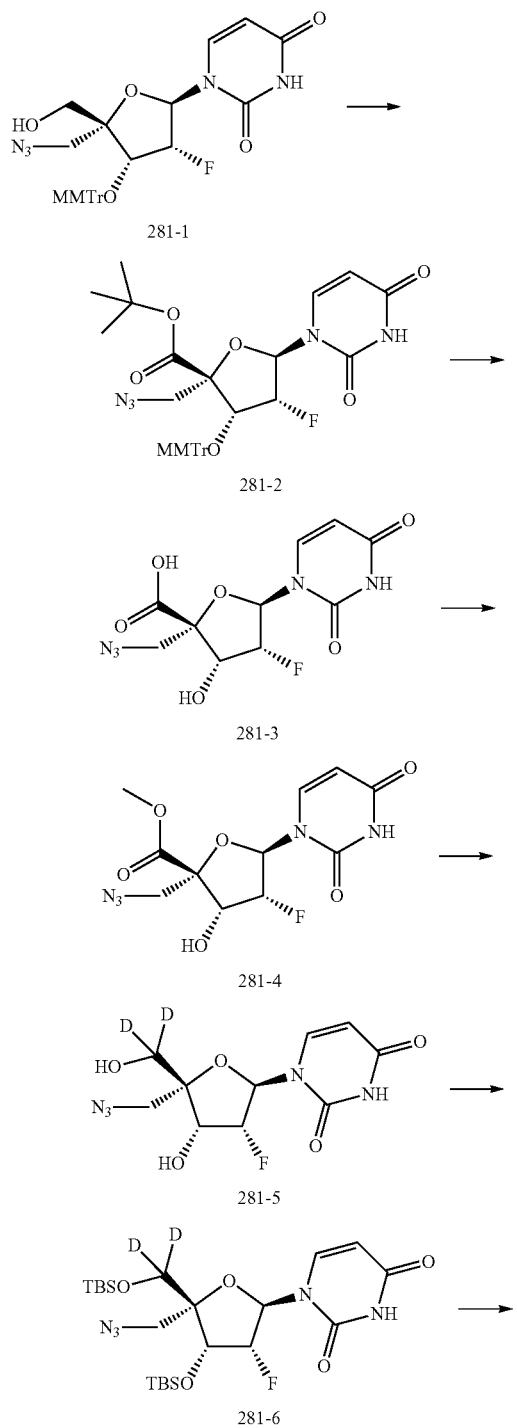

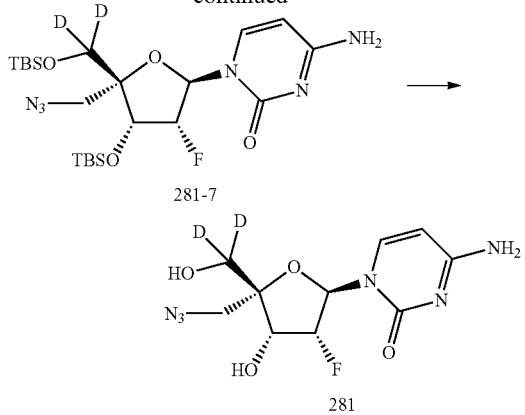

To a stirred solution of 281-1 (3.00 g, 5.23 mmol) in anhydrous DCM (36 mL) was added PDC (3.94 g, 10.46 mmol), Ac$_2$O (5.34 g, 52.30 mmol) and 2-methylpropan-2-ol (7.75 g, 104.60 mmol) at RT. The mixture was stirred at RT for 15 h. The mixture was loaded on a very short silica gel column and eluted with EA. The fractions containing the product were combined and concentrated under reduced pressure. The residue was purified by column chromatography (20% EA in PE) to give 281-2 (2.40 g, 71.3%) as a white foam.

To a stirred solution of 281-2 (2.00 g, 3.26 mmol) in DCM (30 mL) was added TFA (15 mL). The mixture was stirred at RT for 1.5 h. The mixture was concentrated under reduced pressure to give 281-3 (1.00 g, crude), which was used in the next step without further purification.

Crude 281-3 (1.00 g, crude) was dissolved in a mixture of toluene (25 mL) and MeOH (20 mL). TMS-diazomethane (2 M, 3.17 mL) was added. After stirring for 2 h, the mixture was concentrated under reduced pressure at RT. The residue was diluted with EA (25 mL), washed with water (25 mL), dried over anhydrous MgSO$_4$, filtered and concentrated under reduced pressure. The residue was purified by column chromatography (2% MeOH in DCM) to give 281-4 (451 mg, 43.2%) as a white solid. The aqueous phase was concentrated to give 281-3 (500 mg, 50.0%) as a white solid.

To a solution of 281-4 (451 mg, 1.37 mmol) in anhydrous CD$_3$OD (18 mL) was added NaBD$_4$ (344 mg, 8.22 mmol) at RT. The mixture was stirred at RT for 1 h. The reaction was quenched with CD$_3$OD (0.2 mL) and neutralized with AcOH (0.2 mL). The mixture was concentrated under reduced pressure. The residue was purified by column chromatography (4% MeOH in DCM) to give 281-5 (410 mg, 98.7%) as a white solid.

To a stirred solution of 281-5 (410 mg, 1.35 mmol) in pyridine (2.5 mL) was added imidazole (459 mg, 6.75 mmol) and TBSCl (610 mg, 4.05 mmol) at RT. The mixture was stirred at 60° C. for 10 h. The mixture was concentrated under reduced pressure. The residue was diluted with EA (20 mL) and washed with brine (20 mL). The organic layer was dried over MgSO$_4$ and filtered. The filtrate was concentrated under reduced pressure. The residue was purified by column chromatography (10% EA in PE) to give 281-6 (440 mg, 61.3%) as a white solid.

To a solution of 281-6 (440 mg, 827 μmol) in anhydrous MeCN (4 mL) were added DMAP (253 mg, 2.07 mmol), Et$_3$N (209.32 mg, 2.07 mmol) and 2,4,6-triisopropylbenzene-1-sulfonyl chloride (626.50 mg, 2.07 mmol) at RT. The mixture was stirred at RT for 16 h. NH$_3$.H$_2$O (2 mL) was added, and the mixture was stirred for 1 h. The mixture was diluted with EA (20 mL) and washed with sat. aq. NH₄Cl (20 mL). The organic layer was dried over anhydrous Na₂SO₄ and filtered. The filtrate was concentrated under reduced pressure. The residue was purified by column chromatography (2% MeOH in DCM) to give the crude product. The crude product was purified by TLC (10% MeOH in DCM) to give 281-7 (420 mg, 95.63%) as a white solid.

To a solution of 281-7 (420 mg, 791 μmol) in MeOH (4 mL) was added NH₄F (586 mg, 15.83 mmol) at RT. The mixture was stirred at 90-100° C. for 10 h. The mixture was filtered, and the filtrate was concentrated under reduced pressure. The residue was purified by column chromatography (10% MeOH in DCM) to give the crude product. The crude product was purified by prep-HPLC (neutral condition) to give 281 (201 mg, 61.8% yield, 100% deuterium) as a white solid. ESI-TOF-MS: m/z 303.1 [M+H]⁺, 605.2 [2M+H]⁺.

Example 156

Compound 274

To an ice-cold solution of triethylammonium bis(POM) phosphate (7 mmol, prepared from 2.3 g of bis(POM) phosphate and 1 mL of Et₃N) and 274-1 (1.36 g; 4.2 mmol) were added diisopropylethyl amine (3.6 mL; 21 mmol), BOP-Cl (2.68 g; 10.5 mmol) and 3-nitro-1,2,4-triazole (1.20 g; 10.5 mmol). The mixture was stirred at 0° C. for 2 h. The mixture was then diluted with EtOAc, washed with 1 M citric acid, sat. aq. NaHCO₃ and brine and dried with Na₂SO₄. The evaporated residue was purified on silica gel column with i-PrOH/CH₂Cl₂ solvent system (2-12% gradient) to yield 274-2 (2.13 g, 80%).

A solution of 274-2 (2.13 g) in 80% aq. HCOOH (10 mL) was stirred at 45° C. for 8 h. The mixture was cooled and concentrated to obtain a residue. The residue was coevaporated with toluene and MeOH containing few drops of Et₃N. The evaporated residue was purified on silica gel column with MeOH:CH₂Cl₂ (3-10% gradient) to yield 274 as a white foam (1.1 g, 56%). MS: m/z=565 [M−1].

Example 157

Compound 282

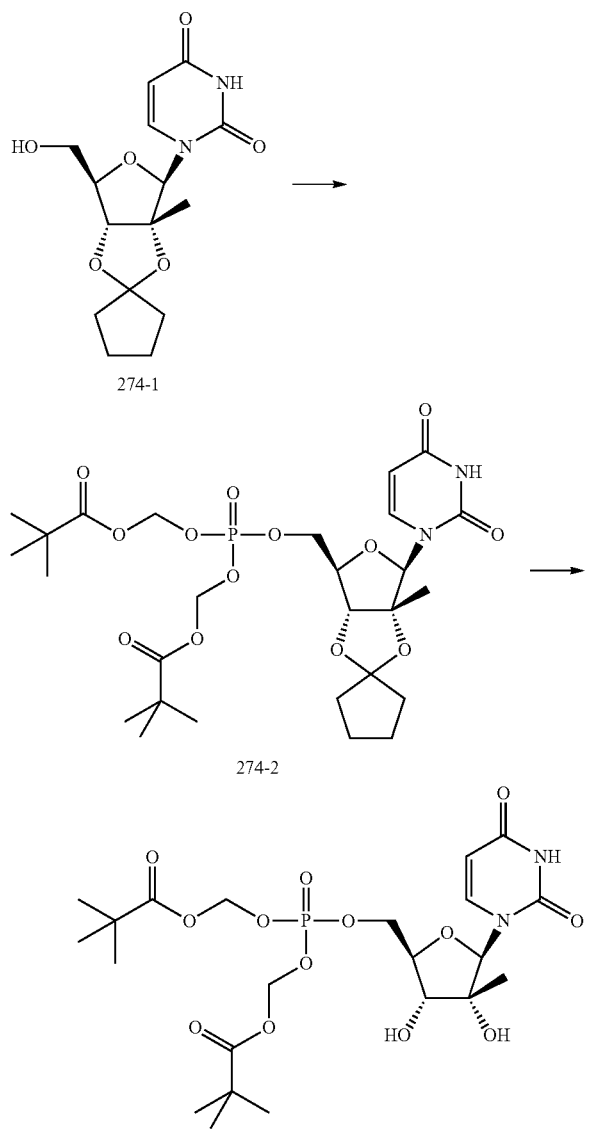

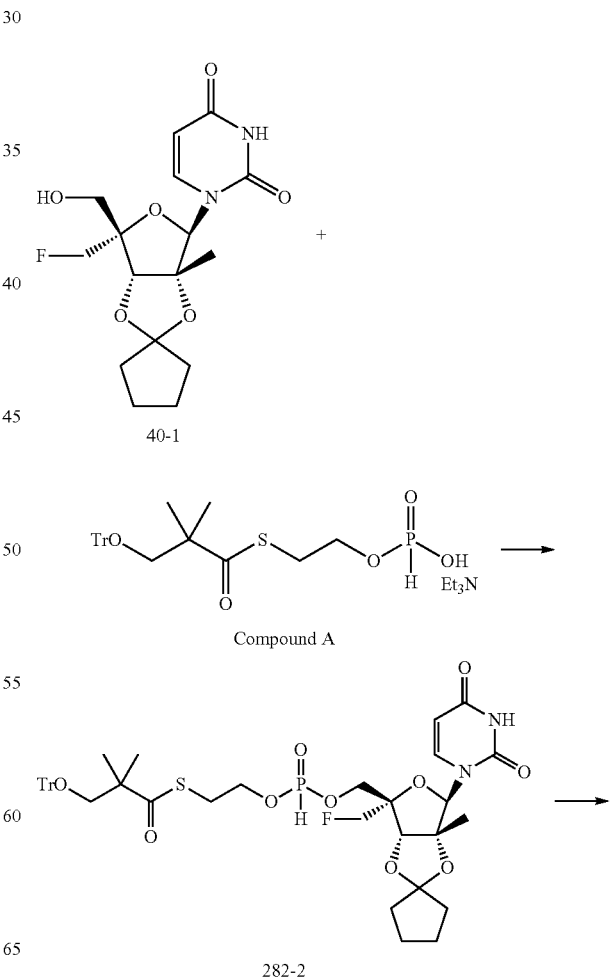

Example 158

Compound 283

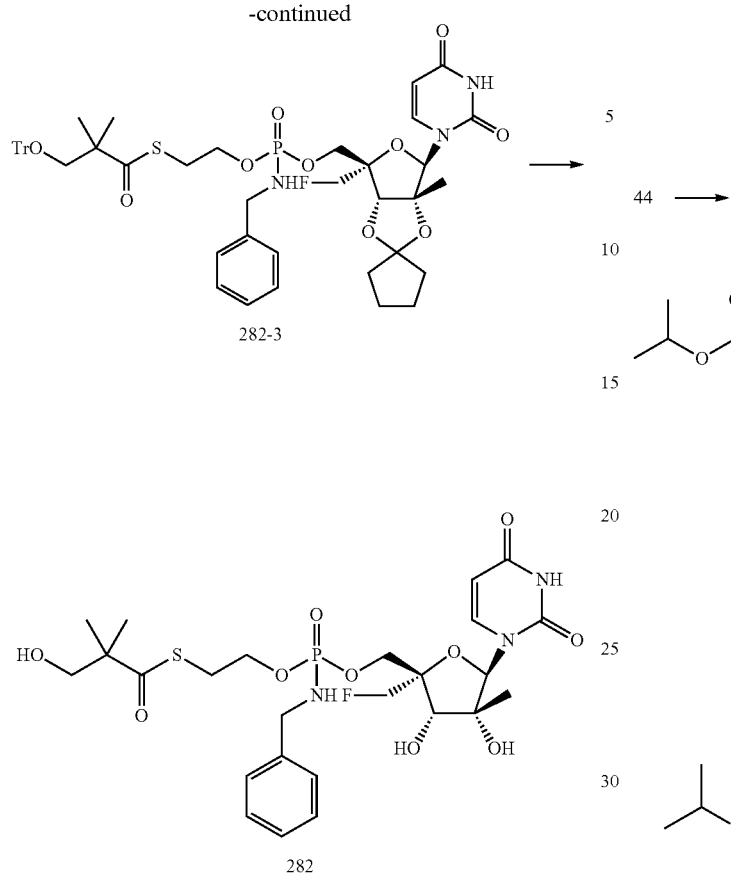

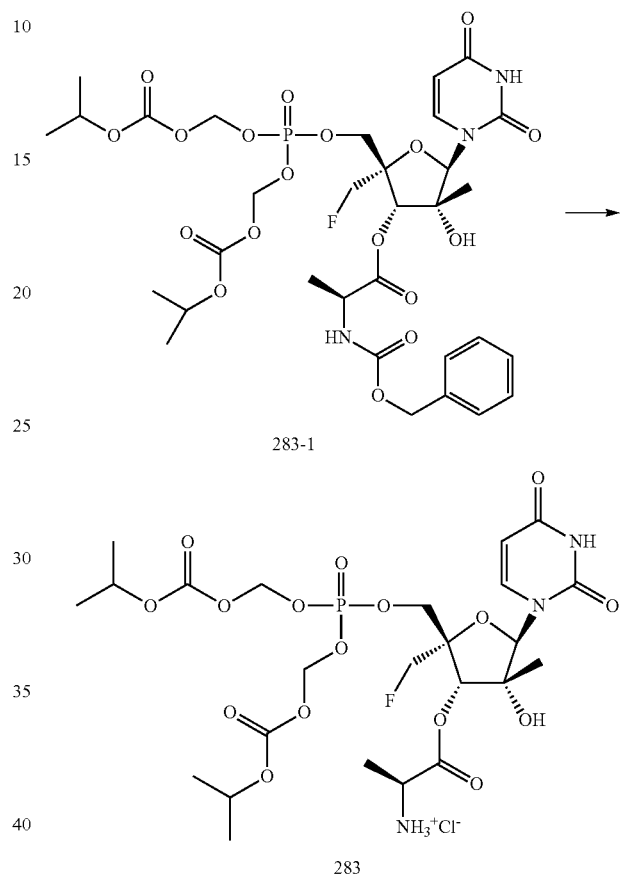

40-1 (1.78 g, 5 mmol) and Compound A (3.22 g, 5.5 mmol; prepared according to the procedure provided in WO 2008/82601 A2) were coevaporated with pyridine and then dissolved in pyridine (70 mL). Pivaloyl chloride (1.22 mL; 10 mmol) was added dropwise at −15° C., and the mixture stirred at −15° C. for 2 h. The mixture was diluted with $CH_2Cl_2$, washed with 0.5 M aq. $NH_4Cl$ and brine, and dried with $Na_2SO_4$. The evaporated residue was purified on a silica column with $CH_2Cl_2$:i-PrOH (4-10% B gradient) to afford 282-2 (2.1 g, 50%).

To a solution of 282-2 (0.51 g, 0.62 mmol) in $CCl_4$ (6 mL) was added benzylamine (0.34 mL, 3.1 mmol) dropwise, and the mixture was stirred at RT for 1 h. The mixture was diluted with EtOAc, washed with 0.5 M aq. citric acid, sat. aq. $NaHCO_3$ and brine, and dried with $Na_2SO_4$. The evaporated residue was purified on a silica column with $CH_2Cl_2$:i-PrOH (4-10% B gradient) to afford 282-3 (0.46 g, 80%).

A mixture of 282-3 (130 mg, 0.14 mmol) and 80% aq. TFA (1.5 mL) was stirred at RT for 2 h. The mixture was evaporated and coevaporated with toluene. The residue was purified on a silica column with $CH_2Cl_2$:MeOH (4-12% B gradient) to afford 282 (32 mg, 37%). MS: m/z=620 [M+1]$^+$.

A solution of Z-Ala-OH (111.6 mg, 0.5 mmol) in anhydrous THF (2 mL) was treated with carbonyldiimidazole (81 mg, 0.5 mmol). The mixture was stirred for 1 h at 40° C. under an Ar atmosphere. This solution was added to a solution of 44 (200 mg, 0.33 mmol), $Et_3N$ (72 μL, 0.5 mmol) and DMAP (4 mg) in DMF (2 mL). The mixture was stirred at RT for 2.5 h. The reaction was quenched by the addition of 1M citric acid (2 mL) at 0 to 5° C. (ice/water bath) and diluted with EA. The organic layer was separated, washed with sodium bicarbonate and brine, dried over $MgSO_4$, filtered and concentrated. The residue was purified by column chromatography in 40 to 90% EA-hexane to give 283-1 (202 mg, 76%) as a white foam.

To a solution of 283-1 (50 mg, 0.062 mmol) in anhydrous EtOH (2 mL), was added 10% Pd/C (5 mg), followed by addition of 4N HCl (31 μL, 0.124 mmol), and the mixture was stirred under $H_2$ atmosphere for 1 h. After completion of the reaction, the mixture was filtered through celite. The catalyst cake was washed with anhydrous EtOH. The washings and the filtrate were combined, and the solvent was removed under vacuum to give 283 (33.3 mg, 79.7%) as an off white foam. MS:m/z=674.1[M+H]$^+$, 1347.2[2M+H]$^+$.

Example 159

Compound 284

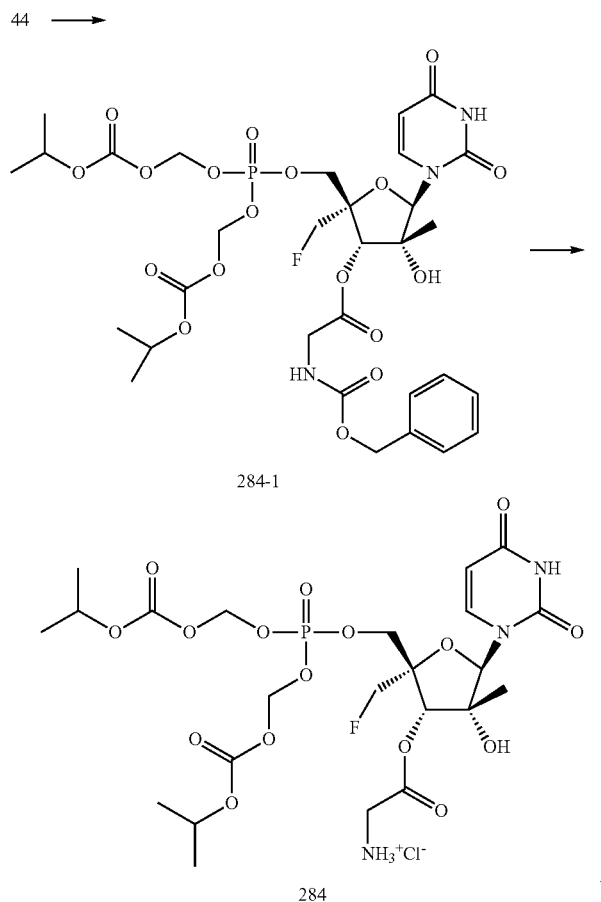

A solution of Z-Gly-OH (105 mg, 0.5 mmol) in anhydrous THF (2 mL) was treated with carbonyldiimidazole (81 mg, 0.5 mmol). The mixture was stirred for 2 h at 40° C., followed by 30 mins at 80° C. under an Ar atmosphere. This solution was added to a solution of 44 (200 mg, 0.33 mmol), Et$_3$N (72 µL, 0.5 mmol) and DMAP (4 mg) in DMF (2 mL). The mixture was stirred at RT for 3 h. The reaction was quenched by the addition of 1M citric acid (2 mL) at 0 to 5° C. (ice/water bath) and diluted with EA. The organic layer was separated, washed with sodium bicarbonate and brine, dried over MgSO$_4$, filtered and concentrated. The residue was purified by column chromatography in 40 to 90% EA-hexane to give 284-1 (208.5 mg, 79.6%) as an off white foam.

To a solution of 284-1 (75 mg, 0.094 mmol) in anhydrous EtOH (3 mL), was added 10% Pd/C (10 mg), followed by the addition of 4N HCl (47 µL, 0.19 mmol). The mixture was stirred under H$_2$ atmosphere for 3 h. After completion of reaction, the mixture was filtered through celite. The catalyst cake was washed with anhydrous EtOH. The washings and the filtrate were combined, and the solvent was removed under vacuum to give 284 (44.3 mg, 71.5%) as an off white foam. MS:m/z=658.05[M+H]$^+$, 1317.05[M+H]$^+$.

Example 160

Compound 285

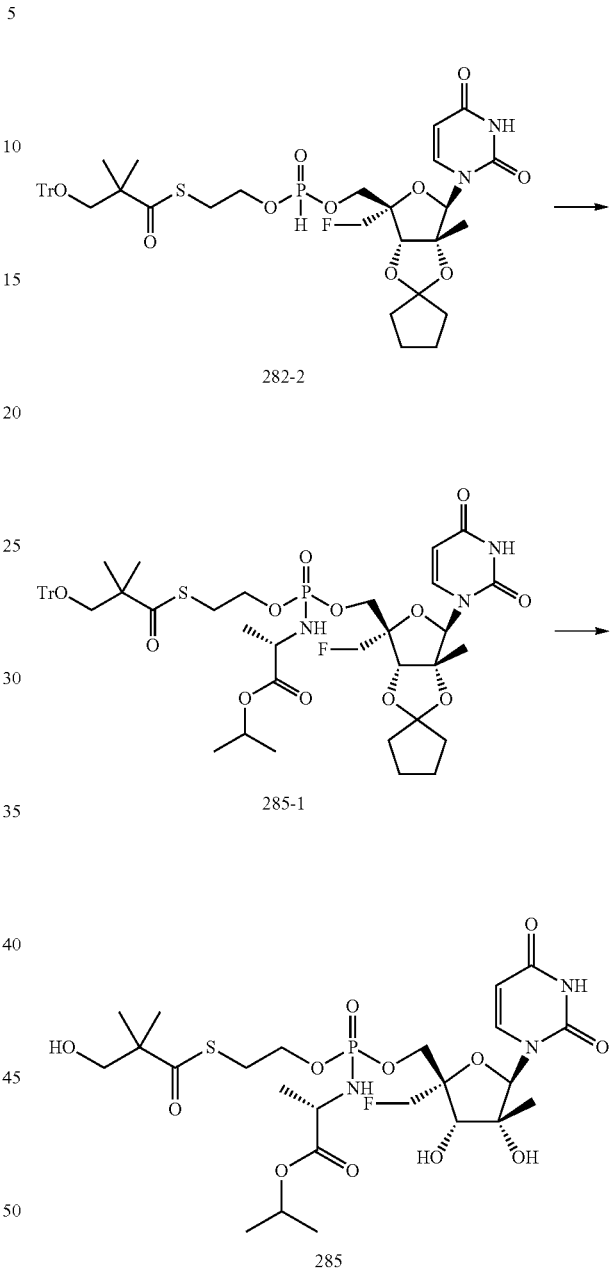

To a solution of 282-2 (223 mg, 0.27 mmol) in CCl$_4$ (3 mL) were added L-alanine isopropyl ester hydrochloride (135 mg, 0.8 mmol) and dropwise Et$_3$N (0.22 mL, 1.6 mmol). The mixture was stirred at RT for 1 h. The mixture was then diluted with CH$_2$Cl$_2$, washed with sat aq. NaHCO$_3$ and brine, and dried with Na$_2$SO$_4$. The evaporated residue was purified on a silica column with CH$_2$Cl$_2$:i-PrOH (3-10% B gradient) to afford 285-1 (0.16 g, 62%).

A mixture of 285-1 (100 mg, 0.11 mmol) and 80% aq. TFA (3 mL) was stirred at RT for 2 h. The mixture was then evaporated and coevaporated with toluene. The residue was purified on a silica column with CH$_2$Cl$_2$:MeOH (4-10% B gradient) to afford 285 (31 mg, 46%). MS:m/z=644 [M+1]$^+$.

Example 161
Compounds 286 and 351
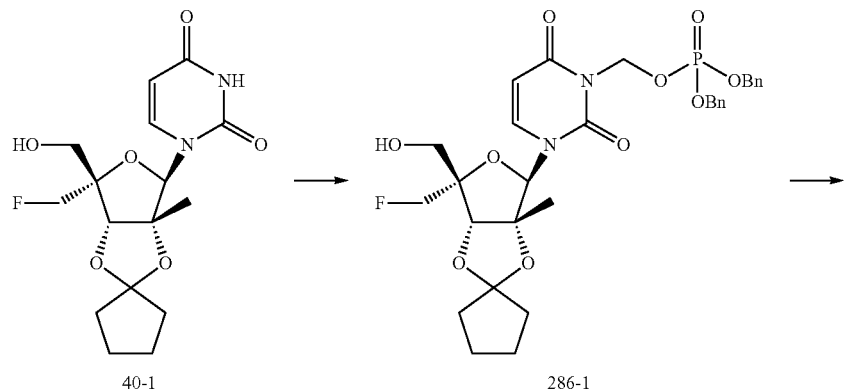
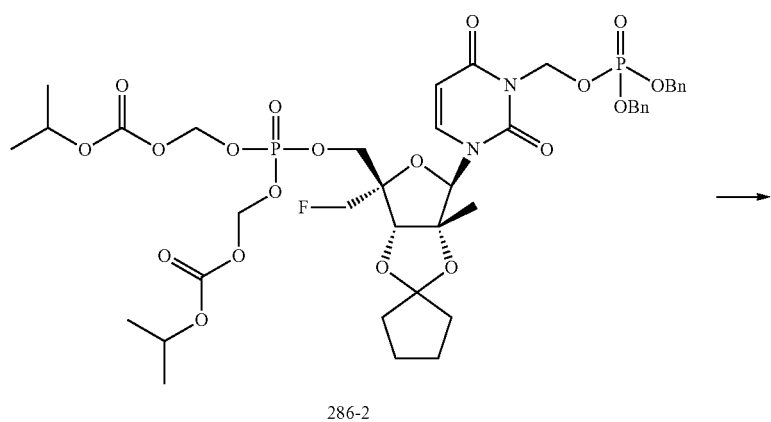
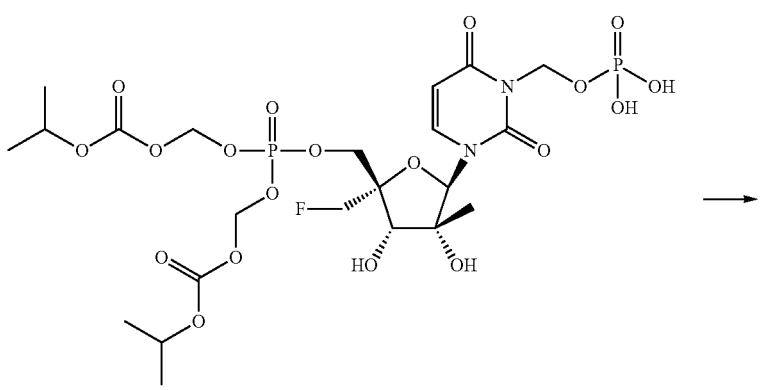

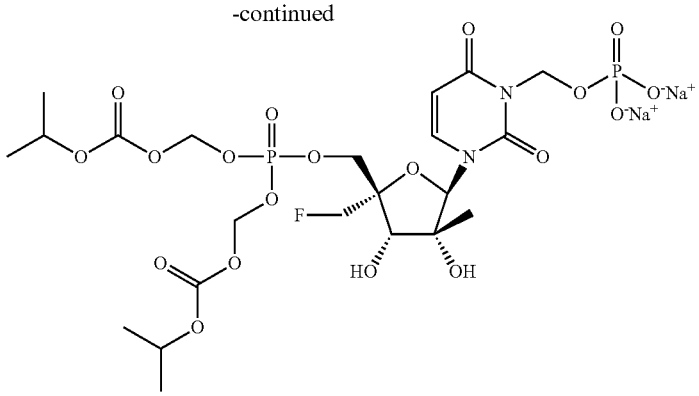

351

To a solution of 40-1 (1.08 g, 3.0 mmol) in N,N-dimethylacetamide (15 mL) was added CsCO$_3$ (1.22 g, 3.7 mmol), and the mixture was stirred at RT for 15 mins. Dibenzyl chloromethylphosphate (1 g, 3.0 mmol) was added, and the mixture was stirred overnight at 40° C. After cooling, the mixture was diluted with methyl tert-butylether and washed with water (3×) and brine, and dried with Na$_2$SO$_4$. The crude evaporated residue was purified on a silica column with CH$_2$Cl$_2$:i-PrOH (3-10% B gradient) to yield 286-1 (580 mg, 30%).

To a solution of triethylammonium bis(isopropyloxycarbonyloxymethyl)phosphate (1.8 mmol, prepared from 0.60 g of bis(isopropyloxycarbonyloxymethyl)phosphate and Et$_3$N) in THF was added 286-1 (0.58 g, 0.9 mmol). The mixture was evaporated and rendered anhydrous by coevaporating with pyridine follow by toluene. The evaporated residue was dissolved in anhydrous THF (9 mL) and cooled in an ice-bath. Diisopropylethyl amine (0.94 mL, 5.4 mmol) was added, followed by BOP-Cl (0.69 g, 2.7 mmol) and 3-nitro-1,2,4-triazole (0.31 g, 2.7 mmol). The mixture was stirred at 0-5° C. for 2 h, diluted with EtOAc, washed with sat. aq. NaHCO$_3$ and brine, and dried with Na$_2$SO$_4$. The evaporated residue was purified on a silica column with CH$_2$Cl$_2$:i-PrOH (3-10% B gradient) to yield 286-2 (0.77 g, 89%).

To a solution of 286-2 (50 mg; 0.05 mmol) in EtOH (2.5 mL) was added 10% Pd/C (8 mg), and the mixture was stirred under H$_2$ (atmospheric pressure) for 1 h. The mixture was filtered through a Celite pad, and the filtrate was evaporated. The residue was treated with 80% aq. HCOOH (2.5 mL) for 3 h, then evaporated and purified by RP-HPLC (A: 50 mM aq. TEAA, B: 50 mM TEAA in MeCN) to afford 286 (22 mg, 44%) as a white solid. MS:m/z=713 [M+1]$^+$.

To a solution of 286 (14 mg, 0.02 mmol) in EtOH (0.3 mL) at 0° C. was added dropwise 0.1 M EtONa in EtOH (0.4 mL; 0.04 mmol). The mixture was allowed to warm to RT and the resulting white solid centrifuged. The supernatant was discarded. The solid was treated with EtOH (0.3 mL) and centrifuged to yield 351 (8 mg). MS:m/z=713 [M+1]$^+$.

Example 162

Compound 287

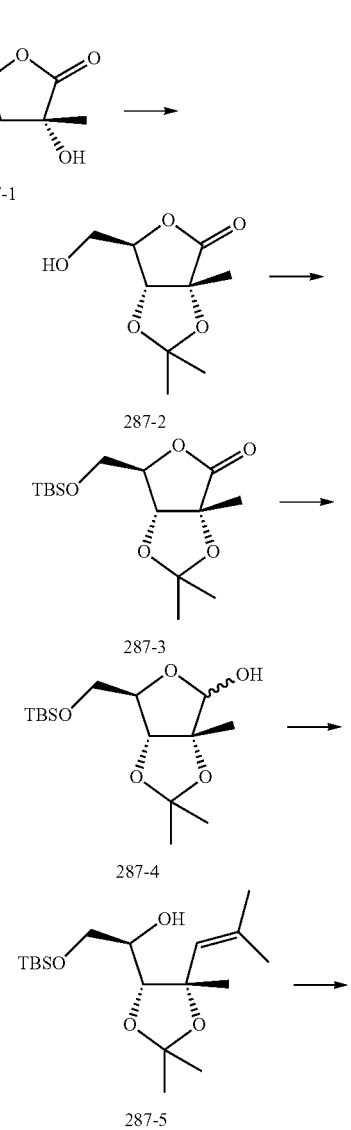

423

-continued

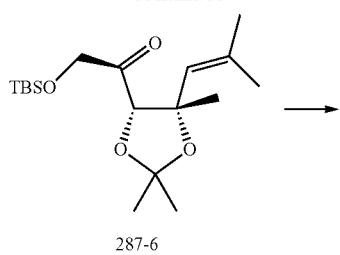

287-6

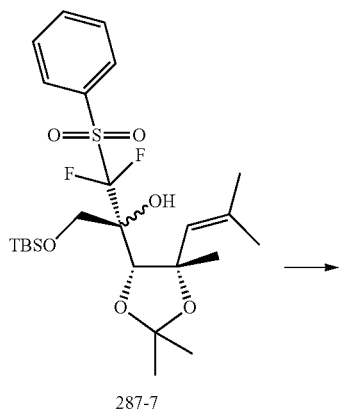

287-7

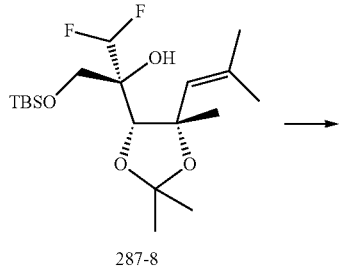

287-8

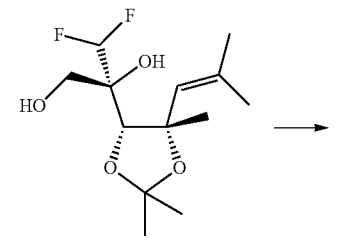

287-9

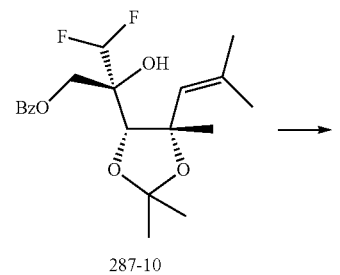

287-10

424

-continued

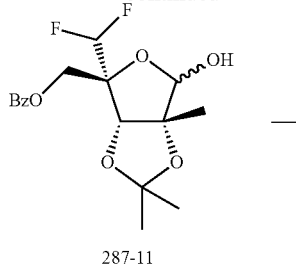

287-11

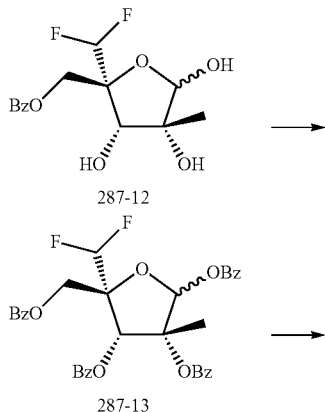

287-12

287-13

287-14

287

To a stirred suspension of 287-1 (300 g, 1.86 mol) in acetone (4 L) was added conc.H$_2$SO$_4$ (56 mL) dropwise at RT. The mixture was stirred at RT for 3 h. The mixture was neutralized with solid NaHCO$_3$ and filtered. The filtrate was evaporated under reduced pressure to give 287-2 (381 g, crude) as a colorless oil, which was used for the next step without further purification.

To a stirred solution of 287-2 (380 g, crude, 1.88 mol) in anhydrous DCM (2 L) was added imidazole (191 g, 2.82 mol) and TBSCl (564 g, 3.76 mol) at 0° C. The mixture was stirred at RT for 12 h, and then filtered. The filtrate was concentrated to dryness, and the residue was purified by silica gel column (2% EA in PE) to give 287-3 (569 g, 97% in 2 steps) as a white solid.

To a solution of 287-3 (150 g, 0.47 mol) in anhydrous THF (2 L) was added DIBAL-H (710 mL, 0.71 mol, 1.0 M in toluene) at −78° C. for 3 h. The reaction was quenched with sat. aq. NH$_4$Cl and then filtered. The filtrate was extracted with EA and washed with brine. The organic layer was dried over Na$_2$SO$_4$ and filtered. The filtrate was concentrated to dryness. The residue was purified by silica gel column (11% EA in PE) to give 287-4 (121 g, 80.5%) as a white solid.

Isopropyltriphenylphosphonium iodide (422.8 g, 0.98 mol) was suspended in anhydrous THF (1 L) and cooled to 0° C. A BuLi solution (2.5M in THF, 391 mL, 0.98 mol) was added dropwise over 0.5 h. The deep red solution was maintained at 0° C. for 0.5 h and 287-4 (207.5 g, 0.65 mol) in THF (1 L) was added slowly over 2 h. The mixture was warmed to ambient temperature and stirred for 12 h. The reaction was quenched with sat. aq. NaHCO$_3$. The precipitated solid was removed by filtration. The filtrate was diluted with EA and washed with brine. The organic layer was dried over anhydrous Na$_2$SO$_4$ and filtered. The filtrate was concentrated at low pressure, and the residue was purified by chromatography on silica gel (10% to 30% EA in PE) to give 287-5 (104.7 g, 47%) as a colorless oil.

To a stirred solution of 287-5 (4.9 g, 14.2 mmol) in anhydrous MeCN (70 mL) was added IBX (7.9 g, 28.4 mmol). The mixture was refluxed for 2 h. The mixture was filtered, and the filtrate was concentrated to dryness. The residue was purified by column chromatography (1% EA in PE) to give 287-6 (4.6 g, 94.8%) as a colorless oil.

To a stirred solution of 287-6 (2.0 g, 5.8 mmol) and difluoromethyl phenyl sulfone (2.24 g, 11.7 mmol) in anhydrous DMF (50 mL) was added LiHMDS (1.0 M in THF, 11.7 mL) dropwise at −78° C. After stirring at −78° C. for 2 h, the reaction was quenched with sat. aq. NH$_4$Cl. The mixture was then stirred at 0° C. for 30 mins. The organic phase was separated, and the aqueous phase was extracted with EA. The combined organic phase was washed with brine, dried over Na$_2$SO$_4$ and filtered. The filtrate was concentrated to dryness. The residue was purified on a silica gel chromatography (0.25% EA in PE) to give 287-7 (1.1 g, 32.1%) as a colorless oil. $^1$H-NMR (CDCl$_3$, 400 MHz) δ=8.01-7.97 (m, 2H), 7.74-7.70 (m, 1H), 7.61-7.57 (m, 2H), 5.80 (d, J=1.6 Hz, 1H), 4.26 (d, J=11.2 Hz, 1H), 4.08 (s, 1H), 4.03 (d, J=11.2 Hz, 1H), 3.86 (s, 1H), 1.82 (s, 3H), 1.69 (s, 3H), 1.54 (s, 3H), 1.41 (d, J=12.4 Hz, 6H), 0.89 (s, 9H), 0.09 (d, J=9.6 Hz, 6H).

To a stirred solution of 287-7 (4.0 g, 7.5 mmol) in DMF (80 mL) and H$_2$O (16 mL) was added Mg (3.6 g, 149.8 mmol) followed by the addition of HOAc (13.5 g, 224.7 mmol). The mixture was stirred at RT for 6 h. The mixture was poured into ice water and filtered. The filtrate was extracted with EA. The combined organic phase was washed with brine, dried over Na$_2$SO$_4$ and filtered. The filtrate was concentrated to dryness, and the residue was purified on the silica gel chromatography (0.2% EA in PE) to give 287-8 (1.12 g, 38%) as a colorless oil. $^1$H-NMR (CDCl$_3$, 400 MHz) δ=5.88-5.74 (m, 2H), 3.98-3.78 (m, 3H), 3.30 (s, 1H), 3.08 (s, 1H), 1.83 (s, 3H), 1.70 (s, 3H), 1.41 (s, 3H), 1.35 (d, J=23.2 Hz, 6H), 0.90 (d, J=4.4 Hz, 9H), 0.08 (d, J=7.6 Hz, 6H).

To a solution of 287-8 (1.12 g, 2.84 mmol) was added a solution (6 mL, 1.0 M) of TBAF in THF, and the mixture was stirred at RT for 30 mins. The mixture was concentrated to dryness, and the residue was purified by silica gel column chromatography (3% EA in PE) to give 287-9 (332 mg, 41.7%) as a colorless oil.

To a solution of 287-9 (415 mg, 1.5 mmol) in anhydrous DCM (7.5 mL) was added Et$_3$N (224 mg, 2.2 mmol) and BzCl (248 mg, 1.7 mmol) at 0° C. The mixture was stirred at RT for 4 h. After the reaction was completed, the reaction was quenched with sat. aq. NaHCO$_3$ and extracted with DCM. The organic layer was dried over Na$_2$SO$_4$ and filtered. The filtrate was evaporated, and the residue was purified by silica gel column chromatography (1% EA in PE) to give 287-10 (441 mg, 77.4%) as colorless oil.

To a stirred solution of 287-10 (440 mg, 1.2 mmol) in anhydrous DCM (10 mL) was bubbled O$_3$ at −78° C. until the solution turned blue. The reaction was then bubbled with O$_2$ until the solution turned to colorless. The organic layer was evaporated to give 287-11 (430 mg, crude), which was used for next step without further purification.

287-11 (441 mg, 1.2 mmol) in 90% TFA (6 mL) was stirred at RT for 12 h. The mixture was concentrated under reduced pressure. The residue was purified via silica gel chromatography (50% EA in PE) to give 287-12 (404 mg, 97%) as a colorless oil.

To a solution of 287-12 (404 mg, 1.3 mmol) in anhydrous DCM (6 mL) was added Et$_3$N (1.0 g, 10.2 mmol), DMAP (44 mg, 0.4 mmol) and BzCl (1.0 g, 7.6 mmol) at 0° C. The mixture was stirred at RT for 4 h. The reaction was quenched with sat. aq. NaHCO$_3$ and extracted with DCM. The organic layer was dried over anhydrous Na$_2$SO$_4$ and filtered. The filtrate was evaporated, and the residue was purified by silica gel column chromatography (1% EA in PE) to give 287-13 (530 mg, 66.2%) as a light yellow foam.

To a stirred solution of uracil (190 mg, 1.7 mmol) in chlorobenzene (2.6 mL) was added N, O-bis (trimethylsilyl) acetamide (680 mg, 3.3 mmol). The solution was stirred at 130° C. for 30 mins, and then cooled to ambient temperature. To a solution of 287-13 (536 mg, 0.8 mmol) in chlorobenzene was added SnCl$_4$ (770 mg, 3.5 mmol) slowly dropwise. The mixture was heated to reflux for 30 mins. The reaction was quenched by sat. aq. NaHCO$_3$ and extracted with EA. The organic layer was dried over anhydrous Na$_2$SO$_4$ and filtered. The filtrate was evaporated, and the residue was purified by silica gel column chromatography (20% EA in PE) to give 287-14 (336 mg, 64.6%) as a white solid.

287-14 (80 mg, 0.1 mmol) was treated with 7.0 M NH$_3$ in MeOH. The mixture was stirred at RT for 12 h. The solvent was removed at low pressure. The residue was purified by silica gel column chromatography (5% MeOH in DCM) to give 287 (36 mg, 90.6%) as a white solid. ESI-LCMS:m/z 309.09 [M+H]$^+$; 331.07 [M+Na]$^+$.

Example 163

Compound 288

51 →

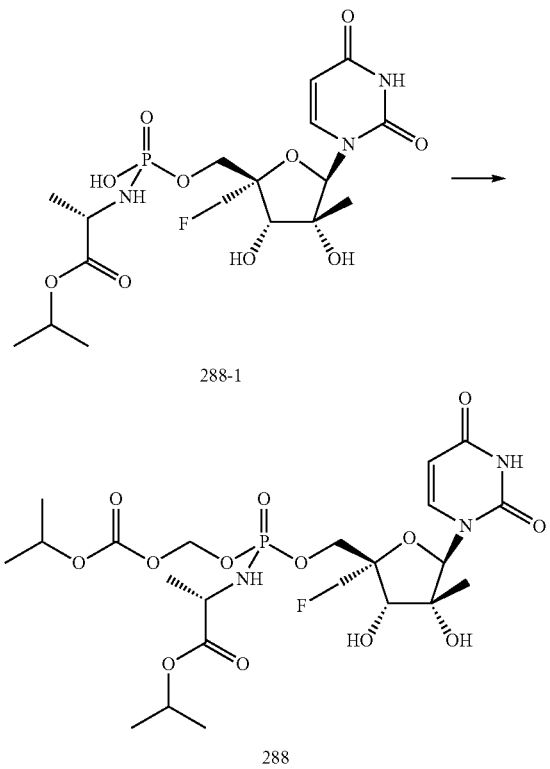

288-1

288

To a mixture of 51 (240 mg, 0.8 mmol) in trimethyl phosphate (4 mL) at 0° C. was added POCl₃ (0.18 mL, 1.6 mmol), and the mixture was stirred at 0° C. for 90 mins. L-alanine isopropyl ester hydrochloride (0.24 g, 1.4 mmol) and Et₃N (0.6 mL, 4.3 mmol) were added. The mixture was warmed to RT and stirring was continued for 1.5 h. The reaction was quenched with 0.5 M aq. TEAA, and the mixture purified by RP-HPLC (A: 50 mM aq. TEAA, B: 50 mM TEAA in MeCN) to yield 288-1 (75 mg).

A mixture of 288-1 (52 mg, 0.1 mmol), DIPEA (0.11 mL, 0.6 mmol) and isopropyloxycarbonyloxymethyl iodide (77 mg, 0.3 mmol) in NMP (1.1 mL) was stirred at RT for 1 h. The mixture was diluted with tert-butyl methylether, washed with sat. aq. NaHCO₃ and brine, and dried with Na₂SO₄. The evaporated residue was purified on a silica column with CH₂Cl₂:MeOH (4-10% B gradient) to yield 288 (12 mg, 20%). MS:m/z=600 [M+1]⁺.

Example 164

Compound 289

44 ⟶

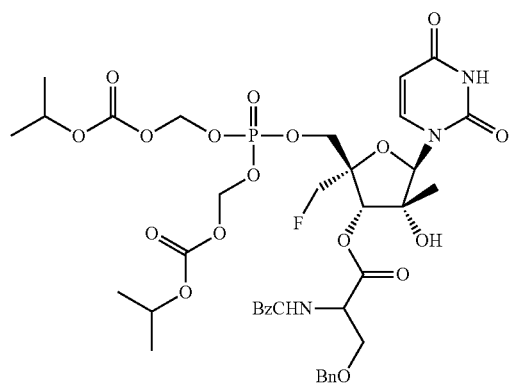

289-1

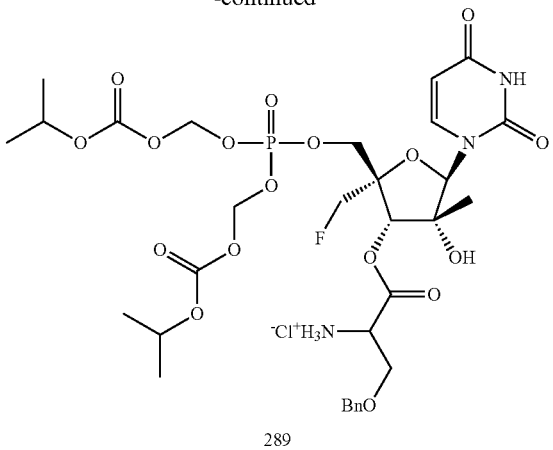

289

To a solution of 44 (200 mg, 0.33 mmol) in anhydrous DCM (6 mL) was added DMAP (4 mg, 0.033 mmol), N-Cbz-O-benzyl-L-serine (164 mg, 0.5 mmol) and EDC (100 mg, 0.52 mmol) at 0 to 5° C. (ice/water bath). The mixture was stirred for 40 h at RT. The mixture was cooled using ice/water bath, diluted with DCM (10 mL), washed sat. NH₄Cl, dried over MgSO₄, filtered and concentrated. The residue was purified by column chromatography in 50 to 90% EA-hexane to give 289-1 (187 mg, 62%) as a white foam.

To a solution of 289-1 (68.7 mg, 0.075 mmol) in anhydrous EtOH (2.5 mL), was added 10% Pd/C (11.4 mg), followed by the addition of 4N HCl (38 µL, 0.15 mmol), and the mixture was stirred under H₂ atmosphere for 3 h. After completion of reaction, the mixture was filtered through celite. The catalyst cake was washed with anhydrous EtOH. The washings and filtrate were combined, and the solvent was removed under vacuum to give 289 (40.1 mg, 77.6%) as an off white foam. MS:m/z=690.1[M+H]⁺.

Example 165

Compound 290

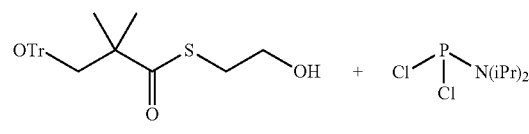

Compound B

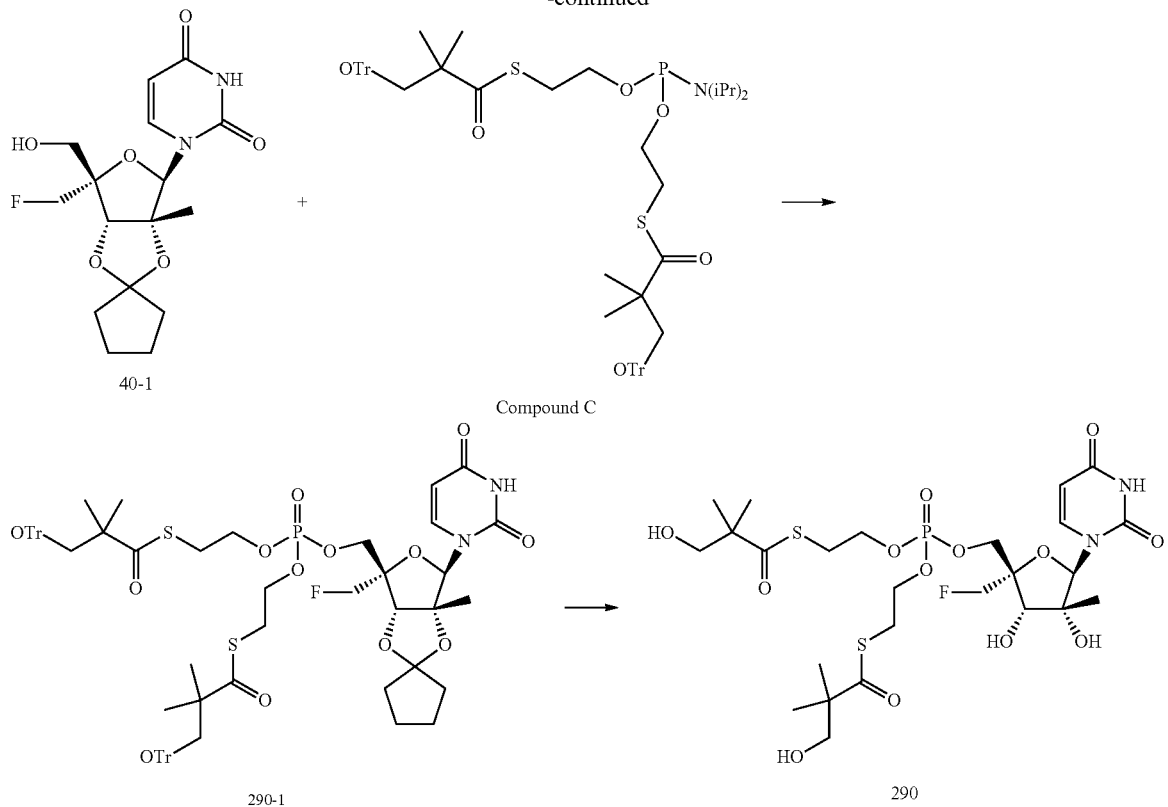

To a mixture of Compound B (0.84 g, 2 mmol; prepared according to Villard et al., *Bioorg. Med. Chem.* (2008) 16:7321-7329) and Et₃N (0.61 mL, 4.4 mmol) in THF (5 mL) at −78° C. was added dropwise a solution of N,N-diisopropyl dichlorophosphoroamidite (184 µL, 1 mmol) in THF (7 mL). The mixture was allowed to warm up and stirred at RT for 2 h. The solids were filtered off. The filtrate was concentrated and purified on a silica gel column with hexanes+1% Et₃N:EtOAc (1-20% B gradient) to yield Compound C (0.38 g).

To a mixture of 40-1 (53 mg, 0.15 mmol) and Compound C (0.17 g, 0.17 mmol) in MeCN (1 mL) was added 5-ethylthio-1H-tetrazole (0.25 M in MeCN; 1.2 mL, 0.3 mmol). The mixture was stirred for 1 h at RT and then cooled to −40° C. A solution of MCPBA (77%; 42 mg, 0.19 mmol) in CH₂Cl₂ (0.5 mL) was added. The mixture was allowed to warm up and stirred at RT for 30 mins. The reaction was quenched with 4% aq. Na₂S₂O₃ in 4% aq. NaHCO₃ (1 mL) and diluted with CH₂Cl₂. The organic layer was washed with sat. aq. NaHCO₃ and brine, and dried with Na₂SO₄. Purification of the evaporated residue on a silica gel column with hexanes:EtOAc (30-100% B gradient) yielded 290-1 (150 mg, 81%).

A solution of 290-1 (120 mg, 0.1 mmol) in 80% aq. TFA (5 mL) was kept at RT for 3 h. The mixture was concentrated, and the residue coevaported with toluene. The crude material was purified on a silica column with CH₂Cl₂:MeOH (4-10% B gradient) to give 290 (25 mg, 36%). MS:m/z=691 [M+1]⁺.

Example 166

Compound 292

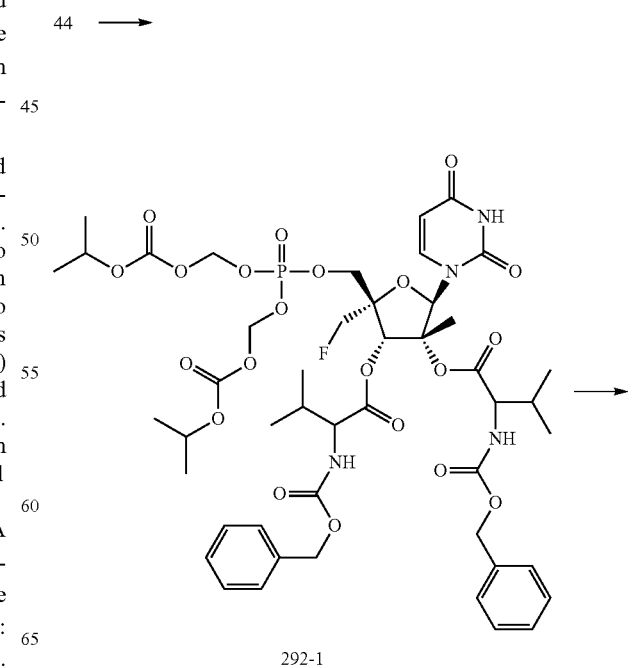

292-1

-continued

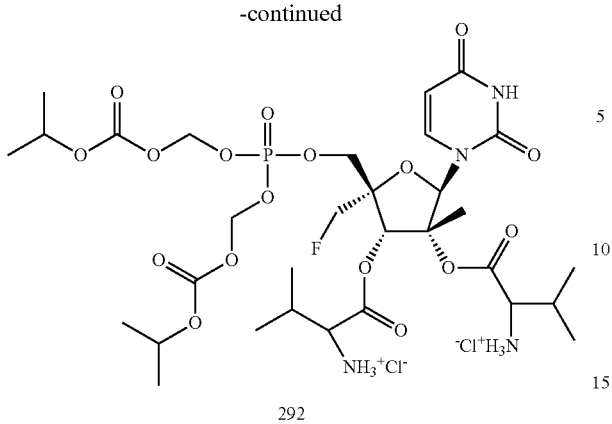

292

To a mixture of DCC (412 mg, 1.98 mmol) in DMF (1 mL), DMAP (244 mg, 1.98 mmol) and Z-Val-OH (502 mg, 1.98 mmol) were added successively, followed by the addition of 44 (200 mg, 0.183 mmol). The mixture was stirred at RT for 1 h. The mixture was filtered, and the filtrate was concentrated with a rotary evaporator until/2 of its original volume. EA was added, and the mixture was washed with water and brine, dried over anhydrous $Na_2SO_4$ and concentrated in vacuo to give a residue. The residue was purified by silica gel with 35-95% EA:hexanes to give 292-1 (107 mg, 31.2%) as a white foam.

To a solution of 292-1 (68 mg, 0.064 mmol) in anhydrous EtOH (2.0 mL) was added 10% Pd/C (12 mg), followed by the addition of 4N HCl (67 µl, 0.25 mmol). The mixture was stirred under $H_2$ atmosphere for 1.5 h. The mixture was filtered through celite, and the catalyst cake was washed with anhydrous EtOH. The washings and the filtrate were combined. The solvent was removed under vacuum to give 292 (41.6 mg, 82%) as a light yellow foam. MS:m/z=801.25 $[M+H]^+$.

Example 167

Compound 293

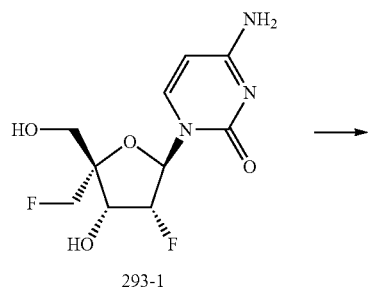

293-1

-continued

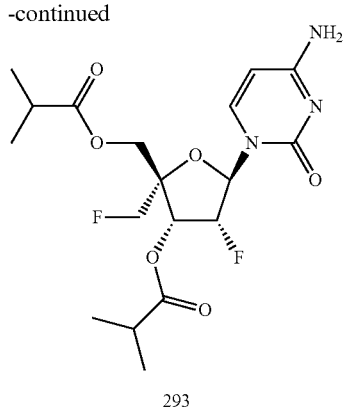

293

To a solution of 293-1 (40 mg, 0.144 mmol) in DMF (2 mL) were added DCC (65 mg, 0.32 mmol), isobutyric acid (28 µl, 0.32 mmol) and DMAP (18 mg, 0.144 mmol). The mixture was stirred at RT overnight. The mixture was filtered, and the filtrate was concentrated with a rotary evaporator to ½ of its original volume. The mixture was then diluted with 25% $DMF/H_2O$ and purified on a reverse-phase HPLC (C18) using $CH_3CN$ and water. Lyophilization gave 293 (17.5 mg, 29%) as a white powder. MS:m/z 416.1 $[M+H]^+$.

Example 168

Compound 294

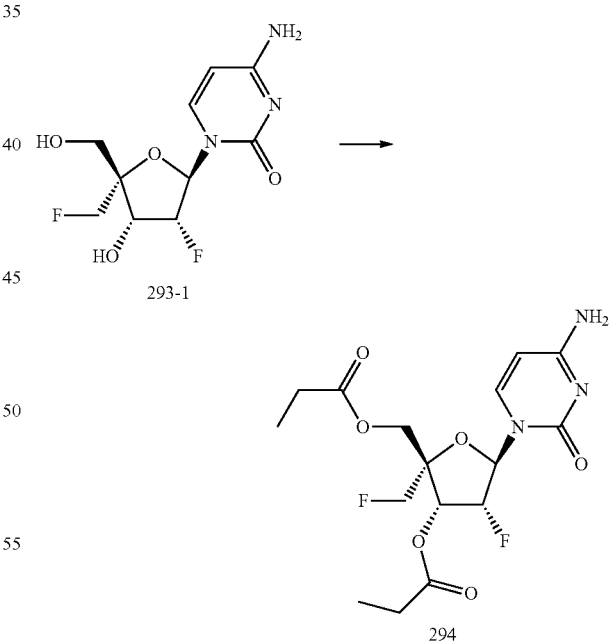

To a solution of 293-1 (50 mg, 0.18 mmol) in DMF (1.5 mL) were added DCC (93 mg, 0.45 mmol), propanoic acid (33.4 µl, 0.45 mmol) and DMAP (22 mg, 0.18 mmol). The mixture was stirred at RT overnight. The mixture was filtered, and then filtrate was concentrated with a rotary evaporator to ½ of its original volume. The mixture was then diluted with 25% $DMF/H_2O$, and purified on a reverse-phase HPLC (C18) using CH₃CN and water. Lyophilization gave 294 (30.2 mg, 43%) as a white powder. MS:m/z 390.1 [M+H]⁺, 388.05 [M−H]⁻.

Example 169

Compound 295

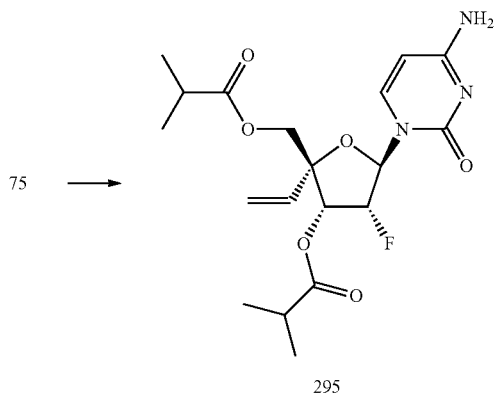 [SMILES: C=C[C@]1(COC(=O)C(C)C)O[C@@H](n2ccc(N)nc2=O)[C@H](F)[C@@H]1OC(=O)C(C)C]

To a solution of 75 (20 mg, 0.073 mmol) in DMF (0.7 mL) were added DCC (37.6 mg, 0.183 mmol), isobutyric acid (16 μl, 0.183 mmol) and DMAP (9 mg, 0.073 mmol). The mixture was stirred at RT overnight. The mixture was filtered, and the filtrate was concentrated with a rotary evaporator to ½ of its original volume. The mixture was then diluted with 25% DMF/H₂O, and purified on a reverse-phase HPLC (C18) using 25-95% CH₃CN:water. Lyophilization gave 295 (12.1 mg, 38.7%) as a white powder. MS:m/z 430.15 [M+H]⁺, 428.10 [M−H]⁻.

Example 170

Compound 296

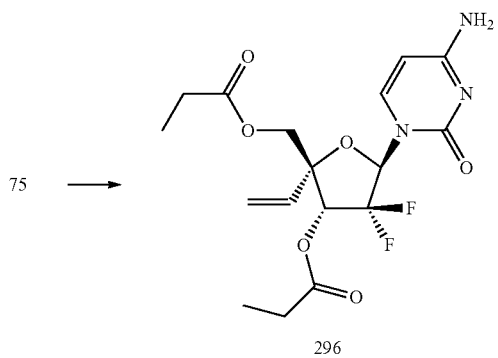

To a solution of 75 (20 mg, 0.073 mmol) in DMF (0.7 mL) were added DCC (37.6 mg, 0.183 mmol), propanoic acid (13.5 μl, 0.183 mmol) and DMAP (9 mg, 0.073 mmol). The mixture was stirred at RT overnight. The mixture was filtered, and then filtrate was concentrated with a rotary evaporator to ½ of its original volume. The mixture was then diluted with 25% DMF/H₂O, and purified on a reverse-phase HPLC (C18) using 25-95% CH₃CN:water Lyophilization gave 296 (14.1 mg, 48%) as a white powder. MS:m/z 402.1 [M+H]⁺.

Example 171

Compound 297

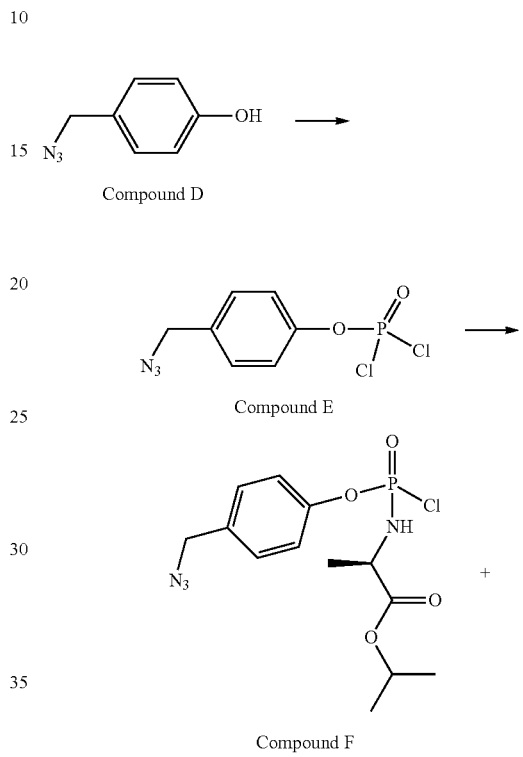

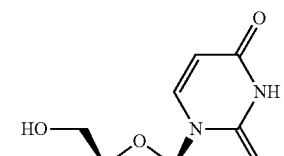

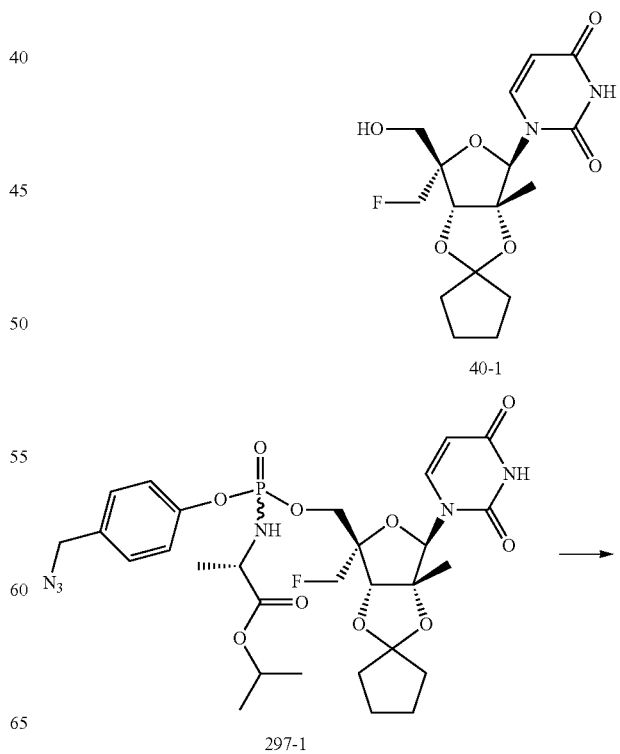

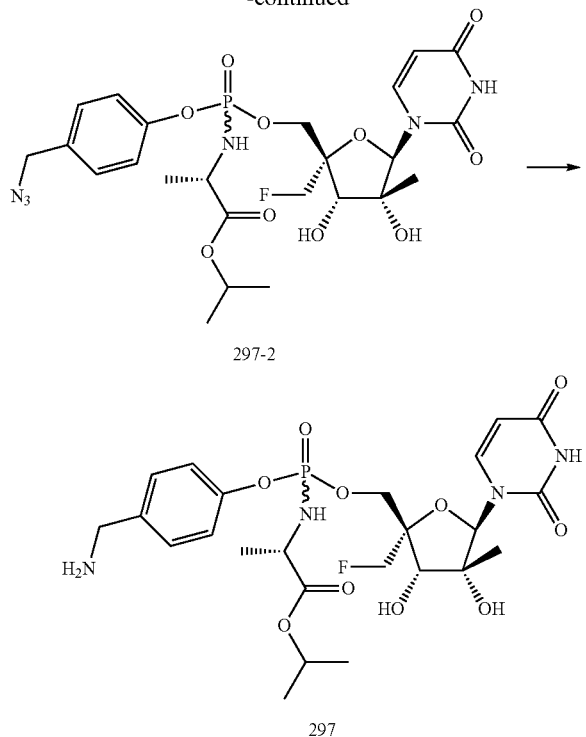

297-2

297

(atmospheric pressure) for 105 mins. The mixture was then filtered through a Celite pad. The evaporated residue was treated with Et$_2$O to yield 297 (55 mg, 63%) as a white solid. MS:m/z=589 [M+1]$^+$.

Example 172

Compound 298

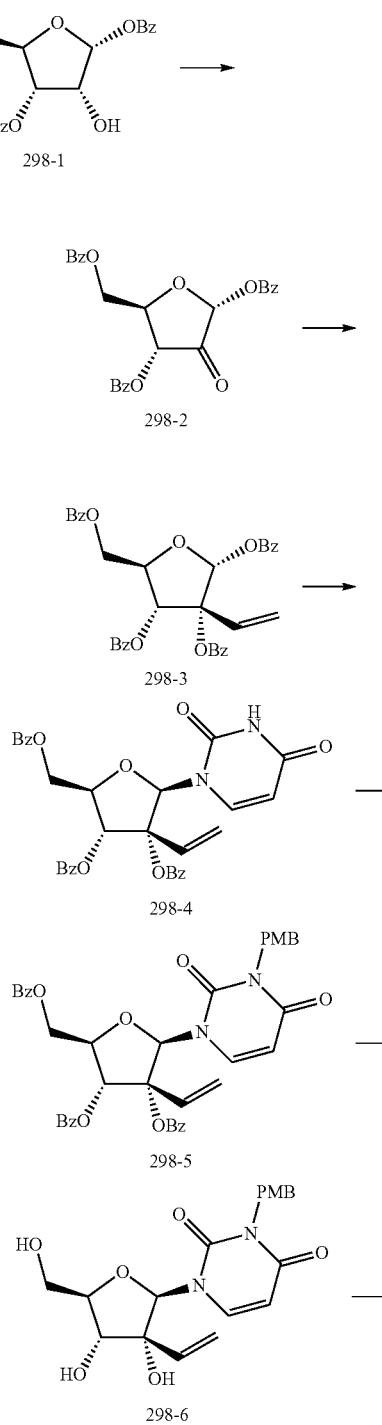

To a mixture of Compound D (0.9 g, 6.0 mmol; prepared according to Qing et al., *Org. Lett.* (2008) 10:545-548) and POCl$_3$ (0.55 mL, 6.0 mmol) in diethyl ether (9 mL) at −78° C. was added Et$_3$N (0.84 mL, 6.0 mmol). The mixture was allowed to warm to RT in 2 h. The mixture was then filtered, and the solids were washed with Et$_2$O. The combined filtrates were evaporated, and the crude Compound E was used without purification.

To a solution of crude Compound E and L-alanine isopropyl ester hydrochloride (1.0 g, 6.0 mmol) in CH$_2$Cl$_2$ (15 mL) at −20° C. was added Et$_3$N (1.67 mL, 1.2 mmol). The mixture was allowed to warm up and stirring at RT for 2 h. The mixture was diluted with hexanes and filtered through a silica pad which was thoroughly washed with CH$_2$Cl$_2$: hexanes 1:1. The combined filtrates were concentrated and purified on a silica column with hexanes:EtOAc (5-50% B gradient) to yield Compound F (0.78 g, 38% for 2 steps).

To a solution of 40-1 (0.36 g, 1.0 mmol) in THF (7.5 mL) at 0° C. was added isopropyl magnesium chloride (2 M in THF; 0.65 mL, 1.3 mmol), and the mixture was stirred at 0° C. for 30 mins. A solution of Compound F (0.78 g, 2.2 mmol) in THF (2 mL) was added, and the mixture stirred at RT for 2 h. The reaction was quenched with sat. aq. NH$_4$Cl, and then diluted with EtOAc. The two layers were separated. The organic layer was washed with water and brine, and dried over Na$_2$SO$_4$. Purification of the evaporated residue on a silica gel column with CH$_2$Cl$_2$:i-PrOH (3-10% B gradient) yielded 297-1 (0.50 g, 74%).

A solution of 297-1 (0.28 g, 0.4 mmol) in 80 aq. TFA (4 mL) was stirred at RT for 4 h. The mixture was evaporated and coevaporated with toluene. The residue was purified on a silica column with CH$_2$Cl$_2$:MeOH (4-10% B gradient) to give 297-2 (0.17 g, 68%).

To a solution of 297-2 (85 mg, 0.14 mmol) in EtOH (3 mL) and HCl (4 N in dioxane; 35 µL, 0.14 mmol) was added 10% Pd/C (8 mg). The mixture was stirred under H$_2$

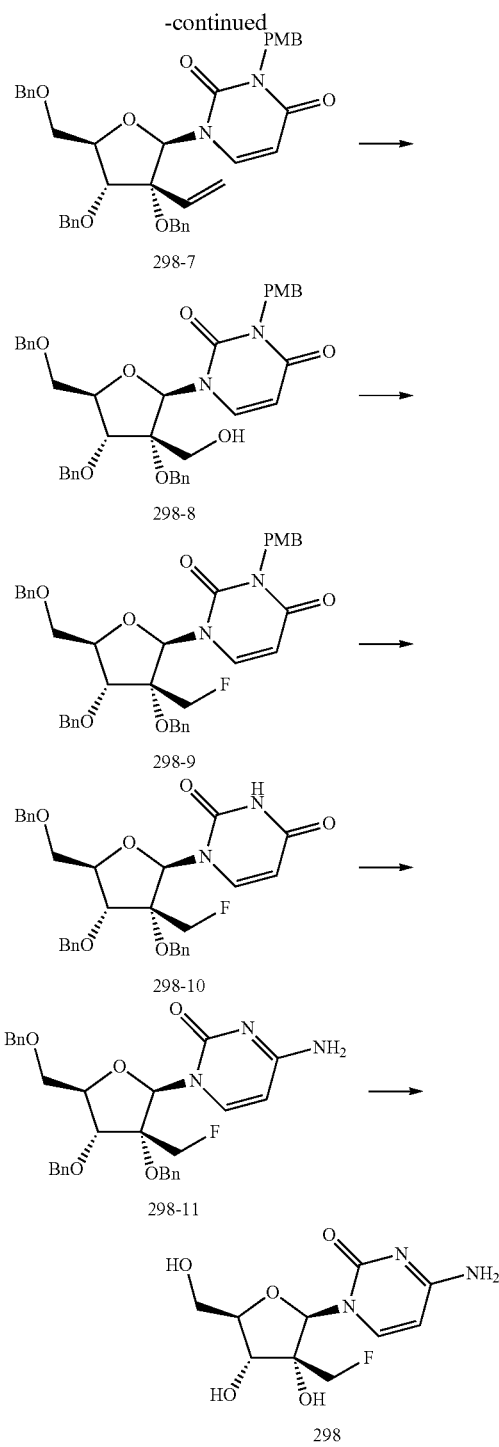

was consumed, the mixture was poured into a sat. NH$_4$Cl solution, and extracted with EA (3×300 mL). The organic layer was washed with brine, dried with anhydrous Na$_2$SO$_4$, filtered and concentrated at low pressure to give the crude intermediate without further purification.

To a solution of this crude intermediate (170 g, 0.346 mol) in anhydrous CH$_2$Cl$_2$ was added TEA (105 g, 1.04 mol) and DMAP (84 g, 0.69 mol), and the mixture was stirred at RT. Benzoyl chloride (146 g, 1.04 mol) was added slowly at RT. After stirring for 12 h at RT, the mixture was diluted with CH$_2$Cl$_2$ and then washed with sat. aq. NaHCO$_3$. The combined aqueous phase was extracted with DCM (100 mL). The combined organic phase was dried with anhydrous Na$_2$SO$_4$, filtered and evaporated to dryness under reduced pressure. The residue was purified by column chromatography (PE:EA=10:1 to 5:1) to give 298-3 (107 g, 52%).

A mixture of uracil (treated by toluene twice) and NOBSA (81.4 g, 0.4 mol) in CH$_3$CN (200 mL) was stirred to reflux for 1.5 h. After the mixture was cooled to RT, 298-3 (59 g, 0.1 mol, treated by toluene) in CH$_3$CN (100 mL) was added. The mixture was treated with TMSOTf (155 g, 0.7 mol), and then warmed to 60-70° C. for 12 h. LCMS showed that no starting material remained. The mixture was poured into a NaHCO$_3$ (sat.) solution. The desired product precipitated. After filtration, pure 298-4 (40 g, 69%) was obtained as a white solid.

To a solution of 298-4 (50 g, 0.086 mol), K$_2$CO$_3$ (17.8 g, 0.13 mol) in DMF (500 mL) was added PMBCl (16 g, 0.1 mol) at 0° C., and the mixture stirred at 25° C. for 12 h. The reaction was quenched with water, and the mixture was extracted with EtOAc (3×150 mL). The solution was washed with brine, dried over anhydrous Na$_2$SO$_4$ and concentrated at low pressure. Crude 298-5 (65 g) was obtained and used directly for the next step.

A mixture of 298-5 (65 g, 0.086 mol) and NaOMe (16.8 g, 0.3 mol) in MeOH:DCM (4:1, 200 mL) was stirred at RT for 2.5 h. LCMS showed that no starting material remained. The reaction was quenched with dry ice. The solution was washed with brine, dried over anhydrous Na$_2$SO$_4$ and concentrated at low pressure. The residue was purified by column chromatography (DCM:MeOH=50:1 to 20:1) to give 298-6 as a yellow foam (25 g, 75%).

To a solution of 298-6 (25.5 g, 0.065 mol) in DMF was added NaH (10.5 g, 0.26 mol) slowly at ice bath, and the mixture was stirred for 30 mins. BnBr (36.3 g, 0.21 mol) was added, and the mixture was stirred at 25° C. for 12 h. TLC showed that the starting material disappeared. The reaction was quenched by sat. aq. NH$_4$Cl and extracted with EtOAc (3×100 mL). The organic phase was washed with brine, dried over anhydrous Na$_2$SO$_4$ and concentrated at low pressure. The residue was purified by column chromatography (PE:EA=5:1 to 3:1 to 1:1) to give 298-7 (20 g, 46%).

To a solution of 298-7 (20 g, 0.03 mol), NMMO (7 g, 0.06 mol) in THF:H$_2$O (5:1, 100 mL) was added OsO$_4$ (2.6 g, 0.01 mol) at 25° C., and the mixture was stirred at 25° C. for 24 h. The reaction was quenched with a sat. Na$_2$S$_2$O$_3$ solution, and extracted with EtOAc (3×100 mL). The organic layer was washed with brine, dried over anhydrous Na$_2$SO$_4$ and concentrated at low pressure. The diol product residue was used directly for next step.

To a solution of diol product (0.03 mol) in MeOH:H$_2$O: THF (170 mL:30 mL:50 mL) was added NaIO$_4$ (9.6 g, 0.045 mol), and the mixture was stirred at 25° C. for 2 h. After the white solid was filtered, the filtrate was used directly for the next step.

The previous solution was treated with NaBH$_4$ (1.8 g, 0.048 mol) at 0° C., and stirred at 25° C. for 30 mins. The A mixture of 298-1 (120 g, 0.26 mol) and IBX (109 g, 0.39 mol) in CH$_3$CN (2.0 L) was heated to reflux and stirred for 12 h. After cooling to RT, the mixture was filtered. The filtrate was concentrated at low pressure and used directly for the next step.

298-2 (130 g, crude, 0.26 mol) was co-evaporated with anhydrous toluene (3×) to remove H$_2$O. Vinyl magnesium bromide (700 mL, 0.78 mol, 1.0 N in THF) was added dropwise into a solution of 298-2 in THF (300 mL) over 30 mins at −78° C. The mixture was stirred for about 1 h. at 25° C. and checked by LCMS trace. When the starting material reaction was quenched with HCl (1 N) solution and adjusted pH to 7-8. The solution was extracted by EtOAc (3×50 mL). The organic phase was washed with brine washed with brine, dried over anhydrous Na₂SO₄ and concentrated at low pressure. The residue was purified by column chromatography (PE:EA=6:1 to 4:1) to give 298-8 (12 g, 61% over 3 steps).

To a solution of 298-8 (14 g, 21 mmol), DMAP (5.1 g, 42 mmol) in DCM (50 mL) was added MsCl (3.1 g, 27 mmol) at 0° C., and the mixture was stirred at 25° C. for 40 mins. LCMS shows that no starting material remained. The reaction was quenched by sat. aq. NaHCO₃ and extracted with DCM (3×100 mL). The solution was washed with HCl (0.2 N) solution, dried over anhydrous Na₂SO₄ and concentrated at low pressure. The residue was purified by column chromatography (PE:EA=10:1 to 5:1) to give the OMs-product (14 g, 90%).

The OMs-product (6.1 g, 8.21 mmol) was dissolved in TBAF (Alfa, 1 N in THF, 120 mL), and the mixture was stirred at 70-80° C. over 3 days. LCMS shows that 50% of the starting material was converted to the desired product. The mixture was concentrated at low pressure. The residue was dissolved in EtOAc (100 mL). The solution was washed by brine, dried over anhydrous Na₂SO₄ and concentrated at low pressure. The residue was purified by column chromatography (PE:EA=10:1 to 5:1) to give 298-9 (1.3 g, 24%).

To a solution of 298-9 (6.3 g, 9.45 mmol) in CAN:H₂O (v:v=3:1, 52 mL) was added CAN (15.5 g, 28.3 mmol), and the mixture was stirred at RT overnight. The reaction was quenched with water, and extracted with EA (3×80 mL). The organic phase was washed with brine, dried over anhydrous Na₂SO₄ and concentrated at low pressure. The residue was purified by column chromatograph (25% EA in PE) to give 298-10 (3.6 g, 71%) as a yellow oil.

To a solution of 298-10 (566 mg, 1.04 mmol), DMAP (253 mg, 2.07 mmol) and TEA (209 mg, 2.07 mmol) in anhydrous MeCN (6 mL) was added TPSCl (627 mg, 2.07 mmol) at 0° C. The mixture was stirred at RT for 2 h. The mixture was treated with NH₃.H₂O (10 mL), and stirred at RT overnight. TLC showed that the reaction was completed. The solution was concentrated at low pressure. The residue was purified by silica gel column chromatography (DCM:MeOH=50:1 to 20:1) to give 298-11 (300 mg, 49%) as a white solid.

To a solution of 298-11 (200 mg, 0.37 mmol) in anhydrous DCM (0.5 mL) was added BCl₃ (2.5 mL, 1 N in DCM) at −70° C., and the mixture was stirred for 2 h at −70° C. TLC showed that no materials remained. The reaction was quenched with MeOH at −70° C., and concentrated at low pressure directly under 40° C. The residue was dissolved in H₂O, and washed with EtOAc over 3 times. The aqueous phase was lyophilized to give 298 (91 mg, 89%) as a white solid. ESI-LCMS:m/z 276.1 [M+H]⁺.

Example 173

Compound 299

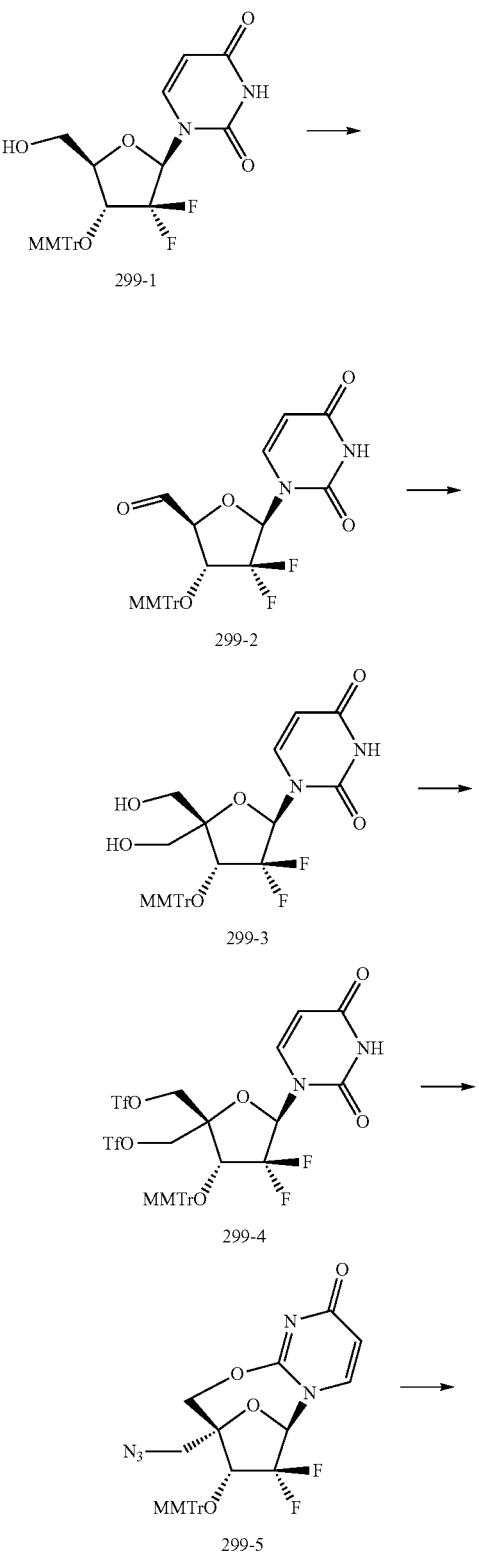

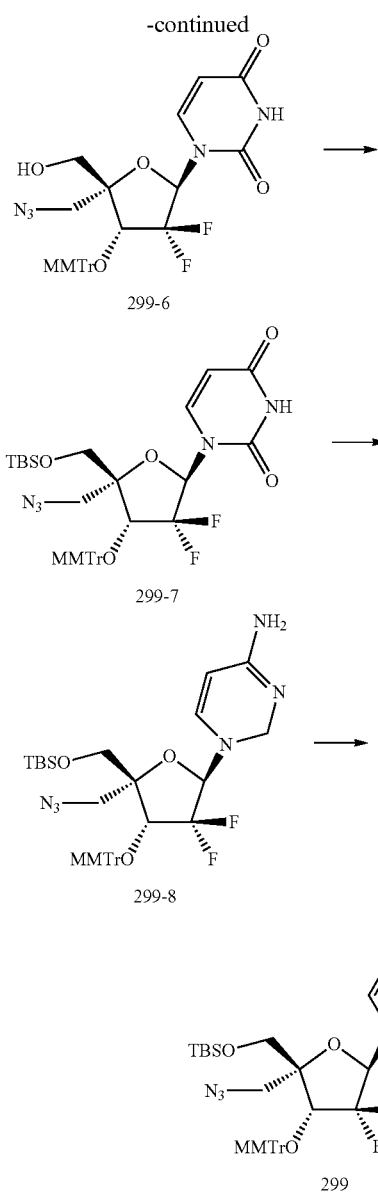

299-6

299-7

299-8

299

To a stirred solution of 299-1 (8.2 g, 15.3 mmol) in anhydrous CH$_3$CN (150 mL) was added IBX (4.7 g, 16.8 mmol) at 20° C. under N$_2$. The suspension was heated to 90° C.~100° C. and stirred at this temperature for 1 h. The mixture was filtered, and the filtrate was concentrated under reduced pressure. The residue, 299-2, (8.2 g, crude) was used in the next step without further purification.

To a solution of 299-2 (8.2 g, 15.4 mmol) in 1,4-dioxane (150 mL) was added aq. NaOH (15.4 mL, 2 M, 30.8 mmol) at 20° C. The mixture was stirred at this temperature for 10 h. The solution was neutralized with AcOH to pH=7, followed by addition of EtOH (50 mL) and NaBH$_4$ (5.8 g, 154.3 mmol) at 0° C. The mixture was stirred at this temperature for 1 h. The reaction was quenched with water (20 mL), extracted with EA (2×40 mL). The combined organic phase was washed with brine, dried over anhydrous MgSO$_4$ and concentrated at low pressure. The residue was purified via silica gel chromatography (50% EA in PE) to give 299-3 (5.5 g, 62.92%) as a white solid.

299-3 (480 mg, 0.8 mmol) was co-evaporated with toluene (2×). The residue was dissolved in anhydrous DCM (5 mL) and pyridine (671 mg, 85 mmol). Tf$_2$O (481 mg, 187 mmol) was added dropwise at 0° C. over 10 mins. The mixture was stirred at this temperature for 40 mins. The mixture was purified by column chromatography (20% EA in PE) to give 299-4 (602 mg, 86.1%) as a brown foam.

To a solution of 299-4 (602.0 mg, 0.72 mmol) in anhydrous DMF (8 mL) was added NaH (34.8 mg, 0.87 mmol) at 0° C. under N$_2$ atmosphere. The reaction was stirred at 20° C. for 1 h, and then NaN$_3$ (1.59 g, 2.5 mmol) was added at 0° C. under N$_2$ atmosphere. The mixture was stirred at 20° C. for 2 h. The reaction was quenched with water at the same temperature, extracted with EA (2×20 mL). The combined organic layer was washed with brine, dried over Na$_2$SO$_4$ and filtered. The filtrate was concentrated to dryness under reduced pressure. The residue, 299-5, (431 mg, crude) was used in next step without further purification.

To a solution of 299-5 (431 mg, crude) in 1,4-dioxane (14 mL) was added aq. NaOH (114.4 mg, 2 M, 2.9 mmol) at 18° C. The mixture was stirred at the same temperature for 3 h. The mixture was diluted with EA (20 mL). The organic layer was washed with brine, dried over MgSO$_4$ and concentrated at low pressure. The residue was purified via silica gel chromatography (30% EA in PE) to give 299-6 (406.0 mg, 47.9%) as a white foam.

To a solution of 299-6 (406.0 mg, 0.68 mmol) in anhydrous DMF (8 mL) was added TBSCl (198.7 mg, 1.3 mmol) and imidazole (119.7 mg, 1.8 mmol) at 30° C. under N$_2$ atmosphere. The solution was stirred at this temperature for 3 h. The solution was diluted with EA (20 mL) and washed with water and brine. The organic phase was dried over MgSO$_4$ and concentrated at low pressure. The residue was purified via silica gel chromatography (50% EA in PE) to give 299-7 (405.0 mg, 65.28%) as a white solid.

To a solution of 299-7 (405.0 mg, 0.57 mmol) in anhydrous CH$_3$CN (6 mL) was added 2,4,6-triisopropylbenzene-1-sulfonyl chloride (343.3 mg, 1.13 mmol), DMAP (138.5 mg, 1.1 mmol) and TEA (114.7 mg, 1.1 mmol) at 30° C. The mixture was stirred at this temperature for 9 h. NH$_3$.H$_2$O (4 mL) was added, and the mixture was stirred for 3 h. The mixture was diluted with EA (20 mL) and washed with brine. The organic layer was dried over Na$_2$SO$_4$ and concentrated at low pressure. The residue was purified via silica gel chromatography (50% EA in PE) to give 299-8 (401.0 mg, crude) as a yellow foam.

299-8 (380.0 mg, 0.54 mmol) was dissolved in 80% HCOOH (25 mL), and the mixture was stirred at 30° C. for 12 h. The reaction was quenched with MeOH and concentrated under reduced pressure. The residue was purified by silica gel chromatography (10% MeOH in DCM) to give 299 (144.0 mg, 83.93%) as a white foam. ESI-MS:m/z 319.1 [M+H]$^+$; 637.2 [2M+H]$^+$.

Example 174

Compound 300

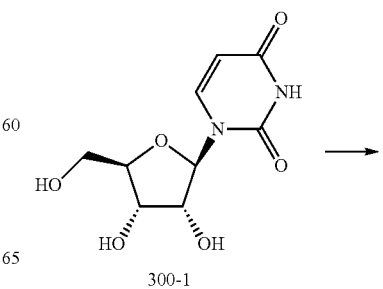

300-1

443
-continued
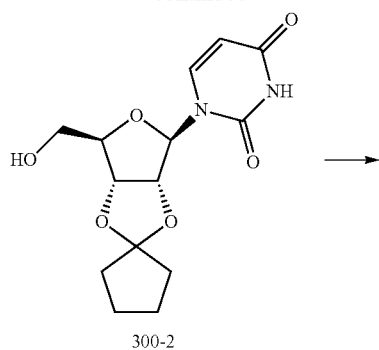
300-2
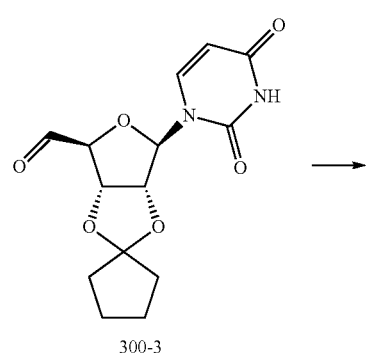
300-3
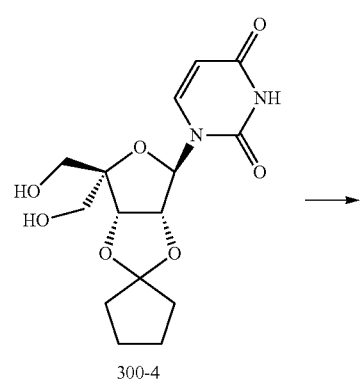
300-4
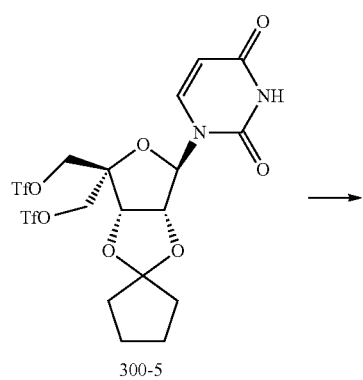
300-5
444
-continued
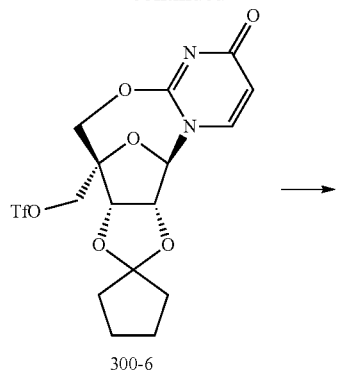
300-6
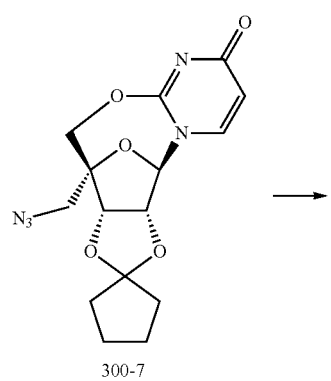
300-7
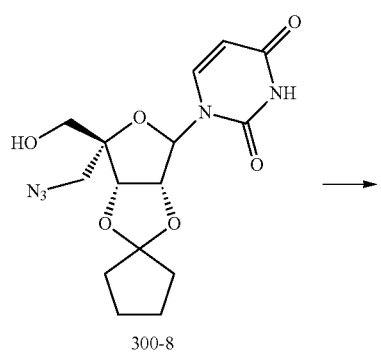
300-8
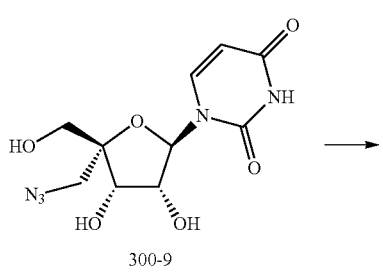
300-9
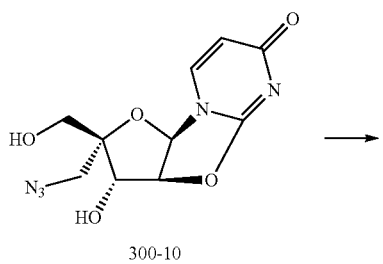
300-10

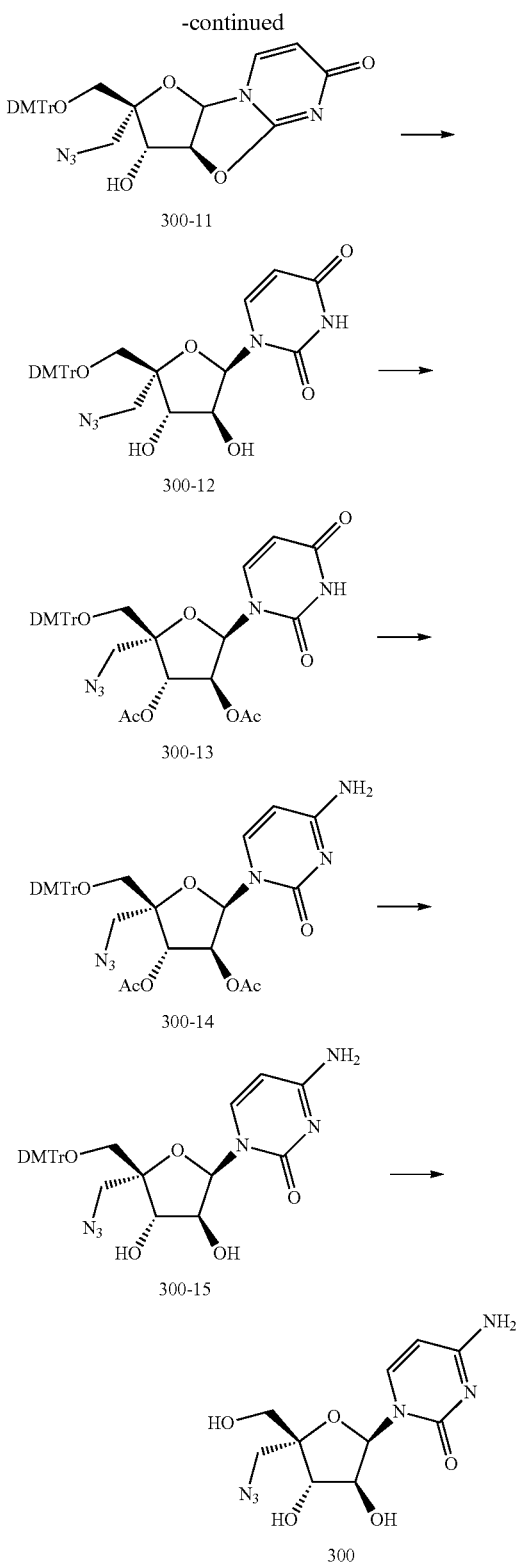

To a solution of 300-1 (30 g, 122.85 mmol) and 1,1-dimethoxycyclopentane (86 g, 660.93 mmol) in DCE (200 mL) was added TsOH.H₂O (2.34 g, 12.29 mmol) in one portion at RT. The mixture was heated to 70° C. and stirred for 14 h. TLC showed that the reaction was completed. The mixture was cooled to RT and concentrated under reduced pressure. The residue was purified by column chromatography (1-10% MeOH in DCM) to give 300-2 (25 g, 65.6%) as a white solid.

To a solution of 300-2 (20 g, 64.45 mmol) in anhydrous CH₃CN (200 mL) was added IBX (19.85 g, 70.9 mmol) at RT. The mixture was refluxed for 18 h. and then cooled to 0° C. The precipitate was filtered-off, and the filtrate was concentrated to give crude 300-3 (20 g, 100%) as a yellow solid.

To a solution of 300-3 (20 g, 64.87 mmol) in 1,4-dioxane (200 mL) were added 37% HCHO (20 mL) and 2.0 M NaOH aq. solution (40 mL) at 0° C. The mixture was stirred at RT overnight and then neutralized with AcOH to pH=7. The solution was treated with NaBH₄ (4.91 g, 129.74 mmol) at 20° C. The mixture was stirred at RT for 1.0 h, and the reaction was quenched with sat. aq. NH₄Cl. The mixture was extracted with EA (3 s 200 mL). The organic layer was dried over anhydrous Na₂SO₄ and concentrated at low pressure. The residue was purified by silica gel column chromatography (1-3% MeOH in DCM) to give 300-4 (9 g, 40.8%) as a white solid.

To an ice cold solution of 300-4 (4.5 g, 13.22 mmol) in anhydrous DCM (50 mL) was added pyridine (10.46 g, 132.20 mmol) and Tf₂O (8.21 g, 29.08 mmol) dropwise at -30° C. The mixture was stirred at the same temperature for 1 h. The reaction was quenched with ice water and extracted with EA (3×60 mL). The organic phase was washed with brine, dried over anhydrous Na₂SO₄ and concentrated at low pressure. The residue was purified on a silica gel column (PE:EA=5:1) to give 300-5 (5 g, 62.57%) as a white solid.

To a stirred solution of 300-5 (5 g, 8.27 mmol) in anhydrous DMF (25 mL) was added NaH (396.96 mg, 9.92 mmol) at 0° C. under N₂. The solution was stirred at RT for 2 h. TLC showed that the reaction was completed. The solution of 300-6 was used in next step without any further workup.

To a stirred solution of 300-6 (3.75 g, 8.25 mmol) was added NaN₃ (1.5 g, 2.50 g, 38.46 mmol) at 0° C. under N2 atmosphere. The solution was stirred at RT for 2 h. The reaction was quenched with water and extracted with EA (3×60 mL). The organic layer was washed with brine, dried over anhydrous Na₂SO₄ and concentrated at low pressure. The residue, 300-7, was used in the next step without further purification.

To a solution of 300-7 (2.87 g, 8.25 mmol) in anhydrous 1,4-dioxane (30 mL) was added NaOH (8.25 mL, 16.50 mmol, 2.0 M in water) at RT. The mixture was stirred at RT for 3 h. TLC showed that the reaction was completed. The mixture was diluted with EA. The solution was washed with brine, dried over anhydrous Na₂SO₄ and concentrated at low pressure. The residue was purified on the silica gel column (PE:EA=10:1 to 2:1) to give 300-8 (2 g, 66.4%) as a white foam. ¹H-NMR (DMSO, 400 MHz), δ=9.02 (s, 1H), 7.40 (d, J=8.0 Hz, 1H), 5.75-5.77 (m, 1H), 5.57 (d, J=3.6 Hz, 1H), 5.13-5.16 (m, 1H), 4.90 (d, J=6.4 Hz, 1H), 3.79-3.85 (m, 2H), 5.51-5.56 (m, 2H), 3.06-3.09 (m, 1H), 2.05-2.09 (m, 2H), 1.65-1.75 (m, 6H).

300-8 (2 g, 5.47 mmol) was dissolved in 80% HCOOH (20 mL) aq. solution, and the mixture was heated to 60° C. for 2 h. The mixture was evaporated at low pressure. The residue was dissolved in MeOH, and the pH was adjusted to 7-8 with NH₃.H₂O. The mixture was stirred for 10 mins, and then concentrated at low pressure. The residue was purified by silica gel column chromatography (DCM:MeOH=20:1) to afford 300-9 (1.4 g, 85.5%) as a white solid.

To a solution of 300-9 (1.00 g, 3.34 mmol) in DMF (5 mL) was added diphenyl carbonate (157.49 mg, 735.20

µmol) and NaHCO₃ (28.06 mg, 0.334 mmol) at 120° C. The mixture was stirred for 16 h. TLC showed that the reaction was completed. The mixture was cooled to RT and concentrated at low pressure. The residue was purified by silica gel chromatography (DCM:MeOH=15:1 to 10:1) to afford 300-10 (600. mg, 63.9%) as a yellow solid. ¹H-NMR (DMSO, 400 MHz), δ=8.49 (s, 1H), 7.83 (d, J=7.2 Hz, 4H), 6.46 (s, 1H), 6.31 (d, J=4.8 Hz, 1H), 5.84 (d, J=6.8 Hz, 1H), 5.27 (d, J=5.6 Hz, 2H), 4.43 (s, 1H), 3.53 (d, J=12.8 Hz, 1H), 3.43 (d, J=13.2 Hz, 1H), 3.12 (d, J=11.2 Hz, 1H).

To a solution of 300-10 (2 g, 7.11 mmol) and AgNO₃ (1.81 g, 10.67 mmol) in Py (20 mL) was added DMTrCl (3.61 g, 10.67 mmol) in one portion at RT. The mixture was stirred at RT for 12 h. TLC showed that the reaction was completed. The mixture was concentrated at low pressure, and the residue was purified by silica gel chromatography (DCM:MeOH=50:1) to afford 300-11 (3 g, 72.3%) as a white solid.

To a solution of 300-11 (1.5 g, 2.57 mmol) in EtOH (5 mL) was added NaOH (5 mL, 2.0 N) in one portion at RT. The mixture was stirred at RT for 0.5 h. TLC showed that the reaction was completed. The aqueous phase was extracted with EA (3×60 mL). The organic phase was washed with brine, dried with anhydrous Na₂SO₄, filtered and concentrated in vacuum to afford 300-12 (1.50 g, 97%) as a yellow solid.

To a solution of 300-12 (1.50 g, 2.49 mmol) in Py (6 mL) was added AC₂O (3 mL) in one portion at RT. The mixture was stirred at RT for 12 h. TLC showed that the reaction was completed. The mixture was concentrated, and the residue was dissolved in water. The aqueous phase was extracted with EA (3×60 mL). The combined organic phase was washed with sat. brine, dried with anhydrous Na₂SO₄, filtered and concentrated in vacuum. The residue was purified by silica gel chromatography (PE:EA=1:1) to afford 300-13 (1.5 g, 87.8%) as a white solid. ¹H-NMR (CDCl₃, 400 MHz), δ=8.10 (s, 1H), 7.29-7.34 (m, 10H), 6.77 (d, J=8.0 Hz, 4H), 6.36 (d, J=5.2 Hz, 1H), 5.36 (d, J=3.6 Hz, 1H), 5.44 (t, J=4.0 Hz, 1H), 5.32 (d, J=8.0 Hz, 1H), 3.80 (s, 6H), 3.58 (d, J=12.8 Hz, 1H), 3.44 (d, J=12.8 Hz, 1H), 3.29 (s, 2H), 2.10 (s, 3H), 1.82 (s, 3H).

To a solution of 300-13 (500 mg, 729.2 µmol) in MeCN (10 mL) was added DMAP (178.17 mg, 1.46 mmol) and TPSCl (430.01 mg, 1.46 mmol) in one portion at RT. The mixture was stirred at RT for 3 h. NH₃/THF (20 mL, sat) was added, and the mixture was stirred for 1 h. The mixture was diluted with EA and washed with water. The combined organic phase was washed with sat. brine, dried with anhydrous Na₂SO₄, filtered and concentrated in vacuum. The residue was purified by silica gel chromatography (DCM:MeOH=50:1) and then purified by pre-HPLC(CH₃CN/H₂O) to afford 300-14 (260 mg, 49.5%) as a yellow solid. ¹H-NMR (MeOD, 400 MHz), δ=7.60 (d, J=7.6 Hz, 1H), 7.46 (d, J=7.6 Hz, 1H), 7.28-7.36 (m, 7H), 6.89 (d, J=8.4 Hz, 4H), 6.44 (d, J=4.8 Hz, 1H), 5.56-5.69 (m, 4H), 3.80 (s, 6H), 3.54 (d, J=13.2 Hz, 1H), 3.39-3.46 (m, 4H), 2.17 (s, 3H), 1.83 (s, 3H).

To a solution of 300-14 (440 mg, 642.6 µmol) in NH₃: MeOH (5 mL, 7N) was stirred at RT for 16 h. TLC showed that the reaction was completed. The mixture was concentrated under reduced pressure at 40° C. The residue was purified by silica gel chromatography (DCM:MeOH=100: 1-20:1) to afford 300-15 (290 mg, 75.13%) as a white solid. ¹H-NMR (MeOD, 400 MHz), δ=7.62 (d, J=7.6 Hz, 1H), 7.43 (d, J=7.6 Hz, 1H), 7.23-7.33 (m, 7H), 6.86 (d, J=8.4 Hz, 4H), 6.31 (d, J=4.8 Hz, 1H), 5.54 (d, J=7.2 Hz, 1H), 4.34 (t, J=4.4 Hz, 1H), 4.27 (d, J=4.0 Hz, 1H), 3.78 (s, 6H), 3.69 (d, J=12.8 Hz, 1H), 3.46 (d, J=12.8 Hz, 1H), 3.41 (s, 2H).

A solution of 300-15 (150 mg, 249.74 µmol) in 80% CH₃COOH (5 mL) was stirred at 60° C. for 2 h. TLC showed that the reaction was completed. The mixture was treated with MeOH and concentrated under reduced pressure at 60° C. The residue was purified by silica gel chromatography (1-10% MeOH in DCM) to afford 300 (65 mg, 78.5%) as a white solid. ESI-MS:m/z 299.1 [M+H]⁺.

Example 175

Compound 302

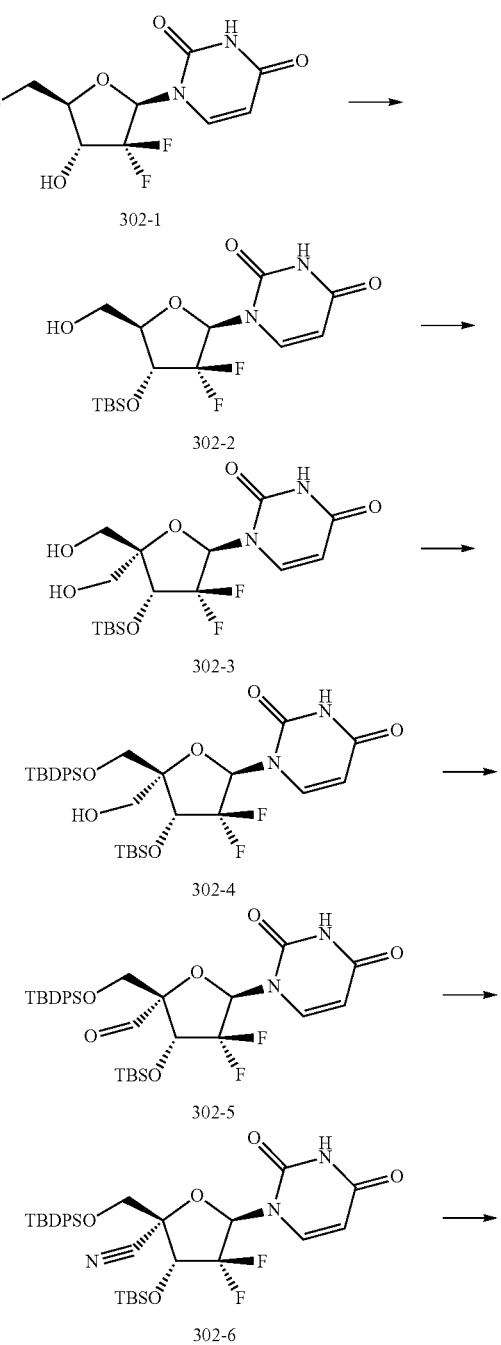

302-1

302-2

302-3

302-4

302-5

302-6

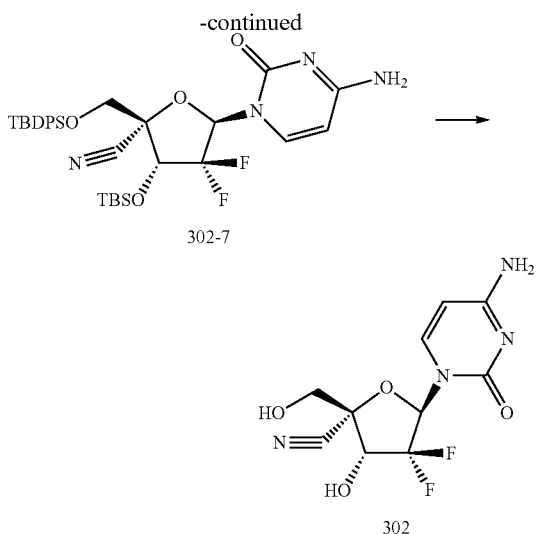

302-7

302

To a solution of 302-1 (12 g, 45.42 mmol) in pyridine (100 mL) was added DMTrCl (16.16 g, 47.69 mmol) in portions at 0° C. over a period of 30 mins under N₂. The mixture was warmed to 25° C. and stirred for 16 h. LCMS and TLC (DCM:MeOH=20:1) showed that the starting material was consumed. The reaction was quenched with MeOH (10 mL) and then concentrated in vacuum. The residue was purified by silica gel chromatography (100-200 mesh silica gel, PE:EA=1:1) to give pure DMTr-302-1 (20 g, 77.7%) as a white solid.

To a solution of DMTr-302-1 (30.00 g, 52.95 mmol) and TBSCl (19.95 g, 132.38 mmol, 2.50 eq.) in DCM (200 mL) was added imidazole (9.00 g, 132.20 mmol, 2.50 eq.) in portions at 0° C. The temperature was maintained below 5° C. The mixture was warmed to 25° C., and stirred for 16 h. TLC (PE:EA=1:1) showed that the starting material was consumed. The reaction was quenched by ice and then extracted with DCM (2×50 mL). The combined organic phase was washed with brine (50 mL), dried over anhydrous Na₂SO₄, filtered and concentrated at low pressure. The residue was purified by chromatography to give the pure product (30.00 g, 83.2%) as a white solid.

The product from the previous step (30.00 g, 44.07 mmol) was dissolved in 80% AcOH aqueous (300 mL), and the mixture was stirred at 25° C. for 16 h. TLC (DCM:MeOH=10:1) showed that the reaction was completed. The reaction was quenched with sat. aq. NaHCO₃ (100 mL) and then extracted with EA (3×100 mL). The organic phase was washed with brine, dried over anhydrous Na₂SO₄ and concentrated under reduced pressure. The residue was purified by a silica gel column (DCM:MeOH=50:1-20:1) to give 302-2 (15.5 g, 92.9%) as a white solid.

To a solution of 302-2 (8.00 g, 21.14 mmol) in MeCN (80 mL) was added IBX (6.51 g, 23.25 mmol, 1.10 eq.) at 25° C. under N₂. The mixture was heated to 81° C. for 1 h. LCMS showed that the starting material was consumed. The mixture was filtered, and the filtrates were concentrated in vacuum. The aldehyde residue (7.50 g, 19.92 mmol) was used in next step without further purification.

To a solution of the aldehyde from the previous step (7.5 g, 19.9 mmol) and aq. formaldehyde (7.85 mL) in dioxane (80 mL) was added 2.0 N aq. NaOH (19.5 mL) in one portion at 25° C. The mixture was stirred at 25° C. for 16 h. TLC showed that the reaction was completed. The mixture was cooled to 0° C. and then neutralized with AcOH to pH=7. The solution were treated with NaBH₄ (4.52 g, 119.52 mmol) at 0° C. The mixture was stirred at 25° C. for 30 mins, and the reaction was quenched with sat. aq. NH₄Cl (100 mL). The mixture was extracted with EA (2×100 mL). The organic phase was dried over anhydrous Na₂SO₄, filtered and concentrated in vacuum. The residue was purified by silica gel chromatography (100-200 mesh silica gel, DCM:MeOH=20:1 to 10:1) to afford 302-3 (4.0 g, 49.2%) as a white solid.

To a solution of 302-3 (4.00 g, 9.79 mmol) in pyridine (20 mL) was added a solution of MMTrCl (3.48 g, 10.28 mmol) in DCM (20 mL) dropwise at 0° C. over a period of 15 mins. The temperature was maintained below 5° C. The mixture was warmed to 25° C. and stirred at 2 5° C. for 16 h. TLC (DCM:MeOH=10:1) showed that the starting material was consumed. The reaction was quenched by MeOH (5 mL) and concentrated in vacuum. The residue was purified by column (DCM:MeOH=50:1) to give a pure intermediate (5.00 g, 71.85%) as a white solid.

To a solution of the above intermediate (5.00 g, 7.03 mmol) and AgNO₃ (2.39 g, 14.06 mmol, 2.00 eq.) in pyridine (40 mL) was added dropwise TBDPSCl (2.90 g, 10.55 mmol) at 0° C. over a period of 10 mins. The mixture was warmed to 25° C. and stirred for 16 h. TLC (PE:EA=1:1) showed that the starting material was consumed. The reaction was quenched by ice and then extracted with EA (3×100 mL). The combined organic phase was washed with sat. brine (2×50 mL), dried over anhydrous Na₂SO₄, filtered and concentrated in vacuum. The residue (5.00 g, crude) was dissolved in 80% aq. AcOH (50 mL), and the mixture was stirred at 25° C. for 2 h. TLC (PE:EA=2:1) showed that the reaction was completed. The reaction was quenched by MeOH (5 mL) and then extracted with DCM (3×100 mL). The organic phase was washed with brine, dried over anhydrous MgSO₄ and concentrated at low pressure. The residue was purified by a silica gel column (PE:EA=5:1 to 2:1) to give 302-4 (2.50 g, 55%) as a yellow solid.

To a solution of 302-4 (400 mg, 618.36 µmol) in DCM (4 mL) was added DMP (393.4 mg, 927.54 µmol, 1.50 eq.) in one portion at 0° C. under N₂. The mixture was stirred at 25° C. for 2 h. TLC (PE:EA=2:1) showed that the reaction was completed. The mixture was cooled to 0° C. and quenched with sat. aq. Na₂SO₃ (5 mL) and aq. NaHCO₃ (5 mL). The aqueous layer was extracted with DCM (3×10 mL). The combined organic phase was washed with sat. brine (10 mL), dried over anhydrous Na₂SO₄, filtered and concentrated in vacuum. The residue was purified by silica gel chromatography (100-200 mesh silica gel, PE:EA=3:1) to afford 302-5 (300.00 mg, 75.24%) as a white solid.

To a solution of 302-5 (500 mg, 775.37 µmol) in pyridine (5 mL) was added hydroxylamine hydrochloride (215.5 mg, 3.10 mmol, 4.00 eq.) in one portion at 0° C. under N₂. The mixture was stirred at 0° C. for 30 mins, and then warmed to 25° C. and stirred for 4 h. LCMS showed that the reaction was completed. The mixture was concentrated in vacuum. The residue was purified by silica gel chromatography (100-200 mesh silica gel, PE:EA=2:1) to afford the oxime (450 mg, 87.95% yield) as a light yellow solid.

To a solution of this oxime (450.00 mg, 681.95 µmol) in DCM (5 mL) was added TEA (208.0 mg, 2.06 mmol) and MsCl (156.0 mg, 1.36 mmol) in one portion at 0° C. The mixture was stirred at 25° C. for 4 h. TLC (PE:EA=2:1) showed that the reaction was completed. The reaction was quenched by sat. aq. NaHCO₃ (5 mL), and the aqueous phases were extracted with DCM (2×20 mL). The combined organic phase was washed with sat. brine (10 mL), dried with anhydrous Na₂SO₄, filtered and concentrated in vacuum. The residue was purified by TLC (PE:EA=2:1) to afford 302-6 (400 mg, 91.4%) as a light yellow solid.

To a solution of 302-6 (450.0 mg, 701.10 μmol), DMAP (171.3 mg, 1.40 mmol) and TEA (212.8 mg, 2.10 mmol) in MeCN (5 mL) was added 2,4,6-triisopropylbenzene-1-sulfonyl chloride (424.7 mg, 1.40 mmol) in one portion at 0° C. The mixture was stirred at 25° C. for 1 h. TLC (PE:EA=2:1) showed that the reaction was completed. The reaction was quenched by sat. aq. NaHCO$_3$ (5 mL) and extracted with EA (2×15 mL). The combined organic phase was washed with sat. brine (10 mL), dried with anhydrous Na$_2$SO$_4$, filtered and concentrated in vacuum. The residue (580.00 mg, 638.59 mol) was dissolved in MeCN (5 mL). The solution was treated with NH$_3$.H$_2$O (10 mL) in one portion at 25° C. The mixture was stirred at 25° C. 16 h. TLC (PE:EA=1:1) showed the reaction was completed. The mixture was extracted with EA (3×10 mL). The combined organic phase was washed with sat. brine (10 mL), dried with anhydrous Na$_2$SO$_4$, filtered and concentrated in vacuum. The residue was purified by silica gel chromatography (100-200 mesh silica gel, DCM:MeOH=40:1 to 25:1) to afford 302-7 (350.00 mg, 85.5%) as a light yellow solid.

To a solution of 302-7 (350.0 mg, 546.13 μmol) in MeOH (10 mL) was added NH$_4$F (405 mg, 10.9 mmol) in one portion at 25° C. The mixture was heated to 65° C. and stirred for 2 h. TLC (EA:MeOH=8:1) showed that the reaction was completed. The mixture was cooled to 25° C. and concentrated under reduced pressure at 40° C. The residue was purified by silica gel chromatography (100-200 mesh silica gel, EA:MeOH=20:1 to 10:1) to afford 302 as a white solid. $^1$H NMR (400 MHz, DMSO-d$_6$), δ=7.59 (d, J=7.28 Hz, 1H), 7.49 (br. s., 2H), 7.25 (br. s., 1H), 6.29 (br. s., 1H), 6.01 (br. s., 1H), 5.82 (d, J=7.53 Hz, 1H), 4.60 (br. s., 1H), 3.88 (br. s., 2H); $^{19}$F NMR (376 MHz, DMSO-d$_6$) d ppm −116.61 (br. s., 1F) −115.98 (br. s., 1F).

Example 176

Compound 303

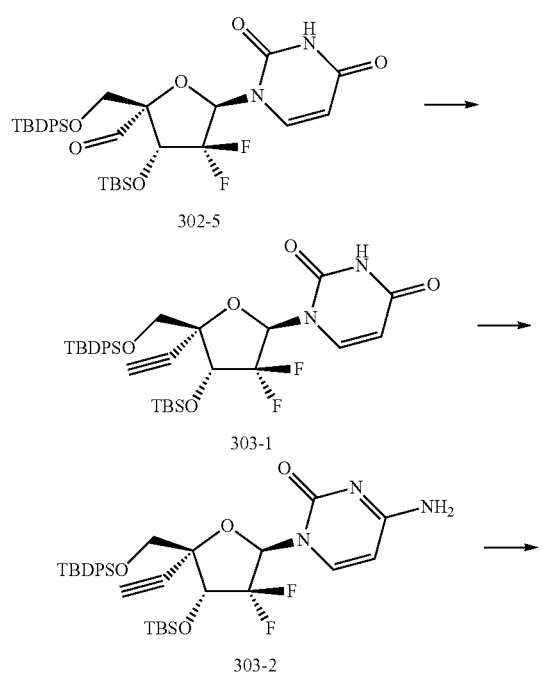

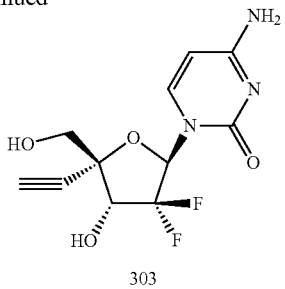

To a solution of K$_2$CO$_3$ (967.5 mg, 7.0 mmol) and TsN$_3$ (552.2 mg, 2.80 mmol) in MeCN (10 mL) was added 1-dimethoxyphosphorylpropan-2-one (465.1 mg, 2.80 mmol) in one portion at 25° C. under N$_2$. The mixture was stirred at 25° C. for 2H. A solution of 302-5 (900.0 mg, 1.40 mmol, 1.00 eq.) in MeOH (10 mL) was added in one portion at 25° C. under N$_2$. The mixture was stirred at 25° C. for 12 h. TLC (PE:EA=2:1) showed that the reaction was completed. The mixture was poured into water (10 mL) and extracted with EA (2×50 mL). The combined organic phase was washed with saturated brine (10 mL), dried with anhydrous Na$_2$SO$_4$, filtered and concentrated in vacuum. The residue was purified by silica gel chromatography (100-200 mesh silica gel, PE:EA=5:1 to 2:1) to afford 303-1 (800 mg, 98.2%) as an off-white solid.

To a solution of 303-1 (500 mg, 780.20 μmol), DMAP (190.6 mg, 1.56 mmol) and TEA (236.9 mg, 2.34 mmol) in MeCN (5 mL), was added 2,4,6-triisopropylbenzene-1-sulfonyl chloride (472.8 mg, 1.56 mmol) in one portion at 0° C. under N$_2$. The mixture was stirred at 0° C. for 30 mins, then warmed to 25° C. and stirred for 2 h. TLC (PE:EA=2:1) showed that the reaction was completed. The reaction was quenched by water (5 mL) and extracted with EA (2×10 mL). The combined organic phase was washed with aq. HCl (1 mL, 0.5 M), dried with anhydrous Na$_2$SO$_4$, filtered and concentrated in vacuum. The residue (650.0 mg, 91.83%) was obtained as a light yellow gum, which was used in next step without further purification.

To a solution of the residue from the previous step (650 mg, 716.4 mol) in MeCN (5 mL) was added NH$_3$.H$_2$O (5 mL) in one portion at 25° C., and the mixture was stirred at 25° C. for 16 h. TLC (DCM:MeOH=20:1) showed that the reaction was completed. The mixture was extracted with EA (2×20 mL). The combined organic phase was washed with brine (10 mL), dried with anhydrous Na$_2$SO$_4$, filtered and concentrated in vacuum. The residue was purified by silica gel chromatography (100-200 mesh silica gel, PE:EA=1:1) to afford 303-2 (350 mg, 76.35%) as an off-white solid.

A mixture of 303-2 (350.0 mg, 546.98 μmol) and NH$_4$F (405.0 mg, 10.93 mmol) in MeOH (5 mL) was heated to 65° C. and stirred for 2 h. LCMS and TLC (EA:MeOH=10:1) showed that the reaction was completed. The mixture was cooled to 25° C. and filtered, and the filtrate was concentrated in vacuum. The residue was purified by silica gel chromatography (300-400 mesh silica gel, EA:MeOH=20:1 to 10:1) to afford 303 (102 mg, 64.93%) as a white solid. $^1$H-NMR (400 MHz, METHANOL-d$_4$), δ=7.73 (d, J=7.28 Hz, 1H), 6.31-6.42 (m, 1H), 5.95 (d, J=7.53 Hz, 1H), 4.47 (t, J=13.55 Hz, 1H), 3.92 (d, J=12.55 Hz, 1H), 3.73-3.80 (m, 1H) 3.25 (s, 1H); $^{19}$F NMR (376 MHz, METHANOL-d$_4$), δ=−115.52−−112.60 (m, 1F).

Example 177
Compound 304
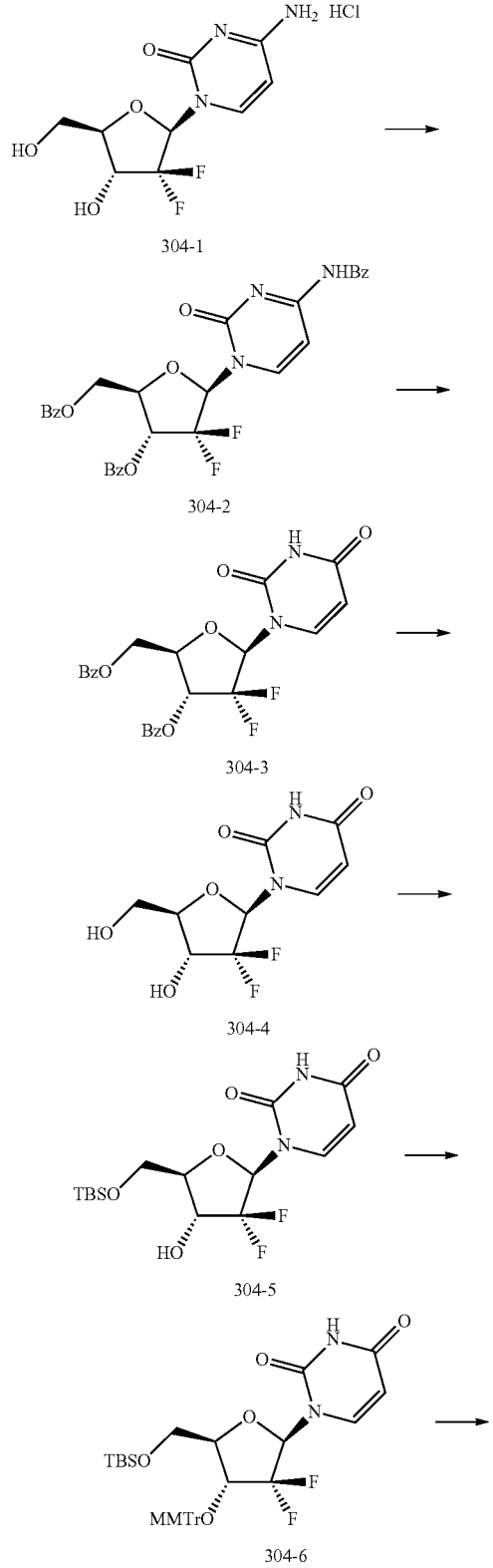
304-1
304-2
304-3
304-4
304-5
304-6
-continued
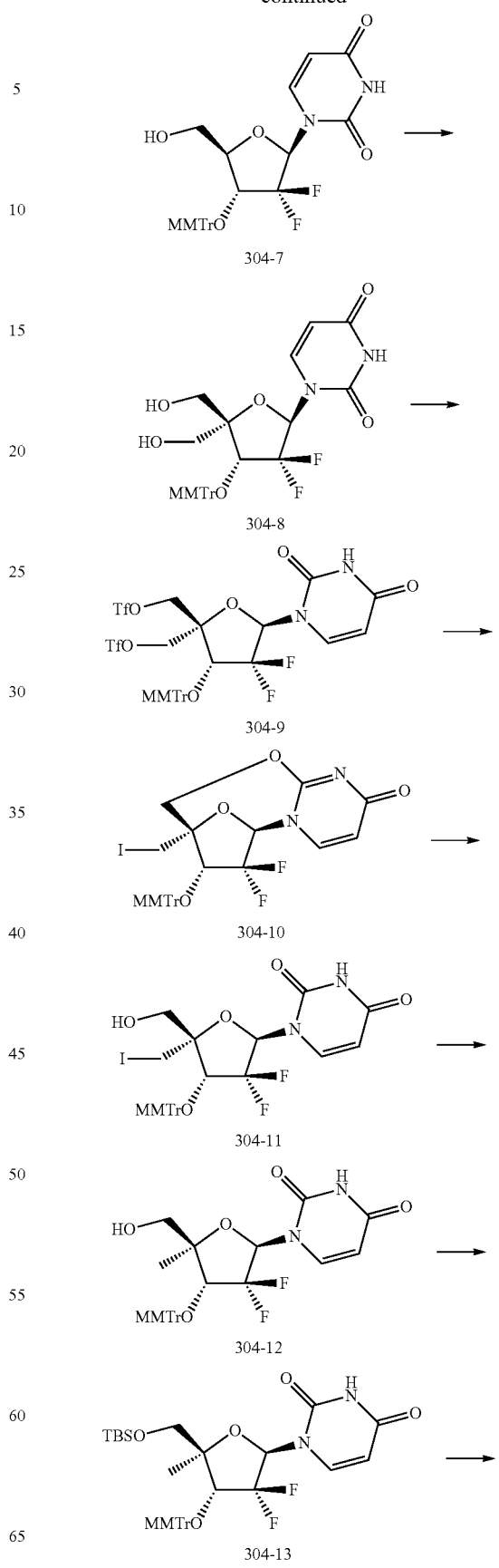
304-7
304-8
304-9
304-10
304-11
304-12
304-13

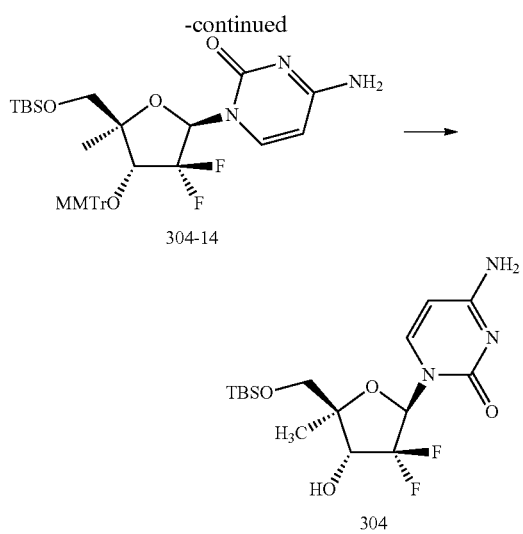

304-14

304

To a solution of 304-1 (20 g, 66.8 mmol) in anhydrous pyridine (180 mL) was added BzCl (30.9 g, 220.3 mmol) at 0° C. under $N_2$. The mixture was stirred at 25° C. for 12 h. The mixture was diluted with EA and washed with sat. aq. $NaHCO_3$. The organic layer was dried over anhydrous $Na_2SO_4$ and filtered, and the filtrate was concentrated to dryness. The residue was purified by silica gel column chromatography (30% EA in PE) to give 304-2 (34.6 g, 90%) as a white solid.

304-2 (33 g, 57.3 mmol) was dissolved in 90% $CH_3COOH$ (360 mL) and heated to 115° C. The mixture was stirred at 115° C. for 12 h. The solvent was removed, and the residue was diluted with EA. The mixture was washed with sat. aq. $NaHCO_3$ and brine. The organic layer was dried over anhydrous $Na_2SO_4$ and filtered. The filtrate was concentrated to give 304-3 (26 g, crude) as a white solid.

304-3 (21 g, 44.5 mmol) was dissolved in a solution (400 mL, 10M) of $NH_3$ in MeOH. The mixture was stirred at 25° C. for 12 h. The mixture was concentrated to give a residue, which was purified by silica gel column chromatography (5% MeOH in DCM) to give 304-4 (9.4 g, 80.4%) as a white solid. $^1$H-NMR ($CD_3OD$, 400 MHz) δ=7.90-7.80 (m, 1H), 6.18-6.09 (m, 1H), 5.71 (d, J=8.2 Hz, 1H), 4.26 (dt, J=8.2, 12.0 Hz, 1H), 3.98-3.84 (m, 2H), 3.76 (dd, J=2.8, 12.5 Hz, 1H), 3.33 (s, 1H).

To a solution of 304-4 (9 g, 34.1 mmol) in anhydrous pyridine (60 mL) was added TBSCl (7.7 g, 51.1 mmol) at 25° C. under $N_2$. The solution was stirred at 50° C. for 12 h. The mixture was concentrated to dryness under reduced pressure. The residue was dissolved in EA. The mixture was washed with sat. aq. $NaHCO_3$ and brine. The organic layer was dried over $MgSO_4$ and concentrated to dryness under reduced pressure. The residue was purified on a silica gel column (20% EA in PE) to give 304-5 (11 g, 85.5%) as a white solid.

To a solution of 304-5 (10.2 g, 27 mmol) in $CH_2Cl_2$ (100 mL) was added $AgNO_3$ (9.2 g, 53.9 mmol), collidine (13.1 g, 107.8 mmol) and MMTrCl (10 g, 32.3 mmol) at 25° C. under $N_2$. The solution was stirred at 25° C. for 12 h. The reaction was quenched with MeOH, and the mixture was filtrated on celite. The filtrate was diluted with $CH_2Cl_2$ and $H_2O$. The organic layer was separated, and the aqueous phase was extracted with $CH_2Cl_2$. The combine organic layer was washed with brine, dried over anhydrous $MgSO_4$ and filtered. The filtrate was concentrated to dryness under reduced pressure. The residue was purified by silica gel chromatography (25% EA in PE) to give 304-6 (15 g, 85.6%) as a white solid.

304-6 (10.5 g, 16.1 mmol) was dissolved in a solution of TBAF in THF (1M, 60 mL) at 25° C. The mixture was stirred at 25° C. for 4 h. The mixture was extracted with EA, and the combined layer was washed with water and brine. The organic layer was dried over $Na_2SO_4$ and filtered. The filtrate was concentrated to give the crude product, which was purified by silica gel column chromatography (30% EA in PE) to give 304-7 (8.1 g, 93.6%) as a white foam.

To a solution of 304-7 (17.0 g, 31.7 mmol) in $CH_3CN$ (150 mL) was added IBX (9.7 g, 34.9 mmol) at 25° C. The mixture was heated to 100° C., and the mixture was stirred at 100° C. for 1 h. The mixture was cooled to 25° C. The mixture was filtered, and the filter cake was washed with MeCN. The filtrate was concentrated under reduce pressure to give a residue (16 g, crude) as a yellow solid. The residue (16 g, crude) was dissolved in 1,4-dioxane (150 mL), and the solution was treated with 37% aq. formaldehyde (18.5 g, 227.5 mmol) and aq. NaOH (2 M, 30 mL) at 25° C. The mixture was stirred at 25° C. for 12 h. EtOH (30 mL) and $NaBH_4$ (10 g, 265.7 mmol) were added at 0° C. After stirring for 1 h at 25° C., the reaction was quenched with sat. aq. $NH_4Cl$ at 0° C. The mixture was diluted with EA. The organic phase was separated, and the aqueous phase was extracted with EA. The combined organic phase was washed with brine and dried over anhydrous $Na_2SO_4$. The organic layer was concentrated in vacuum to give a residue, which was purified by silica gel chromatography (2% MeOH in DCM) to afford 304-8 (8.1 g, 53.1%) as a white solid. $^1$H-NMR (400 MHz, DMSO-$d_6$) δ=11.52 (s, 1H), 7.57 (d, J=8.2 Hz, 1H), 7.46-7.22 (m, 13H), 6.90 (d, J=8.8 Hz, 2H), 6.30 (t, J=8.0 Hz, 1H), 5.61 (d, J=8.2 Hz, 1H), 5.06 (t, J=5.5 Hz, 1H), 4.92-4.86 (m, 1H), 4.61-4.51 (m, 1H), 3.83 (dd, J=5.1, 12.1 Hz, 1H), 3.74 (s, 3H).

To an ice cooled solution of 304-8 (2.5 g, 4.4 mmol) in anhydrous $CH_2Cl_2$ (35 mL) was added pyridine (3.5 g, 44.1 mmol) and $Tf_2O$ (3.7 g, 13.2 mmol) dropwise. The mixture was stirred at 0° C. for 40 mins. The reaction was quenched with ice water and stirred for 10 mins. The mixture was extracted with $CH_2Cl_2$. The organic layer was washed with brine and dried over $MgSO_4$. The organic layer was concentrated to give a residue, which was purified on the silica gel column (15% EA in PE) to give 304-9 (2.6 g, 71%) as a yellow foam.

To a stirred solution of 304-9 (1.8 g, 2.2 mmol) in anhydrous DMF (25 mL) was added NaH (107 mg, 2.7 mmol) at 0° C. under $N_2$. The solution was stirred at 25° C. for 1 h. TLC (PE:EA=1:1) showed the reaction was complete. To the solution was added NaI (3.1 g, 20.6 mmol) at 25° C. The mixture was stirred at 25° C. for 3 h. TLC (PE:EA=1:1) showed the reaction was complete. The mixture was diluted with water and extracted with EA. The organic layer was dried over anhydrous $Na_2SO_4$ and filtered. The filtrate was concentrated at low pressure to give 304-10 (1.4 g, crude) as a yellow solid.

304-10 (1.4 g, crude) was dissolved in 1,4-dioxane (25 mL), and the mixture was treated with aq. NaOH (2 M, 2.7 mL) at 0° C. The solution was stirred for 4 h at 25° C. The reaction was quenched with sat. aq. $NH_4Cl$ and extracted with EA. The organic layer was washed with brine. The organic layer was dried over anhydrous $Na_2SO_4$ and filtered. The filtrate was concentrated to give the crude product, which was purified by silica gel column chromatography (40% EA in PE) to give 304-11 (1.4 g, 94.9%).

To a solution of 304-11 (1.45 g, 2.1 mmol) in EtOH (10 mL) was added Et₃N (434 mg, 4.3 mmol) and Pd/C (101 mg, 88.7 μmol). The mixture was stirred under H₂ (15 psi) for 12 h at 25° C. The suspension was filtered, and the filtrate was concentrated at low pressure. The residue was purified on silica gel column (1% MeOH in DCM) to give 304-12 (1.2 g, 97.6%) as a yellow solid.

To a solution of 304-12 (930 mg, 1.7 mmol) in anhydrous DMF (10 mL) was added imidazole (287 mg, 4.2 mmol) and TBSCl (636 mg, 4.2 mmol) at 25° C. under N₂. The solution was stirred at 25° C. for 5 h. The mixture was concentrated to dryness under reduced pressure, and the residue was dissolved in EA. The mixture was washed with sat. aq. NH₄Cl and brine. The organic layer was dried over MgSO₄ and filtered. The filtrate was concentrated to dryness under reduced pressure. The residue was purified on silica gel column (15% EA in PE) to give 304-13 (968 mg, 86.2%) as a white solid.

To a stirred solution of 304-13 (568 mg, 854.4 μmol) in anhydrous CH₃CN (8 mL) was added DMAP (209 mg, 1.7 mmol), TPSCl (504 mg, 1.7 mmol) and TEA (173 mg, 1.7 mmol) at 25° C. The mixture was stirred at 25° C. for 12 h. NH₃·H₂O (10 mL) was added, and the mixture was stirred for 3 h. The mixture was extracted with EA and washed with sat. aq. NH₄Cl and brine. The organic layer was dried over Na₂SO₄ and filtered. The filtrate was concentrated to give a residue, which was purified on a silica gel column (3% MeOH in DCM) to give 304-14 (480 mg, 84.6%) as a yellow foam. $^1$H-NMR (400 MHz, CDCl₃) δ=7.65-7.40 (m, 13H), 6.97 (d, J=8.8 Hz, 2H), 6.44 (dd, J=6.4, 9.5 Hz, 1H), 5.71 (d, J=7.3 Hz, 1H), 4.76 (dd, J=9.0, 14.4 Hz, 1H), 4.29 (q, J=7.1 Hz, 1H), 3.92-3.92 (m, 1H), 3.95 (s, 3H), 3.60 (d, J=11.2 Hz, 1H), 3.44 (d, J=11.0 Hz, 1H), 1.66-1.55 (m, 3H), 0.95 (s, 9H), 0.08 (s, 3H), 0.00 (s, 3H).

304-14 (501 mg, 753.2 μmol) was dissolved in 80% HCOOH (20 mL), and the mixture was stirred at 25° C. for 4 h. The solvent was removed at low pressure, and the residue was purified on a silica gel column (6% MeOH in DCM) to give 304 (151 mg, 71.8%) as a white solid. ESI-MS:m/z 278.11 [M+H]⁺, 555.18 [2M+H]⁺.

Example 178

Compound 307

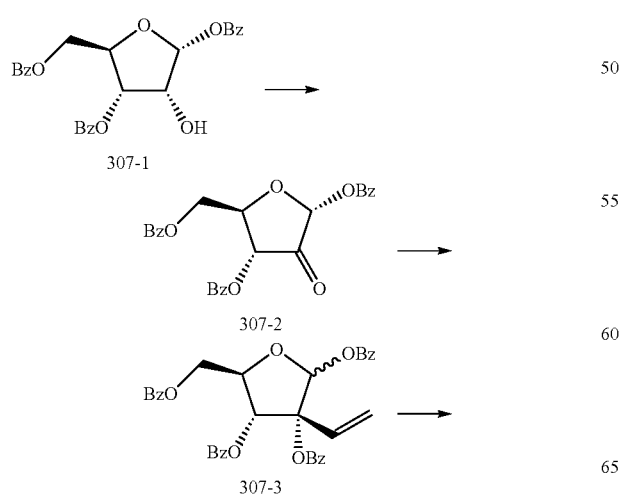

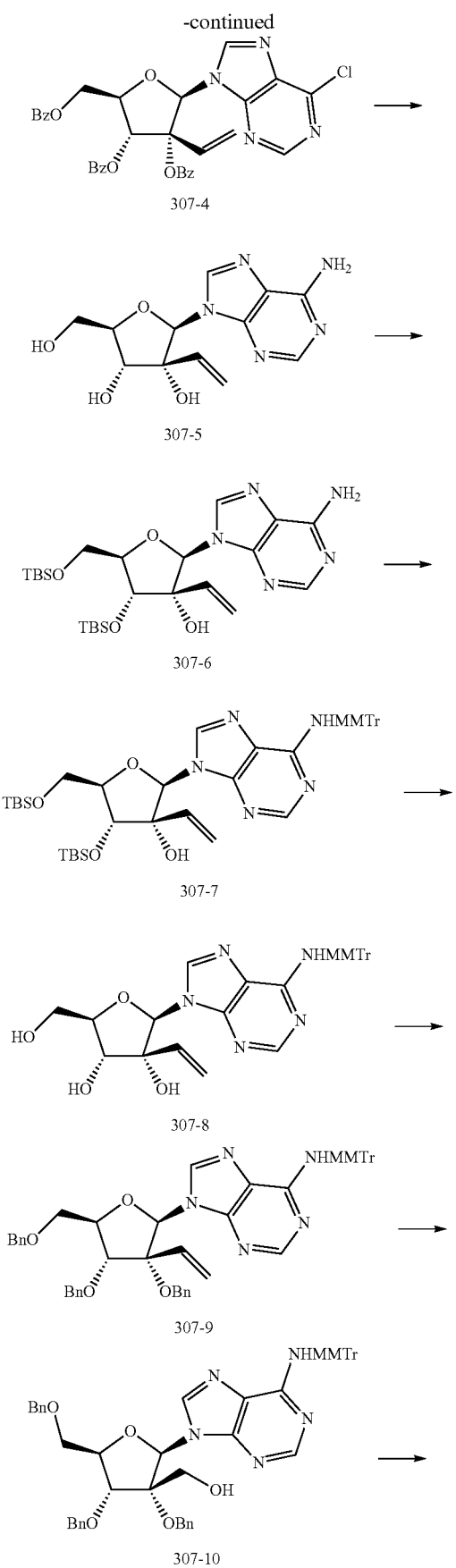

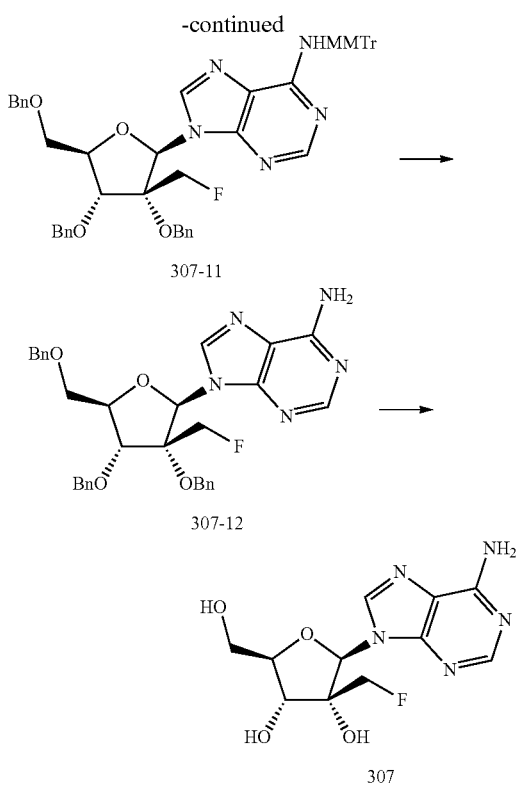

To a solution of 307-1 (120 g, 0.26 mol) in anhydrous MeCN (2 L) was added IBX (109 g, 0.39 mol). The mixture was heated to reflux and stirred for 18 h. The mixture was cooled to 0° C. and filtered. The filtrate was concentrated under vacuum to give 307-2 (142 g) as a brown oil, which was used without purification for the next step.

To a solution of 307-2 (142 g) in anhydrous THF (1.5 L) was added vinylmagnesium bromide (830 mL, 0.83 mol, 1 N) dropwise at −78° C., and the mixture was stirred at −78° C. for 2 h. The reaction was quenched by sat. aq. NH$_4$Cl (2 L) at 0° C. THF was removed under vacuum, and the residue was diluted with EtOAc. The solution was washed with brine, dried over anhydrous Na$_2$SO$_4$, filtered and concentrated to give a light brown oil.

To the light brown oil in anhydrous DCM (2.5 L) was added DMAP (63.5 g, 0.52 mol), Et$_3$N (79 g, 0.78 mol) and BzCl (110 g, 0.78 mol) at 0° C., and the mixture stirred overnight at RT. The mixture was diluted with DCM (2 L) and washed with sat. aq. NaHCO$_3$ (3 L) and brine (1.5 L). The organic phase was dried over anhydrous Na$_2$SO$_4$, filtered and evaporated to dryness under reduced pressure. The residue was purified by silica gel column (PE:EA=20: 1~10:1) to give 307-3 (112.7 g, 72.3%) as a yellow oil.

A stirring mixture of uracil (36.25 g, 323.7 mmol) and N,O-bis(trimethylsilyl) acetamide (131.69 g, 647.4 mmol) in anhydrous MeCN (180 mL) was heated to reflux for 2 h, then cooled to RT. A solution of 307-3 (95.9 g, 161.85 mmol) in anhydrous MeCN (500 mL) was added, followed by treatment with SnCl$_4$ (168.66 g, 647.4 mmol) dropwise at 0° C. The mixture was heated to reflux and stirred for 2 h. The reaction was quenched with sat. aq. NaHCO$_3$ (3 L), and extracted with EtOAc (3×1 L). The organic phase was washed with brine (500 mL), dried over anhydrous Na$_2$SO$_4$, filtered and evaporated to dryness under reduced pressure. The residue was purified by a silica gel column (PE:EA=20: 1~10:1) to give 307-4 (33 g, 35%) as a light yellow oil.

307-4 (33 g, 56.65 mmol) was dissolved in NH$_3$:MeOH (800 mL, 7 N), and the mixture was stirred at RT overnight. The solvent was removed under reduced pressure, and the residue was purified by a column (1% MeOH in DCM) to give 307-5 (12.6 g, 82.4%) as a light yellow foam.

To a solution of 307-5 (2.57 g, 8.76 mmol) in DMF (20 mL) was added AgNO$_3$ (8.93 g, 52.56 mmol) and imidazole (3.58 g, 52.56 mmol), then TBSCl (5.28 g, 35.04 mmol) was added in one portion at 0° C. under N$_2$. The mixture was stirred at 25° C. for 12 h. TLC showed that the reaction was completed. The residue was poured into ice:water (w:w=1: 1) (30 mL). The aqueous phase was extracted with EA (3×100 mL). The combined organic phase was washed with sat. brine (3×20 mL), dried with anhydrous Na$_2$SO$_4$, filtered and concentrated in vacuum. The residue was purified by silica gel chromatography (column height: 250 mm, diameter: 100 mm, 100-200 mesh silica gel, PE:EA=3:1 to 2:1) to afford 307-6 (3.68 g, 80.51%) as a yellow solid.

To a solution of 307-6 (3.48 g, 6.67 mmol) and AgNO$_3$ (3.40 g, 20.01 mmol) in pyridine (30 mL) was added (chloro(4-methoxyphenyl)methylene)dibenzene (4.12 g, 13.34 mmol) in one portion at 25° C. under N$_2$. The mixture was stirred at 25° C. for 16 h. TLC showed that the reaction was completed. The mixture was diluted with EA and filtered. The filtrate was washed with brine and separated. The organic layer was concentrated to dryness. The residue was purified by silica gel chromatography (column height: 250 mm, diameter: 100 mm, 100-200 mesh silica gel, PE:EA=10:1 to 5:1) to afford 307-7 (4.40 g, 83.07%) as a yellow foam.

To a solution of 307-7 (4.30 g, 5.41 mmol) in MeOH (100 mL) was added NH$_4$F (801.55 mg, 21.64 mmol) in one portion at 25° C. The mixture was heated to 68° C. and stirred for 4 h. LCMS trace showed that the reaction was completed. The mixture was cooled to 25° C. and concentrated under reduced pressure. The residue was purified by silica gel chromatography (column height: 250 mm, diameter: 100 mm, 100-200 mesh silica gel, DCM:MeOH: NH$_3$.H$_2$O=30:1:0.05 to 10:1:0.05) to afford 307-8 (3.00 g, 98.04%) as a white solid.

To a solution of 307-8 (3.00 g, 5.30 mmol) in DMF (30 mL) was added NaH (848 mg, 21.20 mmol) in one portion at 0° C. under N$_2$. The mixture was stirred at 0° C. for 30 mins. BnBr (3.63 g, 21.20 mmol) was added at 0° C., and the mixture was stirred for 16 h at 25° C. TLC showed that the reaction was completed. The mixture was poured into ice-water (w:w=1:1) (30 mL). The aqueous phase was extracted with EA (3×50 mL). The combined organic phase was washed with sat. brine (3×20 mL), dried with anhydrous Na$_2$SO$_4$, filtered and concentrated in vacuum. The residue was purified by silica gel chromatography (column height: 250 mm, diameter: 100 mm, 200-300 mesh silica gel, PE:EA=20:1 to 10:1) to afford 307-9 (670 mg, 15.1%).

Ozone was bubbled into a solution of 307-9 (500 mg, 598.10 μmol) in DCM (8 mL) and MeOH (8 mL) at −78° C. for 20 mins. After excess O$_3$ was purged by O$_2$, NaBH$_4$ (113.13 mg, 2.99 mmol) was added at 0° C. The mixture was stirred at 25° C. for 20 mins. TLC showed that the starting material was consumed. The mixture was concentrated to give the crude product, which was purified by silica gel chromatography (PE:EA=5:1) to give 307-10 (167.00 mg, 33.24%) as a yellow solid.

To a solution of 307-10 (216.70 mg, 257.99 μmol) and DMAP (63.04 mg, 515.98 μmol) in DCM (2 mL) was added MsCl (44.33 mg, 386.98 μmol) in one portion at 0° C. under N$_2$. The mixture was stirred at 0° C. for 1 h and then warmed to 25° C. and stirred for 1 h. LCMS showed that the reaction was completed. The residue was poured into ice-water (w:w=1:1) (10 mL), and extracted with EA (3×20 mL). The combined organic phase was washed with sat. brine (3×10 mL), dried with anhydrous Na₂SO₄, filtered and concentrated in vacuum. The residue was purified by silica gel chromatography (column height: 250 mm, diameter: 100 mm, 100-200 mesh silica gel, PE:EA=10:1 to 5:1) to afford a mesylate intermediate (167.00 mg, 70.51%) as a yellow foam.

The mesylated intermediate (167 mg) was dissolved in TBAF:THF (10 mL, 1N) and the mixture was heated to reflux for 12 h. The mixture was slowly cooled to 25° C., and quenched with sat. NH₄Cl solution. The solution was extracted with EA. The combined organic layers were washed with brine, dried over anhydrous Na₂SO₄ and concentrated to dryness. The residue was purified by column chromatography (EA:PE=5:1-2:1) to give 307-11 (80 mg, 43.8%).

307-11 (80.00 mg, 0.087 mmol) was dissolved in 80% AcOH (5 mL) solution, and stirred at 45° C. for 1.0 h. The reaction was quenched with sat. Na₂HCO₃ solution and extracted with EA (3×10 mL). The combined organic layers were washed with brine, dried over anhydrous Na₂SO₄ and concentrated to dryness. The residue was purified by column chromatography to give 307-12 (38 mg, 60%) as a white foam solid. ESI-MS:m/z 570.4 [M+H]⁺.

To a solution of 307-12 (113.8 mg, 0.2 mmol) in DCM (0.5 mL) was added BCl₃/DCM (1.0 N) (1 mL) at −78° C., and the mixture was stirred at −78° C. for 30 mins. The reaction was quenched with MeOH and concentrated to dryness at low pressure. The residue was purified by prep-HPLC with NH₃.H₂O buffer to give 307 (26 mg, 44%) as a white solid.

Example 179

Compound 311

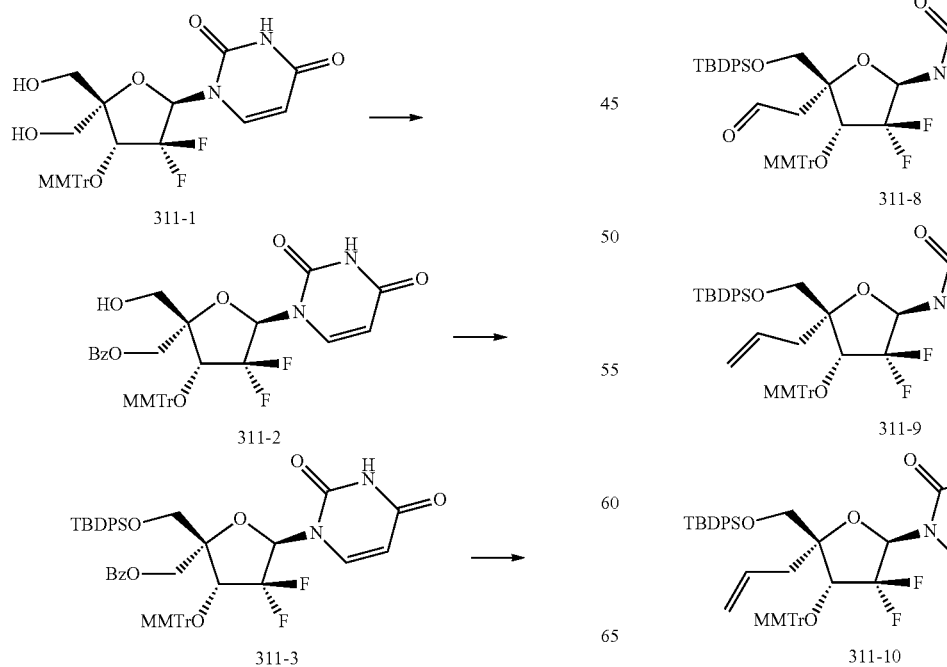
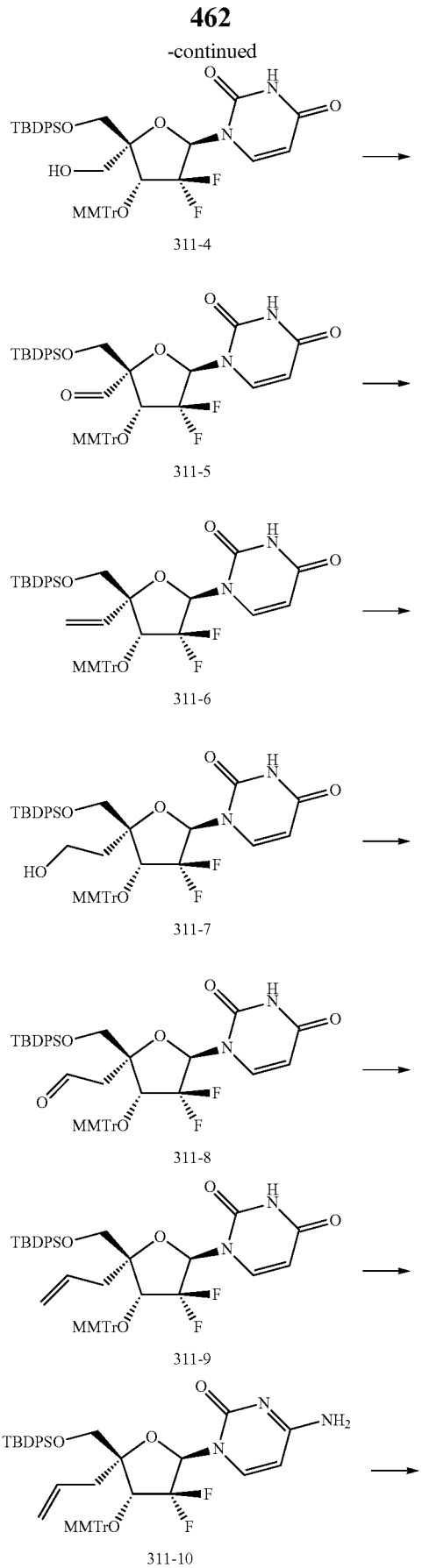

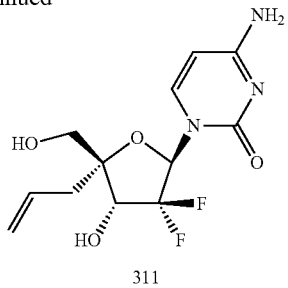

311

To a mixture of 311-1 (2.00 g, 3.5 mmol) in pyridine (10 mL) and DCM (10 mL) was added BzCl (496 mg, 3.5 mmol) dropwise at 0° C. under $N_2$. The mixture was stirred at 0° C. for 30 mins, and then stirred at 25° C. for 6.5 h. The reaction was quenched with sat. aq. NaHCO$_3$ (80 mL). The mixture was extracted with EA (2×100 mL). The organic phase was washed with brine (80 mL), dried over anhydrous Na$_2$SO$_4$ and filtered. The filtrate was concentrated under reduced pressure. The residue was purified by silica gel chromatography (30% EA in PE) to afford 311-2 (1.28 g, 54%) as a white solid.

To a mixture of 311-2 (680 mg, 1.0 mmol) in DMF (5 mL) was added imidazole (412 mg, 6.1 mmol), AgNO$_3$ (514 mg, 3.0 mmol) and TBDPSCl (832 mg, 3.0 mmol) at 25° C. under N$_2$. The mixture was stirred at 25° C. for 12 h. The reaction was quenched with sat. aq. NaHCO$_3$ (30 mL), and then extracted with EA (2×30 mL). The combined organic phase was washed with brine (2×20 mL), dried over anhydrous Na$_2$SO$_4$, filtered and concentrated under reduced pressure. The residue was purified by silica gel chromatography (25% EA in PE) to afford 311-3 (750 mg, 82%) as a white solid.

311-3 (660 mg, 0.7 mmol) was dissolved in NH$_3$:MeOH (15 mL). The mixture was stirred at 25° C. for 36 h in sealed tube, and then concentrated under reduced pressure. The residue was purified by silica gel chromatography (30% EA in PE) to afford 311-4 (430 mg, 73%) as a white solid. $^1$H-NMR (CDCl$_3$, 400 MHz) δ=9.05 (s, 1H), 7.81-7.10 (m, 21H), 6.81 (d, J=9.2 Hz, 2H), 6.42 (m, 1H), 6.20 (m, 1H), 4.13-4.07 (m, 2H), 3.78-3.60 (m, 5H), 2.55 (s, 1H), 0.90-0.74 (m, 9H).

To a mixture of 311-4 (280 mg, 0.3 mmol) in DCM (3.5 mL) was added Dess-Martin (295 mg, 0.7 mmol) in one portion at 0° C. under N$_2$. The mixture was stirred at 25° C. for 3.5 h. The reaction was quenched with sat. aq. NaHCO$_3$ and sat. aq. Na$_2$S$_2$O$_3$. (v:v=1:1, 30 mL). The mixture was extracted with EA (2×20 mL). The combined organic phase was washed with brine (30 mL), dried over anhydrous Na$_2$SO$_4$ and filtered. The filtrate was concentrated in vacuum to afford 311-5 (260 mg, crude) as a yellow solid, which was used in the next step without further purification.

To a stirred solution of Methyl-triphenyl-phosphonium bromide (359 mg, 1.0 mmol) in anhydrous THF (1 mL) was added KOBu-t (1 mL, 1.0 mmol, 1 M in THF) dropwise at 0° C. The mixture was stirred at 25° C. for 1 h. A solution of 311-5 (260 mg, 0.3 mmol) in anhydrous THF (1 mL) was added at 0° C. The mixture was stirred at 25° C. for 16 h. The reaction was quenched with sat. aq. NH$_4$Cl (20 mL) and extracted with EA (30 mL). The organic layer was washed with brine (20 mL), dried over MgSO$_4$, filtered and evaporated to give a light white solid, which was purified by column chromatography (10% EA in PE) to give 311-6 (131 mg, 50%) as a yellow solid. $^1$H-NMR (CDCl$_3$, 400 MHz) δ=8.40 (s, 1H), 7.55-7.21 (m, 21H), 7.10 (dd, J=1.8, 8.2 Hz, 1H), 6.84 (d, J=8.8 Hz, 2H), 6.37 (dd, J=11.0, 17.4 Hz, 1H), 6.09 (dd, J=7.2, 8.9 Hz, 1H), 5.59-5.43 (m, 2H), 5.10-4.92 (m, 2H), 3.85-3.78 (s, 3H), 3.78-3.73 (m, 1H), 3.56 (d, J=11.5 Hz, 1H), 0.99-0.77 (s, 9H).

To a solution of 311-6 (1.50 g, 1.9 mmol) in THF (5 mL) was added 9-BBN (0.5 M, 22.5 mL) at 27° C. under N$_2$. The mixture was heated to 70° C. by microwave and stirred for 0.5 h. Sat. aq. NaHCO$_3$ (15 mL) and H$_2$O$_2$ (7.5 mL) were added at 0° C. The mixture was stirred vigorously at 27° C. for 1.5 h. The reaction was quenched with sat. aq. Na$_2$S$_2$O$_3$ (60 mL). The mixture was extracted with EA (2×50 mL). The organic layer was washed with brine (80 mL), dried over MgSO$_4$, filtered and evaporated to dryness. The residue was purified by silica gel chromatography (30% EA in PE) to afford 311-7 (930 mg, 61%) as a white solid.

To a solution of 311-7 (1.24 g, 1.5 mmol) in DCM (15 mL) was added Dess-Martin (1.28 g, 3.0 mmol) in one portion at 0° C. under N$_2$. The mixture was stirred at 27° C. for 2 h. The reaction was quenched with sat. aq. NaHCO$_3$ and sat. aq. Na$_2$S$_2$O$_3$ (v:v=1:1, 60 mL). The mixture was extracted with EA (2×50 mL). The combined organic phase was washed with brine (80 mL), dried over anhydrous Na$_2$SO$_4$ and filtered. The filtrate was concentrated in vacuum to afford 311-8 (1.21 g, crude) as a yellow solid.

To a stirred solution of Methyl-triphenyl-phosphonium bromide (1.64 g, 4.6 mmol) in anhydrous THF (5.5 mL) was added t-BuOK (1 M, 4.4 mL) at 0° C. dropwise. The mixture was stirred at 27° C. for 1 h. A solution of 311-8 (1.21 g crude, 1.5 mmol) in THF (5 mL) was added at 0° C. The mixture was stirred at 27° C. for 12 h. The reaction was quenched with sat. aq. NH$_4$Cl (70 mL), extracted with EA (2×50 mL). The organic layer was washed with brine (80 mL), dried over MgSO$_4$, filtered and evaporated to dryness to give a light yellow solid, which was purified by column chromatography (15 EA in PE) to give 311-9 (970 mg, 80%) as a white solid.

To a solution of 311-9 (970 mg, 1.2 mmol) in CH$_3$CN (10 mL) was added TPSCl (877 mg, 3.0 mmol), DMAP (363 mg, 3.0 mmol) and TEA (301 mg, 3.0 mmol) at 27° C. under N$_2$. The mixture was stirred at 27° C. for 1.5 h. NH$_3$.H$_2$O (5 mL) was added, and the reaction mixture was stirred at 27° C. for 2 h. The reaction was quenched with sat. aq. NH$_4$Cl (60 mL), and then extracted with EA (2×40 mL). The combined organic phase was washed with brine (60 mL), dried over anhydrous Na$_2$SO$_4$, filtered and concentrated in vacuum. The residue was purified by silica gel chromatography (2% MeOH in DCM) to afford 311-10 (810 mg, 83%) as a white solid.

To a solution of 311-10 (500 mg, 0.6 mmol) in MeOH (15 mL) was added NH$_4$F (455 mg, 12.3 mmol) at 27° C. under N$_2$. The mixture was stirred at 70° C. for 12 h. The mixture was then cooled to RT and filtered. The filtrate was concentrated under reduced pressure. The residue was purified by silica gel chromatography (5% MeOH in DCM) to afford crude 311 (120 mg, crude). The crude was purified by prep-HPLC (neutral condition) to give 311 (86 mg, 45%) as a white solid. MS:m/z=304 [M+H]$^+$.

Example 180
Compound 312
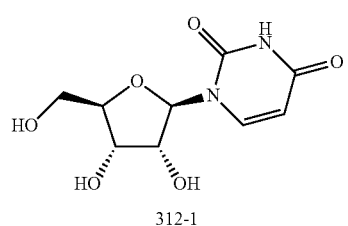
312-1
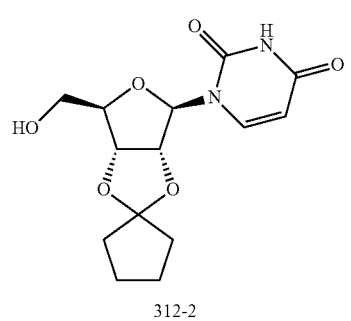
312-2
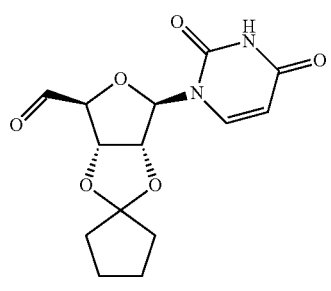
312-3
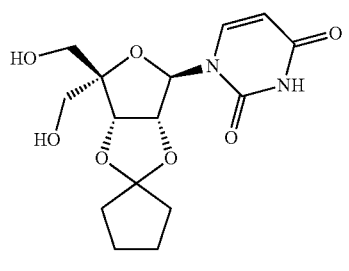
312-4
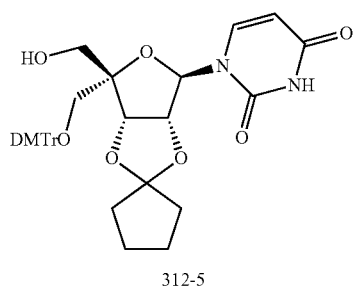
312-5
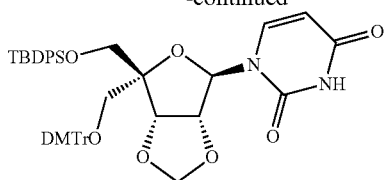
312-6
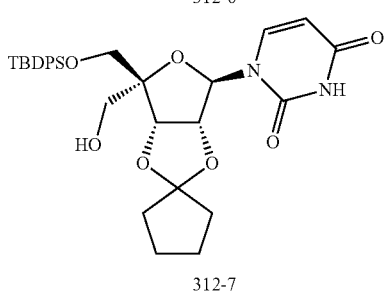
312-7
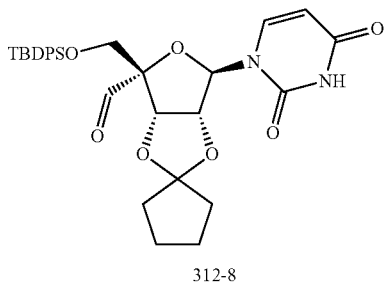
312-8
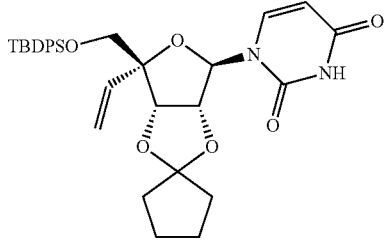
312-9
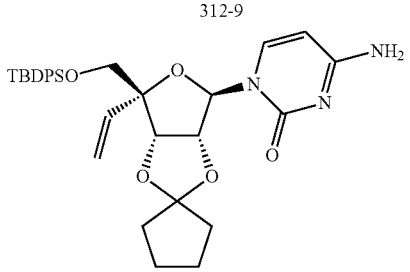
312-10
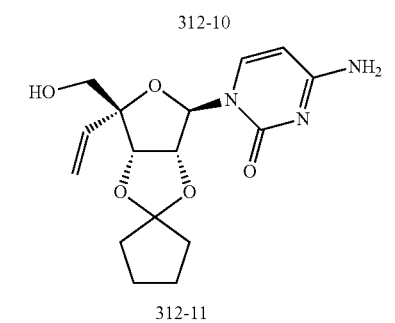
312-11

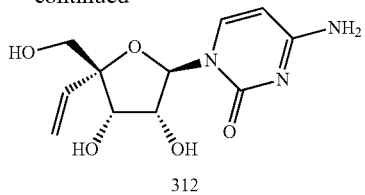

312

To a mixture of 312-1 (30 g, 122.85 mmol) and 1,1-dimethoxycyclopentane (86 g, 660.93 mmol) in DCE (200 mL) was added TsOH.H$_2$O (2.34 g, 12.29 mmol) in one portion at RT. The mixture was heated to 70° C. and stirred for 14 h. The mixture was cooled to RT and concentrated under reduced pressure. The residue was purified by column chromatography (1-10% MeOH in DCM) to give 312-2 (25 g, 65.6%) as a white solid.

To a solution of 312-2 (20 g, 64.45 mmol) in anhydrous CH$_3$CN (200 mL) was added IBX (19.85 g, 70.9 mmol) at RT. The mixture was refluxed for 18 h. and then cooled to 0° C. The precipitate was filtered-off, and the filtrate was concentrated to give crude 312-3 (20 g, 100%) as a yellow solid.

To a solution of 312-3 (20 g, 64.87 mmol) in 1,4-dioxane (200 mL) were added 37% HCHO (20 mL) and 2.0 M NaOH aq. solution (40 mL) at 0° C. The mixture was stirred at RT overnight and then neutralized with AcOH to pH=7. The solution was treated with NaBH$_4$ (4.91 g, 129.74 mmol) at 20° C. The mixture was stirred at RT for 1 h. The reaction was quenched with sat. aq. NH$_4$Cl. The mixture was extracted with EA (3×100 mL). The organic layer was dried over anhydrous Na$_2$SO$_4$ and concentrated at low pressure. The residue was purified by silica gel column chromatography (1-3% MeOH in DCM) to give 312-4 (9 g, 40.8%) as a white solid.

To a solution of 312-4 (15.50 g, 45.54 mmol) in anhydrous pyridine (80.00 mL) was added DMTrCl (18.52 g, 54.65 mmol) in anhydrous DCM (20.00 mL) dropwise at −30° C. The mixture was stirred at 25° C. overnight. The solution was treated with MeOH and concentrated at low pressure. The residue was purified by column chromatography (50% EA in PE) to give 312-5 (10.59 g, yield 32.56%) as a yellow solid.

To a solution of 312-5 (2.90 g, 4.51 mmol) in CH$_2$Cl$_2$ (20.00 mL) was added AgNO$_3$ (1.15 g, 6.77 mmol), imidazole (767.60 mg, 11.28 mmol) and TBDPSCl (1.86 g, 6.77 mmol). The mixture was stirred at 25° C. for 14 h. The precipitate was filtered off, and the filtrate was washed with water and dried over anhydrous Na$_2$SO$_4$. The solvent was removed at low pressure. The crude residue was purified by silica gel chromatography (PE:EA=5:1) to afford 312-6 (2.79 g, 63.19%) as a yellow solid.

312-6 (2.79 g, 3.17 mmol) was dissolved in 80% HOAc aq. solution (50 mL). The mixture was stirred at 25° C. for 4 h. The solution was treated with MeOH and concentrated at low pressure. The residue was purified by silica gel column chromatography (PE:EA=4:1) to give 312-7 (0.9 g, 44%) as a yellow solid.

To a solution of 312-7 (1.50 g, 2.59 mmol) in anhydrous DCM (20 mL) was added Dess-Martin periodinane (1.32 g, 3.11 mmol) at 0° C. under N$_2$. The mixture was stirred at RT for 4 h. The reaction was quenched by the addition of Na$_2$S$_2$O$_3$/sodium bicarbonate saturated aqueous solution. The mixture was stirred for 15 mins. The organic layer was separated, washed with diluted brine and concentrated under reduced pressure. The crude residue was purified by silica gel column chromatography (20% EtOAc in PE) to give 312-8 (1.12 g, yield 67.48%) as a white solid.

To a solution of PPh$_3$CH$_3$Br (1.49 g, 4.16 mmol) in anhydrous THF (15 mL) was added n-BuLi (0.41 mL, 3.47 mmol) at −70° C. under N$_2$. The mixture was stirred at 0° C. for 0.5 hour. A solution of 312-8 (800.00 mg, 1.39 mmol) in anhydrous THF (3 mL) was added dropwise at 0° C. under N$_2$. The mixture was stirred 25° C. for 2 h. The reaction was quenched with sat. NH$_4$Cl solution and extracted with EtOAc (3×60 mL). The organic phase was washed with brine, dried over anhydrous Na$_2$SO$_4$ and concentrated at low pressure. The crude product was purified by silica gel column chromatography (20% EtOAc in PE) to give 312-9 (504 mg, 56.78%) as a white solid.

To a solution of 312-9 (500 mg, 869.96 μmol) in anhydrous CH$_3$CN (10.00 mL) was added 2,4,6-triisopropylbenzenesulfonyl chloride (526.95 mg, 1.74 mmol), DMAP (212.57 mg, 1.74 mmol) and Et$_3$N (1.83 g, 18.04 mmol) at RT. The mixture was stirred at 25° C. for 1 h. NH$_3$.H$_2$O (5.00 mL) was added, and the mixture was stirred for 1 h. The mixture was extracted with EA and washed with brine, 0.1 M HCl and sat. aq. NaHCO$_3$. The organic phase was dried over anhydrous Na$_2$SO$_4$, and concentrated at low pressure. The residue was purified by silica gel chromatography (EtOAc) to give 312-10 (307 mg, 55.36%) as a yellow solid.

To a solution of 312-10 (307 mg, 535.08 μmol) in MeOH (4 mL) was added NH$_4$F (814 mg, 20 mmol) at 25° C. under N$_2$. The mixture was stirred at 65° C. for 16 h. The solution was filtered and evaporated to dryness. The residue was purified by silica gel column (EA:MeOH=50:1) to give 312-11 (130 mg, 65.2%) as a white solid.

312-11 (108 mg, 322.05 μmol) was treated with HCl:MeOH (6 mL, 1N) at 25° C. under N$_2$. The mixture was stirred at 25° C. for 1 h. The aqueous phase was extracted with EA (3×10 mL). The residual aqueous solution was lyophilized to afford 312 (80.00 mg yield 87.65%) as a yellow solid. ESI-MS:m/z 270 [M+H]$^+$.

Example 181

Compound 313

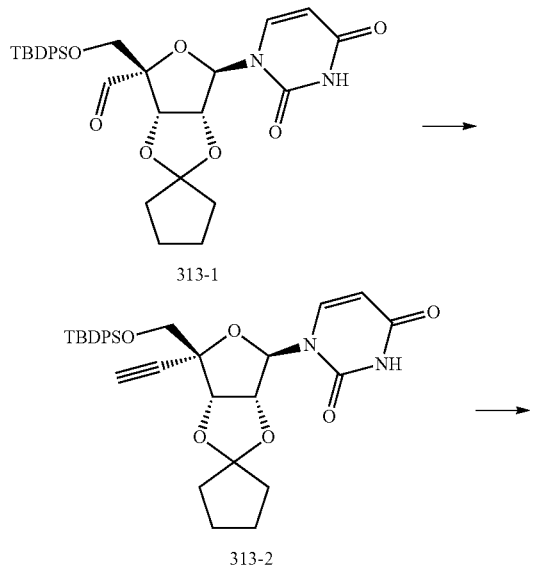

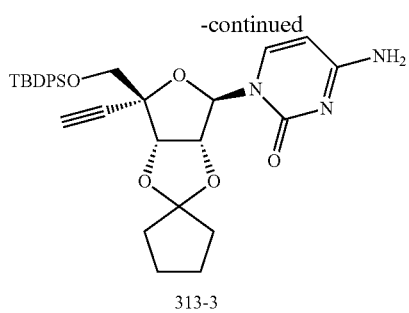

313-3

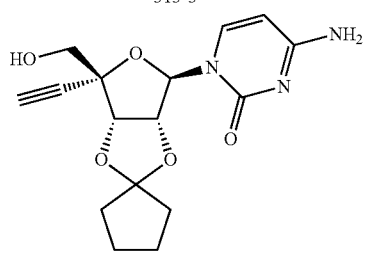

313-4

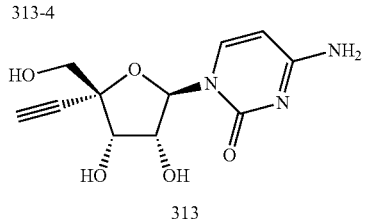

313

To a mixture of K₂CO₃ (2.40 g, 17.35 mmol) and TsN₃ (1.37 g, 6.94 mmol) in CH₃CN (20 mL) was added 1-dimethoxyphosphorylpropan-2-one (1.15 g, 6.94 mmol) in one portion at 25° C. under N₂. The mixture was stirred at 25° C. for 2 h. A solution of 313-1 (2.00 g, 3.47 mmol) in MeOH (20 mL) was added in one portion at 25° C. under N₂, and the mixture was stirred at 25° C. for 16 h. The mixture was poured into water and extracted with EtOAc (2×30 mL). The combined organic phase was washed with brine, dried over anhydrous Na₂SO₄, filtered and concentrated in vacuum. The residue was purified by prep-HPLC (TFA buffer) to give 313-2 (1.50 g, 75%) as a white solid.

To a solution of 313-2 (600 mg, 1.05 mmol) in dry CH₃CN (60 mL) was added TEA (212 mg, 2.10 mmol), DMAP (256 mg, 2.10 mmol) and 2,4,6-triisopropylbenzenesulfonyl chloride (635 mg, 2.10 mmol) at 0° C. The mixture was stirred at 25° C. for 1 h. NH₃.H₂O (10 mL) was added at 25° C. The mixture was stirred at 25° C. for 1 h. The reaction was quenched with sat. NH₄Cl solution, and extracted with EtOAc (2×10 mL). The organic phase was washed with brine, dried over anhydrous Na₂SO₄ and concentrated at low pressure. The residue was purified by silica gel chromatography (PE:EA=3:1 to 0:1), and prep-TLC (DCM:MeOH=10:1) to give 313-3 (380 mg, 63%) as a white solid.

A solution of 313-3 (300 mg, 0.52 mmol) and NH₄F (194 mg, 5.25 mmol) in dry MeOH (5 mL) was stirred at 65° C. for 12 h. The mixture was concentrated at low pressure. The residue was purified by silica gel column chromatography (DCM:MeOH=50:1 to 10:1) to afford 313-4 (140 mg, 80%) as a white solid.

A solution of 313-4 (100 mg, 0.30 mmol) in 1 N HCl: MeOH (5 mL) was stirred at 25° C. for 2 h. The mixture was concentrated under 40° C. The residue was washed with CH₃CN (5×2 mL) to give 313 (61 mg, 67%) as a white solid. ESI-LCMS:m/z 268.1 [M+H]⁺.

Example 182

Compound 314

44 ⟶

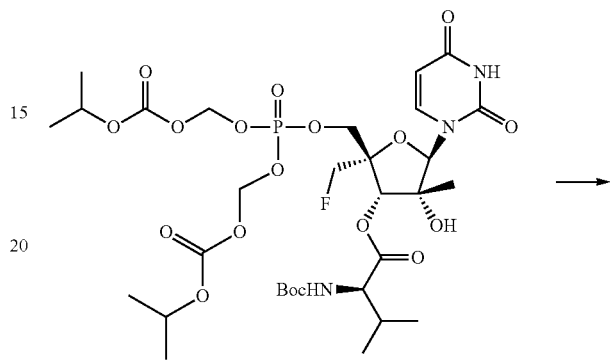

314-1

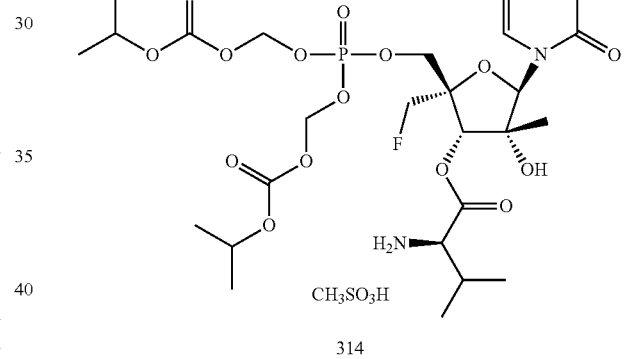

314

To a solution of N-(tert-Butoxycarbonyl)-L-valine (8.06 g, 37.1 mmol, 1.5 eq.) in anhydrous ACN (60 mL) was added carbonyldiimidazole (6.01 g, 37.1 mmol, 1.5 eq.). The reaction was stirred for 1 h at RT and then cooled to 0° C. A solution of 44 (14.9 g, 24.7 mmol, 1 eq.) in anhydrous ACN (50 mL) was added to the cooled solution of N—BOC-valine imidazolide, and the resulting solution was treated with Et₃N (6.4 mL, 49.4 mmol, 2 eq.). The reaction was allowed to proceed for 1 h at 0° C. The reaction was quenched 1M citric acid to pH 2-3 (150 mL), stirred for 15 mins and diluted with IPAC (200 mL). The organic layer was separated, washed sequentially with water and half sat. sodium bicarbonate and water (2×). The organic layer was concentrated under reduced pressure, and the residue was dissolved in MTBE (125 mL) under gentle heating (40° C.) to afford precipitation of the target compound. The solid was aged overnight at 0° C. and isolated by filtration to obtain 314-1 (18.0 g, 90.9%) as a white solid. MS:m/z=802 [M+1]⁺.

A stirred slurry of 314-1 (2.4 g, 3 mmol) in IPAC (45 mL) was treated with methanesulfonic acid (0.39 mL, 6 mmol, 2 eq.), and the mixture was stirred at 40° C. After 1 h, methanesulfonic acid (2×0.2 mL, 6 mmol, 2 eq.) was added, and the temperature was increased to 50° C. After 5 h, the mixture was cooled to RT. The solid was filtered off, washed with IPAC and dried under vacuum to yield 314 (2.0 g, 83%). MS:m/z=702.2 [M+1]+.

Example 183

Triphosphates

Dry nucleoside (0.05 mmol) was dissolved in the mixture of PO(OMe)$_3$ (0.7 mL) and pyridine (0.3 mL). The mixture was evaporated in vacuum for 15 mins at bath temperature (42° C.), than cooled down to RT. N-Methylimidazole (0.009 mL, 0.11 mmol) was added followed by POCl$_3$ (9 µL, 0.11 mmol), and the mixture was kept at RT for 20-40 mins. The reaction was controlled by LCMS and monitored by the appearance of corresponding nucleoside 5'-monophosphate. After completion, tetrabutylammonium salt of pyrophosphate (150 mg) was added, followed by DMF (0.5 mL) to get a homogeneous solution. After 1.5 h at ambient temperature, the reaction was diluted with water (10 mL) and loaded on the column HiLoad 16/10 with Q Sepharose High Performance. Separation was done in a linear gradient of NaCl from 0 to 1N in 50 mM TRIS-buffer (pH 7.5). Triphosphate was eluted at 75-80% B. Corresponding fractions were concentrated. Desalting was achieved by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer. Examples of compound made according to this procedure are provided in Table 2.

TABLE 2

| | Structure | MS [M − 1] | 31P NMR P(α) | P(β) | P(γ) |
|---|---|---|---|---|---|
| 3 | | 540.4 | −10.90 −11.03(d) | −23.38(t) | −11.91 −12.03(d) |
| 19 | | 556.2 | −10.92 −11.03(d) | −23.18(t) | −11.86 −11.98(d) |
| 29 | | 516.1 | −7.49 −7.61(d) | −22.42(t) | −12.17 −12.30(d) |
| 34 | | 568.2 | −5.60 −5.72(d) | −21.13(bs) | −10.93 −11.05(d) |
| 37 | | 539.3 | −10.02 −10.36(d) | −20.72(t) | −11.27 −11.40(d) |

TABLE 2-continued

| | Structure | MS [M − 1] | 31P NMR P(α) | P(β) | P(γ) |
|---|---|---|---|---|---|
| 58 | 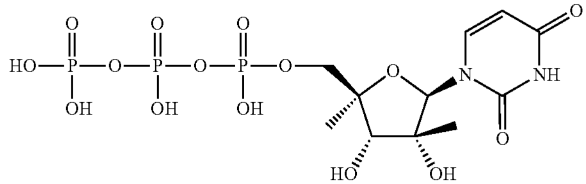 [SMILES: C[C@]1(O)[C@H](n2ccc(=O)[nH]c2=O)O[C@](C)(COP(=O)(O)OP(=O)(O)OP(=O)(O)O)[C@H]1O] | 510.8 | −10.87<br>−10.99(d) | −23.35(t) | −11.76<br>−11.89(d) |
| 59 | 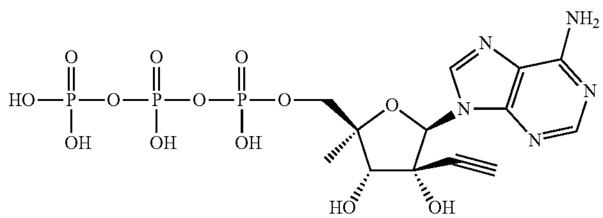 [SMILES: C#C[C@]1(O)[C@H](n2cnc3c(N)ncnc32)O[C@](C)(COP(=O)(O)OP(=O)(O)OP(=O)(O)O)[C@H]1O] | 543.8 | −10.53<br>−10.66(d) | −23.23(t) | −11.63<br>−11.75(d) |
| 61 | 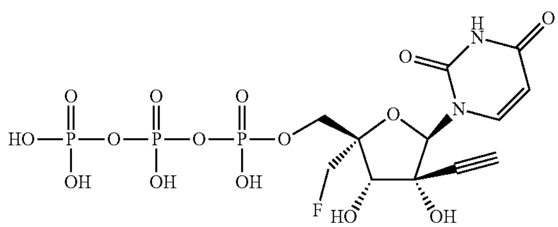 [SMILES: C#C[C@@]1(O)[C@H](O)[C@@](CF)(COP(=O)(O)OP(=O)(O)OP(=O)(O)O)O[C@H]1n1ccc(=O)[nH]c1=O] | 538.9 | −10.61<br>−10.73(d) | −23.20(t) | −11.74<br>−11.86(d) |
| 62 | 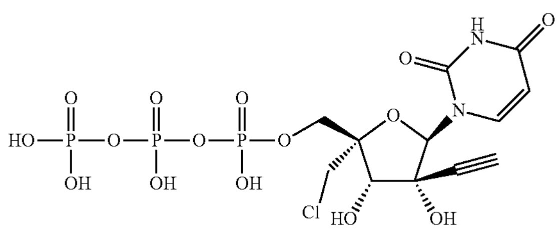 [SMILES: C#C[C@@]1(O)[C@H](O)[C@@](CCl)(COP(=O)(O)OP(=O)(O)OP(=O)(O)O)O[C@H]1n1ccc(=O)[nH]c1=O] | 538.9 | −10.92<br>−11.04(d) | −23.33(t) | −11.81<br>−11.93(d) |
| 72 | 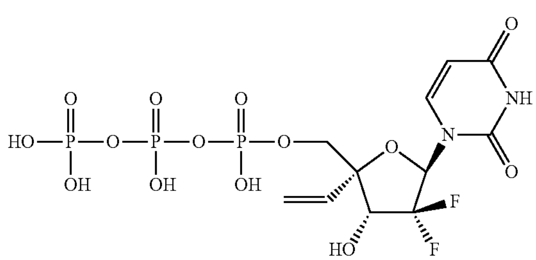 | 529.3 | −5.25<br>−5.37(d) | −20.53(t) | −11.42<br>−11.53(d) |
| 73 | 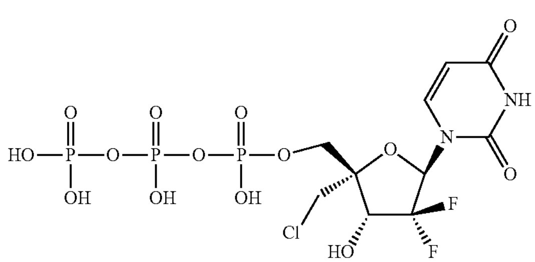 | 551.4 | −10.90<br>−11.02(d) | −23.27(t) | −11.87<br>−11.99(d) |

TABLE 2-continued

| | Structure | MS [M − 1] | 31P NMR P(α) | P(β) | P(γ) |
|---|---|---|---|---|---|
| 74 | 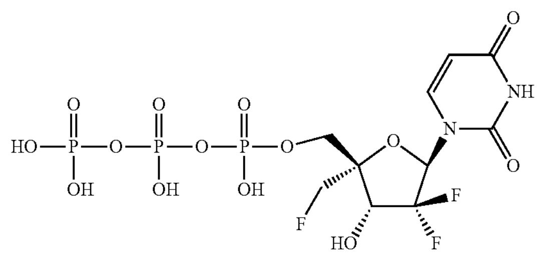 | 535.0 | −5.41<br>−5.53(d) | −23.27(t) | −11.39<br>−11.51(d) |
| 79 | 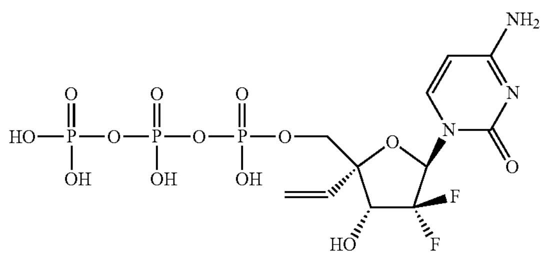 | 529.2 | −10.86<br>−10.98(d) | −23.23(t) | −11.85<br>−11.9(d) |
| 80 | 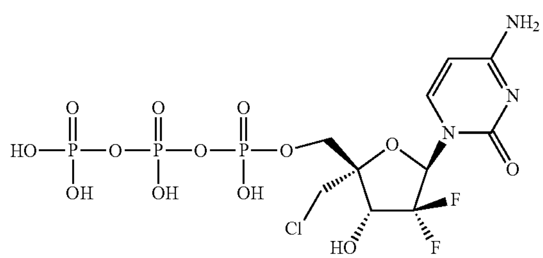 | 535.0 | −10.86<br>−10.98(d) | −23.21(t) | −11.81<br>−11.94(d) |
| 81 | 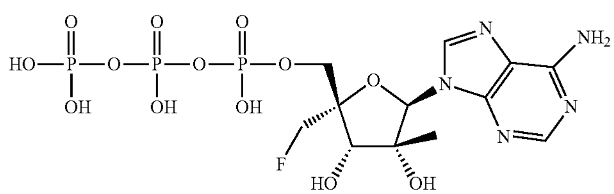 [SMILES: C[C@@]1(O)[C@H](O)[C@@](CF)(COP(=O)(O)OP(=O)(O)OP(=O)(O)O)O[C@H]1n1cnc2c(N)ncnc21] | 529.2 | −10.64<br>−10.73(d) | −20.78(t) | −11.42<br>−11.56(d) |
| 82 | 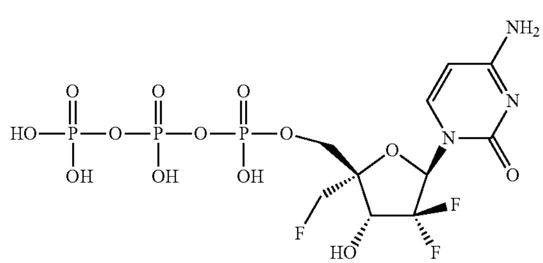 | 534.3 | −10.75<br>−10.89(d) | −23.19(t) | −11.46<br>−11.58(d) |
| 91 | 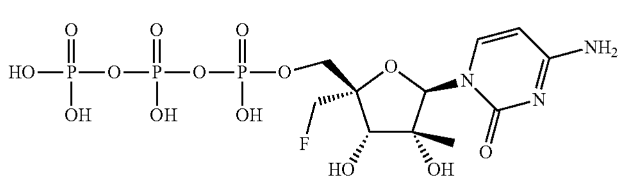 [SMILES: C[C@@]1(O)[C@H](O)[C@@](CF)(COP(=O)(O)OP(=O)(O)OP(=O)(O)O)O[C@H]1n1ccc(N)nc1=O] | 528.0 | −10.13(bs) | −23.16(t) | −11.64<br>−11.81(d) |

TABLE 2-continued

| | Structure | MS [M − 1] | 31P NMR P(α) | P(β) | P(γ) |
|---|---|---|---|---|---|
| 92 | 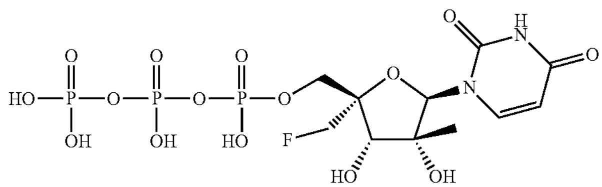 [SMILES: C[C@@]1(O)[C@H](O)[C@@](CF)(COP(=O)(O)OP(=O)(O)OP(=O)(O)O)O[C@H]1n1ccc(=O)[nH]c1=O] | 528.9 | −11.05<br>−11.08(d) | −23.46(t) | −11.79<br>−11.91(d) |
| 93 | 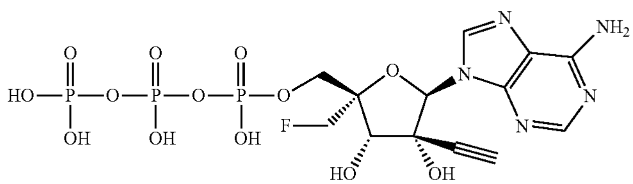 [SMILES: C#C[C@@]1(O)[C@H](O)[C@@](CF)(COP(=O)(O)OP(=O)(O)OP(=O)(O)O)O[C@H]1n1cnc2c(N)ncnc21] | 561.7 | −10.73<br>−10.85(d) | −23.23(t) | −11.63<br>−11.75(d) |
| 94 | 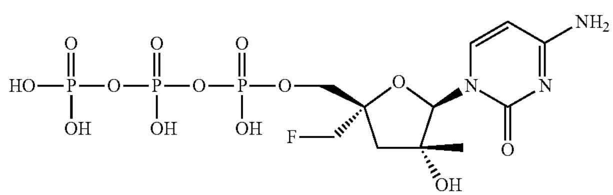 [SMILES: C[C@@]1(O)C[C@@](CF)(COP(=O)(O)OP(=O)(O)OP(=O)(O)O)O[C@H]1n1ccc(N)nc1=O] | 534.0 | −10.92<br>−10.64(d) | −23.38(t) | −11.61<br>−11.73(d) |
| 95 | 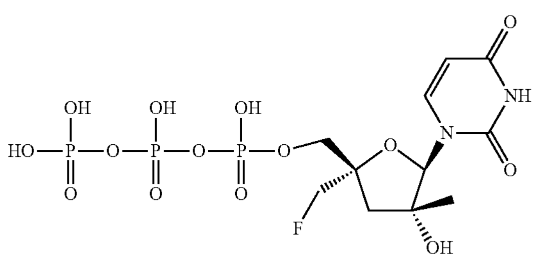 [SMILES: C[C@@]1(O)C[C@@](CF)(COP(=O)(O)OP(=O)(O)OP(=O)(O)O)O[C@H]1n1ccc(=O)[nH]c1=O] | 512.8 | −10.98<br>−11.11(d) | −23.46(t) | −11.70<br>−11.8(d) |
| 101 | 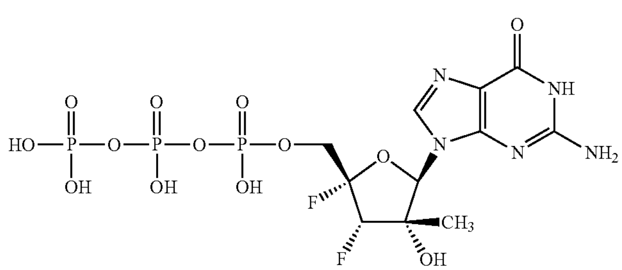 [SMILES: C[C@]1(O)[C@H](n2cnc3c(=O)[nH]c(N)nc32)O[C@](F)(COP(=O)(O)OP(=O)(O)OP(=O)(O)O)[C@H]1F] | 556.2 | −10.92<br>−10.07(d) | −23.34(t) | −11.70<br>−11.82(d) |
| 103 | 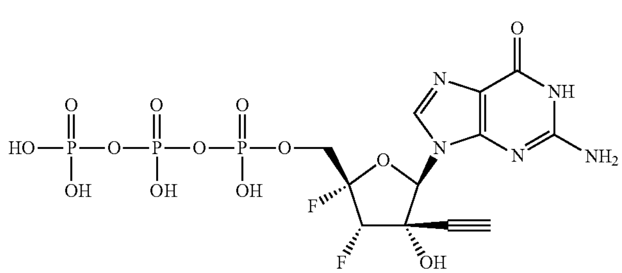 [SMILES: C#C[C@]1(O)[C@H](n2cnc3c(=O)[nH]c(N)nc32)O[C@](F)(COP(=O)(O)OP(=O)(O)OP(=O)(O)O)[C@H]1F] | 566.0 | −6.26<br>−6.39(d) | −22.45(t) | −11.66<br>−11.84(d) |

TABLE 2-continued

| | | MS | 31P NMR | | |
|---|---|---|---|---|---|
| | Structure | [M − 1] | P(α) | P(β) | P(γ) |
| 107 | | 539.3 | −5.36(d) | −20.72(t) | −11.40(d) |
| 111 | | 564.0 | −10.94<br>−11.06(d) | −23.25(t) | −11.85<br>−11.97(d) |
| 114 | | 546.9 | −8.53(bs) | −22.61(bs) | −12.17<br>−12.29(d) |
| 115 | | 564.4 | −11.05(bs) | −23.25(bs) | −11.96<br>−12.08(d) |
| 123 | | 566.0 | −10.92<br>−11.04(d) | −23.18(t) | −11.93<br>−1(d) |
| 124 | | 513.8 | −8.66(bs) | −22.80(t) | −12.17<br>−12.29(d) |

TABLE 2-continued

| | Structure | MS [M − 1] | 31P NMR P(α) | P(β) | P(γ) |
|---|---|---|---|---|---|
| 132 | (triphosphate-5'-O, 4'-CH2N3, 3'-OH, 2'-F guanosine) | 579.4 | −10.31 −10.44(d) | −23.08(t) | −11.81 −11.92(d) |
| 133 | (triphosphate-5'-O, 4'-CH2N3, 3'-OH, 2'-F adenosine) | 563.0 | −10.79 −10.91(d) | −23.24(t) | −11.80 −11.92(d) |
| 147 | (triphosphate-5'-O, 4'-F, 3'-OH, 2'-F, 2'-CH3 uridine) | 517.1 | −13.60 −13.72(d) | −25.98(t) | −15.05 −15.17(d) |
| 149 | (triphosphate-5'-O, 4'-F, 3'-OH, 2'-Cl, 2'-CH3 uridine) | 533.3 | −10.89 −11.01(d) | −23.31(t) | −12.49 −1(d) |
| 162 | (triphosphate-5'-O, 4'-CH2F, 3'-OH, 2'-F, 2'-CH3 guanosine) | 570.4 | −9.25 −9.28(d) | −22.82(t) | −11.29 −11.42(d) |
| 163 | (triphosphate-5'-O, 2'-F, 3'-OH guanosine) | 542.2 | −5.39 −5.40(d) | −20.71(t) | −11.52 −11.63(d) |

TABLE 2-continued

| | Structure | MS [M − 1] | 31P NMR P(α) | P(β) | P(γ) |
|---|---|---|---|---|---|
| 164 | 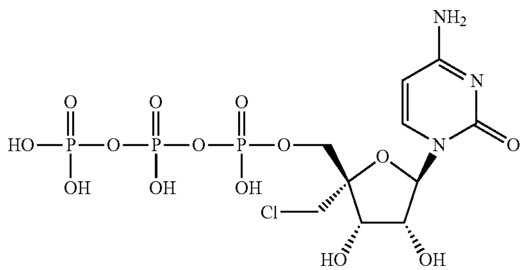 [SMILES: Nc1ccn([C@@H]2O[C@](CCl)(COP(=O)(O)OP(=O)(O)OP(=O)(O)O)[C@@H](O)[C@H]2O)c(=O)n1] | 529.8 | −10.72(bs) | −23.20(t) | −11.73<br>−11.84(d) |
| 166 | 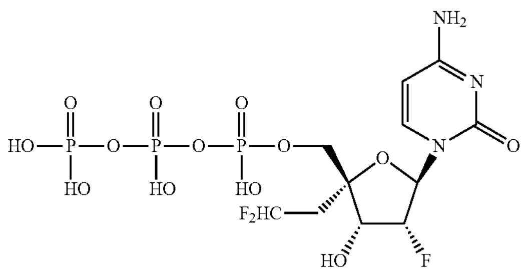 [SMILES: Nc1ccn([C@@H]2O[C@@](COP(=O)(O)OP(=O)(O)OP(=O)(O)O)(CC(F)F)[C@@H](O)[C@H]2F)c(=O)n1] | 548.2 | −10.93<br>−11.05(d) | −23.35(t) | −12.00<br>−12.13(d) |
| 167 | 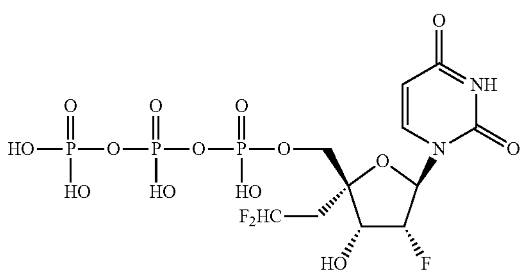 | 535.3 | −12.86<br>−12.98(d) | −25.60(t) | −14.24<br>−14.36(d) |
| 168 | 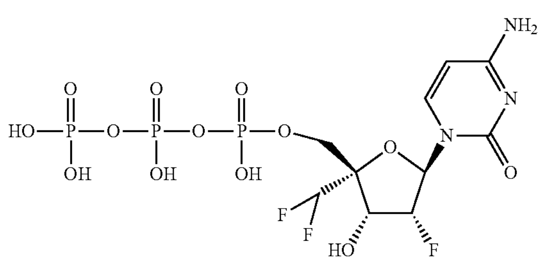 [SMILES: Nc1ccn([C@@H]2O[C@@](COP(=O)(O)OP(=O)(O)OP(=O)(O)O)(C(F)F)[C@@H](O)[C@H]2F)c(=O)n1] | 534.3 | −7.78(bs) | −22.30(t) | −11.70(bs) |
| 184 | 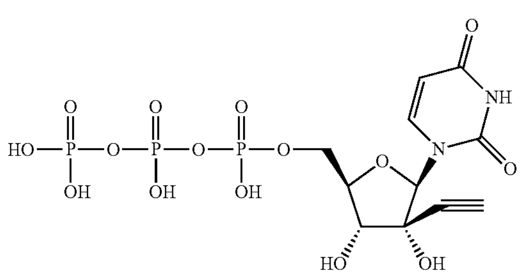 | 523.1 | 42.93 | −23.28 | −7.94 |

TABLE 2-continued

| | | Structure | MS [M − 1] | 31P NMR P(α) | P(β) | P(γ) |
|---|---|---|---|---|---|---|
| 185 | | [structure: uridine 5'-triphosphate with 2'-ethynyl, 2'-OH, 3'-OH; P(R)] | 523.3 | 42.69 | −22.93 | −6.22 |
| 202 | | [structure: adenosine 5'-triphosphate with 2'-ethynyl, 2'-OH, 3'-OH] | 529.8 | −6.53(m) | −22.27(m) | −11.27 |
| 203 | | [structure: guanosine 5'-triphosphate with 2'-ethynyl, 2'-OH, 3'-OH] | 545.9 | −8.6(br) | −22.80(t) | −11.35(d) |
| 205 | | [structure: 7-deazaadenosine 5'-triphosphate with 2'-ethynyl, 2'-OH, 3'-OH] | — | −4.97(m) | −20.04(m) | −10.72(m) |
| 208 | | [structure: cytidine 5'-triphosphate with 2'-F, 2'-methyl, 3'-OH, 3'-N₃] | 539.5 | −7.42(bs) | −22.57(t) | −12.23 −12.34(d) |

TABLE 2-continued

| | Structure | MS [M − 1] | 31P NMR P(α) | P(β) | P(γ) |
|---|---|---|---|---|---|
| 209 | 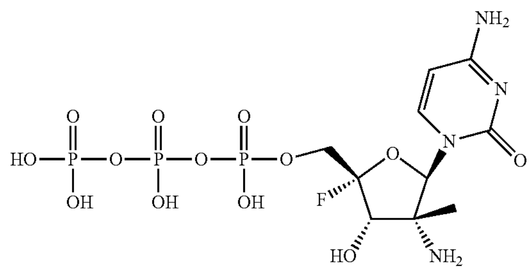 [SMILES: C[C@]1(N)[C@H](n2ccc(N)nc2=O)O[C@](F)(COP(=O)(O)OP(=O)(O)OP(=O)(O)O)[C@H]1O] | 513.1 | −6.36 / −6.49(d) | −22.49(t) | −12.20 / −12.33(d) |
| 210 | 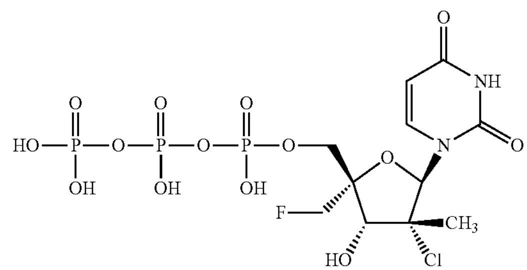 [SMILES: C[C@@]1(Cl)[C@H](O)[C@@](CF)(COP(=O)(O)OP(=O)(O)OP(=O)(O)O)O[C@H]1n1ccc(=O)[nH]c1=O] | 547.3 | −10.95 / −11.07(d) | −23.32(t) | −11.91 / −12.03(d) |
| 215 | 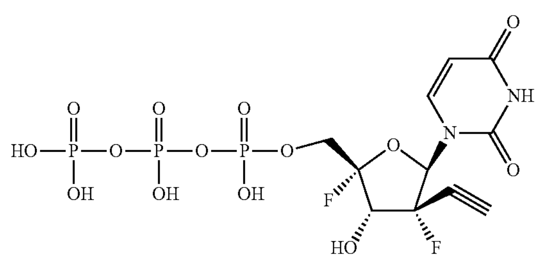 [SMILES: C#C[C@]1(F)[C@H](n2ccc(=O)[nH]c2=O)O[C@](F)(COP(=O)(O)OP(=O)(O)OP(=O)(O)O)[C@H]1O] | 526.8 | −10.96 / −11.08(d) | −23.33(t) | −12.41 / −12.53(d) |
| 236 | 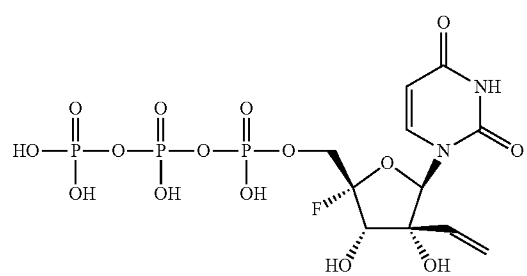 [SMILES: C=C[C@]1(O)[C@H](n2ccc(=O)[nH]c2=O)O[C@](F)(COP(=O)(O)OP(=O)(O)OP(=O)(O)O)[C@H]1O] | 527 | −10.68 / −10.80(d) | −23.35(t) | −12.30 / −12.42(d) |
| 237 | 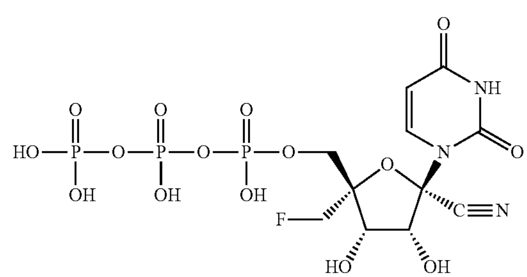 [SMILES: N#C[C@@]1(n2ccc(=O)[nH]c2=O)O[C@](CF)(COP(=O)(O)OP(=O)(O)OP(=O)(O)O)[C@@H](O)[C@H]1O] | 540.5 | −10.91 / −11.03(d) | −23.38(t) | −12.24 / −12.37(d) |

TABLE 2-continued

| | Structure | MS [M − 1] | 31P NMR P(α) | P(β) | P(γ) |
|---|---|---|---|---|---|
| 238 | 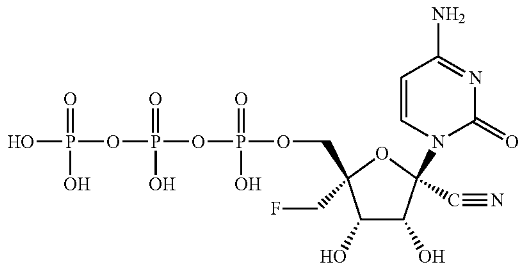 [SMILES: N#C[C@@]1(n2ccc(N)nc2=O)O[C@](CF)(COP(=O)(O)OP(=O)(O)OP(=O)(O)O)[C@@H](O)[C@H]1O] | 539 | −10.88 −10.99(d) | −23.41(t) | −12.15 −12.27(d) |
| 239 | 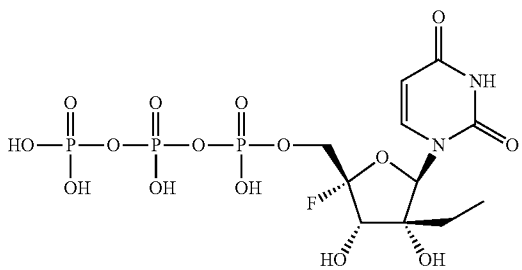 [SMILES: CC[C@]1(O)[C@H](n2ccc(=O)[nH]c2=O)O[C@](F)(COP(=O)(O)OP(=O)(O)OP(=O)(O)O)[C@H]1O] | 529 | −10.83 −10.95(d) | −23.27(t) | −12.25 −12.37(d) |
| 240 | 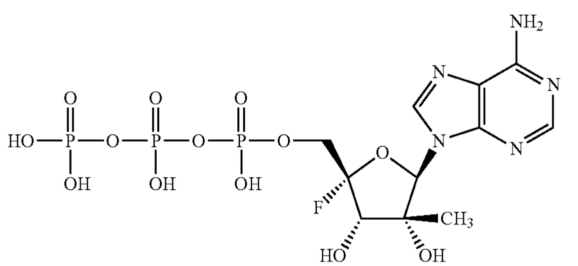 [SMILES: C[C@]1(O)[C@H](n2cnc3c(N)ncnc32)O[C@](F)(COP(=O)(O)OP(=O)(O)OP(=O)(O)O)[C@H]1O] | 538.4 | −9.19(bs) | −22.50(t) | −12.04(bs) |
| 241 | 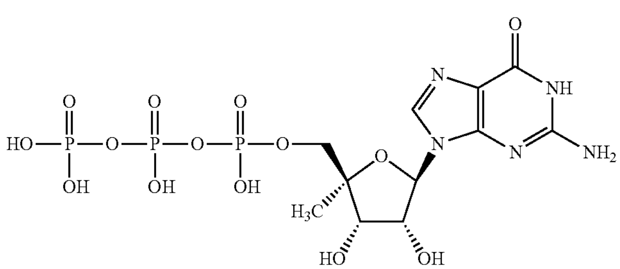 [SMILES: C[C@]1(COP(=O)(O)OP(=O)(O)OP(=O)(O)O)O[C@@H](n2cnc3c(=O)[nH]c(N)nc32)[C@H](O)[C@@H]1O] | 536.0 | −10.69 −10.81(d) | −23.27(t) | −11.72 −12.85(d) |
| 242 | 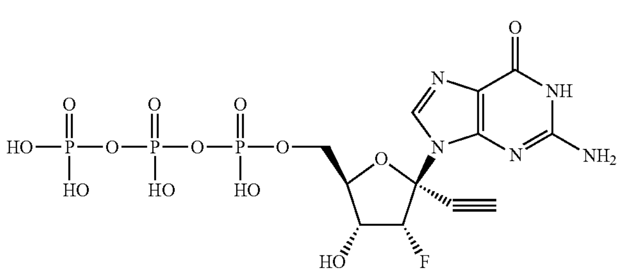 [SMILES: C#C[C@@]1(n2cnc3c(=O)[nH]c(N)nc32)O[C@H](COP(=O)(O)OP(=O)(O)OP(=O)(O)O)[C@@H](O)[C@H]1F] | 548.2 | −10.85 −10.97(d) | −23.27(t) | −11.62 −11.74(d) |

TABLE 2-continued

| | | MS | 31P NMR | | |
|---|---|---|---|---|---|
| | Structure | [M − 1] | P(α) | P(β) | P(γ) |
| 243 | | 510.1 | −10.55<br>−10.67(d) | −23.27(t) | −11.72<br>−12.85(d) |
| 244 | | 544.9 | −10.97<br>−11.05(d) | −23.28(t) | −11.77<br>−12.89(d) |
| 245 | | 577.6 | −10.42<br>−10.54(d) | −23.06(t) | −11.61<br>−12.73(d) |
| 246 | | 554.0 | −10.85<br>−10.96(d) | −23.24(t) | −11.52<br>−11.64(d) |
| 249 | | 552.4 | −6.17(bs) | −21.02(t) | −10.09(bs) |

TABLE 2-continued

| | Structure | MS [M − 1] | 31P NMR P(α) | P(β) | P(γ) |
|---|---|---|---|---|---|
| 251 | 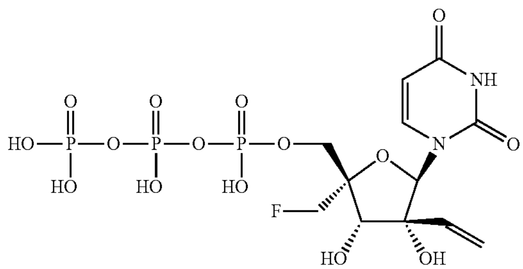 [SMILES: C=C[C@@]1(O)[C@H](O)[C@@](CF)(COP(=O)(O)OP(=O)(O)OP(=O)(O)O)O[C@H]1n1ccc(=O)[nH]c1=O] | 541.4 | −10.87 −11.99(d) | −23.21(t) | −11.72 −11.84(d) |
| 252 | 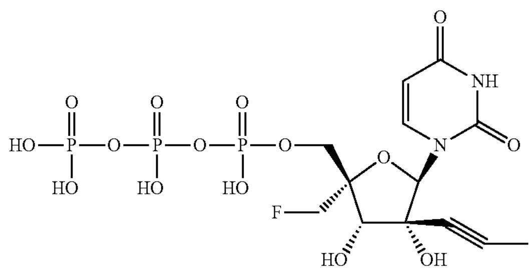 [SMILES: CC#C[C@@]1(O)[C@H](O)[C@@](CF)(COP(=O)(O)OP(=O)(O)OP(=O)(O)O)O[C@H]1n1ccc(=O)[nH]c1=O] | 553.4 | −10.91 −11.03(d) | −23.31(t) | −11.74 −11.87(d) |
| 253 | 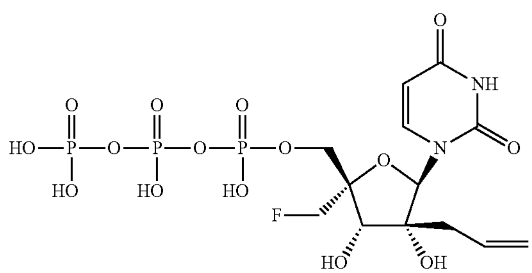 [SMILES: C=CC[C@@]1(O)[C@H](O)[C@@](CF)(COP(=O)(O)OP(=O)(O)OP(=O)(O)O)O[C@H]1n1ccc(=O)[nH]c1=O] | 555.6 | −8.63 −8.76(d) | −24.61(t) | −13.90 −14.03(d) |
| 254 | 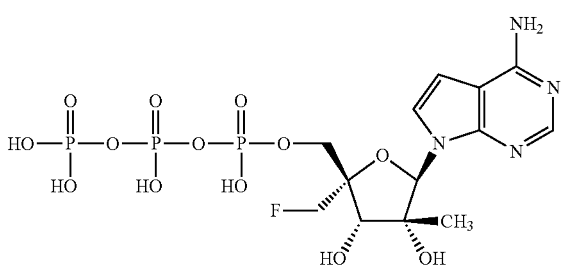 [SMILES: C[C@@]1(O)[C@H](O)[C@@](CF)(COP(=O)(O)OP(=O)(O)OP(=O)(O)O)O[C@H]1n1ccc2c(N)ncnc21] | 551.4 | −9.74 −9.86(d) | −22.89(t) | −11.46 −11.58(d) |
| 255 | 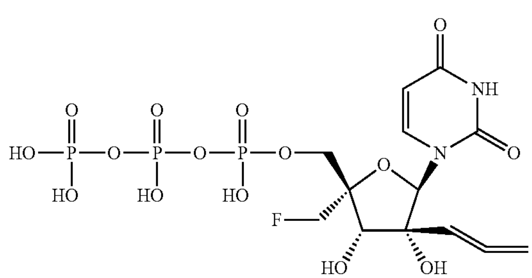 [SMILES: C=C=C[C@@]1(O)[C@H](O)[C@@](CF)(COP(=O)(O)OP(=O)(O)OP(=O)(O)O)O[C@H]1n1ccc(=O)[nH]c1=O] | 553.4 | −10.98 −11.10(d) | −23.38(t) | −11.86 −11.98(d) |

TABLE 2-continued

| | Structure | MS [M − 1] | 31P NMR P(α) | P(β) | P(γ) |
|---|---|---|---|---|---|
| 256 | 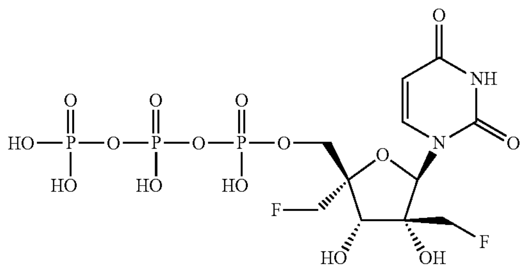 [SMILES: O=c1ccn([C@@H]2O[C@](CF)(COP(=O)(O)OP(=O)(O)OP(=O)(O)O)[C@@H](O)[C@]2(O)CF)c(=O)[nH]1] | 547.2 | −10.91<br>−11.03(d) | −23.33(t) | −11.79<br>−11.91(d) |
| 257 | 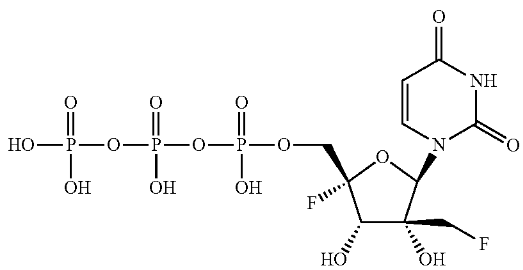 | 533.4 | −10.78(br.s) | −23.22(t) | −12.24<br>−12.36(d) |
| 258 | 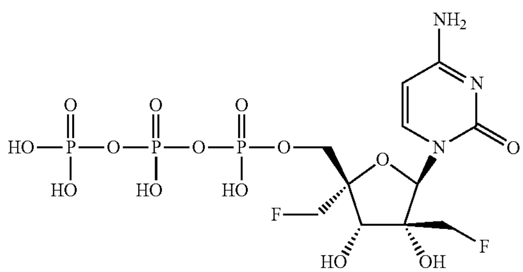 [SMILES: Nc1ccn([C@@H]2O[C@](CF)(COP(=O)(O)OP(=O)(O)OP(=O)(O)O)[C@@H](O)[C@]2(O)CF)c(=O)n1] | 546.3 | −10.52(bs) | −23.05(t) | −11.64<br>−11.76(d) |
| 261 | 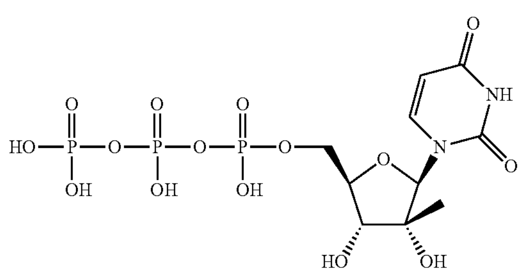 [SMILES: C[C@@]1(O)[C@H](O)[C@@H](COP(=O)(O)OP(=O)(O)OP(=O)(O)O)O[C@H]1n1ccc(=O)[nH]c1=O] | 496.9 | −8.24<br>−8.36(d) | −21.66(t) | −11.14<br>−11.26(d) |
| 262 | 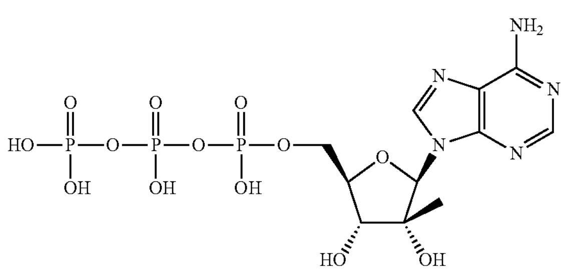 [SMILES: C[C@@]1(O)[C@H](O)[C@@H](COP(=O)(O)OP(=O)(O)OP(=O)(O)O)O[C@H]1n1cnc2c(N)ncnc21] | 520.4 | −10.87<br>−10.97(d) | −23.34(t) | −11.86<br>−11.97(d) |
| 263 | 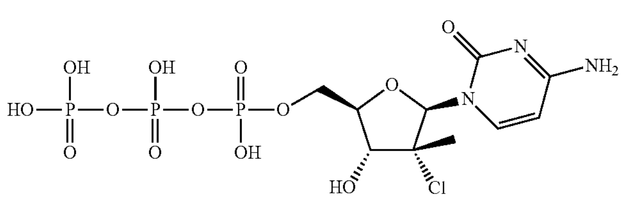 [SMILES: C[C@@]1(Cl)[C@H](O)[C@@H](COP(=O)(O)OP(=O)(O)OP(=O)(O)O)O[C@H]1n1ccc(N)nc1=O] | 513.8 | −8.20(bs) | −22.74(t) | −11.52<br>−11.64(d) |

TABLE 2-continued

| | Structure | MS [M − 1] | 31P NMR P(α) | P(β) | P(γ) |
|---|---|---|---|---|---|
| 264 | 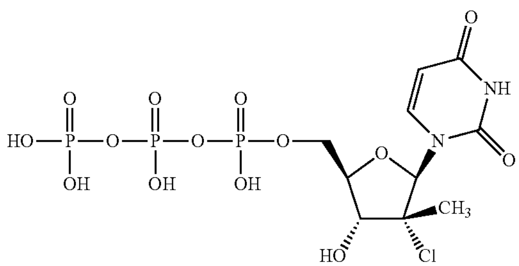 [SMILES: C[C@@]1(Cl)[C@H](O)[C@@H](COP(=O)(O)OP(=O)(O)OP(=O)(O)O)O[C@H]1n1ccc(=O)[nH]c1=O] | 514.9 | −9.95 −10.08(d) | −23.14(t) | −11.64 −11.76(d) |
| 265 | 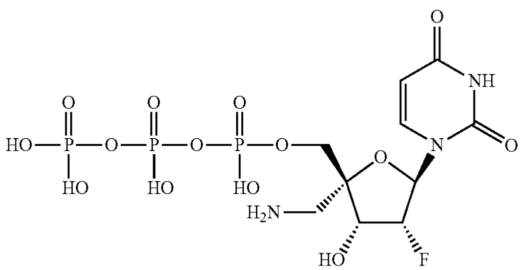 [SMILES: NC[C@]1(COP(=O)(O)OP(=O)(O)OP(=O)(O)O)O[C@@H](n2ccc(=O)[nH]c2=O)[C@H](F)[C@@H]1O] | 514.0 | −6.68 −6.81(d) | −22.25(t) | −11.79 −11.92(d) |
| 266 | 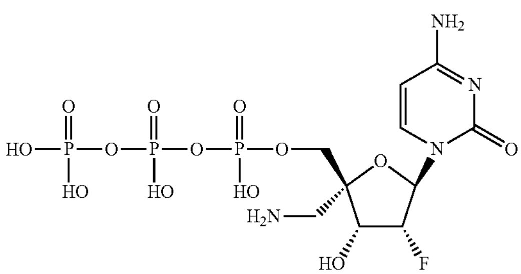 [SMILES: NC[C@]1(COP(=O)(O)OP(=O)(O)OP(=O)(O)O)O[C@@H](n2ccc(N)nc2=O)[C@H](F)[C@@H]1O] | 513 | −5.95 −6.06(d) | −21.38(t) | −11.53 −11.65(d) |
| 267 | 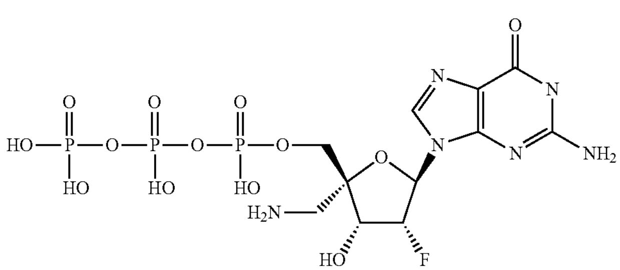 [SMILES: NC[C@]1(COP(=O)(O)OP(=O)(O)OP(=O)(O)O)O[C@@H](n2cnc3c(=O)[nH]c(N)nc32)[C@H](F)[C@@H]1O] | 553 | −9.94 −10.06(d) | −23.83(t) | −11.77 −11.89(d) |
| 268 | 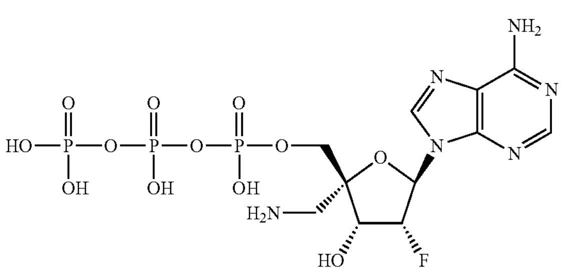 [SMILES: NC[C@]1(COP(=O)(O)OP(=O)(O)OP(=O)(O)O)O[C@@H](n2cnc3c(N)ncnc32)[C@H](F)[C@@H]1O] | 537.0 | −6.48 −6.60(d) | −22.13(t) | −11.76 −11.88(d) |

TABLE 2-continued

| | Structure | MS [M − 1] | 31P NMR P(α) | P(β) | P(γ) |
|---|---|---|---|---|---|
| 270 | 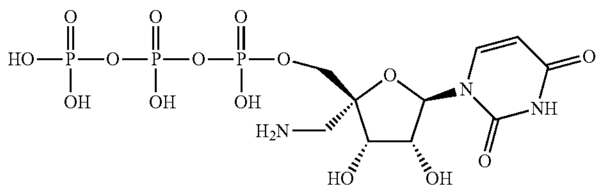 [SMILES: NC[C@]1(COP(=O)(O)OP(=O)(O)OP(=O)(O)O)O[C@@H](n2ccc(=O)[nH]c2=O)[C@H](O)[C@@H]1O] | 526.2 | −7.74(bs) | −21.02(t) | −11.75<br>−11.87(d) |
| 291 | 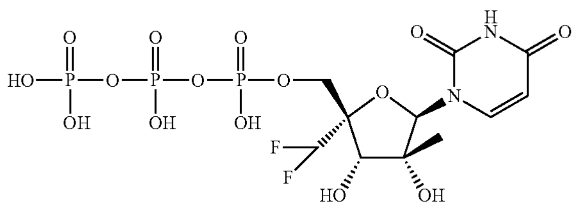 [SMILES: C[C@]1(O)[C@H](n2ccc(=O)[nH]c2=O)O[C@@](COP(=O)(O)OP(=O)(O)OP(=O)(O)O)(C(F)F)[C@H]1O] | 547.0 | −10.78<br>−10.91(d) | −23.31(t) | −11.84<br>−11.96(d) |
| 301 | 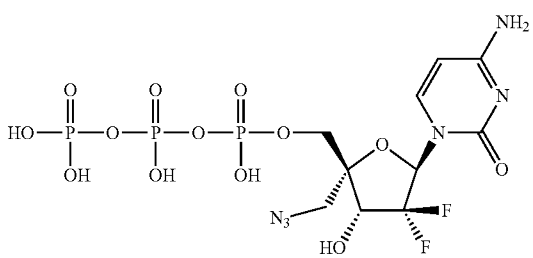 | 557.4 | −10.96<br>−11.09(d) | −23.35(t) | −11.93<br>−12.05(d) |
| 305 | 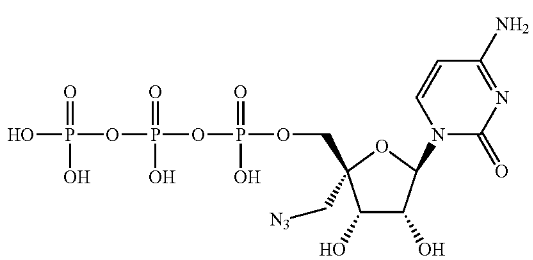 [SMILES: [N-]=[N+]=NC[C@]1(COP(=O)(O)OP(=O)(O)OP(=O)(O)O)O[C@@H](n2ccc(N)nc2=O)[C@H](O)[C@@H]1O] | 537.4 | −10.90<br>−11.03(d) | −23.35(t) | −11.84<br>−11.96(d) |
| 306 | 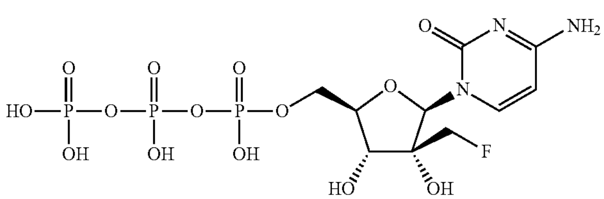 [SMILES: Nc1ccn([C@@H]2O[C@H](COP(=O)(O)OP(=O)(O)OP(=O)(O)O)[C@@H](O)[C@]2(O)CF)c(=O)n1] | 514.0 | −10.27<br>−11.39(d) | −23.18(t) | −11.39<br>−11.51(d) |
| 308 | 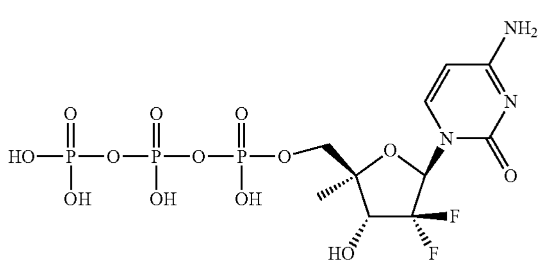 | 516.2 | −9.52(br.s) | −22.74(br.s) | −11.75(br.s) |

TABLE 2-continued

| | Structure | MS [M − 1] | 31P NMR P(α) | P(β) | P(γ) |
|---|---|---|---|---|---|
| 309 | (adenine triphosphate with 2'-OH, 2'-CH2F sugar) | 538.0 | −10.15(br.s) | −22.86(t) | −11.28 −11.40(d) |
| 310 | (cytidine triphosphate with 4'-ethynyl, 2',2'-difluoro sugar) | 526.2 | −9.97(br.s) | −22.81(t) | −12.12 −12.23(d) |
| 367 | (cytidine triphosphate with 4'-allyl, 2'-F sugar) | 524.6 | −11.68(d) | −23.15(t) | −11.72(d) |
| 368 | (cytidine triphosphate with 4'-methyl, 2'-F sugar) | 498.2 | −11.72(d) | −23.30(t) | −10.90(d) |
| 369 | (cytidine triphosphate with 4'-azidomethyl, 2'-deoxy sugar) | 521.3 | −9.23(d) | −22.57(t) | −8.06(d) |
| 370 | (cytidine triphosphate with 4'-CF3, 2'-F sugar) | 552.3 | −12.17(d) | −22.96(t) | −10.23(d) |

TABLE 2-continued

| | Structure | MS [M − 1] | 31P NMR P(α) | P(β) | P(γ) |
|---|---|---|---|---|---|
| 371 | 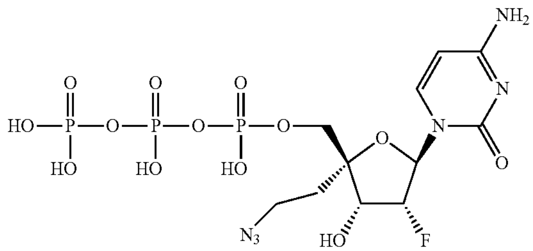 [SMILES: [N-]=[N+]=NCC[C@]1(COP(=O)(O)OP(=O)(O)OP(=O)(O)O)O[C@@H](n2ccc(N)nc2=O)[C@H](F)[C@@H]1O] | 553.0 | −11.79(d) | −22.65(t) | −10.40(br.s) |
| 372 | 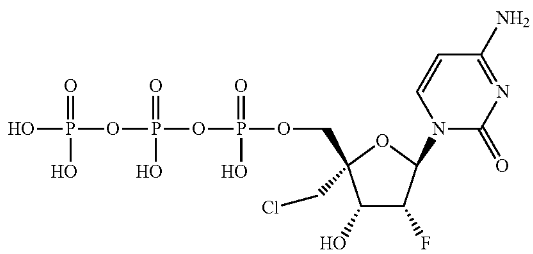 | 553.0 | −11.60(d) | −22.98(t) | −10.70(br.s) |
| 373 | 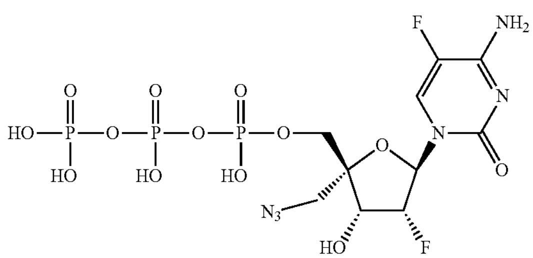 [SMILES: [N-]=[N+]=NC[C@]1(COP(=O)(O)OP(=O)(O)OP(=O)(O)O)O[C@@H](n2cc(F)c(N)nc2=O)[C@H](F)[C@@H]1O] | 557.3 | −11.78(d) | −22.33(t) | −8.76(br.s) |
| 374 | 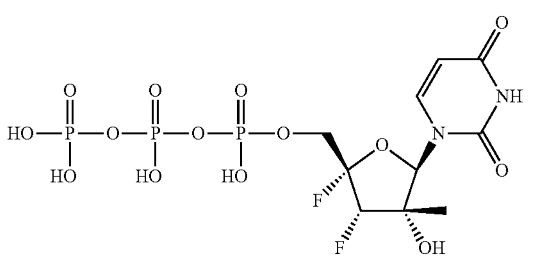 [SMILES: C[C@]1(O)[C@H](n2ccc(=O)[nH]c2=O)O[C@](F)(COP(=O)(O)OP(=O)(O)OP(=O)(O)O)[C@H]1F] | 517.2 | −11.04(d) | −23.42(t) | −12.31(d) |
| 375 | 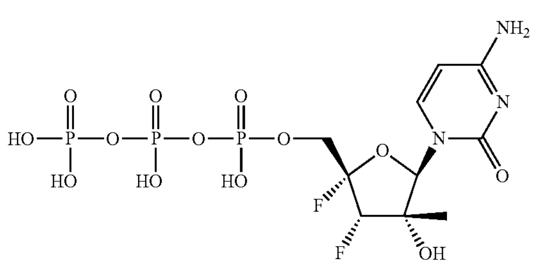 [SMILES: C[C@]1(O)[C@H](n2ccc(N)nc2=O)O[C@](F)(COP(=O)(O)OP(=O)(O)OP(=O)(O)O)[C@H]1F] | 516.6 | −9.80(br.s) | −23.12(t) | −12.09(br.s) |

Example 184
Compounds 315-331
| Compound No. | Structure | Analytical Data |
|---|---|---|
| 315 | 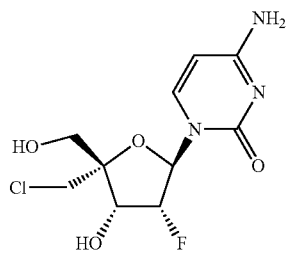 [SMILES: Nc1ccn([C@@H]2O[C@@](CO)(CCl)[C@@H](O)[C@H]2F)c(=O)n1] | 294 [M + H]+<br>587 [2M + H]+ |
| 316 | 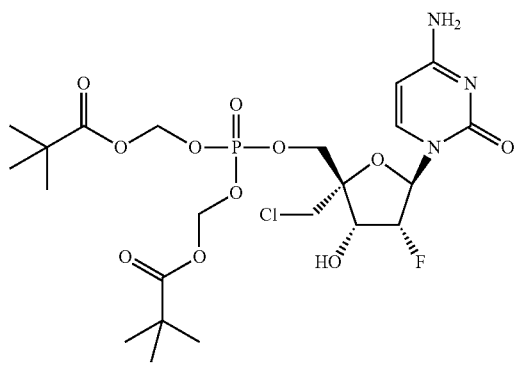 [SMILES: CC(C)(C)C(=O)OCOP(=O)(OCOC(=O)C(C)(C)C)OC[C@@]1(CCl)O[C@@H](n2ccc(N)nc2=O)[C@H](F)[C@@H]1O] | 646 [M + 46 − 1]. |
| 317 | 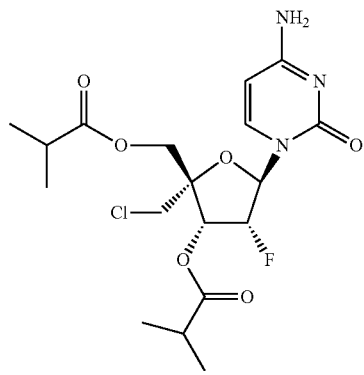 [SMILES: CC(C)C(=O)OC[C@@]1(CCl)O[C@@H](n2ccc(N)nc2=O)[C@H](F)[C@@H]1OC(=O)C(C)C] | 434 [M + 1] |
| 318 | 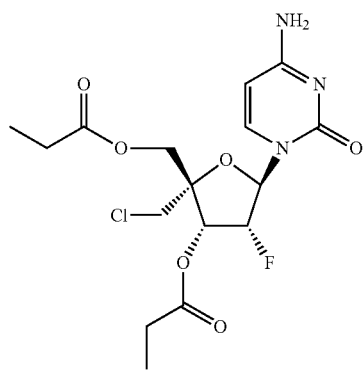 [SMILES: CCC(=O)OC[C@@]1(CCl)O[C@@H](n2ccc(N)nc2=O)[C@H](F)[C@@H]1OC(=O)CC] | 404 [M − 1] |

| Compound No. | Structure | Analytical Data |
|---|---|---|
| 319 | 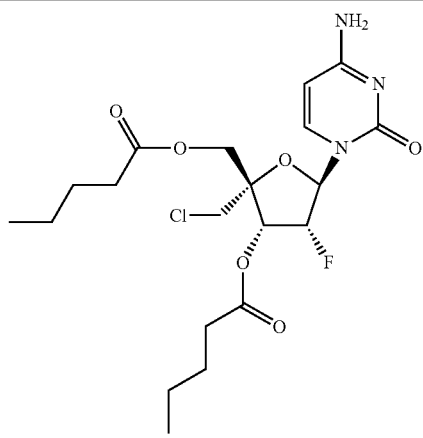 [SMILES: CCCCC(=O)OC[C@@]1(CCl)O[C@@H](n2ccc(N)nc2=O)[C@H](F)[C@@H]1OC(=O)CCCC] | 462 [M + 1] |
| 320 | 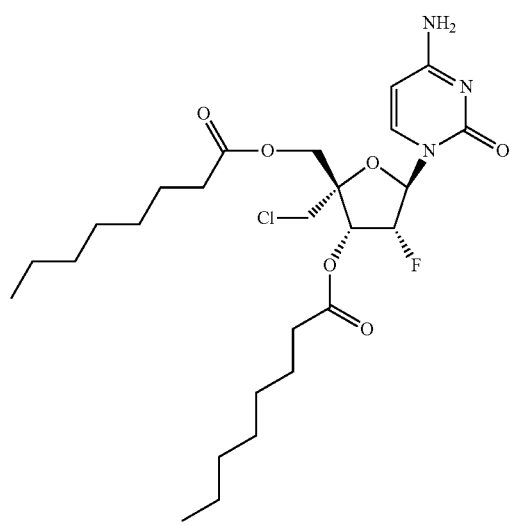 [SMILES: CCCCCCCC(=O)OC[C@@]1(CCl)O[C@@H](n2ccc(N)nc2=O)[C@H](F)[C@@H]1OC(=O)CCCCCCC] | 544 [M − 1] |
| 321 | 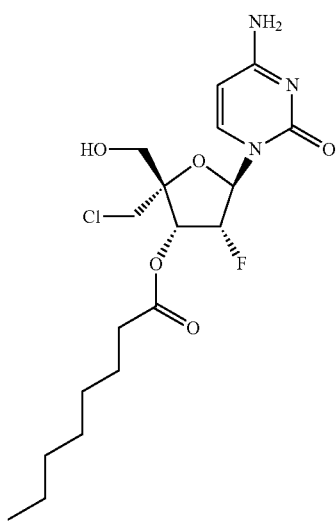 [SMILES: CCCCCCCC(=O)O[C@H]1[C@@H](F)[C@H](n2ccc(N)nc2=O)O[C@@]1(CO)CCl] | 418 [M − 1] |

| Compound No. | Structure | Analytical Data |
| --- | --- | --- |
| 322 | 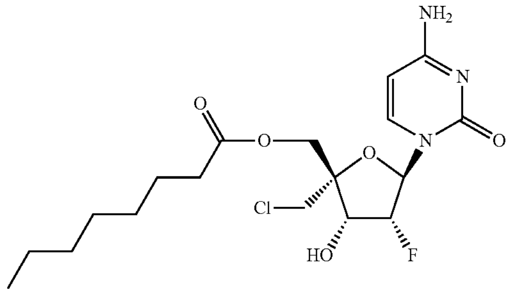 [SMILES: CCCCCCCC(=O)OC[C@@]1(CCl)O[C@@H](n2ccc(N)nc2=O)[C@H](F)[C@@H]1O] | 418 [M − 1] |
| 323 | 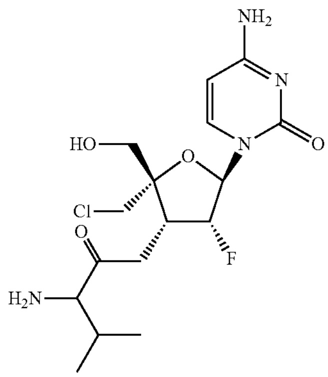 [SMILES: CC(C)C(N)C(=O)C[C@H]1[C@@H](F)[C@H](n2ccc(N)nc2=O)O[C@@]1(CO)CCl] | 391 [M − 1] |
| 324 | 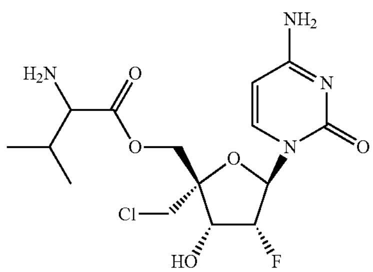 [SMILES: CC(C)C(N)C(=O)OC[C@@]1(CCl)O[C@@H](n2ccc(N)nc2=O)[C@H](F)[C@@H]1O] | 391 [M − 1] |
| 325 | 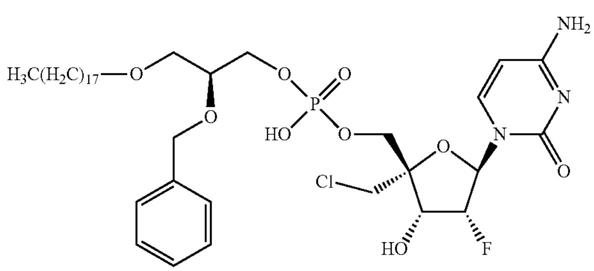 | 788.3 [M − H]+ |
| 326 | 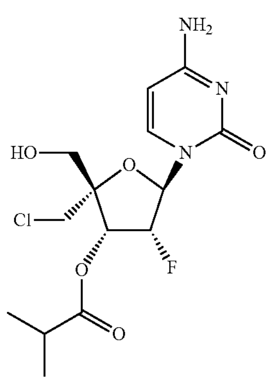 [SMILES: CC(C)C(=O)O[C@H]1[C@@H](F)[C@H](n2ccc(N)nc2=O)O[C@@]1(CO)CCl] | 362.1 [M + 1] |

| Compound No. | Structure | Analytical Data |
| --- | --- | --- |
| 327 | 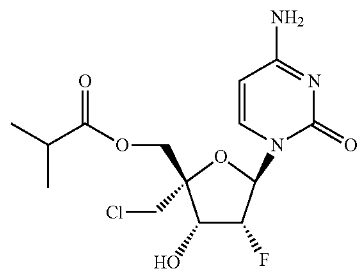 [SMILES: CC(C)C(=O)OC[C@@]1(CCl)O[C@@H](n2ccc(N)nc2=O)[C@H](F)[C@@H]1O] | 364 [M + 1] |
| 328 | 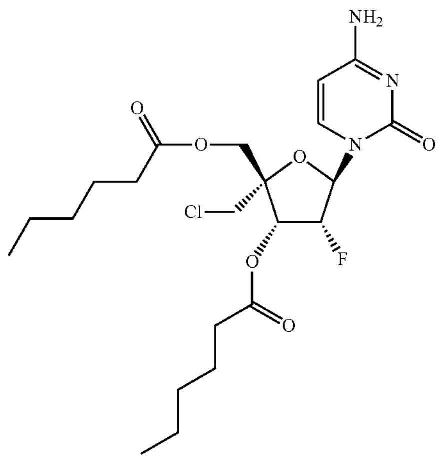 [SMILES: CCCCCC(=O)OC[C@@]1(CCl)O[C@@H](n2ccc(N)nc2=O)[C@H](F)[C@@H]1OC(=O)CCCCC] | 488 [M − 1] |
| 329 | 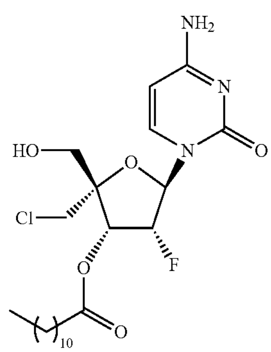 | 474 [M − 1] |
| 330 | 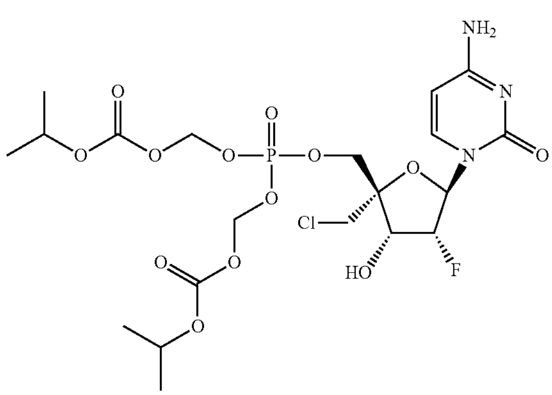 [SMILES: CC(C)OC(=O)OCOP(=O)(OCOC(=O)OC(C)C)OC[C@@]1(CCl)O[C@@H](n2ccc(N)nc2=O)[C@H](F)[C@@H]1O] | 606 [M + 1] |

| Compound No. | Structure | Analytical Data |
|---|---|---|
| 331 | 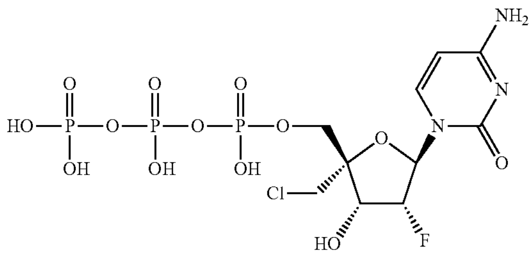 [SMILES: Nc1ccn([C@@H]2O[C@](CCl)(COP(=O)(O)OP(=O)(O)OP(=O)(O)O)[C@@H](O)[C@H]2F)c(=O)n1] | 532.1 [M − 1] |

Compounds 315-331 were prepared as described in U.S. Publication No. 2013/0165400, filed Dec. 20, 2012, PCT Publication WO 2013/096679, filed Dec. 20, 2012 and Publication No. WO 2013/142525, Mar. 19, 2013, which are hereby incorporated by reference in their entireties.

Example 185

Compounds 332 and 333

Compounds 332 and 333 were prepared as described in U.S. Publication No. 2012/0070415, filed Sep. 19, 2011, which are hereby incorporated by reference in its entirety.
332: 287 [M+H]$^+$, 573 [2M+H]$^+$; and 333: 525.3 [M−1].

Example 186

Compounds 346-350

| Compound No. | Structure | Analytical Data |
|---|---|---|
| 346 | 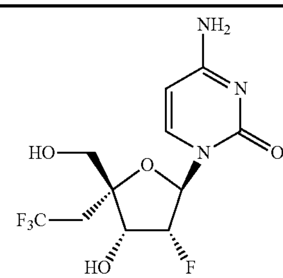 | 327.9 [M + H]$^+$ |
| 347 | 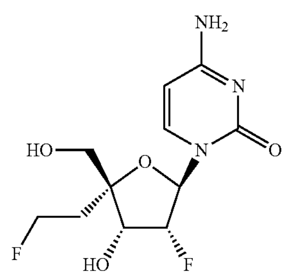 [SMILES: Nc1ccn([C@@H]2O[C@@](CO)(CCF)[C@@H](O)[C@H]2F)c(=O)n1] | 292 [M + H]$^+$ |
| 348 | 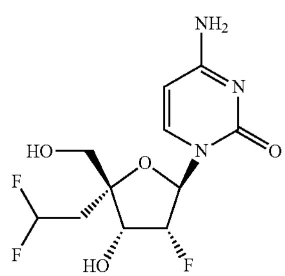 [SMILES: Nc1ccn([C@@H]2O[C@@](CO)(CC(F)F)[C@@H](O)[C@H]2F)c(=O)n1] | 309.9 [M + H]$^+$ |
| 349 | 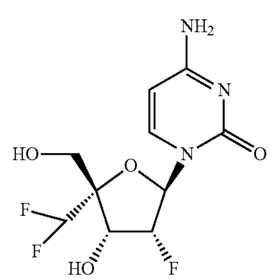 [SMILES: Nc1ccn([C@@H]2O[C@@](CO)(C(F)F)[C@@H](O)[C@H]2F)c(=O)n1] | 294.5 [M − H]$^+$ |

| Compound No. | Structure | Analytical Data |
|---|---|---|
| 350 | 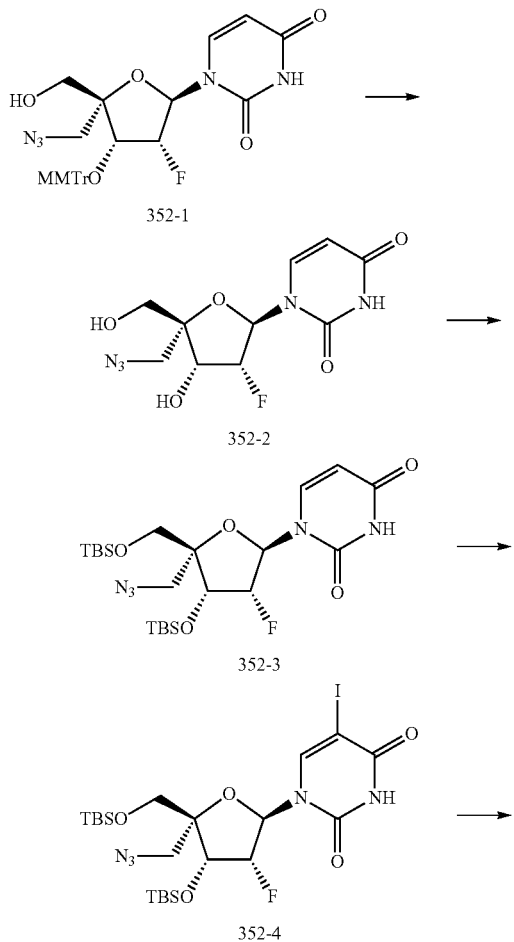 | 326.8 [M + H]+ |

Compounds 346-350 were prepared following one or more of the procedures described herein and using methods known to those skilled in the art.

Example 187

Compound 352

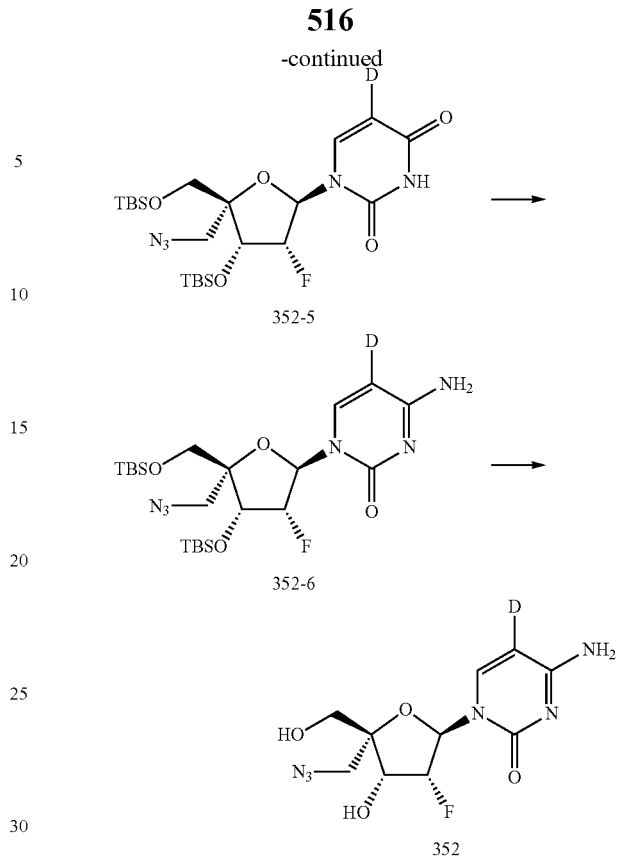

To a solution of 352-1 (1.2 g, 2.09 mmol) in DCE (40 mL) was added TFA (2 mL). The mixture was stirred at RT for 1 h. The mixture was concentrated under reduced pressure, and the residue was purified by column chromatography (3% MeOH in DCM) to give 352-2 (600 mg, 95.3%) as a white solid.

To a solution of 352-2 (600 mg, 1.99 mmol) in pyridine (4 mL) was added imidazole (677 mg, 9.95 mmol) and TBSCl (900 mg, 5.97 mmol) at RT. The mixture was stirred at 60° C. for 16 h, and then concentrated under reduced pressure. The residue was diluted with EA (40 mL) and washed with brine (20 mL). The organic layer was dried over anhydrous $MgSO_4$ and filtered. The filtrate was concentrated under reduced pressure, and the residue was purified by column chromatography (10% EA in PE) to give 352-3 (700 mg, 65.7%) as a white solid.

To a solution of 352-3 (700 mg, 1.32 mmol) in DCM (52 mL) was added NIS (356 mg, 1.58 mmol) and TFA (1.3 mL). The mixture was stirred at 60° C. for 3 h. After cooling to RT, the solution was extracted with DCM (30 mL), washed with sat. aq. $NaHCO_3$ and brine (20 mL), dried over anhydrous $Na_2SO_4$ and filtered. The filtrate was concentrated under reduced pressure. The residue was purified by column chromatography (10% EA in PE) to give 352-4 (400 mg, 46.2%) as a white solid.

A mixture of 352-4 (327 mg, 498 µmol), $Bu_3SnH$ (174 mg, 598 µmol) and 2,2'-azobis(2,4-dimethylvaleronitrile) (25 mg, 100 µmol) in THF-$d_8$ (10 mL) was stirred at 90-100° C. for 3 h. The mixture was concentrated under reduced pressure. and the residue was purified by column chromatography (10% EA in PE) to give 352-5 (180 mg, 68.00%) as a white solid.

To a solution of 352-5 (210 mg, 395 µmol) in anhydrous MeCN (2 mL) were added DMAP (121 mg, 989 µmol), $Et_3N$ (100 mg, 989 μmol) and 2,4,6-triisopropylbenzene-1-sulfonyl chloride (299 mg, 989 μmol) at RT. The mixture was stirred at RT for 16 h. NH$_3$·H$_2$O (1 mL) was added, and the mixture was stirred for 1 h. The mixture was diluted with EA (15 mL) and washed with sat. aq. NH$_4$Cl (15 mL). The organic layer was dried over anhydrous Na$_2$SO$_4$ and filtered. The filtrate was concentrated under reduced pressure, and the residue was purified by column chromatography (2% MeOH in DCM) to give the crude product. The crude product was purified by prep-TLC (10% MeOH in DCM) to give 352-6 (200 mg, 95.42%) as a white solid.

To a solution of 352-6 (200 mg, 0.38 mmol) in MeOH (2 mL) was added NH$_4$F (210 mg, 5.66 mmol) at RT. The mixture was stirred at 90-100° C. for 16 h. The mixture was filtered, and the filtrate was concentrated under reduced pressure. The residue was purified by column chromatography (10% MeOH in DCM) to give the crude product. The crude product was purified by prep-HPLC (neutral condition) to give 352 (70 mg, 61.8% yield, 78.4% deuterium) as a white solid. ESI-TOF-MS: m/z=302.1 [M+H]$^+$, 603.2 [2M+H]$^+$.

Example 188

Compound 353

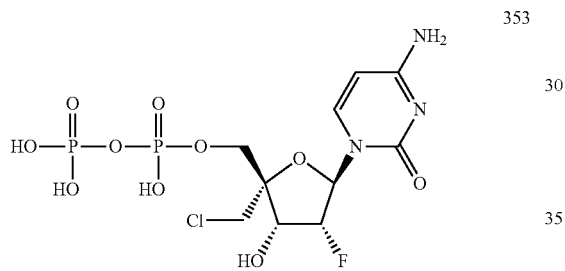
353

The diphosphate, 353, can be prepared using a similar procedure to preparing the triphosphate of Example 183 with the replacement of tetrabutylammonium salt of pyrophosphate with tetrabutylammonium phosphate (75 mg) and using 0.3 mL of DMF to get the homogeneous solution.

Example 189

Compound 354

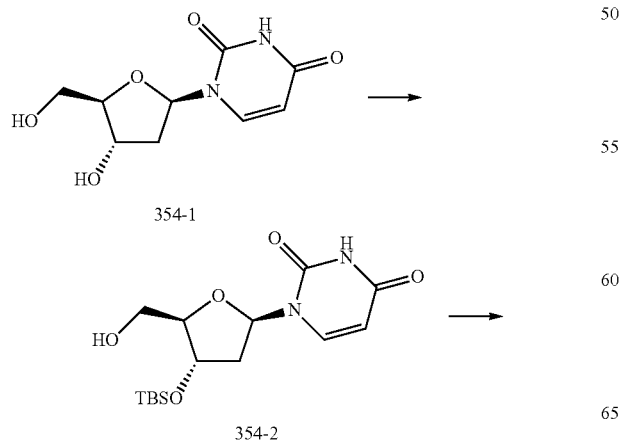

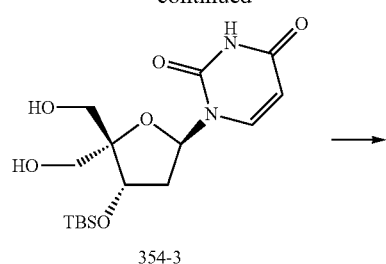
354-3

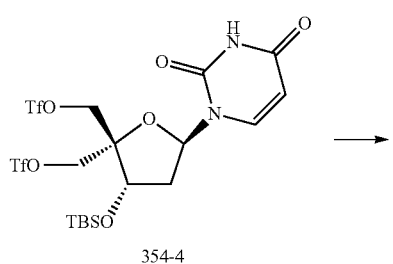
354-4

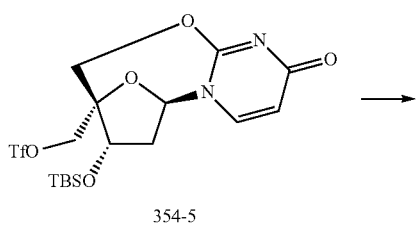
354-5

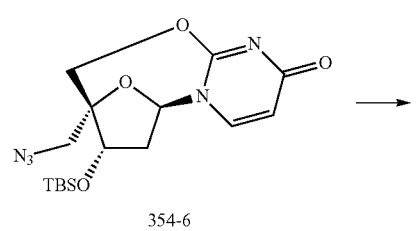
354-6

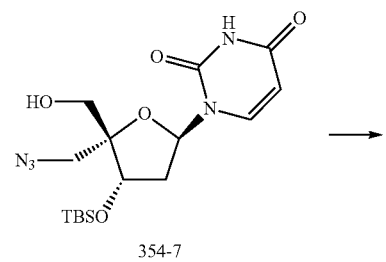
354-7

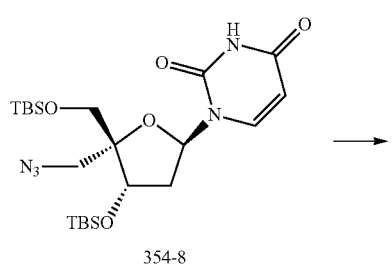
354-8

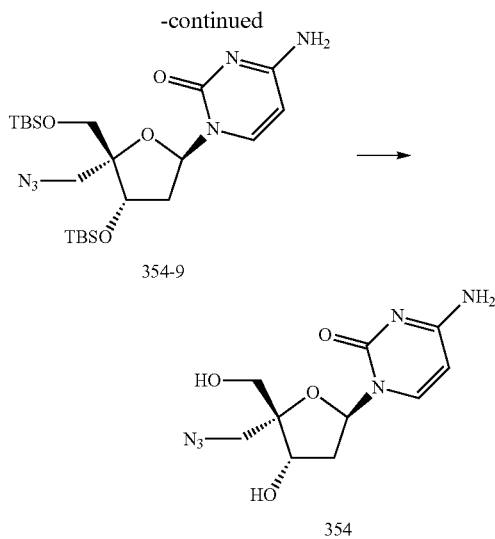

354-9

354

To a solution of 354-1 (22.80 g, 99.91 mmol) in anhydrous pyridine (200 mL) was added DMTCl (37.24 g, 109.90 mmol), and the mixture stirred at 25° C. for 12 h. The reaction was quenched with a sat. NH$_4$Cl solution (200 mL), and extracted with EA (3×200 mL). The combined organic layers were washed with brine (2×100 mL), dried over anhydrous Na$_2$SO$_4$ and concentrated under reduced pressure. The residue was purified by column chromatography (PE:EA=2:1 to 0:1) to give the desired product (43.00 g, 72.94 mmol) as a yellow foam.

To a solution of this product (20.00 g, 37.70 mmol), AgNO$_3$ (6.40 g, 37.70 mmol) and imidazole (5.13 g, 75.39 mmol) in DMF (200.00 mL) was added, followed by TBSCl (8.52 g, 56.54 mmol) at 0° C. The mixture was stirred at 25° C. for 12 h, and then the mixture was concentrated under reduced pressure to remove the DMF. The residue was diluted with ice-water (300 mL) and extracted with EA (3×100 mL). The combined organic layers were washed with brine (3×50 mL), dried over anhydrous Na$_2$SO$_4$, filtered and concentrated under reduced pressure. The residue was purified by column chromatography (PE:EA=3:1 to 1:1) to give 1-[(2R,4S,5R)-5-[[bis(4-methoxyphenyl)-phenyl-methoxy]methyl]-4-[tert-butyl(dimethyl)silyl]oxy-tetrahydrofuran-2-yl]pyrimidine-2,4-dione (15.70 g, 24.35 mmol) as a white solid.

A solution of 1-[(2R,4S,5R)-5-[[bis(4-methoxyphenyl)-phenyl-methoxy]methyl]-4-[tert-butyl(dimethyl) silyl]oxy-tetrahydrofuran-2-yl]pyrimidine-2,4-dione (20.00 g, 31.02 mmol) in AcOH (105 g, 1.40 mol) was stirred at 25° C. for 1 h. The reaction was quenched with MeOH (100 mL), and the mixture was concentrated under reduced pressure. The residue was diluted with water (100 mL). The solution was neutralized with solid NaHCO$_3$ to pH=7, and extracted with EA (3×100 mL). The combined organic layers were washed with brine (100 mL), dried over anhydrous Na$_2$SO$_4$ and concentrated at low pressure. The residue was purified by column chromatography (PE:EA=5:1 to 0:1) to give 354-2 (8.90 g, 20.79 mmol) as a white solid.

To a stirred solution of 354-2 (3.42 g, 9.99 mmol) in dioxane (15.00 mL) and DMSO (3.00 mL) was added DCC (6.18 g, 29.97 mmol) and Py.TFA (1.93 g, 9.99 mmol) at 0° C. The mixture was stirred at 25° C. for 2 h. The solution was diluted with EA (50 mL), and the solid was removed by filtration. The filtrate was washed with brine (30 mL). The organic layer was dried over anhydrous Na$_2$SO$_4$, and concentrated at low pressure. The residue was used in the next step without further purification.

To a solution of the residue from the previous step (3.4 g) and formaldehyde (aq., 3 mL) in dioxane (20 mL) was added 2.0 M NaOH (aq., 5 mL) in one portion at 25° C. The mixture was stirred at 25° C. for 16 h. The mixture was cooled to 0° C. and neutralized with AcOH to pH=7. The solution was treated with NaBH$_4$ (452 mg, 11.952 mmol) at 0° C. The mixture was stirred at 25° C. for 30 mins, and the reaction was then quenched with sat. aq. NH$_4$Cl (100 mL). The mixture was extracted with EA (2×100 mL). The organic phase was dried over anhydrous Na$_2$SO$_4$, filtered and concentrated in vacuum. The residue was purified by column chromatography (DCM:MeOH=20:1 to 10:1) to afford 354-3 (1.43 g, 38.4%) as a white solid.

To a solution of 354-3 (1.43 g, 3.84 mmol) in DCM (10.00 mL) was added Tf$_2$O (2.38 g, 8.45 mmol) and pyridine (1.51 g, 19.2 mmol) at 0° C., and the mixture stirred at 25° C. for 1 h. The reaction was quenched by ice-water (20 mL) at 0° C., and then extracted with DCM (2×30 mL). The combined organic layers were dried over anhydrous Na$_2$SO$_4$, filtered and concentrated under reduced pressure. The residue was purified by column chromatography (DCM:MeOH=40:1) to give 354-4 (1.60 g, 2.14 mmol) as a yellow foam.

To a solution of 354-4 (1.60 g, 2.51 mmol) in DCM (10.00 mL) was added TEA (1.27 g, 12.57 mmol), and the mixture was stirred at 25° C. for 16 h. The reaction was quenched with 1.0 M HCl solution to pH=7, and then extracted with DCM (30 mL). The organic layer was washed with brine (20 mL), dried over anhydrous Na$_2$SO$_4$, and concentrated at low pressure. The residue was purified by column chromatography (DCM:MeOH=40:1 to 30:1) to give 354-5 (1.10 g, 81.07%) as a yellow solid.

To a solution 354-5 (1.10 g, 2.27 mmol) in DMF (10.00 mL) was added NaN$_3$ (441.84 mg, 6.80 mmol), and the mixture was stirred at 25° C. for 12 h. The reaction was quenched with H$_2$O (3 mL), and extracted with EA (3×50 mL). The combined organic layers were washed with brine (50 mL), dried over anhydrous Na$_2$SO$_4$ and concentrated at low pressure to give 354-6 (800.00 mg, 92.87%) as a yellow solid.

To a solution of 354-6 (800.00 mg, 2.11 mmol) in THF (20.00 mL) was added NaOH solution (1.05 mL, 2.11 mmol, 2.0 M), and the mixture was stirred at 25° C. for 12 h. The mixture was diluted with EA (20 mL), and washed with brine (15 mL). The solution was dried over anhydrous Na$_2$SO$_4$ and concentrated under reduced pressure to give 354-7 (821.00 mg, 97.89%) as a yellow solid.

To a solution of 354-7 (596 mg, 1.50 mmol) in DCM (10 mL) was added TBSCl (452.16 mg, 3.00 mmol) and imidazole (306.36 mg, 4.50 mmol), and the mixture stirred at 25° C. for 5 h. The mixture was diluted with DCM (20 mL). The solution was washed with brine, dried over anhydrous Na$_2$SO$_4$ and concentrated under reduced pressure. The residue was purified by column chromatography (DCM: MeOH=40:1 to 30:1) to give 354-8 (750 mg, 87.93%) as a white solid.

To a solution of 354-8 (600 mg, 1.17 mmol) and TEA (296 mg, 2.93 mmol) in CH$_3$CN (10 mL) was added TPSCl (862 mg, 2.93 mmol). The mixture was heated to 40° C. for 5 h. The reaction was quenched with 0.5 M HCl solution to pH=6. The solution was extracted with EA (3×20 mL). The organic layer was dried over anhydrous Na$_2$SO$_4$ and concentrated at low pressure. The residue was treated with NH$_3$/THF (20 mL, 10 M). The solution was stirred at 25° C. for 16 h, and then concentrated under reduced pressure. The residue was purified by column chromatography (DCM:

MeOH=30:1 to 20:1) to give the crude product (500 mg). The crude product was purified by prep-TLC (DCM: MeOH=10:1) to give 354-9 (310 mg, 52%) as a white solid.

To a solution of 354-9 (310 mg, 606.9 μmol) in THF (5 mL) was added TBAF in THF (2 mL, 1.0 M) at 25° C. The solution was stirred at 25° C. for 0.5 h. The mixture was concentrated at low pressure. The residue was purified by prep-HPLC (HCl system) to give 354 (86 mg, 50.2%) as a white solid. ESI-TOF-MS: m/z=283.1 [M+H]$^+$, 565.3 [2M+H]$^+$.

Example 190

Compounds 355 and 356

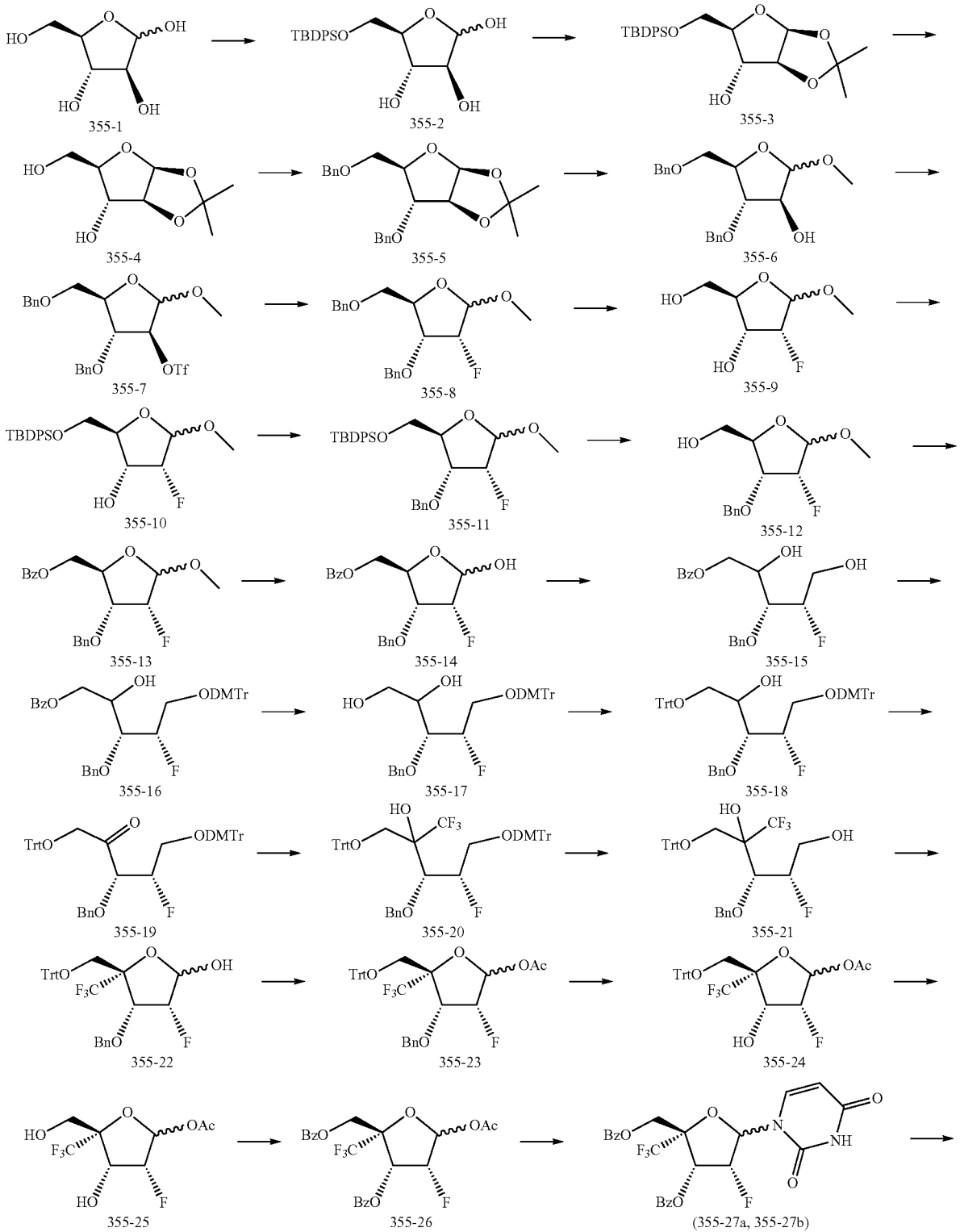

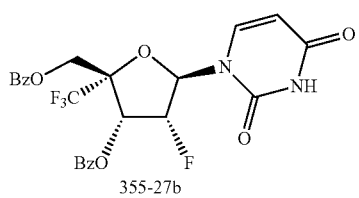
355-27b

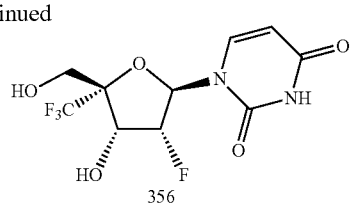
356

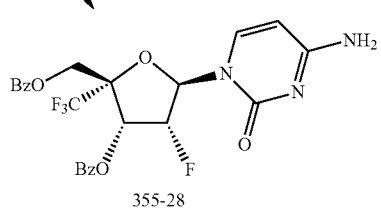
355-28

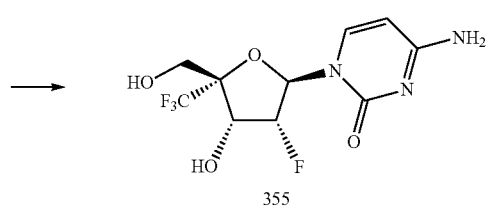
355

To a solution of 355-1 (394 g, 2.62 mol) and imidazole (268 g, 3.93 mol) in DMF (3 L), was added TBDPSCl (756.14 g, 2.75 mol) in one portion at 25° C. The mixture was heated to 50° C. and stirred for 12 h. The mixture was poured into water/brine (v:v=1:1) (6 L) and stirred for 20 mins. The mixture was extracted with EA (2×4 L). The combined organic phase was washed with sat. brine (2×4 L), dried over anhydrous $Na_2SO_4$ and concentrated in vacuum to give 355-2 (800 g, crude) as a yellow solid.

To a solution of 355-2 (1000 g, 2.57 mol) and 2,2-dimethoxypropane (450 g, 4.32 mol) in DCM (6 L), was added TsOH.$H_2O$ (490 g, 2.57 mol) in one portion at 25° C. The mixture was stirred for 0.5 h. The reaction was quenched by water (1 L). The organic layer was washed with water (2×4 L), dried over anhydrous $Na_2SO_4$ and concentrated in vacuum to give 355-3 (1.1 kg, crude), which was used directly for next step.

A mixture of 355-3 (1.0 kg, 2.33 mol) and $NH_4F$ (198 g, 5.36 mol) in MeOH (3 L) was stirred to reflux for 4 h. After the solvent was evaporated, the crude product was purified by silica gel (PE:EA=1:1) directly to give crude 355-4, which was recrystallized (PE:EA=1:1) to give pure 355-4 (170 g, 38.4% yield) as a white solid. $^1$H-NMR (400 MHz, CD3OD), δ=5.90 (d, J=4 Hz, 1H), 4.52 (d, J=4 Hz, 1H), 4.15 (s, 1H), 4.0-3.97 (m, 1H), 3.75-3.65 (m, 2H), 1.50 (s, 3H), 1.31 (s, 3H).

To a solution of 355-4 (300 g, 1.58 mol) in DMF (4 L) was added NaH (83.3 g, 3.47 mol) by portions at 0° C., and the mixture was stirred at 25° C. for 1 h. BnBr (553 g, 3.23 mol) was added, and the mixture was stirred at 25° C. for 1 h. The reaction was quenched by $NH_4Cl$ (sat., 1 L) and water (2 L). The solution was extracted with EA:PE (2×3 L, v:v=1:1). The combined organic layer was concentrated in vacuum. The residue was purified by silica gel chromatography (PE:EA=50:1) to afford 355-5 (505 g, 79.4%) as a yellow oil.

To a solution of 355-5 (330 g, 891 mmol) in MeOH (1500 mL) was added $H_2SO_4$ (conc. 20 mL, 406 mmol) dropwise at 25° C. The mixture was heated to 60° C. for 2 h. After the mixture was cooled to 25° C., the mixture was adjusted to pH to 7-8 with HCl (2 N, ~160 mL). The solution was diluted with EA (1.5 L). The organic layer was washed with $H_2O$ (2×1 L), dried over anhydrous $Na_2SO_4$ and concentrated in vacuum. The residue was purified by silica gel chromatography (PE:EA=5:1) to afford pure 355-6 (280 g, 78.3%) as a yellow oil.

To a solution of 355-6 (150 g, 435.54 mmol) and DMAP (69.2 g, 566 mmol) in DCM (1.5 L) was added $Tf_2O$ (135.2 g, 479 mmol) slowly at −10° C. under $N_2$. The mixture was warmed to 25° C. and stirred for 1.5 h. The reaction was quenched with water (600 mL), and adjusted pH to 4-5 with HCl (1 N). The organic layer was separated, and washed with $NaHCO_3$ (sat., 1 L), brine (1 L), and dried over anhydrous $Na_2SO_4$. The solution was concentrated in vacuum to give 355-7 (207 g, crude) as a yellow oil.

A mixture of 355-7 (207 g, 435.50 mmol) and TBAF (1 M in THF, 870 mL) was stirred at 60-70° C. for 12 h. The solvent was evaporated at low pressure. The residue was dissolved in EA (800 mL). The solution was washed withy water (3×500 mL), brine (500 mL) and dried over anhydrous $Na_2SO_4$. The solution was concentrated at low pressure. The residue was purified by silica gel chromatography (PE:EA=20:1) to afford 355-8 (40 g, 25.46%) as a light yellow oil. $^1$H-NMR (400 MHz, $CD_3OD$) δ=7.36-7.33 (m, 10H), 5.05 (d, J=8 Hz, 1H), 4.87 (m, 0.5H), 4.80-4.70 (m, 1.5H), 4.62-4.53 (m, 3H), 4.36-4.30 (m, 1H), 4.18-4.05 (m, 2H), 3.70-3.53 (m, 2H), 3.36 (s, 3H). $^{19}$F NMR (376 MHz, $CDCl_3$) δ=−209.48.

To a solution of 355-8 (50 g, 144.35 mmol) in MeOH (50 mL) was added $Pd(OH)_2$/C (13 g, 50% $H_2O$) under Ar. The suspension was degassed under vacuum and purged with $H_2$ several times. The mixture was stirred under $H_2$ (40 psi) at 40° C. for 8 h. After the catalyst was filtered off, the filtrate was concentrated in vacuum to give 355-9 (23 g, 91%) as a gray solid.

To a solution of 355-9 (55 g, 331 mmol) and imidazole (31.55 g, 463.4 mmol) in DCM (1 L) was added TBDPSCl (100 g, 364.13 mmol) slowly at 0° C. The mixture was stirred at 25° C. for 12 h. The reaction was quenched with water (100 mL), and then the mixture was concentrated. The residue was dissolved in EA (500 mL). The solution was washed with water (2×500 mL), dried over anhydrous $Na_2SO_4$ and concentrated at low pressure. The residue was purified by silica gel chromatography (PE:EA=5:1) to afford 355-10 (74 g, 55%) as a colorless oil.

To a solution of 355-10 (70 g, 173 mmol) in DMF (750 mL) was added NaH (7.61 g, 190 mmol) at 0° C., and the mixture stirred at 25° C. for 1 hr. BnBr (32.55 g, 190.33 mmol) was added slowly at 0° C. under $N_2$. The mixture was stirred at 25° C. for 2 h, and the reaction was quenched with water (1000 mL). The solution was extracted by EA:PE (v:v=2:1, 2×800 mL). The organic layer was separated and washed with brine:water (v:v=1:1, 2×500 mL). The organic layer was dried over anhydrous $Na_2SO_4$ and concentrated at low pressure to give 355-11 (80 g, crude) as a yellow oil.

A mixture of 355-11 (100 g, 202.1 mmol) and $NH_4F$ (15 g, 404.3 mmol) in MeOH (2000 mL) was stirred at 65° C. for 12 h. The mixture was cooled to 25° C. and concentrated under reduced pressure. The residue was diluted with EA (500 mL) and washed with water (2×500 mL). The organic phase was washed with sat. brine (500 mL), dried with anhydrous $Na_2SO_4$, filtered and concentrated in vacuum. The residue was purified by silica gel chromatography (PE:EA=8:1) to afford 355-12 (36 g, 69.5%) as a yellow oil.

To a solution of 355-12 (36 g, 148.4 mmol) and TEA (22.51 g, 222.4 mmol) in DCM (300 mL) was added BzCl (23 g, 163.1 mmol) dropwise at 25° C. under $N_2$, and the mixture was stirred at 25° C. for 12 h. The reaction was quenched with water (500 mL). The organic layer was separated, washed by water (400 mL) and dried over anhydrous $Na_2SO_4$. The organic layer was concentrated under reduced pressure to give 355-13 (55 g, crude) as a yellow oil.

A mixture of 355-13 (55 g, 152.62 mmol) in $TFA:H_2O$ (500 mL, v:v=9:1) was stirred at 25° C. for 30 h. The solution was evaporated in vacuum. The residue was diluted with EA (200 mL), and washed with $NaHCO_3$ (aq., 200 mL). The organic layer was dried over anhydrous $Na_2SO_4$, and concentrated at low pressure. The residue was purified by silica gel (PE:EA=10:1) to afford 355-14 (45 g, 80.8% yield) as a yellow oil.

To a solution of 355-14 (45 g, 129.9 mmol) in EtOH (500 mL) was added $NaBH_4$ (5.41 g, 142.9 mmol) at 25° C., and the mixture was stirred at 25° C. for 0.5 h. The reaction was quenched with aq. $NH_4Cl$ (500 mL), and extracted with EA (2×300 mL). The organic layer was washed with brine (300 mL), and concentrated under reduced pressure. The residue was purified by column chromatography (PE:EA=2:1) to give 355-15 (42 g, 94% yield) as a white solid. $^1$H-NMR (400 MHz, MeOD), δ=8.05 (d, J=7.2 Hz, 2H), 7.65-7.20 (m, 9H), 4.95 (m, 0.5H), 4.80-4.65 (m, 2H), 4.53-4.47 (m, 2H), 4.15-4.07 (m, 1H), 4.00-3.85 (m, 3H). $^{19}$F NMR (376 MHz, MeOD) δ=−196.75.

A mixture of 355-15 (90 g, 258.4 mmol) in pyridine (500 mL) was treated with DMTrCl (92 g, 271 mmol) at 25° C. for 16 h. The solvent was evaporated in vacuum. The residue was dissolved in EA (500 mL). The solution was washed with water (2×300 mL), dried over anhydrous $Na_2SO_4$ and concentrated at low pressure to give 355-16 (145 g, crude) as a yellow solid.

To a solution of 355-16 (145 g, 223 mmol) in MeOH:THF (2000 mL, v:v=3:1) was added NaOMe (12 g, 53.8 mmol) in one portion. The mixture was stirred at 25° C. for 1 h, and the reaction was quenched with $CO_2$ (solid). The mixture was concentrated at low pressure. The residue was dissolved in EA (200 mL). The solution was washed with water (300 mL) and brine (300 mL), dried over anhydrous $Na_2SO_4$ and concentrated at low pressure. The residue was purified by silica gel chromatography (PE:EA=5:1) to give 355-17 (85 g, 70%) as a yellow oil.

To a solution of 355-17 (35.0 g, 64 mmol) in pyridine (200 mL) was added TrtCl (21.42 g, 76.84 mmol) in one portion at 20° C. The mixture was stirred at 20° C. for 15 h. The solution was evaporated in vacuum. The residue was dissolved in EA (300 mL). The solution was washed with water (2×200 mL). The organic layer was dried over anhydrous $Na_2SO_4$ and concentrated at low pressure. The residue was purified by silica gel chromatography (PE:EA=20:1) to give 355-18 (31 g, 89.5%) as a yellow oil.

To a solution of 355-18 (31 g, 41.8 mmol) in $CH_3CN$ (500 mL) was added IBX (11.7 g, 41.8 mmol) in one portion at 20° C., and the mixture was stirred at 80° C. for 2 h. The mixture was cooled, and then filtered. The filtrate was concentrated at low pressure to give 355-19 (32 g, crude) as a yellow oil.

To a solution of 355-19 (32 g, 40.6 mmol) and CsF (18.53 g, 122 mmol) in THF (300 mL) was added $TMSCF_3$ (17.35 g, 122 mmol) at 15° C., and the mixture was stirred at 15° C. for 18 h. The reaction was quenched with MeOH (5 mL). The solution was extracted with EA (300 mL), and washed with water (2×200 mL). The organic layer was dried over anhydrous $Na_2SO_4$ and concentrated at low pressure. The residue was purified by column chromatography (PE:EA=8:1) to give 355-20 (25 g, 71.7%) as a yellow oil. $^{19}$F NMR (376 MHz, $CDCl_3$) δ=−74.93, −74.95, −186.74, −186.83.

To a solution of 355-20 (50 g, 58.35 mmol) in THF (50 mL) was added AcOH (200 mL, 80%), and the mixture was stirred at 15° C. for 16 h. The mixture was then heated to 45° C. and stirred for 2 h. The solvent was evaporated in vacuum (MeOH was added (5×5 mL) during evaporation). The residue was purified by column chromatography (PE:EA=20:1) to give 355-21 (down spot, desired isomer) (7.4 g, 22.9%) as a yellow solid and the by-product (17.1 g, 52.84%) (up spot) as a yellow solid. Down spot: $^1$H-NMR (400 MHz, $CDCl_3$), δ=7.50-7.25 (m, 20H), 4.85-4.65 (t, 2H), 4.48-4.40 (m, 1H), 4.35 (m, 0.5 H), 4.25 (m, 0.5H), 3.75-3.65 (m, 3H), 3.20 (d, J=12 Hz, 1H). $^{19}$F-NMR (376 MHz, MeOD), δ=−75.55, −190.067. Up spot: $^1$H-NMR (400 MHz, $CDCl_3$), δ=7.50-7.25 (m, 20H), 4.98-4.80 (m, 1H), 4.67 (d, J=12 Hz, 1H), 4.42-4.39 (m, 1H), 4.33-4.29 (m, 1H), 3.85-3.71 (m, 2H), 3.65-3.60 (m, 1H), 3.54-5.52, (m, 2H). $^{19}$F-NMR (376 MHz, MeOD), δ=−75.455 (s, 3F), −189.53 (s, 1F).

To a solution of 355-21 (8.50 g, 15.3 mmol) in THF: DMSO (60 mL) was added IBX (4.29 g, 15.3 mmol), and the mixture was stirred at 35° C. for 2 h. The solution was slowly warmed to 40° C., and the mixture was stirred for 2 h. The mixture was filtered, and the filtrate was concentrated under reduced pressure. The residue was diluted with EA (100 mL) and washed with water (100 mL). The organic phase was dried over anhydrous $Na_2SO_4$, and concentrated under reduced pressure. The residue was purified by column chromatography (PE:EA=25:1) to give 355-22 (8.0 g, 75%) as a yellow oil.

To a solution of 355-22 (4.50 g, 8.14 mmol) in pyridine (50 mL) was added $Ac_2O$ (2.49 g, 24.4 mmol). The mixture was stirred at 15° C. for 3 h. The reaction was quenched with MeOH (1 mL), and the solvent was evaporated via vacuum. The residue was dissolved in EA (40 mL). The solution was washed with water (50 mL), dried over anhydrous $Na_2SO_4$, and concentrated at low pressure. The residue was purified by column chromatography (PE:EA=20:1) to give 355-23 (4.30 g, 88.8%) as a colorless oil. $^1$H-NMR (400 MHz, $CDCl_3$), δ=7.50-7.20 (m, 20H), 6.45 (d, J=12 Hz, 1H), 4.90 (m, 0.5H), 4.77 (m, 0.5H), 4.70-4.55 (m, 3H), 3.40 (dd, J=40 Hz, 2H), 1.79 (s, 3H). $^{19}$F-NMR (376 MHz, MeOD), δ=−73.92 (d, J=18 Hz, 3F), −204.95 (t, 1F).

To a solution of 355-23 (900 mg, 1.51 mmol) in MeOH (20 mL) was added $Pd(OH)_2$/C (50%, 0.6 g) under $N_2$ atmosphere. The suspension was degassed and purged with $H_2$ (3×). The mixture was stirred under $H_2$ (40 psi) at 40° C. for 24 h, and then filtered. The filtrate was concentrated in vacuum. The residue was purified by column chromatography (PE:EA=10:1) to give 355-24 (300 mg, 39.4%) as a yellow oil.

To a solution of 355-24 (200 mg, 396.5 μmol) in DCM (2 mL) was added TFA (153 mg, 1.34 mmol) and Et₃SiH (365 mg, 3.14 mmol). The mixture was stirred at 15° C. for 20 mins. The solvent was evaporated directly in vacuum. The residue was purified by column chromatography (PE:EA=1:1) to give 355-25 (100 mg, 96%) as a white solid.

To a solution of 355-25 (100 mg, 381 μmol) in DCM (2 mL) was added DMAP (46.60 mg, 381 μmol) and TEA (115.8 mg, 1.14 mmol). BzCl (117.96 mg, 839.19 mol) was added, and the mixture was stirred at 15° C. for 0.5 h. The reaction was quenched with HCl (0.3 N, 10 mL). The mixture was extracted with CH₂Cl₂ (3×10 mL), and washed with water (10 mL). The organic phase was dried over anhydrous Na₂SO₄, and concentrated at low pressure. The residue was purified by column chromatography (PE:EA=20:1) to give 355-26 (144 mg, 81%) as a yellow oil. $^1$H-NMR (400 MHz, CDCl₃), δ=8.12 (d, J=7.6 Hz, 1H), 8.04 (d, J=7.6 Hz, 1H), 7.70-7.39 (m, 6H), 6.57 (d, J=11 Hz, 1H), 6.02 (dd, $J_1$=22.8 Hz, $J_2$=4.8 Hz, 1H), 5.28 (dd, $J_1$=52 Hz, $J_2$=4.4 Hz, 1H), 4.74 (t, 2H), 1.96 (s, 3H). $^{19}$F-NMR (376 MHz, MeOD), δ=−74.18 (d, J=18.8 Hz, 3F), −204.08 (t, 1F).

A mixture of uracil (457.54 mg, 4.08 mmol) and HMDS (3.85 g, 23.86 mmol) was stirred at 120° C. for 1 h, and the solvent was evaporated at low pressure. 355-26 (480 mg, 1.02 mmol) was dissolved in CH₃CN (2 mL), and treated with the above mixture. The mixture was taken up into a microwave tube, and was treated with TMSOTf (1.60 g, 7.19 mmol). The mixture was heated at 140° C. for 4 h under microwave irradiation. The reaction was quenched with MeOH, and the mixture was concentrated directly at low pressure. The residue was purified by column chromatography (PE:EA=5:1) to give the crude product (2.5 g), which was purified by prep-HPLC (TFA) to give two isomers (0.92 g). After the residue was purified by SFC (AD-H_6_30-65 6MIN, OJ (250 mm*50 mm, 10 um), Base-MeOH), 355-27a (α-isomer, 470 mg, 22%) and 355-27b (β-isomer, 320 mg, 15%) were obtained as a white solid. 355-27a (α-isomer): $^1$H-NMR (400 MHz, CDCl₃), δ=8.63 (s, 1H), 8.20-8.00 (m, 4H), 7.75-6.95 (m, 6H), 6.63 (d, J=20.8 Hz, 1H), 6.10 (dd, $J_1$=23.6 Hz, $J_2$=4 Hz, 1H), 5.86 (d, J=6.8 Hz, 1H), 5.47 (d, J=54 Hz, 1H), 4.80 (s, 2H). $^{19}$F-NMR (376 MHz, MeOD), δ=−73.65 (d, J=16.4 Hz, 3F), −212.54 (t, 1F). 355-27b (β-isomer): $^1$H-NMR (400 MHz, CDCl₃), δ=8.48 (s, 1H), 8.15-8.00 (m, 4H), 7.60-7.25 (m, 6H), 6.22 (dd, $J_1$=16 Hz, $J_2$=6.4 Hz, 1H), 5.95-5.20 (m, 3H), 4.80 (s, 2H). $^{19}$F-NMR (376 MHz, MeOD), δ=−73.31 (d, J=11 Hz, 3F), −192.56 (t, 1F).

A mixture of 355-27b (180 mg, 344 μmol, 1.0 eq.) in NH₃/MeOH (7 M, 5 mL) was stirred at 15° C. for 16 h. The solvent was concentrated directly in vacuum. The residue was purified by prep-HPLC (neutral condition, NH₄HCO₃) to give 356 (86 mg, 79.4%) as a white solid. ESI-MS: m/z 315.1 [M+H]⁺.

To a solution of 355-27b (200 mg, 383 μmol) in CH₃CN (2 mL) was added DMAP (116 mg, 957 μmol), TEA (97 mg, 957 μmol), and 2,4,6-triisopropylbenzenesulfonyl chloride (290 mg, 957 μmol), and the mixture stirred at 15° C. for 20 mins. The mixture was treated with NH₃.H₂O (2 mL), and the mixture was stirred at 15° C. for 10 mins. The mixture was extracted with EA (2×10 mL). The organic phase was dried over anhydrous Na₂SO₄ and concentrated at low pressure. The residue was purified by column chromatography (PE:EA=2:1) and re-purified by prep-TLC (DCM:MeOH=15:1) to give 355-28 (90 mg, 45%) as a white solid.

A mixture of 355-28 (90 mg, 172.61 μmol) in NH₃/MeOH (7 M, 3 mL) was stirred at 15° C. for 16 h. The solvent was concentrated directly in vacuum. The residue was purified by prep-HPLC (HCl condition) to give 355 (30 mg, 55%) as a white solid. ESI-MS: m/z 314.0 [M+H]⁺.

Example 191

Compound 357

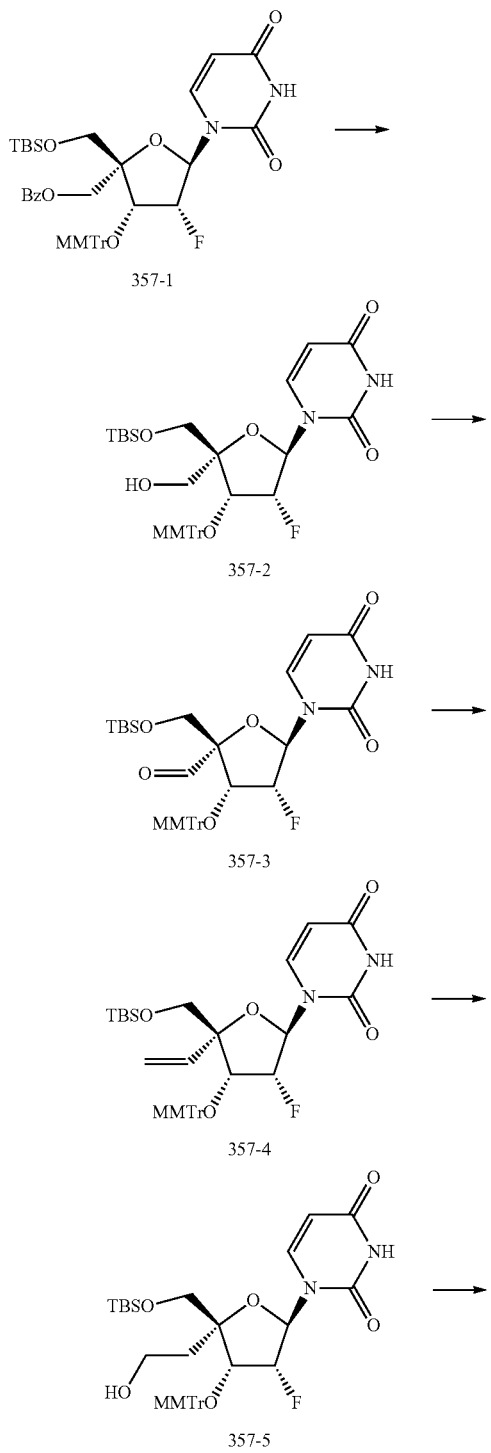

357-1

357-2

357-3

357-4

357-5

-continued

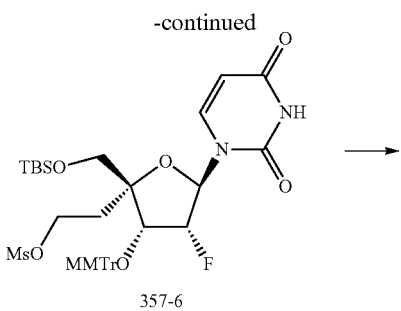

357-6

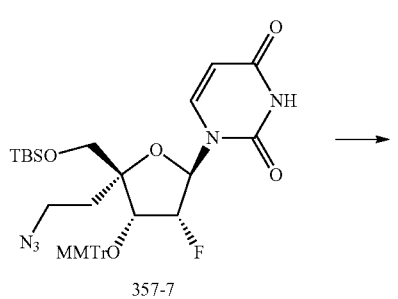

357-7

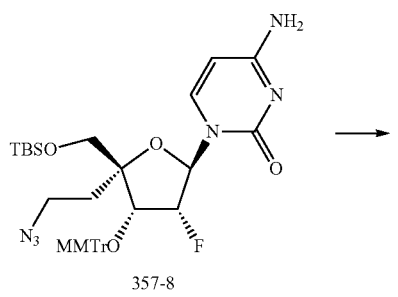

357-8

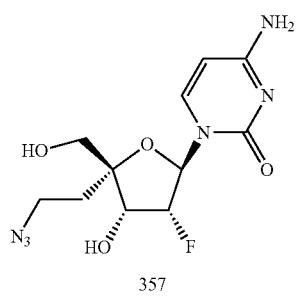

357

357-1 (2.3 g, 3.0 mmol) was treated with NH₃ in MeOH (50 mL, 10 M) at 25° C. The mixture was stirred at 25° C. for 24 h. The mixture was concentrated under reduced pressure. The residue was purified by column chromatography (10%-30% EtOAc in PE) to afford 357-2 (1.5 g, 70.8%) as a white solid.

To a stirred solution of 357-2 (1.5 g, 2.26 mmol) in anhydrous DCM (15.00 mL) was added Dess-Martin (1.6 g, 3.84 mmol) in one portion at 0° C. under N₂. The mixture was stirred at 25° C. for 1.5 h. The reaction was quenched with sat.Na₂S₂O₃ and sat.NaHCO₃ (v:v=1:1, 20 mL) at 0° C. The aqueous phase was extracted with DCM (3×30 mL). The combined organic phase was washed with sat. brine, dried over anhydrous Na₂SO₄, filtered and concentrated in vacuum to give 357-3 (1.6 g, crude), which was used in the next step without further purification.

To a solution of methyl (triphenyl)phosphonium; bromide (3.4 g, 9.4 mmol) in anhydrous THF (12 mL) was added n-BuLi (2.5 M, 3.8 mL) dropwise at 0° C. under N₂. The mixture was stirred at 0° C. for 1 h. 357-3 (1.55 g, 2.35 mmol) in THF (8 mL) was added to the mixture dropwise at 0° C. The solution was warmed and stirred at 25° C. for 12 h. The reaction was quenched with a sat.NH₄Cl solution. The mixture was extracted with EA (3×50 mL). The combined organic phase was washed with brine, dried with anhydrous Na₂SO₄, filtered and concentrated in vacuum. The residue was purified by column chromatography (10%-20% EtOAc in PE) to give 357-4 (1.1 g, 71.05%) as a white solid.

357-4 (501 mg, 758.9 μmol) was dissolved in 9-BBN (0.5 M, 15 mL) in one portion at 25° C. under N₂. The mixture was heated at 80° C. in microwave for 30 mins. Sat. aq. NaHCO₃ (5 mL) and H₂O₂ (30%, 2.5 mL) was added at 0° C. The mixture was stirred at 25° C. for 2 h. The reaction was quenched with sat. Na₂S₂O₃ at 0° C. The mixture was diluted with EA and water. The aqueous phase was back-extracted with EA. The combined organic phase was washed with brine, dried with anhydrous Na₂SO₄, filtered and concentrated in vacuum. The residue was purified by column chromatography (10%-25% EtOAc in PE) to give 357-5 (395 mg, 76.9%) as a white solid.

To a solution of 357-5 (360 mg, 531.8 μmol) in anhydrous DCM (4 mL) was added TEA (215 mg, 2.13 mmol) and MsCl (73 mg, 638.26 μmol) in DCM (1 mL) dropwise at 0° C. The mixture was stirred at 25° C. for 2 h. The reaction was quenched with ice water and extracted with CH₂Cl₂. The organic layer was washed with brine and dried over anhydrous MgSO₄. The solution was filtered and concentrated to 357-6 (395 mg, crude) as a brown solid, which was used in the next step without further purification.

To a solution of 357-6 (380 mg, 504 μmol) in anhydrous DMF (4 mL) was added NaN₃ (98 mg, 1.51 mmol) at 25° C. The mixture was stirred at 70° C. for 3 h. The reaction was quenched with water and extracted with EA. The organic layer was washed with brine, dried over MgSO₄ and filtered. The filtrate was concentrated at low pressure. The residue was purified by column chromatography (10%-30% EtOAc in PE) to give 357-7 (295 mg, 83.5%) as a white solid.

To a stirred solution of 357-7 (295 mg, 420.3 μmol) in anhydrous CH₃CN (3 mL) was added DMAP (102.7 mg, 840.6 μmol), TEA (85.1 mg, 840.6 μmol) and TPSCl (247.9 mg, 840.6 μmol) at 25° C. The mixture was stirred at 25° C. for 3 h. NH₃.H₂O (10 mL, 28%) was added, and the mixture was stirred for 1 h. The mixture was diluted with EA, and washed with brine, dried over anhydrous Na₂SO₄, filtered and concentrated in vacuum. The residue was purified by column chromatography (1%-2% MeOH in DCM) to give 357-8 (260 mg, 88.3%) as a white solid.

357-8 (240 mg, 342.4 μmol) was treated with 80% HCOOH (10 mL) at 25° C. The mixture was stirred at 70° C. for 2 h. The reaction was cooled to 25° C. and then concentrated under reduced pressure. The residue was purified on a silica gel column (2%-6% MeOH in DCM) to give 357 (85 mg, 79.1%) as a white solid. ESI-TOF-MS: m/z=314.9 [M+H]⁺, 629.1 [2M+H]⁺.

Example 192

Compound 358

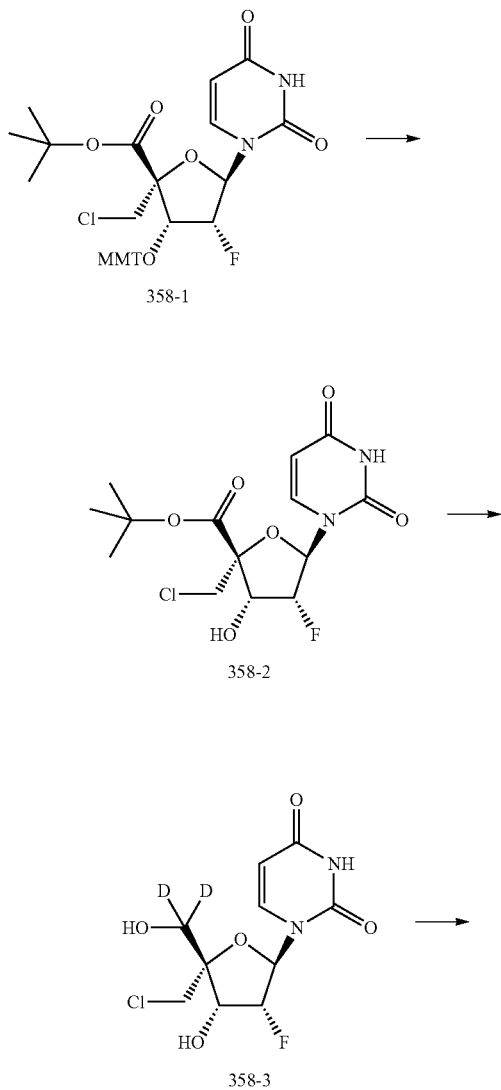

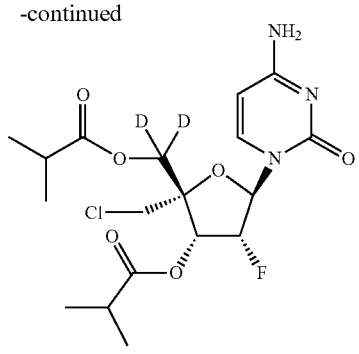

358

A solution of 358-1 (0.68 g, 1.07 mmol) in AcOH (10 mL) and TFA (0.25 mL) was stirred 1 h at RT. The mixture was evaporated, and the residue coevaporated with MeCN and toluene. Purification on silica column with MeOH:CH$_2$Cl$_2$ solvent system (2-12% gradient) afforded 358-1 (0.32 g, 82%).

A mixture of 358-1 (0.32 g, 0.9 mmol) in THF (9 mL) and LiBH$_4$ (94 mg, 3.6 mmol) was stirred 2 d at RT. The reaction was quenched with AcOH:EtOH, and the mixture evaporated. Purification on silica column with MeOH:CH$_2$Cl$_2$ solvent system (4-15% gradient) afforded 358-2 (80 mg, 30%).

A mixture of 358-2 (80 mg, 0.27 mmol) in pyridine (3 mL) and isobutyric anhydride (90 µL, 0.55 mmol) was stirred overnight at RT. The mixture was evaporated, and the residue coevaporated with toluene. Purification on silica column with EtOAc:hexanes solvent system (30-100% gradient) yielded 358-3 (72 mg, 61%) as a white solid.

To a solution of 358-3 (72 mg, 0.17 mmol) in MeCN (2 mL) were added triisopropylphenylsulfonyl chloride (102 mg, 0.34 mmol), DMAP (41 mg, 0.34 mmol) and Et$_3$N (47 µL, 0.34 mmol). The mixture was stirred at RT for 90 mins, and then ammonia was quickly bubbled (<1 min) through. The mixture was stirred for 10 mins. The mixture was diluted with CH$_2$Cl$_2$, washed with 0.1 N HCl, sat. aq. NaHCO$_3$, and brine, and dried with Na$_2$SO$_4$. Purification on silica column with MeOH:CH$_2$Cl$_2$ solvent system (4-12% gradient) afforded 358 (46 mg, 60%). MS: m/z=434.00 [M-1].

Example 193

Compound 359

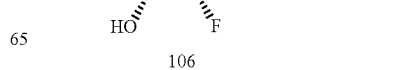

533
-continued

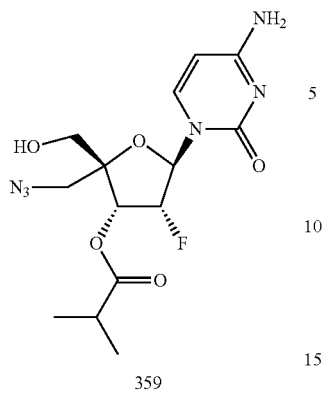

359

To a solution of isobutiric acid (278 µL, 3 mmol) in THF (5 mL) was added CDI (486 mg, 3 mmol). After 1 h the solution of isobutiric acid imidazolide was added to a stirred solution of 106 (600 mg, 2 mmol), triethylamine (560 µL, 4 mmol) and DMAP (0.2 mmol) in DMF (5 mL). The solution was left overnight at RT. The reaction was partitioned between isopropyl acetate and sat. aq. ammonium chloride. The organic phase was washed with water and concentrated under reduced pressure. 359 (500 mg, 67%) was isolated by column chromatography (10 to 15% MeOH in DCM) followed by crystallization from isopropanol:hexane (1:2) as a white solid. MS: m/z 371 [M+H]+.

Example 194

Compound 360

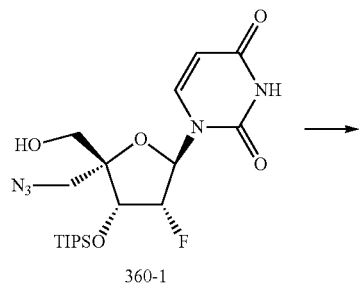

360-1

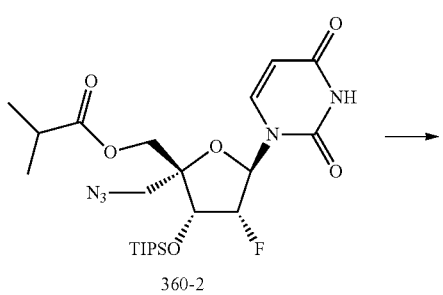

360-2

534
-continued

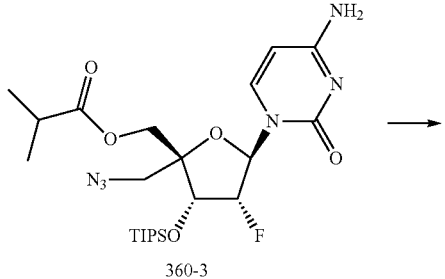

360-3

360

To a stirred solution of 360-1 (2.16 g, 4.73 mmol) in ACN (20 mL) were added triethylamine (1.9 mL, 15 mmol), DMAP (60 mg, 0.5 mmol) and isobutyric anhydride (1.08 mL, 6.5 mmol). The mixture was stirred at RT for 1 h, and then partitioned between isopropyl acetate and sat. aq. sodium bicarbonate solution. The organic phase was separated, washed with water and concentrated. 360-2 (2.1 g, 84%) was isolated by column chromatography using 25 to 50% EA in hexane as a white foam. MS: m/z 528 [M+H]+.

360-2 (2.1 g, 3.98 mmol) was dissolved in ACN (15 mL,) and the solution was cooled to 0° C. Triethylamine (1.1 mL, 8 mmol) and DMAP (537 mg, 4.4 mmol) were added to the solution followed by addition of triisopropylbenzenesulfonyl chloride (1.33 g, 4.4 mmol). The mixture was warmed to RT and then stirred for 1 h. The reaction was quenched with ammonium hydroxide (1 mL). The mixture was stirred for 2 h at RT, diluted with isopropyl acetate and filtered from ammonium salts. The filtrate was washed with water and aq. sodium bicarbonate and then concentrated under reduced pressure. 360-3 (2.1 g, ~100%) was isolated by column chromatography using 4-10% MeOH in CH$_2$Cl$_2$ as a yellowish foam. MS: m/z 527 [M+H]+.

360-3 (1.10 g, 2.09 mmol) was dissolved in THF (6 mL). The solution was cooled to 0° C. and treated with 1M TBAF solution in THF (2.1 mL, 2.1 mmol). The reaction was allowed to proceed for 1 h, and then quenched by the addition of a sat. aq. ammonium chloride solution. 360 (450 mg, 58%) was extracted with isopropyl acetate and isolated by column chromatography in 5-15% MeOH in CH$_2$Cl$_2$ as an off-white foam, MS: m/z 371 [M+H]+.

Example 195

Compound 361

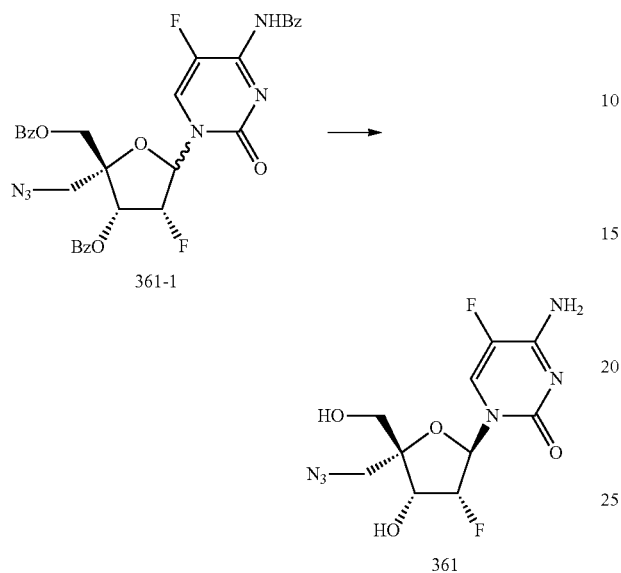

361-1 (400 mg) was dissolved in NH$_3$/methanol (10 mL), and the mixture was kept at ambient temperature over 2 d. The solvent was evaporated, and the residue purified by silica gel chromatography in gradient of MeOH in CH$_2$Cl$_2$ from 3% to 20%. The mixture of products was separated by RP HPLC on Synergy 4 micron Hydro-RP column (Phenominex). A linear gradient of MeOH from 0 to 50% in 50 mM triethylammonium acetate buffer (pH 7.5) was used for elution. The corresponding fractions were collected, concentrated and lyophilized (3×) to remove excess of buffer. The stereochemistry at the 1'-position of both isomers was proved by NOE NMR-experiments. The compound with shorter retention time was 361. MS: m/z 319 [M+1]$^+$, 637 [2M+1]$^+$.

Example 196

Compound 362

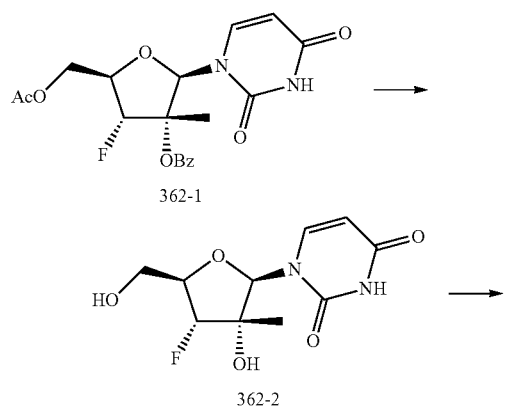

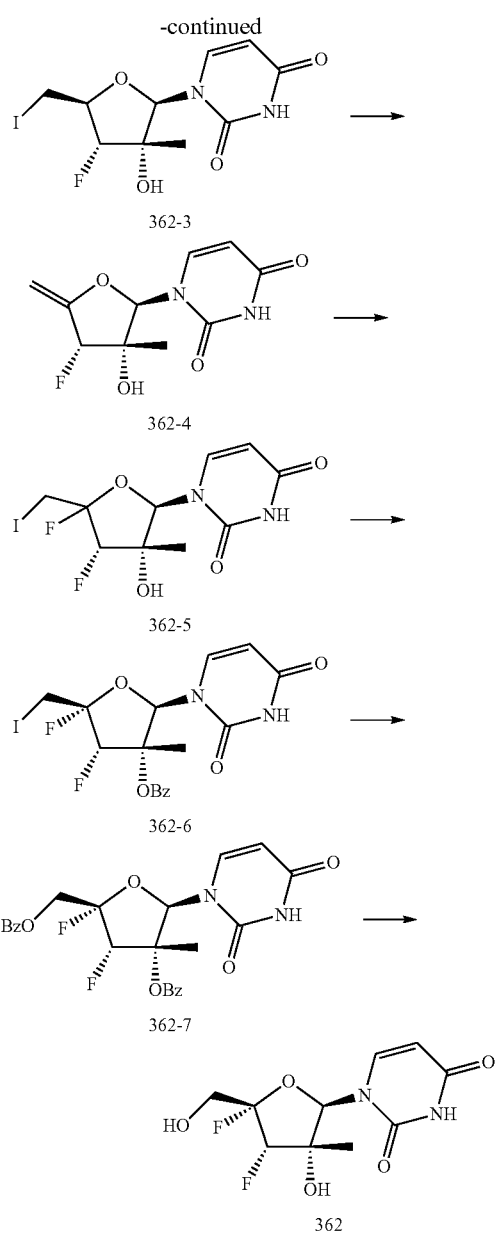

362-1 (6.0 g, 14.77 mmol) was treated with NH$_3$ in MeOH (7.0 M, 150 mL) at RT. The mixture was stirred at 60° C. for 16 h. The mixture was concentrated under reduced pressure. The residue was purified by column chromatography (5% MeOH in DCM) to give 362-2 (3.4 g, 90%) as a white solid.

To a stirred suspension of 362-2 (3.4 g, 13.1 mmol) in anhydrous THF (60 mL) was added pyridine (15 mL), imidazole (1.8 g, 26.5 mol) and PPh$_3$ (5.1 g, 19.5 mol). A solution of I$_2$ (4.3 g, 16.9 mol) in THF (20 mL) was added dropwise at 0° C. The mixture was warmed to RT and stirred for 16 h. The reaction was quenched with sat. aq. Na$_2$S$_2$O$_3$ solution and extracted with EA (3×100 mL). The organic layer was dried over anhydrous Na$_2$SO$_4$, filtered and concentrated under reduced pressure. The residue was purified by column chromatography (40% EA in PE) to afford 362-3 (4.6 g, crude) as a white solid.

To a solution of 362-3 (4.6 g, crude) in THF (35 mL) was added DBU (37.8 g, 247 mmol). The mixture was stirred at RT for 0.5 h. The mixture was neutralized with acetic acid to pH=7 and extracted with EA (3×100 mL). The organic layer was washed with brine, dried over anhydrous Na$_2$SO$_4$ and filtered. The filtrate was concentrated under reduced pressure. The residue was purified by column chromatography (50% EA in PE) to give 362-4 (1.59 g, crude, 84% purity) as a white solid.

To an ice-cold solution of 362-4 (1.59 g, crude) in anhydrous MeCN (35 mL) was added NEt$_3$.3HF (1.06 g, 6.56 mmol 1) and NIS (3.69 g, 16.40 mmol) at 0° C. The mixture was stirred at 0° C. for 1 h. After the reaction was completed, the reaction was quenched with sat. aq. Na$_2$S$_2$O$_3$ solution and sat. aq. NaHCO$_3$ solution and extracted with EA (3×100 mL). The organic layer was dried over anhydrous Na$_2$SO$_4$ and concentrated at low pressure. The residue was purified by column chromatography (50% EA in PE) to give 362-5 (2.0 g, two isomers) as a white solid.

To a solution of 362-5 (2.0 g, 5.15 mmol, two isomers) in anhydrous DCM (30 mL) was added DMAP (1.57 g, 12.88 mmol) and BzCl (1.27 g, 9.01 mmol), and the mixture was stirred at RT for 16 h. The reaction was quenched with sat. aq. NH4Cl solution and extracted with DCM (3×60 mL). The organic layer was dried over anhydrous Na2SO4, filtered and concentrated under reduced pressure. The residue was purified by column chromatography (25% EA in PE) to give the crude product. The crude was further purified by SFC separation (neutral conditions) to give 362-6 (1.60 g, 63.1%) as a white solid.

To a solution of 362-6 (573 mg, 1.16 mmol) in dry DMF (30 mL) was added NaOBz (1.68 g, 11.64 mmol) and 15-crown-5 (3.08 g, 13.97 mmol), and the mixture was stirred at 90-110° C. for 24 h. The mixture was filtered and extracted with EA (3×20 mL). The organic layer was washed with brine, dried over anhydrous Na$_2$SO$_4$, filtered and concentrated at low pressure. The residue was purified by column chromatography (30% EA in PE) to give 362-7 (492 mg, 87.20%) as a white solid.

362-7 (293 mg, 0.6 mmol) was treated with NH$_3$ in MeOH (30 mL, 7.0 M). The mixture was stirred at 60° C. for 16 h, and then concentrated under reduced pressure. The residue was purified by column chromatography (3% isopropanol in DCM) to give the crude product. The crude product was purified by prep-HPLC (FA condition) to give 362 (108 mg, 53.41%) as a white solid. ESI-TOF-MS: m/z=279.1 [M+H]$^+$.

Example 197

Compound 363

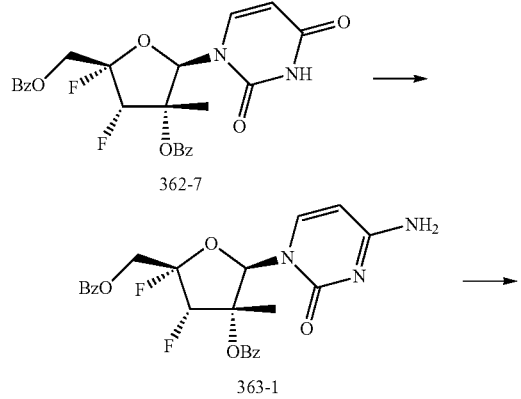

362-7

363-1

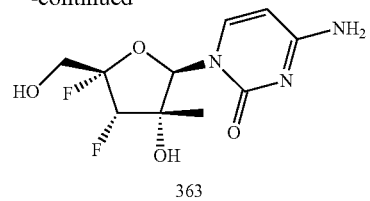

363

To a solution of 362-7 (492 mg, 1.01 mmol) in anhydrous CH$_3$CN (8 mL) were added DMAP (308 mg, 2.53 mmol), Et$_3$N (255 mg, 2.53 mmol) and 2,4,6-triisopropylbenzene-1-sulfonyl chloride (765 mg, 2.53 mmol) at RT. The mixture was stirred at RT overnight. A solution of NH$_3$ in THF (4 mL, 7.0 M) was added, and the mixture was stirred for 30 mins. The solvent was removed under reduced pressure. The residue was diluted with EA. The solution was washed with 0.5% AcOH aq. solution and brine. The organic layer was dried over anhydrous Na$_2$SO$_4$, filtered and concentrated under reduced pressure. The residue was purified by column chromatography (2% MeOH in DCM) and further purified by prep-TLC (10% MeOH in DCM) to give 363-1 (370 mg, 65.6%) as a white solid.

363-1 (370 mg, 0.76 mmol) was treated with NH$_3$ in MeOH (40 mL, 7.0 M). The mixture was stirred at 60° C. for 16 h. The mixture was concentrated under reduced pressure. The residue was purified by column chromatography (8% isopropanol in DCM) to give the crude product. The crude product was purified by prep-HPLC (FA condition) to give 363 (65.6 mg, 30.2%) as a white solid. ESI-TOF-MS: m/z=278.1 [M+H]$^+$, 555.2 [2M+H]$^+$.

Example 198

Compound 364

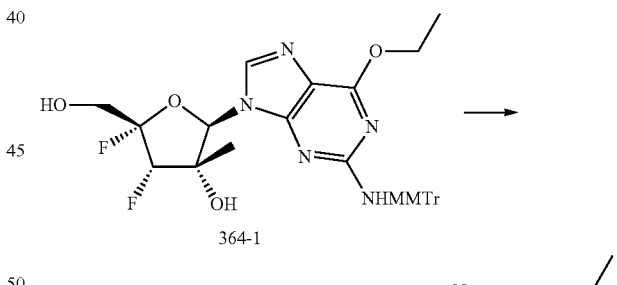

364-1

364

364-1 (50 mg, 0.081 mmol) was dissolved in anhydrous CH$_3$CN (1.0 mL), and 4N HCl in dioxane (81 μL, 0.32 mmol) was added at 0 to 5° C. The mixture was stirred at RT for 1 h. The solvents were evaporated at RT and co-evaporated with toluene (3×). The residue was purified on silica gel column using 15-30% EA:DCM to give 364 (25.6 mg, 92%) as a white solid after evaporation. ESI-LCMS: m/z=346.05 [M+H]$^+$ Example 199
Compound 365
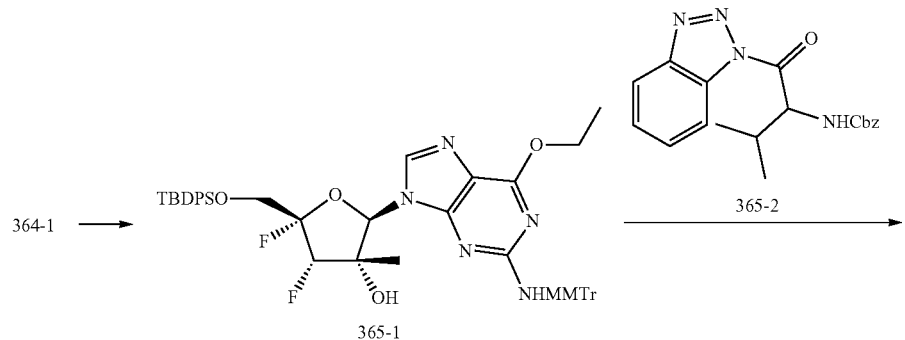
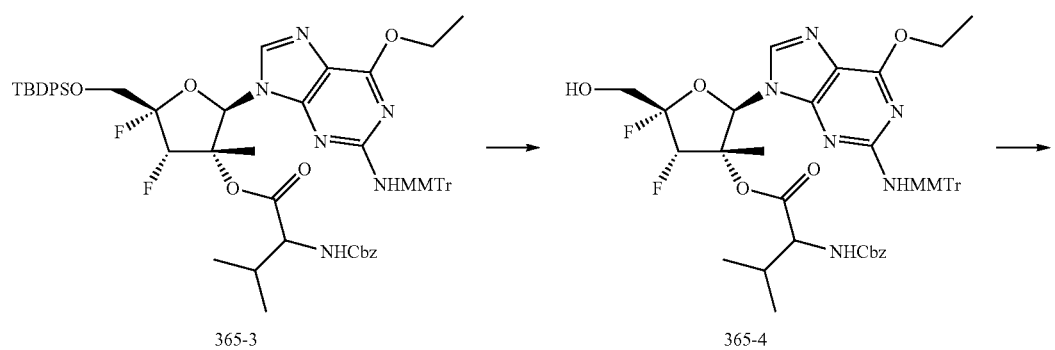
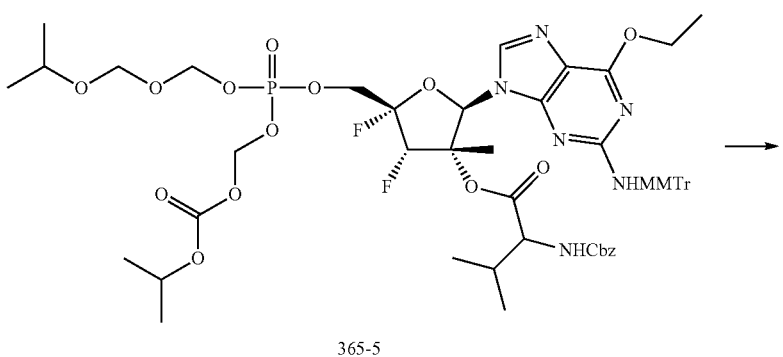
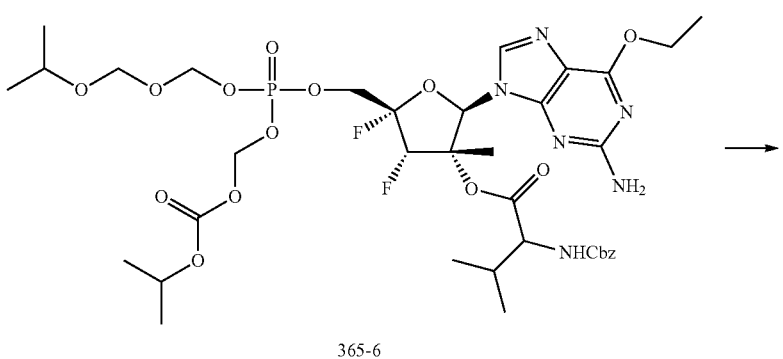

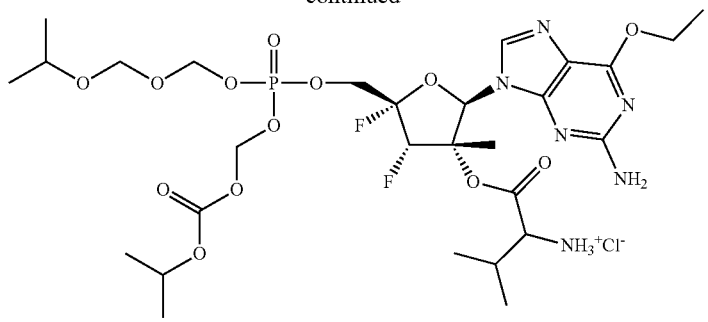

365

To a stirred solution of 364-1 (300 mg, 0.49 mmol) in anhydrous pyridine (3.0 mL) were added TBDPSCl (0.27 mL, 0.97 mmol) and DMAP (119 mg, 0.97 mmol) at 0° C. (ice/water bath). The solution was stirred at RT for 16 h. The mixture was cooled to 0 to 5° C. The reaction was quenched with EtOH (0.3 mL), diluted with EA (100 mL). Water (50 mL) was added to the mixture. The solution was washed with sat. aq. NaHCO$_3$ and brine, and dried with MgSO$_4$. The residue was purified on silica with EA:hexanes (10-100% gradient) to give 365-1 (386 mg, 93%) as an off white foam.

To a stirred solution of 365-1 (300 mg, 0.49 mmol) in anhydrous CH$_3$CN (4.0 mL) were added 365-2 (331.0 mg, 0.94 mmol, was prepared according to procedure described in Katritzky et al., *Synthesis* (2004) 2004(16):2645-2652), DIPEA (0.17 mL, 0.94 mmol) and DMAP (115 mg, 0.94 mmol). The solution was stirred at 70° C. for 16 h. The mixture was cooled to 0 to 5° C., diluted with EA (100 mL) and then water (50 mL) was added. The solution was washed with sat. aq. NaHCO$_3$ and brine, and dried with MgSO$_4$. The residue was purified on silica with EA:hexanes (10-100% gradient) to give 365-3 (174 mg, 70%) as a yellow foam.

To a solution of 365-3 (166 mg, 0.153 mmol) in THF (2 mL), was added 3TEA.HF (98 µL, 0.61 mmol) and TEA (66 µl, 0.46 mmol) at ice bath temperature. The mixture was stirred for 18 h at RT. The mixture was diluted with EA and washed with water and brine. The organic layer was dried and concentrated to give the crude product, which was purified by silica gel column chromatography EA:hexanes (20-100% gradient) to give 365-4 (106 mg, 81.5%) as a white foam.

To a solution of triethylammonium bis (POC) phosphate (0.36 mmol, prepared from 118 mg of bis (POC) phosphate and 0.5 mL of TEA) in THF (3 mL) was added 365-4 (102 mg, 0.12 mmol) followed by 3-nitro-1,2,4-triazole (48 mg, 0.42 mmol), diisopropylethyl amine (0.11 mL, 0.6 mmol) and BOP-Cl (107 mg, 0.42 mmol) at 0 to 5° C. (ice water bath). The mixture was stirred at 2 h, diluted with EtOAc and washed with water and brine. The organic layer was separated, dried over anhydrous Na$_2$SO$_4$ and filtered. The filtrate was concentrated in vacuum to give a white solid, which was purified on silica gel column (EA:hexanes 5 to 60%) to give 365-5 as a light yellow foam (106 mg, 78%).

365-5 (102 mg, 0.088 mmol) was dissolved in anhydrous CH$_3$CN (0.7 mL), and 4N HCl in dioxane (55 µL, 0.22 mmol) was added at 0 to 5° C. The mixture was stirred at RT for 1 h, and then anhydrous EtOH (100 µL) was added. The solvents were evaporated at RT and co-evaporated with toluene (3×). The product was purified on silica gel column (EA:hexanes 15 to 100%) to give 365-6 as a white foam (60.3 mg, 77%)

365-6 (40 mg, 0.044 mmol) was dissolved in anhydrous EtOH (1.3 mL), degassed (3×), flushed H$_2$, and then 10% Pd/C (6 mg) and 4N HCl in dioxane (22 µL, 0.089 mmol) were added. The mixture was stirred under H$_2$ atmosphere at RT for 2 h. The mixture was filtered through celite, and the celite was washed with anhydrous EtOH (1.5 mL). The solvents were evaporated, and triturated with anhydrous diethyl ether (3×1.5 mL). The ether layer was decanted, and the solid obtained was dried in high vacuum to give 365 (26.8 mg, 79.7%, hydrochloride salt) as a white solid. ESI-LCMS: m/z=757.2 [M+H]$^+$.

Example 200

Compound 366

362 ⟶

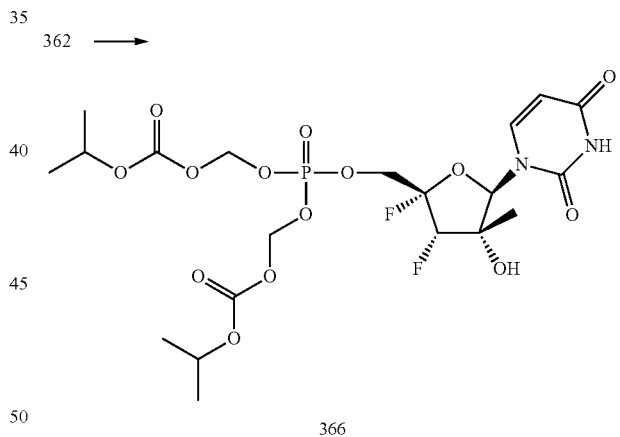

366

366 was prepared according to the procedure described for 365-5 starting from 362 (36.5 mg, 0.13 mmol) and a solution of triethylammonium bis (POC) phosphate (0.26 mmol, prepared from bis (POC) phosphate (85 mg) and TEA (0.5 mL) in THF (1 mL)). ESI-LCMS: m/z=589.0 [M−H]$^−$.

Example 201

Compounds of Formula (I)

Some compounds of Formula (I) are commercially available. For some compounds, the foregoing syntheses are exemplary and can be used as a starting point to prepare additional compounds of Formula (I). Examples of additional compounds of Formula (I) are shown below. These compounds can be prepared in various ways, including those synthetic schemes shown and described herein. Those skilled in the art will be able to recognize modifications of the disclosed syntheses and to devise routes based on the disclosures herein; all such modifications and alternate routes are within the scope of the claims.
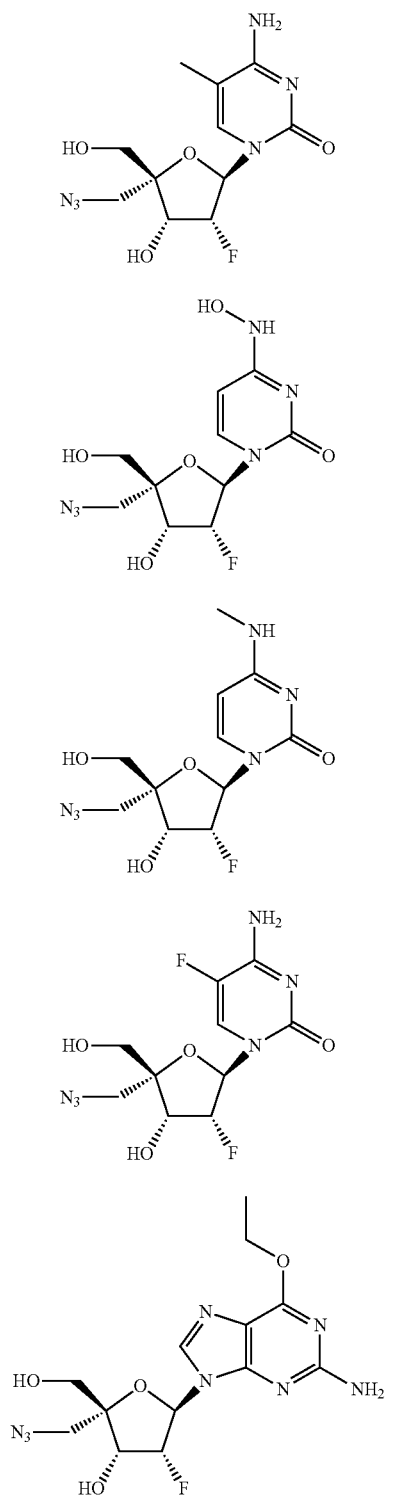
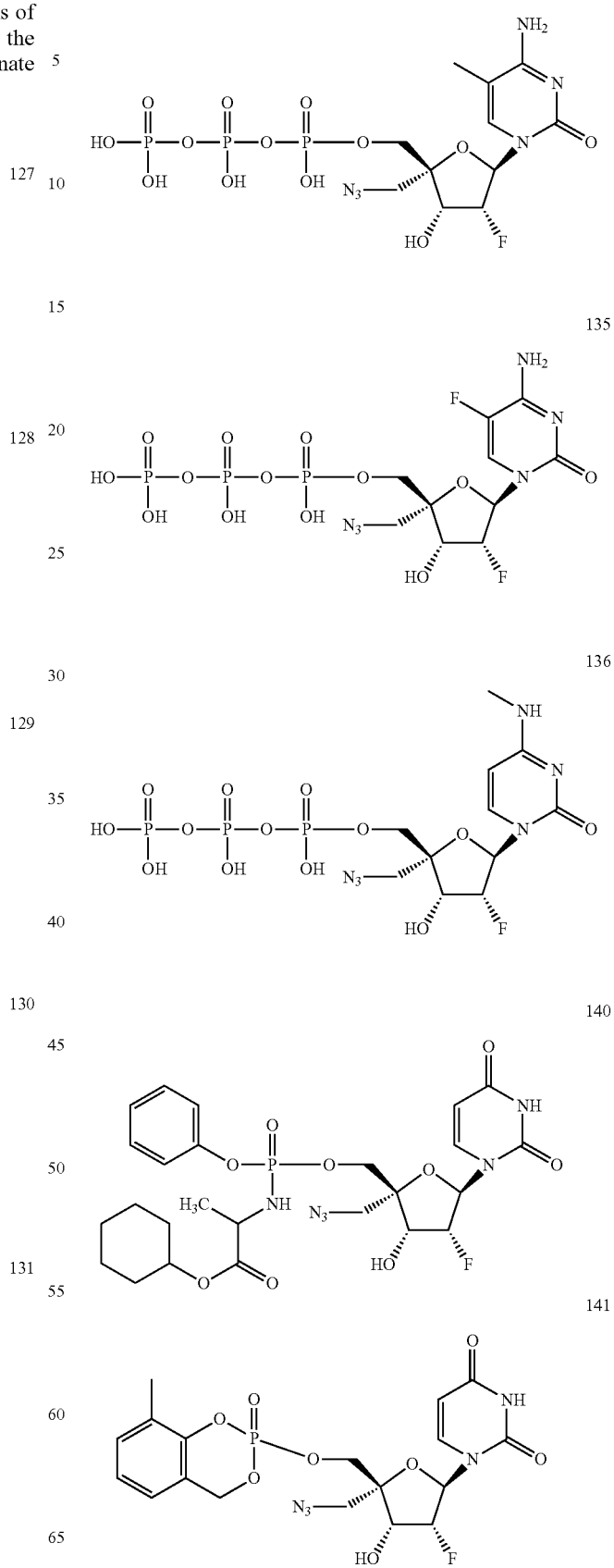

142
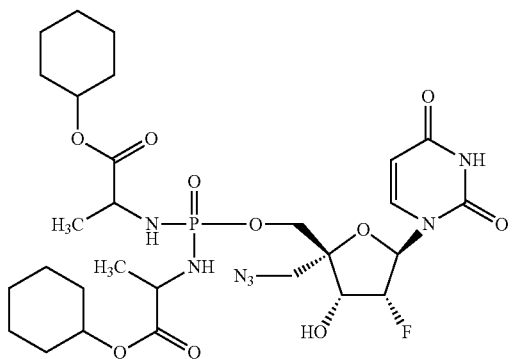
144
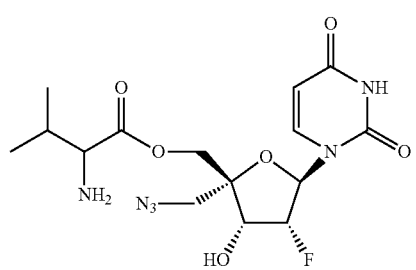
217
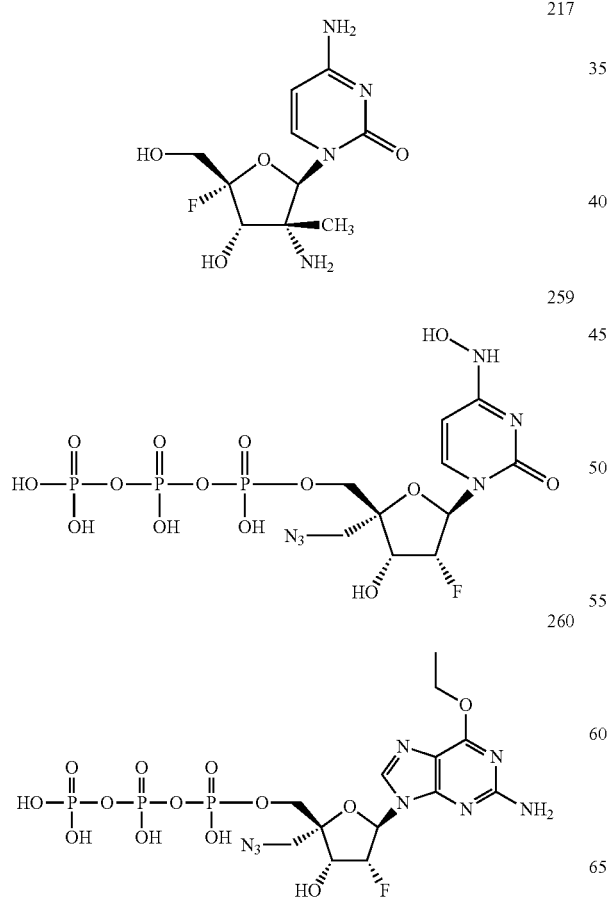
259
260
271
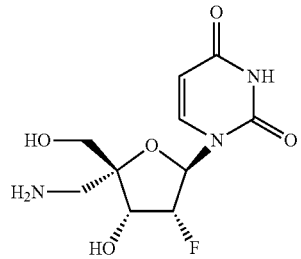
272
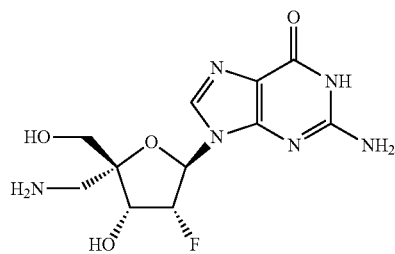
273
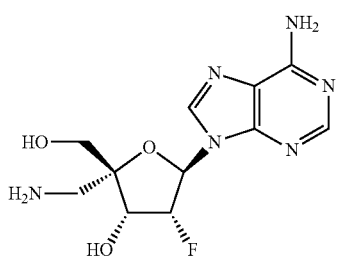
334
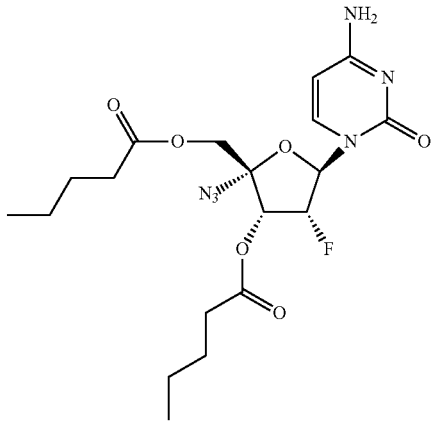
335
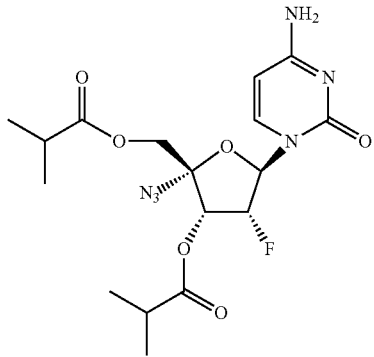

337
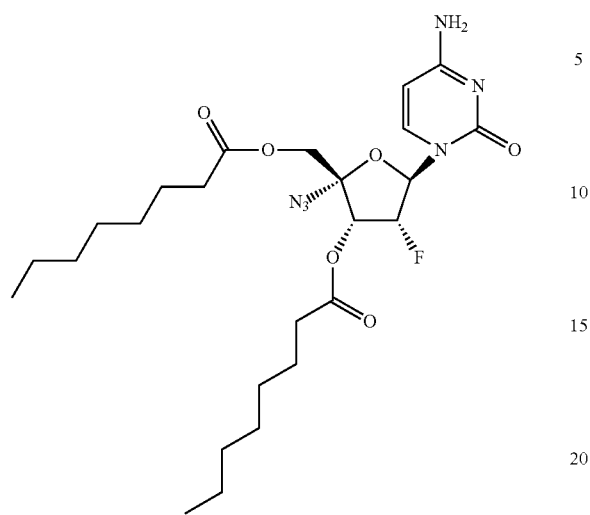
338
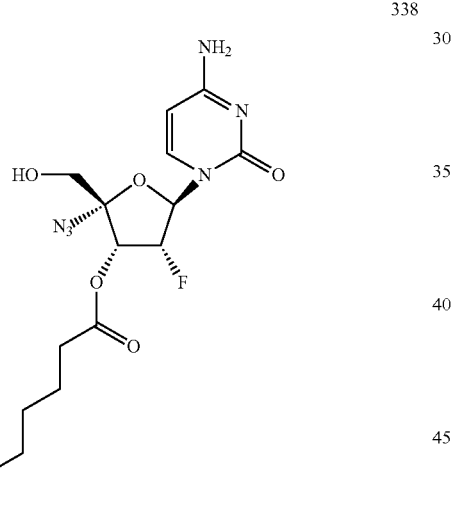
339
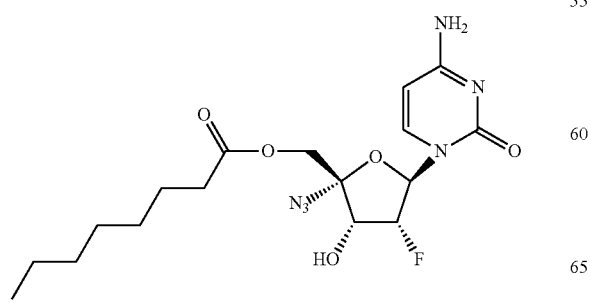
340
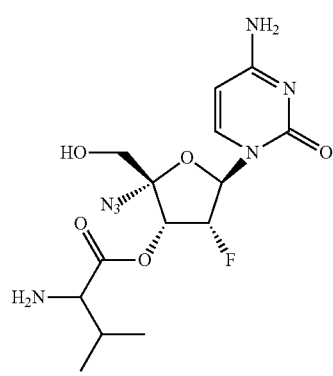
341
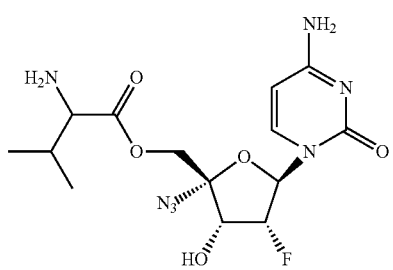
342
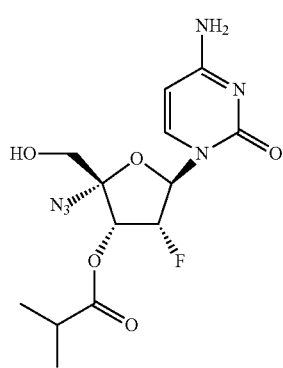
343
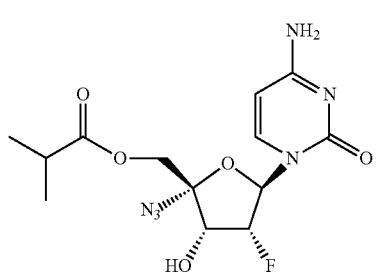

344

[Chemical structure: cytidine analog with 2'-F, 4'-N₃, and 5' and 3' hexanoate esters]

345

[Chemical structure: cytidine analog with 2'-F, 4'-N₃, 5'-OH, and 3'-O-acyl (C11) ester]

376

[Chemical structure: uridine triphosphate analog with 4'-CF₃, 2'-F, 3'-OH]

377

[Chemical structure: guanosine triphosphate analog with 2',4'-diF, 3'-OH, and methyl group]

Example 202

Filoviruses Assay

Compounds of Formula (I) were tested for activity against a filoviruses using methods described in Panchal et al., *J. Biomolecular Screening* (2010) 15(7):755-765. Several compounds of Formula (I) and described herein were active against a filovirus with an activity of $EC_{50} < 25$ µM. For example, compound 315 had an $EC_{50} < 25$ µM against Ebola, and compounds 106 and 332 both had an $EC_{50} < 2$ µM against Ebola in HeLa cells.

Example 203

Combination Studies

Compounds were tested in combination using a recombinant Ebola virus (EBOV) Zaire engineered to express the enhanced green fluorescent protein (EBOV-eGFP) in a HeLa cell culture system. EBOV infection was performed at a multiplicity of infection (MOI) of 0.5. Compounds were tested in 10 point titrations starting at either 20 µM or 100 µM with 2-fold step dilutions. Consensus interferon (CIFN) was tested with each compound at 9 concentrations starting from a top concentration of 10 ng/mL with 3-fold step dilutions. HeLa cells were treated with CIFN 18-20 h prior to EBOV infection, and compounds were added to the cells 2 h before infection. The cells were then incubated with no compound as a control, with the test compounds, or the combination of compounds for a further 48 h. The direct effects of the combination of the test compounds were examined by fixing cells in formalin, washing (3×) in phosphate-buffered saline and assessing the numbers of EBOV-eGFP infected cells by high content imaging. Dose-response curves were determined for individual compounds and fixed ratio combinations of the two test compounds.

MacSynergy II software was kindly provided by Dr. M. Prichard (University of Michigan). This program allows the three-dimensional examination of drug interactions of all data points generated from the checkerboard combination of two inhibitors with Bliss-Independence model. Confidence bounds are determined from replicate data. If the 95% confidence limits (CL) do not overlap the theoretic additive surface, then the interaction between the two drugs differs significantly from additive. The volumes of synergy or antagonism can be determined and graphically depicted in three dimensions and represent the relative quantity of synergism or antagonism per change in the two drug concentrations. Synergy and antagonism volumes are based on the Bliss independence model, which assumes that both compounds act independently on different targets. A set of predicted fractional responses faAB under the Bliss independence model is calculated as faAB=faA+faB−faA·faB with faA and faB representing the fraction of possible responses, e.g. % inhibition, of compounds A and B at amounts dA and dB, respectively, and describes the % inhibition of a combination of compounds A and B at amount (dA+dB). If faAB>faA+faB−faA·faB then we have Bliss synergy; if faAB<faA+faB−faA·faB then we have Bliss antagonism. The 95% synergy/antagonism volumes are the summation of the differences between the observed inhibition and the 95% confidence limit on the prediction of faAB under the Bliss independence model. MacSynergy II was used for data analysis.

MacSynergy II Volume Descriptions: <25 $\mu M^2\%$=Additive; 25-50 $\mu M^2\%$=Minor synergism; 50-100 $\mu M^2\%$=Significant synergism; and >100 $\mu M^2\%$=Strong synergism. Combinations of Infergen® with compound 106, Infergen® with compound 315 and Infergen® with compound 332 with all showed strong synergy.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for ameliorating or treating a Filoviridae viral infection comprising contacting a cell infected with a Filoviridae virus with an effective amount of a compound of Formula (I), or a pharmaceutically acceptable salt thereof, wherein the compound of Formula (I) has the structure:

[Structure of Formula (I) showing a furanose ring with substituents $R^{a1}$, $R^{a2}$, $R^{1A}O$, $R^{2A}$, $B^{1A}$, $R^A$, H, $R^{5A}$, $R^{3A}$, $R^{4A}$]

wherein:
$B^{1A}$ is selected from the group consisting of:

[Uracil and cytosine structures]
and ;

$R^{3A}$ is selected from the group consisting of OH, —OC(=O)$R^{"A}$ and an optionally substituted O-linked α-amino acid;
$R^{4A}$ is halogen;
$R^{a1}$ and $R^{a2}$ are independently hydrogen or deuterium;
$R^A$ is hydrogen;
$R^{1A}$ is selected from the group consisting of hydrogen, an optionally substituted acyl, an optionally substituted O-linked α-amino acid,

[Three phosphate structures: $R^{6A}O-P(=Z^{1A})(OR^{7A})-$, $R^{8A}O-P(=Z^{2A})(R^{9A})-$, and $R^{10A}-P(=Z^{3A})(R^{11A})-$]

$R^{2A}$ is —(CH$_2$)$_{1-6}$Cl or —(CH$_2$)$_{1-6}$N$_3$;
$R^{5A}$ is hydrogen or halogen;
$R^{6A}$ and $R^{7A}$ are independently selected from the group consisting of absent, hydrogen,

[Structure with $R^{22A}$, $R^{23A}$, $Z^{4A}$, O, $R^{24A}$, s]
and

[Structure with O, w, S, $R^{25A}$];

or $R^{6A}$ is

[Structure: $R^{12A}O-P(=O)(OR^{13A})-[O-P(=O)(R^{14A})-]_m$]

and $R^{7A}$ is absent or hydrogen;
$R^{8A}$ is an optionally substituted aryl;
$R^{9A}$ is N-alanine, N-valine, N-leucine, N-alanine isopropyl ester, N-alanine cyclohexyl ester, N-alanine neopentyl ester, N-valine isopropyl ester or N-leucine isopropyl ester;
$R^{10A}$ and $R^{11A}$ are independently N-alanine, N-valine, N-leucine, N-alanine isopropyl ester, N-alanine cyclohexyl ester, N-alanine neopentyl ester, N-valine isopropyl ester or N-leucine isopropyl ester;
$R^{12A}$ and $R^{13A}$ are independently absent or hydrogen;
$R^{14A}$ is O$^-$ or OH;
$R^{22A}$ and $R^{23A}$ are each hydrogen;
$R^{24A}$ is selected from the group consisting of hydrogen, an optionally substituted C$_{1-24}$ alkyl and an optionally substituted —O—C$_{1-24}$ alkyl;
$R^{25A}$ is an optionally substituted C$_{1-24}$ alkyl;
$R^{"A}$ is an optionally substituted C$_{1-24}$ alkyl;
m is 0 or 1;
w is 0;
s is 0; and
$Z^{1A}$, $Z^{2A}$, $Z^{3A}$ and $Z^{4A}$ are each O.

2. The method of claim 1, wherein the Filoviridae virus is Ebola virus.

3. The method of claim 1, wherein the Filoviridae virus is Marburg virus.

4. The method of claim 1, wherein the $R^{2A}$ is (CH$_2$)$_{1-6}$N$_3$.

5. The method of claim 4, wherein $R^{1A}$ is hydrogen.

6. The method of claim 4, wherein $R^{1A}$ is an optionally substituted acyl.

7. The method of claim 6, wherein the optionally substituted acyl has the formula of C(=O)$R^{39A}$, wherein $R^{39A}$ is an optionally substituted C$_{1-12}$ alkyl.

8. The method of claim 4, wherein $R^{1A}$ is C(=O)-unsubstituted C$_{1-4}$ alkyl.

9. The method of claim 4, wherein $R^{1A}$ is

[Structure: $R^{6A}O-P(=Z^{1A})(OR^{7A})-$];

$R^{6A}$ is

[Structure: $R^{12A}O-P(=O)(OR^{13A})-[O-P(=O)(R^{14A})-]_m$];

$R^{7A}$ is absent or hydrogen; $R^{12A}$ and $R^{13A}$ are independently absent or hydrogen; and $R^{14A}$ is O$^-$ or OH.

10. The method of claim 4, wherein $R^{3A}$ is OH.

11. The method of claim 4, wherein $R^{3A}$ is —OC(=O)$R^{"A}$.

12. The method of claim 11, wherein $R''^A$ is an unsubstituted $C_{1-4}$ alkyl.
13. The method of claim 4, wherein $R^{4A}$ is F.
14. The method of claim 4, wherein $R^{5A}$ is hydrogen.
15. The method of claim 7, wherein $R^{3A}$ is —OC(=O)$R''^A$.
16. The method of claim 15, wherein $R''^A$ is an unsubstituted $C_{1-4}$ alkyl.
17. The method of claim 1, wherein the compound is selected from the group consisting of:
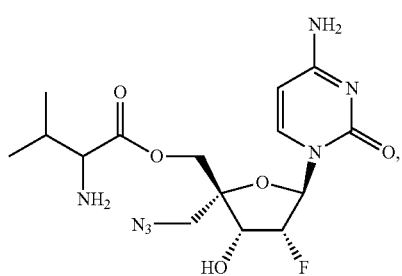
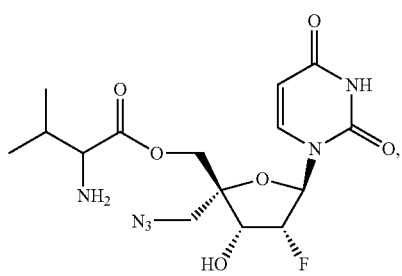
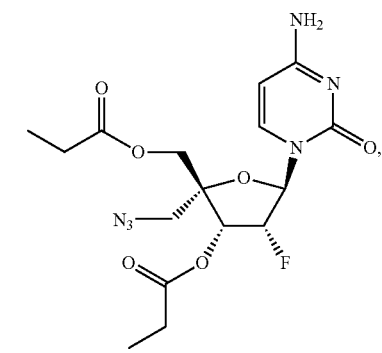
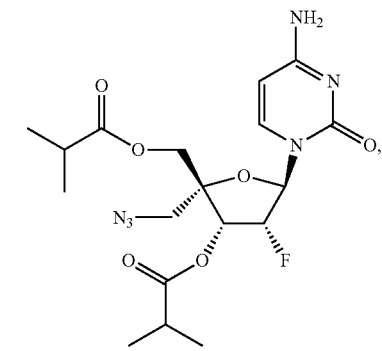
-continued
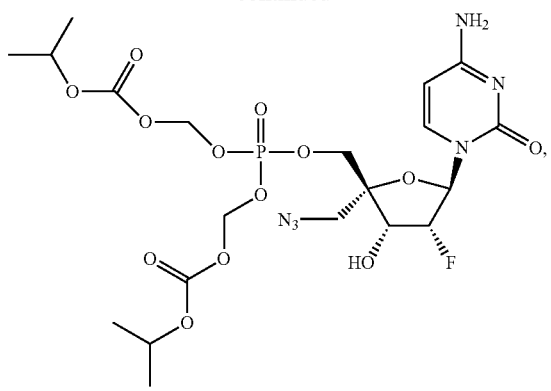
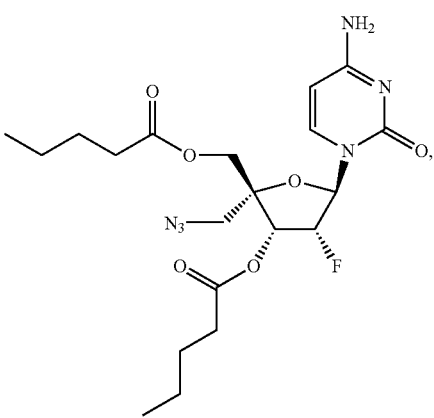
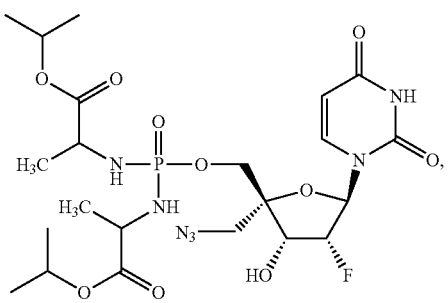
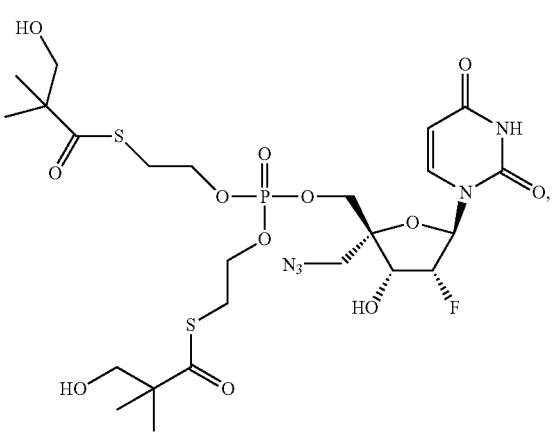

555
-continued
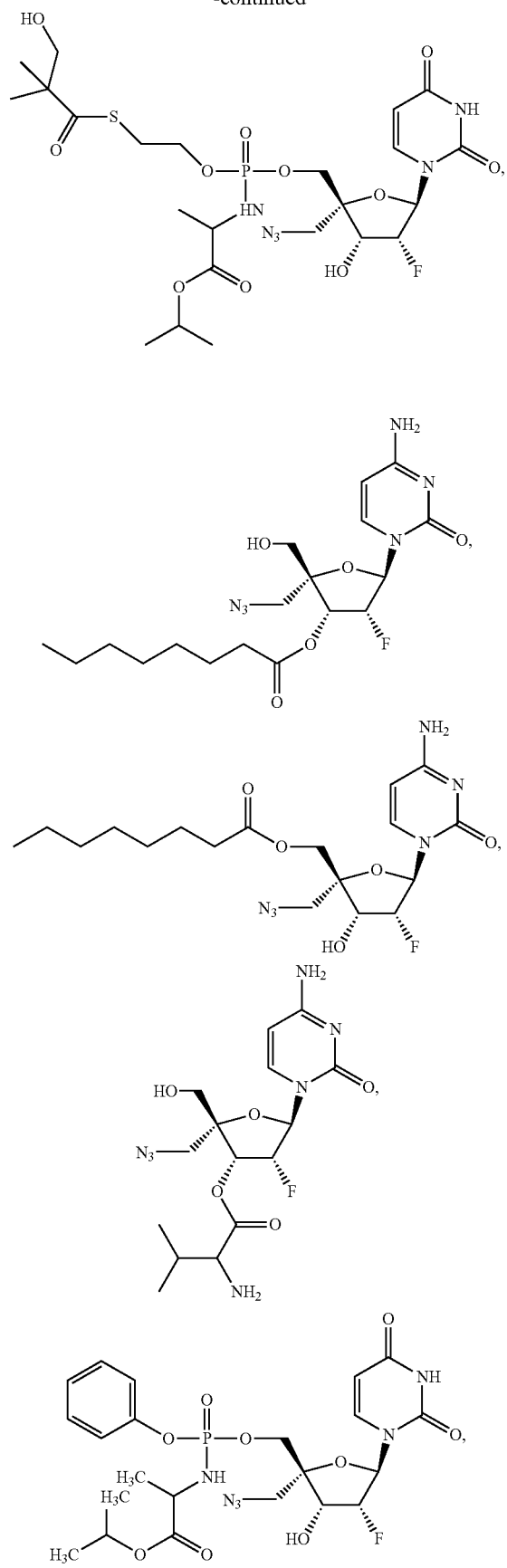
556
-continued
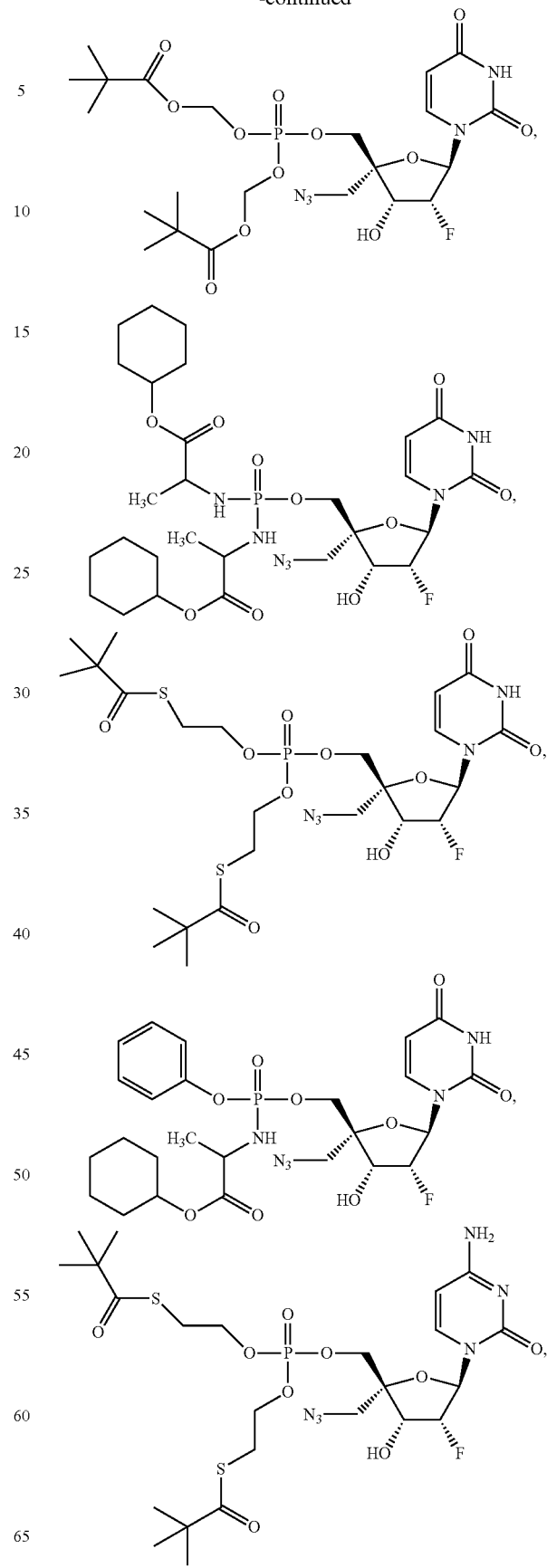

557
-continued
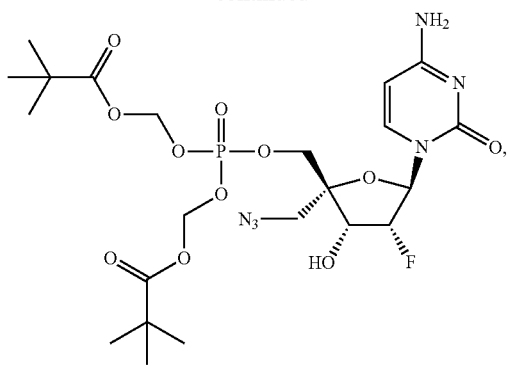
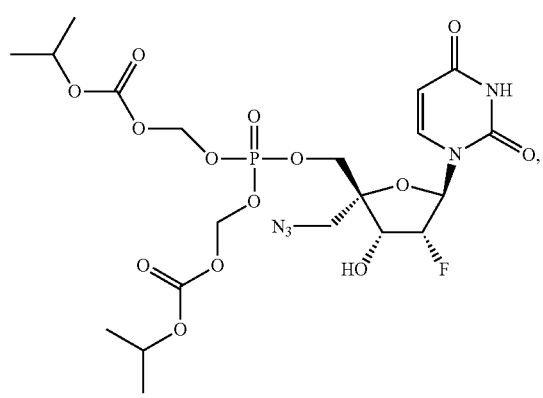
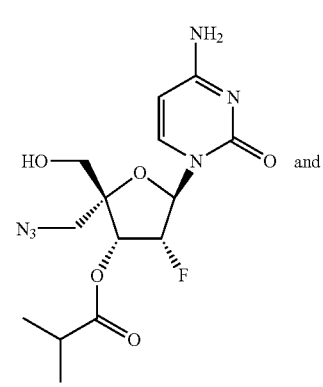 and
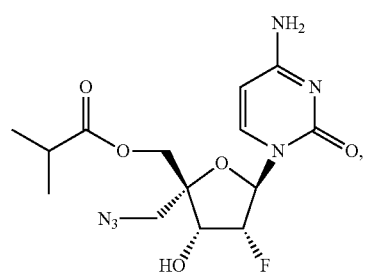
or a pharmaceutically acceptable salt of any of the foregoing.
18. The method of claim 1, wherein the compound is selected from the group consisting of:
558
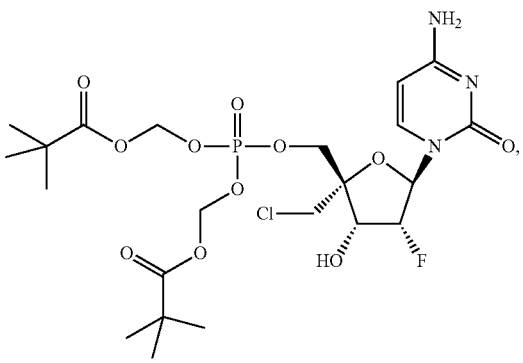
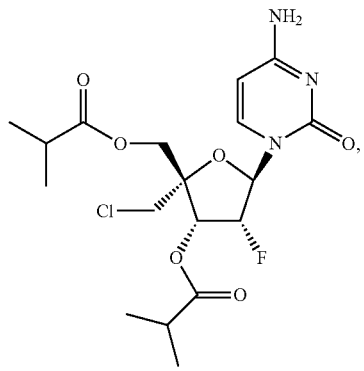
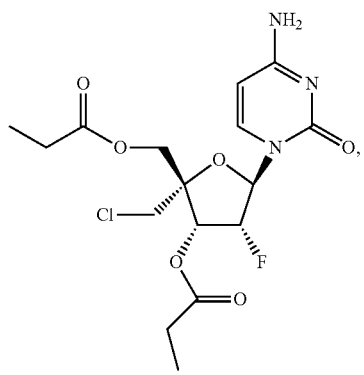
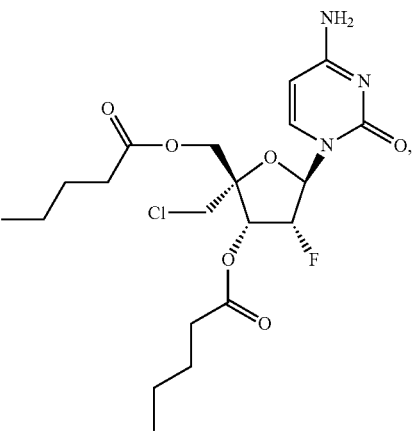

559
-continued
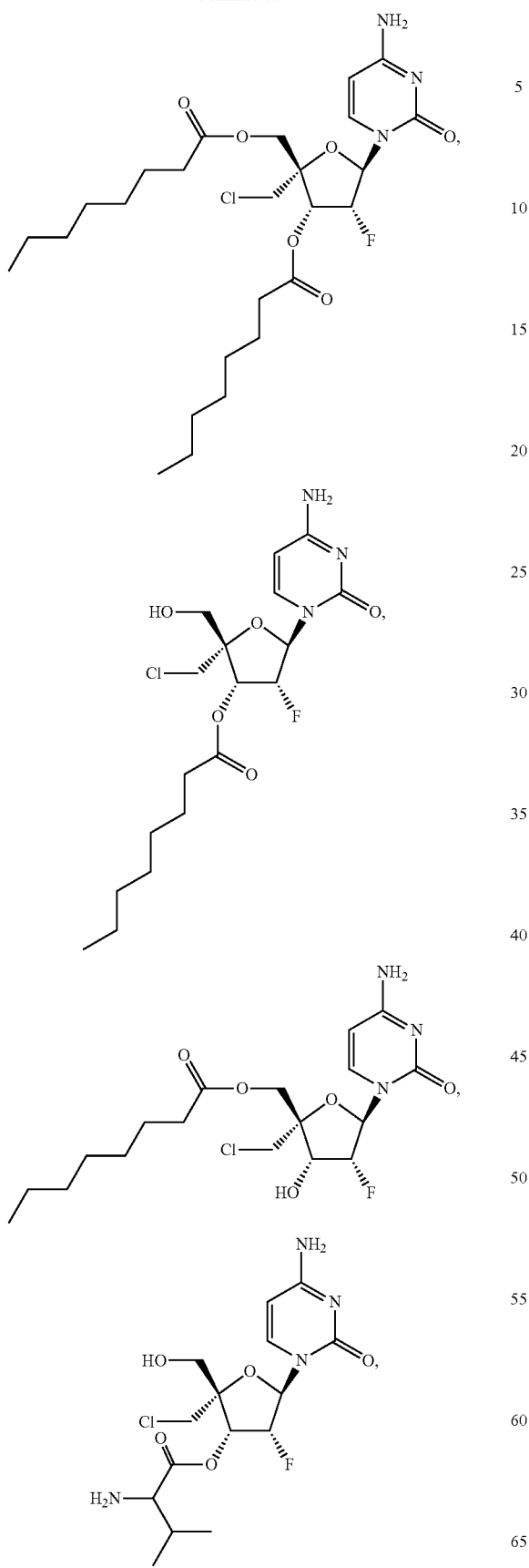
560
-continued
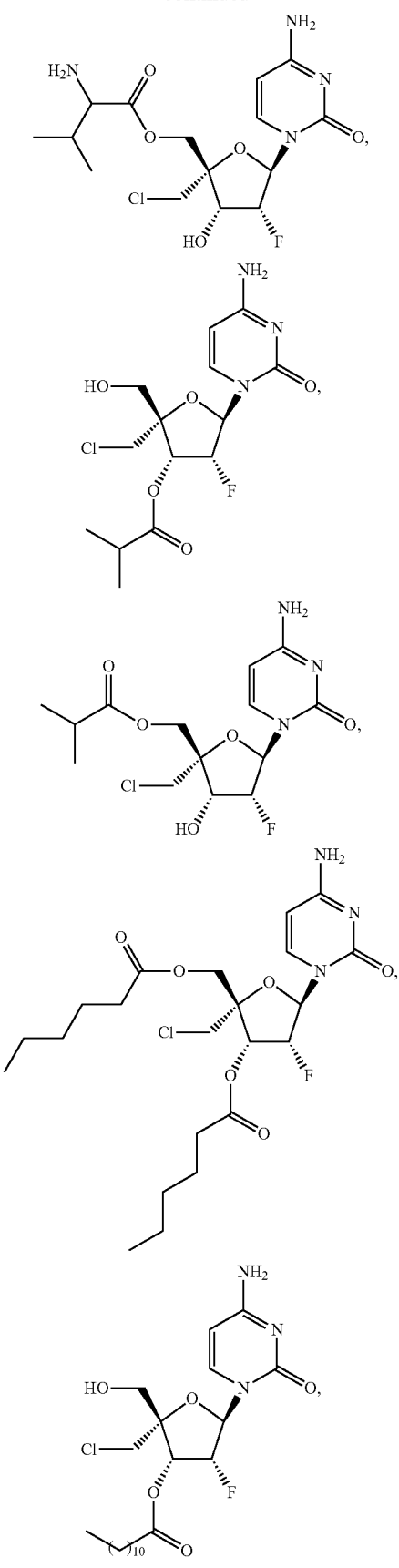

-continued

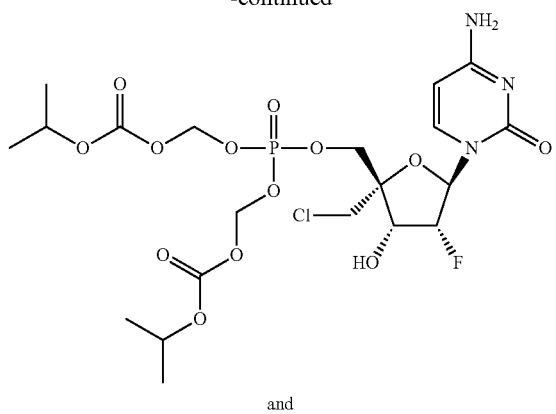

and

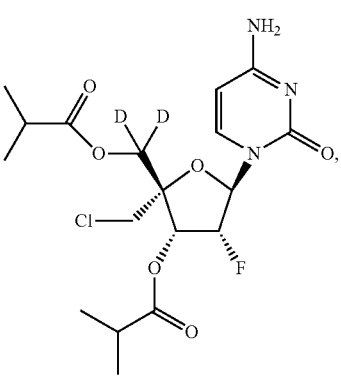

or a pharmaceutically acceptable salt of any of the foregoing.

19. The method of claim 1, wherein the compound is

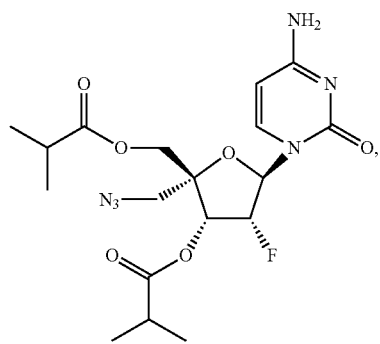

or a pharmaceutically acceptable salt thereof.

20. The method of claim 1, wherein the compound is

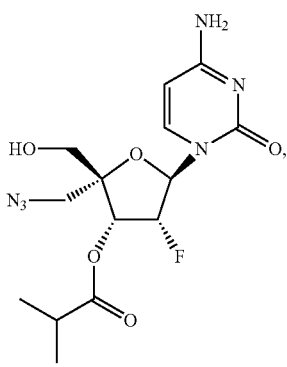

or a pharmaceutically acceptable salt thereof.

21. The method of claim 1, wherein the compound is

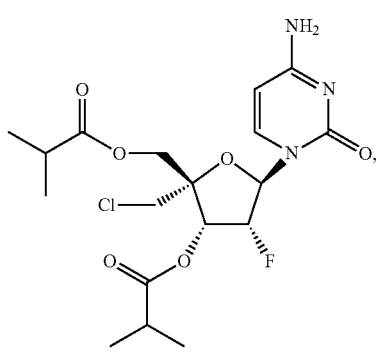 [SMILES: CC(C)C(=O)OC[C@@]1(CCl)O[C@@H](n2ccc(N)nc2=O)[C@H](F)[C@@H]1OC(=O)C(C)C]

or a pharmaceutically acceptable salt thereof.

22. The method of claim 1, wherein the compound is

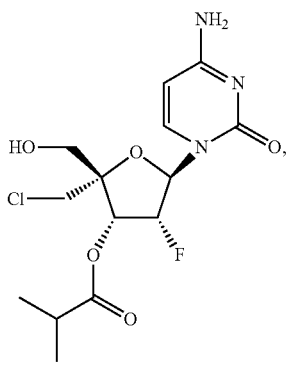 [SMILES: CC(C)C(=O)O[C@H]1[C@@H](F)[C@H](n2ccc(N)nc2=O)O[C@@]1(CO)CCl]

or a pharmaceutically acceptable salt thereof.

* * * * *